(12) United States Patent
Voigt et al.

(10) Patent No.: US 11,441,162 B2
(45) Date of Patent: Sep. 13, 2022

(54) HUMAN GUT MICROBIOME-DERIVED BIOSYNTHETIC ENZYMES FOR PRODUCTION OF FATTY ACID AMIDES

(71) Applicant: Massachusetts Institute of Technology, Cambridge, MA (US)

(72) Inventors: Christopher A. Voigt, Belmont, MA (US); Fang-Yuan Chang, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 7 days.

(21) Appl. No.: 16/812,196

(22) Filed: Mar. 6, 2020

(65) Prior Publication Data
US 2020/0299738 A1    Sep. 24, 2020

Related U.S. Application Data

(60) Provisional application No. 62/816,021, filed on Mar. 8, 2019.

(51) Int. Cl.
*C12P 13/02*    (2006.01)

(52) U.S. Cl.
CPC ....... *C12P 13/02* (2013.01); *C12Y 203/01041* (2013.01)

(58) Field of Classification Search
None
See application file for complete search history.

(56) References Cited

U.S. PATENT DOCUMENTS

2015/0079643 A1*  3/2015  Lutes ............... C12P 13/02
                                                    435/129
2020/0299738 A1*  9/2020  Voigt ................ C07K 14/33

FOREIGN PATENT DOCUMENTS

WO   WO 2013/173576 A1   11/2013
WO   WO 2015/077752 A1    5/2015
WO   WO 2018/0213554 A1  11/2018

OTHER PUBLICATIONS

PCT/US2020/021578, May 4, 2020, International Search Report and Written Opinion.
International Search Report and Written Opinion dated May 4, 2020 for Application No. PCT/US2020/021578.
Kim et al., Mind-altering With the Gut: Modulation of the Gut-Brain Axis With Probiotics. J Microbiol. Mar. 2018;56(3):172-182. doi: 10.1007/s12275-018-8032-4.

* cited by examiner

*Primary Examiner* — Richard C Ekstrom
(74) *Attorney, Agent, or Firm* — Wolf, Greenfield & Sacks, P.C.

(57) ABSTRACT

Disclosed herein, in some embodiments, are vectors encoding biosynthetic enzymes from gut microbiome-derived bacterium (e.g., Clostridia enzymes), engineered cells comprising the vectors, and methods of using biosynthetic enzymes from gut microbiome-derived bacterium (e.g., Clostridia enzymes) to produce fatty acid amides.

31 Claims, 96 Drawing Sheets

Specification includes a Sequence Listing.

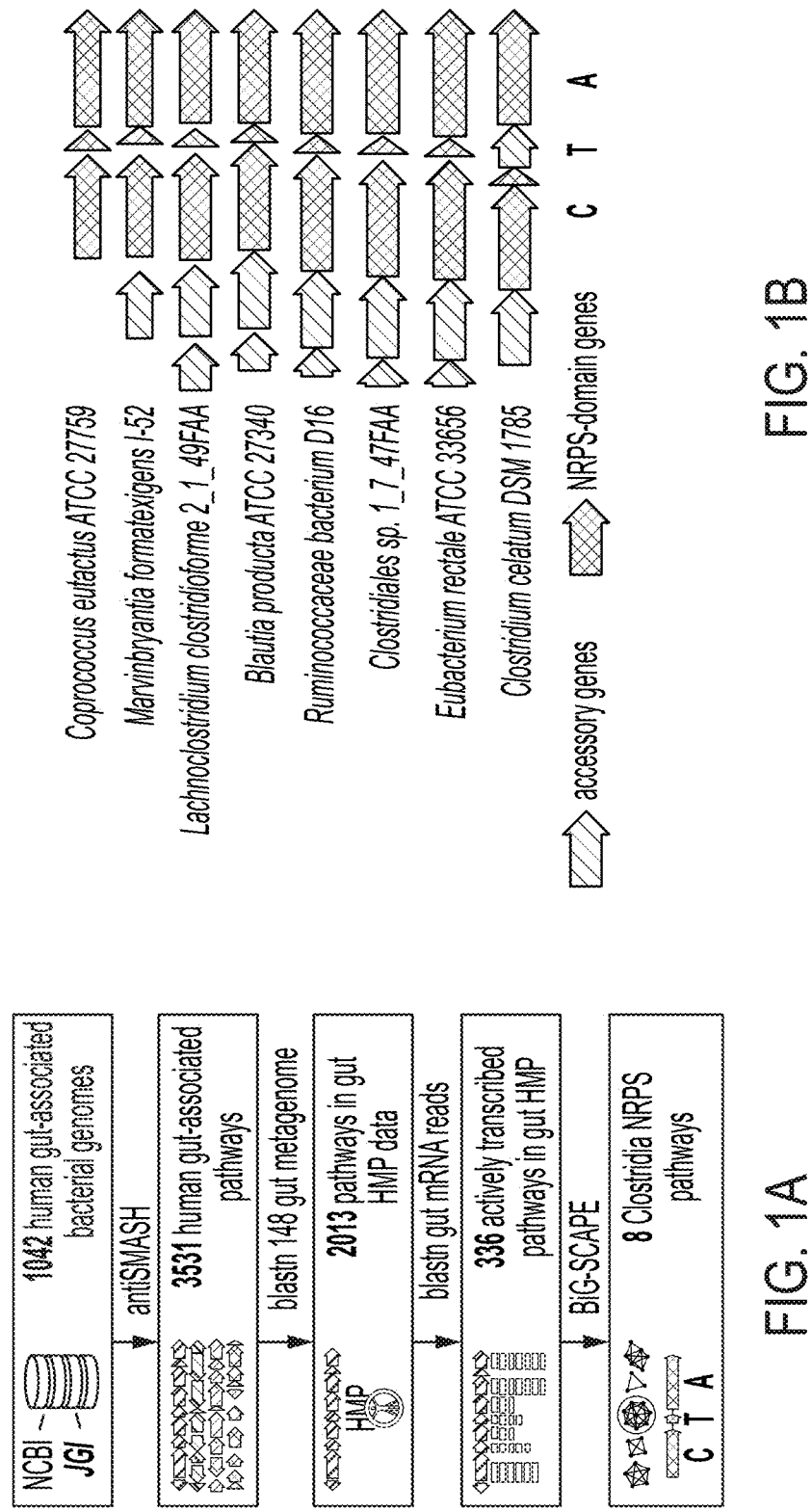

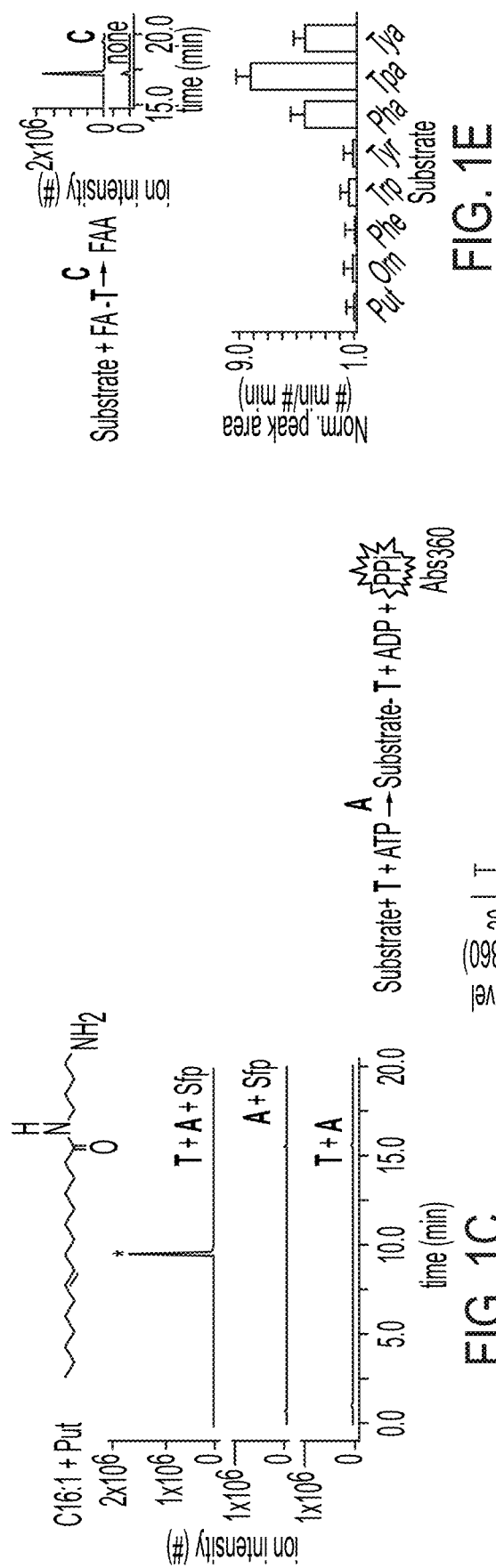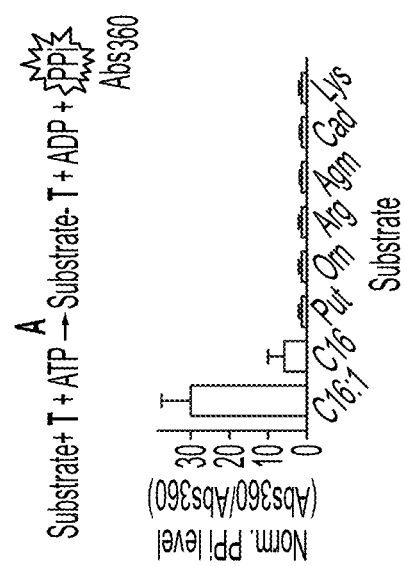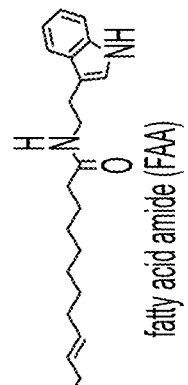

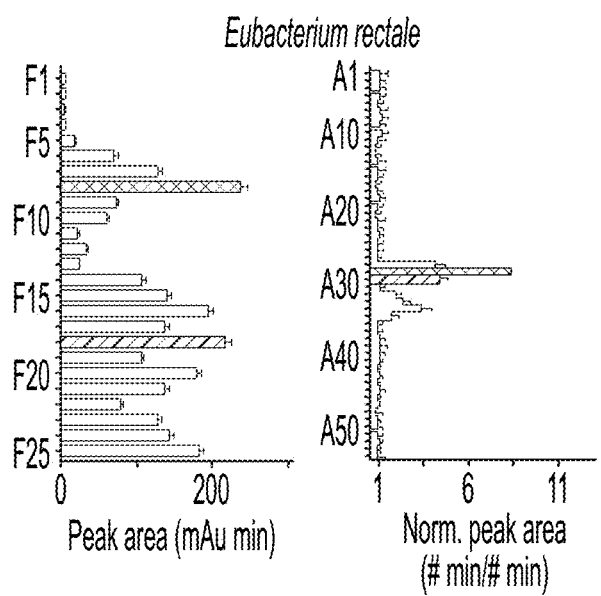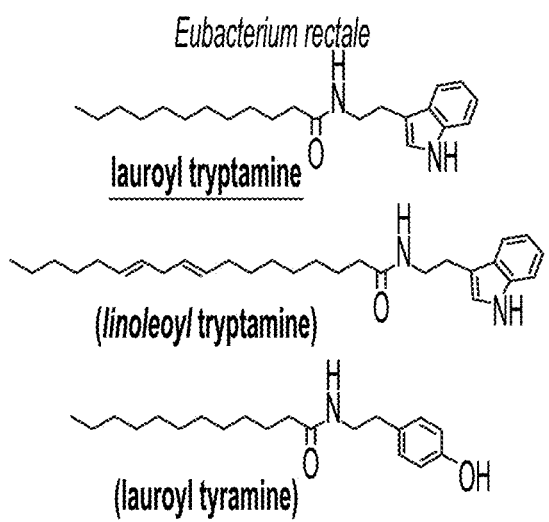
FIG. 2E
CONTINUED

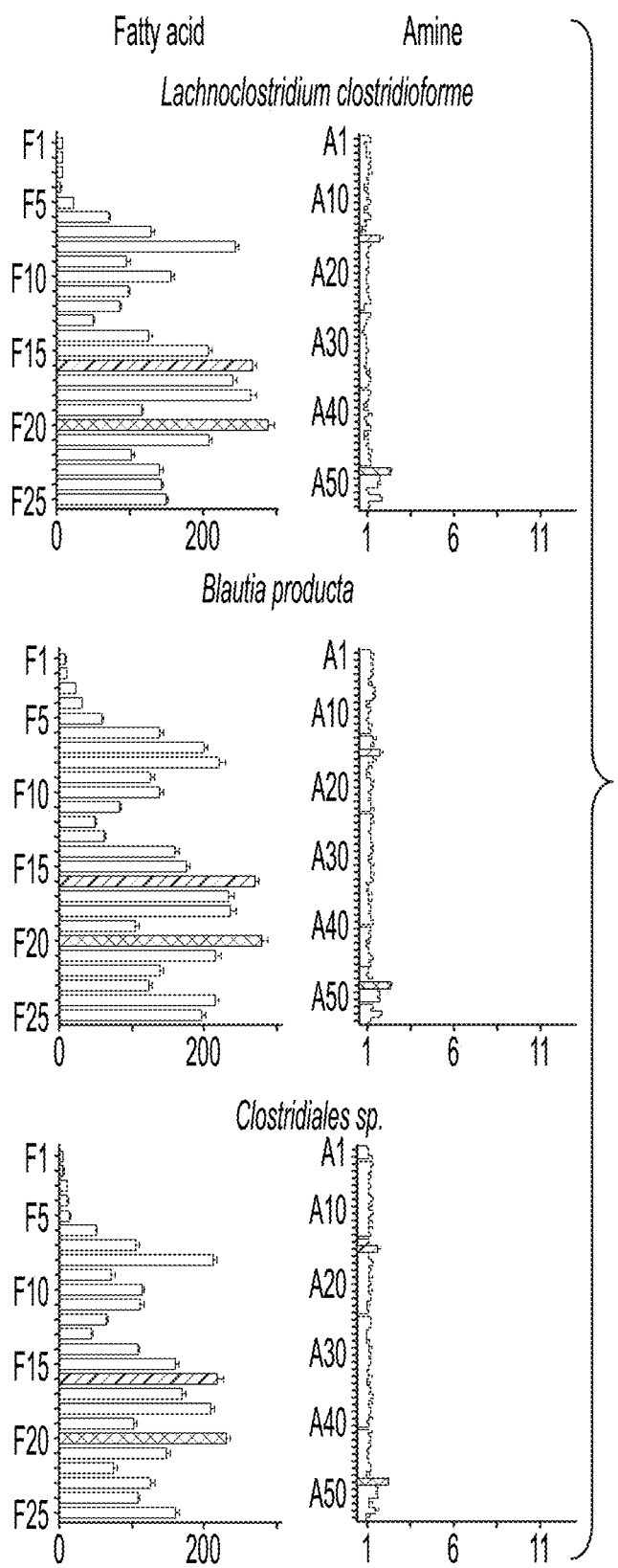
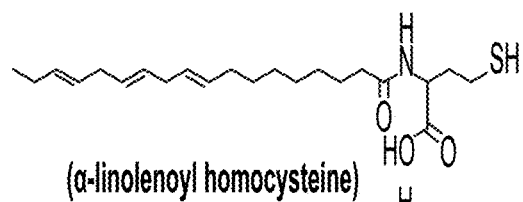
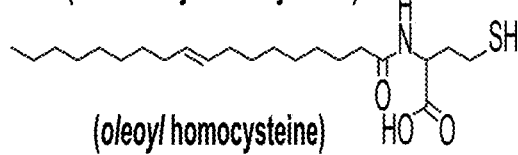
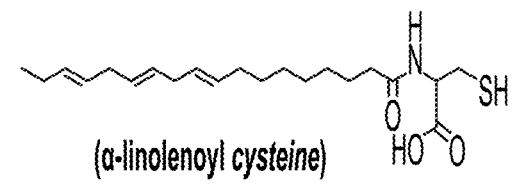
FIG. 2E CONTINUED

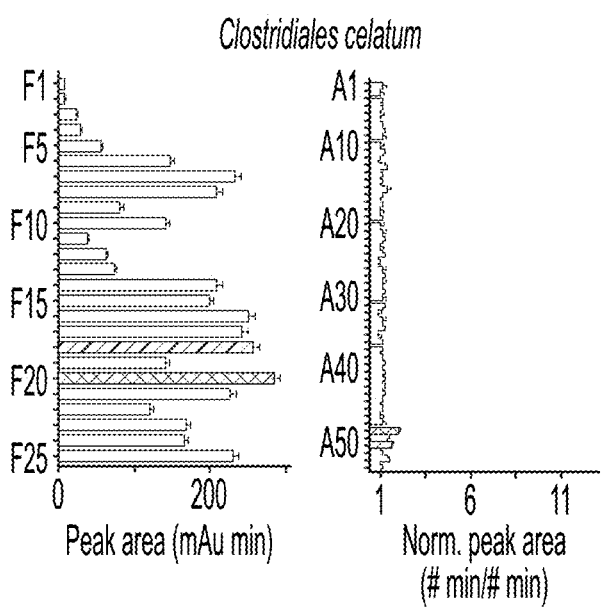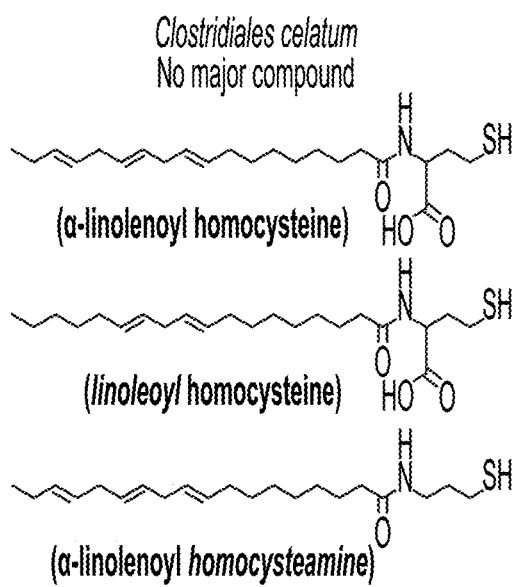
FIG. 2E
CONTINUED

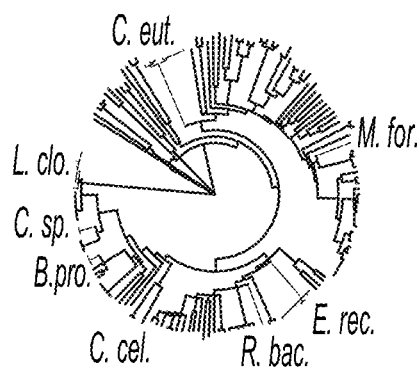
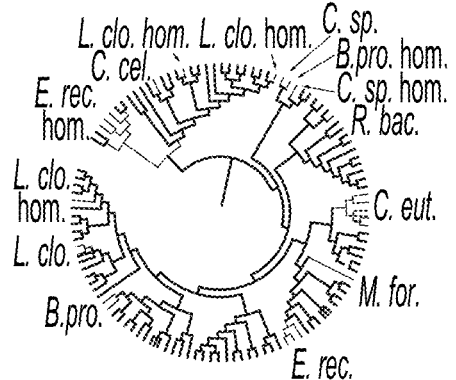
FIG. 4
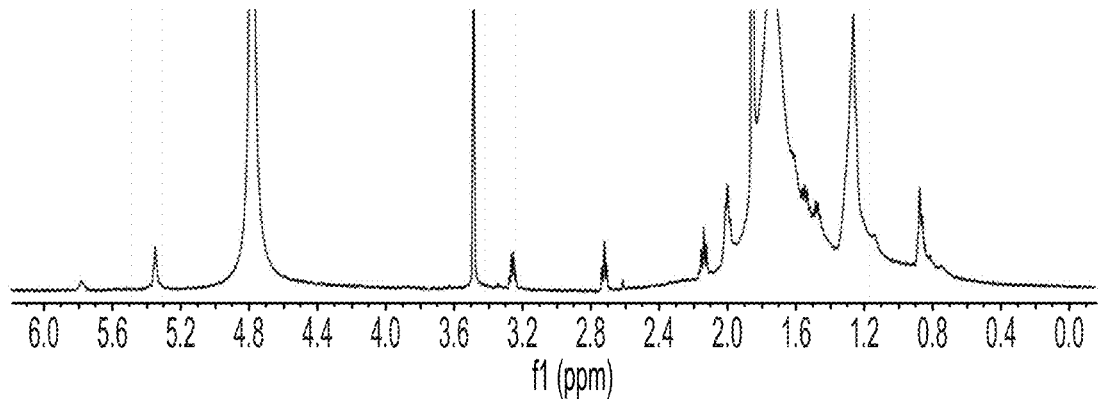
FIG. 5A
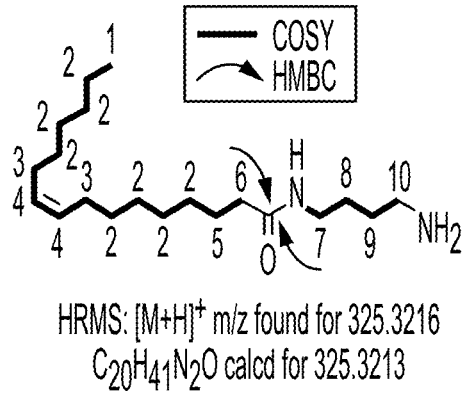
HRMS: [M+H]+ m/z found for 325.3216
C20H41N2O calcd for 325.3213
FIG. 5B
| Position | Integration | δH (J in Hz) | COSY | HSQC δC |
|---|---|---|---|---|
| 1 | 3H | 0.88, t (6.4) | 2 | 14.5 |
| 2 | 16H | 1.28, m | 1, 3, 5 | 29.9 |
| 3 | 4H | 2.01, q (7.4) | 2, 4 | 27.7 |
| 4 | 2H | 5.35, dt (9.8, 7.2) | 3 | 130.2 |
| 5 | 2H | 1.62, m | 2, 6 | 26.3 |
| 6 | 2H | 2.15, t (6.5) | 5 | 37.6 |
| 7 | 2H | 3.26, t (7.5) | NH, 8 | 39.8 |
| 8 | 2H | 1.55, m | 7, 9 | 27.7 |
| 9 | 2H | 1.49, m | 8, 10 | 30.9 |
| 10 | 2H | 2.73, t (6.8) | 9 | 42.7 |
| NH (amide) | 1H | 5.78, bs | 7 | |
FIG. 5C

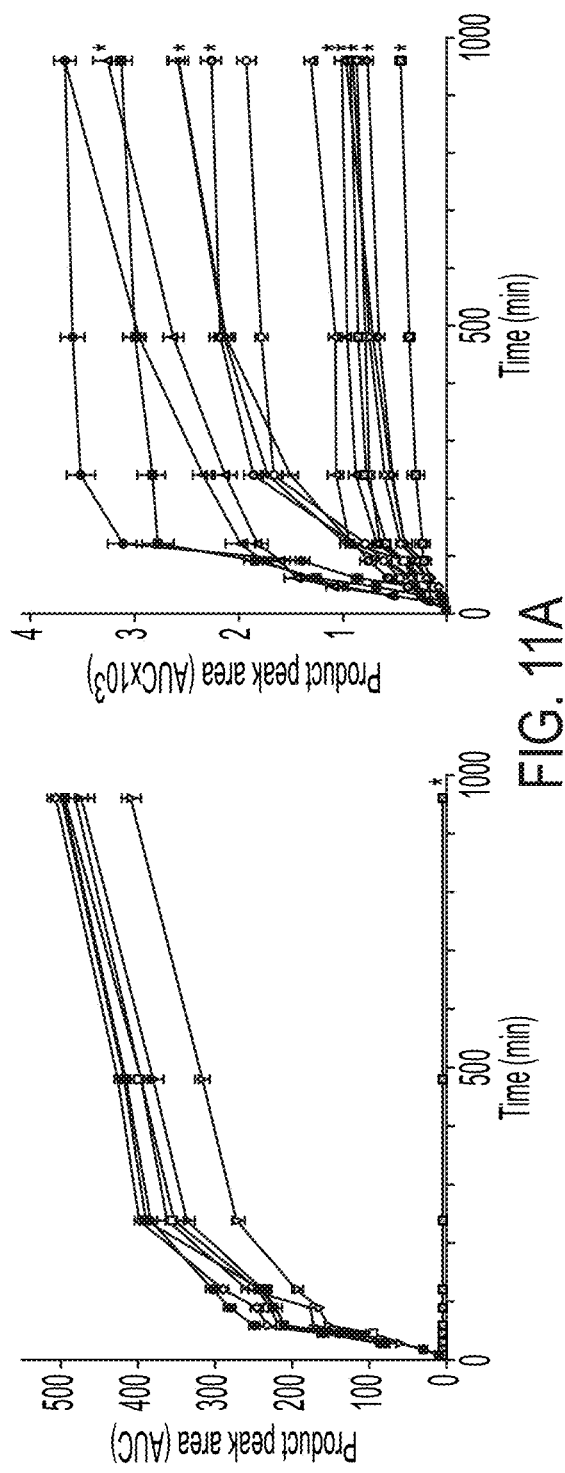
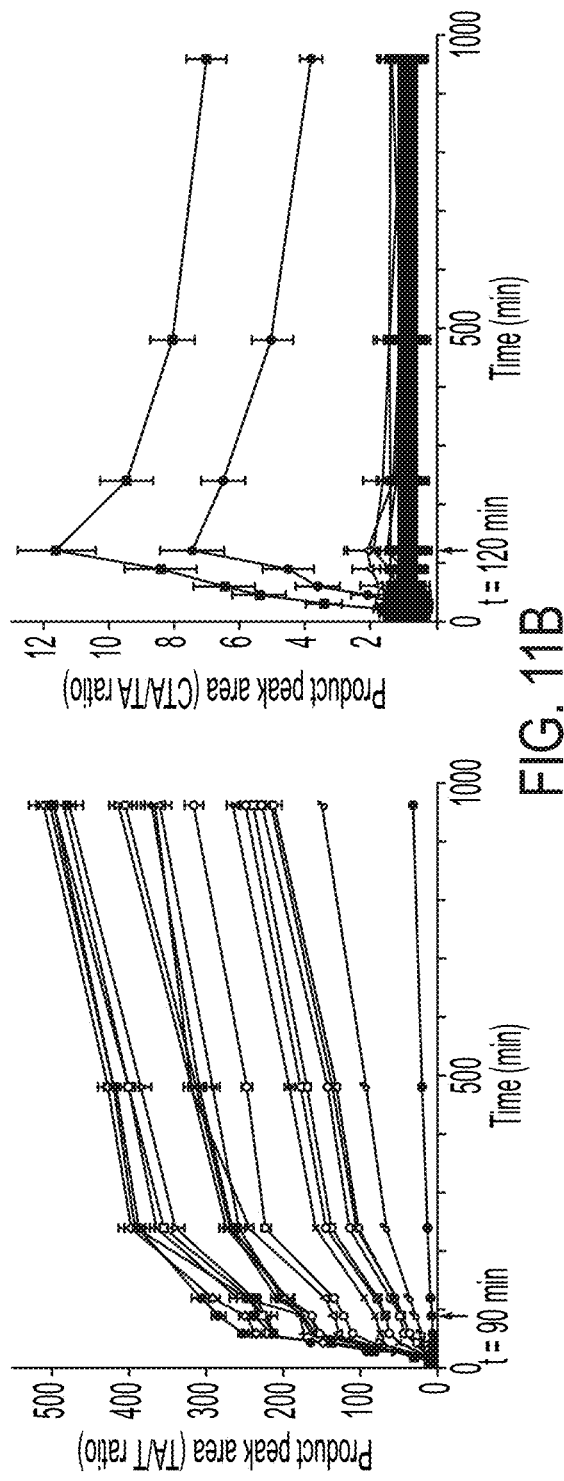
FIG. 11A
FIG. 11B

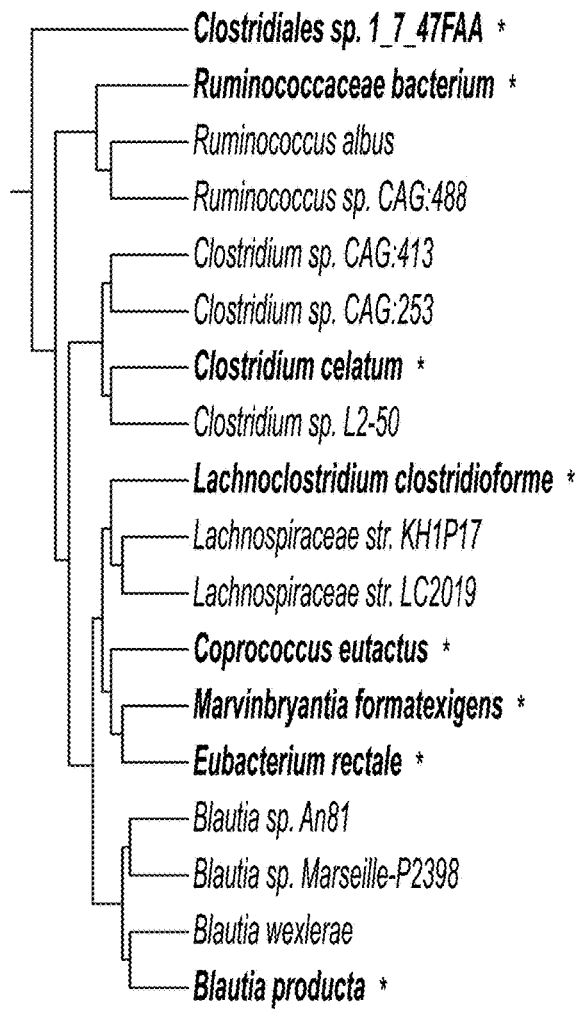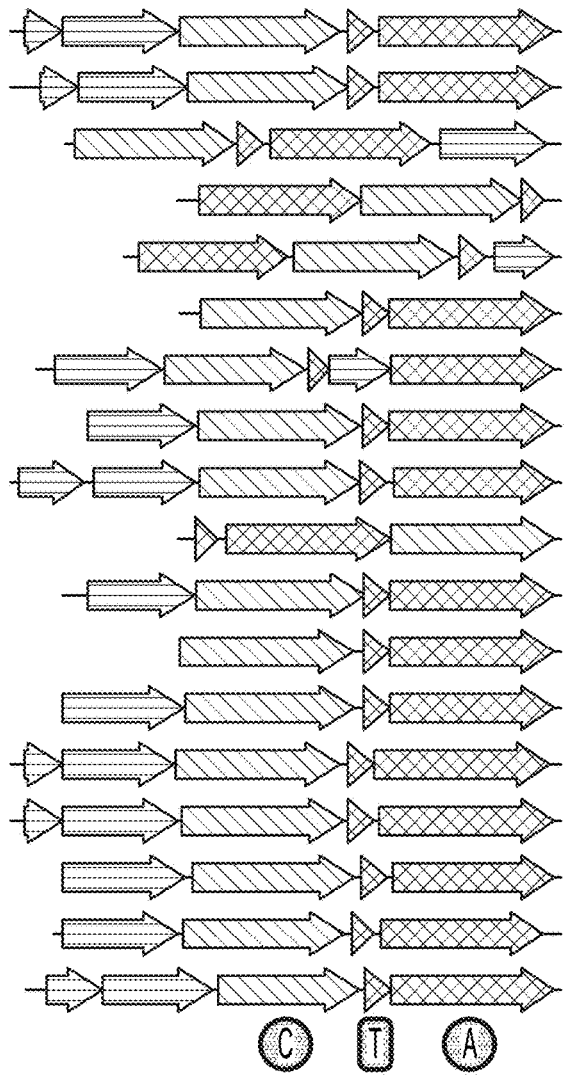
FIG. 15A

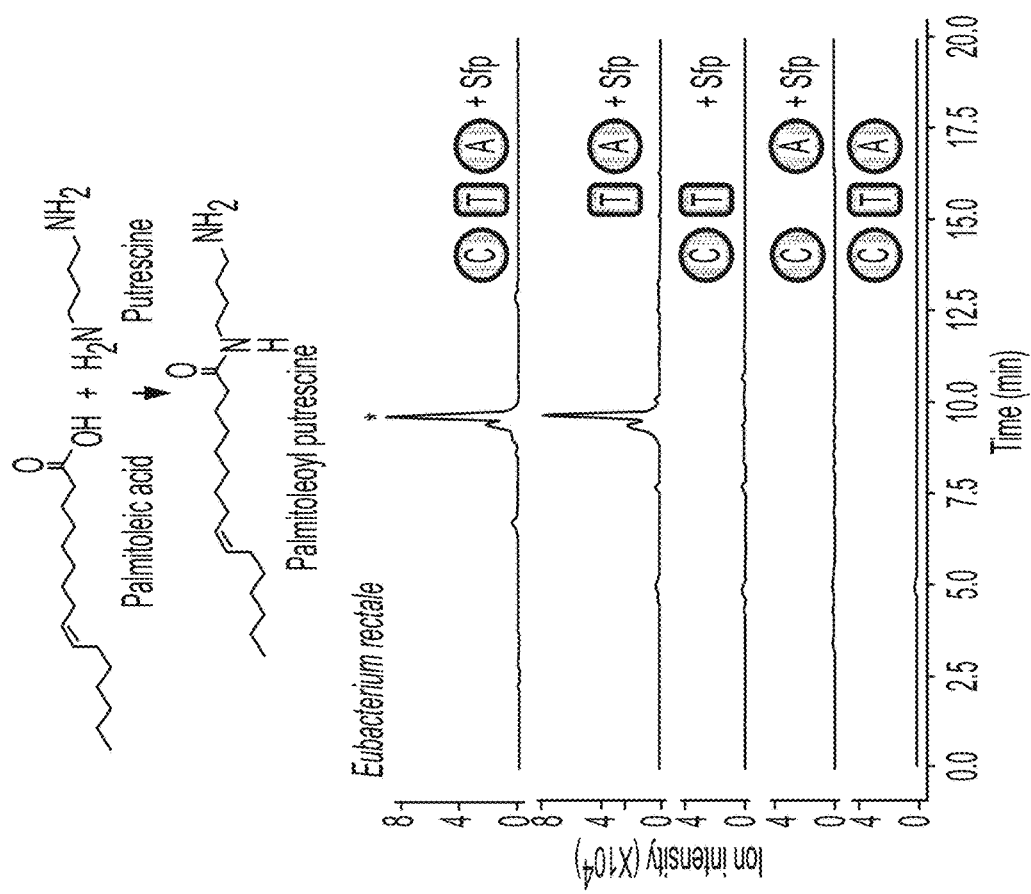
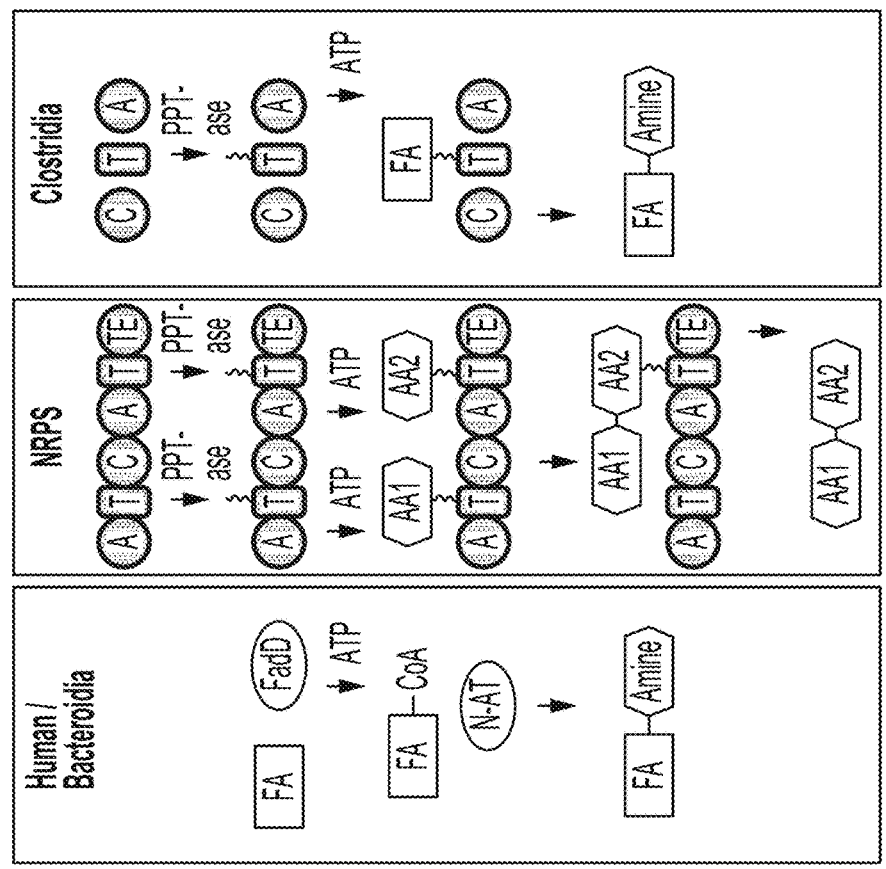
FIG. 16B
FIG. 16A

*Eubacterium rectale* 

| # | Name (NCBI #) | Close nonidentical homolog (NCBI #) | Homolog in/near NAA pathway (Y/N) |
|---|---|---|---|
| 16 | PD-(D/E)XK nuclease family transposase (WP_015516882) | *Ruminococcus torques* (CUN24676) | No |
| 17 | Hypothetical protein (CBK91075) | *Vibrio coralliilyticus* (WP_080555927) | No |
| 7 | TetR regulator (WP_015516884) | *Lachnoclostridium sp. An76* (WP_087178539) | Yes |
| 6 | SCP2 sterol-binding domain protein (WP_015516885) | *Lachnoclostridium sp. An298* (WP_087151249) | Yes |
| 4 | Alpha/beta hydrolase (WP_015516886) | *Ruminococcus torques* (CUN26251) | Yes |
| 1 | Non-ribosomal peptide synthetase (WP_015516887) | *Ruminococcus torques* (CUN05859) | Yes |
| 2 | Acyl carrier protein (WP_015516888) | *Lachnoclostridium sp. An169* (WP_087160605) | Yes |
| 3 | Long-chain-fatty-acid-CoA ligase (WP_118342301) | *Ruminococcus torques* (CUN26274) | Yes |
| 12 | Cell wall glycosyltransferase (WP_015568930) | *Roseburia sp. MUC/ MUC-530-WT-4D* (WP_154429335) | No |
| 18 | Nucleotidyltransferase domain protein (WP_012741894) | *Roseburia sp. MUC/ MUC-530-WT-4D* (WP_154429007) | No |
| 19 | Nucleotidyltransferase (WP_015516891) | *Roseburia sp. MUC/ MUC-530-WT-4D* (WP_154429009) | No |

FIG. 20B

| | |
|---|---|
| pBsmC | bsmC |
| pBsmT | bsmT |
| pBsmA | bsmA |
| pRalC | ralC |
| pRalT | ralT |
| pRalA | ralA |
| pCscC | cscC |
| pCscT | cscT |
| pCscA | cscA |
| pLbkC | lbkC |
| pLbkT | lbkT |
| pLbkA | lbkA |
| pBsaC | bsaC |
| pBsaT | bsaT |
| pBsaA | bsaA |
| pBweC | bweC |
| pBweT | bweT |
| pBweA | bweA |
| pLblC | lblC |
| pLblT | lblT |
| pLblA | lblA |
| pRscC | rscC |
| pRscT | rscT |
| pRscA | rscA |
| pCslC | cslC |
| pCslT | cslT |
| pCslA | cslA |
| pCcaC | ccaC |
| pCcaT | ccaT |
| pCcaA | ccaA |
| pEreC* | ereC*(H144V) |

FIG. 21B
CONTINUED

| Ion detected | Theoretical mass (Da) | Experimental mass (Da) |
|---|---|---|
| $b_2$ | 279.1162 | 279.1183 |
| $b_3$ | 408.1588 | 408.1530 |
| $b_4$ | 523.1857 | 523.1812 |
| $y_2$ | 248.1605 | 248.1637 |
| $y_3$ | 376.2191 | 376.2231 |
| $y_4$ | 505.2617 | 505.2573 |
| $y_6$ | 747.3883 | 747.3803 |
| $y_{31}$ | 4173.8632 | 4174.7372 |

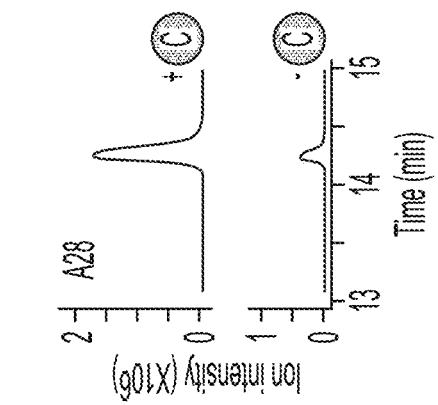
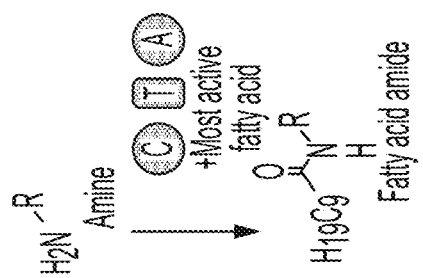
FIG. 25B
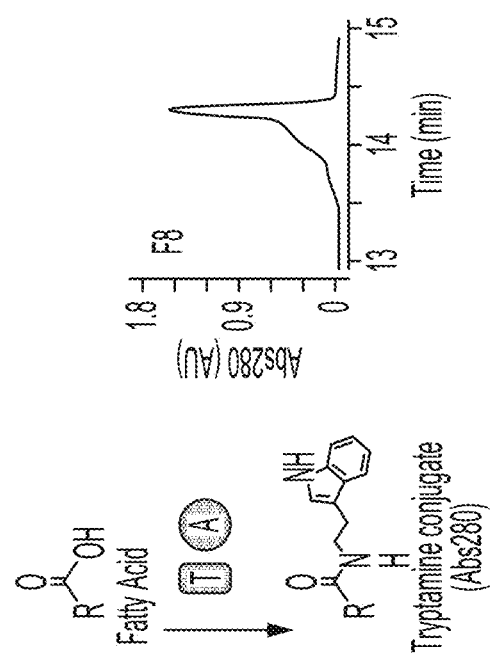
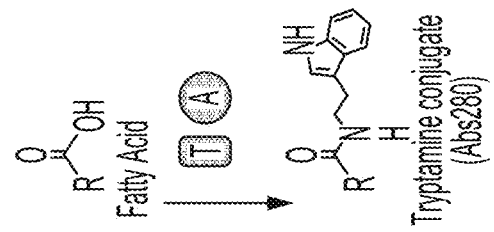
FIG. 25A

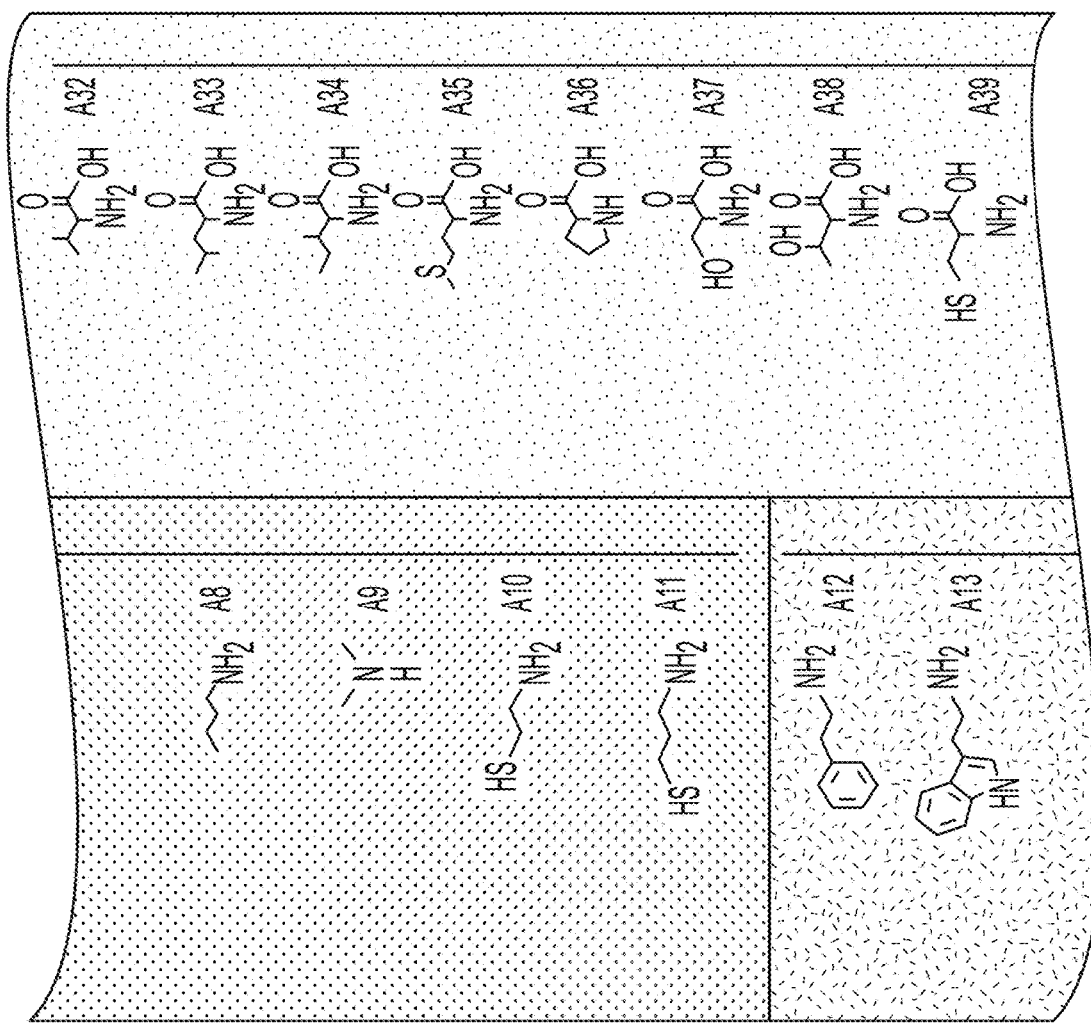
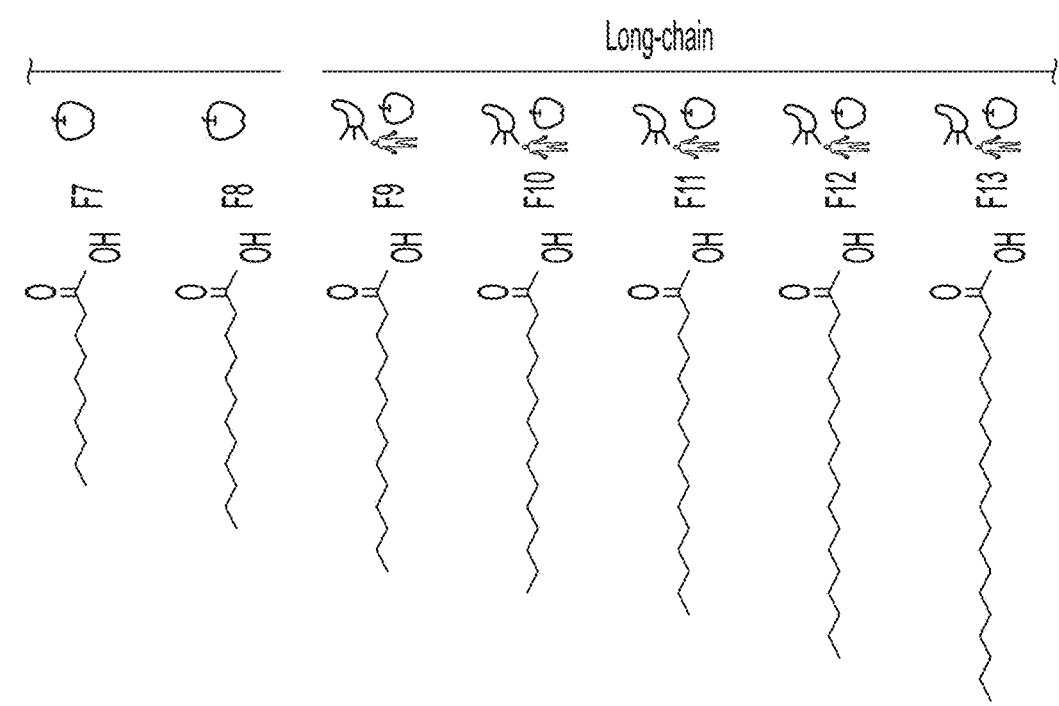
FIG. 25C CONTINUED

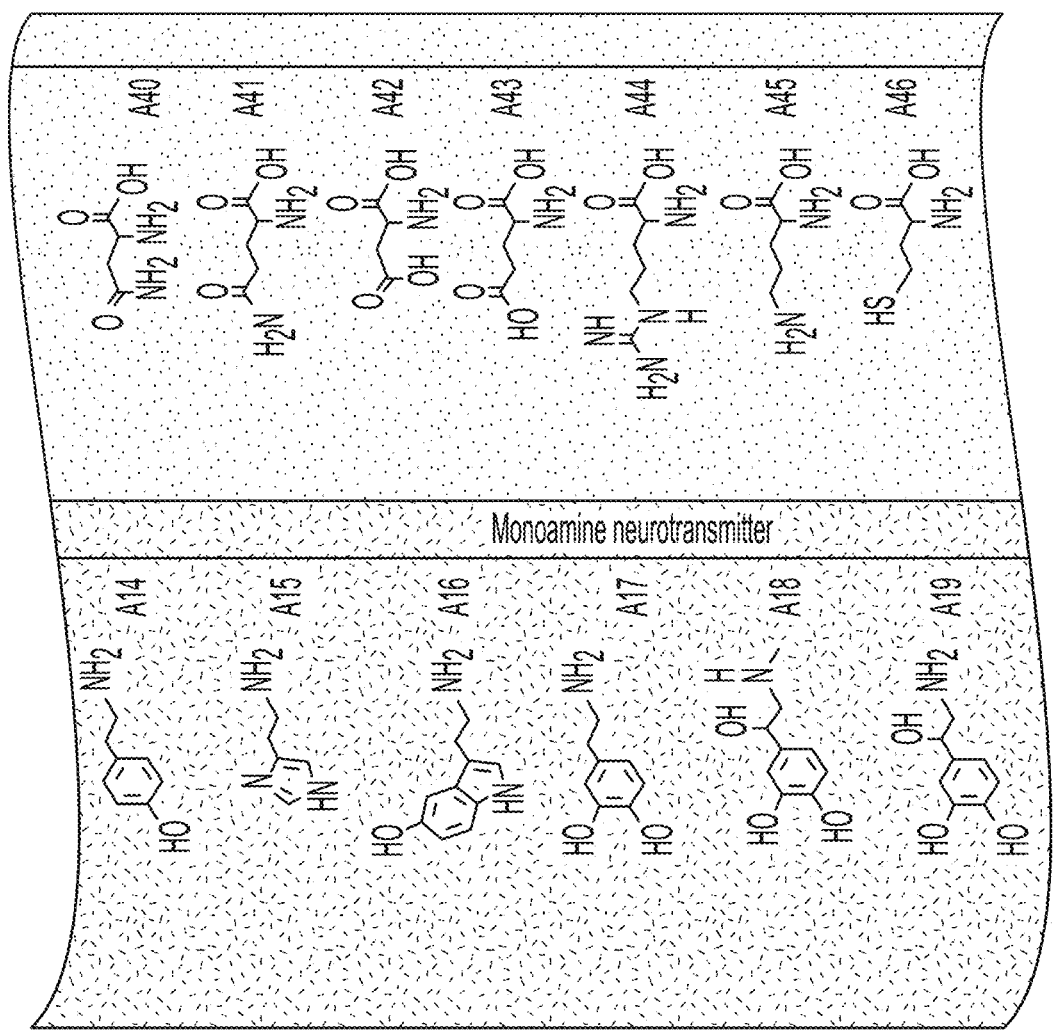
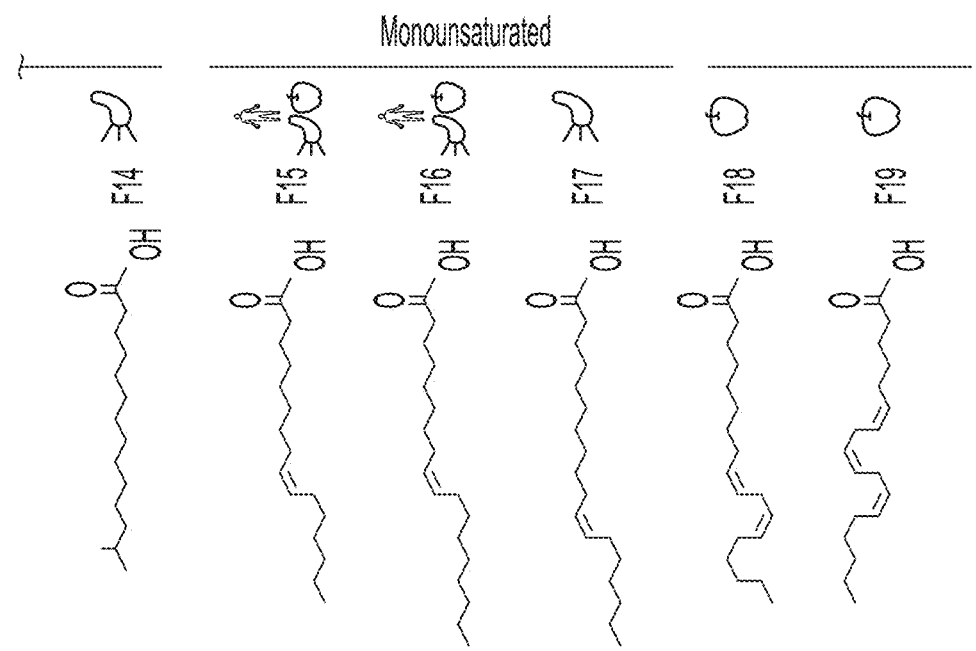
FIG. 25C CONTINUED

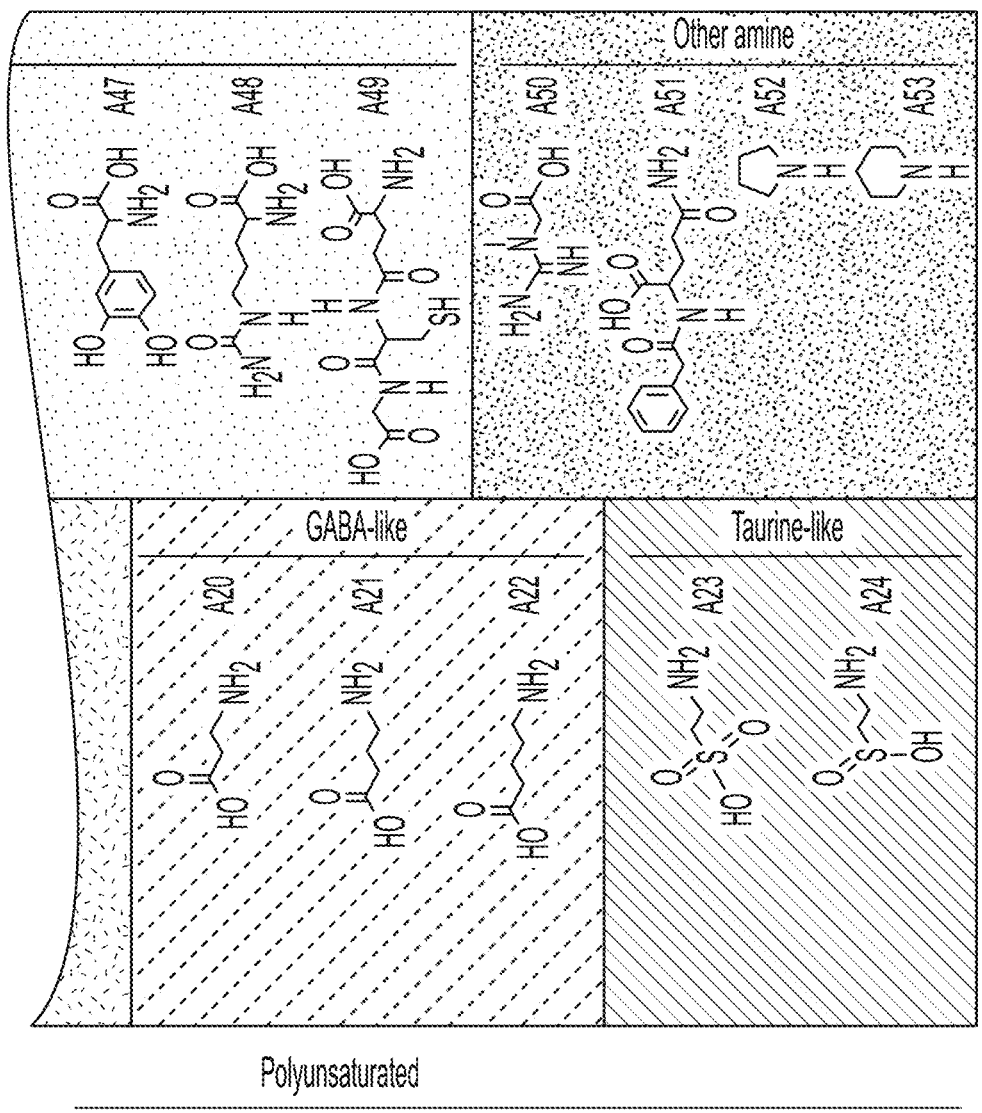
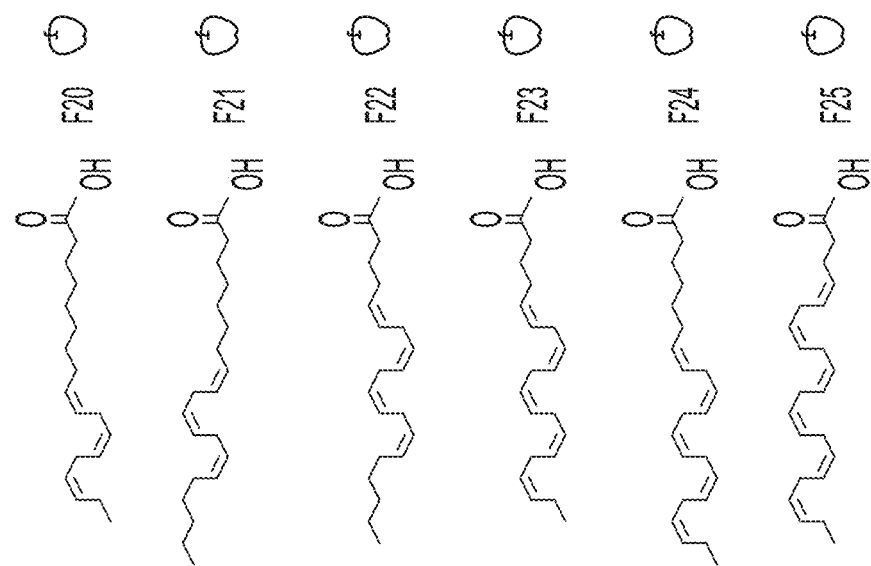
FIG. 25C CONTINUED

*Lachnoclostridium clostridioforme*
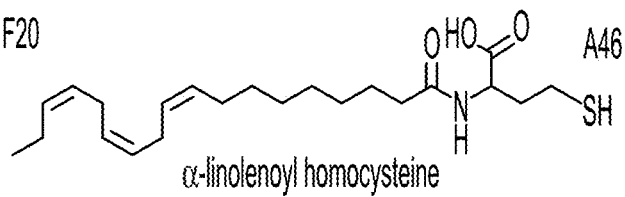
α-linolenoyl homocysteine
*Blautia producta*
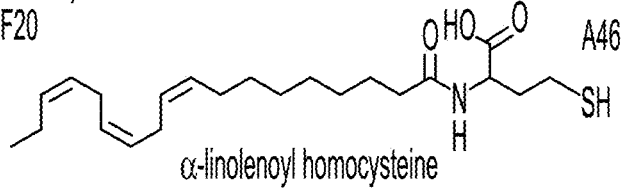
α-linolenoyl homocysteine
FIG. 28A

*Clostridiales celatum*
F20 α-linolenoyl homocysteine A46
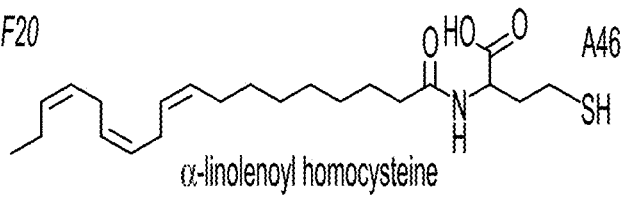
*Clostridium sp. CAG:413*
F8 Lauroyl tryptamine A13
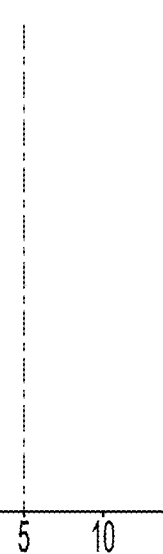
FIG. 28A
CONTINUED

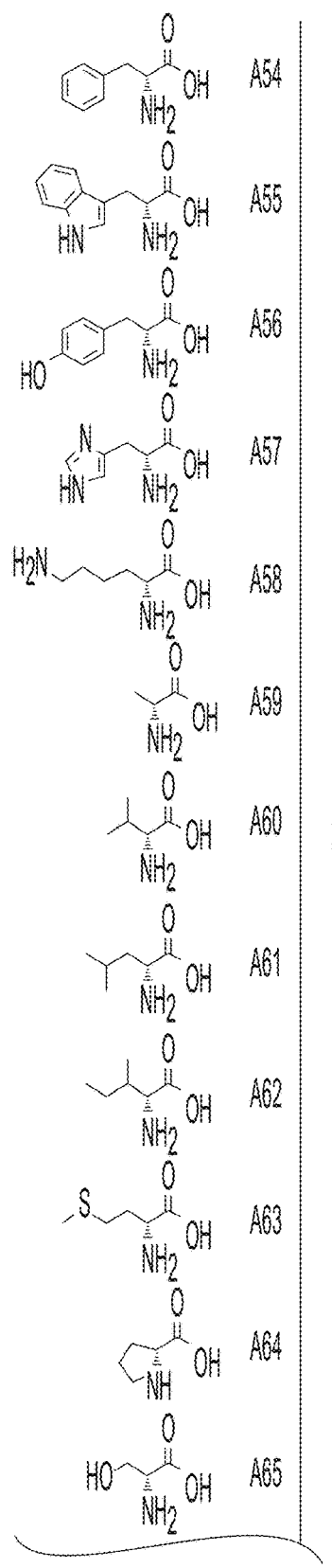
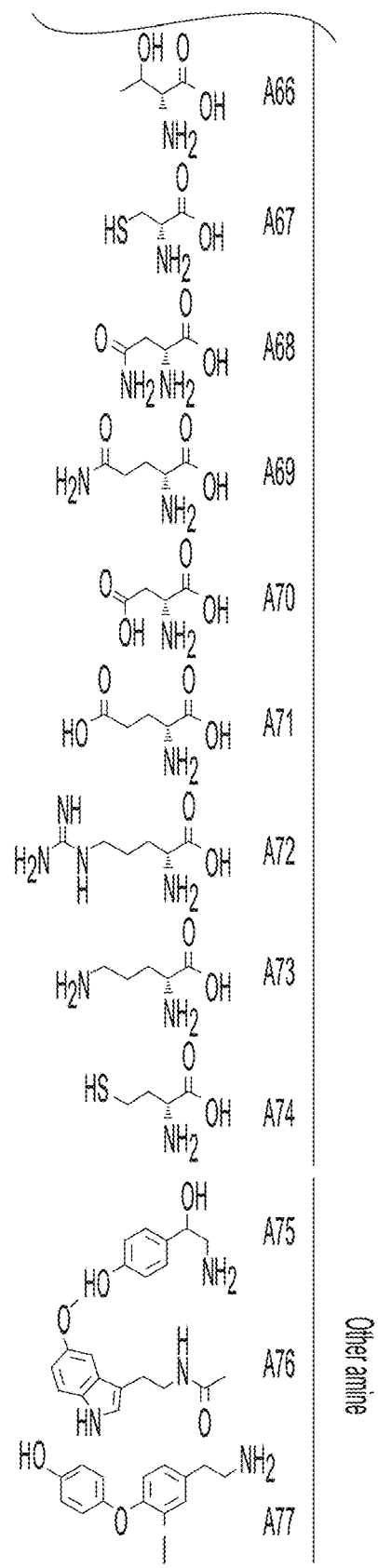
FIG. 28B
FIG. 28B CONTINUED

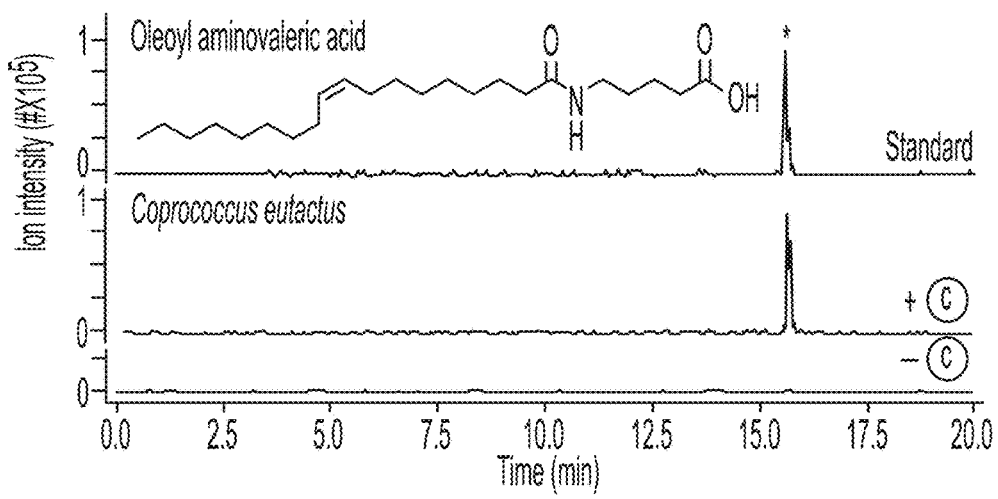
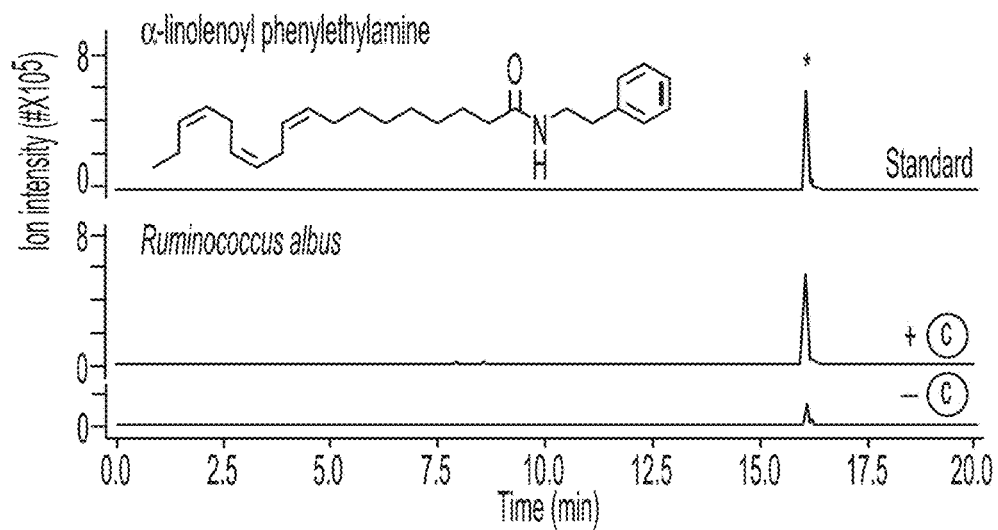
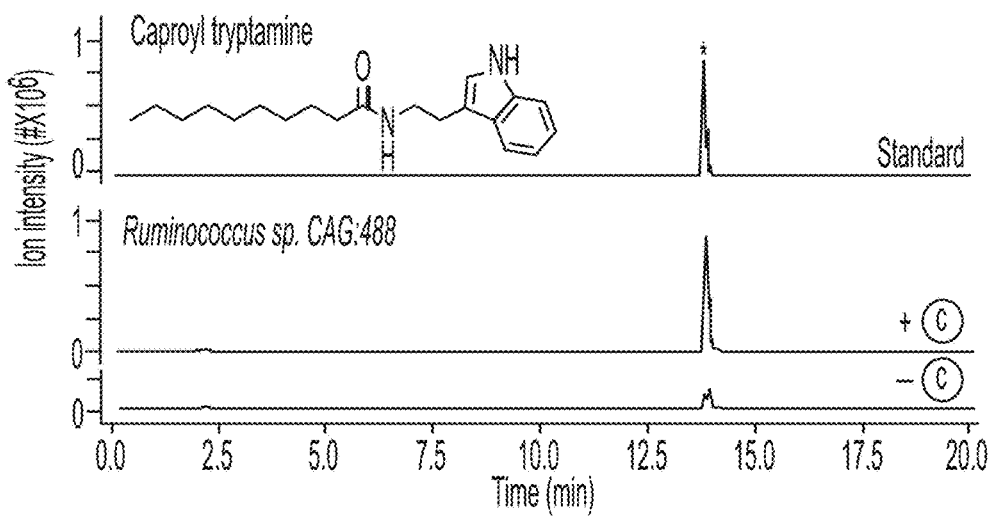
FIG. 29 CONTINUED

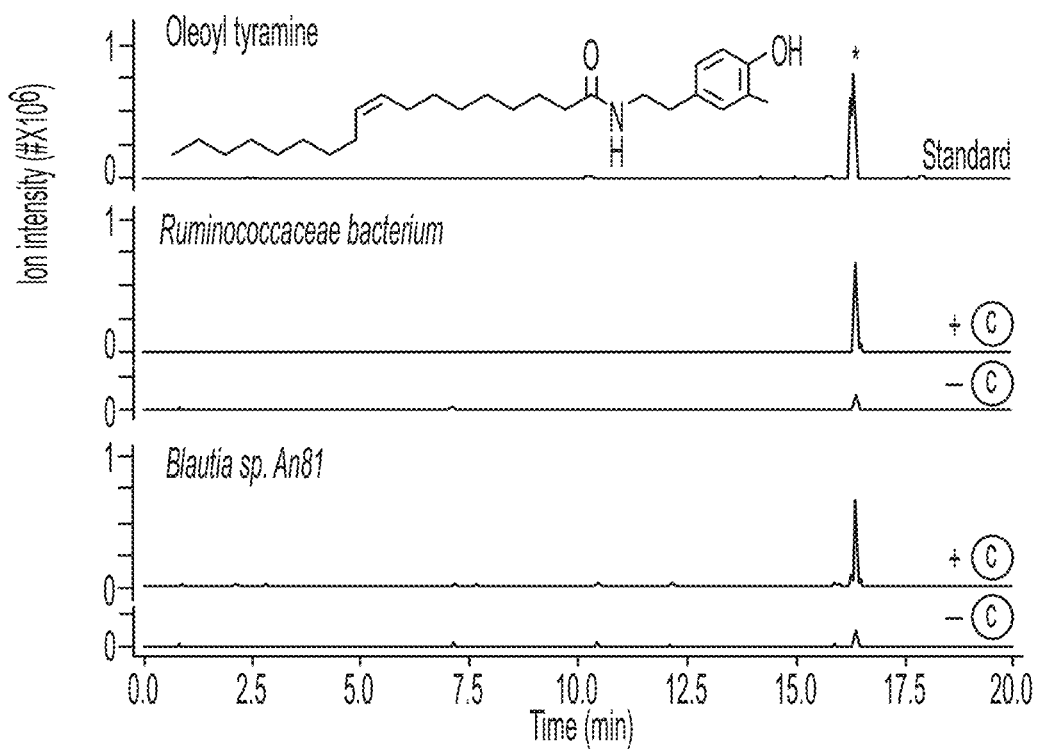
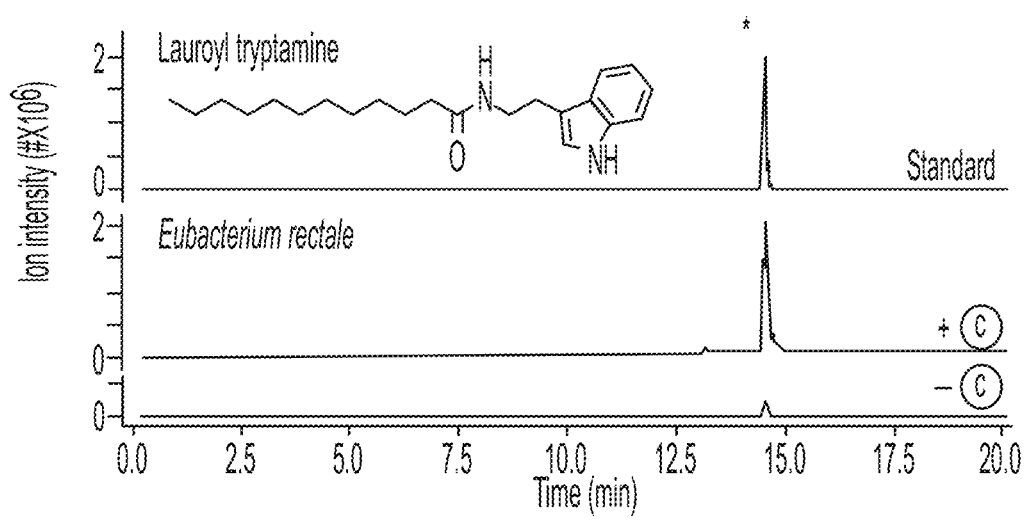
FIG. 29
CONTINUED

| Clostridia major FAAs | Known human FAAs | Known GPCR targets |
|---|---|---|
| Oleoyl dopamine | | |
| Oleoyl tyramine | Oleoyl dopamine | CNR1<br>DRD2<br>GPR119 |
| α-linolenoyl phenylethylamine | | |
| Lauroyl tryptamine | Palmitoyl serotonin | |
| Caproyl tryptamine | Oleoyl serotonin | GPR119 |
| | Docosahexaenoyl serotonin | |
| Oleoyl aminovaleric acid | Oleoyl γ-aminobutryic acid | GPR92 |
| | Arachidonoyl γ-aminobutryic acid | |

FIG. 30

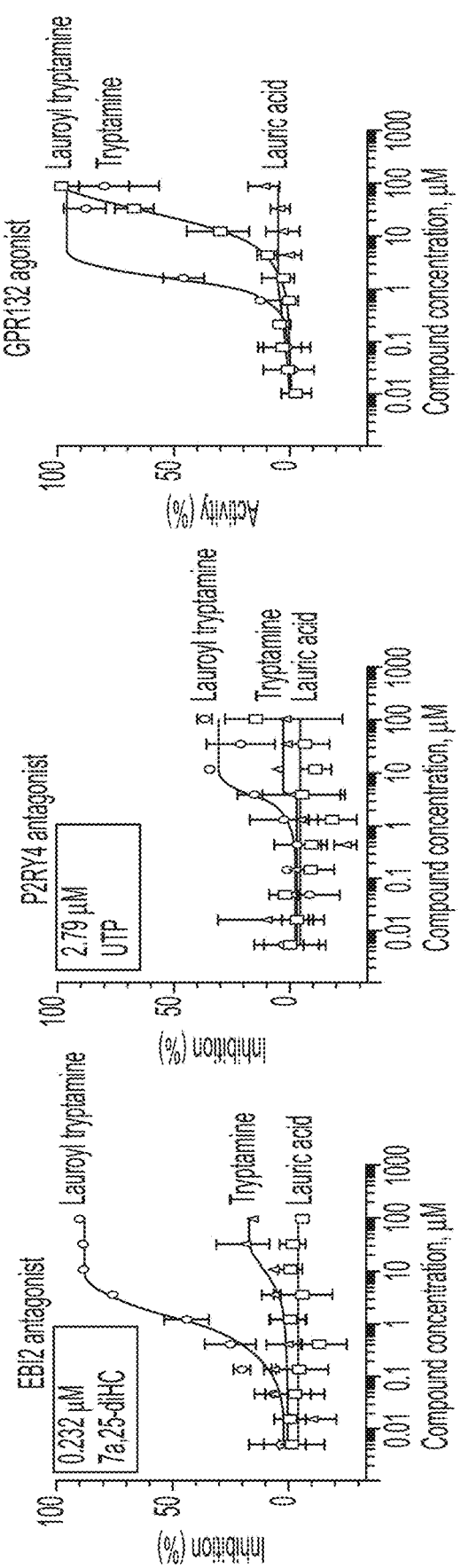
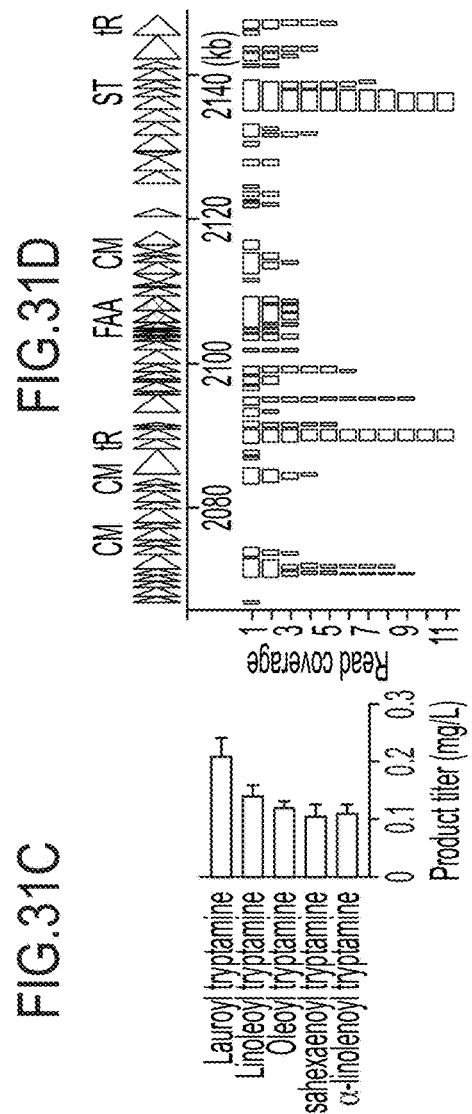
FIG. 31B
FIG. 31C
FIG. 31D
FIG. 31E
FIG. 31F
FIG. 31G

FIG. 34
CONTINUED

HUMAN GUT MICROBIOME-DERIVED BIOSYNTHETIC ENZYMES FOR PRODUCTION OF FATTY ACID AMIDES

RELATED APPLICATIONS

This application claims priority under 35 U.S.C. § 119(e) to U.S. Provisional Application No. 62/816,021, filed Mar. 8, 2019, and entitled "Human Gut Microbiome-Derived Biosynthetic Enzymes for Production of Fatty Acid Amides," which is incorporated herein by reference in its entirety for all purposes.

GOVERNMENT SUPPORT

This invention was made with Government support under Grant No. HR0011-15-C-0084 awarded by the Defense Advanced Research Projects Agency (DARPA). The government has certain rights in the invention.

BACKGROUND OF THE INVENTION

Fatty acid amides (FAAs) represent a class of compounds produced by humans and other mammals that have been implicated as important signaling molecules.[1] FAAs comprise a hydrophobic acyl tail group and a head group and these groups may contribute to the bioactivity of FAAs.[2] The first FAA identified was arachidonoyl ethanolamide (anandamide), a linear hydrophobic FAA that activates the $CB_1$ and $CB_2$ endocannabinoid G protein coupled receptors (GPCRs).[3] It is present at low levels with short half-life due to hydrolysis by the enzyme fatty acid amide hydrolase (FAAH).[4] Nonetheless, it has been suggested to induce motivation and pleasure via $CB_1$ activation,[3] suppress immune function via $CB_2$ activation,[5] and promote obesity via an unknown mechanism.[6] Since then, a second family of FAAs has been found with fatty acids linked to monoamine neurotransmitters. One member is oleoyl dopamine, a nanomolar activator of vanilloid receptor 1 involved in sensing pain,[7] which has also been proposed to act via other mechanisms including $CB_1$ agonism,[7] FAAH antagonism,[7] calcium channel antagonism,[8] glucose homeostasis receptor agonism,[9] dopamine transporter antagonism,[10] and a as general carrier of dopamine across the blood-brain barrier.[11] Other examples include docosahexaenoyl serotonin that attenuates cytokine production[12] and arachidonoyl γ-aminobutryic acid (GABA) that suppresses pain and motor activity in mice via an uncharacterized mechanism.[13] Moreover, a third family of FAAs with amino acid conjugates is known, and includes arachidonoyl serine which shows vascular modulation activity via interaction with a noncannabinoid GPCR receptor.[14] Although the primary biological roles for these FAAs are still largely left for investigation, they have been shown to target diverse molecular targets to control various physiopathological conditions. Given the diverse molecular targets of FAAs, efficient and high throughput methods of producing FAAs are needed.

SUMMARY OF THE INVENTION

Aspects of the present disclosure relate to methods of producing fatty acid amides, comprising contacting a composition, comprising one or more exogenous fatty acids and one or more amines, with a set of biosynthetic enzymes which are human gut microbiome-derived clostridia biosynthetic enzymes in an effective amount to produce a fatty acid amide.

In some embodiments, the biosynthetic enzymes comprise a fatty-acyl transferase. In some embodiments, the biosynthetic enzymes comprise an acyl carrier protein (ACP). In some embodiments, the biosynthetic enzymes comprise a fatty acyl-ACP synthetase. In some embodiments, the method is performed in vitro. In some embodiments, the composition is a culture broth. In some embodiments, the set of biosynthetic enzymes are isolated from human gut microbiome-derived clostridia. In some embodiments, the method further comprises isolating acyl carrier protein from a human gut microbiome-derived clostridia. In some embodiments, the biosynthetic enzymes comprise a hydrolase. In some embodiments, the biosynthetic enzymes comprise a lipid transfer protein. In some embodiments, the biosynthetic enzymes comprise a glycosyltransferase.

In some embodiments, the set of biosynthetic enzymes are synthetic proteins. In some embodiments, the set of biosynthetic enzymes are recombinant proteins expressed from one or more vectors. In some embodiments, the set of biosynthetic enzymes are recombinant proteins expressed from a vector comprising a single operon, wherein the operon comprises genes encoding at least a fatty acyl transferase, an acyl carrier protein, and a fatty acyl-ACP synthetase. In some embodiments, the set of biosynthetic enzymes are recombinant proteins expressed from a plurality of vectors comprising a first vector, a second vector, and a third vector, wherein each of the plurality of vectors comprises a gene in a single operon and under the control of a regulatory element.

In some embodiments, the one or more exogenous fatty acids are selected from a group consisting of acetic acid, propionic acid, butyric acid, valeric acid, hexanoic acid, octanoic acid, capric acid, lauric acid, myristic acid, pentadecanoic acid, palmitic acid, stearic acid, arachidic acid, iso-pentadecanoic acid, palmitoleic acid, oleic acid, vaccenic acid, linoleic acid, γ-linolenic acid, α-linolenic acid, dihomo-γ-linolenic acid, arachidonic acid, eicosapentaenoic acid, docosapentaenoic acid, docosahexaenoic acid, 8-methyl-6-nonenoic acid, octynoic acid, myristic acid alkyne, and palmitic acid alkyne.

In some embodiments, the one or more exogenous amines are selected from a group consisting of phenylalanine, tryptophan, tyrosine, histidine, lysine, glycine, alanine, valine, leucine, isoleucine, methionine, proline, serine, threonine, cysteine, asparagine, glutamine, aspartic acid, glutamic acid, arginine, ornithine, β-alanine, L-DOPA, creatine, citrulline, phenylacetylglutamine, phenylethylamine, tryptamine, tyramine, histamine, serotonin, dopamine, epinephrine, norepinephrine, γ-aminobutryic acid (GABA), aminovaleric acid, ethanolamine, cadaverine, putrescine, spermine, spermidine, agmatine, propylamine, butylamine, dimethylamine, pyrollidine, piperidine, homocysteine, cysteamine, homocysteamine, taurine, hypotaurine, glutathione, octopamine, 3-iodothyronamine, melatonin, and vanillylamide.

Further aspects of the present disclosure relate to methods of producing a fatty acid amide, comprising: (i) administering to a host a plurality of vectors comprising a first vector, a second vector, and a third vector, wherein each of the plurality of vectors comprises a human gut microbiome-derived bacterium gene under the control of a regulatory element; and wherein the gene on the first vector, the second vector and the third vector encode a fatty acyl transferase, an acyl carrier protein, and fatty acyl-ACP synthetase, respectively; and (ii) contacting the host with a composition in an effective amount to produce a fatty acid amide in the host.

In some embodiments, the composition is a culture broth. In some embodiments, the gene is in a single operon. In some embodiments, the regulatory element is an inducible promoter, optionally wherein the inducible promoter is an IPTG-inducible promoter. In some embodiments, the regulatory element is a constitutive promoter. In some embodiments, the regulatory element is a repressible promoter, optionally, wherein the repressible promoter comprises a lac operon. In some embodiments, the regulatory element comprises a T7 promoter. In some embodiments, the method further comprises administering a vector encoding T7 RNA polymerase. In some embodiments, the vector further comprises a ribosomal binding site. In some embodiments, at least one gene is codon-optimized. In some embodiments, the gene is an open reading frame. In some embodiments, the host is an E. coli. In some embodiments, the gut microbiome-derived bacterium is from Clostridia. In some embodiments, the gene is codon-optimized for production in E. coli.

In some embodiments, the fatty acid amide is palmitoleyl-putrescine, oleoyl aminovaleric acid, α-linolenoyl aminovaleric acid, oleoyl γ-aminobutyric acid, oleoyl dopamine, oleoyl tyramine, palmitoleoyl dopamine, α-linolenoyl tyramine, oleoyl phenethylamine, lauroyl tyrptamine, lineoleoyl tryptamine, lauroyl tyramine, α-linolenoyl homocysteine, oleoyl homocysteine, α-linolenoyl cysteine, linoleoyl homocysteine, oleoyl-aminopentanoic acid, or α-linolenoyl homocysteamine.

In some embodiments, the plurality of vectors further comprises a vector having a gene encoding Sfp 4'-phosphopantetheinyl transferase. In some embodiments, the first vector, the second vector, or the third vector further comprises a gene encoding Sfp 4'-phosphopantetheinyl transferase.

In some embodiments, the composition does not comprise an exogenous fatty acid. In some embodiments, the composition does not comprise an exogenous amine. In some embodiments, the composition comprises one or more exogenous fatty acids selected from a group consisting of acetic acid, propionic acid, butyric acid, valeric acid, hexanoic acid, octanoic acid, capric acid, lauric acid, myristic acid, pentadecanoic acid, palmitic acid, stearic acid, arachidic acid, iso-pentadecanoic acid, palmitoleic acid, oleic acid, vaccenic acid, linoleic acid, γ-linolenic acid, α-linolenic acid, dihomo-γ-linolenic acid, arachidonic acid, eicosapentaenoic acid, docosapentaenoic acid, docosahexaenoic acid, 8-methyl-6-nonenoic acid, octynoic acid, myristic acid alkyne, and palmitic acid alkyne.

In some embodiments, the composition comprises one or more exogenous amines selected from a group consisting of phenylalanine, tryptophan, tyrosine, histidine, lysine, glycine, alanine, valine, leucine, isoleucine, methionine, proline, serine, threonine, cysteine, asparagine, glutamine, aspartic acid, glutamic acid, arginine, ornithine, β-alanine, L-DOPA, creatine, citrulline, phenylacetylglutamine, phenylethylamine, tryptamine, tyramine, histamine, serotonin, dopamine, epinephrine, norepinephrine, γ-aminobutyric acid (GABA), aminovaleric acid, ethanolamine, cadaverine, putrescine, spermine, spermidine, agmatine, propylamine, butylamine, dimethylamine, pyrollidine, piperidine, homocysteine, cysteamine, homocysteamine, taurine, hypotaurine, glutathione, octopamine, 3-iodothyronamine, melatonin, and vanillylamide.

Further aspects of the present disclosure provide vectors for the production of fatty acid amides, comprising genes, wherein each of the genes is under the control of a regulatory element, wherein each of the genes is derived from gut microbiome-derived bacterium, and wherein the genes encode at least a fatty acyl transferase, an acyl carrier protein, and a fatty acyl-ACP synthetase. In some embodiments, the regulatory element is an inducible promoter. In some embodiments, the regulatory element is a constitutive promoter. In some embodiments, the regulatory element is a repressible promoter. In some embodiments, the regulatory element comprises a T7 promoter. In some embodiments, the vector further encodes a T7 RNA polymerase. In some embodiments, the vector further comprises a ribosomal binding site.

In some embodiments, the genes are codon-optimized. In some embodiments, the genes are open reading frames. In some embodiments, the genes are codon-optimized for production in E. coli. In some embodiments, the gut microbiome-derived bacterium is from Clostridia. In some embodiments, the genes also encode a hydrolase. In some embodiments, the genes also encode a lipid transfer protein. In some embodiments, the genes also encode a glycosyltransferase. In some embodiments, the genes encode Sfp 4'-phosphopantetheinyl transferase. In some embodiments, the genes are in a single operon.

Further aspects of the present disclosure provide methods of producing a fatty acid amide comprising: (i) administering to a host a vector comprising genes, wherein each of the genes is under the control of a regulatory element, wherein each of the genes is derived from a human gut microbiome-derived bacterium, and wherein the genes encode a fatty acyl transferase, an acyl carrier protein, and fatty acyl-ACP synthetase; and (ii) contacting the host with a composition in an effective amount to produce a fatty acid amide in the host.

In some embodiments, the composition is a culture broth. In some embodiments, the regulatory element is an inducible promoter. In some embodiments, the regulatory element is a constitutive promoter. In some embodiments, the regulatory element is a repressible promoter. In some embodiments, the regulatory element is a T7 promoter. In some embodiments, the vector further encodes a T7 RNA polymerase. In some embodiments, the vector further comprises a ribosomal binding site. In some embodiments, wherein the genes are codon-optimized. In some embodiments, the genes are open reading frames. In some embodiments, the host is E. coli. In some embodiments, the gut microbiome-derived bacterium is from Clostridia. In some embodiments, the genes are codon-optimized for production in E. coli.

In some embodiments, the fatty acid amide is palmitoleyl-putrescine, oleoyl aminovaleric acid, α-linolenoyl aminovaleric acid, oleoyl γ-aminobutyric acid, oleoyl dopamine, oleoyl tyramine, palmitoleoyl dopamine, α-linolenoyl tyramine, oleoyl phenethylamine, lauroyl tyrptamine, lineoleoyl tryptamine, lauroyl tyramine, α-linolenoyl homocysteine, oleoyl homocysteine, α-linolenoyl cysteine, linoleoyl homocysteine, oleoyl-aminopentanoic acid, or α-linolenoyl homocysteamine.

In some embodiments, the genes further comprise a gene encoding Sfp 4'-phosphopantetheinyl transferase. In some embodiments, the genes are in a single operon. In some embodiments, the composition does not comprise an exogenous fatty acid. In some embodiments, the composition does not comprise an exogenous amine.

In some embodiments, the composition comprises one or more exogenous fatty acids selected from a group consisting of acetic acid, propionic acid, butyric acid, valeric acid, hexanoic acid, octanoic acid, capric acid, lauric acid, myristic acid, pentadecanoic acid, palmitic acid, stearic acid, arachidic acid, iso-pentadecanoic acid, palmitoleic acid, oleic acid, vaccenic acid, linoleic acid, γ-linolenic acid, α-linolenic acid, dihomo-γ-linolenic acid, arachidonic acid, eicosapentaenoic acid, docosapentaenoic acid, docosahexaenoic acid, 8-methyl-6-nonenoic acid, octynoic acid, myristic acid alkyne, and palmitic acid alkyne.

In some embodiments, the composition comprises one or more exogenous amines selected from a group consisting of phenylalanine, tryptophan, tyrosine, histidine, lysine, glycine, alanine, valine, leucine, isoleucine, methionine, proline, serine, threonine, cysteine, asparagine, glutamine, aspartic acid, glutamic acid, arginine, ornithine, β-alanine, L-DOPA, creatine, citrulline, phenylacetylglutamine, phenylethylamine, tryptamine, tyramine, histamine, serotonin, dopamine, epinephrine, norepinephrine, γ-aminobutryic acid (GABA), aminovaleric acid, ethanolamine, cadaverine, putrescine, spermine, spermidine, agmatine, propylamine, butylamine, dimethylamine, pyrollidine, piperidine, homocysteine, cysteamine, homocysteamine, taurine, hypotaurine, glutathione, octopamine, 3-iodothyronamine, melatonin, and vanillylamide.

Further aspects of the present disclosure relate to engineered cells comprising any of the vectors described herein.

Further aspects of the present disclosure relate to methods of producing fatty acid amides, the method comprising: contacting a composition, comprising one or more exogenous fatty acids and one or more amines, with a set of biosynthetic enzymes which are human gut microbiome-derived clostridia biosynthetic enzymes in an effective amount to produce a fatty acid amide, wherein the set of biosynthetic enzymes comprise a fatty acyl transferase, an acyl carrier protein, and a fatty acyl-ACP synthetase.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. For purposes of clarity, not every component may be labeled in every drawing. It is to be understood that the data illustrated in the drawings in no way limit the scope of the disclosure. In the drawings:

FIGS. 1A-1F show FAA pathways from human gut microbiome-derived Clostridia. a, Computational workflow from DNA sequencing data to gut Clostridia NRPS pathways. b, Arrow diagram of the eight NRPS pathways with the source Clostridia strain indicated on the left. Darker arrows=conserved biosynthetic genes with homology to condensation (C), thiolation (T), and adenylation (A) domains from NRPS. Lighter arrows=accessory genes. c, MS chromatogram (EIC ESI+m/z 325.3213, [M+H]$^+$ of palmitoeyl putrescine, as shown) of the in vivo extract of E. coli expressing different combinations of E. rectale biosynthetic genes and sfp gene. * denotes peak corresponding to the shown compound. The fatty acid olefin is in cis (Z) conformation. d, Adenylation activity assay based on absorbance of pyrophosphate (PPi) fluorogenic dye (Abs$_{360}$), normalized to no adenylation enzyme control. e, Condensation activity assay, based on MS ion intensity of the final product, normalized to product level with no condensation enzyme. f, Biosynthetic scheme for FAA formation, where T is an acyl carrier protein, A is a fatty acyl-ACP synthetase, and C is a N-fatty acyltransferase. Substrate labels for d and e: C16:1=palmitoleic acid, C16: palmitic acid, Put=putrescine, Orn=ornithine, Arg=argnine, Agm=agmatine, Cad=cadaverine, Lys=lysine, Phe=phenylalanine, Trp=tryptophan, Tyr=tyrosine, Pha=phenethylamine, Tpa=tryptamine, Tya=tyramine. All error bars are the s.d. of three replicates conducted on different days.

FIG. 4 shows pathway phylogeny analysis. Left: A phylogenetic tree (MUSCLE alignment, Neighbor Joining, best tree, MacVector) based on the adenylation gene of 148 Clostridia FAA pathways. Eight representative HMP-derived pathways and their close homologs (>98% sequence identity) are labeled with the originating species. Right: A phylogenetic tree (phyloT) based on NCBI taxon ID of the bacterial strain harboring the pathway. The HMP-derived pathways are labeled according to species or the pathway to which they are homologous ("hom."). Pathways without unique NCBI taxon ID are not included.

FIGS. 5A-5C show structural elucidation of E. coli in vivo compound. a, $^1$H NMR (600 MHz) of major compound from E. rectale-derived pathway harboring E. coli BAP1. b, Key spectral data in structure determination. c, NMR data summary. $^1$H-$^1$H COSY show two coupling networks. The first network consists of four methylene systems with deshielded carbons (δ39.8, 42.7) at each end with one end connected to an amide proton system, suggestive of a 1,4-butanediamine substructure. The second network consists of two olefin, twelve methylene, and one methyl systems, which are correlated to form a hexadecene substructure (double bond position inferred based on its biosynthetic origin). The two networks are connected by a $^1$H-$^{13}$C HMBC correlation from H6 and H7 to the same remaining carbonyl carbon (δ177.1). The purified compound was found to be spectroscopically identical to an authentic standard that has been chemically synthesized based on the elucidated structure.

FIG. 11A-11B shows a substrate panel assay time course. Fatty acid (left; 25 substrates) and amine (right; 53 substrates) substrate panel assay for *C. eutactus* pathway proteins over the course of ten time points (10, 20, 30, 45, 60, 90, 120, 240, 480, and 960 min). a, For eight representative fatty acid (left) or amine (right) substrates, unnormalized data of product level with (unmarked curves) and without (curves marked with *) adenylation protein is shown (left), or product level with (unmarked curves) and without (curves marked with *) condensation protein is shown (right). b, For all 25 fatty acid (left) or 53 amine (right) substrates, normalized activity data is shown over the ten time points. The time point with the largest difference between the highest point and the rest is marked with an arrow. All error bars are the s.d. of three replicates conducted on different days.

FIGS. 15A-15C show computational identification of Clostridia-derived NRPS-like pathways from human gut metagenome. a, Genetic diagrams for the eighteen Clostridia pathways ordered based on their 16S rRNA phylogeny (left tree). Eight pathways were screened from the Human Microbiome Project human gut metagenome (indicated with *) and ten were selected from NCBI nr database. Biosynthetic genes: condensation domain protein (large diagonally-hashed arrows), thiolation domain protein (small solid arrows), adenylation domain protein (large solid arrows). Accessory genes (horizontally-striped arrows): alpha/beta-fold hydrolase, PPTase, sterol transfer protein. b, Similarity network map of 3531 human gut-associated pathways represented as nodes and connected with edges based on protein sequence- and domain-level similarity (BiG-SCAPE) at a cutoff of 0.9. c, Similarity network map of 346 human gut-derived and actively transcribed pathways, with edges at a cutoff of 0.75. The Clostridia NRPS group is circled.

FIGS. 16A-16D show FAA production from Clostridia-derived pathways. a, Comparison of biosynthetic mechanisms. The Clostridia condensation, thiolation, or adenylation-like protein contains the Pfam condensation (PF00668), PP-binding (PF00550), or AMP-binding (PF00501) domain that is present in its corresponding NRPS homolog. The Clostridia proteins show no sequence homology to known FAA biosynthetic enzymes. Abbreviations: FA=fatty acid substrate, FadD=fatty acyl-CoA synthetase, N-AT=N-acyltransferase, A=adenylation, T=thiolation, C=condensation, TE=thioesterase, PPTase=phosphopantetheinyl transferase, AA=amino acid substrate. b, In vivo production of palmitoleoyl putrescine FAA in *E. coli* host. MS chromatogram (EIC ESI+[M+H]+ of palmitoleoyl putrescine: theoretical=325.3213, experimental=325.2874) of the in vivo extract of *E. coli* expressing different combinations of biosynthetic genes and sfp gene. The * denotes the palmitoleoyl putrescine peak. c, In vitro adenylation activity assay on possible fatty acid or amine substrates, as measured by absorbance (Abs360) of pyrophosphate (PPi) fluorogenic dye relative to no adenylation enzyme control (TA/T ratio). d, Left bar graph: In vitro condensation activity assay on possible amine substrates, as measured by MS ion intensity of the resulting palmitoleoylated FAA product relative to no condensation enzyme control (CTA/TA ratio). Right bar graph: In vitro condensation assay of lauroyl tryptamine production with the condensation domain protein (EreC), without the protein, or with the H144V mutated condensation domain protein. For c and d, the data was taken in triplicate per day. The reported data is the average of the mean triplicate normalized values conducted on three different days, with the error bar being the s.d. of the three mean triplicate values.

Figure 17:
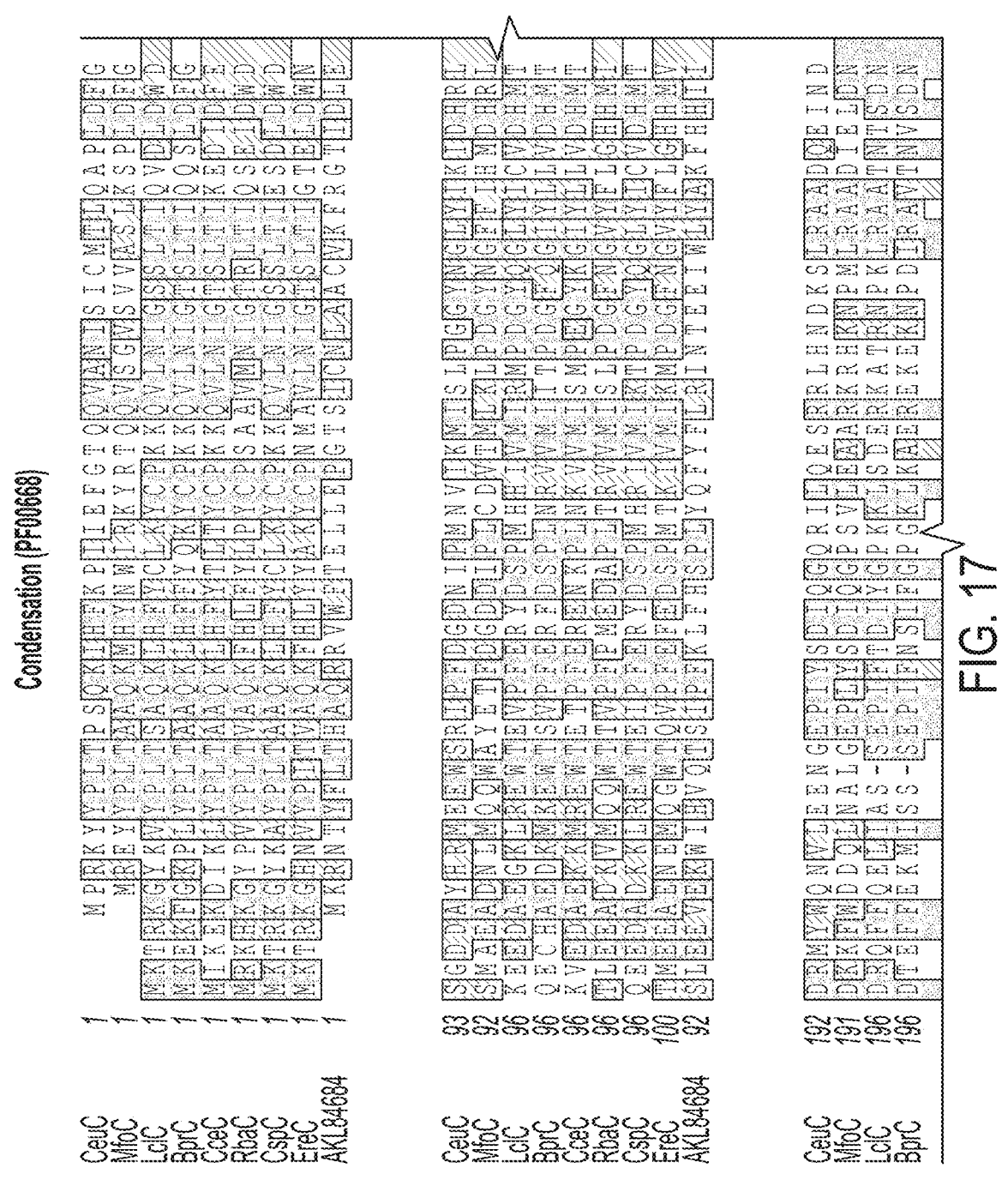
Figure 17:
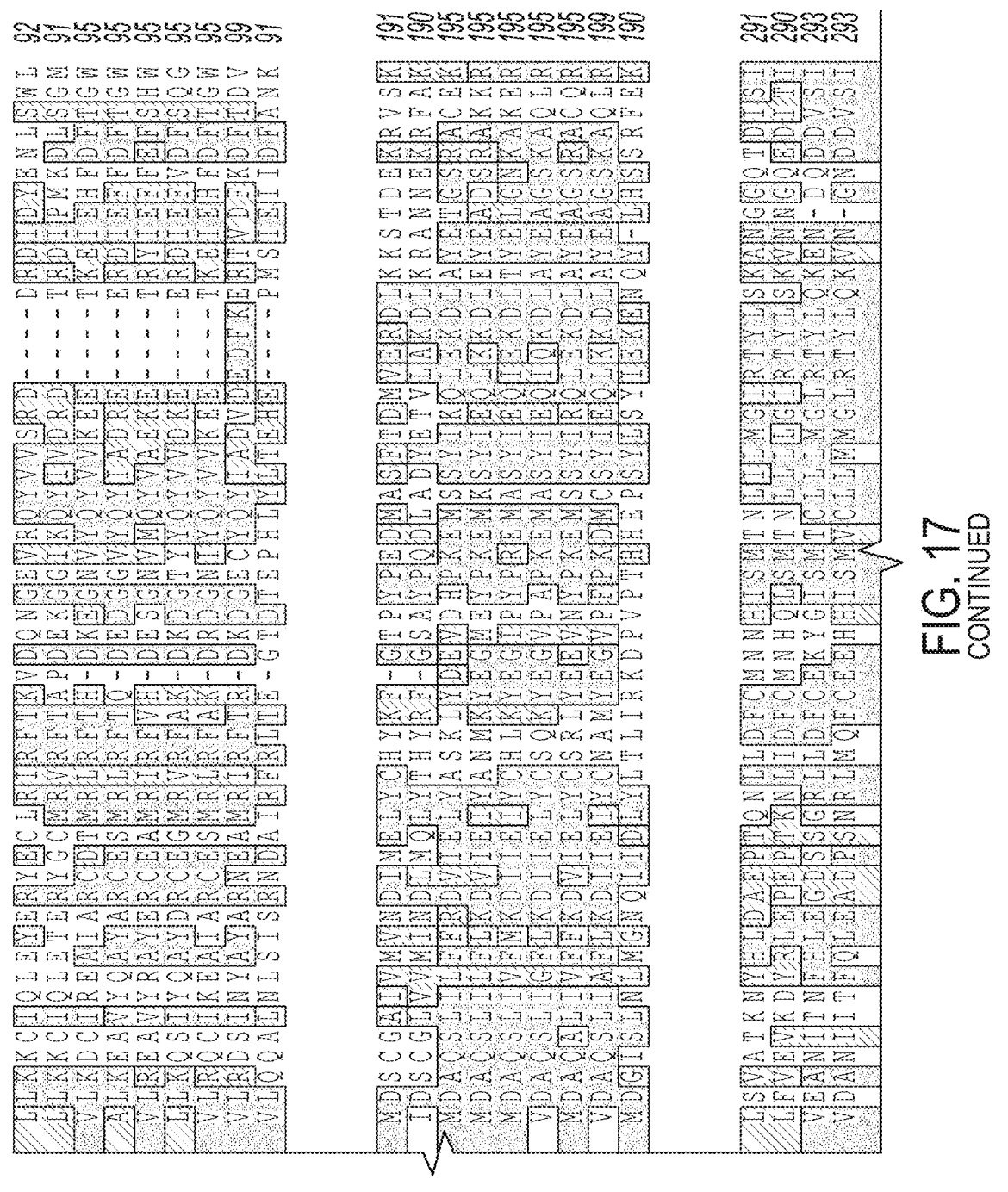
Figure 17:
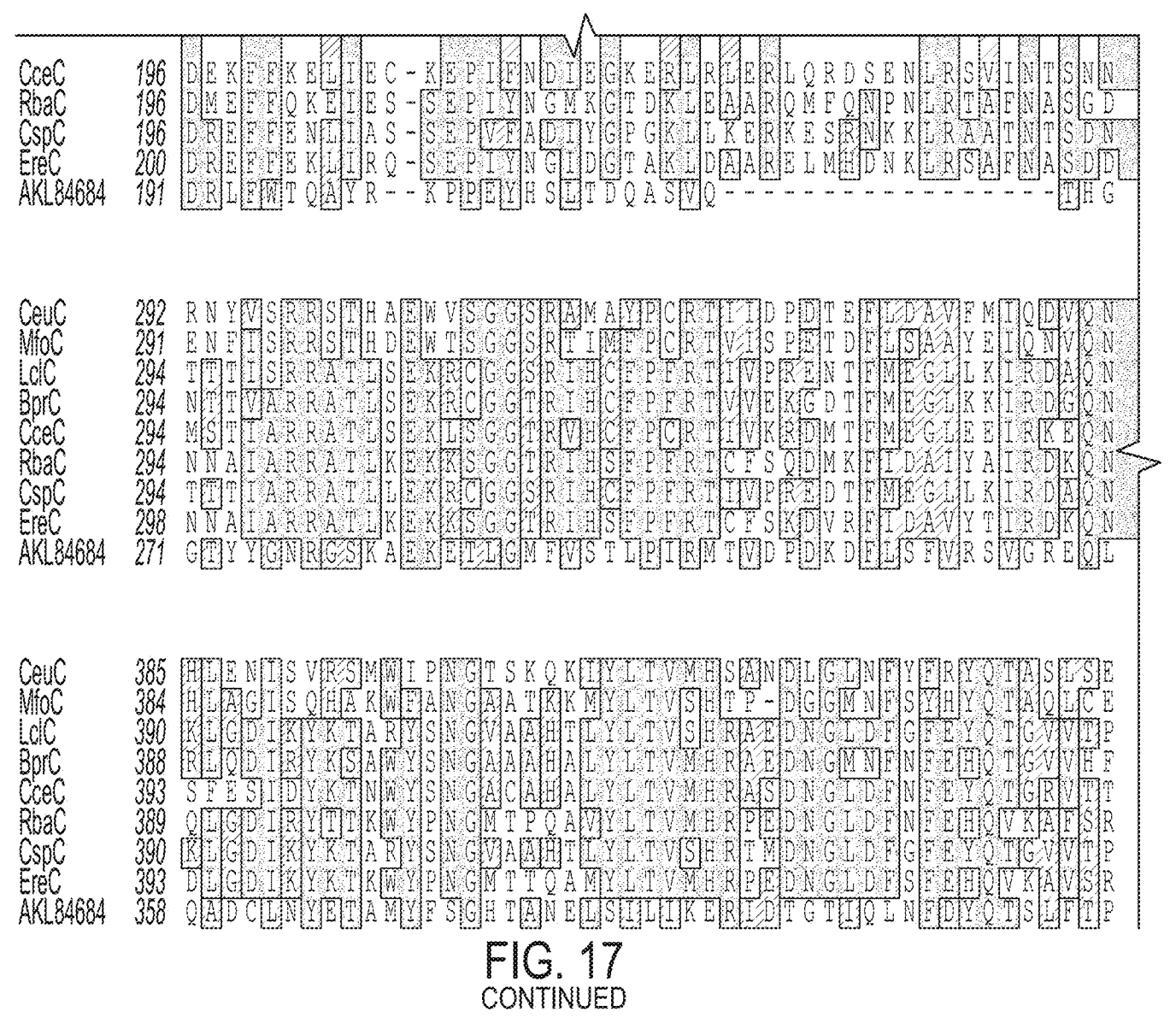
Figure 17:
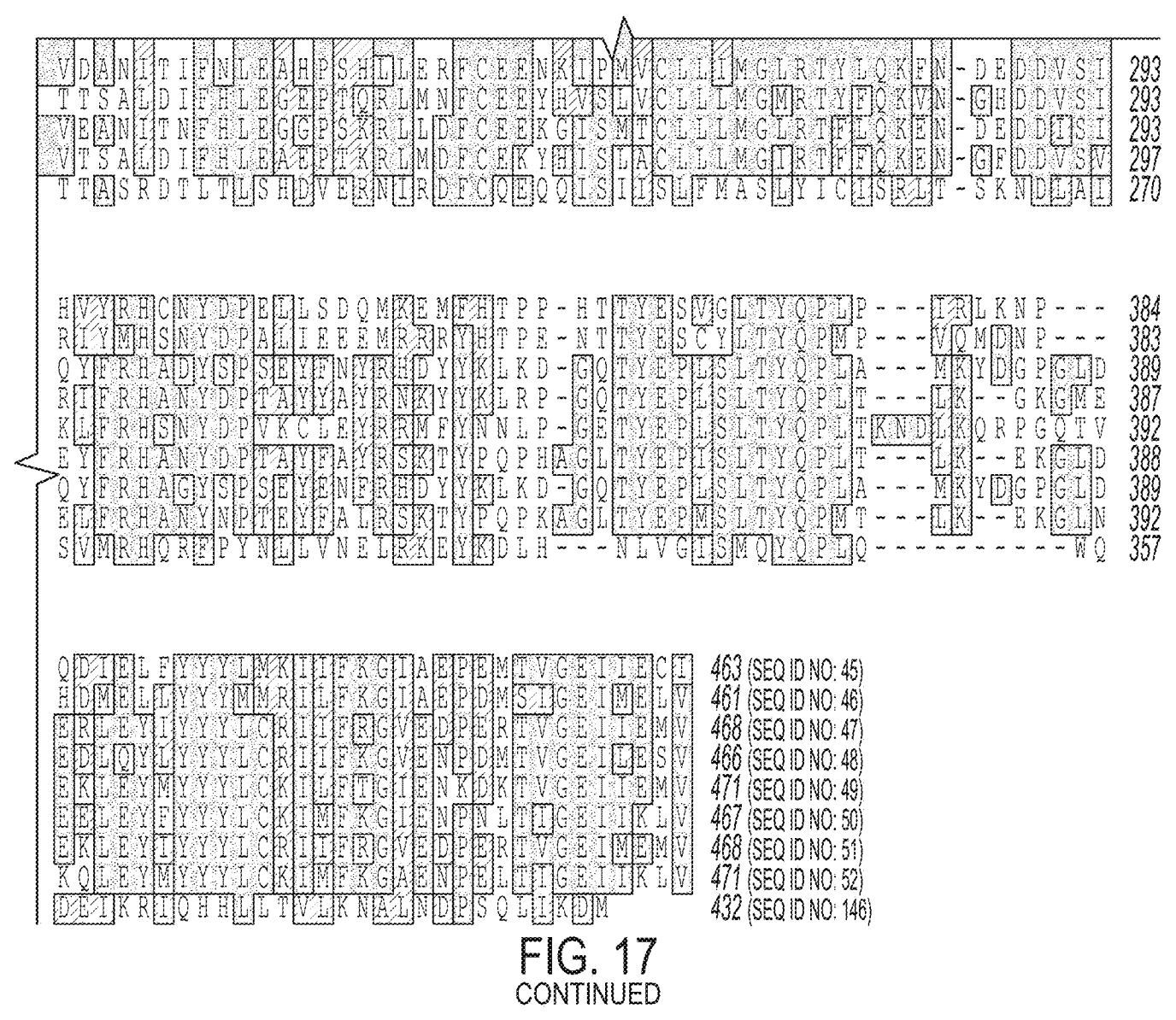

FIG. 17 shows condensation domain protein sequence alignment. MUSCLE alignment of the eight condensation domain (Pfam: PF00668) containing proteins from the eight HMP-derived Clostridia pathways, along with the closest NRPS homolog in the NCBI nr database (NCBI Accession: AKL84684).

Figure 19:
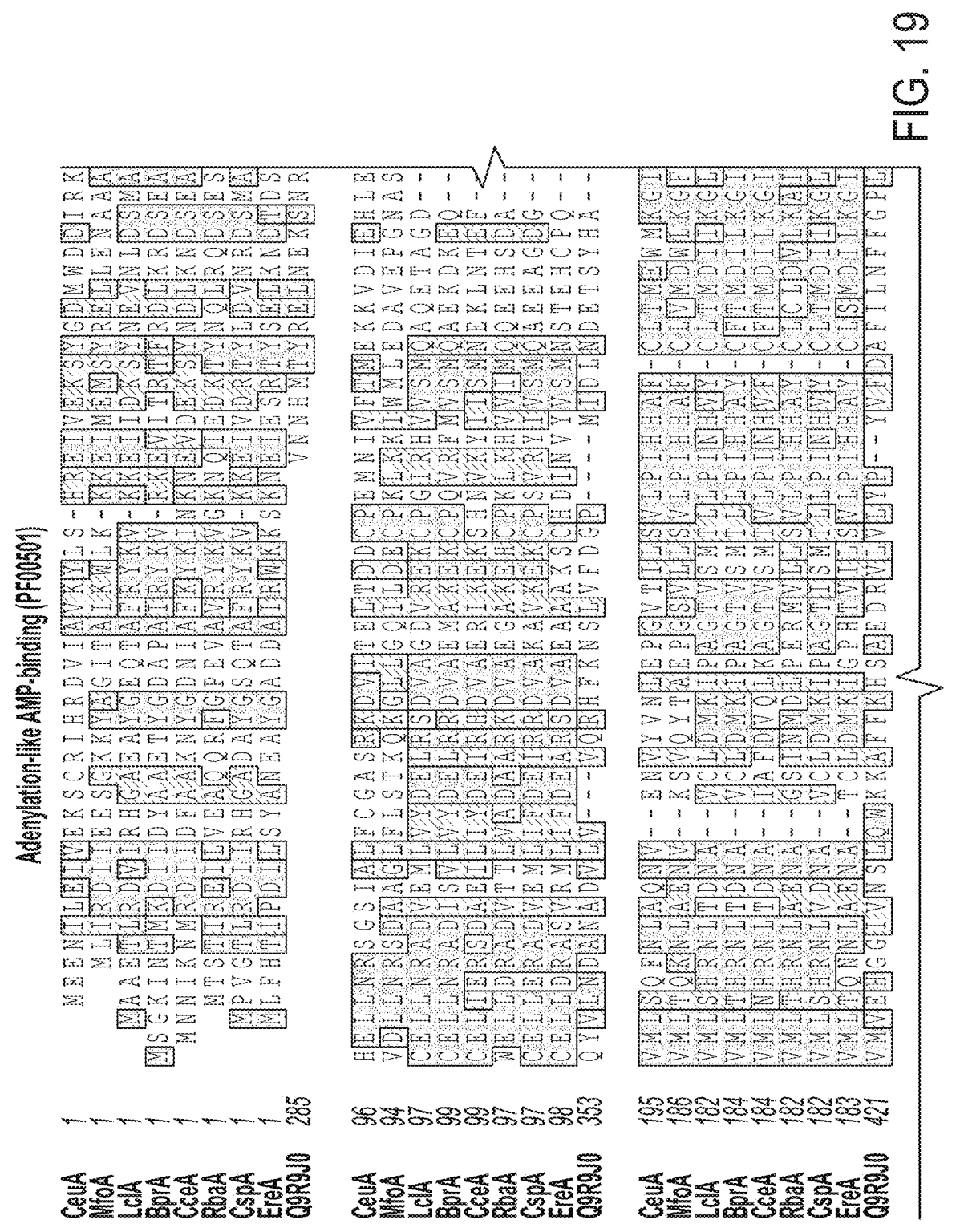
Figure 19:
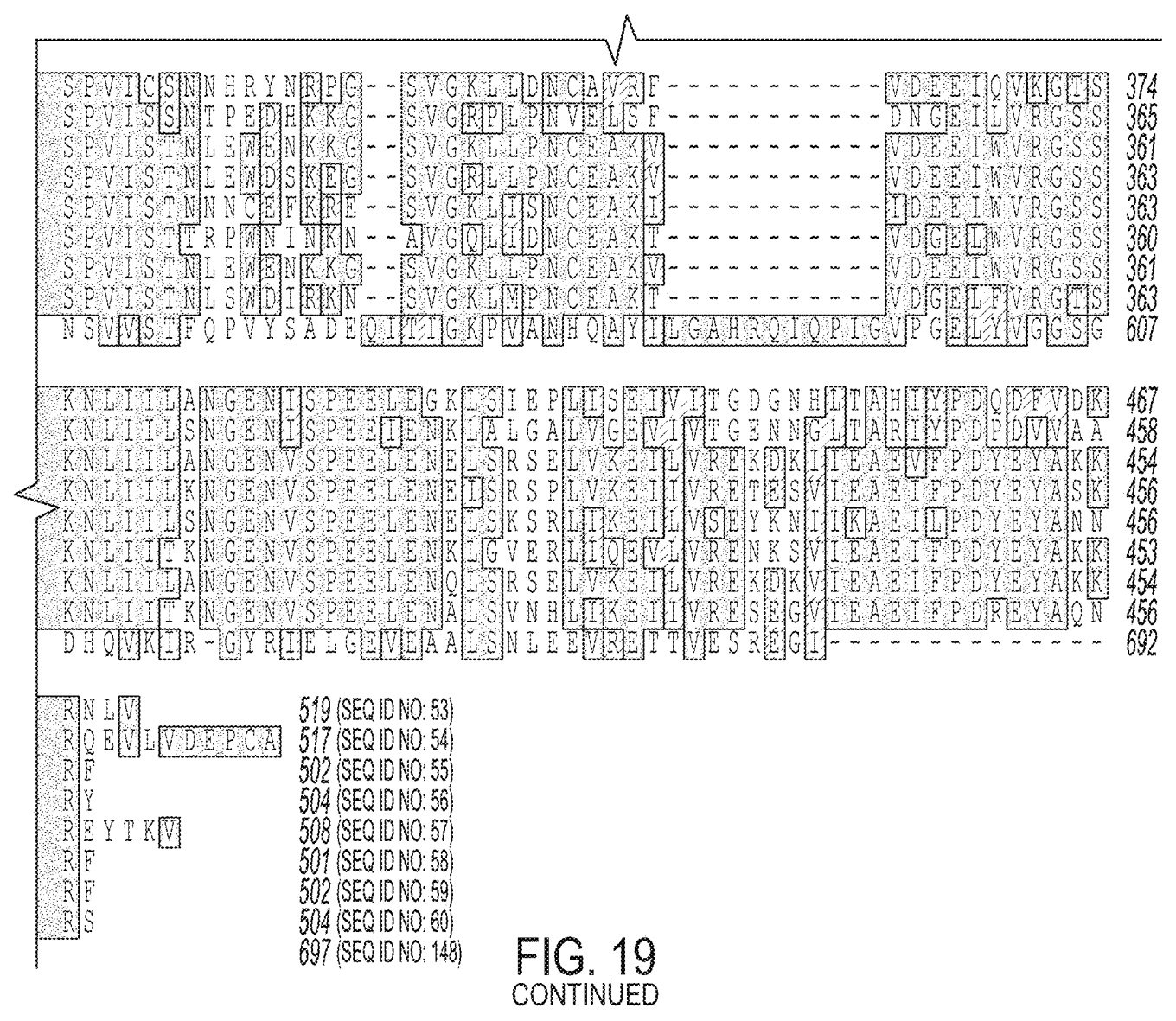

FIG. 19 shows adenylation domain protein sequence alignment. MUSCLE alignment of the eight adenylation-like AMP-binding domain (Pfam: PF00501) containing proteins from the eight HMP-derived Clostridia pathways, along with the closest NRPS homolog in the NCBI nr database (NCBI Accession: Q9R9J0).

FIGS. 20A-20B show pathway boundary analysis. a, Genetic diagrams for the eighteen Clostridia pathways, consisting of the eight HMP-derived pathways (top) and the ten NCBI nr database (bottom), with pathway boundaries predicted by antiSMASH. b, Annotation of the *E. rectale* pathway including two additional genes outside of the antiSMASH-predicted boundary. Each gene was investigated for the presence of a homolog in other FAA pathways.

FIG. 23 shows the adenylation domain catalytic region sequence alignment. MUSCLE alignment of the catalytic region of the eight adenylation-like AMP-binding domain (Pfam: PF00501) containing proteins from the eight HMP-derived Clostridia pathways, along with the closest NRPS homolog in the NCBI nr database (NCBI Accession: Q9R9J0) and the reference NRPS A domain PheA (GrsA). Sequence location of aspartic acid (D) residues of a canonical NRPS adenylation domains that interact with the α-amino group is indicated with an arrow.

FIG. 24 shows condensation domain sequence alignment and point mutation. MUSCLE alignment of the catalytic region of the condensation domain (Pfam: PF00668) containing proteins from the eight HMP-derived Clostridia pathways, along with the closest NRPS homolog in the NCBI nr database (NCBI Accession: AKL84684) and the reference NRPS A domain TycB (ProCAT). Sequence location of histidine (H) residues known to be essential for catalytic activity is indicated with an arrow.

FIGS. 25A-25D show the in vitro substrate panel assay. a, Adenylation activity on a panel of fatty acid substrates, as measured by absorbance (Abs280) of tryptamine conjugated product relative to no adenylation control (TA/T ratio), analyzed on LCMS. b, Condensation activity on a panel of amine substrates, as measured by MS ion intensity of FAA product (consisting of fatty acid with highest activity on adenylation assay) relative to no condensation control (CTA/TA ratio). c, Panel of 25 fatty acids and 53 amines tested. The sources of the fatty acids in the human gut are indicated (symbols on the right of each compound; multiple symbols displayed for multiple sources, with the top symbol signifying the primary source). d, Six Clostridia-derived pathways encoding for unique major FAA compounds. Top: Major compound based on fatty acid and amine substrate with highest activity level in the panel assay. Bottom: Bar graph representing adenylation and condensation activity from the substrate panel assay. The data was taken in triplicate per day. The reported data is the average of the mean triplicate normalized values conducted on three different days, with the error bar being the s.d. of the three mean triplicate values. A threshold level is marked (dotted line) at TA/T ratio>50 for fatty acid incorporation activity and CTA/TA ratio>5 for amine incorporation activity.

FIGS. 28A-28B show pathways with no observable major amine substrate. a, Six Clostridia-derived pathways that showed no major FAA compound production based on not meeting the threshold of CTA/TA ratio>5 for amine incorporation activity. Top: Compound based on fatty acid and amine substrate with highest activity level in the panel assay. Bottom: Bar graph representing adenylation and condensation activity from the substrate panel assay. The data was taken in triplicate per day. The reported data is the average of the mean triplicate normalized values conducted on three different days, with the error bar being the s.d. of the three mean triplicate values. A threshold level is marked (dotted line) at TA/T ratio>50 for fatty acid incorporation activity and CTA/TA ratio>5 for amine incorporation activity. b, An expanded list of amines tested for these pathways.

FIG. 30 shows structural homology of Clostridia and human FAAs. The major compounds characterized from the Clostridia FAA pathways (left) in comparison to known human FAAs (middle), suggesting structural and functional mimicry. GPCR targets with which known human FAAs are reported to interact are summarized to the right.

FIGS. 31A-31H show GPCR activity assay of lauroyl tryptamine. a, Cell-based β-arrestin reporter assay (DiscoveRx) with a panel of 168 GPCRs with known ligands in agonist mode and antagonist mode, and also 73 orphan GPCRs in agonist mode at 10 uM. Agonist mode measures % activity of target GPCR by the compound, relative to the baseline value (0% activity) and maximum value with a known ligand, or twofold increase over baseline for orphan GPCR (100% activation). Antagonist mode measures % inhibition of target GPCR by the compound in the presence of a known ligand, relative to the value at the EC80 (0% inhibition) and basal value (100% inhibition). GPCR targets with activity/inhibition higher than the empirical threshold provided by DiscoverX (30%, 35%, or 50% for GPCR agonist, GPCR antagonist, or orphan GPCR agonist, respectively; plotted as dotted line) suggest that the interaction is potentially significant. EBI2 antagonist activity (81%) is marked with an asterisk (*). b, Concentration-dose response curves of the inhibitory activity of lauroyl tryptamine, tryptamine, and lauric acid on EBI2 in the presence of the native agonist 7α,25-dihydroxycholesterol (7a,25-diHC) at 0.232 uM (EC80). IC50: lauroyl tryptamine=0.98 uM; tryptamine>100 uM; lauric acid>100 uM. c, Concentration-dose response curves of the inhibitory activity of lauroyl tryptamine, tryptamine, and lauric acid on P2RY4 in the presence of the native agonist UTP at 2.79 uM (EC80). IC50>100 uM for all three compounds. d, Concentration-dose response curves of the stimulatory activity of lauroyl tryptamine, tryptamine, and lauric acid on GPR132. EC50: lauroyl tryptamine=1.45 uM; lauric acid=25.2 uM; tryptamine>100 uM. For b, c, d, the curves span ten concentration points in duplicates from 100 to 0.0051 uM, with the error bar being the s.d. from duplicates. e, MS chromatogram (EIC ESI+ [M+H]+ m/z of lauroyl tryptamine, theoretical=343.2744, experimental=343.2369) of the in vivo extract of E. rectale in RCM media (with no fed substrates). The samples are injected alongside a chemically synthesized and structurally verified standard. The * denotes lauroyl tryptamine. The production titer was determined to be 0.04 mg/L. f, Product titer of fatty acyl tryptamine from the in vivo extract of E. rectale in RCM, when fed with exogenous fatty acid (lauric acid, linoleic acid, oleic acid, docosahexaenoic acid, or α-linolenic acid). g, Mapping of human gut metatranscriptomic reads from subject subX316701492 (accession: SRX247340) onto a 80 kb region of the E. rectale genome centered on the FAA pathway (darker arrows, labeled "FAA"). The mean coverage of the 80 kb segment was 0.8 (SD=3.3), while the mean coverage of the FAA pathway by itself was 1.5 (SD=1.1). Housekeeping genes within this segment include tRNA synthetase (tR), carbohydrate metabolism (CM), and sugar transporter (ST) genes. h, Immunological and development role of the EBI2-oxysterol axis and its suppression by E. rectale-derived lauroyl tryptamine to possibly protect against IBD.

DETAILED DESCRIPTION OF THE INVENTION

Figure 2A:
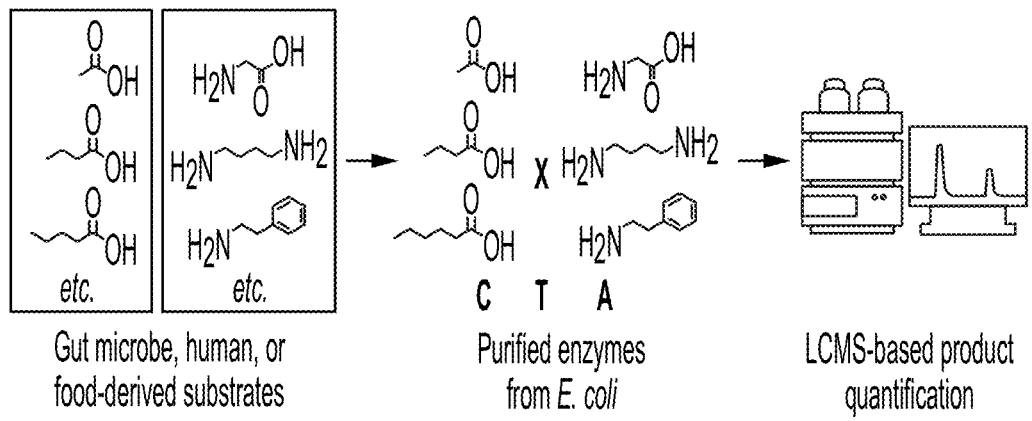
FIGS. 2A-2E show in vitro substrate screening assay. a, Experimental workflow of the assay. b, Adenylation activity with panel of fatty acid substrates, based on absorbance of tryptamine conjugated product (Abs$_{280}$). c, Condensation activity with panel of amine substrates, based on MS ion intensity of fatty acid conjugated product, normalized to product level with no condensation enzyme. d, Panel of 25 fatty acids (labeled F1-F25) and 53 biogenic amines (labeled A1-A53) tested for substrate screening assay, with indication of the primary source in the human gut (bacteria, human, food). The fatty acid olefins are all in cis (Z) conformation. e, Left: Bar graphs representing adenylation and condensation enzyme activity on a panel of fatty acid and amine substrates, respectively, for the eight pathways. Error bars are the s.d. of three replicates conducted on different days. Right: Major compound from each pathway based on the fatty acid and amine substrate with highest activity level (and also surpasses 2 fold-difference threshold), as well as examples of minor compounds based on substrates with second highest activity level. The fatty acid olefins are all in cis (Z) conformation.

Fatty acid amides comprise a diverse class of organic compounds and have been implicated as neuromodulatory lipids and as regulators of human physiopathological conditions. Production of fatty acid amides, however, using conventional laboratory host cells often has low yield. For example, in laboratory strains of E. coli, exogenous fatty acids are often converted into fatty acyl-CoAs, which are rapidly degraded and rebuilt by *E. coli*'s fatty acid biosynthesis machinery (FASII) into their endogenous pool of fatty acyl-ACPs. Without being bound by a particular theory, in *E. coli*, the endogenous fatty acyl-transferase enzyme that conducts the lipidation of these molecules does not use free fatty acid as its substrate, but instead uses a fatty acid conjugated onto either coenzyme A (fatty acyl-CoA) or acyl carrier protein (fatty acyl-ACP). Therefore, when a foreign biosynthetic pathway comprising a fatty acyl-transferse is expressed in *E. coli*, the addition of an exogenous fatty acid in the culture broth generally does not lead to the incorporation of the desired fatty acid onto the final product, but rather a fatty acid that is endogenously made by the host.

This disclosure is premised, at least in part, on the unexpected finding that host cells may be engineered to efficiently produce fatty acid amides from free fatty acids. Accordingly, provided herein, in some embodiments, are vectors encoding biosynthetic enzymes derived from gut microbiome bacteria, engineered cells comprising the same, and methods of using biosynthetic enzymes derived from gut microbiome bacteria to produce fatty acid amides. Biosynthetic enzymes are enzymes that are capable of promoting synthesis of organic compounds and include fatty acyl-transferase, acyl carrier protein (ACP), fatty acyl-ACP synthetase, hydrolases, lipid transfer proteins, and glycosyl-transferases. In some instances, a biosynthetic enzyme is a metabolic enzyme.

Fatty acid amides (FAAs) comprise a hydrophobic acyl tail group and a head group and are formed from a fatty acid and an amine. Non-limiting examples of fatty acid amides include oleoyl aminovaleric acid, α-linolenoyl aminovaleric acid, oleoyl γ-aminobutyric acid, oleoyl dopamine, oleoyl tyramine, palmitoleoyl dopamine, α-linolenoyl tyramine, oleoyl phenethylamine, lauroyl tyrptamine, lineoleoyl tryptamine, lauroyl tyramine, α-linolenoyl homocysteine, oleoyl homocysteine, α-linolenoyl cysteine, linoleoyl homocysteine, oleoyl-aminopentanoic acid, palmitoleyl-putrescine, and α-linolenoyl homocysteamine. FAAs produced by humans include arachidonoyl γ-aminobutryic acid, oleoyl dopamine, docosahexaenoyl serotonin, and arachidonoyl serine. See also, FIGS. 2E, 9 and 32. In some embodiments, the fatty acid amides produced by the methods described herein are structural analogs (also referred to herein as structural homologs) of FAAs that are naturally produced by a cell or subject. See, e.g., FIGS. 9 and 32. In some instances, the FAAs produced by the methods described herein are functional analogs that share one or more biological activities with a FAA that is naturally produced by a cell or subject. As a non-limiting example, a FAA produced by the methods described herein may activate a particular cellular pathway that is activated by a naturally occurring structural analog. In some instances, the subject is a human.

Other than human cells, the human gut microbiome can likewise produce diffusible metabolites that interact with human cellular targets to modulate human signaling pathways.[15,16] For example, a phenotypic assay of DNA damage-inducing *Escherichia coli* or colitis-inducing *Klebsiella oxytoca* led to discovery of pathway responsible for the production of the compounds colibactin[17,18] and tilivalline,[19] respectively. Human microbiome sequencing studies show that, while healthy individuals differ remarkably in the bacterial strains that constitute the microbiome at a taxonomical level, the metabolic pathways remain fairly constant.[20] Taxonomical identification of the human microbiota is therefore not sufficient in associating them with different health states. Elucidating the chemical modulators and connecting them back to specific bacterial genes provide the means to glean functional outputs from DNA sequencing data and ultimately control the underlying mechanisms by therapeutic interventions.

A forward genetics-based approach, like phenotypic assay, has been instrumental in compound discovery, but it is intrinsically designed to be characterized one molecule or bacterial strain at a time. Alternatively, metabolites can be elucidated in a reverse genetics-based manner by bioinformatically mining putative compound-encoding biosynthetic pathways from DNA sequencing data. As an example, a focused search on biosynthetic genes encoding the N-acyl synthase protein domain (PF13444), followed by *E. coli* heterologous expression of representative genes, led to the isolation of FAAs that modulate human health by structurally mimicking human endogenous FAAs, primarily of the amino acid conjugate type from Gram-negative gut commensal bacteria.[21] A more generalized computational search using a detection algorithm (antiSMASH)[22] based on pattern recognition from known pathways identified 14,000 putative pathways from microbiome sequencing data, select groups of which have been characterized to produce compound classes, like lactocillin-based antibiotics[23] and peptide aldehyde-based protease inhibitors.[24] Without being bound by a particular theory, sequence-based methods provide the means to leverage the growing number of available genomic datasets to identify large unexplored groups of pathways that are likely to produce compounds significant in the human gut and systematically characterize them en masse.

Putative pathways identified from sequence data have largely been characterized in vivo by fermentation of the pathway-harboring native or heterologous bacterial strain in laboratory media. However, such laboratory in vivo systems often fail to elucidate pathways that rely on substrates that are absent from or found in insufficient levels in the host strain or culture broth, including bacterial pathways that convert bile acids endogenously produced by human liver cells into more cytotoxic secondary bile acids, like deoxycholic acid and lithocholic acid.[25] The human gut lumen contains a complex mixture of metabolites from gut microbes, human cells, and dietary intake, which is difficult to recapitulate in vivo. On the other hand, pathways can be investigated with precise control of substrates and enzymes by in vitro reconstitution, like the characterization of colibactin biosynthesis.[26] However, this requires a priori biochemical knowledge of the pathways to predict the substrates and enzymatic conditions, which are often lacking for pathways gleaned from sequence data.

One natural product superclass that is widely used by bacteria is the nonribosomal peptide synthetase (NRPS) class.[27] NRPS is known to produce peptide-based compounds of various structures (e.g. cyclic, D-amino acids) and bioactivities (e.g. antibiotics, immunosuppressants). The biosynthetic machinery consists of multiple modules, each of which is generally responsible for incorporating a specific amino acid subunit. The minimal module contains three protein domains: a carrier protein or thiolation domain (T; PF00550) that requires a 4'-phospho-pantetheine (PPT) arm, added by a separate PPTase (e.g. Sfp);[28] an adenylation domain (A; PF00501) that uses ATP to load a specific amino acid onto the T domain to form aminoacyl-T thiotemplated intermediate; and a condensation domain (C; PF00668) that catalyzes amide bond formation between the upstream and downstream aminoacyl-T to generate peptidyl-T thiotemplated intermediate. A termination domain then releases the elongated peptidyl-T from the machinery to form the final product. The chemical ecology in various habitats evolutionarily subjects the bacteria to produce unique secondary metabolites made by specialized NRPS machineries, such as the iterative module of gut *E. coli* enterobactin biosynthesis[29] and the bisintercalator loading domain of marine *Micromonospora* thiocoraline biosynthesis.[30]

As described herein, in some embodiments, genome mining was coupled with in vitro reconstitution to characterize a group of noncanonical NRPS-like pathways from the Gram-positive human gut Clostridia. Putative biosynthetic pathways were computationally detected from publically available human-associated bacterial genomes, and further mapped with metagenomic and metatranscriptomic reads from human gut samples of the Human Microbiome Project to identify eight unprecedented NRPS-like pathways that are ubiquitously present and actively transcribed in the human gut.

Each of the three conserved biosynthetic genes encodes for exactly one protein domain (C, T, or A) that together constitute the NRPS minimal module. Surprisingly, *E. coli* heterologous expression resulted in the production of a FAA. By in vitro reconstitution of the pathway, the C domain was found to load an exogenous fatty acid, instead of an amino acid as predicted from conventional NRPS enzymology, onto the T domain. Furthermore, contrary to NRPS C domain that catalyzes the conjugation of two thiotemplated substrates,[31] this pathway's C domain was characterized to conjugate a thiotemplated fatty acid with a free amine, providing the flexibility to incorporate monoamine neurotransmitter as substrate. Without being bound by a particular theory, because the FAA isolated from *E. coli* was found to be an artifact, the pathways were screened for their preferred substrates with a panel of bacteria-, human-, and food-derived fatty acids and amines known to be abundant in the human gut, resulting in the characterization of four major neurotransmitter conjugate FAA products. In some instances, the chemical structures of the gut Clostridia FAAs are either identical or otherwise homologous to known human FAAs, making them likely to interact with similar human endogenous cellular targets involved in various signaling pathways and serve as a way to modulate human health.

Without being bound by a particular theory, genome mining across multiple sequencing datasets serves as an effective approach for the systematic discovery of human microbiome-derived chemical effectors that scales with the exponential growth of publically available sequence data with minimal prior knowledge.[53] However, the conventional method for sequence-to-compound production relies on heterologous expression, which may fail due to the lack of proper substrates in the heterologous host's metabolic pool.[54] Coupling of sequence mining with in vitro substrate panel screening to analyze enzyme activity with defined substrates to systematically characterize human gut microbiome-derived biosynthetic pathways encoding for chemical compounds is described herein. Without being bound by a particular theory, this allowed for the characterization of the highly abundant and actively transcribed gut Clostridia NRPS-like pathways that preferentially incorporated substrates abundant in the human gut that may not be readily available in conventional laboratory host strains and culture media. Lauric acid and α-linolenic acid are examples of such substrates, found mostly in plants as part of human diet.[55] Although oleic acid occurs naturally across diverse biological systems, the fact that it is the most abundant fatty acid in human adipose tissue[56] suggests that Clostridia pathways have also likely incorporated fatty acids from the human gut lumen. For the amine substrates, dopamine, tyramine, tryptamine, and aminovaleric acid may be absent from or found in insufficient levels in *E. coli* host strains, but are found endogenously in humans, as well as secreted by gut commensal bacteria.[57] Thus, instead of encoding for substrate biosynthesis, the FAA pathways encode a mechanism to incorporate substrates from the host, a phenomenon that has been observed for known biosynthetic pathways in symbiotic systems.[58]

Figure 9A:
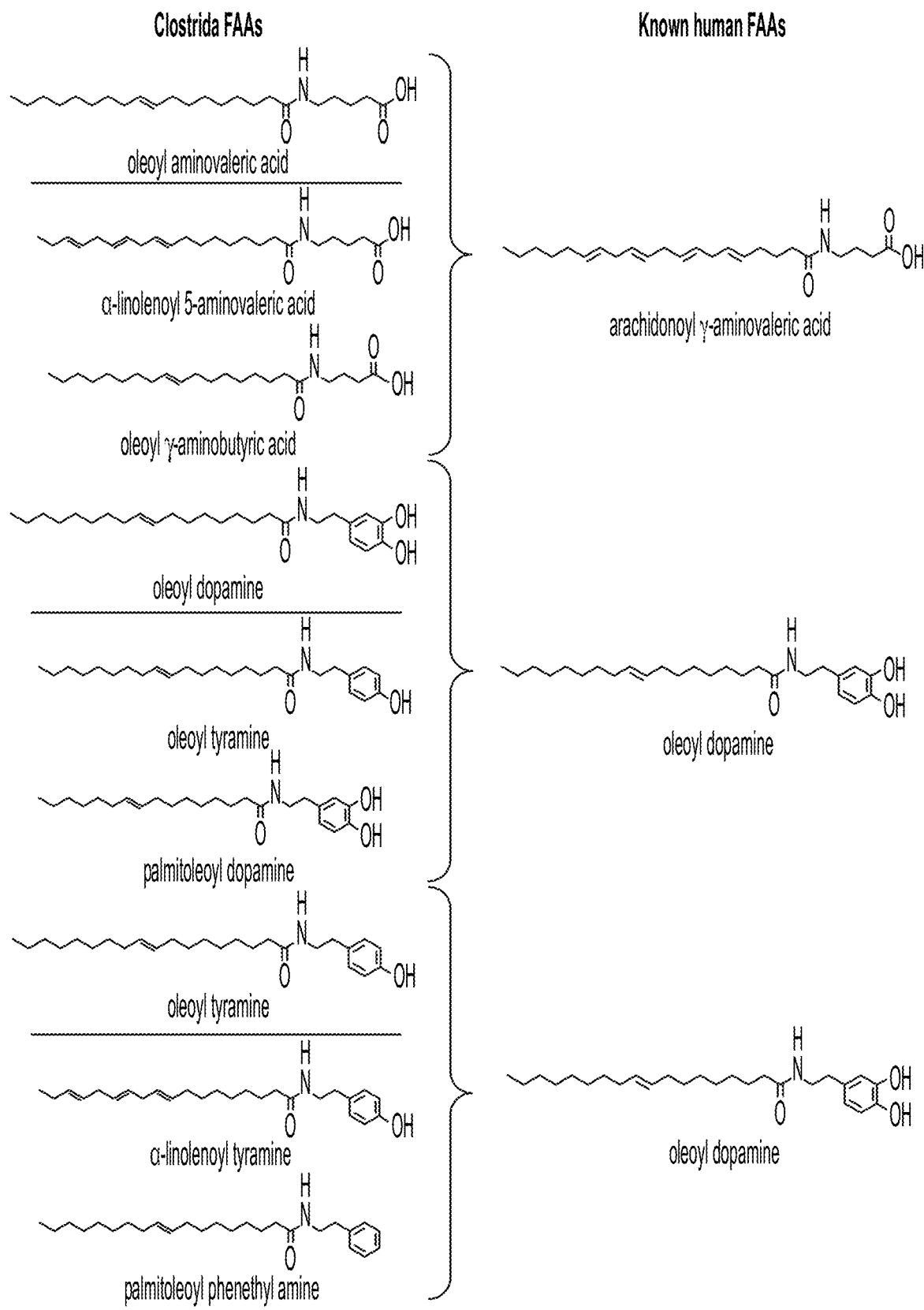
FIGS. 9A-9B show structural homology of Clostridia and human FAAs. The major and minor compounds characterized from the Clostridia FAA pathways (left) in comparison to known human FAAs (right), suggesting structural and functional mimicry.
Figure 9B:
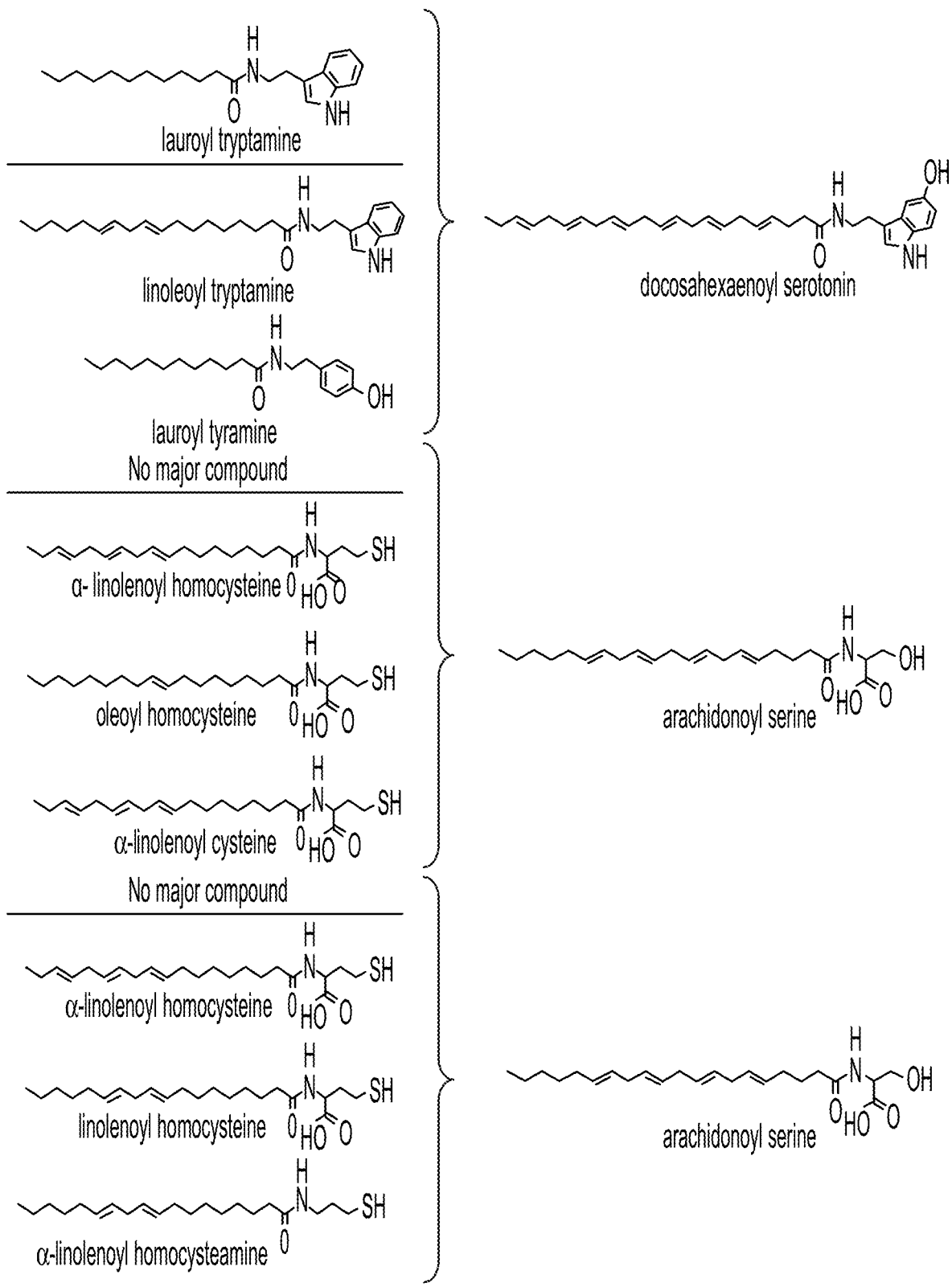

The Clostridia pathways were characterized to produce four major compounds of the FAA type, the same class of signaling molecules produced by human cells to interact with various signaling pathways involved in human health (FIG. 9). One Clostridia-derived compound, oleoyl dopamine, is a known human endogenous FAA. Two of the other compounds, oleoyl tyramine and lauroyl tryptamine, are structurally analogous to known human FAAs, including oleoyl dopamine and docosahexanoyl serotonin. These FAAs are aryl neurotransmitter conjugates that have anandamide-like fatty acid tail and dopamine-like aryl head group, thereby providing the potential to interact with various neurotransmitter receptor sites. The remaining Clostridia-derived FAA, oleoyl aminovaleric acid, is structurally similar to the known human FAA, arachidonoyl GABA. These neurotransmitter conjugates have a GABA-like linear head group, allowing for the interaction with neurotransmitter receptor sites distinct from the arylamine conjugates.

The human gut is referred to as the "second brain" because of the multitude of neurons, otherwise called the enteric nervous system, that embed the walls of the gastrointestinal tract.[59] Neurotransmitters within the gut have been investigated to interact with these receptors to not only influence host neurological, but also immune, metabolic, and vasculature states.[60] The known human endogenous FAAs have also been suggested to interact with these receptors to modulate conditions, such as pain, mood, inflammation, and obesity.[61] Considering the structural mimicry, these Clostridia-derived FAAs are likely the missing chemical link that enables human gut Clostridia to interact with a diverse set of host signaling pathways to influence a variety of physiopathological conditions. The systematic elucidation of these functional outputs will ultimately allow for the deterministic manipulation of these chemical modulators and their targets as an effective mode for human microbiome-based therapy.

Reference numbers in the preceding section correspond to those listed in Reference Section 1.

Gut Microbiome Bacterium

Any of the biosynthetic enzymes (e.g., fatty acyl-transferase, acyl carrier protein (ACP), fatty acyl-ACP synthetase, hydrolases, lipid transfer proteins, and glycosyltransferases) described herein may be derived from a gut microbiome bacterium. A human gut microbiome bacterium is a bacterium that is found in the gastrointestinal tract of a human.

The gut microbiome bacterium may be from any species. For example, the gut microbiome bacterium may be *Bacteroides* spp., *Enterococcus* spp., *Escherichia* spp., *Enterobacter* spp., *Klebsiella* spp., *Bifidobacterium* spp., *Staphylococcus* spp., *Lactobacillus*, *Clostridium* spp., *Proteus* spp., *Pseudomonas* spp., *Coprococcus* spp., *Lachnoclostridum* spp., *Eubacterium* spp., *Salmonella* spp., *Faecalibacterium* spp., *Peptostreptococcus* spp., or *Peptococcus* spp. See also, e.g., Lloyd-Price Nature. 2017 Oct. 5; 550(7674):61-66.

In some instances, a biosynthetic enzyme is a human gut microbiome-derived Clostridia enzyme. Clostridia comprise a class of anaerobic bacteria that are polyphyletic. Non-limiting orders of Clostridia include *Clostridiales*, *Halan-*

*aerobiales, Natranaerobiales, Thermoanaerobacteriales,* and *Negativicutes.* Genera of Clostridia include *Coprococcus, Marvinbryantia, Lachnoclostridum, Blautia, Ruminococcaceae, Eubacterium,* and *Clostridium.* For example, a biosynthetic enzyme may be derived from *Coprococcus eutactus, Marvinbryantia formatexigens, Lachnoclostridium clostridioforme, Blautia producta, Rumiococcaceae bacterium, Clostridiales* sp., *Eubacterium rectale,* or *Clostridium celatum.* Non-limiting examples of human gut-associated bacteria include *Bacteroides fragilis* NCTC 9343, *Bacteroides fragilis* YCH46, *Bacteroides thetaiotaomicron* VPI-5482, *Bifidobacterium longum* NCC2705, *Enterococcus faecalis* V583, *Escherichia coli* sv. O6:K15:H31 536, *Escherichia coli* O157:H7 EDL933 (EHEC), *Escherichia coli* O157:H7 Sakai (EHEC), *Escherichia coli* UTI89 (UPEC), *Helicobacter hepaticus* 3B1, ATCC 51449, *Helicobacter pylori* 26695, *Helicobacter pylori* HPAG1, *Helicobacter pylori* J99, *Lactobacillus acidophilus* NCFM, *Lactobacillus delbrueckii bulgaricus* sv. E Lb14, *Lactobacillus johnsonii* NCC 533, *Lactobacillus salivarius salivarius* UCC118, *Lawsonia intracellularis* PHE/MN1-00, *Listeria monocytogenes* sv. 1/2a EGD-e, *Listeria monocytogenes* sv. 4b F2365, *Porphyromonas gingivalis* W83, *Vibrio cholerae* sv. O1 bv. El Tor N16961, *Campylobacter jejuni jejuni* HB93-13, *Campylobacter upsaliensis* RM3195, *Escherichia coli* O148:H28 B7A (CS6:LT+:ST+) (ETEC), *Escherichia coli* O111:H9 E110019 (EPEC), *Escherichia coli* O139:H28 F11 (ETEC), *Listeria monocytogenes* sv. 1/2a F6854, *Listeria monocytogenes* 4b H7858, *Yersinia bercovieri* ATCC 43970, *Bifidobacterium adolescentis* ATCC 15703, *Lactobacillus brevis* ATCC 367, *Lactobacillus casei* ATCC 334, *Lactobacillus delbrueckii bulgaricus* ATCC BAA-365, *Lactobacillus gasseri* ATCC 33323, *Collinsella aerofaciens* ATCC 25986, *Bacteroides vulgatus* ATCC 8482, *Campylobacter concisus* 13826, *Campylobacter curvus* 525.92, *Campylobacter hominis* ATCC BAA-381, *Citrobacter koseri* ATCC BAA-895, *Escherichia coli* sv. O139:H28 E24377A (ETEC), *Escherichia coli* sv. O9 HS, *Parabacteroides distasonis* ATCC 8503, *Yersinia pseudotuberculosis* sv. O:1b IP 31758, *Vibrio cholerae* sv. O14 MZO-2, *Pseudoflavonifractor capillosus* ATCC 29799, *Bifidobacterium adolescentis* L2-32, *Parabacteroides merdae* ATCC 43184, *Eubacterium ventriosum* ATCC 27560, *Bacteroides caccae* ATCC 43185, *Blautia obeum* ATCC 29174, *Ruminococcus torques* ATCC 27756, *Campylobacter jejuni* CG8486, *Dorea longicatena* DSM 13814, *Listeria monocytogenes* sv. 4b HPB2262, *Ruminococcus gnavus* ATCC 29149, *Listeria monocytogenes* sv. 1/2a1 FSL N3-165, *Lactobacillus helveticus* DPC 4571, *Faecalibacterium prausnitzii* M21/2, *Parvimonas micra* ATCC 33270, *Coprococcus eutactus* ATCC 27759, *Clostridium leptum* DSM 753, *Lachnoclostridium bolteae* ATCC BAA-613, *Absiella dolichum* DSM 3991, *Bacteroides uniformis* ATCC 8492, *Clostridium* sp. L2-50, *Bacteroides ovatus* ATCC 8483, *Escherichia coli* C ATCC 8739, *Escherichia coli* DH10B, *Finegoldia magna* ATCC 29328, *Intestinibacter bartlettii* DSM 16795, *Burkholderia oklahomensis* EO147, *Dorea formicigenerans* ATCC 27755, *Escherichia albertii* TW07627, *Clostridium spiroforme* DSM 1552, *Streptococcus infantarius infantarius* ATCC BAA-102, *Providencia stuartii* ATCC 25827, *Eubacterium siraeum* DSM 15702, *Bifidobacterium dentium* ATCC 27678, *Anaerofustis stercorihominis* DSM 17244, *Bacteroides stercoris* ATCC 43183, *Lachnoclostridium scindens* ATCC 35704, *Alistipes putredinis* DSM 17216, *Escherichia coli* O157:H7 EC508, *Anaerostipes caccae* DSM 14662, *Bifidobacterium animalis lactis* HN019, *Listeria monocytogenes* FSL J2-071, *Listeria monocytogenes* sv. 1/2b FSL J2-064, *Clostridium* sp. SS2/1, *Anaerotruncus colihominis* DSM 17241, *Akkermansia muciniphila* ATCC BAA-835, *Bifidobacterium longum* DJO10A, *Helicobacter pylori* Shi470, *Lactobacillus casei casei* BL23, *Ruminococcus lactaris* ATCC 29176, *Bacteroides coprocola* M16, DSM 17136, *Clostridium sporogenes* ATCC 15579, *Bacteroides intestinalis* 341, DSM 17393, *Bifidobacterium catenulatum* DSM 16992, JCM 1194, LMG 11043, *Desulfovibrio piger* ATCC 29098, *Providencia alcalifaciens* sv. 019:H2 DSM 30120, *Providencia rustigianii* DSM 4541, *Collinsella stercoris* DSM 13279, *Anaerococcus hydrogenalis* DSM 7454, *Helicobacter pylori* HPKX_438_AG0C1, *Helicobacter pylori* 98-10, *Helicobacter pylori* B128, *Helicobacter pylori* HPKX_438_CA4C1, *Bacteroides eggerthii* DSM 20697, *Bacteroides pectinophilus* ATCC 43243, *Bacteroides plebeius* M12, DSM 17135, *Parabacteroides johnsonii* DSM 18315, *Lachnoclostridium hylemonae* DSM 15053, *Holdemanella biformis* DSM 3989, *Lactobacillus rhamnosus* HN001, *Tyzzerella nexilis* DSM 1787, *Bacteroides dorei* DSM 17855, *Clostridium hiranonis* TO-931 DSM 13275, *Bacillus cereus* AH187 (F4810/72), *Bacillus cereus* G9842, *Bifidobacterium animalis lactis* AD011, *Bifidobacterium longum infantis* ATCC 15697, *Escherichia coli* O81 ED1a, *Escherichia coli* SE11, *Helicobacter pylori* G27, *Helicobacter pylori* P12, *Listeria monocytogenes* sv. 4a HCC23, *Roseburia inulinivorans* DSM 16841, *Clostridiales* sp. 1_7_47FAA, *Lactobacillus acidophilus* ATCC 4796, *Bifidobacterium bifidum* NCIMB 41171, *Lactobacillus hilgardii* ATCC 8290, *Lactobacillus ultunensis* DSM 16047, *Lactobacillus salivarius* HO66, ATCC 11741, *Lactobacillus paracasei* ATCC 25302, *Acidaminococcus intestini* D21, *Lactobacillus brevis gravesensis* ATCC 27305, *Lactobacillus fermentum* ATCC 14931, *Lactobacillus buchneri* ATCC 11577, *Enterococcus faecalis* TX1322, *Enterococcus faecalis* TX0104, *Bifidobacterium breve* DSM 20213, JCM 1192, *Holdemania filiformis* VPI J1-31B-1, DSM 12042, *Leuconostoc mesenteroides cremoris* ATCC 19254, *Catenibacterium mitsuokai* DSM 15897, *Bacteroides cellulosilyticus* DSM 14838, *Lachnoclostridium asparagiforme* DSM 15981, *Coprococcus comes* ATCC 27758, *Proteus penneri* ATCC 35198, *Enterococcus faecium* TX1330, *Lactobacillus rhamnosus* LMS2-1, *Lactobacillus paracasei* 8700:2, *Bifidobacterium longum longum* ATCC 55813, *Helicobacter cinaedi* CCUG 18818, *Bacteroides coprophilus* DSM 18228, JCM 13818, *Blautia hydrogenotrophica* DSM 10507, *Eubacterium hallii* DSM 3353, *Clostridium methylpentosum* R2, DSM 5476, *Helicobacter canadensis* MIT 98-5491, ATCC 700968, *Bifidobacterium longum longum* CCUG 52486, *Helicobacter pullorum* MIT 98-5489, *Bifidobacterium animalis lactis* B1-04, ATCC SD5219, *Bifidobacterium animalis lactis* DSM 10140, *Eubacterium eligens* ATCC 27750, *Eubacterium rectale* ATCC 33656, *Helicobacter pylori* B38, *Lactobacillus plantarum* JDM1, *Lactobacillus rhamnosus* GG, *Acinetobacter baumannii* AB900, *Parabacteroides* sp. 2_1_7, *Bacteroides fragilis* 3_1_12, *Weissella paramesenteroides* ATCC 33313, *Fusobacterium nucleatum* subsp. *animalis* D11, *Escherichia coli* D9, *Fusobacterium gonidiaformans* ATCC 25563, *Faecalibacterium prausnitzii* A2-165, *Butyrivibrio crossotus* DSM 2876, *Hungatella hathewayi* DSM 13479, *Lactobacillus antri* DSM 16041, *Lactobacillus helveticus* DSM 20075, *Fusobacterium gonidiaformans* 3-1-5R, *Oxalobacter formigenes* HOxBLS, *Coprobacillus* sp. D7, *Fusobacterium nucleatum animalis* 7_1, *Fusobacterium nucleatum* subsp. *vincentii* 4_1_13, *Fusobacterium mortiferum* ATCC 9817, *Helicobacter winghamensis* ATCC BAA-430, *Citrobacter portucalensis* 30_2, *Bacteroides dorei* 5_1_36/D4, *Escherichia* sp. 3_2_53FAA, *Clostridium* sp. 7_2_43FAA, *Escherichia* sp. 1_1_43, *Fusobacterium periodonticum* 2_1_31, *Bacteroides* sp. 9_1_42FAA, *Bacteroides* sp. D1, *Oxalobacter formigenes* OXCC13, *Bacteroides* sp. 2_2_4, *Bacteroides thetaiotaomicron* 1_1_6, *Bacteroides* sp. 4_3_47FAA, *Fusobacterium varium* ATCC 27725, *Parabacteroides* sp. D13, *Clostridioides difficile* CD196, *Clostridioides difficile* R20291, *Escherichia coli* K-12, MG1655, *Mycoplasma hominis* PG21, ATCC 23114, *Veillonella parvula* Te3, DSM 2008, *Bifidobacterium longum longum* JDM301, *Escherichia coli* O55:H7 CB9615, *Lactobacillus johnsonii* FI9785, *Bifidobacterium animalis lactis* BB-12, *Bifidobacterium animalis lactis* V9, *Escherichia coli* O44:H18 042 (EAEC), *Escherichia coli* O18:K1:H7 IHE3034, *Escherichia coli* O150:H5 SE15, *Helicobacter pylori* 51, *Helicobacter pylori* v225, *Lactobacillus rhamnosus* GG, *Acetomicrobium hydrogeniformans* ATCC BAA-1850, *Bacteroides ovatus* SD CC 2a, *Bacteroides ovatus* SD CMC 3f, *Bacteroides vulgatus* PC510, *Bacteroides xylanisolvens* SD CC 1b, *Clostridioides difficile* NAP07, *Clostridioides difficile* NAP08, *Corynebacterium ammoniagenes* DSM 20306, *Edwardsiella tarda* ATCC 23685, *Enterococcus faecium* PC4.1, *Enterococcus faecium* E1071, *Grimontia hollisae* CIP 101886, *Lactobacillus amylolyticus* DSM 11664, *Turicibacter sanguinis* PC909, *Vibrio cholerae* CT 5369-93, *Vibrio cholerae* sv. Inaba INDRE 91/1, *Vibrio cholerae* sv. O1 RC27, *Vibrio furnissii* sv. II CIP 102972, *Vibrio mimicus* MB-451, *Bacteroides fragilis* 2_1_16, *Bacteroides* sp. 2_1_22, *Bacteroides* sp. 2_1_33B, *Bacteroides* sp. 3_1_33FAA, *Bacteroides* sp. D20, *Enterococcus faecalis* X98, ATCC 27276, *Enterococcus faecium* 1,141,733, *Enterococcus faecium* 1,231,501, *Enterococcus faecium* Com12, *Enterococcus faecium* Com15, *Fusobacterium periodonticum* 1_1_41FAA, *Klebsiella variicola* 1_1_55, *Pediococcus acidilactici* 7_4, *Streptococcus* sp. 2_1_36FAA, *Veillonella* sp. 3_1_44, *Veillonella* sp. 6_1_27, *Escherichia coli* O26:H11 11368, *Helicobacter pylori* PeCan4, *Helicobacter pylori* SJM180, *Campylobacter jejuni jejuni* M1, *Edwardsiella tarda* FL6-60, *Escherichia coli* AIEC UM146, *Helicobacter pylori* 908, *Helicobacter pylori* Cuz20, *Helicobacter pylori* Sat464, *Campylobacter coli* JV20, *Enterococcus faecalis* TX2134, *Escherichia coli* MS 107-1, *Escherichia coli* MS 115-1, *Escherichia coli* MS 116-1, *Escherichia coli* MS 119-7, *Escherichia coli* MS 124-1, *Escherichia coli* MS 146-1, *Escherichia coli* MS 175-1, *Escherichia coli* MS 182-1, *Escherichia coli* MS 185-1, *Escherichia coli* MS 187-1, *Escherichia coli* MS 196-1, *Escherichia coli* MS 198-1, *Escherichia coli* MS 200-1, *Escherichia coli* MS 21-1, *Escherichia coli* MS 45-1, *Escherichia coli* MS 69-1, *Escherichia coli* MS 78-1, *Escherichia coli* MS 84-1, *Bacteroides* sp. 1_1_14, *Parabacteroides* sp. 20_3, *Bacteroides* sp. 3_1_19, *Bacteroides* sp. 3_1_23, *Bacteroides* sp. D22, *Burkholderiales bacterium* 1_1_47, *Bifidobacterium bifidum* PRL2010, *Bifidobacterium bifidum* S17, *Bifidobacterium longum infantis* 157F-NC, *Bifidobacterium longum longum* BBMN68, *Bifidobacterium longum longum* JCM 1217, *Campylobacter jejuni jejuni* ICDCCJ07001, *Helicobacter felis* CS1, ATCC 49179, *Helicobacter pylori* B8, *Lactobacillus delbrueckii bulgaricus* ND02, *Odoribacter splanchnicus* 1651/6, DSM 20712, *Anaerostipes* sp. 3_2_56FAA, *Arcobacter butzleri* JV22, *Bacteroides eggerthii* 1_2_48FAA, *Bacteroides* sp. 3_1_40A, *Bacteroides* sp. 4_1_36, *Bifidobacterium* sp. 12_1_47BFAA, *Campylobacter upsaliensis* JV21, *Clostridium* sp. HGF2, *Lachnoclostridium symbiosum* WAL-14163, *Lachnoclostridium symbiosum* WAL-14673, *Coprobacillus cateniformis* 29_1, *Eggerthella* sp. 1_3_56FAA, *Erysipelotrichaceae bacterium* sp. 3_1_53, *Escherichia coli* MS 145-7, *Faecalibacterium* cf. *prausnitzii* KLE1255, *Helicobacter suis* HS1, *Helicobacter suis* HS5, *Lachnospiraceae bacterium* sp. 5_1_63FAA, *Lachnospiraceae bacterium* sp. 8_1_57FAA, *Pediococcus acidilactici* DSM 20284, *Phascolarctobacterium succinatutens* YIT 12067, *Prevotella salivae* DSM 15606, *Ralstonia* sp. 5_7_47FAA, *Streptococcus anginosus* 1_2_62CV, *Streptococcus equinus* ATCC 9812, *Succinatimonas hippei* YIT 12066, *Sutterella wadsworthensis* 3_1_45B, *Alistipes shahii* WAL 8301, *Bacteroides fragilis* 638R, *Bacteroides xylanisolvens* XB1A, *Bifidobacterium longum longum* F8, *Butyrivibrio fibrisolvens* 16/4, *Lachnoclostridium* cf. *saccharolyticum* K10, *Coprococcus catus* GD/7, *Enterobacter cloacae cloacae* NCTC 9394, *Enterococcus faecalis* 62, *Enterococcus faecalis* 7L76, *Faecalitalea cylindroides* T2-87, *Eubacterium rectale* DSM 17629, *Eubacterium rectale* M104/1, *Eubacterium siraeum* 70/3, *Faecalibacterium prausnitzii* SL3/3, *Faecalibacterium prausnitzii* L2-6, *Gordonibacter pamelaeae* 7-10-1-bT, DSM 19378, *Helicobacter pylori* Gambia94/24, *Helicobacter pylori* India7, *Helicobacter pylori* Lithuania75, *Helicobacter pylori* SouthAfrica7, *Lactobacillus delbrueckii bulgaricus* 2038, *Listeria monocytogenes* sv. 4a L99, *Megamonas hypermegale* ART12/1, *Roseburia intestinalis* M50/1, *Roseburia intestinalis* XB6B4, *Ruminococcus bromii* L2-63, *Blautia obeum* A2-162, *Ruminococcus* sp. SR1/5, *Ruminococcus* sp. 18P13, *Ruminococcus torques* L2-14, *Clostridiales* sp. SS3/4, *Anaerostipes hadrus* SSC/2, *Victivallis vadensis* ATCC BAA-548, *Clostridium* sp. SY8519, *Eggerthella* sp. YY7918, *Helicobacter bizzozeronii* CIII-1, *Bifidobacterium animalis lactis* CNCM 1-2494, *Bifidobacterium breve* UCC2003 (NCIMB8807), *Bifidobacterium longum infantis* JCM 1222, *Escherichia coli* DH1 (ME8569), *Escherichia coli* LF82, *Helicobacter pylori* 2017, *Helicobacter pylori* 2018, *Helicobacter pylori* 83, *Helicobacter pylori* F16, *Helicobacter pylori* F30, *Helicobacter pylori* F32, *Helicobacter pylori* F57, *Lactobacillus amylovorus* GRL 1118, *Lactobacillus johnsonii* DPC 6026, *Yersinia enterocolitica palearctica* sv. O:3 bt. 4 Y11, *Clostridium* sp. D5, *Bacteroides clarus* YIT 12056, *Bacteroides fluxus* YIT 12057, *Bacteroides ovatus* 3_8_47FAA, *Bacteroides* sp. 1_1_30, *Bacteroides fragilis* 2_1_56FAA, *Eggerthella* sp. HGA1, *Fusobacterium nucleatum* subsp. *animalis* 11_3_2, *Klebsiella* sp. MS 92-3, *Lachnospiraceae bacterium* 1_1_57FAA, *Lachnospiraceae bacterium* 1_4_56FAA, *Lachnospiraceae bacterium* 2_1_58FAA, *Lachnospiraceae bacterium* 3_1_46FAA, *Lachnospiraceae bacterium* 6_1_37FAA, *Lachnospiraceae bacterium* 5_1_57FAA, *Lachnospiraceae bacterium* 6_1_63FAA, *Lachnospiraceae bacterium* 9_1_43BFAA, *Neisseria macacae* ATCC 33926, *Paenibacillus* sp. HGF5, *Paenibacillus* sp. HGF7, *Paraprevotella xylaniphila* YIT 11841, *Parasutterella excrementihominis* YIT 11859, *Turicibacter* sp. HGF1, *Lactobacillus reuteri* CF48-3A, *Bifidobacterium pseudocatenulatum* D2CA, *Bdellovibrio bacteriovorus* W, *Alistipes finegoldii* AHN 2437, DSM 17242, *Microcystis aeruginosa* PCC 7806, *Megasphaera elsdenii* DSM 20460, *Acidaminococcus intestini* RyC-MR95, *Roseburia hominis* A2-183, DSM 16839, *Enterococcus faecalis* OG1RF, ATCC 47077, *Helicobacter pylori* Puno135, *Pseudomonas aeruginosa* NCGM2.S1, *Helicobacter pylori* 35A, *Listeria monocytogenes* sv. 1/2a 10403S, *Listeria monocytogenes* FSL R2-561, *Listeria monocytogenes* sv. 1/2a J0161, *Listeria monocytogenes* Finland 1988, *Helicobacter pylori* Puno120, *Corynebacterium appendicis* CIP 107643, *Alistipes* sp. HGB5, *Bifidobacterium breve* SC95, *Bifidobacterium longum infantis* SC142, *Bifidobacterium breve* SC154, *Bifidobacterium bifidum SC555, *Bifidobacterium longum longum* SC596, *Bifidobacterium longum longum* SC664, *Bifidobacterium breve* JCM 7019, *Helicobacter cetorum* MIT 99-5656, *Helicobacter cetorum* MIT 00-7128, *Helicobacter pylori* Shi11 2, *Helicobacter pylori* Shi169, *Helicobacter pylori* Shi417, *Helicobacter pylori* PeCan18, *Bifidobacterium animalis animalis* ATCC 25527, *Pseudomonas* sp. 2_1_26, *Klebsiella* sp. 4_1_44FAA, *Citrobacter freundii* 4_7_47CFAA, *Tannerella* sp. 6_1_58FAA_CT1, *Hungatella hathewayi* WAL-18680, *Alistipes indistinctus* YIT 12060, *Odoribacter laneus* YIT 12061, *Flavonifractor plautii* ATCC 29863, *Campylobacter* sp. 10_1_50, *Synergistes* sp. 3_1_syn1, *Subdoligranulum* sp. 4_3_54A2FAA, *Enterococcus saccharolyticus* 30_1, *Lachnoclostridium clostridioforme* 2_1_49FAA, *Prevotella stercorea* DSM 18206, *Enterococcus faecalis* PC1.1, *Bilophila* sp. 4_1_30, *Desulfovibrio* sp. 6_1_46AFAA, *Bacillus* sp. 7_6_55CFAA_CT2, *Lachnospiraceae bacterium* sp. 7_1_58FAA, *Fusobacterium necrophorum funduliforme* 1_1_36S, *Erysipelotrichaceae bacterium* sp. 21_3, *Dorea formicigenerans* 4_6_53AFAA, *Collinsella tanakaei* YIT 12063, *Erysipelotrichaceae* sp. 2_2_44A, *Eubacterium* sp. 3_1_31, *Dialister succinatiphilus* YIT 11850, *Lachnoclostridium citroniae* WAL-17108, *Coprobacillus* sp. 8_2_54BFAA, *Clostridium* sp. 7_3_54FAA, *Sutterella parvirubra* YIT 11816, *Coprobacillus* sp. 3_3_56FAA, *Hafnia alvei* ATCC 51873, *Bacillus smithii* 7_3_47FAA, *Propionibacterium* sp. 5_U_42AFAA, *Paraprevotella clara* YIT 11840, *Lactobacillus* sp. 7_1_47FAA, *Megamonas funiformis* YIT 11815, *Blautia producta* ATCC 27340, *Acetomicrobium hydrogeniformans* ATCC BAA-1850, *Listeria monocytogenes* NKB04_01, *Listeria monocytogenes* sv. 4b NKB04_02, *Listeria monocytogenes* sv. 4b NKB04_03, *Listeria monocytogenes* sv. 1/2b NKB06_01, *Listeria monocytogenes* NKB06_03, *Vibrio cholerae* sv. O1 Ogava P-18785, *Escherichia coli* HM605, *Helicobacter pylori* XZ274, *Eubacterium siraeum* DSM 15702, *Lactobacillus helveticus* R0052, *Lawsonia intracellularis* N343, *Escherichia coli* DEC15E, *Escherichia coli* DEC15D, *Escherichia coli* DEC15C, *Desulfitobacterium hafniense* DP7, *Bifidobacterium longum* D2957, *Vibrio cholerae* ZWU0020, *Helicobacter pylori* 26695, *Clostridium celatum* DSM 1785, *Helicobacter pylori* Hp P-15b, *Helicobacter pylori* Hp P-25c, *Helicobacter pylori* Hp P-25d, *Helicobacter pylori* Hp P-28b, *Escherichia coli* DEC15A, *Escherichia coli* DEC15B, *Escherichia coli* DEC14D, *Escherichia coli* DEC13C, *Escherichia coli* DEC13D, *Escherichia coli* DEC14A, *Escherichia coli* DEC9E, *Escherichia coli* DEC5B, *Escherichia coli* DEC13A, *Escherichia coli* DEC11D, *Escherichia coli* DEC11C, *Escherichia coli* DEC12A, *Escherichia coli* DEC12C, *Escherichia coli* DEC12B, *Escherichia coli* DEC12D, *Helicobacter pylori* NQ4076, *Helicobacter pylori* NQ4044, *Helicobacter pylori* NQ4110, *Helicobacter pylori* Hp A-5, *Helicobacter pylori* Hp A-4, *Helicobacter pylori* Hp A-9, *Escherichia coli* DEC10E, *Escherichia coli* DEC10F, *Escherichia coli* DEC10C, *Escherichia coli* DEC10D, *Escherichia coli* DEC10A, *Escherichia coli* DEC10B, *Escherichia coli* DEC9D, *Escherichia coli* DEC11A, *Escherichia coli* DEC11B, *Helicobacter pylori* Hp H-43, *Escherichia coli* DEC9A, *Escherichia coli* DEC8D, *Escherichia coli* DEC8C, *Escherichia coli* DEC9B, *Listeria monocytogenes* sv. 1/2c SLCC 2372, *Listeria monocytogenes* sv. 1/2b SLCC 2755, *Listeria monocytogenes* sv. 4e SLCC 2378, *Bifidobacterium bifidum* BGN4, *Listeria monocytogenes* sv. 3b SLCC 2540, *Bifidobacterium longum* E18, *Escherichia coli* DEC14B, *Escherichia coli* DEC14C, *Escherichia coli* DEC13E, *Enterococcus faecalis* TX2137, *Enterococcus faecalis* TX4244, *Escherichia coli* MS 57-2, *Escherichia coli* DEC5D, *Escherichia coli* DEC5E, *Escherichia coli* DEC6A, *Escherichia coli* DEC6B, *Escherichia coli* DEC6C, *Escherichia coli* DEC6D, *Escherichia coli* DEC6E, *Escherichia coli* DEC7A, *Escherichia coli* DEC7B, *Escherichia coli* DEC7C, *Aeromonas veronii* AMC34, *Aeromonas hydrophila* SSU, *Escherichia coli* DEC1D, *Escherichia coli* DEC1E, *Escherichia coli* DEC1B, *Escherichia coli* DEC1C, *Escherichia coli* DEC1A, *Barnesiella intestinihominis* YIT 11860, *Slackia piriformis* YIT 12062, *Helicobacter pylori* GAM118Bi, *Helicobacter pylori* GAM115Ai, *Helicobacter pylori* GAM114Ai, *Helicobacter pylori* GAM112Ai, *Helicobacter pylori* GAM105Ai, *Helicobacter pylori* GAM103Bi, *Helicobacter pylori* GAM101Biv, *Helicobacter pylori* GAM120Ai, *Helicobacter pylori* GAM119Bi, *Campylobacter jejuni jejuni* 2008-979, *Shigella dysenteriae* CDC 74-1112, *Helicobacter pylori* CPY6311, *Helicobacter pylori* NQ4216, *Helicobacter pylori* NQ4200, *Helicobacter pylori* NQ4228, *Helicobacter pylori* CPY6081, *Helicobacter pylori* CPY6261, *Helicobacter pylori* CPY6271, *Helicobacter pylori* NQ4099, *Helicobacter pylori* NQ4053, *Escherichia coli* DEC3D, *Escherichia coli* DEC3E, *Escherichia coli* DEC2C, *Escherichia coli* DEC2D, *Escherichia coli* DEC2A, *Escherichia coli* DEC2B, *Escherichia coli* DEC3C, *Escherichia coli* DEC3B, *Escherichia coli* DEC2E, *Escherichia coli* DEC3A, *Escherichia coli* O104:H4 11-4522, *Helicobacter pylori* Hp H-41, *Helicobacter pylori* Hp H-36, *Helicobacter pylori* Hp H-30, *Helicobacter pylori* Hp H-27, *Helicobacter pylori* Hp H-28, *Helicobacter pylori* Hp H-24, *Helicobacter pylori* HP250ASi, *Helicobacter pylori* HP250AFiV, *Helicobacter pylori* GAMchJs124i, *Helicobacter pylori* GAMchJs117Ai, *Helicobacter pylori* GAMchJs114i, *Helicobacter pylori* HP250AFiii, *Helicobacter pylori* HP250AFii, *Helicobacter pylori* HP116Bi, *Helicobacter pylori* GAMchJsl36i, *Bifidobacterium longum longum* 44B, *Escherichia coli* HM605, *Helicobacter pylori* GAM260Bi, *Helicobacter pylori* GAM260ASi, *Helicobacter pylori* GAM263BFi, *Helicobacter pylori* GAM260BSi, *Helicobacter pylori* GAM252Bi, *Helicobacter pylori* GAM250T, *Helicobacter pylori* GAM254Ai, *Helicobacter pylori* GAM252T, *Helicobacter pylori* GAM265BSii, *Helicobacter pylori* GAM264Ai, *Bacteroides* sp. HPS0048, *Enterococcus faecium* ERV165, *Enterococcus faecium* TX1337RF, *Escherichia coli* MS 85-1, *Escherichia coli* MS 79-10, *Listeria monocytogenes* sv. 1/2b FSL R2-503, *Listeria monocytogenes* FSL J1-194, *Bacteroides* salyersiae WAL 10018, DSM 18765, JCM 12988, *Enterococcus faecalis* TX1341, *Enterococcus faecalis* TX1302, *Escherichia coli* 4_1_47FAA, *Erysipelotrichaceae bacterium* sp. 6_1_45, *Helicobacter pylori* Hp H-19, *Helicobacter pylori* Hp H-21, *Bifidobacterium longum longum* 2-2B, *Escherichia coli* MS 60-1, *Sutterella wadsworthensis* 2_1_59BFAA, *Helicobacter pylori* Hp P-1, *Helicobacter pylori* Hp P-3, *Helicobacter pylori* Hp P-4, *Helicobacter pylori* Hp H-23, *Helicobacter pylori* Hp H-34, *Helicobacter pylori* Hp P-8, *Acinetobacter baumannii* OIFC047, *Helicobacter pylori* Hp H-11, *Helicobacter pylori* Hp H-24b, *Helicobacter pylori* Hp H-24c, *Helicobacter pylori* Hp H-5b, *Helicobacter pylori* Hp P-74, *Helicobacter pylori* Hp P-41, *Helicobacter pylori* Hp P-62, *Mycobacterium avium* paratuberculosis S397, *Shigella boydii* serotype 7 AMC 4006, ATCC 9905, *Anaerostipes hadrus* comb. nov. VPI 82-52, DSM 3319, *Helicobacter pylori* Hp M1, *Escherichia coli* MS 117-3, *Escherichia coli* MS 110-3, *Escherichia coli* MS 16-3, *Escherichia coli* MS 153-1, *Escherichia coli* DEC13B, Escherichia coli DEC11E, Escherichia coli DEC12E, Enterococcus faecalis TX1346, Enterococcus faecalis TX1342, Enterococcus faecalis TX1467, Escherichia coli DEC8B, Escherichia coli DEC8A, Escherichia coli DEC7E, Escherichia coli DEC7D, Escherichia coli DEC8E, Escherichia coli DEC9C, Bacteroides oleiciplenus YIT 12058, Helicobacter pylori CPY1124, Lactobacillus rhamnosus ATCC 21052, Helicobacter pylori CPY1662, Helicobacter pylori CPY1313, Helicobacter pylori CPY3281, Helicobacter pylori CPY1962, Escherichia coli DEC5C, Escherichia coli DEC4E, Escherichia coli DEC4D, Escherichia coli DEC5A, Escherichia coli DEC4F, Escherichia coli DEC4A, Escherichia coli DEC3F, Escherichia coli DEC4C, Escherichia coli DEC4B, Helicobacter pylori Hp P-2, Clostridioides difficile 002-P50-2011, Clostridioides difficile 050-P50-2011, Helicobacter pylori GAM239Bi, Helicobacter pylori GAM244Ai, Helicobacter pylori GAM245Ai, Helicobacter pylori GAM246Ai, Helicobacter pylori GAM121Aii, Helicobacter pylori GAM201Ai, Helicobacter pylori GAM210Bi, Helicobacter pylori GAM231Ai, Helicobacter pylori GAM249T, Helicobacter pylori GAM250AFi, Escherichia coli O104:H4 LB226692, Helicobacter pylori HP260Bi, Acinetobacter junii CIP 64.5, Helicobacter pylori NQ4161, Helicobacter pylori Hp A-11, Helicobacter pylori Hp A-20, Helicobacter pylori Hp A-17, Lactobacillus delbrueckii lactis DSM 20072, Helicobacter pylori GAM100Ai, Campylobacter concisus UNSWCD, Helicobacter pylori HP260ASii, Helicobacter pylori HP260BFii, Helicobacter pylori HP250ASii, Helicobacter pylori HP250BFi, Helicobacter pylori HP250BFii, Helicobacter pylori HP250BFiii, Helicobacter pylori HP250BFiV, Helicobacter pylori HP250BSi, Helicobacter pylori HP260AFi, Helicobacter pylori HP260AFii, Yokenella regensburgei ATCC 43003, Helicobacter pylori Hp P-2b, Helicobacter pylori GAM42Ai, Helicobacter pylori GAM71Ai, Helicobacter pylori GAM268Bii, Helicobacter pylori GAM270ASi, Helicobacter pylori GAM83T, Helicobacter pylori GAM93Bi, Helicobacter pylori GAM80Ai, Helicobacter pylori GAM83Bi, Helicobacter pylori GAM96Ai, Helicobacter pylori GAMchJs106B, Bifidobacterium breve 26M2, Listeria innocua ATCC 33091, Escherichia coli Nissle 1917, Helicobacter pylori Hp A-27, Helicobacter pylori Hp A-26, Clostridioides difficile 70-100-2010, Butyricicoccus pullicaecorum 1.2, Helicobacter pylori Hp H-45, Helicobacter pylori Hp H-44, Helicobacter pylori Hp A-16, Helicobacter pylori Hp A-8, Helicobacter pylori Hp A-6, Klebsiella pneumoniae WGLW5, Klebsiella pneumoniae WGLW3, Proteus mirabilis WGLW6, Bifidobacterium longum 1-6B, Clostridium perfringens WAL-14572, Clostridiales sp. OBRC5-5, Helicobacter pylori Hp H-42, Helicobacter pylori Hp H-29, Helicobacter pylori Hp H-16, Lactobacillus saerimneri 30a, Helicobacter pylori Hp P-26, Helicobacter pylori Hp P-25, Helicobacter pylori Hp P-23, Helicobacter pylori Hp P-16, Helicobacter pylori Hp P-15, Helicobacter pylori Hp P-13, Helicobacter pylori Hp P-11, Helicobacter pylori Hp P-30, Helicobacter pylori Hp H-1, Helicobacter pylori Hp H-3, Helicobacter pylori Hp H-4, Helicobacter pylori Hp H-6, Helicobacter pylori Hp H-9, Helicobacter pylori Hp H-10, Helicobacter pylori Hp H-18, Helicobacter pylori Hp P-11b, Helicobacter pylori Hp P-3b, Helicobacter pylori Hp P-4d, Helicobacter pylori Hp P-4c, Helicobacter pylori Hp P-8b, Helicobacter pylori Hp P-13b, Helicobacter pylori Hp P-11b, Lactobacillus johnsonii pf01 GCA_000219475, Helicobacter pylori Hp A-14, Helicobacter pylori Hp M5, Helicobacter pylori Hp M4, Helicobacter pylori Hp M3, Helicobacter pylori Hp M2, Helicobacter pylori Hp M9, Helicobacter pylori Hp M6, Fusobacterium nucleatum animalis ATCC 51191, Bifidobacterium animalis lactis Bi-07, Listeria monocytogenes SLCC 7179, Cedecea davisae 005, DSM 4568, Corynebacterium sp. HFHOO82, Paenibacillus sp. HGH0039, Coprococcus sp. HPP0048, Coprococcus sp. HPP0074, Streptomyces sp. HGB0020, Paenisporosarcina sp. HGH0030, Prevotella oralis HGA0225, Sutterella wadsworthensis HGA0223, Veillonella sp. HPA0037, Actinomyces sp. HPA0247, Acidaminococcus sp. HPA0509, Streptococcus sp. HPH0090, Bifidobacterium breve HPH0326, Dermabacter sp. HFH0086, Propionibacterium sp. HGH0353, Streptomyces sp. HPH0547, Bifidobacterium bifidum ATCC 29521, Helicobacter pylori GAM117Ai, Enterococcus faecalis V583, Clostridioides difficile CD196, Blautia sp. KLE 1732, Listeria monocytogenes LO28, Listeria monocytogenes FSL J1-208, Enterococcus faecalis V583, Enterococcus asini ATCC 700915, Megasphaera sp. NM10, Streptococcus sp. I-G2, Streptococcus sp. I-P16, Listeria monocytogenes FSL J1-208, Listeria monocytogenes FSL F2-515, Coprobacillus cateniformis D6, Escherichia coli K-12 MG1655star, Campylobacter jejuni jejuni H22082, Listeria monocytogenes sv. 4b Scott A, Mycobacterium avium paratuberculosis CLIJ644, Kocuria rhizophila P7-4, Bifidobacterium breve DPC 6330, Metakosakonia massiliensis JC163, Alistipes senegalensis JC50, Anaerococcus senegalensis JC48, Peptoniphilus senegalensis JC140, Brevibacterium senegalense JC43, Kurthia massiliensis JC30, Bacillus timonensis MM10403188, Paenibacillus senegalensis JC66, Dielma fastidiosa JC118, Senegalimassilia anaerobia JC110, Anaerococcus vaginalis PH9, Peptoniphilus grossensis ph5, Brevibacillus massiliensis phR, Enorma massiliensis phI, Alistipes obesi ph8, Cellulomonas massiliensis JC225, Timonella senegalensis JC301, Noviherbaspirillum massiliense JC206, Bacillus massilioosenegalensis JC6, Bacillus massilioanorexius AP8, Megasphaera massiliensis NP3, Peptoniphilus obesi ph1, Edwardsiella tarda 080813, Edwardsiella tarda ATCC 15947, Mycobacterium avium paratuberculosis Pt139, Mycobacterium avium paratuberculosis Pt144, Mycobacterium avium paratuberculosis Pt145, Mycobacterium avium paratuberculosis Pt146, Mycobacterium avium paratuberculosis Pt154, Mycobacterium avium paratuberculosis Pt155, Mycobacterium avium paratuberculosis Pt164, Mycobacterium avium paratuberculosis CLIJ623, Escherichia coli O104:H4 TY-2482, Mycobacterium avium paratuberculosis CLIJ361, Listeria monocytogenes FSL J2-003, Escherichia coli O104:H4 H112180541, Clostridioides difficile CD37, Oceanobacillus massiliensis Ndiop, Mycobacterium avium paratuberculosis 4B, Holdemania massiliensis AP2, Collinsella massiliensis GD3, Fusobacterium nucleatum subsp. animalis 4_8, Streptococcus anginosus C1051, Streptococcus anginosus C238, Fusobacterium nucleatum vincentii 3_1_36A2, Bacteroides sp. 3_2_5, Oscillibacter sp. 40911, Fusobacterium nucleatum 13_3C, Helicobacter macacae MIT 99-5501, Helicobacter canis NCTC 12740, Cetobacterium somerae ATCC BAA-474, Faecalitalea cylindroides ATCC 27803, Pseudomonas sp. HPB0071, Bifidobacterium breve S27, Listeria monocytogenes sv. 7 SLCC 2482, Vibrio cholerae V51, Vibrio cholerae sv. O37 V52, Listeria monocytogenes sv. 1/2a F6900, Listeria monocytogenes sv. 1/2a J2818, Subdoligranulum variabile DSM 15176, Clostridium sp M62/1, Marvinbryantia formatexigens 1-52, Citrobacter youngae ATCC 29220, Fusobacterium ulcerans 12-1B, Blautia hansenii VPI C7-24, DSM 20583, Providencia rettgeri DSM 1131, Ralstonia sp. 5_2_56FAA, Bacteroides finegoldii DSM 17565, Bifidobacterium angulatum DSM 20098, Bifidobacterium gallicum DSM 20093, LMG 11596, *Bifidobacterium pseudocatenulatum* DSM 20438, JCM 1200, LMG 10505, *Collinsella intestinalis* DSM 13280, *Desulfovibrio* sp. 3_1_syn3, *Enterobacter cancerogenus* ATCC 35316, *Escherichia* sp. 4_1_40B, *Fusobacterium nucleatum* subsp. *animalis* 3_1_33, *Fusobacterium ulcerans* ATCC 49185, *Helicobacter bilis* ATCC 43879, *Listeria grayi* DSM 20601, *Mitsuokella multacida* DSM 20544, *Roseburia intestinalis* L1-82, *Ruminococcus* sp. 5_1_39BFAA, *Erysipelotrichaceae bacterium* 5_2_54FAA, *Enterobacteriaceae bacterium* 9_2_54FAA, *Prevotella copri* CB7, DSM 18205, *Bacteroides* sp. D2, *Bilophila wadsworthia* 3_1_6, *Fusobacterium necrophorum* D12, *Lactobacillus plantarum* ATCC 14917, *Ruminococcaceae bacterium* D16, *Lachnospiraceae bacterium* 3_1_57FAA_CT1, *Lachnospiraceae bacterium* 2_1_46FAA, *Fusobacterium nucleatum vincentii* 3_1_27, *Escherichia coli* O104:H4 GOS1, *Escherichia coli* O104:H4 GOS2, *Aneurinibacillus aneurinilyticus* ATCC 12856, *Fusobacterium nucleatum* CTI-1, *Fusobacterium nucleatum* CTI-2, *Fusobacterium nucleatum* CTI-3, *Providencia alcalifaciens* F90-2004, *Providencia alcalifaciens* 205/92, *Providencia alcalifaciens* R90-1475, *Providencia alcalifaciens* RIMD 1656011, *Providencia alcalifaciens* PAL-1, *Providencia alcalifaciens* PAL-2, *Providencia alcalifaciens* PAL-3, *Klebsiella oxytoca* OK-1, *Klebsiella oxytoca* KA-2, *Coprococcus* sp. ART55/1, *Eubacterium siraeum* V10Sc8a, *Fusobacterium nucleatum* CTI-6, *Fusobacterium nucleatum* CTI-7, *Fusobacterium nucleatum* CTI-5, *Bifidobacterium animalis* RH, *Enterococcus faecalis* 918, *Campylobacter jejuni jejuni* HB93-13, *Ruminococcus bicirculans* 80/3, *Klebsiella oxytoca* KONIH1, *Bifidobacterium longum* BXY01, *Escherichia coli* Nissle 1917, *Serratia marcescens marcescens* db11, *Enorma timonensis* GD5, *Bacteroides salyersiae* WAL 10018, DSM 18765, JCM 12988, *Intestinibacter bartlettii* DSM 16795, *Eubacterium ruminantium* ATCC 17233, *Clostridioides difficile* 630, *Porphyromonas* sp. 31_2, *Klebsiella pneumoniae pneumoniae* KPNIH28, *Bifidobacterium breve* JCM 7019, *Escherichia coli* B7A, *Hafnia alvei* Stuart 32011, ATCC 13337, *Flavonifractor plautii* 1_3_50AFAA, *Collinsella* sp. 4_8_47FAA, *Shigella flexneri* 2003036 (contamination screened), *Shigella flexneri* Shi06HN006 (contamination screened), *Salmonella enterica enterica* sv. *typhimurium* ATCC 13311, *Vibrio cholerae* sv. O1 bv. El Tor MAK676, *Ruminococcus callidus* ATCC 27760, *Lachnoclostridium symbiosum* ATCC 14940, *Clostridium* sp. ATCC BAA-442, *Eubacterium ramulus* VPI C6-27, ATCC 29099, *Lactobacillus brevis* ATCC 14869, *Marvinbryantia formatexigens* 1-52, *Clostridium* sp. VPI C48-50, *Oscillibacter* sp. KLE 1728, *Oscillibacter* sp. KLE 1745, *Clostridium* sp. KLE 1755, *Clostridium ihumii* AP5, *Corynebacterium ihumii* GD7, *Escherichia albertii* GTC 14781, *Nesterenkonia massiliensis* NP1, *Clostridium bolteae* WAL-14578 JGI Assembly and Annotation, *Bacteroides neonati* MS4, *Bacteroides xylanisolvens* SD CC 1b, *Gorillibacterium massiliense* G5, *Vibrio cholerae* sv. O1 bv. El Tor 5/66, *Helicobacter heilmannii* ASB 1.4, *Peptoniphilus timonensis* JC401, *Akkermansia muciniphila* ATCC BAA-835, *Clostridium saudiense* JCC, *Clostridium jeddahense* JCD, *Eggerthella lenta* 1_1_60AFAA, *Parabacteroides* sp. HGS0025, *Parabacteroides goldsteinii* WAL 12034, *Clostridiales* sp. SM4/1, *Corynebacterium ammoniagenes* DSM 20306 Genome sequencing, *Bacteroides cellulosilyticus* WH2, *Lactobacillus casei casei* ATCC 393, *Bacteroides* sp. 3_1_13, *Klebsiella oxytoca* 09-7231, *Parabacteroides* sp. D26, *Lachnoclostridium citroniae* WAL-19142, *Coprobacillus* sp. 8_1_38FAA, *Vibrio cholerae* sv. O14 MZO-2, *Aeromicrobium massiliense* JC14, *Dorea* sp. D27, *Klebsiella oxytoca* 10-5244, *Bacteroides eggerthii* 1_2_48FAA, *Escherichia coli* ST540an, *Lachnoclostridium clostridioforme* WAL-7855, *Clostridium* sp. 1_1_41A1FAA, *Escherichia coli* ST540a, *Escherichia coli* ST2747, *Fusobacterium nucleatum animalis* 7_1, *Eubacterium* sp. 3_1_31, *Bifidobacterium bifidum* NCIMB 41171, *Fusobacterium nucleatum* subsp. *animalis* 21_1A, *Helicobacter pylori* J99, *Lactobacillus antri* DSM 16041, *Lactobacillus amylolyticus* DSM 11664, *Vibrio fluvialis* NBRC 103150, *Bacteroides ovatus* ATCC 8483, *Bacteroides clarus* DSM 22519, *Lactobacillus ultunensis* DSM 16047, *Bifidobacterium angulatum* DSM 20098, *Vibrio cholerae* ZWU0020, *Escherichia coli* D9, *Bifidobacterium breve* DSM 20213, JCM 1192, *Coprobacillus cateniformis* JCM 10604, *Ruminococcus faecis* JCM 15917, *Dielma fastidiosa* DSM 26099, *Blautia hansenii* DSM 20583, *Citrobacter portucalensis* 30_2, *Oxalobacter formigenes* OXCC13, bacterium MS4, bacterium OL-1, *Akkermansia* sp. KLE1605, *Clostridium* sp. CL-2, *Clostridium amazonitimonense* LF2, *Bacillus andreraoultii* KW-12, *Helicobacter pylori* B508A-T4, *Flavonifractor plautii* DSM 6740, *Pantoea septica* LMG 5345, *Helicobacter canadensis* MIT 98-5491, ATCC 700968, *Bacteroides caccae* ATCC 43185, *Fusobacterium mortiferum* ATCC 9817, *Fusobacterium gonidiaformans* ATCC 25563, *Fusobacterium ulcerans* ATCC 49185, *Blautia* sp. Marseille-P2398, *Ruminococcus albus*, *Clostridium* sp. CAG:413, *Lachnospiraceae* str. KH1P17, *Blautia* sp. An81, *Blautia wexlerae*, *Lachnospiraceae* str. LC2019, *Ruminococcus* sp. CAG:488, *Clostridium* sp. L2-50, and *Clostridium* sp. CAG:253.

Acyl Carrier Protein (ACP)

Acyl carrier proteins (ACPs or T proteins) comprise a 4'-phosphopantetheine moiety and are capable of catalyzing the addition of a thioester to the phosphopantetheine moiety. The 4'-phosphopantetheine moiety may be post-translationally added to a serine residue on an ACP by a 4'-phosphopantetheinyl transferase (PPTase). Non-limiting examples of 4'-phosphopantetheinyl transferases include Sfp (e.g., UniProtKB-P39135 (SFP_BACSU)).

In some instances, an ACP comprises a sequence that has at least 50% (e.g., at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity with an ACP sequence shown in Table 1.

Figure 12:
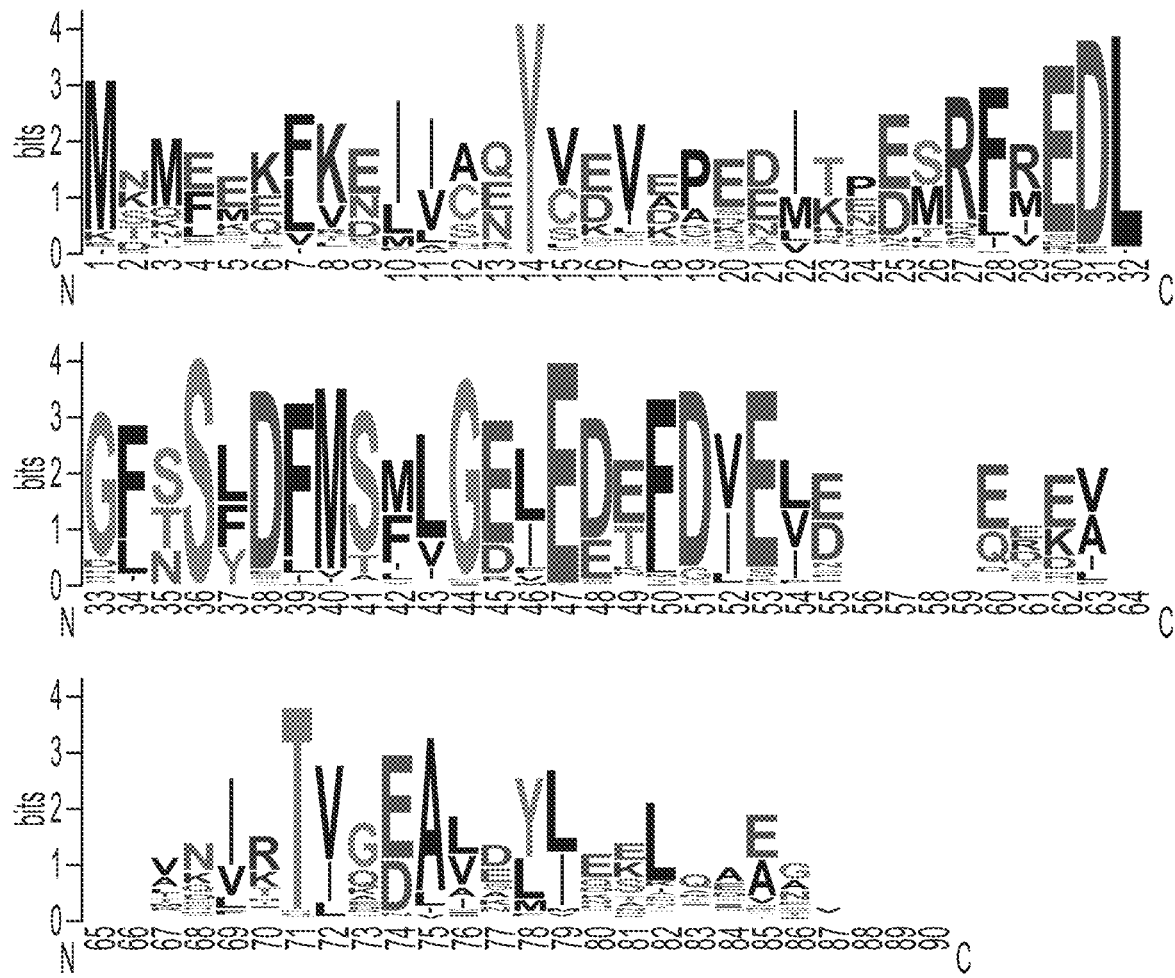
FIG. 12 shows a non-limiting example of an acyl carrier protein (ACP or T protein) sequence logo. The sequence logo was created using WebLogo. See, e.g., Crooks et al., Genome Research, 14:1188-1190, (2004); Schneider et al., Nucleic Acids Res. 18:6097-6100 (1990).
Figure 13A:
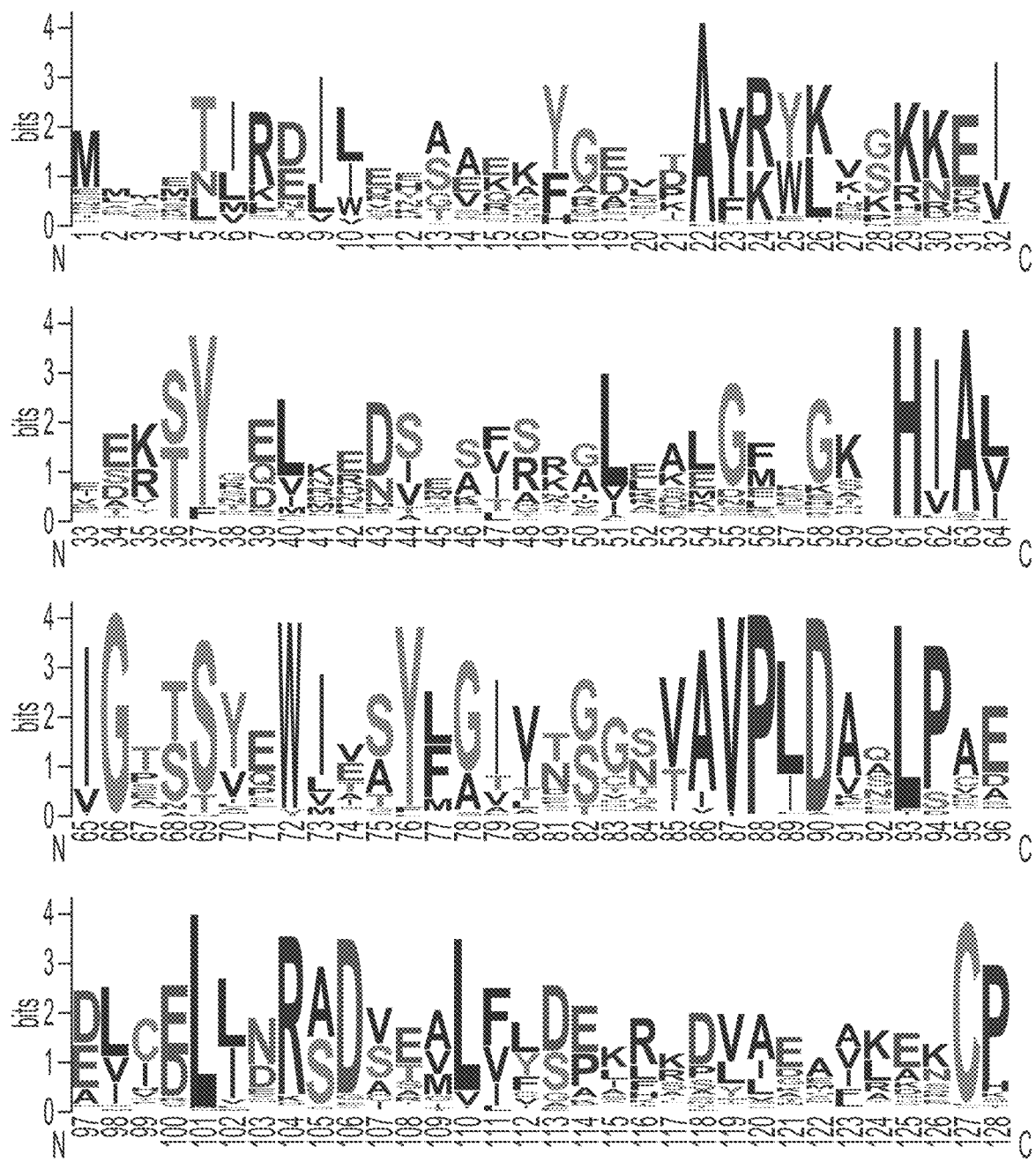
FIGS. 13A-13D show a non-limiting example of a fatty acyl-ACP synthetase (A protein) sequence logo. The sequence logo was created using WebLogo. See, e.g., Crooks et al., Genome Research, 14:1188-1190, (2004); Schneider et al., Nucleic Acids Res. 18:6097-6100 (1990).
Figure 13B:
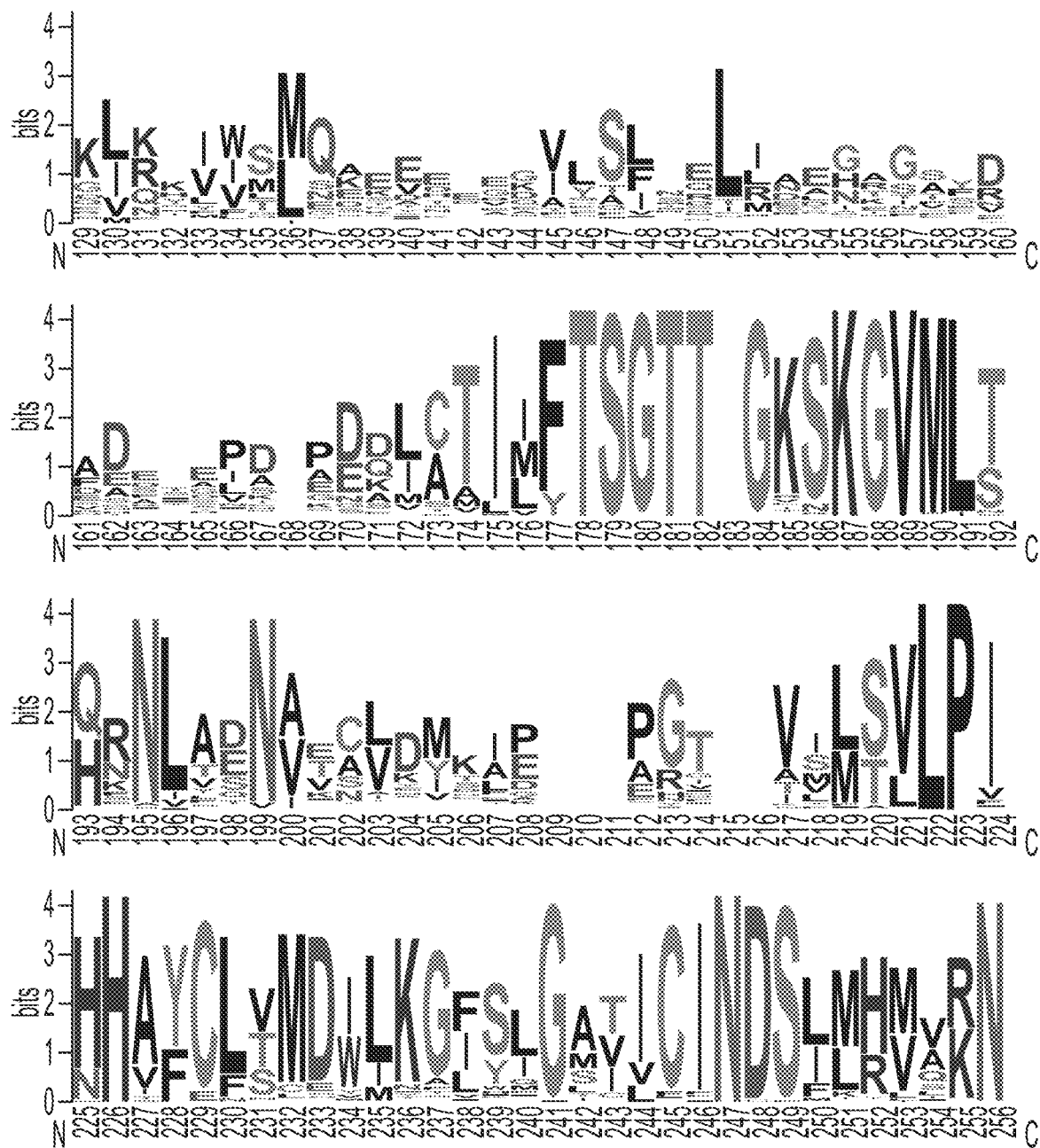
Figure 13C:
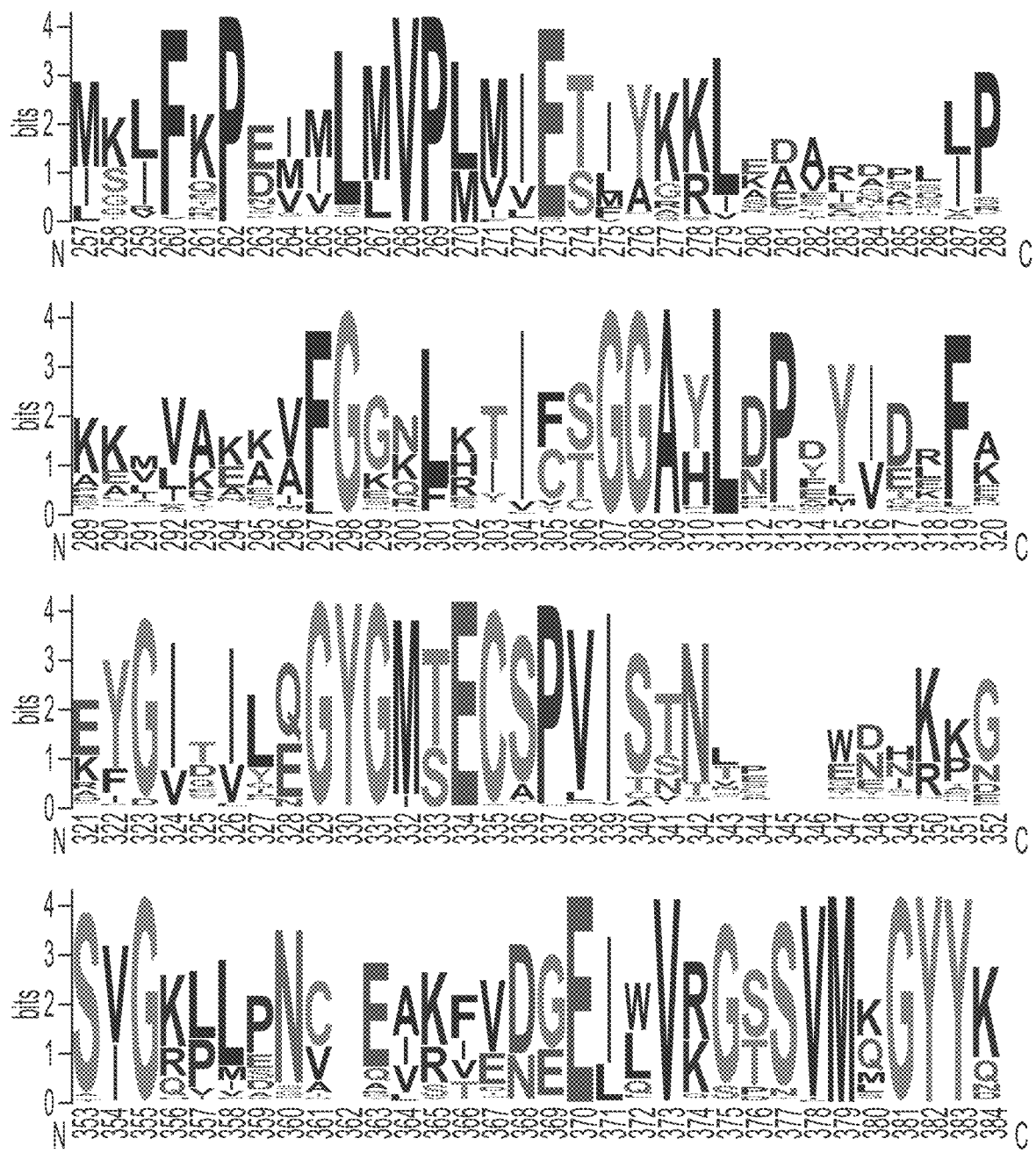
Figure 13D:
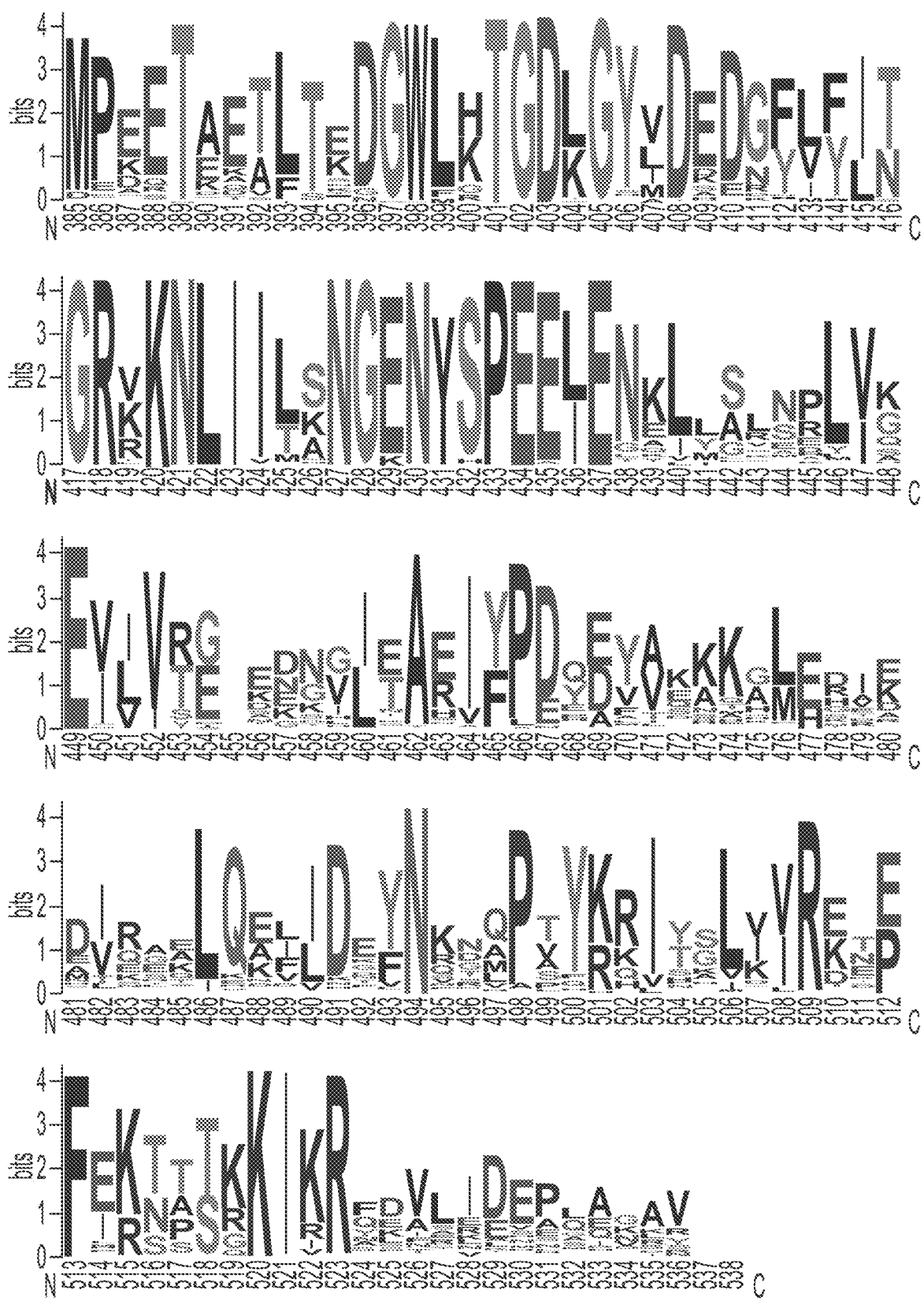
Figure 14A:
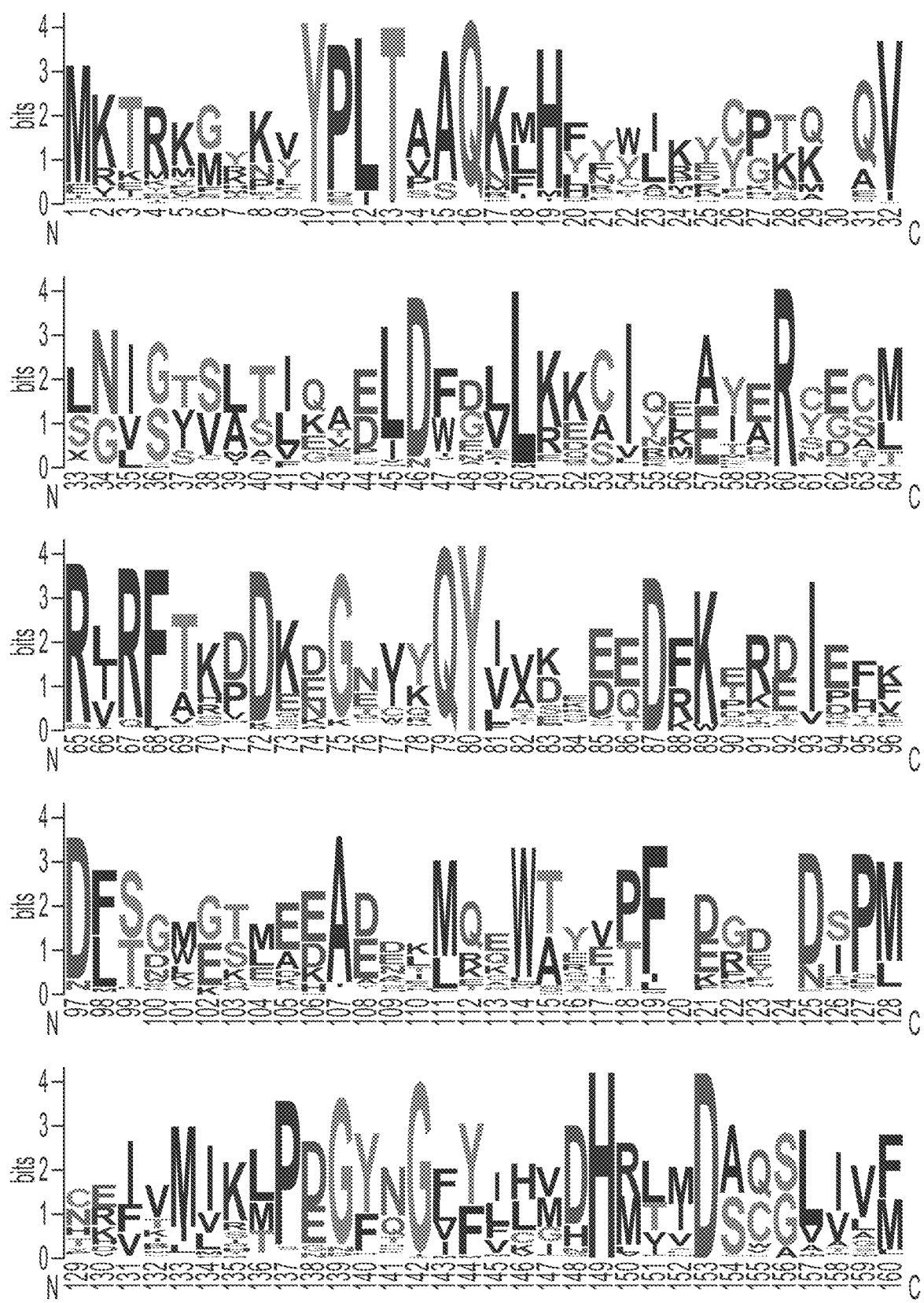
FIGS. 14A-14D show a non-limiting example of a fatty acyl-transferase (C protein) sequence logo. The sequence logo was created using WebLogo. See, e.g., Crooks et al., Genome Research, 14:1188-1190, (2004); Schneider et al., Nucleic Acids Res. 18:6097-6100 (1990).
Figure 14B:
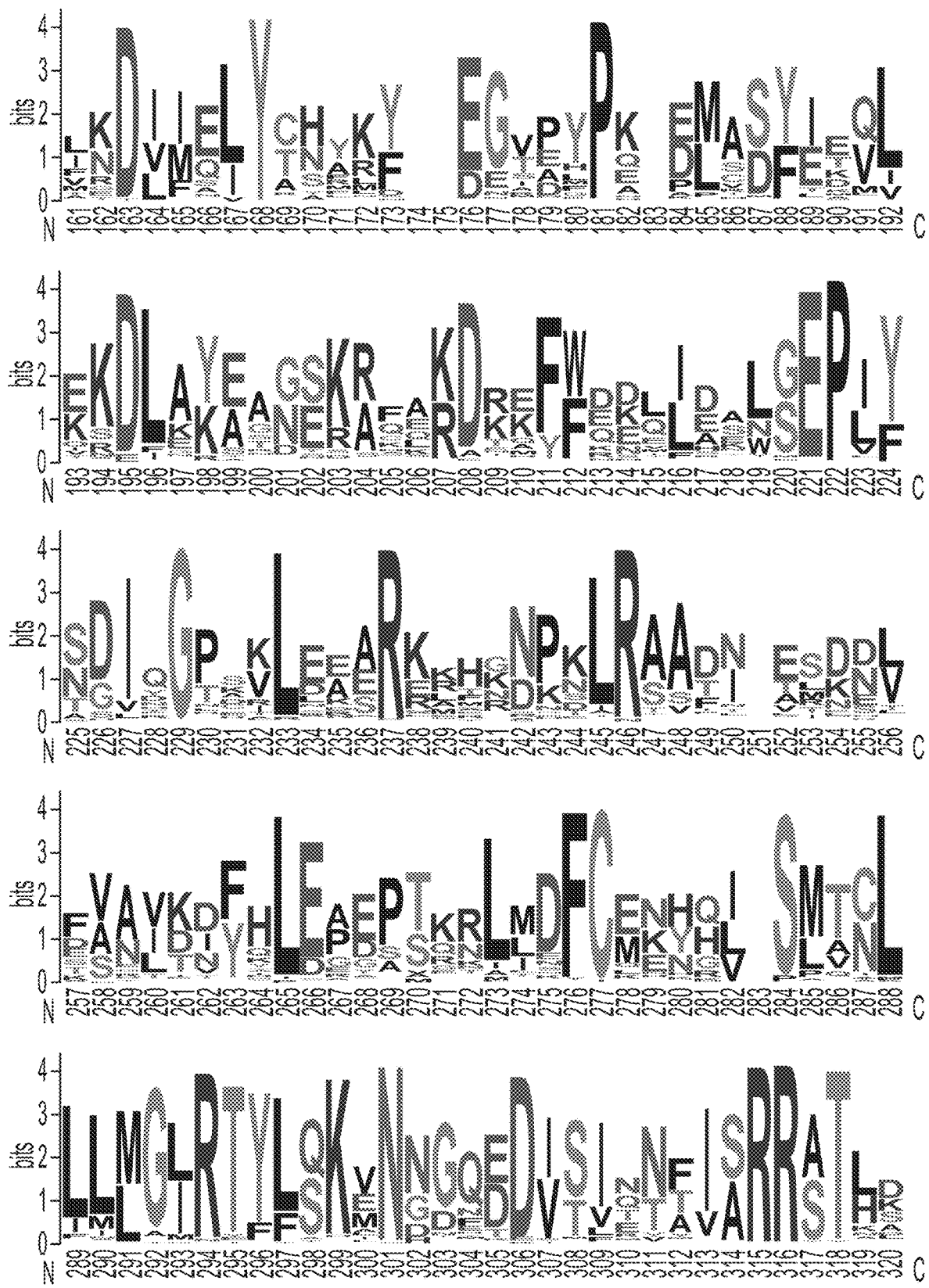
Figure 14C:
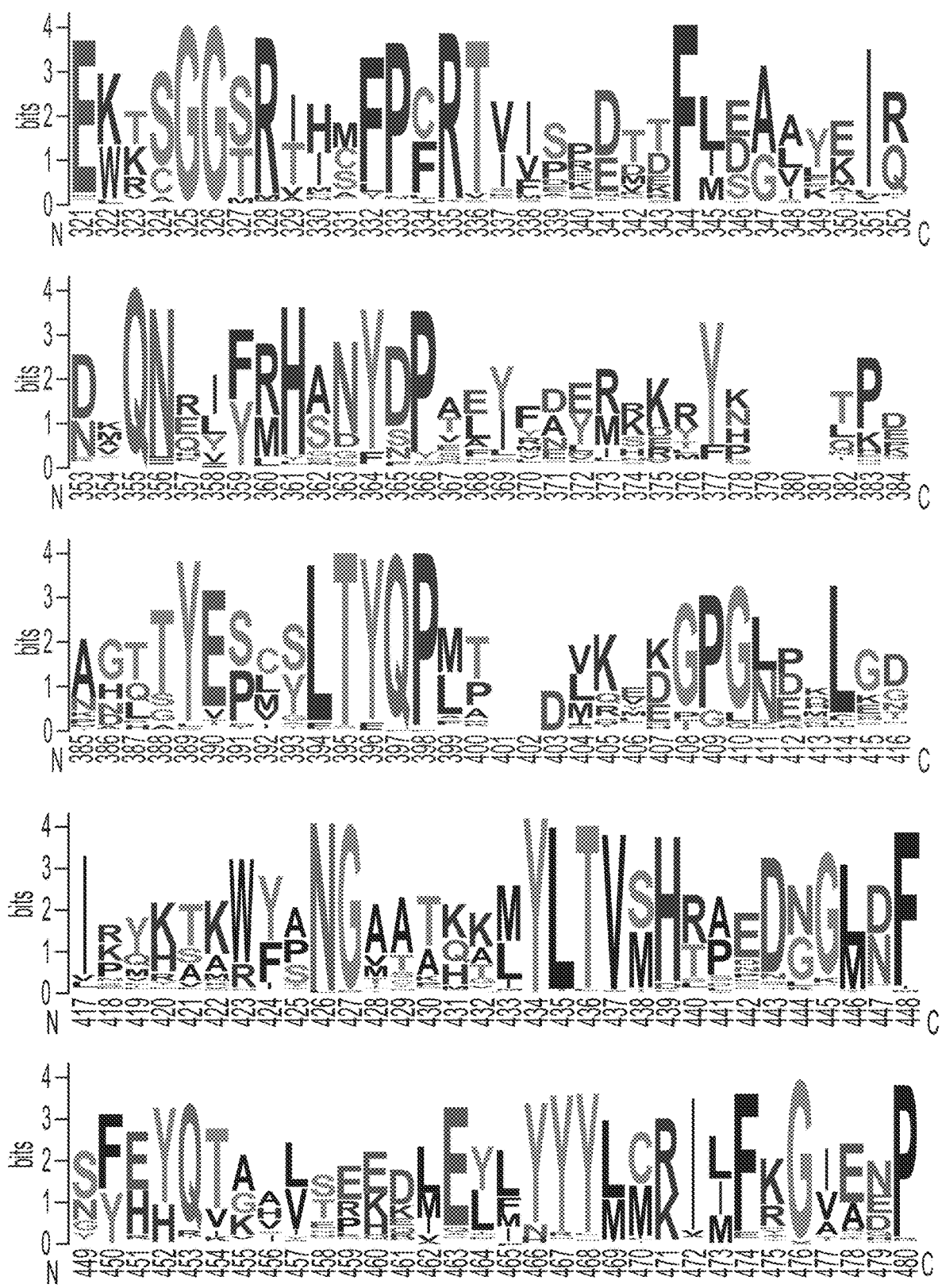
Figure 14D:
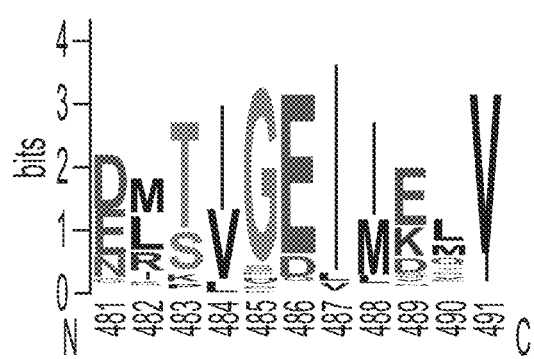

A non-limiting example of a sequence logo for ACP proteins is shown in FIG. 12.

Fatty Acyl-ACP Synthetase

As used herein, fatty acyl-ACP synthetases or A proteins are capable of conjugating a fatty acid substrate onto an acyl carrier protein (ACP). The fatty acid substrate may be endogenous or exogenous to a host cell or composition (e.g., cell lysate or cell culture broth). A fatty acyl-ACP synthetase may use any type of fatty acid. For example, a fatty acyl-ACP synthetase may use a medium-chain fatty acid or a long-chain fatty acid as a substrate.

Fatty acyl-ACP synthetases use ATP to catalyze the production of fatty acyl-ACPs. The activity of a fatty acyl-ACP synthetase activity may be measured using suitable method known in the art or described in the Examples section below. ATP consumption by a fatty acyl-ACP synthetase may be measured using an in vitro assay. For example, 2-amino-6- mercapto-7-methylpurine riboside (MESG) substrate, which is converted to ribose 1-phosphate and 2-amino-6-mercapto-7-methylpurine product in the presence of inorganic phosphate purine nucleoside phosphorylase (PNP) enzyme, can be used to determine the amount of ATP consumed by a fatty acyl-ACP synthetase in the presence of a fatty acid substrate.

In some instances, a fatty acyl-ACP synthetase comprises a sequence that has at least 50% (e.g., at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity with a fatty acyl-ACP synthetase sequence shown in Table 1

A non-limiting example of a sequence logo for fatty acyl-ACP synthetases (A proteins) is shown in FIGS. 13A-13D.

Fatty Acids

Fatty acids are carboxylic acids with aliphatic chains. They can be classified as either saturated or unsaturated. Saturated fatty acids do not have double bonds in their aliphatic chain and have the formula $CH_3(CH_2)_nCOOH$, where C is carbon, H is hydrogen, O is oxygen, and n is any non-negative integer (e.g., n may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100 or higher, including any values in between). In contrast, unsaturated fatty acids have at least one double bond in their aliphatic chain, resulting in either a cis (hydrogen atoms on the same side of the double bond) or trans hydrogen configuration.

Fatty acids may also be classified by length. Short-chain fatty acids (SCFAs) have aliphatic chains of up to 5 carbons. Medium-chain fatty acids (MCFAs) have aliphatic chains of 6 to 12 carbons (e.g., 6 carbons, 7 carbons, 8 carbons, 9 carbons, 10 carbons, 11 carbons, 12 carbons, 6 to 8 carbons, 6 to 9 carbons, 6 to 10 carbons, 6 to 11 carbons, 7 to 9 carbons, 7 to 10 carbons, 7 to 11 carbons, 7 to 12 carbons, 8 to 10 carbons, 8 to 11 carbons, 8 and 12 carbons, 9 to 11 carbons, 9 to 12 carbons, or 10 to 12 carbons), inclusive. MCFAs include hexanoic acid, octanoic acid, decanoic acid, and dodecanoic acid. Long-chain fatty acids (LCFAs) have aliphatic chains ranging from 13 to 21 carbons (e.g., 13 carbons, 14 carbons, 15 carbons, 16 carbons, 17 carbons, 18 carbons, 19 carbons, 20 carbons, 21 carbons, or 15 to 20 carbons), inclusive. Non-limiting examples of LCFAs include oleic acid, palmitoleic acid, and nervonic acid. Very long chain fatty acids (VLCFAs) comprise aliphatic chains of 22 or more carbons (e.g., at least 23, at least 25, at least 30, at least 35, at least 40, at least 50, at least 60, at least 70, at least 80, at least 90, or at least 100, including all values in between). Non-limiting examples of VLCFAs include lignoceric acid and hexacosanoic acid. Most naturally-occurring fatty acids have unbranched aliphatic chains and have an even number of carbons.

In some embodiments, a fatty acid comprises a straight-chain alkyl chain. In some embodiments, the straight-chain alkyl chain comprises 10-12 carbons.

In some embodiments, a fatty acid comprises a cis-9 double bond.

A fatty acid may be a free fatty acid. A free fatty acid is a non-esterified fatty acid (NEFA).

Non-limiting examples of fatty acids include acetic acid, propionic acid, butyric acid, valeric acid, hexanoic acid, octanoic acid, capric acid, lauric acid, myristic acid, pentadecanoic acid, palmitic acid, stearic acid, arachidic acid, iso-pentadecanoic acid, palmitoleic acid, oleic acid, vaccenic acid, linoleic acid, γ-linolenic acid, α-linolenic acid, dihomo-γ-linolenic acid, arachidonic acid, eicosapentaenoic acid, docosapentaenoic acid, docosahexaenoic acid, 8-methyl-6-nonenoic acid, octynoic acid, myristic acid alkyne, and palmitic acid alkyne. See, e.g., Table 3.

A fatty acid may be exogenous or endogenous in reference to a host cell or a composition. As used herein an exogenous fatty acid refers to a fatty acid that is introduced. The exogenous fatty acid may be a fatty acid that is introduced to a host cell or added to a composition (e.g., a cell culture broth or cell lysate). In some instances, the host cell is a *bacterium* (e.g., *Escherichia coli*). An exogenous fatty acid may be derived from another cell or produced synthetically. As a non-limiting example, a host cell may naturally produce a particular fatty acid but the same fatty acid may be derived from an exogenous source and the exogenous fatty acid may be introduced to the cell. In some embodiments, an exogenous fatty acid is not naturally produced by a host cell.

In some embodiments, an exogenous fatty acid is acetic acid, propionic acid, butyric acid, valeric acid, hexanoic acid, octanoic acid, capric acid, lauric acid, myristic acid, pentadecanoic acid, palmitic acid, stearic acid, arachidic acid, iso-pentadecanoic acid, palmitoleic acid, oleic acid, vaccenic acid, linoleic acid, γ-linolenic acid, α-linolenic acid, dihomo-γ-linolenic acid, arachidonic acid, eicosapentaenoic acid, docosapentaenoic acid, docosahexaenoic acid, 8-methyl-6-nonenoic acid, octynoic acid, myristic acid alkyne, or palmitic acid alkyne. See, e.g., Table 3.

In contrast, an endogenous fatty acid refers to a fatty acid that is present in a host cell or composition (e.g. a cell lystate or a cell culture broth). In some embodiments, an endogenous fatty acid is acetic acid, propionic acid, butyric acid, valeric acid, hexanoic acid, octanoic acid, capric acid, lauric acid, myristic acid, pentadecanoic acid, palmitic acid, stearic acid, arachidic acid, iso-pentadecanoic acid, palmitoleic acid, oleic acid, vaccenic acid, linoleic acid, γ-linolenic acid, α-linolenic acid, dihomo-γ-linolenic acid, arachidonic acid, eicosapentaenoic acid, docosapentaenoic acid, docosahexaenoic acid, 8-methyl-6-nonenoic acid, octynoic acid, myristic acid alkyne, or palmitic acid alkyne. See, e.g., Table 3.

Fatty Acyl-Transferases

The fatty acyl-transferases of the present disclosure are capable of conjugating an amine to a thiotemplated fatty acid (e.g., a fatty acyl-ACP) to produce a fatty acid amide and may be referred to as C proteins. The amine may be endogenous or exogenous to a host cell or composition (e.g., cell lysate or cell culture broth).

In some instances, a fatty acyl-transferase comprises a sequence that has at least 50% (e.g., at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%) sequence identity with a fatty acyl-transferase sequence shown in Table 1.

FIGS. 14A-14D show a non-limiting example of a fatty acyl-transferase (C protein) sequence logo.

Amines

Amines are derivatives of ammonia, wherein one or more of the hydrogen atoms have been replaced with a substituent group (R group). Non-limiting examples of amines include phenylalanine, tryptophan, tyrosine, histidine, lysine, glycine, alanine, valine, leucine, isoleucine, methionine, proline, serine, threonine, cysteine, asparagine, glutamine, aspartic acid, glutamic acid, arginine, ornithine, β-alanine, L-DOPA, creatine, citrulline, phenylacetylglutamine, phenylethylamine, tryptamine, tyramine, histamine, serotonin, dopamine, epinephrine, norepinephrine, γ-aminobutyric acid (GABA), aminovaleric acid, ethanolamine, cadaverine, putrescine, spermine, spermidine, agmatine, propylamine, butylamine, dimethylamine, pyrollidine, piperidine, homocysteine, cysteamine, homocysteamine, taurine, hypotaurine, glutathione, octopamine, 3-iodothyronamine, melatonin, and vanillylamide. See, e.g., Table 3.

An amine may be endogenous or exogenous to a host cell or a composition. As used herein an exogenous amine refers to an amine that is introduced. The exogenous amine may be an amine that is introduced to a host cell or added to a composition (e.g., a cell culture broth or cell lysate). In some instances, the host cell is a *bacterium* (e.g., *Escherichia coli*). An exogenous amine may be derived from another cell or produced synthetically. As a non-limiting example, a host cell may naturally produce a particular amine but the same amine may be derived from an exogenous source and the exogenous amine may be introduced to the cell. In some instances, an exogenous amine is not naturally produced by a particular host cell.

Variants

Variants of the sequences (e.g., biosynthetic enzymes), including nucleic acid or amino acid sequences described herein are also encompassed by the present disclosure. A variant may share at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with a reference sequence, including all values in between. Sequence identity to a particular reference sequence may be determined by sequence alignment programs and parameters described herein and known to those skilled in the art.

The comparison of sequences and determination of percent identity between two sequences can be accomplished using a mathematical algorithm. Techniques for determining identity are codified in publicly available computer programs. Exemplary computer software to determine homology between two sequences include, but are not limited to, the GCG program package (Devereux, J. et al. Nucleic Acids Research, 12(1): 387, 1984), the BLAST suite (Altschul, S. F. et al. Nucleic Acids Res. 25: 3389, 1997), and FASTA (Altschul, S. F. et al. J. Molec. Biol. 215: 403, 1990). Other techniques include: the Smith-Waterman algorithm (Smith, T. F. et al. J. Mol. Biol. 147: 195, 1981); the Needleman-Wunsch algorithm (Needleman, S. B. et al. J. Mol. Biol. 48: 443, 1970); and the Fast Optimal Global Sequence Alignment Algorithm (FOGSAA) (Chakraborty, A. et al. Sci Rep. 3: 1746, 2013).

In some instances, a biosynthetic enzyme comprises a conservative amino acid substitution relative to a reference sequence disclosed herein. A conservative amino acid substitution is an amino acid substitution that does not alter the relative charge or size characteristics of the protein or peptide in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Variants can be prepared according to methods for altering polypeptide sequences known to one of ordinary skill in the art such as those are found in references that compile such methods (see, e.g., Current Protocols in Molecular Biology, Ausubel, F. M., et al., New York: John Wiley & Sons, 2006; Molecular Cloning: A Laboratory Manual, Green, M. R. and Sambrook J., New York: Cold Spring Harbor Laboratory Press, 2012; Gibson, D. G., et al., Nature Methods 6(5):343-345 (2009), the teachings of which relating to polypeptide preparation and modifications are herein incorporated by reference).

As a non-limiting example, any of the biosynthetic enzymes may be from one of the homologous pathways listed in Table 4.

TABLE 4

Homologous pathways in non-redundant database

| NCBI Protein Accession | NCBI taxonomy ID |
|---|---|
| WP_062807977 | 1805476 |
| WP_074960409 | 1264 |
| OKZ85230 | 1896982 |
| SKB82813 | 1898203 |
| OUN25501 | 1965659 |
| OUN90421 | 1965636 |
| WP_094177321 | 1898203 |
| CDA18795 | 1262959 |
| CDA90273 | 1262961 |
| CDB75482 | 1262787 |
| CDC11311 | 1262803 |
| WP_022756671 | 1280697 |
| CDM68196 | 1216932 |
| WP_025485643 | 2302989 |
| WP_026649047 | 418240 |
| WP_027640220 | 1280692 |
| WP_044914561 | 1410611 |
| WP_055272765 | 411474 |
| ANU46418 | 1834196 |
| ANU76734 | 1796616 |
| SCH92732 | 458253 |
| SCG94715 | 165186 |
| SCH24189 | 765821 |
| SCH04233 | 765821 |
| SCH67917 | 765821 |
| SCH34388 | 765821 |
| SCZ76358 | 185007 |
| SDB30726 | 1520802 |
| SDL46385 | 1798184 |
| SEA64537 | 1520801 |
| SEF93625 | 42322 |
| SEQ03931 | 1520823 |
| SEK99881 | 1264 |
| SES30790 | 831 |
| SET14983 | 1531 |
| SFO23886 | 1798185 |
| SFI12108 | 1798186 |
| SFB96813 | 1520812 |
| SHJ66668 | 1123012 |
| SHI22409 | 1121131 |
| OKZ58607 | 1897047 |
| OKZ60972 | 1897043 |
| OKZ92810 | 1896997 |
| OLA73747 | 1897018 |
| OLR60781 | 1261634 |
| OUO80577 | 1965603 |
| WP_090167850 | 1855344 |
| WP_092045784 | 1520809 |
| EDO56526 | 411489 |
| EDP17324 | 411902 |

TABLE 4-continued

Homologous pathways in non-redundant database

| NCBI Protein Accession | NCBI taxonomy ID |
|---|---|
| EDP26494 | 411474 |
| ACR74791 | 515619 |
| EEQ58445 | 457421 |
| EES76357 | 457412 |
| EET59992 | 478749 |
| CBK73404 | 657324 |
| CBK91081 | 657318 |
| CBK93983 | 657317 |
| CBL27452 | 657313 |
| CBK83162 | 751585 |
| EGJ47862 | 552398 |
| EHE97033 | 742733 |
| EHI58297 | 742737 |
| EIM58172 | 633697 |
| EMZ25486 | 97139 |
| EMZ37363 | 1235802 |
| ENZ16072 | 999407 |
| ENZ39981 | 997895 |
| ENZ45351 | 997897 |
| ENZ53889 | 997893 |
| EOS27406 | 397291 |
| EOS40633 | 1235792 |
| EOS45712 | 1235793 |
| WP_018593829 | 1121114 |
| WP_019162631 | 1095771 |
| CDC16546 | 1262960 |
| CCX97935 | 1263064 |
| CCY31720 | 1262964 |
| CCY60264 | 1262786 |
| CDA26009 | 1262943 |
| CDB64527 | 1263065 |
| CDB78847 | 1262862 |
| CDB88948 | 1262785 |
| CDC71196 | 1263079 |
| CDE70434 | 1262790 |
| WP_022754580 | 1280696 |
| WP_022779847 | 1280666 |
| EXM39836 | 1341156 |
| WP_027293796 | 1469950 |
| WP_027641883 | 742735 |
| WP_027870868 | 1408436 |
| WP_028528860 | 438033 |
| WP_029470012 | 1232442 |
| KJJ68302 | 1609975 |
| KLU70291 | 1504536 |
| KMW11489 | 742736 |
| KMW19636 | 742734 |
| CUQ71892 | 33039 |
| CUQ85104 | 33039 |
| CUM73550 | 33043 |
| CUN43486 | 33043 |
| CUN74017 | 33043 |
| CUN93414 | 40520 |
| CUN00699 | 39491 |
| CUO54074 | 40520 |
| CUP17825 | 40520 |
| CUN52161 | 418240 |
| CUO37617 | 40520 |
| CUQ02385 | 40520 |
| CUO14476 | 1531 |
| CUN26274 | 33039 |
| CUN05905 | 33039 |
| CUQ58744 | 33039 |
| CRL34458 | 39491 |
| CUX73241 | 1776046 |
| SCI93813 | 59620 |
| SCJ94142 | 59620 |
| WP_066544197 | 1720194 |
| SDA29827 | 1352374 |
| EDM89219 | 411459 |
| EKY22234 | 545697 |
| WP_024856059 | 1264 |
| WP_029321096 | 1506994 |
| WP_033141306 | 33035 |
| WP_044919162 | 1408323 |
| SDI83657 | 398199 |
| SFN28053 | 398199 |
| WP_089973574 | 1855374 |
| WP_095171663 | 2025493 |
| WP_034230866 | 1458462 |
| WP_035627896 | 1410622 |
| WP_093041603 | 1520817 |
| OLA15608 | 1897003 |
| WP_087175350 | 1965547 |
| WP_070040448 | 180332 |
| WP_033126296 | 1519438 |
| OUO28396 | 1965627 |
| OUP49472 | 1965575 |
| OUP66376 | 1965573 |
| WP_087160604 | 1965569 |
| OKZ83901 | 1896984 |
| WP_087154053 | 1965583 |
| WP_087163958 | 1965555 |
| OUP03257 | 1965589 |
| OUN34155 | 1965654 |
| WP_070088698 | 1653435 |
| WP_055157043 | 33039 |
| WP_044292898 | 180332 |

Vectors

Provided herein, in some embodiments, are vectors encoding human gut microbiome-derived bacterium genes involved in biosynthesis. In some embodiments, a vector encodes at least one human gut microbiome-derived bacterium gene selected from a fatty acyl transferase, an acyl carrier protein, and a fatty acyl-ACP synthetase. In some embodiments, a vector encodes at least two human gut microbiome-derived bacterium genes selected from a fatty acyl transferase, an acyl carrier protein, and a fatty acyl-ACP synthetase. In some embodiments, a vector encodes at least three human gut microbiome-derived bacterium genes selected from a fatty acyl transferase, an acyl carrier protein, and a fatty acyl-ACP synthetase. A vector may further encode a hydrolase, a lipid transfer protein, a glycosyltransferase, or any combination thereof.

In some embodiments, a vector comprises an open reading frame encoding at least one biosynthetic enzyme. An open reading frame is a nucleic acid sequence that is transcribed continuously into an mRNA molecule, and then translated continuously into an amino acid sequence, uninterrupted by stop codons. The translated open reading frame may be all or a portion of a gene encoding a protein or polypeptide.

The vectors comprise at least one regulatory element controlling expression of at least one biosynthetic gene from a human gut microbiome-derived bacterium. The regulatory element may be a promoter. In some instances, all biosynthetic genes in a vector are in a single operon and are regulated by one regulatory element. In some instances, at least 2, 3, 4, 5, 6, 7, 8, 9, 10, or more biosynthetic genes in a vector are in a single operon and are regulated by one regulatory element. A vector may comprise 1, 2, 3, 4, 5, 6, 7, 8, 9, 10, or more operons.

For example, a vector may comprise at least one promoter operably linked to a nucleic acid encoding a fatty acyl transferase, an acyl carrier protein, a fatty acyl-ACP synthetase, or any combination thereof. In some embodiments, a vector comprises one promoter operably linked to a nucleic acid encoding a human gut microbiome-derived bacterium fatty acyl transferase, a human gut microbiome-derived bacterium acyl carrier protein, and a human gut microbiome-derived bacterium fatty acyl-ACP synthetase. In some embodiments, nucleic acids encoding the fatty acyl transferase, the acyl carrier protein, and the fatty acyl-ACP synthetase are each operably linked to a separate promoter in a vector.

A vector may comprise a nucleic acid encoding a biosynthetic enzyme from a human gut microbiome-derived bacterium, and the nucleic acid may be codon optimized for heterologous expression in a host cell. For example, the nucleic acid may be codon optimized for expression in an *E. coli* host cell. A codon usage database may be used to improve expression of a heterologous sequence in a host cell. See, e.g., Gustafsson et al., Trends Biotechnol. 2004 July; 22(7):346-53.

A promoter is a control region of a nucleic acid sequence through which initiation and rate of transcription of the remainder of a nucleic acid sequence are controlled. A promoter may also contain sub-regions at which regulatory proteins and molecules, such as RNA polymerase and other transcription factors, may bind. A promoter drives expression or drives transcription of the nucleic acid sequence that it regulates. A promoter is considered to be "operably linked" to a nucleotide sequence when it is in a correct functional location and orientation in relation to the nucleotide sequence to control ("drive") transcriptional initiation and/or expression of that sequence. Promoters may be constitutive or inducible. An inducible promoter is a promoter that is regulated (e.g., activated or inactivated) by the presence or absence of a particular factor.

Inducible promoters for use in accordance with the present disclosure include those that function in bacteria. An exemplary inducible promoter for use herein is an isopropyl β-D-1-thiogalactopyranoside (IPTG)-inducible promoter or a tetracycline-inducible promoter (e.g., when used with a reverse tetracycline-controlled transactivator (rtTA)). In some embodiments, the IPTG-inducible promoter is an inducible T7 promoter. The vector may further encode a lac repressor (LacI).

In some embodiments, a vector may encode a repressible promoter, which inactivates expression of an operably linked nucleic acid in the presence of a factor. For example, a tetracycline-sensitive promoter may be used with a tetracycline-controlled transactivator (tTA), such that in the presence of tetracycline, the tTA binds to the tetracycline-sensitive promoter and prevents expression of the operably linked nucleic acid.

In some embodiments, a vector further encodes a selection marker. Suitable selection markers include antibiotic resistance genes (e.g., genes encoding resistance to kanamaycin, spectinomycin, ampicillin, carbenicillin, bleomycin, chloramphenicol, coumermycin, gentamycin, tetracycline, or any combination thereof).

In some instances, a vector encodes a ribosomal binding site (RBS). Ribosomal binding sites promote ribosomal recruitment during initiation of protein translation and are located upstream of a start codon. In prokaryotes, the RBS may be referred to as a Shine-Dalgarno sequence. A RBS sequence may comprise AGGAGG. As a non-limiting example, a RBS for use in *E. coli* may comprise the sequence AGGAGGU.

Examples of vectors for expressing include, but are not limited to, plasmids, phagemids and bacterial artificial chromosomes (BACs). The vectors of the present disclosure may be generated using standard molecular cloning methods (see, e.g., Current Protocols in Molecular Biology, Ausubel, F. M., et al., New York: John Wiley & Sons, 2006; Molecular Cloning: A Laboratory Manual, Green, M. R. and Sambrook J., New York: Cold Spring Harbor Laboratory Press, 2012; Gibson, D. G., et al., Nature Methods 6(5):343-345 (2009), the teachings of which relating to molecular cloning are herein incorporated by reference).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Engineered Cells

Any of the vectors described herein may be introduced into a host cell to produce an engineered cell using routine methods known in the art. An engineered cell comprises at least one engineered nucleic acid or is otherwise structurally or functionally distinct from a wildtype counterpart. Thus, a host cell comprising a vector encoding at least one biosynthetic enzyme that is from a human gut microbiome-derived bacterium is considered an engineered cell. In some instances, an engineered cell comprises at least three human gut microbiome-derived bacterium biosynthetic enzymes, including a fatty-acyl transferase, an acyl carrier protein synthase, and a fatty acyl-ACP synthetase. In some instances, all three enzymes (a fatty-acyl transferase, an acyl carrier protein synthase, and a fatty acyl-ACP synthetase) are derived from the same species of human gut microbiome bacterium. In some embodiments, at least two of the three enzymes (a fatty-acyl transferase, an acyl carrier protein synthase, and/or a fatty acyl-ACP synthetase) are derived from the same species of human gut microbiome bacterium. In some embodiments, all three enzymes (a fatty-acyl transferase, an acyl carrier protein synthase, and a fatty acyl-ACP synthetase) are derived from distinct species of human gut microbiome bacteria. In some embodiments, one or more of the enzymes (a fatty-acyl transferase, an acyl carrier protein synthase, and/or a fatty acyl-ACP synthetase) are derived from the same species of human gut microbiome bacterium, and other one or more of the enzymes are derived from a different one or more species of human gut microbiome bacteria. In some instances, the human gut microbiome bacterium is from the Clostridia class.

The engineered cells of the present disclosure may further comprise other biosynthetic enzymes from human gut microbiome-derived bacterium. For example, the engineered cells may comprise a hydrolase, a lipid transfer protein, a glycosyltransferase, or any combination thereof. Lipid transfer proteins, which may also be referred to as sterol carrier proteins or sterol transfer proteins, are capable of transferring steroids between cellular membranes. See, e.g., Pfam Identifier: PF02036. The hydrolases may be from the alpha/beta hydrolase superfamily and comprise eight beta strands connected by 6 alpha helices. See, e.g., Pfam Identifier: PF12146. Glycosyltransferases are capable of catalyzing the transfer of sugars from donor molecules to acceptor molecules. See, e.g., Lozupone et al., Proc Natl Acad Sci USA. 2008 Sep. 30; 105(39):15076-81; Bhattacharya et al., PLoS One. 2015 Nov. 6; 10(11):e0142038; Brockhausen, Front Immunol. 2014 Oct. 20; 5:492.

A non-limiting example of a glycosyltransferase is: EreG: (*E. rectale* pathway):

(SEQ ID NO: 145)
MHNQTAILFFYKGKKMKLLSFAIPCYNSKDYMEHCIESILPGGDDVEIII

VDDGSKDETAAIADRYAAEYPDIVKAVHQENGGHGEAVNTGLKNATGKYF

KVVDSDDWVDLDSYKKILDKLREFEQENTQIDMLLANYVYEKEGAKRKKV

MRQTGFPRNEIFTWSDIKHIYKGHYILMHSVIYRTELLRSCGLKLPKHTF

YVDNIYVYKPLPYVRTMYYLDVDFYRYFIGRDDQSVNEQVMIRRIDQQIR

VNKIMFDDVKLHEITNEMCRKYMYSYLEIITTISTILAIISGTDENMAKK

DELWAYMKEHDEETYKKLRHGVMGQLMNLPGKGGRKVAIGAYKLSQKVVG

FN

In some instances, at least two, at least three, at least four, at least five, at least six, at least seven, at least eight, at least nine, at least ten, or more of the biosynthetic enzymes in an engineered cell are from the same species of human gut microbiome-derived bacterium. In some instances, all biosynthetic enzymes from human gut microbiome-derived bacteria are from different species of human gut microbiome-derived bacteria. In some instances, all biosynthetic enzymes from human gut microbiome-derived bacteria are from the same species of human gut microbiome-derived bacteria.

The host cell may be, for example, *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp.

In some instances, the host cell is a yeast cell.

The engineered cells of the present disclosure may be propagated under conditions well known in the art (e.g. temperature, culture broth and incubation times). In some embodiments, in which the engineered cells comprise nucleic acids operably linked to inducible promoters, the engineered cells are cultured in the presence of an effective amount inducing agent to induce expression from the inducible promoter. In some embodiments, the inducible promoter driving expression of a nucleic acid encoding a heterologous protein is a IPTG-inducible promoter, thus, the engineered cells are cultured in an effective amount of IPTG to induce expression from the tetracycline-inducible promoter. In some embodiments, a vector encoding T7 RNA polymerase may also be introduced into a cell with a IPTG-inducible promoter. In some embodiments, the inducible promoter driving expression of a nucleic acid encoding a heterologous protein is a tetracycline-inducible promoter, thus, the engineered cells are cultured in an effective amount of tetracycline to induce expression from the tetracycline-inducible promoter.

Methods of Producing Fatty Acid Amides

Some aspects of the present disclosure provide methods for producing a fatty acid amide using human gut microbiome-derived bacterium biosynthetic enzymes. Biosynthetic enzymes include fatty acyl-transferase, acyl carrier protein (ACP), fatty acyl-ACP synthetase, hydrolases, lipid transfer proteins, and glycosyltransferases.

The methods comprise contacting a composition comprising at least one fatty acid and at least one amine with one or more of the biosynthetic enzymes described herein. A set of biosynthetic enzymes (e.g., at least 2, at least 3, at least 4, at least 5, at least 6, at least 7, at least 8, at least 9, at least 10, or more) may be used to produce fatty acid amides. In some instances, at least 2, at least 3, at least 4, at least 5, at least 6, at least 7, at least 8, at least 9, at least 10, or more of the biosynthetic enzymes are from the same species of human gut microbiome-derived bacterium. In some instances, the set of biosynthetic enzymes may be all from the same species of human gut microbiome-derived bacterium. In some instances, the set of biosynthetic enzymes are all from different species of human gut microbiome-derived bacterium. In some embodiments, the set of biosynthetic enzymes comprises a fatty acyl-transferase, an acyl carrier protein (ACP), and a fatty acyl-ACP synthetase.

For example, at least 1, at least 2, at least 3, at least 4, at least 5, at least 6, at least 7, at least 8, at least 9, at least 10, or more of the microbiome-derived bacterium biosynthetic enzymes in a set may be from the Clostridia class. In sets with more than one Clostridia biosynthetic enzyme, at least 1, at least 2, at least 3, at least 4, at least 5, at least 6, at least 7, at least 8, at least 9, at least 10, or more of the biosynthetic enzymes may be from the same order, family, genus, species, or any combination thereof.

The fatty acid may be a free fatty acid. In some instances, at least 1, at least 2, at least 3, at least 4, at least 5, at least 6, at least 7, at least 8, at least 9, at least 10, at least 15, at least 16, at least 17, at least 18, at least 19, at least 20, at least 30, at least 40, at least 50, at least 60, at least 70, at least 80, at least 90, at least 100, or more fatty acids, including all values in between, may be used. A composition may comprise fatty acids that are all of the same type, fatty acids that are all different, or some fatty acids that are the same and some fatty acids that are different. In some instances, at least 1, at least 2, at least 3, at least 4, at least 5, at least 6, at least 7, at least 8, at least 9, at least 10, at least 15, at least 16, at least 17, at least 18, at least 19, at least 20, at least 30, at least 40, at least 50, at least 60, at least 70, at least 80, at least 90, at least 100, or more fatty acids, including all values in between, may be used.

A composition may comprise amines that are all of the same type, amines that are all different, or some amines that are the same and some amines that are different. In some instances, at least 1, at least 2, at least 3, at least 4, at least 5, at least 6, at least 7, at least 8, at least 9, at least 10, at least 15, at least 16, at least 17, at least 18, at least 19, at least 20, at least 30, at least 40, at least 50, at least 60, at least 70, at least 80, at least 90, at least 100, or more amines, including all values in between, may be used.

As one of ordinary skill in the art would appreciate, selection of a particular fatty acid and amine pair may be dependent upon the fatty acid amide of interest. As a non-limiting example, palmitoeyl putrescine is a fatty acid amide (FAA) that is formed by the conjugation of palmitoleic acid and putrescine. To make palmitoeyl putrescine, palmitoleic acid would be selected as the fatty acid and putrescine would be selected as the amine.

The methods may comprise using one or more purified biosynthetic enzymes, a lysate comprising one or more biosynthetic enzymes, or culturing a cell comprising a vector encoding one or more biosynthetic enzymes.

Protein purification methods include, but are not limited, to size exclusion chromatography, ammonium sulfate precipitation, ion exchange chromatography, immobilized metal chelate chromatography, thiophilic adsorption, melon gel chromatography and antibody ligand chromatography, any of which may be used as provided herein to recover a protein The engineered cells of the present disclosure may be propagated under conditions well known in the art (e.g. temperature, culture media and incubation times). In some embodiments, in which the engineered cell comprises nucleic acids operably linked to inducible promoters, the engineered cells are cultured in the presence of an effective amount inducing agent to induce expression from the inducible promoter. In some embodiments, the inducible promoter driving expression of a nucleic acid encoding a heterologous protein is a IPTG-inducible promoter, thus, the engineered cells are cultured in an effective amount of IPTG to induce expression from the IPTG inducible promoter.

Any of the compounds described herein, including fatty acids, amines, and fatty acid amides, disclosed herein may be identified and extracted using any method known in the art. Mass spectrometry (e.g., LC-MS, GC-MS) is a non-limiting example of a method for identification and may be used to extract a compound of interest.

EXAMPLES

Example 1

Clostridia NRPS-Like Pathways Identified from Human Gut Sequencing Data

Figure 3:
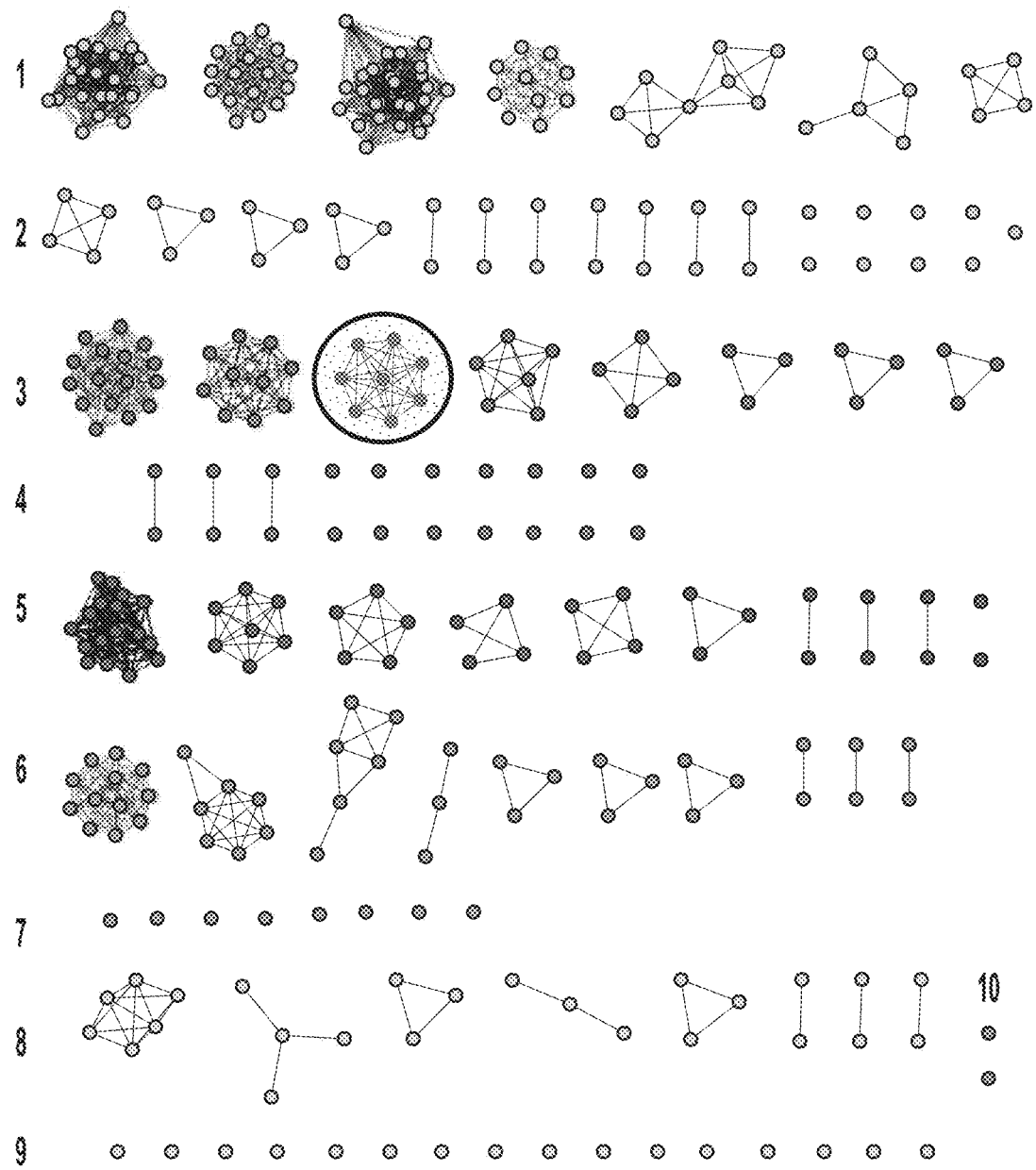
FIG. 3 shows a pathway similarity network map. Network map of 346 human gut-derived and actively transcribed pathways, represented as nodes. Edges are calculated using BiG-SCAPE based on the protein sequence- and domain-level (dis)similarity of pairs of pathway with a cutoff of 0.75. Clostridia NRPS group is circled. Groups labeled 1 and 2 show saccharides, 3 and 4 show NRPS products, 5 shows PKS products, 6 and 7 show hybrid products, 8 and 9 show RiPP products, and 10 shows other products.

The human gut microbiome genomic datasets were systematically screening for the presence of metabolite-encoding biosynthetic pathways (FIG. 1A). Metadata from the Joint Genome Institute (JGI) was used to identify 1042 bacterial genomic datasets associated with the human gastrointestinal tract, which were retrieved from either JGI or the National Center for Biotechnology Information (NCBI) database. The software antiSMASH,[22] which employs a pattern recognition algorithm based on protein domains from known natural product pathways, was used to bioinformatically detect 3531 putative pathways from the genomic datasets. The pathways were further narrowed to those that are prevalent and actively transcribed in healthy human subjects, reasoning that they are more likely encode for small molecule modulators that are relevant and mechanistically conserved across different human gut strains. To screen by prevalence, the antiSMASH-detected pathways were analyzed for their representation in the shotgun metagenomic sequencing data collected from the Human Microbiome Project (HMP; 148 gut samples of healthy subjects).[20] The resulting 2013 human gut-associated pathways were narrowed based on transcription by examining their presence in RNA sequencing datasets from the stool samples of eight healthy subjects from the HMP.[32] The 336 transcribed pathways were organized using the software BiG-SCAPE,[33] which uses network-similarity algorithms to group the pathways into pathway families (FIG. 3). The network groups were then manually inspected to disregard the known families, such as polysaccharide A,[15] catecholate-type siderophores,[34] and aldehyde-type protease inhibitors.[24]

Among the HMP-derived, transcribed, and uncharacterized pathways, a family of eight pathways specific to the Clostridia bacterial class was chosen for investigation (FIG. 1B). Analysis with MetaQuery[35] confirms that these pathways are prevalent in the human gut, with at least one pathway appearing in 99.6% of the >2000 publically available human gut metagenomes. Three biosynthetic genes that are conserved amongst all eight pathways encode for the signature C, T, and A domains of the NRPS minimal module. The system comprises three unique characteristics: 1) the presence of only one NRPS module; 2) a lack of termination domain for product release; and 3) the architecture of each NRPS domain encoded as a separate, standalone protein. Bioinformatics analysis thereby suggests that this family encodes for an as-yet uncharacterized chemical modulatory mechanism that is highly utilized across diverse gut commensal Clostridia.

FAA Pathway Phylogeny and Taxonomical Phylogeny are Different

To investigate the representation and distribution of the eight HMP-derived pathways with respect to other members in a general database, homologous pathways were computationally searched on the NCBI nonredundant (nr) database and a total of 148 pathways were identified. When these pathways were organized based on protein sequence phylogeny, the *Coprococcus eutactus*, *Lachnoclostridium clostridioforme*, and *Eubacterium rectale* pathways from HMP data were found to be particularly represented across multiple strains, with eight to nine instances each at >98% sequence identity (FIG. 4). While all of the pathways come from the Clostridia class, analysis by re-organizing the pathways based on taxonomical phylogeny reveals that they are encoded by diverse Clostridia species. Notably, the strains that harbor close homologs of *C. eutactus* form one distinct taxonomical clade, while each of the *L. clostridioforme*, and *E. rectale* pathways form multiple taxonomical clades. Therefore, while there is some correlation between the pathway- and taxonomy-based phylogenic distributions (e.g., *C. eutactus* pathways), they are different in many cases (e.g., *L. clostridioforme*, and *E. rectale* pathways). As a result, taxonomical classification of the bacterial strains is not sufficient in predicting the FAA pathway types and any health-related functional outputs that they encode for.

Fatty Acid Amide Isolated from Gut Clostridia Pathways

Considering that some of the pathways were identified using metagenomic data and the host organisms were never isolated, *E. coli* heterologous expression was first attempted as a characterization strategy. The eight pathways were synthesized from genome or metagenome sequence with *E. coli* optimized codons. Each gene in the pathway was placed under a strong T7 promoter and ribosomal binding site for robust and inducible expression. The resulting redesigned pathways were introduced into *E. coli* BAP1 host that expresses Sfp PPTase to ensure proper activity of the heterologous NRPS machinery.[28] Various fermentation and extraction conditions were attempted for the eight pathways, but clone-specific compound production was detected with sufficient titers for only the *E. rectale* pathway (FIG. 1C). The major compound was found to be palmitoeyl putrescine, as elucidated by 1- and 2-D NMR and then confirmed by comparison with a synthetic sample (FIG. 5).

Figure 6A:
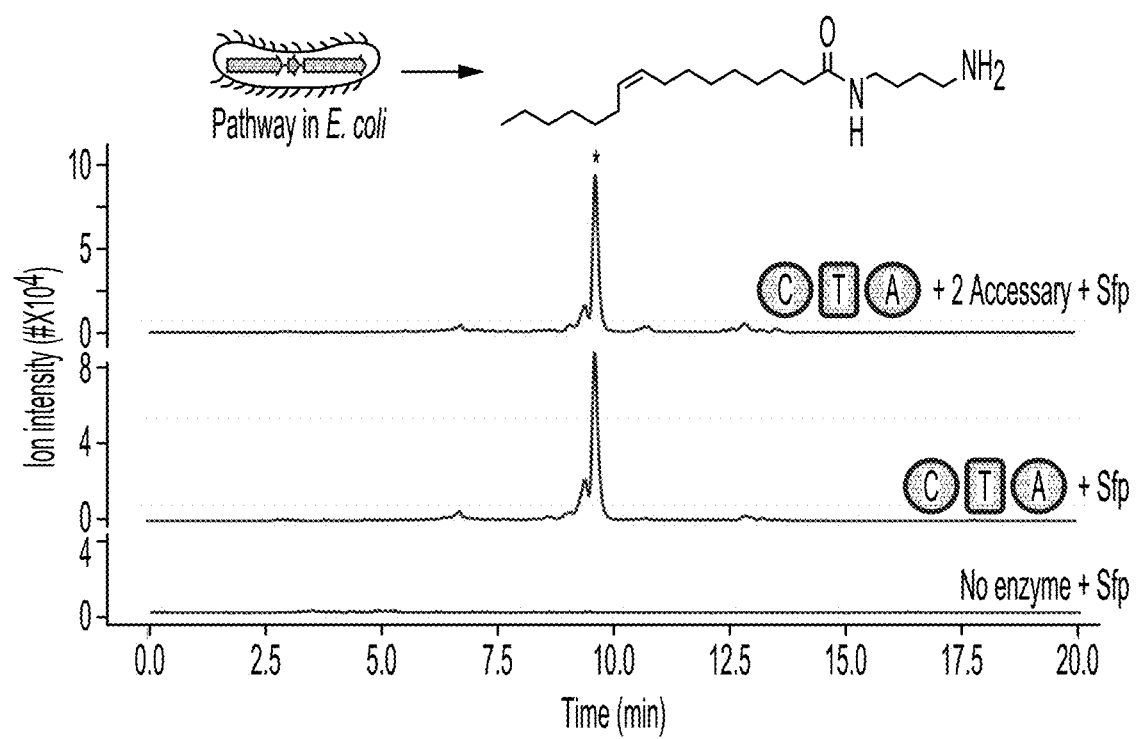
FIGS. 6A-6B show *E. coli* heterologous production. a, MS chromatogram (EIC ESI+m/z 325.3213, [M+H]+ of palmitoeyl putrescine, as shown) of the in vivo extract of *E. coli* expressing the *E. rectale* biosynthetic genes (C, T, A), sfp gene, and with or without the 2 accessory genes encoding alpha/beta hydrolase and sterol transfer proteins. * denotes peak corresponding to the shown compound, palmitoeyl putrescine. b, MS chromatogram of the in vivo extract of *E. rectale* pathway-expressing *E. coli* with either tryptamine (Tpa) or octanoic acid (C8) fed into culture broth. Top: EIC ESI+m/z 397.3213. Bottom: EIC ESI+m/z 215.2118. * denotes peak corresponding to the shown product compound.

The three NRPS domain-containing biosynthetic genes are the only genes conserved across all eight characterized FAA pathways. However, some pathways also contained genes encoding a sterol transfer protein (Pfam: PF02036) and an alpha/beta hydrolase protein (Pfam: PF12146) (Table 1). The exclusion of these genes had no effect on FAA production in a heterologous expression system (FIG. 6A). They are thus predicted to be accessory genes, with the sterol transfer protein facilitating the transport of exogenous fatty acids from the human gut lumen to the bacterial cytoplasm,[36] while the hydrolase acts to either cleave human endogenous FAAs to generate free substrates for the pathway, or to degrade the FAA pathway product as a negative regulatory mechanism in much the same way as human FAA hydrolases do.[37]

Mechanism Elucidated for Clostridia FAA Biosynthesis

Figure 6B:
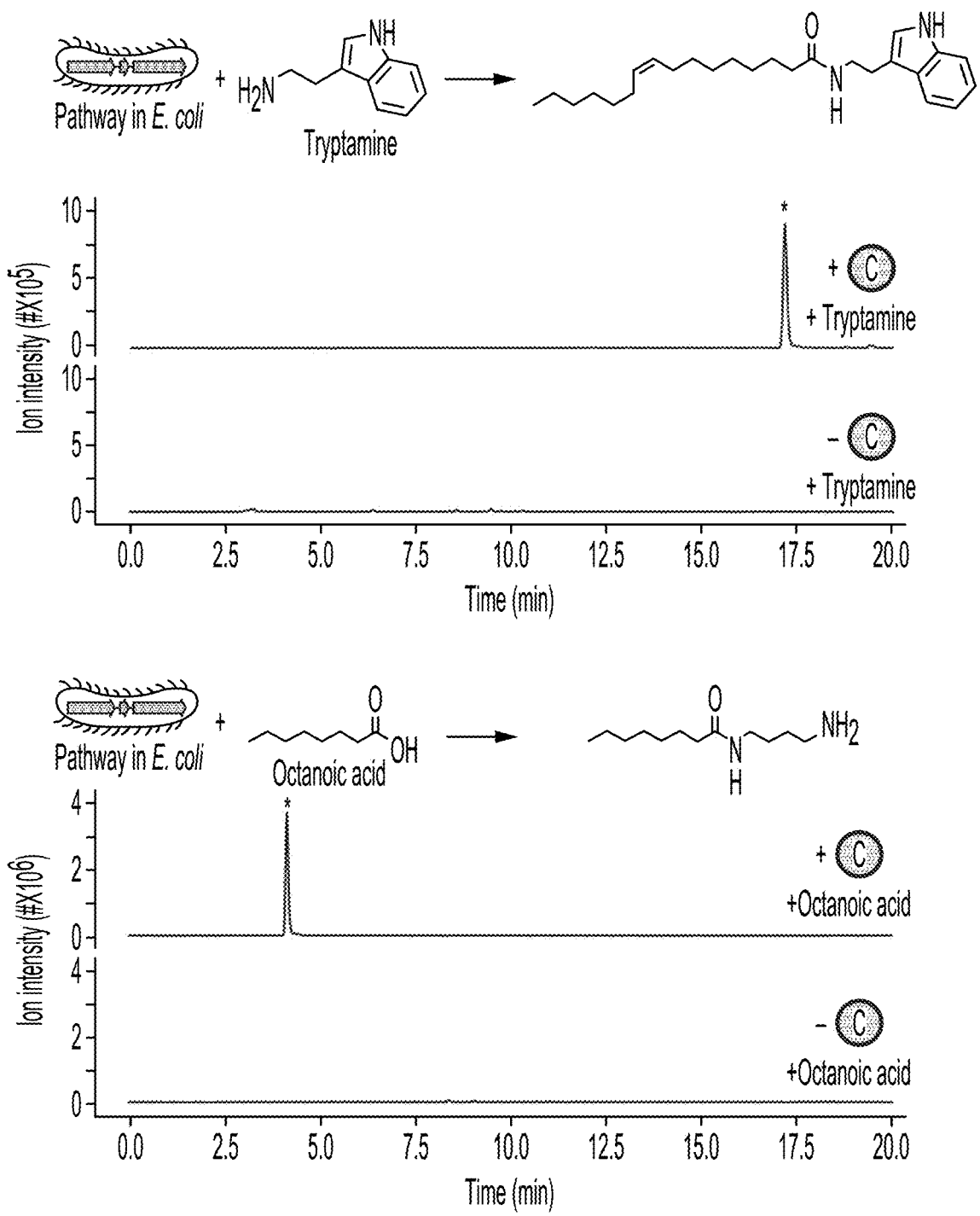

Palmitoeyl putrescine is a fatty acid amide (FAA) that is formed by the conjugation of palmitoleic acid and putrescine. Much like peptide bond formation, it is biochemically viable for NRPS domains to join a fatty acid and an amine to generate a FAA. However, considering that putrescine is highly produced in E. coli, but deficient in Clostridia,[38] it is questionable as to whether palmitoleic acid and putrescine are actually the preferred substrates of this pathway. To investigate the contribution of the biosynthetic enzymes, single-gene knockout pathways without one of the biosynthetic genes were constructed and tested for production in E. coli. Removing either the A, T, or Sfp PPTase gene demolished compound production, thereby confirming the thiotemplating activity of A onto T in FAA production. However, removing the C gene had no effect on production, indicating that palmitoeyl putrescine is a shunt product that formed as a result of a different metabolic pool in E. coli host (FIG. 1C). Moreover, feeding the culture broth of the E. coli host harboring the wildtype pathway with either octanoic acid or tryptamine led to the production of octanoyl putrescine or palmitoeyl tryptamine, respectively (FIG. 6B). The pathway is therefore capable of incorporating a different fatty acid or amine that is exogenously available in the environment.

To further investigate the biosynthetic mechanism of FAA production, each of the three biosynthetic genes in the palmitoeyl putrescine-producing E. rectale pathway were cloned in a separate construct, expressed for protein purification, and reconstituted in vitro, such that the A and C activity can be measured independently with defined substrates. The A activity was first measured based on the amount of inorganic pyrophosphate (PPi) that was formed from ATP consumption. Up to 30-fold increase in PPi level relative to negative control was observed with fatty acid substrates, while no difference was observed with amino acid substrates (FIG. 1D). Therefore, as opposed to the conventional NRPS adenylation enzyme that tethers an amino acid, the A protein in this pathway tethers a fatty acid onto the T protein. This is consistent with the fact that the conserved aspartic acid residue that interacts with the α-amino group of an amino acid substrate in canonical NRPS A domain[39] is lacking in this A protein, thereby being similar to other acyl-coenzyme A synthetase enzymes.[40]

On the other hand, although the result from E. coli heterologous production suggests that the C protein does not catalyze a reaction involving putrescine, it may instead recognize a different amine. Since the condensation enzyme does not consume ATP, the amount of the product FAA itself was used as the metric for enzyme activity. Because different compounds ionize at varying intensities, ion abundance as measured by LCMS cannot be directly compared between FAAs of different amine moieties. However, based on the observation that the amine substrate, such as putrescine, can non-enzymatically release the tethered fatty acid to generate FAA, the FAA level was normalized in the presence of the C enzyme relative to the level in its absence. Among the small set of biological amines that were tested, the C enzyme showed preference towards incorporation of tryptamine, with about 8-fold higher activity than putrescine (FIG. 1E).

Based on in vivo gene knockout and in vitro reconstitution studies, a biosynthetic scheme for FAA formation can be constructed, where T is an acyl carrier protein, A is a fatty acyl-acyl carrier protein synthetase, and C is a N-fatty acyltransferase (FIG. 1F). Upon Sfp-dependent activation of the T protein with PPT arm, the A enzyme selects an exogenous fatty acid substrate and tethers it onto T. The C enzyme then selects an exogenous amine and conjugates it onto the thiotemplated fatty acid (fatty acyl-T) to form the FAA product.

Bioinformatics has at times permitted the prediction of compound structure from primary sequence data alone,[41] but structure prediction was misleading for these pathways. While a peptide-based structure can be predicted from the sequence based on the presence of NRPS domains, it instead produced FAA with a biosynthetic machinery that shows limited homology to previously known FAA pathways.[42] Surprisingly, as described herein, this NRPS condensation domain protein could be used to catalyze the incorporation of an untethered substrate, like tryptamine, that does not have a carboxylate moiety.

Preferred FAA Products Characterized by In Vitro Substrate Combinatorics

Figure 2B:
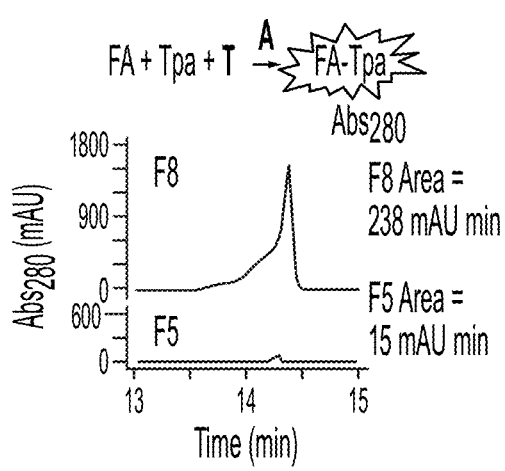
Figure 2C:
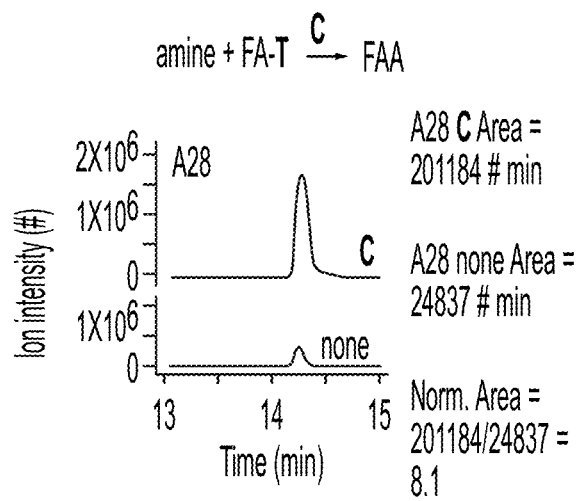
Figure 2D:
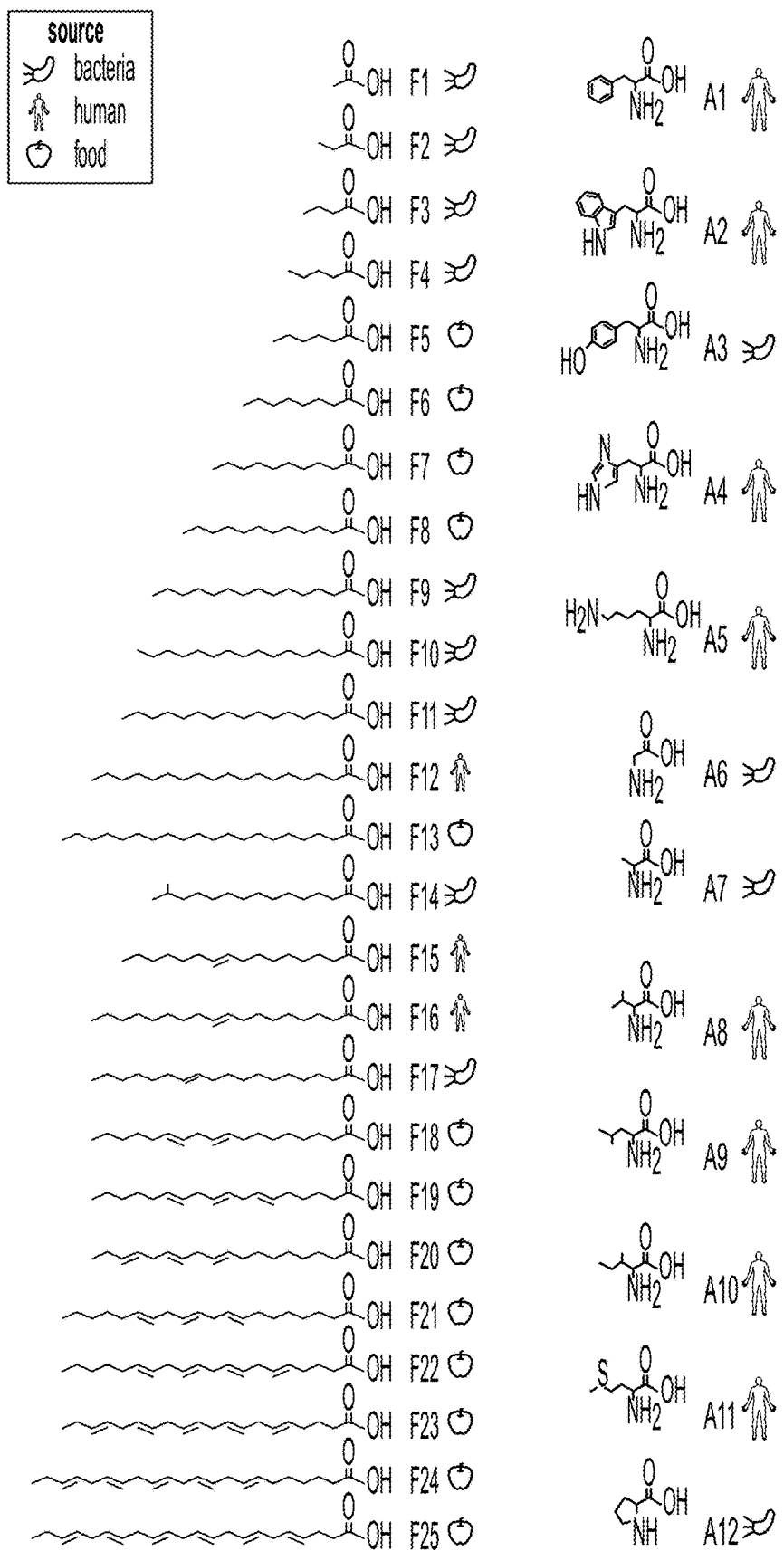
Figure 2D:
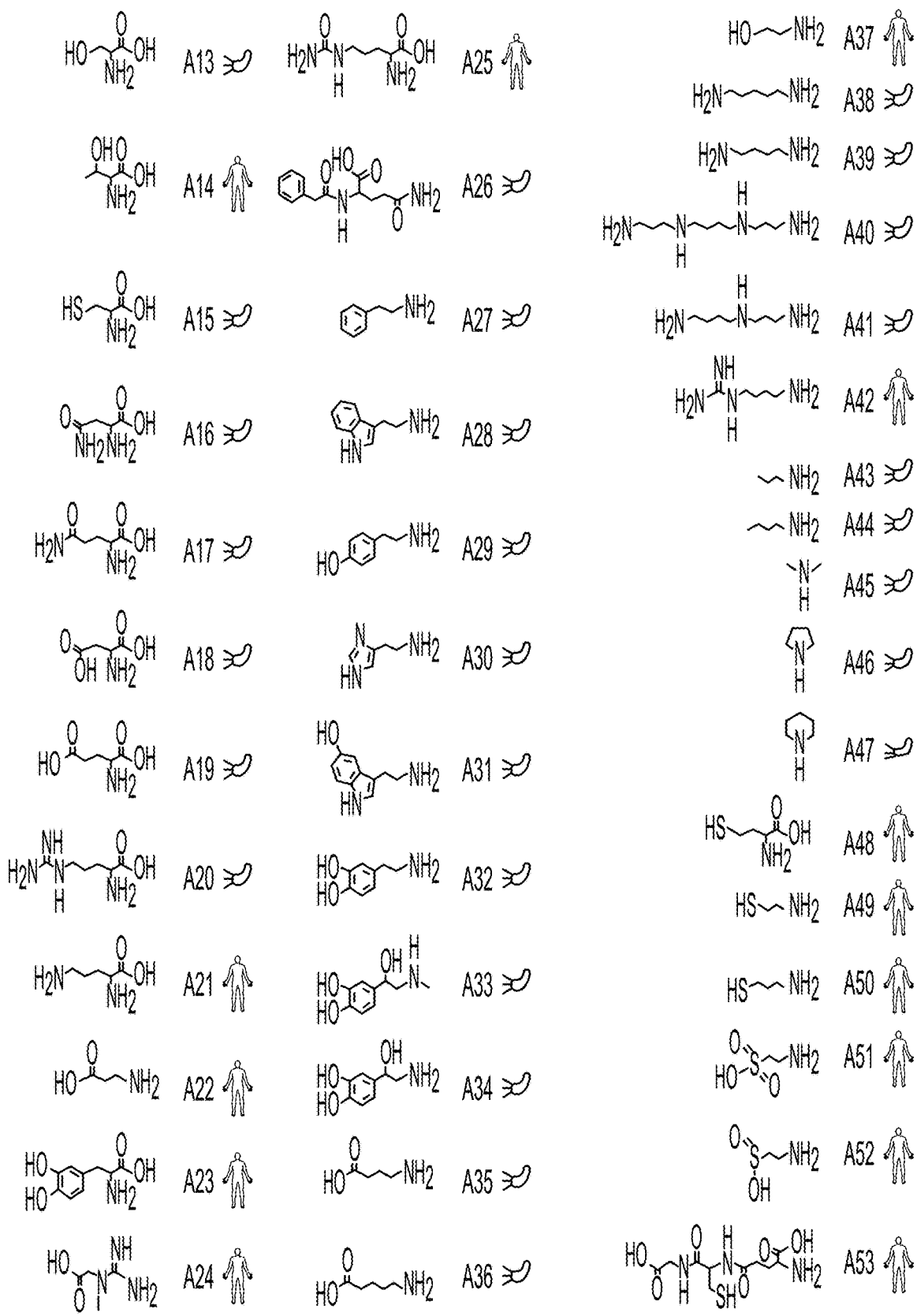

The human gut lumen consists of various fatty acid and amine substrates from different sources that the pathway can incorporate for FAA production. To characterize the preferred product, an in vitro substrate panel assay was set up to investigate substrate selectivity of the biosynthetic enzymes for each of the eight identified HMP-derived pathways (FIG. 2A). A and C enzyme activity was measured for defined fatty acid and amines, respectively, to determine the substrates that each pathway prefers to incorporate for FAA production (FIG. 2B-2C). A panel of 25 fatty acids and 53 biogenic amines derived from Clostridia, human cells, and human diet that are known to be abundant in the human gut was selected (FIG. 2D).[43,44,45,46,47] For consistency, FAA product level, instead of PPi level, was used as the metric of A activity for the panel assay by adding tryptamine for all query fatty acid substrates to measure the level of C-independent FAA formation based on the UV absorbance of the indole chromophore (FIG. 2B). For C activity, the fatty acid that generated the highest A activity was added for all of the query amine substrates, with the metric being the normalized FAA product level as described previously (FIG. 2C). To alleviate the bottleneck of LCMS sample runtime, the number of runs was reduced by subpooling the query substrates together and then separating the FAA products by LC to measure enzymatic activity for each substrate. In this manner, the enzymatic activity of the A and C proteins for each pathway was elucidated for each fatty acid and amine substrates in the panel, respectively (FIG. 2E).

The A protein had a higher enzymatic activity than the C protein, with around 40-60 fold difference in the A protein between the highest and lowest substrates, compared to 5-15 fold difference in the C protein for the C. eutactus, M. formatexigens, R. bacterium, E. rectale pathways. This can be partially attributed to the fact that the enzymatic activity of the C protein is competing with nonenzymatic release of the tethered substrate, a phenomenon that is known in multimodular assembly reaction.[48] However, even taking that into consideration, the observed enzymatic activity of the C protein for the L. clostridioforme, B. producta, C. celatum, C. sp pathways was low, with 2 fold difference with homocysteine substrate being the highest. Because of the lack of precedence for this type of condensation enzyme, the possibility that this 2 fold difference in activity is relevant in the context of this in vitro system and that homocysteine is the preferred amine substrate for these four pathways cannot be discounted. However, considering that previously characterized product release domains in NRPS systems compete against nonenzymatic release with at least 2 fold higher activity,[49,50] it is more likely that the amine panel does not contain the appropriate substrate for these four pathways to observe C enzymatic activity higher than the 2 fold-difference threshold.

On the other hand, the C protein show higher substrate selectivity than the A protein, with 25-100% higher activity between the highest and second highest substrates in the C protein, compared to 8-40% in the A protein. Barring for differences in rank order, the A proteins in all pathways generally preferred to incorporate either middle-chain fatty acid (e.g. lauric acid) or long-chain fatty acid with cis-9 double bond (e.g. oleic acid), both of which fit in a hydrophilic pocket that selects for a straight-chain alkyl chain of 10-12 carbons in length from the amide bond. Meanwhile, the C proteins show diversity in substrate selectivity, from the straight-chain amine (e.g. aminovaleric acid) of the *C. eutactus* pathway to the arylamine (e.g. tryptamine) of the *E. rectale* pathway.

Figure 2E:
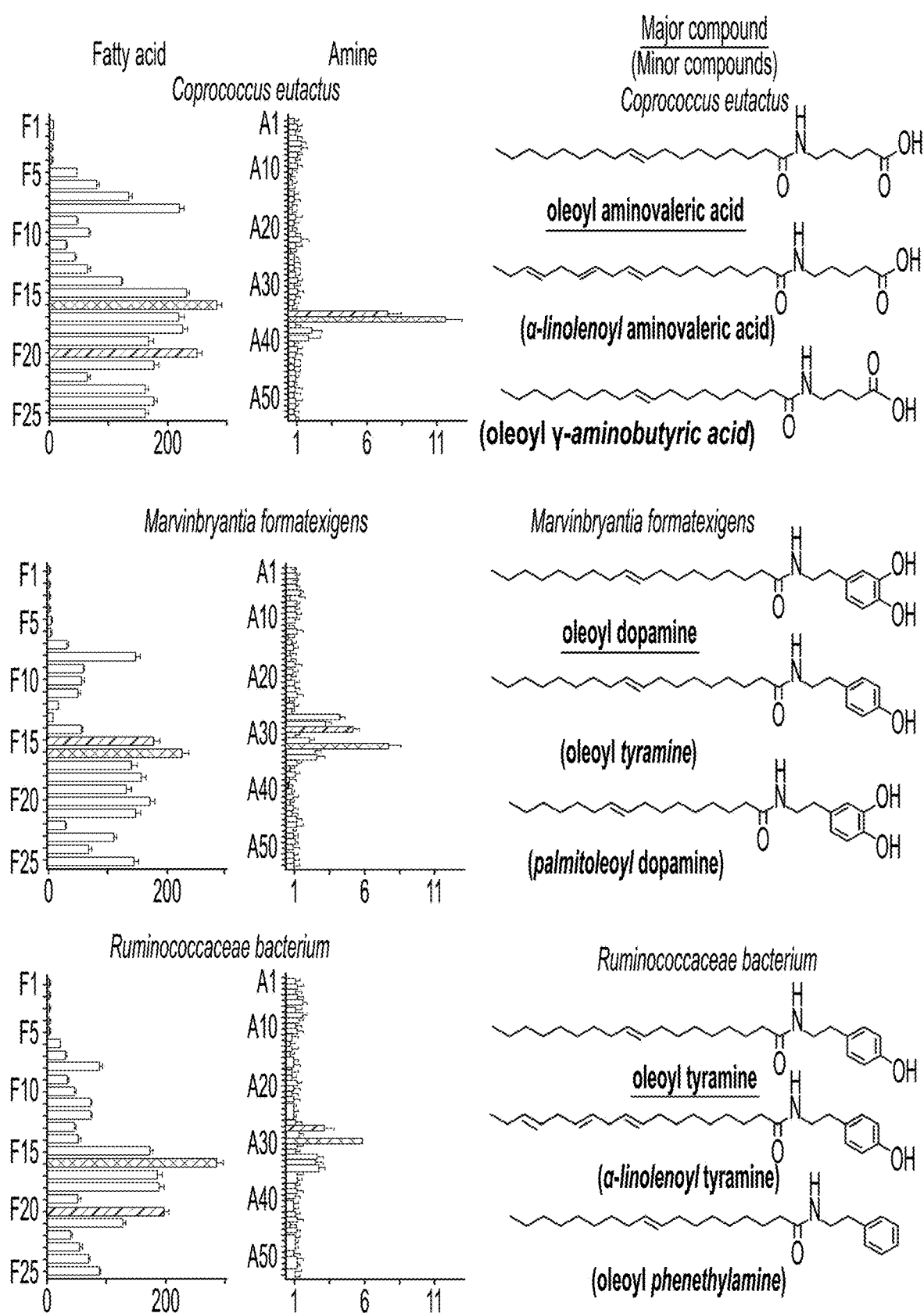
Figure 7:
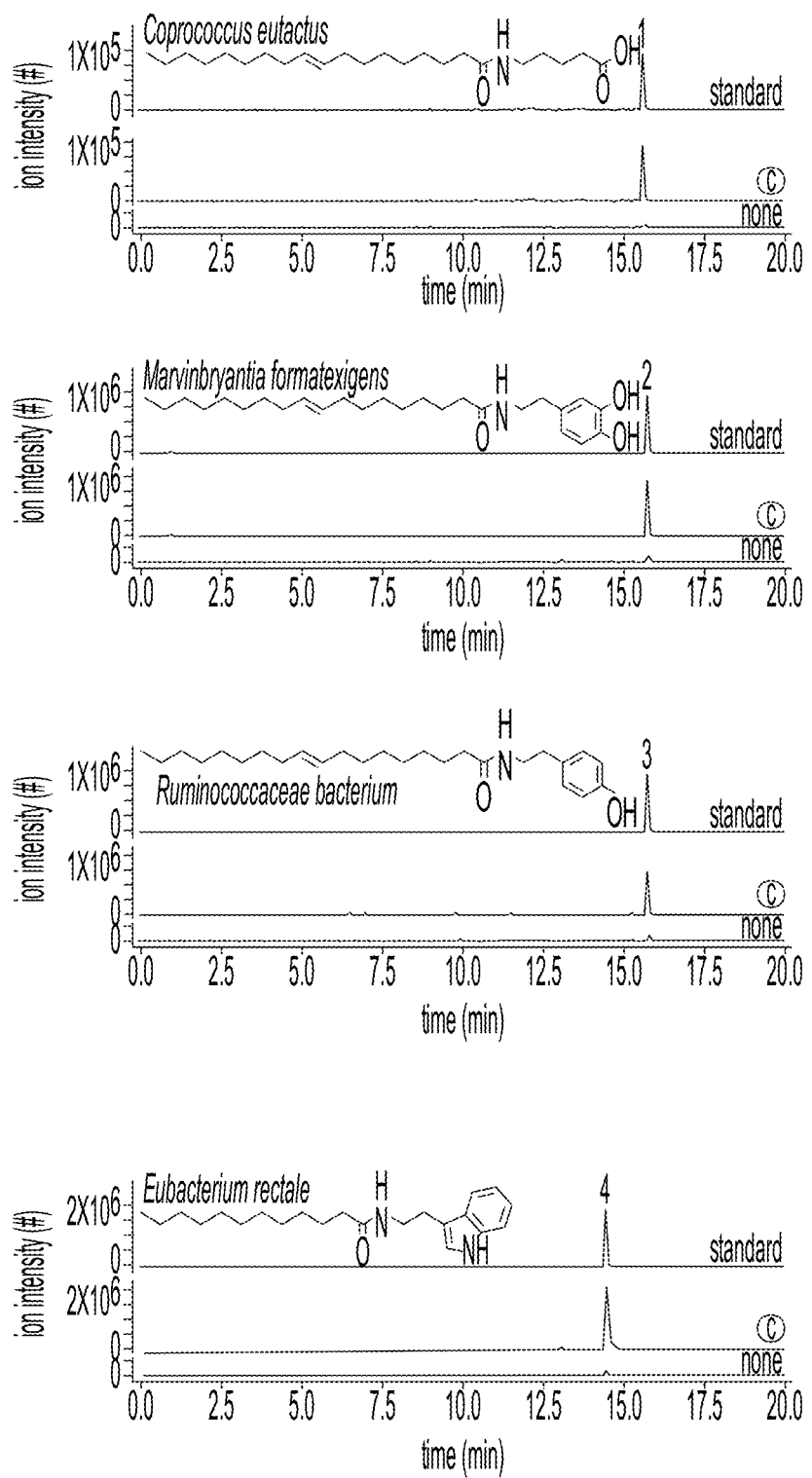
FIG. 7 shows in vitro compound production. MS chromatogram of the reaction in amine in vitro substrate panel assay at EIC ESI+ corresponding to m/z of the preferred product with highest enzymatic activity (1: 382.3316, 2: 418.3316, 3: 402.3367, 4: 343.2744, 5: 396.2567). Labels: standard=chemically synthesized authentic standard; C=in vitro extract with condensation enzyme; none=in vitro extract without condensation enzyme.
Figure 7:
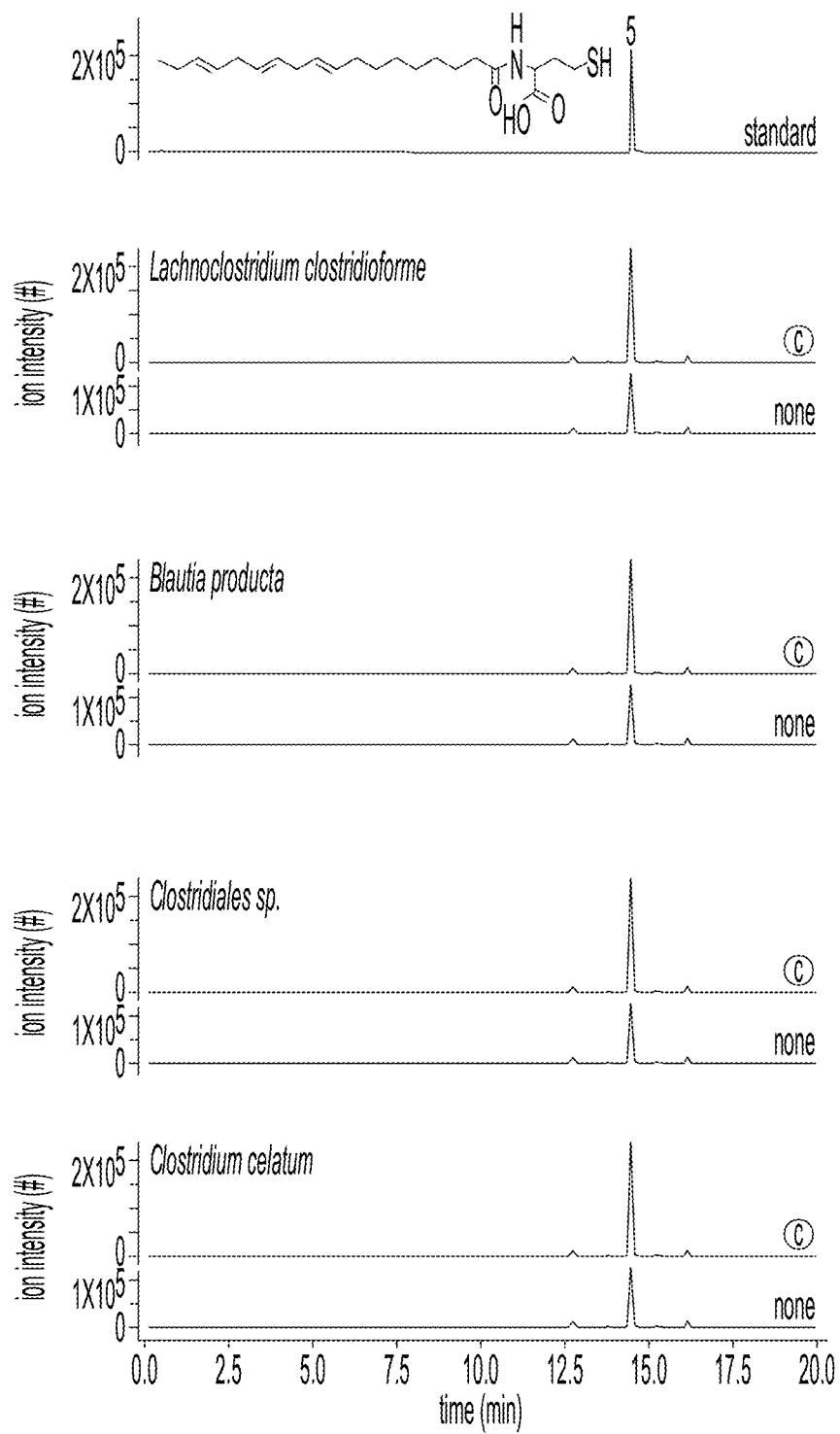

The fatty acid and amine substrates yielding the highest enzymatic activity were determined for each pathway, leading to the production of oleoyl aminovaleric acid for the *C. eutactus* pathway, oleoyl dopamine for the *M. formatexigens* pathway, oleoyl tyramine for the *R. bacterium* pathway, and lauroyl tryptamine for the *E. rectale* pathway as the major FAA (FIG. 2E and FIG. 7). The production of α-linolenoyl homocysteine yielded the highest enzymatic activity for the *L. clostridioforme, B. producta, C. celatum,* and *C.* sp. pathways, but the low C enzymatic activity diminishes its likelihood as being the major FAA. The products that are generated by the incorporation of second highest fatty acid or amine are also listed as examples of minor FAAs (FIG. 2E). These may become relevant depending on the abundance of the fatty acid and amine substrates that the native strains are subjected to in the human gut environment.

C and T Protein Interaction is Pathway Specific

Figure 8:
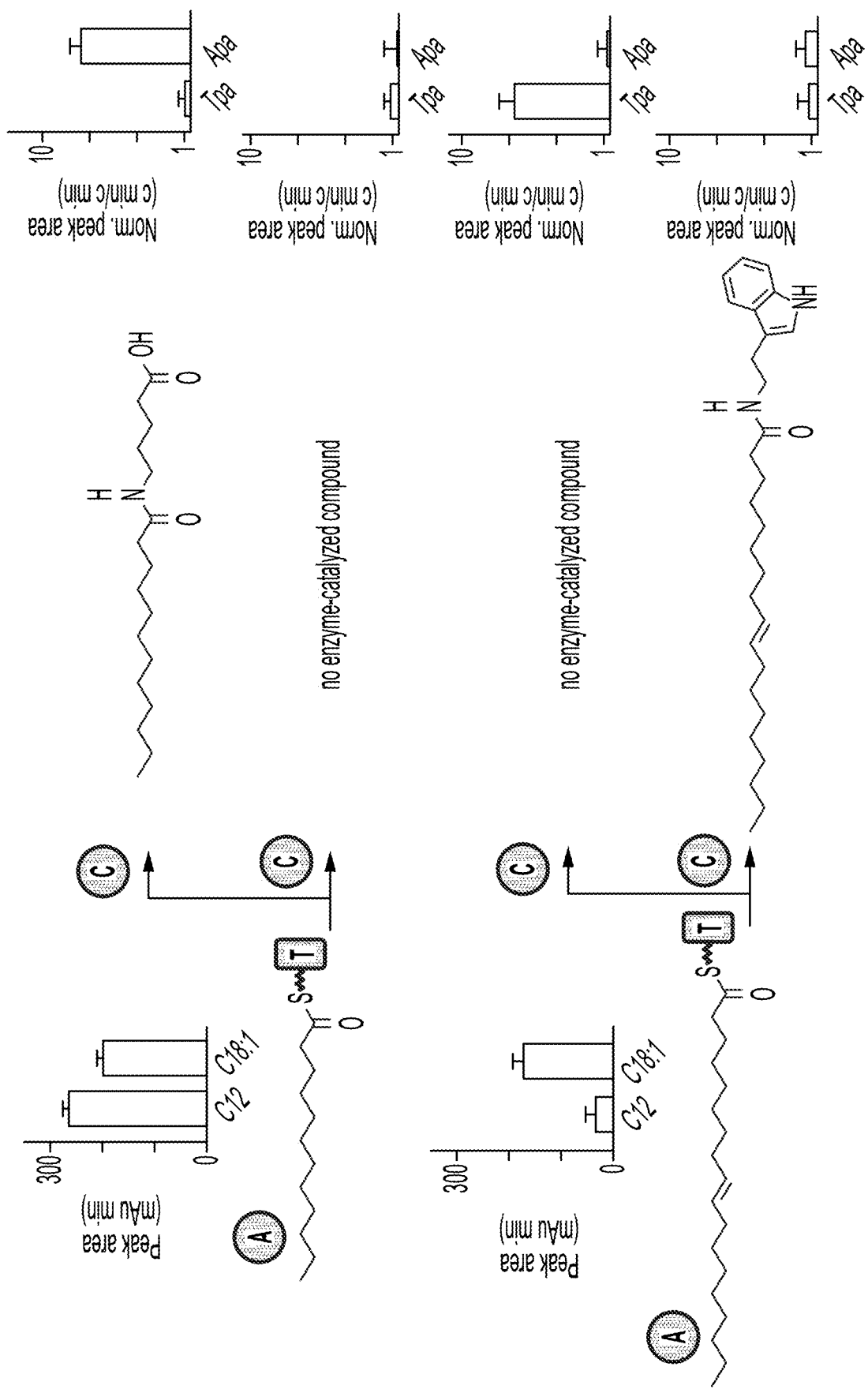
FIG. 8 shows inter-pathway domain swapping. Adenylation (left graph) and condensation activity (right graph) level and corresponding enzyme-catalyzed product formation (if any) for different combinations of biosynthetic proteins (C, T, A) from the *C. eutactus* (lighter shade) and *E. rectale* (darker shade) pathways. The fatty acid olefin is in cis (Z) conformation. Substrate labels: C12=lauric acid, C18:1 oleic acid, Tpa=tryptamine, Apa=aminovaleric acid. All error bars are the s.d. of three replicates conducted on different days.

Organisms use acyl carrier proteins homologous to the FAA pathway's T protein to make endogenous fatty acids.[51] Therefore, in order for the FAA pathway to utilize exogenous fatty acids, the biosynthetic proteins may have a mechanism that prevents crosstalk with other homologous proteins. To investigate such pathway-specific interactions, the biosynthetic proteins from the two FAA pathways that make oleoyl aminovaleric acid and lauroyl tryptamine were swapped and their effect on enzyme activity was measured. While the C protein lost activity, the A protein retained activity after swapping the T protein. Swapping the A domain, while retaining the T and C protein pair from the same pathway, permitted the enzymatic production of hybrid FAA that incorporated the substrates from two different pathways (FIG. 8). This suggests that the T and C proteins interact in a pathway-specific manner, possibly by containing donor and acceptor communication-mediating domains found in known NRPS systems.[52] This has implications in pathway engineering, where the communication between the T and C protein from the same pathway needs to be retained when considering the combinatorial biosynthesis of these pathways for the production of FAA chemical library.

Methods

Strains and Plasmids

*Escherichia coli* DH10B (New England BioLabs) was used for routine cloning. *E. coli* BAP1 *E. coli* BAP1 containing T7 DNA polymerase and Sfp phosphopantetheinyl transferase was used for heterologous expression of re-designed pathways.[28] *E. coli* BL21(DE3) (Sigma-Aldrich) was used for protein expression and pathway expression in the absence of Sfp. Plasmid was introduced by electroporation, with electrocompetent cells prepared for the non-commercially available BAP1 strains using published protocol.[62] Vector pET28a (Novagen) was used as backbone for all pathway and protein expression constructs. Kanamycin was used as for selection at 30 μg/ml.

Figure 10A:
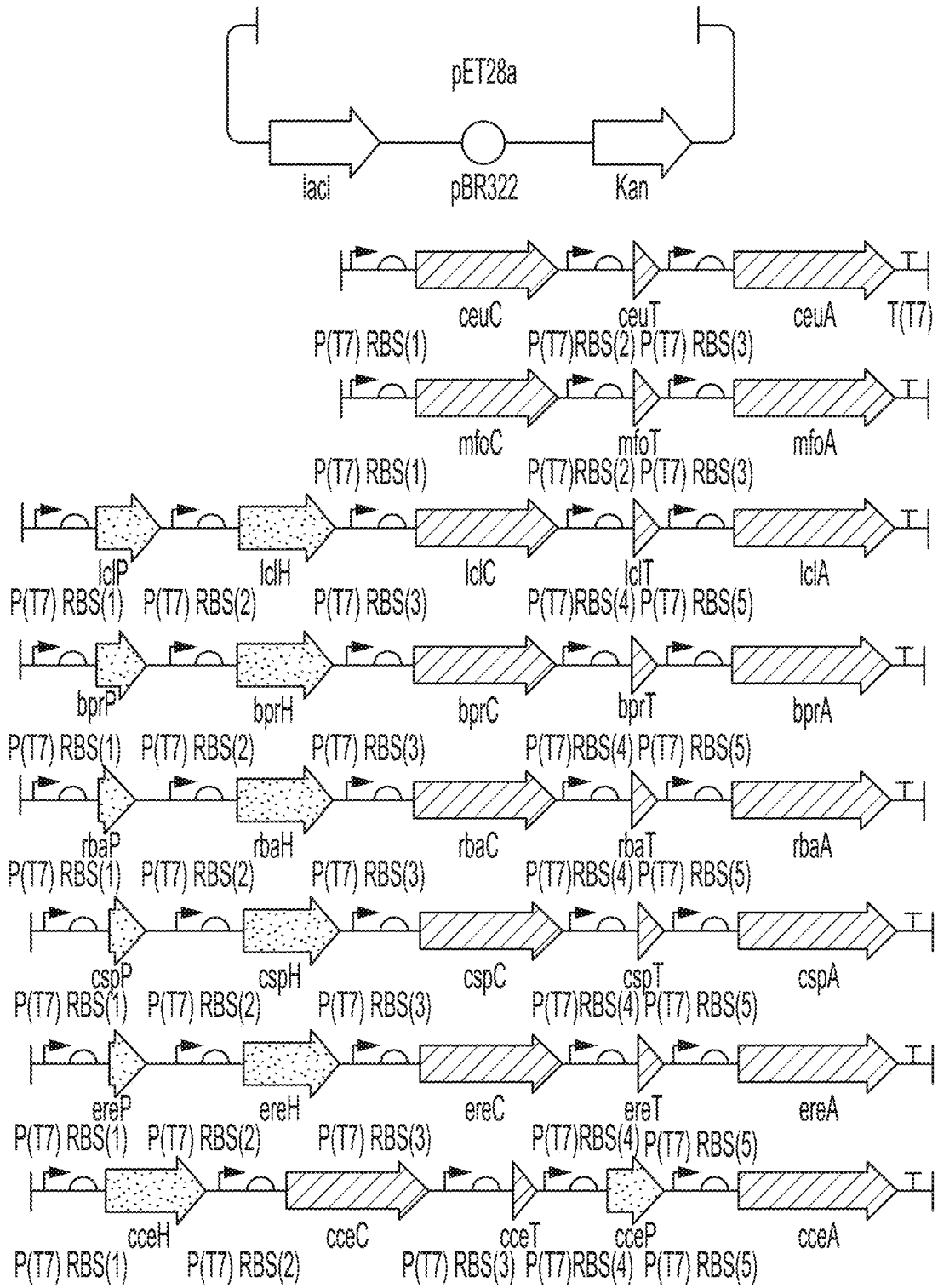
FIGS. 10A-10C show expression vector design. Cloning into pET28a (Novagen) for constructs containing a, redesigned complete pathways, b, gene knockout pathways, and c, single gene expression for protein purification. Sequences of genes and vector components are in Tables 1 and 2.
Figure 10B:
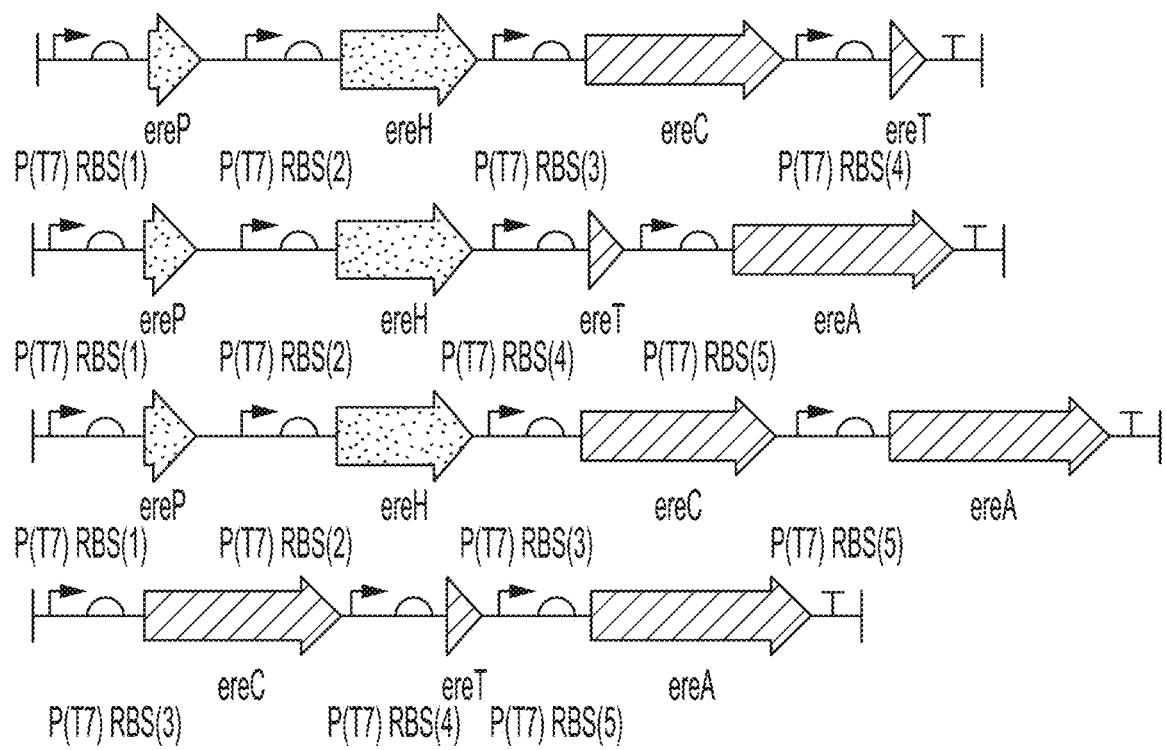
Figure 10C:
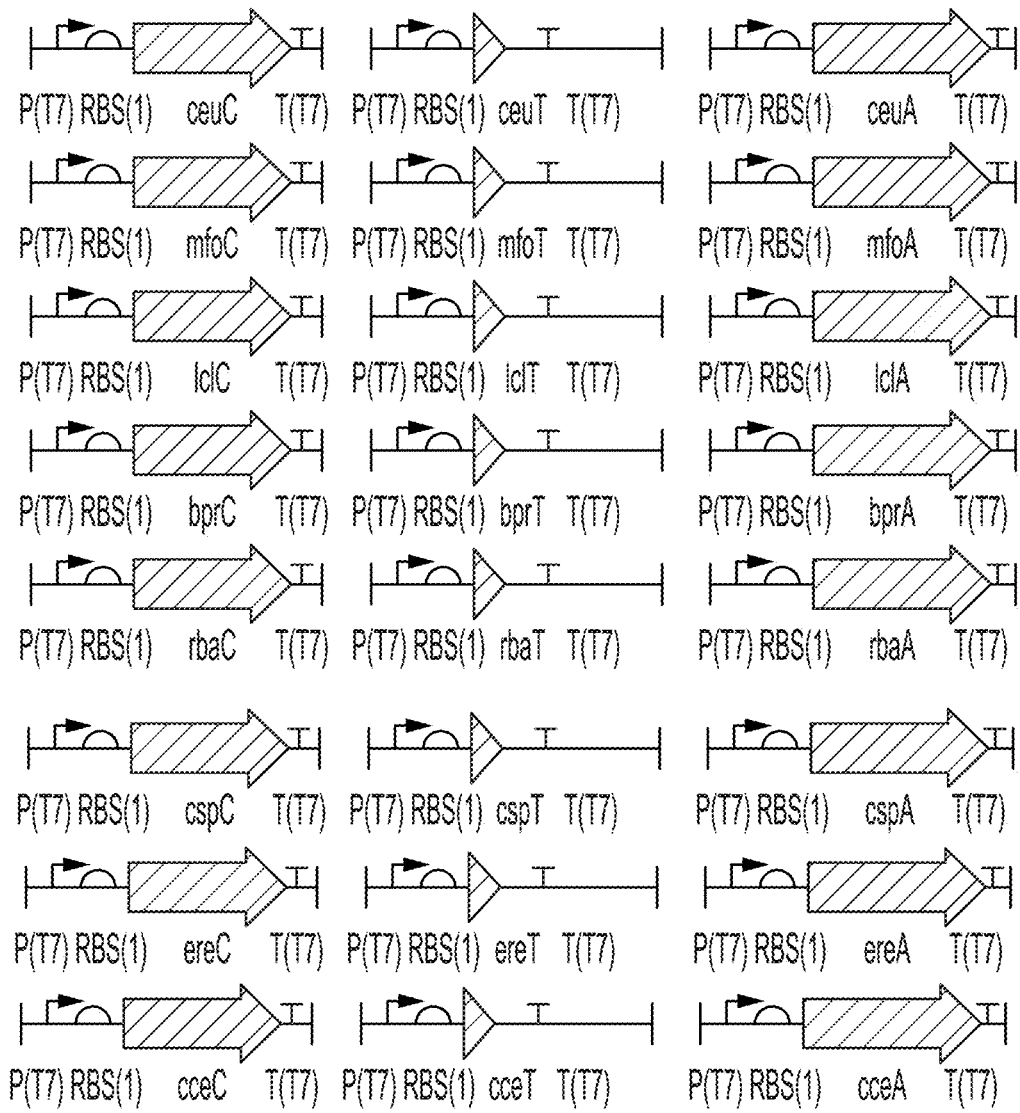

Pathways including the biosynthetic and accessory genes were re-designed such that each gene was codon optimized for *E. coli* without Type IIS restriction sites (GeneArt CodonOptimizer), placed under T7 promoter (with lacO operator) and RBS parts from pET28a (Novagen), and arranged in the same direction in the order that they appear natively (FIG. 10, Tables 1 and 2). The re-designed pathways were synthesized by either Invitrogen or Gen9 with flanking BsaI sites. The synthesized pathways, either as purified fragments or cloned in default vector, were cloned into pET28a using Golden Gate assembly and transformed into *E. coli* BAP1. In Table 1, genes with names that end with "C" at the end encode fatty acyl-transferases (e.g., ceuC, mfoC, etc.). In Table 1, genes with names that end with "A" at the end encode fatty acyl-ACP synthetases (e.g., ceuA, mfoA, etc.). In Table 1, genes with names that end with "T" at the end encode acyl carrier proteins (ACPs) (e.g., ereT, ceuT, mfoT).

TABLE 1

Non-limiting examples of biosynthetic enzymes from human gut microbiome-derived bacterium.

| Enzyme | Gene | Source | Nucleotide Sequence | Amino Acid Sequence |
| --- | --- | --- | --- | --- |
| Sfp synthase | sfp | *B. subtilis* | ATGAAGATTTACGGAATTTA TATGGACCGCCCGCTTTCACA GGAAGAAAATGAACGGTTCA TGACTTTCATATCACCTGAAA AACGGGAGAAATGCCGGAGA TTTTATCATAAAGAAGATGCT CACCGCACCCTGCTGGGAGA TGTGCTCGTTCGCTCAGTCAT AAGCAGGCAGTATCAGTTGG ACAAATCCGATATCCGCTTTA GCACGCAGGAATACGGGAAG CCGTGCATCCCTGATCTTCCC GACGCTCATTTCAACATTTCT CACTCCGGCCGCTGGGTCATT GGTGCGTTTGATTCACAGCC GATCGGCATAGATATCGAAA AAACGAAACCGATCAGCCTT GAGATCGCCAAGCGCTTCTTT TCAAAAACAGAGTACAGCGA | MKIYGIYMDRPLSQEENE RPMTFISPEKREKCRRFY HKEDAHRTLLGDVLVRS VISRQYQLDKSDIRFSTQE YGKPCIPDLPDAHFNISHS GRWVIGAFDSQPIGIDIEK TKPISLEIAKRFFSKTEYS DLLAKDKDEQTDYFYHL WSMKESFIKQEGKGLSLP LDSFSVRLHQDGQVSIEL PDSHSPCYIKTYEVDPGY KNIAVCAAHPDFPEDITM VSYEELL (SEQ ID NO: 84) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | CCTTTTAGCAAAAGACAAGG ACGAGCAGACAGACTATTTT TATCATCTATGGTCAATGAA AGAAAGCTTTATCAAACAGG AAGGCAAAGGCTTATCGCTT CCGCTTGATTCCTTTTCAGTG CGCCTGCATCAGGACGGACA AGTATCCATTGAGCTTCCGG ACAGCCATTCCCCATGCTATA TCAAAACGTATGAGGTCGAT CCCGGCTACAAAATGGCTGT ATGCGCCGCACACCCTGATTT CCCCGAGGATATCACAATGG TCTCGTACGAAGAGCTTTTAT AA (SEQ ID NO: 82) | |
| 4'-phosphopantetheinyl transferase | cceP C. celatum | ATGAGCATTCTGCAGCCGTA CAAATACAAGATCTTCTATA AACAAATCCCGCTGAAAAAG GGCATCAGCAAACTGGAACA GAACAAAATTATGCATGATG CCGGTATTAACCTGCTGGAT GAAAAACTGGAAGAAATCTT CAACGTGAAAAACGCACGTG AAAACTATTGTAGCAGCCTG AATGGTAAACCGTATCTGAA AAATAGCAGCATCAACTTCA ACATCAGCCACTGCAATAAC ATTGTGGTGGTGATTATCAGC AATAAGAACGTGGGCATTGA TATCGAGGATATCAAAGAGT TCAAAAAAAGCATCATCCGC AAAGTGCTGACCAACAATGA ACTGATTGATCTGCTGAGCG CCAACAACAAAAAAGAGTAT TTTTTCAAACTGTGGACCCTG AAAGAGAGCTTTCTGAAAGC CATTGGCACCGGTCTGAGCT ATGGTATGCAGAATATTGAA TTCAGCATCAAAGACAAAAA CATTATCTGCAACAAGATCG GCTTCCTGTTCAAACAAGAA AGCCTGATCTTTAACAACAA CAAGTACATTGTGAGCATCA CCTGGGAAGTGTAA (SEQ ID NO: 32) | MSILQPYKYKIFYKQIPLK KGISKLEQNKIMHDAGIN LLDEKLEEIFNVKNAREN YCSSLNGKPYLKNSSINF NISHCNNIVVVIISNKNVG IDIEDIKEFKKSIIRKVLTN NELIDLLSANNKKEYFFK LWTLKESFLKAIGTGLSY GMQNIEFSIKDKNIICNKI GFLFKQESLIFNNNKYIVS ITWEV (SEQ ID NO: 68) |
| 4'-phosphopantetheinyl transferase | lclP L. clostridioforme | ATGATTTATCTGGCCACCTAT GAACCTGGTGGTAGCCTGTA TAATCGTGAACGTGAACATA TTCTGGGTCGTAGCCTGCTGA ATTTTGGTCTGATGAAAGAA TATGGTCGTACCTGGGAAGT TGAACAAGAAACCGGTAGCA AACCGTGTCTGAAAGGTGCA GAAGATGTGGAATTTAACAT TAGTCATACCCGTGGTCTGGT TGTTTGTGCAGTTGCAGATCG TGCACTGGGTGTTGATACCG AACGTATTCGTCCGTTTAAAG AAGGTCTGATGCGTCGTGTTT GTAGCGAAAGCGAACGTGGT TTTGTTCTGGAAGGTCGTAGC GAAGCAGCACGTCAAGAACG TTTTTTTCGTCTGTGGACCCT GAAAGAAAGCTTTGTTAAAG CCATTGGTCGCGGTCTGGCAT TTCCGCTGGGTGATATTACCT TTAGCCTGGAAGAAGGTGCA GTTAAAGGTAGCATTCCTGG TTGGCGTTTTTATCAGAGCCG TGTGTATCAGAGCTATATTAT CAGCGTTTGTGCCGCAGATG | MIYLATYEPGGSLYNRER EHILGRSLLNFGLMKEYG RTWEVEQETGSKPCLKG AEDVEFNISHTRGLVVCA VADRALGVDTERIRPFKE GLMRRVCSESERGFVLEG RSEAARQERFFRLWTLKE SFVKAIGRGLAFPLGDITF SLEEGAVKGSIPGWRFYQ SRVYQSYIISVCAADEKA VFAFTTGKLKVEGSLEKA LMLQKFV (SEQ ID NO: 67) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | AAAAAGCAGTTTTTGCATTTA CCACCGGCAAACTGAAAGTT GAAGGTAGTCTGGAAAAAGC ACTGATGCTGCAGAAATTTG TGTAA (SEQ ID NO: 31) | |
| acyl carrier protein | bprT B. producta | ATGTTCGAGAAACTGAAAGA CATGATCTGCGAATATGTGG AAGTGGATAAAAATGCCGTT ACCGAAAATAGCCGTTTTGTT GAAGATCTGGGTTTCACCAG CTATGATTTTATGAGCATGAT TGGCGAACTGGAAGAAACCT ATGATATCGAAGTTGAAGAA CGTCAGGCAGCAGAAATTCG TACCGTTGGTGAAGCAGTTC GTTATATTGAAAGCCTGCAG GATTAA (SEQ ID NO: 4) | MFEKLKDMICEYVEVDK NAVTENSRFVEDLGFTSY DFMSMIGELEETYDIEVE ERQAAEIRTVGEAVRYIE SLQD (SEQ ID NO: 40) |
| acyl carrier protein | cceT C. celatum | ATGCTGGAAAAACTGCGTGA ACTGCTGAGCGAATATGTTG AAGTTGCACGTGAAGATATT ACCGTGGAAAGCAAACTGGT TGAAGATCTGGGTCTGAACA GCTATGAATTTATGACCCTGG TTGGTGATCTGGAAGAGGAA TTTGATGTGGAAGTTAATGA ACGTGAAGTGGCCAAAGTTA ATACCATTGGCGATATCATC GAATACATTACCGCACTGCA GGTCTAA (SEQ ID NO: 5) | MLEKLRELLSEYVEVARE DITVESKLVEDLGLNSYE FMTLVGDLEEEFDVEVNE REVAKVNTIGDIIEYITAL QV (SEQ ID NO: 41) |
| acyl carrier protein | ceuT C. eutactus | ATGAACAACAACATCACCTT TCTGAACATCGTTGCCGAAT ATTGTAATACACCGGCAGAT GAAATTACCAACGATATGCG CTTTATTGAAGATCTGGGTTT TAGCAGCCTGGACTTTATGA CCTTTCTGGGTGATCTGGAAG ATACCTTTGATGTGGAAATC AACGAAGATGAGATCATCAA CATCCACACCATTGAAGATG CCATCAAATATCTGGATAAT CTGACCAGCAGCAGCGCAAG CGTTTAA (SEQ ID NO: 1) | MNNNITFLNIVAEYCNTP ADEITNDMRFIEDLGFSSL DFMTFLGDLEDTFDVEIN EDEIINIHTIEDAIKYLDNL TSSSASV (SEQ ID NO: 37) |
| acyl carrier protein | cspT Clostridiales sp. | ATGTTCGAGGAACTGAAAGA ACTGATCTGCGAATATGTTG ATGTTGATCCGAGCGCCATT AAAGAAGAAAGCCGTTTTAT TGAAGATCTGGGCTTCAACA GCTATGACTTTATGAGCATG GTTGGCGAAATCGAAGAAAC CTTTGATGTGGAAGTTGAAG AACGTGAAGTGGTGAATGTT AAAACCGTTAAAGATGCCGT GGAATATATCCAGAGCCTGC AGGATTAA (SEQ ID NO: 7) | MFEELKELICEYVDVDPS AIKEESRFIEDLGFNSYDF MSMVGEIEETFDVEVEER EVVNVKTVKDAVEYIQS LQD (SEQ ID NO: 43) |
| acyl carrier protein | ereT E. rectale | ATGTTCGATGAACTGGTGGA AATCATCTGCAATTATGTTGA TGTTCAGCCTGCCGATGTTCA TGAAGAAAGCCGTTTTATGG AAGATCTGGGTTTTACCAGCT TTGACTTTATGAGCATGCTGG GCGAAATTGAAGATACCTTT GATGTGGAAATCGAACAGAC CAAAGCAGCAGAAATTCGTA CCGTTCAAGAAGCAGTTGAT TATCTGGAAACCCTGAAAGA TGCCTAA (SEQ ID NO: 8) | MFDELVEIICNYVDVQPA DVHEESRFMEDLGFTSFD FMSMLGEIEDTFDVEIEQ TKAAEIRTVQEAVDYLET LKDA (SEQ ID NO: 44) |

TABLE 1-continued

Non-limiting examples of biosynthetic enzymes from human gut microbiome-derived bacterium.

| Enzyme | Gene Source | Nucleotide Sequence | Amino Acid Sequence |
| --- | --- | --- | --- |
| acyl carrier protein | lclT *L. clostridioforme* | ATGTTCGAGGAACTGAAAGA AATCATCTGCGAATATGTTG ATGTTGCACCGGAAACCATT AAAGAAAACAGCCGCTTTAT TGAAGATCTGGGCTTTAACA GCTATGATTTCATGAGCATG GTGGGCGAAATCGAAGAAAA ATTTGATGTGGAAGTGGAAG AACGCGAAGTGGTTAATGTT AAAACCGTTAAAGATGCCGT GGATTATATTCAGAGTCTGC AGGCAGAATAA (SEQ ID NO: 3) | MFEELKEIICEYVDVAPET IKENSRFIEDLGFNSYDFM SMVGEIEEKFDVEVEERE VVNVKTVKDAVDYIQSL QAE (SEQ ID NO: 39) |
| acyl carrier protein | mfoT *M. formatexigens* | ATGACCCAAGAGATGCAGTT TAAAACCATTGCAGCACAGT ATTGTGGTGTGAAACCGGAA GATATGACCAATGATATGCG TTTTCGTGAAGATCTGGGTT TAGCAGCCTGGATTTTATGA GCTTTCTGGGTGAACTGGAA GATACCTTTGATGTTGAGCTG GAAGAAGAAGAGGTTGTTAA AATTCTGACCGTTGCAGAAG CACTGGCACTGCTGGAAAAA CTGCAAGAAGAATAA (SEQ ID NO: 2) | MTQEMQFKTIAAQYCGV KPEDMTNDMRFREDLGF SSLDFMSFLGELEDTFDV ELEEEEVVKILTVAEALA LLEKLQEE (SEQ ID NO: 38) |
| acyl carrier protein | rbaT *R. bacterium* | ATGTTCGAGAAACTGGTGGA AATCATCTGCAATTATGTTGA AGTTGAGCCGGAAAAAATCA CCAGCGATAGCCGTTTTATG GAAGATCTGGGTTTTACCAG CTTTGACTTTATGAGCATGCT GGGCGAAATTGAAGATACCT TTGATATCGAAGTGGATGAA ACGGAAGTGGTGAAAATTCG TACCGTTGGTGAAGCCGTTG ATTATATTCAGAGCCTGGCA GATTAA (SEQ ID NO: 6) | MFEKLVEIICNYVEVEPE KITSDSRFMEDLGFTSFDF MSMLGEIEDTFDIEVDET EVVKIRTVGEAVDYIQSL AD (SEQ ID NO: 42) |
| acyl-CoA thioester hydrolase | ceuA *C. eutactus* | ATGGAAGAGAACATTCTGGA AATCGTGGAAAAAGCTGTC GCATTCATCGTGATGTTATCG CCGTTAAATATCTGAGCCATC GTGAGATTGTTGAGAAAAGC TATGGTGATATGTGGGATGA TATTCGTAAAACCGCAGTGA TTCTGCGTAATAATGGTCTGT GTGGCACCCATATTGCACTG GTTGGTAGCAGCAGCTATGA ATGGATTTGTGCATATATGGC CATTCTGTTTACCGGCAATAC CGCAGTTCCGCTGGATGCAA ATCTGAGCGTTAGCGAACTG CATGAACTGCTGAATCGTAG CGGTAGCATTGCACTGTTTTG TGGTGCAAGCCGTAAAGATG TTATTACCGAACTGACCGAT GATTGTCCGGAAATGAATAT TGTGTTCACCATGGAAAAAA AAGTGGACATCGAACATCTG GAAGGTGCAGATAGCAATCC GCAGCTGGCAATTCTGAGCT TTGAACAGCTGCGTAATGAA ATTACCATTCCGGATGATTTT GCATTCGCCGATCAGGATAA AGATAAAATGTGTACCCTGA TGTATACCAGCGGCACCACC GGTAAAAGCAAAGGTGTTAT GCTGAGCCAGTTTAATCTGG CACAGAATGTTGAAAACGTG TACGTTAATCTGGAACCGGG TGTTACCATTCTGAGCGTGCT | MEENILEIVEKSCRIHRDV IAVKYLSHREIVEKSYGD MWDDIRKTAVILRNNGL CGTHIALVGSSSYEWICA YMAILFTGNTAVPLDANL SVSELHELLNRSGSIALFC GASRKDVITELTDDCPEM NIVFTMEKKVDIEHLEGA DSNPQLAILSFEQLRNEITI PDDFAFADQDKDKMCTL MYTSGTTGKSKGVMLSQ FNLAQNVENVYVNLEPG VTILSVLPIHHAFCLTME WMKGISLGATICINDSLL HMLKNMKRFQPVGMLM VPLMVETIYKKLKDVNPL LPKKLVAKEAFGGKLEYI FCGGAYLDPMYVTEFKK YGIDILQGYGMTECSPVIC SNNHRYNRPGSVGKLLD NCAVRFVDEEIQVKGTSV MSGYYDMPNETAEAFQD GWLCTGDLGYLDSDGFM YITGRKKNLIILANGENIS PEELEGKLSIEPLISEIVITG DGNHLTAHIYPDQDFVD KKHMDAARTSEKLQKII D TFNKNQPTYKRISALDIR KEPFEKSSTKKIKRNLV (SEQ ID NO: 53) |

TABLE 1-continued

Non-limiting examples of biosynthetic enzymes from human gut microbiome-derived bacterium.

| Enzyme | Gene | Source | Nucleotide Sequence | Amino Acid Sequence |
|---|---|---|---|---|
| | | | GCCGATTCATCATGCATTTTG<br>TCTGACCATGGAATGGATGA<br>AAGGTATTAGCCTGGGTGCA<br>ACCATTTGCATTAATGATAGC<br>CTGCTGCACATGCTGAAAAA<br>CATGAAACGTTTTCAGCCGG<br>TTGGTATGCTGATGGTTCCGC<br>TGATGGTGGAAACCATTTAC<br>AAAAAACTGAAAGATGTGAA<br>TCCGCTGCTGCCGAAAAAAC<br>TGGTTGCAAAAGAAGCATTT<br>GGCGGTAAACTGGAATATAT<br>CTTTTGCGGTGGTGCATATCT<br>GGATCCGATGTATGTTACCG<br>AGTTTAAAAAGTATGGCATC<br>GATATCCTGCAAGGTTATGG<br>TATGACCGAATGTAGTCCGG<br>TTATTTGCAGCAATAATCACC<br>GTTATAATCGTCCGGGTAGC<br>GTTGGTAAACTGCTGGATAA<br>TTGTGCAGTTCGTTTTGTGGA<br>TGAAGAGATTCAGGTTAAAG<br>GCACCAGCGTTATGAGCGGT<br>TATTATGATATGCCGAACGA<br>AACAGCCGAAGCATTTCAGG<br>ATGGTTGGCTGTGTACCGGT<br>GATCTGGGTTATCTGGATAGT<br>GATGGCTTTATGTATATTACC<br>GGTCGCAAAAAGAACCTGAT<br>TATTCTGGCCAATGGCGAAA<br>ACATTAGTCCGGAAGAACTG<br>GAAGGTAAACTGAGTATTGA<br>ACCGCTGATTAGCGAAATTG<br>TGATTACAGGTGATGGTAAT<br>CATCTGACCGCACATATTTAT<br>CCGGATCAGGATTTCGTGGA<br>CAAAAAACACATGGATGCAG<br>CACGTACCAGCGAAAAACTG<br>CAGAAAATTATCGACACCTT<br>CAACAAAAATCAGCCGACCT<br>ATAAACGTATTAGCGCACTG<br>GATATTCGCAAAGAACCGTT<br>TGAAAAAAGCAGCACCAAAA<br>AGATTAAACGCAACCTGGTG<br>TAA (SEQ ID NO: 17) | |
| acyl-CoA thioester hydrolase | mfoA | M. formatexigens | ATGCTGATTCGCGATATTATT<br>GAAGAAAGCGGCAAAAAAT<br>ACGCAGGCATTACCGCAATT<br>AAATGGCTGAAAAAGAAAGA<br>AATCATGGAAATGAGCTATC<br>GCGAACTGCTGGAAAATGCA<br>GCAGCCGTTCGTCGTGGTCTG<br>CTGGCCGAAGGTTTTGCCGG<br>TGCACATCTGGCACTGATTG<br>GTAGCAGCAGCGCAGAATGG<br>GTTGAAAGCTATCTGGGTATT<br>ATTACCGGCAATACCGTTGC<br>AGTTCCGCTGGATGCAAATC<br>TGCCTGGTGAAGATCTGGTT<br>GATCTGCTGAATCGTAGTGA<br>TGCAGCAGGTCTGTTTCTGAG<br>CACCAAACAGAAAGGCCTGC<br>TGGGTCAGATTCTGGATGAA<br>TGTCCGAAACTGAAAAAAAT<br>CTGGATGCTGGAAGATGCCG<br>TTGAACCGGGTAATGCAAGC<br>GGTGCAGAAGTTACCAGCCT<br>GGCAGATCTGAAAGCAGCCG<br>GTGCAGGTAGCGTTGCAGAT<br>GCAGATCGTCCGGATCCTGA<br>AAGCATTGCAACCATTATCTT | MLIRDIIEESGKKYAGITA<br>IKWLKKKEIMEMSYRELL<br>ENAAAVRRGLLAEGFAG<br>AHLALIGSSSAEWVESYL<br>GIITGNTVAVPLDANLPG<br>EDLVDLLNRSDAAGLFLS<br>TKQKGLLGQILDECPKLK<br>KIWMLEDAVEPGNASGA<br>EVTSLADLKAAGAGSVA<br>DADRPDPESIATIIFTSGTT<br>GKSKGVMLTQKNLAENV<br>KSVQYTAEPGSVLLSVLPI<br>HHAFCLVMDWLKGFSLG<br>TTVCINDSLLHMVKNMG<br>VFQPQVMLMVPLMVETI<br>YKRLAGADASIPKQMVA<br>KAVFGGRLHTIFTGGAHL<br>DPYYIDRFAEYGVEVLEG<br>YGMSECSPVISSNTPEDH<br>KKGSVGRPLPNVELSFDN<br>GEILVRGSSVMKGYYQM<br>PQETADTLKDGWLHTGD<br>KGYLDEDGPLFINGRVKN<br>LIILSNGENISPEEIENKLA<br>LGALVGEVIVTGENNGLT<br>ARIYPDPDVVAAKGMDA |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | TACCAGCGGCACCACCGGTA AAAGCAAAGGTGTTATGCTG ACCCAGAAAAACCTGGCCGA AAATGTTAAAAGCGTTCAGT ATACCGCAGAACCGGGTTCA GTTCTGCTGAGCGTTCTGCCG ATTCATCATGCATTTTGTCTG GTTATGGATTGGCTGAAAGG TTTTAGCCTGGGTACAACCGT TTGTATTAATGATAGCCTGCT GCACATGGTGAAAAATATGG GTGTGTTTCAGCCGCAGGTA ATGCTGATGGTTCCGCTGATG GTGGAAACCATCTATAAACG TCTGGCAGGCGCAGATGCAA GCATTCCGAAACAAATGGTT GCCAAAGCAGTTTTTGGTGG TCGTCTGCATACCATTTTTAC AGGTGGCGCTCATCTGGATC CGTATTATATCGATCGTTTTG CCGAATATGGTGTGGAAGTT CTGGAAGGTTATGGTATGAG CGAATGTAGTCCGGTTATTA GCAGCAATACACCGGAAGAT CATAAAAAAGGTAGCGTGGG TCGTCCGCTGCCGAATGTTGA ACTGAGCTTTGATAATGGTG AAATTCTGGTTCGTGGTTCCA GCGTTATGAAAGGTTATTATC AGATGCCGCAAGAAACCGCA GATACCCTGAAAGATGGTTG GCTGCATACCGGTGATAAAG GTTATCTGGATGAGGATGGT TTTCTGTTTATTAACGGTCGC GTGAAGAACCTGATTATTCT GAGCAATGGCGAAAACATTA GTCCGGAAGAAATCGAAAAT AAACTGGCACTGGGTGCACT GGTTGGTGAAGTTATTGTTAC CGGTGAAAATAATGGTCTGA CCGCACGTATTTATCCTGATC CGGATGTTGTTGCAGCAAAA GGTATGGATGCAGAAGCAGT TCAGACCGAACTGCAGGCAT TTCTGGATCAGTACAATAAA ACCCAGCCGAGCTATCGTCA GATTACCGGTCTGGTTGTTCG TAAAAATCCGTTTATCAAAA GCGCGACCCGTAAAATCAAA CGTCAAGAGGTTCTGGTGGA TGAACCGTGTGCATAA (SEQ ID NO: 18) | EAVQTELQAFLDQYNKT QPSYRQITGLVVRKNPFIK SATRKIKRQEVLVDEPCA (SEQ ID NO: 54) |
| alpha/beta hydrolase | bprH B. producta | ATGAATGGTTGGAGCCTGCT GTTAGGTGCCGGTGCACTGG CAGCAGCCGGTGAATATGGT ATTGCAAGCTATTTTTCCGT CGTACCATGCTGCGTCAGAA TGCAGCAACCAAACGTACCA TGGATATGGCAGGTACAAAT TGGGATCTGTATATTCCGGA AATCGGCAAAATGAAACAGT GGATGCTGGAACAAGAACGC GAAGATGTTTATATTCGTAGC GGTGATGGTCTGAAACTGCA TGGCACCTATTTTCCAGGTCA AGGTAGCGGTAAACTGGTGA TTTGTTTTCATGGTTATACCA GCAAAGGCATGAGCGATTAT ATTGGTCTGAGCAACTATTAT CTGCCTCGTGGTTATCAGATG CTGCTGGTTGATGAACGTGC ACATGGTGATAGCGAAGGCA CCTATATTGGTTTTGGTTGTC TGGATCGTGAAGATGCACTG | MNGWSLLLGAGALAAA GEYGIASYFFRRTMLRQN AATKRTMDMAGTNWDL YIPEIGKMKQWMLEQER EDVYIRSGDGLKLHGTYF PGQGSGKLVICFHGYTSK GMSDYIGLSNYYLPRGY QMLLVDERAHGDSEGTY IGFGCLDREDALLWITYA VKRFGSGCQIWLHGTSM GASTVLMASGLKLPPQV RGIVSDCAFTTAWDVFA HVLKDQYHLPAYPILKLS DSMCRKKAGYGLKQCSA SEEVKRAKVPILFIHGDA DTFVPCRMCYEIYENCAS KKDMLIVHGAGHVEAFY KEQALYEQKLTEFLETAG EAWAPAGKSIYVSDVTG EGSTGDSVPV (SEQ ID NO: 62) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | CTGTGGATTACCTATGCAGTT AAACGTTTTGGTAGCGGTTGT CAGATTTGGCTGCATGGTAC AAGCATGGGTGCAAGCACCG TTCTGATGGCAAGCGGTCTG AAATTACCGCCTCAGGTTCGT GGTATTGTTAGCGATTGTGCA TTTACCACCGCATGGGATGTT TTTGCACATGTTCTGAAAGAT CAGTATCATCTGCCTGCATAT CCGATCCTGAAACTGAGCGA TAGCATGTGTCGTAAAAAAG CAGGTTATGGCCTGAAACAA TGTAGCGCAAGCGAAGAAGT TAAACGCGCAAAAGTTCCGA TTCTGTTTATTCATGGTGATG CCGATACCTTTGTTCCGTGTC GTATGTGCTATGAAATCTATG AAAATTGCGCCAGCAAAAAA GACATGCTGATTGTTCATGGT GCAGGTCATGTTGAAGCCTT CTATAAAGAACAGGCACTGT ATGAACAGAAACTGACCGAA TTTCTGGAAACCGCAGGCGA AGCATGGGCACCAGCAGGTA AAAGCATTTATGTTAGTGAT GTTACCGGTGAAGGTAGCAC CGGTGATAGTGTTCCGGTTTA A (SEQ ID NO: 26) | |
| alpha/beta hydrolase | cceH C. celatum | ATGAGCAAACGCCTGTTTATT GGTGCAGGTATTATTGGTCTG GCAGCACTGACCGAAGTTGT TATGGCACGTTATCTGCTGGA ACGTGTTCTGATTCGTAAAA ACGTTAAAACCGAACGCACC CAGAAAATGAGCGGTACAAA TTGGGATAACTATATCCCGTT TATCAAAGAACGTAAAGCAT GGCTGATGCTGCAAGAACGT GAAGATGTGTATATTACCAG TGATGATGGTCTGCGTCTGCA TGGTGTTCTGGTTCCGAATGA AAATAGCAAAAAAACCGTGA TCTGCTTCCATGGCTATAGCA GCAAAGGTGCAACCAGCGAT TTTGCAGCAATTAGCAAATTC TACAAAGAGAACGACTTTAA CATCCTGATGGTTGATGCAC GTGCCCATGGTGAAAGTGAT GGCAAATATATCGGTTTTGGT TGTCTGGATCGTATGGATGTT CTGAAATGGATTAACTACGT GGTGGAAAAATTTGGCGAAG AATGTCAGATTCTGCTGCATG GTATTAGCATGGGTGGTGCA ACCGTGGTTATGGCAAGCGG TCTGCATCTGCCGAATAATGT GAAATTTATCATTAGCGATTG CGCCTTTACCAGTCCGTGGG AAGTTTTTAGTGATGTGCTGA AAAACATGTATCACATTCCG CCTTTTCCGGTGATTAACATT GTTAGCAACATGTGCAAAAA GATGGCAGGCTACAACTTTA AAGAATGCAACGCCGATATT GAAGTTCGTCGTGCCACCGTT CCGATTCTGTTTATTCATGGT GCAAATGATACCTTTGTTCCG TGTCGTATGTGCCACGATATT TATGATAATTGCCACAGCGA TAAAGAAATCCTGATTGTTA AGAAGCAGGTCACGCAGAG AGCTATTACAAAGAAACCGA AATCTACGAAGAAAACATCA | MSKRLFIGAGIIGLAALTE VVMARYLLERVLIRKNV KTERTQKMSGTNWDNYI PFIKERKAWLMLQERED VYITSDDGLRLHGVLVPN ENSKKTVICFHGYSSKGA TSDFAAISKFYKENDFNIL MVDARAHGESDGKYIGF GCLDRMDVLKWINYVVE KFGEECQILLHGISMGGA TVVMASGLHLPNNVKFII SDCAFTSPWEVFSDVLKN MYHIPPFPVINIVSNMCK KMAGYNFKECNADIEVR RATVPILFIHGANDTFVPC RMCHDIYDNCHSDKEILI VKEAGHAESYYKETEIYE ENIKKFISKYILDEIGAGN NDKRKRY (SEQ ID NO: 63) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | AAAAATTCATCAGCAAATAC<br>ATCCTGGATGAAATTGGCGC<br>AGGCAATAACGATAAACGCA<br>AACGCTATTAA (SEQ ID NO: 27) | |
| alpha/beta hydrolase | cspH Clostridiales sp. | ATGGGTAAAATTGGTCTGCT<br>GTTTGGTCTGGCAGCAGCCG<br>GTGCAGCGGGTGAATATGGT<br>ATTGCACGTTATTTCTTTCAT<br>CGTACCGTTGTTCGTGGTAAT<br>GCAAAACGTGAACGTACCCA<br>GAAAATGGCAGGCACCGATT<br>GGGATGCATATATTCCGGGT<br>ATTCGTGCAAGCAAAGAATG<br>GCTGAGCGGTAAACCGCAAG<br>AAGATGTGTATATTACCAGT<br>GATGATGGTCTGCGTCTGCAT<br>GGCACCTTTTTCCGTGTCCG<br>GGTAGCGATCGTGCAGTTAT<br>TTGTTTTCATGGTTATACCAG<br>CGAAGGCCTGAATGATTTTA<br>GCAGCATTGCCCGTTTTTATC<br>TGGAACAGGGTTTTAATCTG<br>ATGGTGGTTGATGAACGTGC<br>ACATGGTCGTAGCGAAGGCA<br>CCTATATTGGTTTTGGTTGTC<br>TGGATCGTATGGATGCACGT<br>CTGTGGATTGAATATGTGATT<br>GAACGTCTGGGTCAAGATTG<br>TCAGGTTATGCTGCATGGTAT<br>TAGCATGGGTGGTGCAACCG<br>TTCTGATGACCACCGGTCTGA<br>GCCTGCCTCCGCAGGTTAAA<br>GCAGCAGTTAGCGATTGTGG<br>TTTTACCAGTGCATGGGAAG<br>TTTTTAGCTATGTGCTGAAAA<br>GCATGTATCACATGCCACCG<br>TTTCCGATTATGCAGATTGCA<br>GATCGCATGGCACGTCAAGA<br>GGCAGGTTATGGTCTGGATC<br>AGTGTAATGCACGTGATGAA<br>GTTAAAAAAGCCCGTATTCC<br>GATCCTGTTTATTCATGGTGA<br>TGCAGATACCTTTGTGCCGTG<br>TAGCATGGTTTATCAGCTGTA<br>TGGTGCATGTCGTAGCGGTA<br>AAGAACTGCTGGTTATTAGC<br>GGTGCAGCACATGCAGAAGC<br>ATATTACAAAGATACCAAAA<br>GCTATGAACGCGCAGTTACC<br>GAACTGATTGGTCGTACCATT<br>GAACCGCTGGGTGATCGTCA<br>TGAAGGTCGTGATAGCCGTG<br>ATGAAAAAGGTGAATAA<br>(SEQ ID NO: 29) | MGKIGLLFGLAAAGAAG<br>EYGIARYFFHRTVVRGNA<br>KRERTQKMAGTDWDAYI<br>PGIRASKEWLSGKPQEDV<br>YITSDDGLRLHGTFFPCPG<br>SDRAVICFHGYTSEGLND<br>FSSIARFYLEQGFNLMVV<br>DERAHGRSEGTYIGFGCL<br>DRMDARLWIEYVIERLG<br>QDCQVMLHGISMGGATV<br>LMTTGLSLPPQVKAAVSD<br>CGFTSAWEVFSYVLKSM<br>YHMPPFPIMQIADRMARQ<br>EAGYGLDQCNARDEVKK<br>ARIPILFIHGDADTFVPCS<br>MVYQLYGACRSGKELLV<br>ISGAAHAEAYYKDTKSYE<br>RAVTELIGRTIEPLGDRHE<br>GRDSRDEKGE (SEQ ID NO: 65) |
| alpha/beta hydrolase | ereH E. rectale | ATGCGTATGAAATGGGGTAT<br>TATTGCCGGTGTTTTAGGTGG<br>TATTGCAGCAGCCGAAGCCG<br>GTGGTAGCGCATATTTCTATC<br>GTCGTACCATGATGCGTTAC<br>AACGCAAAAAAGAACGCAC<br>CATGAAAATGAGCGGTGTTG<br>ATTGGGAAAGCTATTACAGC<br>TTTATGAAACCGCATGGTGA<br>ATGGATGCGTGCACAGACCC<br>ATGAAGATGTTTGGATTAAA<br>AGTGATGATGGTCTGCGTCT<br>GCATGCAACCTATTTTCCGGG<br>TATTGATGGTGGTAATCCGG<br>ATAAAGCAGTGATTTGCTTTC | MRMKWGIIAGVLGGIAA<br>AEAGGSAYFYRRTMMRY<br>NAKKERTMKMSGVDWE<br>SYYSFMKPHGEWMRAQT<br>HEDVWIKSDDGLRLHAT<br>YFPGIDGGNPDKAVICFH<br>GYTSEAMSDYSSISNYYL<br>KKGYSMLLVDARAHGQS<br>EGKFIGFGCKDRYDALK<br>WIDWMIKKAGNGIRIVL<br>MGNSMGGATVLMASGL<br>NLPEQVKGIVSDCAFTSP<br>KAVFTHVLHSMYHLPAF<br>PMIQIADFVNRKMAGYG<br>LDECNAAKEVQKAKLPIL |

TABLE 1-continued

Non-limiting examples of biosynthetic enzymes from human gut microbiome-derived bacterium.

| Enzyme | Gene Source | Nucleotide Sequence | Amino Acid Sequence |
| --- | --- | --- | --- |
| | | ATGGTTATACCAGCGAAGCA<br>ATGAGCGATTATAGCAGCAT<br>TAGCAACTACTACCTGAAAA<br>AAGGTTATAGCATGCTGCTG<br>GTTGATGCACGTGCCCATGG<br>TCAGAGCGAAGGCAAATTTA<br>TCGGTTTTGGTTGCAAAGATC<br>GTTACGATGCACTGAAATGG<br>ATTGACTGGATGATCAAAAA<br>AGCCGGTAATGGTATTCGTA<br>TTGTGCTGATGGGTAATAGC<br>ATGGGTGGTGCAACCGTTCT<br>GATGGCAAGCGGTCTGAATC<br>TGCCGGAACAGGTTAAAGGT<br>ATTGTTAGCGATTGTGCATTT<br>ACCAGTCCGAAAGCAGTTTT<br>TACCCATGTTCTGCATAGCAT<br>GTATCATCTGCCTGCATTTCC<br>GATGATTCAGATTGCCGATTT<br>TGTGAATCGTAAAATGGCAG<br>GTTATGGTCTGGATGAATGT<br>AATGCAGCAAAAGAAGTTCA<br>GAAAGCCAAACTGCCGATTC<br>TGTTTATTCATGGCGATAAAG<br>ATACCTTTGTTCCGTGTAGCA<br>TGTGTGATGAACTGTATGCA<br>AGCTGTGCAAGCCAGAAAAC<br>AAAACTGATTGTTAAAGGTG<br>CCGGTCACTGCGAATCCTATT<br>ACAAAAATACCAAAGCCTTT<br>GAGGATGCCCTGGATAAATT<br>TCTGGAAGGTGTTATGCGTTA<br>A (SEQ ID NO: 30) | FIHGDKDTFVPCSMCDEL<br>YASCASQKTKLIVKGAG<br>HCESYYKNTKAFEDALD<br>KFLEGVMR (SEQ ID NO:<br>66) |
| alpha/beta<br>hydrolase | 1c1H *L.*<br>*clostridioforme* | ATGGGTATTAAAGGCTGGAT<br>TCTGGGTTTAGCAGCAGCCG<br>GTGCAGCGGGTGAATATGGT<br>ATTGCACGTTATTTCTTTCAT<br>CGTACCGTTGTTCGTGGTAAT<br>GCAAAACGTGATCGTACCCG<br>TAAAATGGCAGGCACCGATT<br>GGGATGCATATATTCCGGGT<br>ATTCGTGCAAGCCGTGAATG<br>GCTGGCAGGTCAGCCGCAAG<br>AAGAAGTGTATATTACCAGC<br>CGTGATGGTCTGCGTCTGCAT<br>GGCACCTTTTTTTGTTGTGAA<br>GGTAGCGGTAAAGCCGTTGT<br>TTGTTTTCATGGTTATACCAG<br>CGAAGGCCTGAATGATTATA<br>CCAGTATTGCCAAATTCTATC<br>TGAGCCAGGGTTTTAGCCTG<br>ATGGCAGTTGATGAACGTGC<br>ACATGGTAAAAGCGAAGGCA<br>CCTATATTGGTTTTGGTTGTC<br>TGGATCGTAATGATGCAAAA<br>CAGTGGATGGAATACATGGT<br>TGAACGTCTGGGTGAAGATT<br>GTGAACTGATGCTGCATGGT<br>ATTAGCATGGGTGCAGCAAC<br>CGTTCTGATGAGCACCGGTCT<br>GAATCTGCCGAAACAGGTTC<br>GTGCAGCAGTTAGCGATTGT<br>GCATTTACCAGCGCATGGGA<br>AGTTTTTAGCCATGTTCTGCG<br>TAGCATGTATCACATGCCTGC<br>ATTTCCGGTTATGCAGATTGC<br>AGATCGTATGGCACGTAGCG<br>AAGCAGGTTATGGTCTGGAT<br>GAATGTAATGCACGTGAAGA<br>AGTTAAAAAAGCCCGTATTC<br>CGATCCTGTTTATTCATGGTG<br>ATCGTGATACCTTTGTTCCGT<br>GTAGCATGGTTTATGAACTGT<br>ATGAAGCATGTGCAAGCCCG | MGIKGWILGLAAAGAAG<br>EYGIARYFFHRTVVRGNA<br>KRDRTRKMAGTDWDAYI<br>PGIRASREWLAGQPQEEV<br>YITSRDGLRLHGTFFCCE<br>GSGKAVVCFHGYTSEGL<br>NDYTSIAKFYLSQGFSLM<br>AVDERAHGKSEGTYIGFG<br>CLDRNDAKQWMEYMVE<br>RLGEDCELMLHGISMGA<br>ATVLMSTGLNLPKQVRA<br>AVSDCAFTSAWEVFSHV<br>LRSMYHMPAFPVMQIAD<br>RMARSEAGYGLDECNAR<br>EEVKKARIPILFIHGDRDT<br>FVPCSMVYELYEACASPK<br>ELLVIPGASHAEAYYKEA<br>DRYEHAIEELIARFFGKEE<br>NKV (SEQ ID NO: 61) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | AAAGAACTGCTGGTGATTCC GGGTGCAAGCCATGCCGAAG CATACTATAAAGAAGCAGAT CGTTACGAACATGCCATCGA AGAACTGATTGCCCGTTTTT TGGCAAAGAAGAGAACAAA GTCTAA (SEQ ID NO: 25) | |
| alpha/beta hydrolase | rbaH R. bacterium | ATGGGCCTGCTGAAAAAAGC AGCAGTTCTGGCAGGTCTGG CAGCAGCAGCCGAAGGTCTG GGCACCGCATATTTCTATCGT CGTACCATGATTCGTACCAAT GCAAAACCGGAACGTAGCGC AAAAATGAGCGGTATTGATT GGAGCCAGTATTATCCGCGT ATGCATGAAAATCGTGATTG GCTGCTGCAACAGCCGCATG AAGAAGTTGGTATTCTGAGC CATGATGGTCTGAAACTGCA TGGCACCTATTTTCCAGGTCC GGGTAATAAAGTTGTGATTT GCTTTCATGGCTATACCAGCT ATGGTATGGGTGAATATCCG AGCCTGGCACGTTGTTTTATG AGCCGTGGTTTTGGTGCACTG ATTATTGATCAGCGTAGCCAT GGTGAAAGCGAAGGCAAATA TATCGGTTTTGGTTGTATGGA TCGTCTGGATGCACTGGAAT GGATTCGTTGGACCATTGAT AAAGTTGGTCAGGATGCACA GATTATTCTGCATGGTGGTAG CATGGGTGGTGCAACCGTTT GTATGGTTAGCGGTCTGGAT CTGCCTCCGCAGGTTAAAGG TATTATTAGCGATAGCGCATT TACGAGCCCGAAATATGTTTT TACCCATGTTCTGCACAGCAT GTATCATCTGCCTGCAACACC GATGATTCCGCTGGCAGATA AAGTTAATAAACGCCTGGCA GGTTATGGTCTGGATGATTGT AATGCAGCACGTGAAGTTCG TAAAGCAAAAGTTCCGATGC TGTTTATTCATGGCAGCAAA GATACCTTTGTTCCGCCTTAT ATGTGTGATGAACTGTATGA AAATTGTGCCGCACCGAAAA CCAAACTGATTGTTGAAGGT GCAGGTCATGTTGAGAGCTA TTACAAAAACACCCAAGAAT ATGAAGAGGCCCTGGATAAA TTCATTGGTGGCATCATCAAA TAA (SEQ ID NO: 28) | MGLLKKAAVLAGLAAA AEGLGTAYFYRRTMIRTN AKPERSAKMSGIDWSQY YPRMHENRDWLLQQPHE EVGILSHDGLKLHGTYFP GPGNKVVICFHGYTSYG MGEYPSLARCFMSRGFG ALIIDQRSHGESEGKYIGF GCMDRLDALEWIRWTID KVGQDAQIILHGGSMGG ATVCMVSGLDLPPQVKGI ISDSAFTSPKYVFTHVLHS MYHLPATPMIPLADKVN KRLAGYGLDDCNAAREV RKAKVPMLFIHGSKDTFV PPYMCDELYENCAAPKT KLIVEGAGHVESYYKNT QEYEEALDKFIGGIIK (SEQ ID NO: 64) |
| AMP-binding protein | cceA C. celatum | ATGAACAACATCAAAAACAT GCGCGACATCATTGATTTCGC AGCCAAAAACTATGGCGATA ATATCGCGTTCAAGTATAAA ATCAACAAAAACGAAGTGGA TGAAAAAAGCTATAACGATC TGAAAAACGATAGCGAAGCA GTTAGCAATGCACTGAAAAG CCTGAATATGATTGGTAAAC ATGTTGCCATTGTTGGCCAGA CCAGCTATCCGTGGATTGTTA GCTATTTTGGTGTTGTTAATA GCGGTGGTGTTATTGTTCCGA TTGATGTTCAGCTGCCTGCAG ATGATATTTGCGAACTGATTG AACGTAGTGATGCCGAAATT CTGATCTATGATGAAATTCGT CATGATGTGGCCGAACGCAT TAAAGAAAAAAGCCACAACG | MNNIKNMRDIIDFAAKNY GDNIAFKYKINKNEVDEK SYNDLKNDSEAVSNALK SLNMIGKHVAIVGQTSYP WIVSYFGVVNSGGVIVPI DVQLPADDICELIERSDAE ILIYDEIRHDVAERIKEKS HNVKYIISMNEKLNTEFA LSLNELMAENRSSFHIEID EEKLCTILFTSGTTGKSKG VMLNHRNLTDNAIAFDV QLKAGTVSMTVLPINHVF CFTMDILKGIHLGLCICIN DSVMRVLKNLKLFKPQV MCLVPMIIESLYNKLIDES KDICKEVVAKVALGGNL KTIYSGGAYLNPEIIDGM NDFGIEVIQGYGMTECSP VISTNNNCEFKRESVGKLI |

TABLE 1-continued

Non-limiting examples of biosynthetic enzymes from human gut microbiome-derived bacterium.

| Enzyme | Gene | Source | Nucleotide Sequence | Amino Acid Sequence |
|---|---|---|---|---|
| | | | TGAAGTACATCATCAGCATG AATGAAAAACTGAACACCGA ATTTGCACTGAGCCTGAATG AACTGATGGCAGAAAATCGT AGCAGCTTTCATATCGAAAT CGACGAAGAAAAACTGTGCA CCATTCTGTTTACCAGCGGCA CCACCGGTAAAAGCAAAGGT GTTATGCTGAATCATCGTAAC CTGACCGATAATGCCATTGC ATTCGATGTGCAGCTGAAAG CAGGCACCGTTAGCATGACC GTTCTGCCGATTAATCATGTT TTTTGCTTCACCATGGATATC CTGAAAGGTATTCATCTGGG TCTGTGCATTTGCATTAATGA TAGCGTTATGCGCGTGCTGA AAAATCTGAAACTGTTTAAA CCGCAGGTTATGTGTCTGGTG CCGATGATTATTGAAAGCCT GTATAACAAACTGATCGACG AGAGCAAAGATATCTGCAAA GAAGTTGTTGCCAAAGTTGC CTTAGGTGGTAATCTGAAAA CCATTTATAGTGGTGGTGCAT ATCTGAACCCGGAAATTATT GATGGCATGAACGATTTTGG CATCGAAGTGATTCAAGGTT ATGGTATGACCGAATGTAGT CCGGTTATTAGCACCAACAA TAACTGCGAATTCAAACGTG AAAGCGTGGGCAAACTGATT AGTAATTGTGAAGCCAAAAT CATTGATGAAGAGATTTGGG TTCGTGGTAGCAGCGTTATG ATGGGTTATTACAAAATGCC GAAAGAAACCGAAGAGGCA CTGGTTGATGGTTGGCTGAA AACCGGTGATCTGGGTTATA TCGATGAAGATAACTTTGTGT TTATCACCGGTCGCAAAAAG AACCTGATTATTCTGAGCAAT GGCGAAAATGTTAGTCCGGA AGAACTGGAAAATGAGCTGA GCAAAAGCCGTCTGATCAAA GAAATTCTGGTGAGCGAGTA CAAGAACATCATTAAAGCGG AAATTCTGCCGGATTATGAG TATGCCAATAACAACGGCAT TAACGATATCGAAAACGAAA TTCGCAATCTGGTGGACAAA TATAACTGTGAACTGCCGAC CTATAAACGCATTGGTATGG TTATTATTCGCGATACCGAAT TCGAAAAAACCACGAGCAAA AAAATCAAACGCGAGTACAC CAAAGTGTAA (SEQ ID NO: 21) | SNCEAKIIDEEIWVRGSSV MMGYYKMPKETEEALV DGWLKTGDLGYIDEDNF VFITGRKKNLIILSNGENV SPEELENELSKSRLIKEILV SEYKNIIKAEILPDYEYAN NNGINDIENEIRNLVDKY NCELPTYKRIGMVIIRDTE FEKTTSKKIKREYTKV (SEQ ID NO: 57) |
| condensation domain protein | cceC | C. celatum | ATGATCAAAGAGAAGGACAT CAAACTGTATCCGCTGACCG CAGCACAGAAACTGCACTTT TATACCCTGACCTATTGTCCG AAAAAACAGGTTCTGAATAT TGGCACCAGCCTGACCATTA AAGAAGATATCGATTTTGAA GTTCTGCGCGAAGCAGTTTAT CGTGCCTATGAACGTTGTGA AGCAATGCGTATTCGTTTTGT TCATGATGAAAGCGGTAACG TGATGCAGTATGTTGCAGAA AAAGAAACCCGCTATATCGA GTTTTTTGAATTCAGCCATTG GAAGGTTGAAGATGCCGAGA AAAAAATGCGTGAATGGACC | MIKEKDIKLYPLTAAQKL HFYTLTYCPKKQVLNIGT SLTIKEDIDFEVLREAVYR AYERCEAMRIRFVHDESG NVMQYVAEKETRYIEFFE FSHWKVEDAEKKMREW TETPFERENKPLNKVVMI SMPEGYKGIYLLVDHMT MDAQSLIVFMKDIIEIYCH LKYEGIPYPREMASYIEQI EKDLTYELGNKAKERDE KFFKELIECKEPIFNDIEG KERLRLERLQRDSENLRS VINTSNNVDANITIFNLEA HPSHLLERFCEENKIPMV CLLIMGLRTYLQKFNDED |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | GAAACACCGTTTGAACGTGA<br>AAACAAACCGCTGAATAAAG<br>TGGTGATGATTAGCATGCCG<br>GAAGGCTATAAAGGTATTTA<br>TCTGCTGGTTGATCACATGAC<br>CATGGATGCACAGAGCCTGA<br>TTGTTTTTATGAAAGACATCA<br>TCGAGATCTATTGCCACCTGA<br>AATATGAAGGTATTCCGTAT<br>CCGCGTGAAATGGCAAGCTA<br>TATTGAGCAGATTGAAAAAG<br>ACCTGACGTATGAACTGGGC<br>AACAAAGCAAAGAACGTGA<br>CGAGAAATTCTTCAAAGAAC<br>TGATCGAATGCAAAGAGCCG<br>ATCTTTAACGATATTGAAGGT<br>AAAGAACGTCTGCGTCTGGA<br>ACGCCTGCAGCGTGATAGCG<br>AAAATCTGCGTAGCGTGATT<br>AATACCAGCAATAATGTGGA<br>TGCCAACATTACCATCTTTAA<br>CCTGGAAGCACATCCGAGCC<br>ATCTGCTGGAACGTTTTTGTG<br>AAGAAAACAAAATTCCGATG<br>GTGTGCCTGCTGATTATGGGT<br>CTGCGTACCTATCTGCAGAA<br>ATTCAATGATGAAGATGACG<br>TGAGCATCATGAGCACCATT<br>GCACGTCGTGCGACCCTGAG<br>CGAAAAACTGAGCGGTGGCA<br>CCCGTGTTCATTGTTTTCCGT<br>GTCGTACCATTGTTAAACGC<br>GATATGACCTTTATGGAAGG<br>CCTGGAAGAAATCCGTAAAG<br>AACAGAATAAACTGTTCCGC<br>CACAGCAATTATGATCCGGT<br>TAAATGTCTGGAATATCGTC<br>GCATGTTCTATAATAACCTGC<br>CTGGTGAAACCTATGAACCG<br>CTGAGTCTGACCTATCAGCC<br>GCTGACCAAAAATGATCTGA<br>AACAGCGTCCGGGTCAGACC<br>GTTAGCTTTGAAAGCATTGAT<br>TACAAAACCAACTGGTATAG<br>CAATGGCGCATGTGCCCATG<br>CACTGTATCTGACCGTTATGC<br>ATCGTGCAAGCGATAATGGT<br>CTGGATTTTAACTTTGAATAT<br>CAGACCGGTCGTGTGACCAC<br>AGAAAAACTGGAATACATGT<br>ACTACTACCTGTGCAAAATTC<br>TGTTTACCGGCATCGAGAAC<br>AAAGATAAAACCGTGGGTGA<br>AATCATCGAAATGGTGTAA<br>(SEQ ID NO: 13) | DVSIMSTIARRATLSEKLS<br>GGTRVHCFPCRTIVKRDM<br>TFMEGLEEIRKEQNKLFR<br>HSNYDPVKCLEYRRMFY<br>NNLPGETYEPLSLTYQPL<br>TKNDLKQRPGQTVSFESI<br>DYKTNWYSNGACAHAL<br>YLTVMHRASDNGLDFNF<br>EYQTGRVTTEKLEYMYY<br>YLCKILFTGIENKDKTVG<br>EIIEMV (SEQ ID NO: 49) |
| condensation domain protein | ceuC C. eutactus | ATGCCTCGTAAATACTATCCG<br>CTGACACCGAGCCAGAAAAT<br>TCATTTTAAACCGATCATTGA<br>ATTCGGCACCCAGCAGGTTG<br>CAAATATTAGCATTTGTATGA<br>CCCTGCAGGCACCGCTGGAT<br>TTTGGTCTGCTGAAAAAATGT<br>ATTCAGCTGGAATATGAACG<br>CTATGAATGTCTGCGTATTCG<br>CTTTACCAAAGTGGATCAGA<br>ATGGTGAAGTTCGTCAGTAT<br>GTTGTTAGCCGTGATGATCGC<br>GATATCGATTATGAAAATCT<br>GAGCTGGCTGAGCGGTGATG<br>ATGCATATCATCGTATGGAA<br>GAATGGTCAAGAATTCCGTT<br>TGATGGCGATAATATTCCGA<br>TGAACGTGATCAAAATGATT<br>AGCCTGCCTGGTGGTTATAAT | MPRKYYPLTPSQKIHFKPI<br>IEFGTQQVANISICMTLQA<br>PLDFGLLKKCIQLEYERY<br>ECLRIRFTKVDQNGEVRQ<br>YVVSRDDRDIDYENLSW<br>LSGDDAYHRMEEWSRIPF<br>DGDNIPMNVIKMISLPGG<br>YNGLYIKIDHRLMDSCGA<br>IVMVNDIMELYCHYKFG<br>TPYPEDMASFTDMVERD<br>LKKSTDEKRVSKDRMYW<br>QNVLEENGEPIYSDIQGQ<br>RILQESRRLHNDKSLRAA<br>DQEINDLSVATKNYHLD<br>AEPTQNLLDFCMNNHISM<br>TNLILMGIRTYLSKANGG<br>QTDISIRNYVSRRSTHAE<br>WVSGGSRAMAYPCRTIID<br>PDTEFLDAVFMIQDVQNH |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | GGCCTGTATATCAAAATTGA TCACCGCCTGATGGATAGCT GTGGTGCCATTGTTATGGTGA ACGATATTATGGAACTGTAC TGCCACTACAAATTTGGCAC CCCGTATCCGGAAGATATGG CAAGCTTTACCGATATGGTTG AACGCGATCTGAAAAAAAGC ACCGATGAAAAACGTGTGAG CAAAGATCGTATGTATTGGC AGAATGTGCTGGAAGAAAAT GGCGAACCGATTTATAGCGA TATTCAGGGTCAGCGTATTCT GCAAGAAAGCCGTCGTCTGC ATAATGATAAAAGCCTGCGT GCAGCAGATCAAGAAATTAA TGATCTGAGCGTTGCCACCA AAAACTATCATCTGGATGCA GAACCGACACAAAATCTGCT GGATTTCTGCATGAATAACC ATATCAGCATGACCAACCTG ATTCTGATGGGTATTCGTACC TATCTGAGCAAAGCAAATGG TGGTCAGACCGATATTTCCAT TCGTAATTATGTGAGCCGTCG TAGCACCCATGCAGAATGGG TTAGCGGTGGTAGCCGTGCA ATGGCATATCCGTGTCGTACC ATTATTGATCCGGATACCGA ATTTCTGGATGCCGTTTTTAT GATTCAGGATGTGCAGAATC ATGTGTATCGCCATTGCAACT ATGATCCGGAACTGCTGAGC GATCAGATGAAAGAAATGTT TCATACCCCTCCGCATACCAC CTATGAAAGCGTTGGTCTGA CCTATCAGCCGCTGCCGATTC GTCTGAAAAATCCGCATCTG GAAAACATTAGCGTTCGTAG CATGTGGATTCCGAATGGTA CAAGCAAACAGAAAATCTAT CTGACCGTTATGCATAGCGC AAATGATCTGGGTCTGAATTT CTATTTTCGTTATCAGACCGC AAGCCTGAGCGAACAGGATA TTGAACTGTTTTATTATTATC TGATGAAAATCATCTTTAAA GGCATTGCCGAACCGGAAAT GACCGTTGGTGAAATTATTG AATGCATTTAA (SEQ ID NO: 9) | VYRHCNYDPELLSDQMK EMFHTPPHTTYESVGLTY QPLPIRLKNPHLENISVRS MWIPNGTSKQKIYLTVM HSANDLGLNFYFRYQTAS LSEQDIELFYYYLMKIIFK GIAEPEMTVGEIIECI (SEQ ID NO: 45) |
| lichenysin synthetase A | mfoC *M. formatexigens* | ATGCGCGAATATTATCCGCT GACCGCAGCACAGAAAATGC ATTATAACTGGATTCGTAAAT ATCGCACCCAGCAGGTTAGC GGTGTTAGCGTTGTTGCAAG CCTGAAAAGTCCGCTGGATT TTGGTCTGCTGAAAAAATGT ATTCAGCTGGAAACCGAACG TTATGGTTGTATGCGTGTTCG TTTTACCGCACCGGATGAAA AAGGTGGTATTAAACAGTAT ATTGTGGATCGCGATACCCG TGATATTCCGATGAAAGATC TGAGCGGTATGAGCATGGCC GAAGCAGATAATCTGATGCA GCAGTGGGCCTATGAAACCT TTGATGGTGATGATATCCCG TGTGTGATGTTACCATGCTGA AACTGCCGGATGGTTATAAT GGCTTTTTTATCCACATGGAT CACCGCCTGATTGATAGCTGT GGTCTGGTTGTTATGATTAAT GATCTTATGCAGCTGTATACC | MREYYPLTAAQKMHYN WIRKYRTQQVSGVSVVA SLKSPLDFGLLKKCIQLET ERYGCMRVRFTAPDEKG GIKQYIVDRDTRDIPMKD LSGMSMAEADNLMQQW AYETFDGDDIPLCDVTML KLPDGYNGFFIHMDHRLI DSCGLVVMINDLMQLYT HYRFGSAYPQDLADYET VLAKDLKRANNEKRFAK DKKFWDDQLNALGEPLY SDIQGPSVLEAARKRHKN PMLRAADIELDNLFVEVK DYRLEPEPTKNLIDFCMN HQLSMTNLLLLGIRTYLS KVNNGQEDITIENFISRRS THDEWTSGGSRTIMFPCR TVISPETDFLSAAYEIQNV QNRIYMHSNYDPALIEEE MRRRYHTPENTTYESCYL TYQPMPVQMDNPHLAGI SQHAKWFANGAATKKM |

TABLE 1-continued

Non-limiting examples of biosynthetic enzymes from human gut microbiome-derived bacterium.

| Enzyme | Gene | Source | Nucleotide Sequence | Amino Acid Sequence |
|---|---|---|---|---|
| | | | CACTATCGTTTTGGTAGCGCA<br>TATCCGCAGGATCTGGCAGA<br>TTATGAAACCGTTCTGGCAA<br>AAGACCTGAAACGTGCCAAT<br>AATGAAAAACGCTTTGCCAA<br>AGACAAAAAATTCTGGGATG<br>ATCAGCTGAATGCACTGGGT<br>GAACCGCTGTATAGCGATAT<br>TCAGGGTCCGAGCGTTCTGG<br>AAGCAGCACGTAAACGTCAT<br>AAAAATCCGATGCTGCGTGC<br>AGCAGATATTGAACTGGATA<br>ACCTGTTTGTGGAAGTGAAA<br>GATTATCGTCTGGAACCGGA<br>ACCGACCAAAAATCTGATTG<br>ATTTTTGCATGAATCATCAGC<br>TGAGCATGACCAATCTGCTG<br>CTGCTGGGTATTCGTACCTAT<br>CTGAGCAAAGTTAATAACGG<br>CCAAGAAGATATCACCATCG<br>AAAACTTTATTAGCCGTCGTA<br>GCACCCATGATGAATGGACC<br>AGCGGTGGTAGCCGTACCAT<br>TATGTTTCCGTGTCGTACCGT<br>TATTAGTCCGGAAACCGATTT<br>TCTGAGCGCAGCGTATGAAA<br>TTCAGAATGTTCAGAACCGC<br>ATCTACATGCACAGCAATTA<br>TGATCCGGCACTGATTGAAG<br>AAGAAATGCGTCGTCGTTAT<br>CATACACCGGAAAACACCAC<br>CTATGAAAGCTGTTATCTGAC<br>CTATCAGCCGATGCCGGTTC<br>AGATGGATAATCCGCATCTG<br>GCAGGTATTAGCCAGCATGC<br>AAAAATGGTTTGCAAATGGTG<br>CAGCAACCAAAAAGATGTAT<br>CTGACCGTTAGTCATACCCCT<br>GATGGTGGTATGAATTTCAG<br>CTATCATTATCAGACAGCCC<br>AGCTGTGTGAACATGATATG<br>GAACTGCTGTATTATTACATG<br>ATGCGGATCCTGTTTAAAGG<br>TATTGCAGAACCGGATATGA<br>GCATTGGCGAAATCATGGAA<br>CTGGTCTAA (SEQ ID NO: 10) | YLTVSHTPDGGMNFSYH<br>YQTAQLCEHDMELLYYY<br>MMRILFKGIAEPDMSIGEI<br>MELV (SEQ ID NO: 46) |
| long-chain-<br>fatty-acid--CoA<br>ligase | bprA | B. producta | ATGAGCGGCAAAATCAACAC<br>CATGAAAGATATCATTGATT<br>ATGCAGCCGAAACCTATGGT<br>GATGCACCGGCAATTCGTTA<br>TAAAGTTCGTAAAGAAGTTA<br>TCACCCGTACCTTTCGTGATC<br>TGAAACGTGATAGCGAAGCA<br>TTTTGTCGTGCACTGGATAGC<br>ATGGGTATGCTGGGTAAACA<br>TGTTGCAGTTATTGGTCCGAC<br>CACCTATGAATGGATTCTGG<br>CATATTTTGGTGCAGCAAAT<br>AGCGGTTGTGTTATTGTTCCG<br>CTGGATGCACAGCTGCCTGC<br>AGCAGATGTTTGTGAACTGC<br>TGAATCGTGCAGATATTAGC<br>GTTCTGGTTTATGATGAACTG<br>CGTCGTGATGTTGCAGAAAT<br>GGCAAAAGAAAAATGTCCGC<br>AGGTTCGTTTTATGGTTAGCA<br>TGCAGGCAGAAAAAGATAAA<br>GAACAGGTTCTGAGCCTGAC<br>CAGCCTGCTGAAAAAACATG<br>CAGGTAGCTTTAGCTGTGAA<br>CTGGATCCGGATAAACTGTG | MSGKINTMKDIIDYAAET<br>YGDAPAIRYKVRKEVITR<br>TFRDLKRDSEAFCRALDS<br>MGMLGKHVAVIGPTTYE<br>WILAYFGAANSGCVIVPL<br>DAQLPAADVCELLNRADI<br>SVLVYDELRRDVAEMAK<br>EKCPQVRFMVSMQAEKD<br>KEQVLSLTSLLKKHAGSF<br>SCELDPDKLCAILFTSGTT<br>GKSKGVMLTHRNLTDNA<br>VCLDMKIPAGTVSMTLLP<br>IHHAYCFTMDILKGIYIG<br>MVICINDSIMHVSKNMKL<br>FKPEIVLLVPMVIESIYKK<br>LKESTGILPKKMVAKAAF<br>GGNLKTICSGGAYLPPEM<br>VGAFAEYGITILQGYGMT<br>ECSPVISTNLEWDSKEGS<br>VGRLLPNCEAKVVDEEI<br>WVRGSSVMMGYYKMPA<br>ETEEALEDGWLKTGDLG<br>YVDQDDFVFLTGRKKNLI<br>ILKNGENVSPEELENEISR<br>SPLVKEIIVRETESVIEAEI |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | TGCAATTCTGTTTACCAGCGG<br>CACCACCGGTAAAAGCAAAG<br>GTGTTATGCTGACCCATCGTA<br>ATCTGACCGATAATGCAGTTT<br>GTCTGGATATGAAAATTCCG<br>GCAGGCACCGTTAGCATGAC<br>CCTGCTGCCGATTCATCATGC<br>ATATTGTTTTACCATGGATAT<br>CCTGAAGGGCATCTATATTG<br>GTATGGTGATTTGCATCAAC<br>GACAGCATTATGCATGTGAG<br>CAAAAACATGAAACTGTTTA<br>AGCCGGAAATTGTTCTGCTG<br>GTTCCGATGGTTATTGAGAG<br>CATTTACAAAAAGCTGAAAG<br>AAAGCACCGGTATCCTGCCG<br>AAAAAAATGGTTGCAAAAGC<br>AGCATTTGGTGGCAACCTGA<br>AAACCATTTGTAGCGGTGGT<br>GCATATCTGCCTCCGGAAAT<br>GGTTGGTGCATTTGCCGAAT<br>ATGGTATTACCATTCTGCAAG<br>GTTATGGTATGACCGAATGT<br>AGTCCGGTTATTAGCACCAA<br>TCTGGAATGGGATAGCAAAG<br>AAGGTAGCGTTGGTCGTCTG<br>CTGCCTAATTGTGAAGCAAA<br>AGTTGTGGATGAAGAAATTT<br>GGGTTCGTGGTAGCAGCGTT<br>ATGATGGGTTATTACAAAAT<br>GCCTGCAGAAACCGAAGAGG<br>CACTGGAAGATGGTTGGCTG<br>AAAACCGGTGATCTGGGTTA<br>TGTTGATCAGGATGATTTTGT<br>TTTTCTGACCGGTCGCAAAA<br>AGAACCTGATTATTCTGAAA<br>AATGGCGAGAATGTGTCACC<br>GGAAGAACTGGAAAATGAAA<br>TCAGCCGTAGTCCGCTGGTG<br>AAAGAAATTATTGTTCGTGA<br>AACCGAAAGCGTGATTGAAG<br>CAGAAATTTTTCCGGATTATG<br>AGTATGCCAGCAAAAAACGT<br>ATTCGTGATGTGCGTGAAAA<br>ACTGCAAGAAGTGATCGATA<br>ACTTTAATCGTGGTCTGCCAC<br>CGTACAAAAAAATCCATGGT<br>CTGAAAATTCGCGAGGAAGA<br>ATTTGAAAAAACCCCGAGCA<br>AAAAGATCAAGCGCTATTAA<br>(SEQ ID NO: 20) | FPDYEYASKKRIRDVREK<br>LQEVIDNFNRGLPPYKKI<br>HGLKIREEEFEKTPSKKIK<br>RY (SEQ ID NO: 56) |
| long-chain-<br>fatty-acid--CoA<br>ligase | cspA Clostridiales sp. | ATGCCGGTTGGCACCCTGCG<br>TGATATTATTCGTCATGGTGC<br>AGATGCCTATGGTAGCCAGA<br>CCGCATTTCGTTATAAAGTGA<br>AAAAAGAAATCGTGGACCGC<br>ACCTATCTGGATGTTAATCGT<br>GATAGCATGGCAGTTAGCCG<br>TATGCTGGAAAGCATGGGTA<br>TGGAAGGTAAACATATTGCA<br>CTGATTGGCACCACCACCTAT<br>CAGTGGATTGTTGGTTATTTT<br>GGTATTGTTGGTAGCGGTAG<br>CGTTGCAGTTCCGATTGATGC<br>ACAGCTGCCTGCAGATGCAG<br>TTTGTGAACTGCTGGAACGT<br>GCAGATGTTGAAATGCTGAT<br>TTTTGATGAAATTCGTCGTGA<br>TGTTGCCAAAGCCGTTAAAG<br>AAAAATGTCCGAGCGTTCGT<br>TATATTGTTAGCATGCAGGCC<br>GAAGAAGCAGGCGACGGTAT<br>TCAGAGCCTGAGCATGCTGA<br>TGGCACTGCATGCCGGTGAA | MPVGTLRDIIRHGADAYG<br>SQTAFRYKVKKEIVDRTY<br>LDVNRDSMAVSRMLESM<br>GMEGKHIALIGTTTYQWI<br>VGYFGIVGSGSVAVPIDA<br>QLPADAVCELLERADVE<br>MLIFDEIRRDVAKAVKEK<br>CPSVRYIVSMQAEEAGDG<br>IQSLSMLMALHAGEYEKE<br>LSGDQLATILFTSGTTGKS<br>KGVMLSHRNLVDNAVCL<br>DMKIPAGTISMTLLPINHV<br>YCLTMDIIKGLHIGLVICI<br>NDSIMHVQRNMKLFKPEI<br>VLLVPLVIESIYGKLKDA<br>GSLIPKKMVAKAAFGGN<br>LRIICSGGAYLDPDYVDK<br>FKEYGITILQGYGMTECS<br>PVISTNLEWENKKGSVGK<br>LLPNCEAKVVDEEIWVR<br>GSSVMQGYYKMPEQTAE<br>TLEDGWLKTGDLGYVDE<br>DRFVYITGRRKNLIILANG |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | TATGAAAAAGAACTGAGCGG<br>TGATCAGCTGGCAACCATTCT<br>GTTTACCAGCGGCACCACCG<br>GTAAAAGCAAAGGTGTTATG<br>CTGAGCCATCGTAATCTGGTT<br>GATAATGCCGTTTGTCTGGAT<br>ATGAAAATTCCGGCAGGCAC<br>CATTAGCATGACCCTGCTGCC<br>GATTAATCATGTTTATTGTCT<br>GACCATGGACATCATCAAAG<br>GTCTGCATATTGGTCTGGTGA<br>TTTGCATTAACGATAGCATTA<br>TGCATGTGCAGCGCAACATG<br>AAACTGTTTAAACCGGAAAT<br>TGTTCTGCTGGTTCCGCTGGT<br>TATTGAAAGCATTTATGGCA<br>AACTGAAAGATGCCGGTAGC<br>CTGATTCCGAAAAAATGGT<br>TGCAAAAGCAGCCTTTGGTG<br>GTAATCTGCGTATTATTTGTA<br>GCGGTGGTGCATATCTGGAT<br>CCGGATTATGTTGATAAGTTC<br>AAAGAATACGGCATCACCAT<br>TCTGCAAGGTTATGGTATGA<br>CCGAATGTAGTCCGGTTATTA<br>GCACCAATCTGGAATGGGAA<br>AACAAAAAAGGTAGCGTGGG<br>TAAACTGCTGCCTAATTGTGA<br>AGCAAAAGTTGTGGATGAAG<br>AAATTTGGGTTCGTGGTAGC<br>AGCGTTATGCAGGGTTATTA<br>CAAAATGCCGGAACAGACCG<br>CAGAAACCCTGGAAGATGGT<br>TGGCTGAAAACCGGTGATCT<br>GGGCTATGTTGATGAAGATC<br>GTTTTGTGTATATTACCGGTC<br>GTCGCAAAAACCTGATTATT<br>CTGGCAAATGGTGAAAACGT<br>TAGTCCGGAAGAACTGGAAA<br>ATCAGCTGAGCCGTAGCGAA<br>CTGGTGAAAGAAATTCTGGT<br>GCGTGAAAAGATAAAGTGA<br>TCGAAGCAGAAATCTTCCCG<br>GATTACGAATACGCCAAAAA<br>AAAGCATGTGAAAGACGTTG<br>AAGGGAAACTGCAAGAACTG<br>GTGGATGATTTCAATAAAGA<br>TATGCCGGTGTACAAACGCA<br>TCTATAGTCTGATTGTTCGCG<br>AAACCGAATTTGAAAAAACC<br>CCGAGCAAAAAATCAAACG<br>CTTTTAA (SEQ ID NO: 23) | ENVSPEELENQLSRSELV<br>KEILVREKDKVIEAEIFPD<br>YEYAKKKHVKDVEGKLQ<br>ELVDDFNKDMPVYKRIY<br>SLIVRETEFEKTPSKKIKR<br>F (SEQ ID NO: 59) |
| long-chain-<br>fatty-acid--CoA<br>ligase | ereA E. rectale | ATGCTGTTTCATACCATTCCG<br>GATATTCTGAGCTATGCCAAT<br>GAAGCCTATGGTGCAGATGA<br>TGCAATTCGTTGGAAAAAAA<br>GCAAAAACGAAATTGAGAGC<br>CGCACCTATAGCGAACTGAA<br>AAATGATACCGATAGCTTTG<br>CCAACGCCATTGAAAAACTG<br>GGTAAAAAAGGTCAGCATAT<br>CGCAGTTATTGGTCCGAGCA<br>GCTATGAATGGATTGTTAGCT<br>ATCTGGCAATTACCGAAAGC<br>GGTAGCGTTGCAGTTCCGATT<br>GATGCAAGCCTGCCTGCAGC<br>AGATATTTGTGAACTGCTGG<br>ATCGTGCAAGCGTTCGTATG<br>CTGATTTTTGATGAAGCACGT<br>AGTGATGTTCAGAAGCAGC<br>AGCAAAAGCTGCCATGATA<br>TTAATGTTTACGTGAGCATGA<br>ACAGCACCGAACATTGTCCG<br>CAGGTTCTGAGCTTTAAAGG | MLFHTIPDILSYANEAYG<br>ADDAIRWKKSKNEIESRT<br>YSELKNDTDSFANAIEKL<br>GKKGQHIAVIGPSSYEWI<br>VSYLAITESGSVAVPIDAS<br>LPAADICELLDRASVRML<br>IFDEARSDVAEAAAKSCH<br>DINVYVSMNSTEHCPQVL<br>SFKGLIDDNRGSYEPAVA<br>EDALCTIMFTSGTTGKSK<br>GVMLTQNNLAENATCLD<br>MKIGPHTVILSVLPIHHAY<br>CLSMDILKGISLGSVICIN<br>DSIMRMAKNIQLFTPDMI<br>LMVPLMIETFARKLEEVR<br>AAGLPAEPVRKKMFGER<br>LHTICSGGAYLNPDYVDL<br>FAEFGITILQGYGMTECSP<br>VISTNLSWDIRKNSVGKL<br>MPNCEAKTVDGELFVRG<br>TSVMQGYYKMPKETEET<br>LSDGWLHTGDLGYVDED |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | TCTGATTGATGATAATCGCG<br>GTAGCTATGAACCGGCAGTT<br>GCCGAAGATGCACTGTGTAC<br>CATTATGTTTACCAGCGGCAC<br>CACCGGTAAAAGCAAAGGTG<br>TGATGCTGACCCAGAATAAT<br>CTGGCAGAAAATGCAACCTG<br>TCTGGACATGAAAATTGGTC<br>CGCATACCGTGATTCTGAGC<br>GTTCTGCCGATTCATCATGCA<br>TATTGTCTGAGCATGGATATC<br>CTGAAAGGTATTAGCCTGGG<br>TAGCGTGATTTGTATTAACGA<br>TAGCATTATGCGCATGGCCA<br>AAAACATTCAGCTGTTTACA<br>CCGGATATGATTCTGATGGTT<br>CCGCTGATGATTGAAACCTTT<br>GCACGTAAACTGGAAGAAGT<br>TCGCGCAGCAGGTCTGCCTG<br>CCGAACCGGTGCGCAAAAAA<br>ATGTTTGGTGAACGTCTGCAT<br>ACCATTTGTAGCGGTGGTGC<br>ATATCTGAACCCGGATTATGT<br>TGACCTGTTTGCCGAATTTGG<br>TATTACCATTCTGCAAGGTTA<br>TGGTATGACCGAATGTAGTC<br>CGGTTATTAGCACCAATCTG<br>AGCTGGGATATTCGTAAAAA<br>TAGCGTGGGTAAACTGATGC<br>CGAATTGTGAAGCCAAAACC<br>GTTGATGGTGAACTGTTTGTT<br>CGTGGCACCAGCGTTATGCA<br>GGGTTATTACAAAATGCCGA<br>AAGAAACCGAAGAAACCCTG<br>AGTGATGGTTGGCTGCATAC<br>CGGTGATCTGGGTTATGTTGA<br>TGAAGATGGTTATATCTATCT<br>GACCGGTCGTCGCAAAAATC<br>TGATTATTACCAAAAATGGC<br>GAAAACGTGAGTCCGGAAGA<br>ACTGGAAAATGCACTGAGCG<br>TTAATCACCTGATCAAAGAA<br>ATTATTGTGCGCGAAAGCGA<br>AGGTGTTATTGAAGCAGAAA<br>TTTTTCCGGATCGTGAATATG<br>CACAGAATACCGGCATTGCA<br>GATATTCGTTCAGCACTGCA<br>GGCACTGATCGATGAATATA<br>ATGTTAATGCCCCTGCCTACA<br>AACGCATCTATAGCATTAAA<br>GTTCGTGAAAGCGAATTCGA<br>AAAAACCGCAAGCCGTAAAA<br>TCAAACGCAGCTAA (SEQ ID<br>NO: 24) | |
| long-chain-<br>fatty-acid--CoA<br>ligase | lclA *L.*<br>*clostridioforme* | ATGGCAGCAGAAACCCTGCG<br>TGATGTTATTCGTCATGGTGC<br>CGAAGCCTATGGTGAACAGA<br>CCGCATTTCGTTACAAAGTG<br>AAAAAAGAGATCATCGATAA<br>AAGCTACAACGAGGTGAATC<br>TGGATAGCATGGCAGTTAGC<br>CGTGCAGTTGAAGCACTGGG<br>TATGAAAGGTAAACATATTG<br>CCGTTATTGGCACCACCAGTT<br>ATCAGTGGATTACCGCATATT<br>TTGGCATTGTTAATAGCGGTA<br>GCGTTGCAGTTCCGATTGATG<br>CACAGTTTCCAGCCGAAGCA<br>ATTTGTGAACTGCTGAATCGT<br>GCAGATGTTGAAATGCTGGT<br>TTATGATGAACTGCGTAGTG<br>ATGTTGCCGGTGATGTTCGTG<br>AAAAAATGTCCGGGTATTCGC<br>CATGTTGTTAGCATGCAGGC | MAAETLRDVIRHGAEAY<br>GEQTAFRYKVKKEIIDKS<br>YNEVNLDSMAVSRAVEA<br>LGMKGKHIAVIGTTSYQ<br>WITAYFGIVNSGSVAVPI<br>DAQFPAEAICELLNRADV<br>EMLVYDELRSDVAGDVR<br>EKCPGIRHVVSMQAQET<br>AGDVLSLSRLIAENAGTY<br>ETELSGSQLCTILFTSGTT<br>GRSKGVMLSHRNLTDNA<br>VCLDMKIPAGTVSMTLLP<br>INHVYCLTMDIIKGLYIG<br>MIICINDSIMHVQRNMKL<br>FKPEIVLLVPLVIESIYGKL<br>KDAGSLIPKKMVAKAAF<br>GGNLRIICSGGAYLDPDY<br>VDRFKEYGITILQGYGMT<br>ECSPVISTNLEWENKKGS<br>VGKLLPNCEAKVVDEEI |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | ACAAGAAACAGCGGGTGATG TGCTGAGCCTGAGCCGTCTG ATTGCAGAAAATGCAGGTAC GTATGAAACCGAACTGAGCG GTAGCCAGCTGTGTACCATTC TGTTTACCAGCGGCACCACC GGTCGTAGCAAAGGTGTTAT GCTGAGCCATCGTAATCTGA CCGATAATGCAGTTTGTCTGG ATATGAAAATTCCGGCAGGC ACCGTTAGCATGACCCTGCT GCCGATTAATCATGTTTATTG TCTGACCATGGACATCATCA AAGGTCTGTATATTGGCATG ATCATCTGCATCAACGATAG CATTATGCATGTGCAGCGTA ACATGAAACTGTTCAAACCG GAAATTGTTCTGCTGGTTCCG CTGGTTATTGAAAGCATTTAT GGCAAACTGAAAGATGCCGG TAGCCTGATTCCGAAAAAAA TGGTTGCAAAAGCAGCCTTT GGTGGTAATCTGCGTATTATT TGTAGCGGTGGTGCATATCT GGATCCGGATTATGTTGATC GCTTTAAAGAATATGGCATC ACCATTCTGCAAGGTTATGGT ATGACCGAATGTAGTCCGGT TATTAGCACCAATCTGGAAT GGGAAAACAAAAAAGGTAG CGTGGGTAAACTGCTGCCTA ATTGTGAAGCAAAAGTTGTG GATGAAGAAATTTGGGTTCG TGGTAGCAGCGTTATGCAGG GTTATTACAAAATGCCGGAA CGTACCGCAGAAACACTGGA AGATGGTTGGCTGAAAACCG GTGATCTGGGCTATGTAGAT GAAGATAACTTTGTGTATATT ACCGGTCGCCGTAAAAACCT GATTATTCTGGCAAATGGTG AAAACGTTAGTCCGGAAGAA CTGGAAAATGAACTGAGCCG TTCAGAACTGGTTAAAGAAA TTCTGGTGCGCGAGAAAGAT AAAATCATTGAAGCCGAAGT TTTTCCCGGATTACGAATACGC AAAAAAGAAACACATCAAAG ATATTCGTGGCACCCTGCAA GAACTGATTGATGGTTTTAAC AAAGATATGCCGGTGTACAA ACGCATCTATAGTCTGATTGT TCGCGAAACCGAATTTGAAA AAACCCCGAGCAAAAAAATC AAACGCTTTTAA (SEQ ID NO: 19) | WVRGSSVMQGYYKMPE RTAETLEDGWLKTGDLG YVDEDNFVYITGRRKNLII LANGENVSPEELENELSR SELVKEILVREKDKIIEAE VFPDYEYAKKKHIKDIRG TLQELIDGFNKDMPVYKR IYSLIVRETEFEKTPSKKIK RF (SEQ ID NO: 55) |
| long-chain- fatty-acid--CoA ligase | rbaA R. bacterium | ATGACCAGCACCATTCGTGA AATTCTGGTTGAAGCACAGC AGCGTTTTGGTCCGGAAGTT GCAGTTCGTTATAAAGTGGG TAAAAACCAGATCGAGGACA AAACCTATAATCAGCTGCGT CAGGATAGCGAAAGCTTTAG CAGCGCACTGGCAGCACTGG GTGAACAGGGTAGCCATATT GCAGTTATTGGTCCGACCAG CTATCGTTGGATGGTTACCTA TCTGGGTATTGTTAATAGCGG TAGCGTTGCCGTTCCGCTGGA TGCAAGCCTGCCTGCAGCAG ATGTTTGGGAACTGCTGGAT CGTGCAGATGTTACCACACT GGTTGCAGATGCAGCACGTA AAGATGTTGCAGAAGGTGCA | MTSTIREILVEAQQRFGPE VAVRYKVGKNQIEDKTY NQLRQDSESFSSALAALG EQGSHIAVIGPTSYRWMV TYLGIVNSGSVAVPLDAS LPAADVWELLDRADVTT LVADAARKDVAEGAKEH CPKLKHVVIMQQEEHSD AALFLPQLLAEHQTAFDF EPQPDQLCTIMFTSGTTG KSKGVMLTHRNLAENAG SINMDLPERMVLLSVLPI HHAYCLCLDVLKAISLGS IICINDSLLRVMKNIQLFK PEMILMVPLMIETIAKKLE DNTLLPPKLVKNAVFGK QLTKISSGGAYLDPSYIDL PEKYGITILQGYGMTECS |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | AAAGAACATTGCCCGAAACT GAAACATGTTGTGATTATGC AGCAAGAAGAACATAGCGAC GCAGCACTGTTTCTGCCGCA GCTGCTGGCCGAACATCAGA CCGCATTTGATTTTGAACCGC AGCCGGATCAGCTGTGTACC ATTATGTTTACCAGCGGCACC ACCGGTAAAAGCAAAGGTGT TATGCTGACCCATCGTAATCT GGCAGAAAATGCAGGTAGCA TTAATATGGATCTGCCGGAA CGTATGGTTCTGCTGAGCGTT CTGCCGATTCATCATGCATAT TGTCTGTGTCTGGATGTGCTG AAAGCAATTAGCCTGGGTAG TATTATTTGCATTAATGATAG CCTGCTGCGCGTGATGAAAA ACATTCAGCTGTTTAAACCG GAAATGATTCTGATGGTTCC GCTGATGATTGAAACGATTG CAAAAAAGCTGGAAGATAAT ACCCTGCTGCCTCCGAAACT GGTTAAAAATGCAGTTTTTG GTAAGCAGCTGACGAAAATT AGCAGCGGTGGTGCATATCT GGATCCGAGCTATATTGACC TGTTTGAGAAATATGGCATC ACCATTCTGCAAGGTTATGGT ATGACCGAATGTAGTCCGGT TATTAGCACCACACGTCCGT GGAACATTAACAAAAATGCC GTTGGTCAGCTGATCGATAA TTGTGAAGCAAAAACCGTTG ATGGTGAACTGTGGGTTCGT GGTAGCAGCGTTATGCAGGG TTATTACAAAATGCCGGAAG AAACCGCAGCAACCCTGGAA GATGGTTGGCTGAAAACCGG TGATCTGGGTTATGTTGATGA AGATGGCTTTGTTTATCTGAC CGGTCGCAAAAAAAACCTGA TCATCACCAAAAATGGCGAA AATGTTAGTCCGGAAGAACT GGAAAATAAACTGGGTGTTG AACGCCTGATTCAAGAAGTT CTGGTTCGCGAAAACAAAAG CGTTATTGAAGCAGAAATCT TCCCGGATTATGAGTACGCC AAAAAAAAGCACATTAAAGA TGTGCGTGCAGCCCTGCAAG AAATCATTGATCAGTATAAT CTGCAGGCACCGCCTCACAA AAAAATCTATAGCCTGATTG TTCGTGAAACCGAGTTTGAA AAAACCCCGAGCAAAAAGAT CAAACGCTTCTAA (SEQ ID NO: 22) | PVISTTRPWNINKNAVGQ LIDNCEAKTVDGELWVR GSSVMQGYYKMPEETAA TLEDGWLKTGDLGYVDE DGFVYLTGRKKNLIITKN GENVSPEELENKLGVERL IQEVLVRENKSVIEAEIFP DYEYAKKKHIKDVRAAL QEIIDQYNLQAPPHKKIYS LIVRETEFEKTPSKKIKRF (SEQ ID NO: 58) |
| non-ribosomal peptide synthetase | ereC E. rectale | ATGAAAACCCGCAAAGGCCA TAATGTTTATCCGATTACCGT TGCGCAGAAATTCCATCTGT ATTATGCAAAATATTGCCCG AATATGGCCGTGCTGAATAT TGGCACCAGCCTGACCATTG GCACCGAACTGGATTGGAAT GTGCTGCGTGATAGCATTAA CTATGCCTATGCACGTAATG AAGCAATGCGTATTCGTTTCA CCCGTGATAAAGATGGTGAG TGCTATCAGTATATTGCCGAT GTGGATGAAGATTTTAAAGA ACGCACCGTGGATTTCAAAG ATTTTACCGATGTTACCATGG AAGAGGCCGAAAATGAAATG | MKTRKGHNVYPITVAQK FHLYYAKYCPNMAVLNI GTSLTIGTELDWNVLRDS INYAYARNEAMRIRFTRD KDGECYQYIADVDEDFK ERTVDFKDFTDVTMEEA ENEMQGWTQVPFEFEDS PMTKIVMIKMPDGFNGV YFLGHHMVVDAQSLIAFL KDIIEIYCNAMYEGVPFPK DMCSYIEQLKKDLAYEA GSKAQLRDREFFEKLIRQ SEPIYNGIDGTAKLDAAR ELMHDNKLRSAFNASDD VTSALDIFHLEAEPTKRL MDFCEKYHISLACLLLMG |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | CAAGGTTGGACCCAGGTTCC GTTTGAATTTGAAGATAGCC CGATGACCAAAATCGTGATG ATCAAAATGCCGGATGGTTT TAACGGTGTGTATTTCTGGG TCATCACATGGTTGTTGATGC ACAGAGCCTGATTGCATTTCT GAAAGATATCATCGAGATCT ACTGCAACGCAATGTATGAA GGTGTTCCGTTTCCTAAAGAT ATGTGCAGCTATATCGAGCA GCTGAAAAAAGATCTGGCCT ATGAAGCAGGTAGCAAAGCA CAGCTGCGCGATCGTGAATT TTTTGAAAAACTGATTCGTCA GAGCGAGCCGATTTATAACG GTATTGATGGCACCGCAAAA CTGGATGCAGCACGTGAACT GATGCATGATAATAAACTGC GTAGCGCATTTAACGCCAGT GATGATGTGACCAGCGCACT GGATATTTTTCATCTGGAAGC AGAACCGACCAAACGTCTGA TGGATTTTTGTGAGAAATATC ATATTAGCCTGGCATGTCTGC TGCTGATGGGTATTCGTACAT TTTTCCAGAAAGAAAACGGC TTTGATGACGTGAGCGTTAAT AATGCCATTGCACGTCGTGC GACCCTGAAAGAGAAAAAAT CAGGCGGTACACGTATTCAC AGCTTTCCGTTTCGTACCTGT TTTAGCAAAGATGTGCGTTTT ATTGATGCCGTGTATACCATT CGCGATAAACAGAATGAACT GTTTCGTCACGCAAACTATA ATCCGACCGAATATTTCGCCC TGCGTAGCAAAACCTATCCG CAGCCGAAAGCCGGTCTGAC CTATGAACCGATGAGCCTGA CATATCAGCCGATGACACTG AAAGAAAAAGGTCTGAATGA TCTGGGCGACATCAAATACA AAACCAAATGGTATCCGAAT GGCATGACCACACAGGCAAT GTATCTGACCGTTATGCATCG TCCGGAAGATAATGGTCTGG ATTTCAGCTTTGAACATCAGG TTAAAGCAGTTAGCCGTAAA CAGCTGGAATACATGTACTA TTACCTGTGCAAGATCATGTT TAAAGGTGCCGAAAATCCGG AACTGACGATTGGTGAAATT ATCAAACTGGTGTAA (SEQ ID NO: 16) | IRTFFQKENGFDDVSVNN AIARRATLKEKKSGGTRI HSFPFRTCFSKDVRFIDAV YTIRDKQNELFRHANYNP TEYFALRSKTYPQPKAGL TYEPMSLTYQPMTLKEK GLNDLGDIKYKTKWYPN GMTTQAMYLTVMHRPE DNGLDFSFEHQVKAVSR KQLEYMYYYLCKIMFKG AENPELTIGEIIKLV (SEQ ID NO: 52) |
| peptide synthetase | bprC B. producta | ATGAAAGAGAAATTTGGCAA ACCGCTGTATCCGCTGACCG CAGCACAGAAACTGCATTTT TTCTATCAGAAATACTGCCCG AAAAAACAGGTGCTGAATAT TGGCACCAGCCTGACCATTC AGCAGAGCCTGGATTTTGGT GCACTGAAAGAAGCAGTTTA TCAGGCCTATGCACGTTGTG AAAGCATGCGTCTGCGTTTTA CCCAGGATGAAGATGGTGGT GTTTATCAGTATATTGCCGAT CGTGAAGAACGCGATATCGA ATTTTTTGATTTCACCGGTTG GCAAGAATGTCACGCCGAAG ATAAAATGAAAGAATGGACC AGCGTTCCGTTTGAACGTTT TGATAGTCCGCTGAATCGTGT GGTGATGATTATTACACCGG | MKEKFGKPLYPLTAAQK LHFFYQKYCPKKQVLNIG TSLTIQQSLDFGALKEAV YQAYARCESMRLRFTQD EDGGVYQYIADREERDIE FFDFTGWQECHAEDKMK EWTSVPFERFDSPLNRVV MIITPDGFQGIYLLVDHM TMDAQSLILFLKDVIEIYA NMKYEGMEYPKEMKSYI EQLKKDLEYEADSRAKK RDTEFFEKMISSSEPIFNSI FGPGKLKAEREKEKNPDI RAVTNVSDNVDANIITFQ LEADPSNRLMQFCEEHHI SMVCLLMMGLRTYLQKV NGNDDVSINTTVARRATL SEKRCGGTRIHCFPFRTV VEKGDTFMEGLKKIRDG |

TABLE 1-continued

Non-limiting examples of biosynthetic enzymes from human gut microbiome-derived bacterium.

| Enzyme | Gene | Source | Nucleotide Sequence | Amino Acid Sequence |
|---|---|---|---|---|
| | | | ATGGTTTTCAGGGTATCTATC TGCTGGTTGATCACATGACC ATGGATGCACAGAGCCTGAT TCTGTTTCTGAAAGATGTGAT TGAGATCTATGCCAACATGA AGTATGAAGGCATGGAATAT CCGAAAGAAATGAAAAGCTA TATCGAACAGCTGAAAAAAG ATCTGGAATATGAAGCAGAT AGCCGTGCCAAAAAACGTGA TACAGAATTCTTCGAGAAAA TGATCAGCAGCAGCGAACCG ATTTTTAACAGCATTTTTGGT CCGGGTAAACTGAAAGCAGA ACGCGAAAAGAAAAAAAC CCGGATATTCGTGCAGTTACC AATGTTAGCGATAATGTGGA TGCGAACATTATCACCTTTCA GCTGGAAGCAGATCCGAGCA ATCGTCTGATGCAGTTTTGCG AAGAACATCATATTAGCATG GTTTGCCTGCTGATGATGGGT CTGCGTACCTATCTGCAGAA AGTTAATGGTAATGATGACG TGAGCATTAATACCACCGTT GCACGTCGTGCGACCCTGAG CGAAAAACGTTGTGGTGGCA CCCGTATTCATTGTTTTCCGT TTCGTACCGTTGTGGAAAAA GGCGATACCTTTATGGAAGG CCTGAAAAAAATCCGTGATG GTCAGAATCGTATTTTTCGCC ATGCAAATTATGATCCGACC GCCTATTATGCCTATCGCAAC AAATACTATAAACTGCGTCC GGGTCAGACCTATGAACCGC TGAGCCTGACCTATCAGCCG CTGACACTGAAAGGTAAAGG TATGGAACGTCTGCAGGATA TTCGCTATAAAAGCGCATGG TATAGCAATGGTGCAGCAGC ACATGCACTGTATCTGACCGT TATGCATCGTGCGGAAGATA ATGGTATGAACTTTAACTTTG AACACCAGACCGGTGTTGTG CATTTTGAAGATCTGCAGTAT CTGTACTATTATCTGTGCCGC ATTATCTTTAAAGGCGTGGA AAATCCGGATATGACCGTTG GTGAAATTCTGGAAAGCGTG TAA (SEQ ID NO: 12) | QNRIFRHANYDPTAYYA YRNKYYKLRPGQTYEPLS LTYQPLTLKGKGMERLQ DIRYKSAWYSNGAAAHA LYLTVMHRAEDNGMNFN PEHQTGVVHFEDLQYLY YYLCRIIFKGVENPDMTV GEILESV (SEQ ID NO: 48) |
| peptide synthetase | cspC | Clostridiales sp. | ATGAAAACCCGCAAAGGCTA TAAAGCATATCCGCTGACCG CAGCACAGAAACTGCACTTT TATTGTCTGAAATACTGCCCG AAAAAACAGGTGCTGAATAT TGGTAGCAGCCTGACCATTG AAAGCGATCTGGATTGGGAT GTTCTGCGTCAGTGTATTAAA GAAGCCATTGCACGTTGCGA AAGCATGCGTCTGCGTTTTGC CAAAGATCGTGATGGTAACA TTTATCAGTATGTGGTGAAA GAAGAAACCAAAGAGATCGA GCACTTTGATTTTACCGGTTG GCAAGAGGAAGATGCCGATA AAAAACTGCGTGAATGGACC GAAATTCCGTTTGAACGTTAT GATAGCCCTATGCATCGTATC GTGATGATTAAAACACCGGA TGGTTATCAGGGTCTGTATAT TTGTGTTGATCACATGACCAT GGATGCACAGGCACTGATTG TTTTTTTCAAAGATGTGATCG | MKTRKGYKAYPLTAAQK LHFYCLKYCPKKQVLNIG SSLTIESDLDWDVLRQCI KEAIARCESMRLRFAKDR DGNIYQYVVKEETKEIEH FDFTGWQEEDADKKLRE WTEIPFERYDSPMHRIVM IKTPDGYQGLYICVDHMT MDAQALIVFFKDVIELYC SRLYEEVNYPKEMSSYIR QLEKDLAYEAGSRACQR DREFFENLIASSEPVFADI YGPGKLLKERKESRNKK LRAATNTSDNVEANITNF HLEGGPSKRLLDFCEEKG ISMTCLLLMGLRTFLQKE NDEDDISITTTIARRATLL EKRCGGSRIHCFPPFRTIVP REDTFMEGLLKIRDAQNQ YFRHAGYSPSEYFNFRHD YYKLKDGQTYEPLSLTY QPLAMKYDGPGLDKLGD IKYKTARYSNGVAAHTL |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | AGCTGTATTGCAGCCGTCTGT ATGAAGAAGTTAACTATCCG AAAGAAATGAGCAGCTATAT TCGCCAGCTGGAAAAAGATC TGGCCTATGAAGCAGGTAGC CGTGCATGTCAGCGTGATCG TGAATTTTTTGAAAATCTGAT TGCAAGCAGCGAACCGGTTT TTGCAGATATTTATGGTCCGG GTAAACTGCTGAAAGAACGT AAAGAAAGCCGCAACAAAA AGCTGCGTGCAGCAACCAAT ACCAGCGATAATGTTGAAGC CAACATCACCAATTTTCATCT GGAAGGTGGTCCGAGCAAAC GTCTGCTGGATTTTTGTGAAG AAAAAGGCATTAGCATGACC TGTCTGCTGCTGATGGGTCTG CGTACCTTCCTGCAGAAAGA AAATGATGAAGATGATATCA GCATCACCACCACCATTGCG CGTCGTGCAACCCTGTTAGA AAAACGTTGTGGTGGTAGCC GTATTCATTGTTTTCCGTTTC GTACCATTGTTCCGCGTGAA GATACCTTTATGGAAGGTCT GCTGAAAATCCGTGATGCAC AGAATCAGTATTTTCGTCATG CAGGTTATAGCCCGAGCGAA TATTTCAATTTTCGCCACGAT TACTACAAACTGAAAGATGG TCAGACCTATGAACCGCTGA GCCTGACCTATCAGCCGCTG GCAATGAAATATGATGGTCC TGGTCTGGATAAACTGGGCG ATATCAAATACAAAACCGCA CGTTATAGCAATGGTGTTGC AGCACATACCCTGTATCTGA CCGTTAGCCATCGTACCATG GATAATGGCCTGGATTTTGGT TTTGAATATCAGACCGGTGTT GTGACACCGGAAAAACTGGA ATATATCTACTATTATCTGTG CCGCATTATCTTTCGTGGTGT TGAAGATCCGGAACGTACCG TTGGTGAAATTATGGAAATG GTGTAA (SEQ ID NO: 15) | YLTVSHRTMDNGLDFGF EYQTGVVTPEKLEYIYYY LCRIIFRGVEDPERTVGEI MEMV (SEQ ID NO: 51) |
| peptide synthetase | lclC *L. clostridioforme* | ATGAAAACCCGCAAAGGCTA TAAAGTTTATCCGCTGACCA GCGCACAGAAACTGCACTTT TATTGTCTGAAATACTGCCCG AAAAAACAGGTGCTGAATAT TGGTAGCAGCCTGACCATTC AGGTTGATCTGGATTGGGAT GTTCTGAAAGATTGTATTCGT GAAGCCATTGCACGTTGTGA TACCATGCGTCTGCGTTTTAC CCATGATAAAGAAGGTAACG TCTATCAGTATGTGGTGAAA GAAGAAACCAAAGAGATCGA GCACTTTGATTTTACCGGTTG GAAAGAAGAGGACGCCGAA GGTAAACTGCGTGAATGGAC CGAAGTTCCGTTTGAACGTTA TGATAGCCCGATGCATCATA TTGTGATGATTCGTATGCCGG ATGGTTATCAGGGTCTGTATA TTTGTGTTGATCACATGACCA TGGATGCACAGAGCCTGATT CTGTTTTTCCGTGATGTTATT GAACTGTACGCCAGCAAACT GTATGATGAAGTTGATCATC CGAAAGAAATGAGCAGCTAT ATCAAACAGCTGGAAAAAGA | MKTRKGYKVYPLTSAQK LHFYCLKYCPKKQVLNIG SSLTIQVDLDWDVLKDCI REAIARCDTMRLRFTHDK EGNVYQYVVKEETKEIEH FDFTGWKEEDAEGKLRE WTEVPFERYDSPMHHIV MIRMPDGYQGLYICVDH MTMDAQSLILFFRDVIEL YASKLYDEVDHPKEMSS YIKQLEKDLAYETGSRAC EKDRQFFQELIASSEPIFT DIYGPKKLSDERKATRNP KLRAATNTSDNVEANITN FHLEGDSSGRLLDFCEKY GISMTCLLLMGLRTYLQK ENDQDDVSITTTISRRATL SEKRCGGSRIHCFPFRTIV PRENTFMEGLLKIRDAQN QYFRHADYSPSEYFNYRH DYYKLKDGQTYEPLSLT YQPLAMKYDGPGLDKLG DIKYKTARYSNGVAAHT LYLTVSHRAEDNGLDFGF EYQTGVVTPERLEYIYYY LCRIIFRGVEDPERTVGEII EMV (SEQ ID NO: 47) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | TCTGGCCTATGAAACCGGTA<br>GCCGTGCATGTGAGAAAGAT<br>CGTCAGTTTTTTCAAGAACTG<br>ATTGCAAGCAGCGAACCGAT<br>TTTTACCGATATTATGGCCC<br>TAAAAAACTGTCCGATGAAC<br>GTAAAGCAACCCGTAATCCG<br>AAATTACGTGCAGCAACCAA<br>TACCAGCGATAATGTTGAAG<br>CCAACATCACCAATTTTCATC<br>TGGAAGGTGATAGCAGCGGT<br>CGTCTGCTGGATTTTTGTGAA<br>AAATATGGTATTAGCATGAC<br>CTGCCTGCTGCTGATGGGTCT<br>GCGTACCTATCTGCAGAAAG<br>AAAATGATCAGGATGATGTG<br>AGCATTACCACCACCATTAG<br>CCGTCGTGCAACCCTGAGCG<br>AAAAACGTTGTGGTGGTAGC<br>CGTATTCATTGTTTTCCGTTT<br>CGTACCATTGTTCCGCGTGAA<br>AATACCTTTATGGAAGGCCT<br>GCTGAAAATCCGTGATGCCC<br>AGAATCAGTATTTTCGTCATG<br>CAGATTATAGCCCGAGCGAG<br>TATTTTAACTATCGCCACGAT<br>TACTACAAACTGAAAGATGG<br>TCAGACCTATGAACCGCTGA<br>GCCTGACCTATCAGCCGCTG<br>GCAATGAAATATGATGGTCC<br>TGGTCTGGATAAACTGGGCG<br>ATATCAAATACAAAACCGCA<br>CGTTATAGCAATGGTGTTGC<br>AGCACATACCCTGTATCTGA<br>CCGTTAGCCATCGTGCCGAA<br>GATAATGGCCTGGATTTTGGT<br>TTTGAATATCAGACCGGTGTT<br>GTTACACCGGAACGTCTGGA<br>ATATATCTATTATTACCTGTG<br>CCGCATTATCTTTCGTGGTGT<br>TGAAGATCCGGAACGTACCG<br>TTGGTGAAATTATTGAAATG<br>GTGTAA (SEQ ID NO: 11) | |
| peptide synthetase | rbaC R. bacterium | ATGCGCAAACATAAAGGTTA<br>TCCGGTTTATCCGCTGACCGT<br>TGCACAGAAATTTCACCTGTT<br>TTATCTGCCGTATTGTCCGAG<br>CGCAGCAGTTATGAATATTG<br>GCACCCGTCTGACCATTCAG<br>AGCGAAATTGATTGGGATCT<br>GCTGAAACAGAGCATTTATC<br>AGGCCTATGATCGTTGTGAA<br>GGTATGCGTGTTCGTTTCGCA<br>AAAGATAAAGATGGCACCTA<br>TTATCAGTACGTGGTGGATA<br>AAGAAGAACGCGATATTGAA<br>TTTGTGGATTTTAGCCAGGGC<br>ACCCTGGAAGAGGCCGATAA<br>AGTTATGCAGCAGTGGACCA<br>CCGTTCCGTTTCCGATGGAAG<br>ATGCACCGCTGACACGTGTT<br>GTTATGATTAGCCTGCCGGAT<br>GGTTTTAATGGTGTTTATTTT<br>CTGGGCCATCACATGATTGTT<br>GATGCACAGAGCCTGATTGG<br>TTTTCTGAAAGATATCATCGA<br>ACTGTATTGCAGCCAGAAAT<br>ATGAAGGTGTTCCGGCACCG<br>AAAGAAATGGCAAGCTATAT<br>TGAGCAGATTCAGAAAGATC<br>TGGCCTATGAAGCAGGTAGC<br>AAAGCACAGCTGCGTGATAT<br>GGAATTTTTCCAGAAAGAAA<br>TCGAAAGCAGCGAGCCGATT | MRKHKGYPVYPLTVAQK<br>FHLFYLPYCPSAAVMNIG<br>TRLTIQSEIDWDLLKQSIY<br>QAYDRCEGMRVRFAKDK<br>DGTYYQYVVDKEERDIEF<br>VDFSQGTLEEADKVMQQ<br>WTTVPFPMEDAPLTRVV<br>MISLPDGFNGVYFLGHH<br>MIVDAQSLIGFLKDIIELY<br>CSQKYEGVPAPKEMASYI<br>EQIQKDLAYEAGSKAQLR<br>DMEFFQKEIESSEPIYNG<br>MKGTDKLEAARQMFQNP<br>NLRTAFNASGDTTSALDI<br>FHLEGEPTQRLMNFCEEY<br>HVSLVCLLLMGMRTYFQ<br>KVNGHDDVSINNAIARRA<br>TLKEKKSGGTRIHSFPFRT<br>CFSQDMKFIDAIYAIRDK<br>QNEYFRHANYDPTAYFA<br>YRSKTYPQPHAGLTYEPI<br>SLTYQPLTLKEKGLDQLG<br>DIRYTTKWYPNGMTPQA<br>VYLTVMHRPEDNGLDFN<br>FEHQVKAFSREELEYFYY<br>YLCKIMFKGIENPNLTIGE<br>IIKLV (SEQ ID NO: 50) |

TABLE 1-continued

Non-limiting examples of biosynthetic enzymes from human gut microbiome-derived bacterium.

| Enzyme | Gene Source | Nucleotide Sequence | Amino Acid Sequence |
| --- | --- | --- | --- |
| | | TATAACGGTATGAAAGGCAC CGATAAACTGGAAGCAGCAC GTCAGATGTTTCAGAATCCG AATCTGCGTACCGCATTTAAT GCAAGCGGTGATACCACCTC AGCACTGGATATTTTTCATCT GGAAGGTGAACCGACACAGC GTCTGATGAATTTTTGTGAAG AATATCATGTTAGCCTGGTTT GTCTGCTGCTGATGGGTATGC GTACCTATTTTCAGAAAGTTA ACGGTCATGATGACGTGAGC ATTAATAACGCCATTGCACG TCGTGCGACCCTGAAAGAGA AAAAATCAGGCGGTACACGT ATTCACAGCTTTCCGTTTCGT ACCTGTTTTTCACAGGACATG AAATTCATCGATGCCATTTAT GCCATTCGCGATAAACAGAA CGAATATTTTCGCCACGCAA ATTATGATCCGACCGCATATT TTGCATATCGCAGCAAAACC TATCCGCAGCCGCATGCCGG TCTGACCTATGAACCGATTTC ACTGACCTATCAGCCGCTGA CGCTGAAAGAAAAAGGTCTG GATCAGCTGGGCGATATTCG TTATACCACCAAATGGTATCC GAATGGTATGACACCGCAGG CAGTTTATCTGACCGTTATGC ATCGTCCGGAAGATAATGGT CTGGATTTCAATTTTGAACAC CAGGTGAAAGCATTTAGCCG TGAAGAACTGGAATACTTCT ATTATTACCTGTGCAAAATCA TGTTCAAAGGCATCGAAAAT CCGAACCTGACCATTGGCGA AATTATCAAACTGGTGTAA (SEQ ID NO: 14) | |
| SCP2 sterol-binding domain-containing protein | bprS B. producta | ATGACCTATCAAGAACTGGT GAGCGAAATTCGTGGCATTT TTATGCAGGCAGATGTGAGC GGTATTAAAGAACATATTGC CTACCAGTTTAACATTCGTGG TGAAGCCGAAGGTGCATTCT ATGCAGAAGTTCTGGAAGGC AAACTGTATATCGAACCGTA TGAGTATTATGATCGTGATGT TCTGTTTACCACCACCGCAGA TACCCTGCTGAGCATTGCAA CCGGCACCATGGATGCAGTT GCAGCATTTACCCTGGGCAA ACTGCAGGTTGAAGGTAGCT TTGATAAAGCACTGCTGCTG CAGAGTTTTAGCAAACAGGC AGGTCGTGAAAAAAAGAAAA TGAAAGCCGAAGAAAAACGC CAGCAGAAAGCAGAAGAGA AAGAACTGCAGAAAGCCGTT GAAAAAGAAAGCCAGAAAG TTGTGGAAAAAGTTGCCCAG AAAACGGAAGAAAAAACCG CCAAAAAAACCGTTCGTCGT CTGCTGAAAAAATAA (SEQ ID NO: 33) | MTYQELVSEIRGIFMQAD VSGIKEHIAYQFNIRGEAE GAFYAEVLEGKLYIEPYE YYDRDVLFTTTADTLLSI ATGTMDAVAAFTLGKLQ VEGSFDKALLLQSFSKQA GREKKKMKAEEKRQQK AEEKELQKAVEKESQKV VEKVAQKTEEKTAKKTV RRLLKK (SEQ ID NO: 69) |
| SCP2 sterol-binding domain-containing protein | cspS Clostridiales sp. | ATGACCTTCGAGAAAGTTTTC GAAACCGTGAAAGAAATCTT CATGAAAGCCGATGTTAGCA AAGTGGATGAACATCTGGCA TTTCAGTTTAACATTACCGGT GAAGGTGAAGGCATCTTTTA TGCCGAAGCAAAAGATGGTA AACTGTATGTGGAACCGTAT | MTFEKVFETVKEIFMKAD VSKVDEHLAFQFNITGEG EGIFYAEAKDGKLYVEPY EYYDRDAIFICSADTLLKL AAGKLDPVFAFTTGKLK VEGSLEKALKLQKFV (SEQ ID NO: 71) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | GAGTATTATGATCGTGATGC CATTTTTATCTGTAGCGCAGA TACCCTGCTGAAACTGGCAG CAGGTAAACTGGATCCGGTT TTTGCATTTACCACCGGCAAA CTGAAAGTTGAAGGTAGCCT GGAAAAAGCACTGAAACTGC AGAAATTTGTGTAA (SEQ ID NO: 35) | |
| SCP2 sterol-binding domain-containing protein | ereS E. rectale | ATGACCTATGCCGATATGTTC AGCAAAGTGAAAGGTCTGTT TATGGAAAGTGATGTGAGCG ATATTAGCGAACATCTGGCA TTTCAGTTTAACATTACCGGT GAAGCCGAAGGTATCTTTTA TGCCGAAGTTAAAGATGGTG TTCTGGCAGTTGAACCGTATG AATATTTTGATCGTGATGCCA TCTTTATCTGTAGCGCAGAAA CCCTGTTTAAACTGGCAGAA GGTCGTATTGATCCGATTCTG GCCTTTACCACCGGCAAACT GAAAGTTGAAGGCAATATTG ATAAAGCCCTGCGTCTGAAG CAGATCATCGATAGCAAAAA AGCCTAA (SEQ ID NO: 36) | MTYADMFSKVKGLFMES DVSDISEHLAFQFNITGEA EGIFYAEVKDGVLAVEPY EYFDRDAIFICSAETLFKL AEGRIDPILAFTTGKLKVE GNIDKALRLKQIIDSKKA (SEQ ID NO: 72) |
| SCP2 sterol-binding domain-containing protein | rbaS R. bacterium | ATGACCTATGCCGATATGTTT AGCGAAGTTAAAGGTATGCT GGCAGGCGCAGATGTTAGCG ATATTCAAGAACATCTGGCC TATCAGTTTAACATTATTGGT GAAGCCGAAGGCATCTTTTA TGCCGAAGTGAAAGAAGGCA AACTGTATATCGAACCGTAT GAGTATTTTGATCGCGACGT GATGTTTATTTGTACCGCAGA TACCCTGTTTAAACTGGCAA AAGGTAAAACCGATCCGGTT CTGGCATTTACCACCGGTAA ACTGAAAGTGGAAGGCAATA TTGATAAAGCCCTGAAACTG GGTGATCTGCTGGCACGTAA ACGTAAAGGTTAA (SEQ ID NO: 34) | MTYADMFSEVKGMLAG ADVSDIQEHLAYQFNIIGE AEGIFYAEVKEGKLYIEP YEYFDRDVMFICTADTLF KLAKGKTDPVLAFTTGK LKVEGNIDKALKLGDLLA RKRKG (SEQ ID NO: 70) |
| chromosome condensation protein | bsmC Blautia sp. | ATGACCAACTATTATCCGCTG ACCGCAGCACAGAAAATGCA TCATAATTGGATCATGGATTA TGGCACCCAGCAGGTTAGCG GTGTTAGCGTTGTTGCAAGC GTTCAGGCAGAACTGGATTT TGGTCTGCTGAAAAAATGCA TTCAGATGGAAACCGAACGT AGCGGTTGTACCCGTATTCGT TTTACCAAACCGGATAAAGA TGGTAACGTTCAGCAGTATCT GGTTAAACAAGATCCGCGTG ATATCGGCTTTAAAGATCTG AGCGGTATGGGTAGCCTGGC AAAAGCAGATGAACTGATGC AGCAGTGGGCCTATGAAACC TTTGATGGTGATGATATTCCG ATGTGCGAATTCACCATGCT GAAACTGCCGGAAGGTTATA ATGGTTTTTTTGTGCACATGG ATCACCGCCTGATTGATAGCT GTGGTCTGGTTGTTATGATTG GTGATCTTTTTCAGCTGTATA CCTACTACAAATATGGCACC GCATATCCGCAAGAACTGGC AGATTTTGAAACCGTCCTGA AAAAAGATCTGGCCAAAGCA GGTAATGAAAAACGCTTTGC | MTNYYPLTAAQKMHHN WIMDYGTQQVSGVSVVA SVQAELDFGLLKKCIQME TERSGCTRIRFTKPDKDG NVQQYLVKQDPRDIGFK DLSGMGSLAKADELMQQ WAYETFDGDDIPMCEFT MLKLPEGYNGFFVHMDH RLIDSCGLVVMIGDLFQL YTYYKYGTAYPQELADF ETVLKKDLAKAGNEKRF AKDKKFWDDQLDALGEP LYSDVQGPSVLEEARKRH GNPKLRSSDIEMKDLFVA VKDYYLEPGPTKNLIDFC MNHQLSMTNLLLLGIRTY LSKVNNGQEDITIQNFISR RSTHDEWTSGGSRTIMFP CRTVIAPETDFLSAAYEIQ NMQNRIYMHSNYDPAFI MDEMRKRYNTPEHTGYE SCYLTYQPMTVKVENEM LGTIRQHAKWFANGAAT KKMYLTVSHTEDGGMNF SYHYQTAHLEEHDMELL YYYMMRILFKGIAEPDMS IGEIMELV (SEQ ID NO: 86) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | CAAAGACAAAAAATTCTGGG<br>ATGATCAGCTGGATGCACTG<br>GGTGAACCGCTGTATAGTGA<br>TGTTCAGGGTCCGAGCGTTCT<br>GGAAGAGGCACGTAAACGTC<br>ATGGTAATCCGAAACTGCGT<br>AGCAGCGATATTGAAATGAA<br>AGACCTGTTTGTTGCCGTGAA<br>AGATTATTATCTGGAACCGG<br>GTCCGACCAAAAATCTGATT<br>GATTTTTGTATGAACCATCAG<br>CTGAGCATGACCAATCTGCT<br>GCTGCTGGGTATTCGTACCTA<br>TCTGAGCAAAGTTAATAACG<br>GCCAAGAAGATATTACCATC<br>CAGAACTTTATTAGCCGTCGT<br>AGCACCCATGATGAATGGAC<br>CAGCGGTGGTAGCCGTACCA<br>TTATGTTTCCGTGTCGTACCG<br>TTATTGCACCGGAAACCGAT<br>TTTCTGAGCGCAGCGTATGA<br>AATTCAGAATATGCAGAACC<br>GCATCTACATGCACAGTAAT<br>TATGATCCGGCATTTATCATG<br>GATGAAATGCGCAAACGTTA<br>TAACACACCGGAACACACAG<br>GTTATGAAAGCTGTTATCTGA<br>CCTATCAGCCGATGACCGTT<br>AAAGTGGAAAATGAAATGCT<br>GGGCACCATTCGTCAGCATG<br>CAAAATGGTTTGCAAATGGT<br>GCAGCAACCAAAAAAATGTA<br>TCTGACCGTTAGCCATACCG<br>AAGATGGTGGTATGAATTTC<br>AGCTATCATTATCAGACCGC<br>ACATCTGGAAGAACATGATA<br>TGGAACTGCTGTACTATTATA<br>TGATGCGCATTCTGTTTAAAG<br>GCATTGCCGAACCGGATATG<br>AGCATTGGTGAAATCATGGA<br>ACTGGTGTAA (SEQ ID NO: 85) | |
| acyl carrier protein | bsmT Blautia sp. | ATGAATCAAGAGATGGAATT<br>CAAGAACATCGTTGCCCAGT<br>ATAGCAAAGTTGCAAGCGAA<br>GAAATGAATAACGAAATGCG<br>TTTTCGTGAAGATCTGGGTTT<br>TAGCAGCCTGGATTTTATGA<br>GCTTTCTGGGTGAACTGGAA<br>GATACCTTTGATCTGGAACTG<br>GATGAAAGCGAAGTGCTGAA<br>AATTACCACACTGGGTGAAG<br>CACTGAATCTGCTGGAAGAA<br>CTGCAGTAA (SEQ ID NO: 87) | MNQEMEFKNIVAQYSKV<br>ASEEMNNEMRFREDLGF<br>SSLDFMSFLGELEDTFDL<br>ELDESEVLKITTLGEALNL<br>LEELQ (SEQ ID NO: 88) |
| AMP-binding protein | bsmA Blautia sp. | ATGCTGATTCGCAACATTCTG<br>GAAGAAAGCGTGCGTAAATT<br>TGATGAAGTTAAAGCCGTTA<br>AATGGCTGAAAAAGAAAGAA<br>ATCATGGAACGCAGCTATGG<br>CGAACTGATGGAAAATGTTG<br>TTAGCACCCGTAAAGGTCTG<br>CTGGCAGAAGGTTTTGAAGG<br>TAAACATATTGCACTGATTG<br>GCACCAGCAGCGTTGAATGG<br>ATGGAAAGCTATCTGGGTAT<br>TATTACCGGTTGTACCACCGC<br>AGTTCCGCTGGATGCAGCAC<br>TGCCGTGTGAAGATCTGATT<br>GATCTGCTGAATCGTAGCGA<br>TAGCGCAGCACTGTTTCTGA<br>GCCCGAAACTGAAACCGTAT<br>CTGGATGCATTTCTGGAAAA<br>TTGTCCGAAACTGCAGAAAG<br>TTTGGATGCTGCAAGAAGAA | MLIRNILEESVRKFDEVK<br>AVKWLKKKEIMERSYGE<br>LMENVVSTRKGLLAEGF<br>EGKHIALIGTSSVEWMES<br>YLGIITGCTTAVPLDAALP<br>CEDLIDLLNRSDSAALFLS<br>PKLKPYLDAFLENCPKLQ<br>KVWMLQEEVEDAPAKV<br>YGIGELRNAGKSASADSV<br>CPDAEDIATIIFTSGTTGK<br>SKGVMLTQNNLASNVEA<br>VKITAEPGTAVLSVLPIHH<br>AFCLVMDWLKGFSLGAT<br>LCINDSLLHMVRNMSIFK<br>PEIMLMVPMMIETIYKRL<br>AAADPSIPKTVLAEKVFG<br>GKLRIIFTGGAHLDPYYID<br>RFAEYGVEVLEGYGMSE<br>CSPVISNNTLENNKKGSIG<br>KPLENAEIRFENGEILVKG |

TABLE 1-continued

Non-limiting examples of biosynthetic enzymes from human gut microbiome-derived bacterium.

| Enzyme | Gene | Source | Nucleotide Sequence | Amino Acid Sequence |
|---|---|---|---|---|
| | | | GTTGAGGACGCACCGGCAAA AGTTTATGGTATTGGTGAACT GCGTAATGCAGGTAAAAGCG CAAGCGCAGATAGCGTTTGT CCGGATGCAGAAGATATTGC AACCATTATCTTTACCAGCGG CACCACCGGTAAAAGCAAAG GTGTTATGCTGACCCAGAAT AATCTGGCAAGCAATGTTGA AGCAGTGAAAATTACCGCAG AACCGGGTACAGCAGTTCTG AGCGTTCTGCCGATTCATCAT GCATTTTGTCTGGTTATGGAT TGGCTGAAAGGTTTTAGCCT GGGTGCAACCCTGTGTATTA ATGATAGCCTGCTGCACATG GTTCGTAACATGAGCATCTTT AAACCGGAAATTATGCTGAT GGTGCCGATGATGATTGAAA CCATCTATAAACGTCTGGCA GCAGCAGATCCGAGCATTCC GAAAACCGTTCTGGCAGAAA AAGTTTTTGGTGGTAAACTGC GCATTATTTTCACCGGTGGCG CACATCTGGACCCGTATTATA TCGATCGTTTTGCAGAATATG GTGTCGAAGTTCTGGAAGGT TATGGTATGAGCGAATGTAG TCCGGTGATTAGCAATAATA CGCTGGAAAACAACAAAAAA GGCAGCATTGGTAAACCACT GGAAAATGCGGAAATTCGCT TTGAAAATGGTGAGATTCTG GTTAAAGGTAGCAGCGTGAT GAAAGGCTATTATCAGATGC CGGATGAAACCGCAGAAACC CTGAAAGATGGTTGGCTGCA TACCGGTGATAAAGGTTATA TGGATGAAGATGGCTACCTG TTTATTAACGGTCGTGTGAAA AATCTGATCATTCTGAGCAAT GGCGAAAATGTTAGTCCGGA AGAAATCGAAAATAAACTGG CACTGAATCCGCTGATTGGT GAAGTTATTGTTACGGGTGA AGATAACGGTCTGACCGCAC GTATTTATCCGGAAACAGGCA GTTGTTGAAGCCAAAGCACT GGATGCCGAAGCAATTCAGG CACAGCTGCAGGCCTTTCTG GATGAATATAATCGTAATCA GCCGACCTATCGTCGCATTAC CGGTCTGGTTGTTCGTAAAA ATCCGTTTATTCGTAACACCA CCAAGAAAATTCGTCGTCAG GATGTGCTGATTGATGAACC GCTGGAATAA (SEQ ID NO: 89) | SSVMKGYYQMPDETAET LKDGWLHTGDKGYMDE DGYLFINGRVKNLIILSNG ENVSPEEIENKLALNPLIG EVIVTGEDNGLTARIYPE QAVVEAKALDAEAIQAQ LQAFLDEYNRNQPTYRRI TGLVVRKNPFIRNTTKKI RRQDVLIDEPLE (SEQ ID NO: 90) |
| chromosome condensation protein | ralC | Ruminococcus albus | ATGGAAAAACGCTATGAACT GACCGCAGCACAGAAAATGC ATTATCGTTGGATTAAAGAA TATGGCACCCAGCAGGTTAG CGGTCTGAGCATTGTTGCAG CATTTGGTGCAGAACTGGAT ATTGGTCTGCTGAAAAAATG TATCGAGCTGGAAAAACAGC GTTATAGCTGTCTGCGTCTGC GTTTTACCAAACCGGATGAT AATGGTGAGATCAAACAGTA TATTGCCGAATATCAGCCGG AAGAAATCAAAGAATACGAT CTGCGTGATATGACCCTGCC GGAAGCAGATGACATTATGC AGAATTGGGCCTATGAAACC | MEKRYELTAAQKMHYR WIKEYGTQQVSGLSIVAA FGAELDIGLLKKCIELEKQ RYSCLRLRFTKPDDNGEI KQYIAEYQPEEIKEYDLR DMTLPEADDIMQNWAYE TFDGDDIPMCEFRIVMLP EGYTGFFVHMDHRLNDS VGVAVMATDIMNLYKHF KFGDEEPAPLADFEKVLI NDLEKASNEKRHAKAKR FWDEELDELGEPLYSDIQ GTSVLEEARRKHNAPNLR AADIERKELFVAVKDYQL EVDSMQRAINFCLHNQIS PTNLILLVIRTYLSKVNGG |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | TTTGATGGTGATGATATTCCG<br>ATGTGCGAATTTCGTATTGTT<br>ATGCTGCCTGAAGGTTATAC<br>CGGTTTTTTTGTTCACATGGA<br>TCATCGTCTGAATGATAGCGT<br>TGGTGTTGCAGTTATGGCAA<br>CCGATATTATGAACCTGTAC<br>AAGCACTTCAAATTTGGTGA<br>TGAAGAACCGGCACCGCTGG<br>CAGATTTTGAAAAAGTTCTG<br>ATTAACGACCTGGAAAAAGC<br>CAGCAATGAAAACGTCATG<br>CAAAAGCCAAACGCTTCTGG<br>GATGAAGAATTAGATGAACT<br>GGGTGAACCGCTGTATAGCG<br>ATATTCAGGGCACCAGCGTT<br>CTGGAAGAAGCACGTCGTAA<br>ACATAATGCACCGAATCTGC<br>GTGCAGCCGATATTGAACGT<br>AAAGAACTGTTTGTTGCCGT<br>GAAAGATTATCAGCTGGAAG<br>TTGATAGCATGCAGCGTGCA<br>ATTAACTTTTGCCTGCATAAT<br>CAGATTAGCCCGACCAATCT<br>GATTCTGCTGGTTATTCGTAC<br>CTATCTGAGCAAAGTTAATG<br>GTGGCCAAGAAGATATTACC<br>GTCGAAAACTTTATTAGCCGT<br>CGTAGCACCCATGATGAGCT<br>GACCAGCGGTGGTAGTCGTA<br>CCCTGTGTTTTCCGTGTCGTA<br>CCGTTATTAGCGGTGATACC<br>ACCTTTATTGATGCAGCACGT<br>AAAATTCAGAATCATCAGAA<br>CCGCATCTATATGTTCAGCGG<br>TTATGATCCGGAATTTATTCG<br>CGACGAAATGAAAAAGCGCT<br>ATAATACCCCTGATGATACC<br>ACGTATGTTTCAGTGTATCTG<br>ACCTATCAGCCTCCGATGAC<br>CAGCCAGGATCTGGACCCGA<br>ATGCACAGAAACTGCCGCTG<br>TATGTTAAATGGTTTGCAAAT<br>GGTGCAGCCACGAAAAAGAT<br>GTACCTGACCGTTAGCCATCT<br>GCCGGATCGTAAACTGAATT<br>TCAGCTATCATTATCAGACCG<br>CACATCTGACCGAGAAAGAT<br>GCCGAACTGATGTATTATTAC<br>ATGATGCGTATTCTGTTCCGT<br>GGCATTGAAGATCCGGGTCG<br>TACCATTAGCGAAATTATTG<br>ATATGGTGTAA (SEQ ID NO:<br>91) | QEDITVENFISRRSTHDEL<br>TSGGSRTLCFPCRTVISGD<br>TTFIDAARKIQNHQNRIY<br>MFSGYDPEFIRDEMKKRY<br>NTPDDTTYVSVYLTYQPP<br>MTSQDLDPNAQKLPLYV<br>KWFANGAATKKMYLTV<br>SHLPDRKLNFSYHYQTAH<br>LTEKDAELMYYYMMRIL<br>FRGIEDPGRTISEIIDMV<br>(SEQ ID NO: 92) |
| acyl carrier protein | ralT *Ruminococcus albus* | ATGGAACAGAAGTTTAAAGA<br>AATCGCCAGCCGTTATTGCA<br>AAGGTGATGTTGGTGAAATC<br>ACACCGGAAATGGCAATTCG<br>TGAAGATCTGGGTCTGAGCA<br>GCCTGGATCTGATGACCTTTC<br>TGGGTGATCTGGAAGATGAA<br>TTTGATATCGAGTTTGATTTT<br>GGTGCCGATGAACAGAAACT<br>GGGTAATATTCGTACCGTTG<br>GTGATGCCATTGGTCTGCTGA<br>ATGAATATGTTGGTTAA (SEQ ID NO: 93) | MEQKFKEIASRYCKGDV<br>GEITPEMAIREDLGLSSLD<br>LMTFLGDLEDEFDIEFDF<br>GADEQKLGNIRTVGDAIG<br>LLNEYVG (SEQ ID NO: 94) |
| AMP-binding protein | ralA *Ruminococcus albus* | ATGAAAAAGACCATTCACAC<br>CCTGTGGAATCGTAGCGCAA<br>AGATTATGCCGATCTGCCT<br>GCAGTTCGTTGGCTGGTTAA<br>AAAAGATATCAAAGAAATCA<br>GCTACAAGCAGGCCGATGAA | MKKTIHTLWNRSAKDYA<br>DLPAVRWLVKKDIKEISY<br>KQADEVISGLRKGAYAL<br>GFEHRHIALVGTNSAEWI<br>EAYMSVVTSTNTAVPLDS<br>ALPAHDLIDLIDRSDSEGV |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | GTTATTAGCGGTCTGCGTAA<br>AGGTGCCTATGCACTGGGTTT<br>TGAACATCGTCATATTGCACT<br>GGTTGGCACCAATAGCGCAG<br>AATGGATTGAAGCATATATG<br>AGCGTTGTTACCAGTACCAA<br>TACCGCAGTTCCGCTGGATA<br>GCGCACTGCCTGCACATGAT<br>CTGATCGATCTGATTGATCGT<br>AGCGATAGCGAAGGTGTTTT<br>TCTGGACCCGAAATTTGCAA<br>GCCTGGCAACCGAAATCAAA<br>GACAAATGCAAAAAAGTGAA<br>AAAAATCTGGATGCTGAGCG<br>ACGAAGCCATTGAAGGCACC<br>GAAAGCCTGAAAGACCTGAT<br>TGCAGCCGGTGAAGGTGCAG<br>ATGAACCGAGCGCACCGGAA<br>GAGGATGATATTAGCATGAT<br>TGTTTTTACCAGCGGCACCAC<br>CGGTAAAAGCAAAGGTGTTA<br>TGCTGACCCAGAGCAATCTG<br>TATACCAATATTGAAGCCAT<br>CCTGTATGATATGGACCCTG<br>GTCTGATTTTTCTGAGCGTTC<br>TGCCGGTTCATCATTGTTTTT<br>GTCTGGTTATGGATTGGCTGA<br>ATGGTTTTTGGATGGGTGCA<br>GTTCTGTGTATTAATGATAGC<br>CTGATGCACATGGTTCGTAA<br>CATGACCATTTTTAACCCGGA<br>TGTGATGCTGATGGTTCCGCT<br>GATGGTGGAAACCATCTATA<br>AACGTCTGCGTACCTTAGATC<br>CGAGCATTCCGCCTGAAGTT<br>GTGAGCGAAAAAGTGTTTGG<br>TAAGAACCTGAAATACATTT<br>TTACAGGTGGCGCACATCTG<br>GAACCGTATTATATCGAAGA<br>GTTCAACAAATATGGCATCG<br>ATGTGTATGAAGGTTATGGT<br>ATGAGCGAATGTAGTCCGGT<br>TATTAGCAGCAACAAAATTG<br>GTGATAGCAAACCGGGTAGC<br>ATTGGTCGTCCGCTGCCGAAT<br>GTTGAAATCAAATTTGTTGAT<br>GGCGAAATTCTGGTTCGTAG<br>CACCAGCGTTATGAAAGGCT<br>ATTACAAGATGGAAAAAGAA<br>ACCGAAGAAACCCTGAAGGA<br>TGGTTGGCTGCATACCGGTG<br>ATAAAGGTTATATTGATGAA<br>GATGGCTTCCTGTTTATTAAC<br>GGTCGTGTGAAAAATCTGAT<br>CATTCTGAGCAATGGCGAAA<br>ACATTAGTCCGGAAGAAATT<br>GAAAATCGTCTGGCACTGAA<br>TGACCTTATTGGTGAAATTGT<br>TGTTACCGGTGAAGATAATC<br>TGCTGACCGCACGTATTTTTC<br>CAGATCCGGATATGACCGGT<br>GGTATGAGTGATGAAGAAAT<br>TCGTAATGCCCTGCAAGAAA<br>TCCTGAACGATTATAACAAA<br>CAGCAGCCGACCTATAAACA<br>GCTGAGCAAACTGGTTGTTC<br>GCAAATATCCGTTTCTGAAA<br>AACACGACCCGTAAAATCAT<br>TCGTGCCGAAGTTTATCGTGA<br>TGAACAGGGTGCATAA (SEQ<br>ID NO: 95) | FLDPKFASLATEIKDKCK<br>KVKKIWMLSDEAIEGTES<br>LKDLIAAGEGADEPSAPE<br>EDDISMIVFTSGTTGKSK<br>GVMLTQSNLYTNIEAILY<br>DMDPGLIFLSVLPVHHCF<br>CLVMDWLNGFWMGAVL<br>CINDSLMHMVRNMTIFNP<br>DVMLMVPLMVETIYKRL<br>RTLDPSIPPEVVSEKVFGK<br>NLKYIFTGGAHLEPYYIEE<br>FNKYGIDVYEGYGMSEC<br>SPVISSNKIGDSKPGSIGRP<br>LPNVEIKFVDGEILVRSTS<br>VMKGYYKMEKETEETLK<br>DGWLHTGDKGYIDEDGF<br>LFINGRVKNLIILSNGENIS<br>PEEIENRLALNDLIGEIVV<br>TGEDNLLTARIFPDPDMT<br>GGMSDEEIRNALQEILND<br>YNKQQPTYKQLSKLVVR<br>KYPFLKNTTRKIIRAEVY<br>RDEQGA (SEQ ID NO: 96) |

TABLE 1-continued

Non-limiting examples of biosynthetic enzymes from human gut microbiome-derived bacterium.

| Enzyme | Gene Source | Nucleotide Sequence | Amino Acid Sequence |
| --- | --- | --- | --- |
| putative uncharacterized protein | cscC *Clostridium* sp. | ATGCTGGAATATACCCTGCC GGATGGTCGTACCGTTGAAA GCTATCCGCTGACACCGGCA CAGCAGCTGATGCTGTATCT GAGCATTCAGTATGGTAATC ATGTTCCGGTTCTGAATATTT GCACCGGCTATTATTTCCAGG GTGAGTTTGATAGCAAAGTG ATGAAAGAAGCAGTTCTGGA AGCCATTGATCGTTGTGATGT TATGCGTCTGCGTTTTGCCAA ACATCCGCTGTTTAAAGTTGT TCAGTATCTGGCAGATGAAG CCGGTATTGAAGTTGAAGAA GAGGATCTGAGCAATATGCC GTGGGATGAAGCACATGAAT TTATCAAAGAACGTGGCCAT AGCCTGATTGATACCTTTGCA GATGCACCGCTGCATCAGAT TAAAATCATTCATCTGGAAA ACGACTACAACGGCATCTAT CTGAAACTGCATCATCTGGG TTTTGATGGCTATAGCAGCA AAATGCTGATTAGCGATATT ATGGCCATTTACCTGAGCAA AAAATACGGTAAACCGTATC CGAAACCGATGCGTAGCTAT TTTGAATGCCTGGATAAAGA ATTTGCCTATGCAGAAAGCG ATCGCCATGATGAAGATATT GATTATTGGGTTAGCACCATT ACCGATCGTCCGGAAGCAAT TTATACCGATTATGTTCGTCC GAGCCGTCTGATTGAACAGC GTATTCGTGAAAATAAACCG GATCTGCGTATTGCAAGCGTT CATGATGGTGATGATCCGAG CAGTAAAACCCTGCGTTATA GCCTGAGTAAAGAAACCAGC GATAAAATCATGAGCCTGTG TGCAGAAAAGGTCTGAGCG TTCCGTGTGTTATGATGATGG GTCTGCGTTGTGCACTGAGC AGCTTTAATGATAATGAAGA AGATGTGAGCTTCAAACTGA TGGTTAATCGTCGTGCAACCC TGCTGGAAAAGAAAAGCGGT GGTATGCGTATGCACTTTTTT AGCATGCGTAGCATTGTTAA ACCGGAAATGACCTTCCTGG AAGCCCTGAAAGTTATTGAA CAGGCACAGAATGAAGTGTT TGAACATAGCAATCTGAGCA GCCTGGAAGCGATTGCAGTT CGTCATAAAGCAATGGGTAA TGAAACCCACGATGTGTATG AAAGCATGAGCTTTAGCTAT CAGCCGTATATGCCGGTTCC GTGTCTGGATGAAAAAATGC GTGATAGCAGCCGTGGTTTTT GGTATAATAACGATGCAAGC ATGCAGAATCTGTACCTGAC CGTTATGCATCGTAGCAATG ATGCAGGTCTGGATTTCAATT ATGAATACCGCACCAAAAAC AACCCGATTAATGAACTGGG CATCTTCCATAACAAACTGAT CAAAAGCATTCTGCTGGGCA CCCGTAATACCGGCATTACC GTTGGTGAAATTCTGGATGA GATCAAAGAAGATGAGGTCG ATATTTACGCCTAA (SEQ ID NO: 97) | MLEYTLPDGRTVESYPLT PAQQLMLYLSIQYGNHVP VLNICTGYYFQGEFDSKV MKEAVLEAIDRCDVMRL RFAKHPLFKVVQYLADE AGIEVEEEDLSNMPWDE AHEFIKERGHSLIDTFADA PLHQIKIIHLENDYNGIYL KLHHLGFDGYSSKMLISD IMAIYLSKKYGKPYPKPM RSYFECLDKEFAYAESDR HDEDIDYWVSTITDRPEAI YTDYVRPSRLIEQRIRENK PDLRIASVHDGDDPSSKT LRYSLSKETSDKIMSLCA EKGLSVPCVMMMGLRCA LSSFNDNEEDVSFKLMVN RRATLLEKKSGGMRMHF FSMRSIVKPEMTFLEALK VIEQAQNEVFEHSNLSSL EAIAVRHKAMGNETHDV YESMSFSYQPYMPVPCLD EKMRDSSRGFWYNNDAS MQNLYLTVMHRSNDAGL DFNYEYRTKNNPINELGIF HNKLIKSILLGTRNTGITV GEILDEIKEDEVDIYA (SEQ ID NO: 98) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| acyl carrier protein | cscT Clostridium sp. | ATGCTGGAAAAAATCGTGGA CATCATCCTGAATTATGTGGA ACCGGATGATGAAATTACAC CGGATACACGTATTAAAAGC GAACTGGGTATGTCCTCATTT GATCTGGTTTGTTTTGGTGAT GATCTGTATGATGAATTCGG CGTTAAAATTGGTGCCGATG ATTTTCGTCGTTGTGATACCG TTGGTAAACTGGCAGCATAT ATTGGTGCAAATTGCTAA (SEQ ID NO: 99) | MLEKIVDIILNYVEPDDEI TPDTRIKSELGMSSFDLV CFGDDLYDEFGVKIGAD DFRRCDTVGKLAAYIGA NC (SEQ ID NO: 100) |
| putative uncharacterized protein | cscA Clostridium sp. | ATGGCAAGCGAACAGAATCG CCTGGAATATTATGCAAAAG TTAATACCGTTCGCGATCTGA TTGATCTGGCAGCAGAACGT TATGGTGATAAACCGTTTATT AAGTATCTGGAAGGTGATCG CATTACCGAAAAAAGCTTTA GCGAACTGCGTAGCAATAGC CTGGCACTGAGCCGTTATATT CGTAGCATTTGTCCGCGTCGT ATGCATATTGCAGTTATTGGT CGTACCACCTATGAATATATC ACCGCACTGACCGGTACACT GGTTAGCGGTAATGTTTTTGT TCCGTTTGCACCGAACATTAG CGTTAATGAAGCATGTGAAC TGTTTGCCGATGGTGATGTTG AAGCACTGTTTTATGAAGCC GATTTTGATGAACGTGCCAA AGAAATCGCAAAAAAATGTC CGCAGCTGAAAACCGTTGTT AATATGGGTGATGCAGAACA TTTTGCCAGCATCTATGCAGA ATATGGTGAAGGTAGCGAAT ATGCAACCCTGAGCGAAGTT GAACTGGACCCGGATGATTG TGCAGCAATTATCTATACCA GCGGCACCACCGGTGTTCGT AAAGGTGTTATGCTGAGCAG CCGTAATCTGATTAGCAATGT TACCTATACCGAACTGGCGTT AGATCCGAATGATGTGATGC TGAGCGTTCTGCCGATGCATC ACATTTTTTGTATTAGCTGCG ATTACTTCAAACCGCTGCTGG ATGGTATTACCGTTTGTCTGA ATGGTGAAATTAGCAATATT GGTCGCAGCCTGGCAACCTT TAAACCGACCACCATGCGTG CAGTTCCGATGATTTGTGATA CCCTGATCAAAAAAGTGCAC ATGCTGCATAAAAAGTATCC GGAACTGACCGATCGTCAGG CAGCCGAACTGGTTTTTGGTG AAAACTTTAAATGGATTGCA GTTGGTGGTGCAGCATTAGG TAAAGGTCTGGTTGCAGATT ATGAAAAACATGGTATTATG CTGCGCCAAGGTTATGGTAT GACCGAAGTTAGCCCGAAAA TTTCAACCGCAGATTTTGGTG ATGAATGCAAAGATAGCAGC GGTAAAATTCTGCGTAGTATT GGTGATGTGCGTATTGTTGAT GGCGAAATTCAGGTTAAAGG TAGCAGCGTTATGATGGGCT ATTATAAGAAACCGGAAGAA ACCGCCAAAGTGTTTACCGA AGATGGTTATCTGAAAACAG GTGATCTGGGTCGTATTACCA GCAGCGATCATATTTATGTG ACCGGTCGTCTGAAAAACCT | MASEQNRLEYYAKVNTV RDLIDLAAERYGDKPFIK YLEGDRITEKSFSELRSNS LALSRYIRSICPRRMHIAV IGRTTYEYITALTGTLVSG NVFVPFAPNISVNEACELF ADGDVEALFYEADFDER AKEIAKKCPQLKTVVNM GDAEHFASIYAEYGEGSE YATLSEVELDPDDCAAII YTSGTTGVRKGVMLSSR NLISNVTYTELALDPNDV MLSVLPMHHIFCISCDYF KPLLDGITVCLNGEISNIG RSLATFKPTTMRAVPMIC DTLIKKVHMLHKKYPELT DRQAAELVFGENFKWIA VGGAALGKGLVADYEKH GIMLRQGYGMTEVSPKIS TADFGDECKDSSGKILRSI GDVRIVDGEIQVKGSSVM MGYYKKPEETAKVFTED GYLKTGDLGRITSSDHIY VTGRLKNLIILSNGENVSP EMLENKFADEKVIKEIVV YGDKDRIVAEIFPDAEYA SAAGIDDIKGYLEAKAQQ LNDSEPEERRIAEIRLRDK PFEKTTTGKIKRTAVKIEY (SEQ ID NO: 102) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | GATTATTCTGAGCAATGGCG AAAATGTTAGTCCGGAAATG CTGGAAAACAAATTCGCCGA TGAAAAGGTGATCAAAGAAA TTGTGGTGTATGGCGATAAA GATCGTATTGTGGCAGAAAT TTTTCCGGATGCCGAATATGC CAGCGCAGCAGGTATTGATG ATATTAAAGGTTACCTGGAA GCAAAAGCACAGCAGCTGAA TGATAGCGAACCTGAAGAAC GTCGTATTGCAGAAATTCGTC TGCGCGATAAACCTTTTGAA AAAACCACCACCGGCAAAAT CAAACGTACCGCAGTTAAAA TCGAGTATTAA (SEQ ID NO: 101) | |
| condensation domain-containing protein | lbkC *Lachnospiraceae bacterium* | ATGACCGAACGTCTGATTAA TGGTGTTATGGTTAAAACCTG GCCTCTGACCGATGTTCAAG GTGGTCTGTATAAAGTTTTTG CACATTATGCCAGCATCCAA GAAATGAATTTAGGTGTGGG CTTCTACTTCAAGATGGATAT GAATGAAGAACTGATGCGTC AGAGCATGCGTGAAGCCATT GGTTATATGGAAGCACTGAA TGTTCGTTTTGGCCAGGATGA AAATGGTGAGATGTATCAGT ATATTAACCCGGAACCGTGG AACGAAGAAATGCCGCTGTG GGATCTGAGCGATCTGTCAG AAAAAGAAGCAAAAGAGTA CCTGACCAAAGTTACCAGCG AACCGATTGATTATCTGCAC AAAAACATGACCATTGTGAG CCTGGTTAAACTGCGTGATG GTTTTAGCGGTGTGTATATCA ATTTCAATCACATGCTGGCA GATGGCTATAGCATCAATAT GTTTATGACCTATCTGGCCGT GATCTATTTCAGCCATGCAGC AGGTAAAGAAATTGATCTGC CTCGTAAAAGCGACTATATC AAAATGATCGAGAAAGAACT GGAATACAAAGGTAGCGAAC GTGAAAAAGCCGATCATGAA TTTTGGAATAGCACCCTGGA AGAAGGTGAACCGATTTATA CCCATCCGACCGCAGCACCG AATAATGCACGTGTTCGTCA GCTGCGCGAAAAAGGTGAAA CCCGTTATTTTGAAAATACGA TTAGCCCGAAAGCCAGCATT GATAGCGAAATTATTGGTGG TGAACGTGCCGAAAAACTGG TTGATGCCATTGCAGAAAAT AAACTGAGCGAAAATGCACT GGCAACCCTGGCACTGCGTA GTACCCTGAGCCTGCTGAAT CATCGTGAAACCGATATTGC AGCACGTGTTATTGTTAATCG TCGCGGTACAATTAATGAAC GTTATAGCGGTGGTAATCGC ATGACCTTTCTGACCTGGCGT AGCATTATTGATGATGATAT GCCGGTTCGTGATGCCCTGA AAGAAATGATTGATAGCCAG AAAAAAATCTTTCGCCACGC CGATTATAACAGCATGAAAC GTCTGGCAGAACGTGGTCAG TATTTTGGTAATCCGCCTCTG GCAACCTATGAAAGCGTTAC CTTTACCTATCAGCCGAATAC | MTERLINGVMVKTWPLT DVQGGLYKVFAHYASIQ EMNLGVGFYFKMDMNE ELMRQSMREAIGYMEAL NVRFGQDENGEMYQYIN PEPWNEEMPLWDLSDLS EKEAKEYLTKVTSEPIDY LHKNMTIVSLVKLRDGFS GVYINFNHMLADGYSIN MFMTYLAVIYFSHAAGK EIDLPRKSDYIKMIEKELE YKGSEREKADHEFWNST LEEGEPIYTHPTAAPNNA RVRQLREKGETRYFENTI SPKASIDSEIIGGERAEKL VDAIAENKLSENALATLA LRSTESLENHRETDIAAR VIVNRRGTINERYSGGNR MTFLTWRSIIDDDMPVRD ALKEMIDSQKKIFRHADY NSMKRLAERGQYFGNPP LATYESVTFTYQPNTVQI DPRLPEMKAVWYSNSST SNICYLTLEHMLGKKDY VFIYERRVEEMSEEEMHF FTELMMECMESAVEHLD GTIGEVLDEVQARHPELC ESEMRAV (SEQ ID NO: 104) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | CGTTCAGATTGATCCGCGTCT GCCGGAAATGAAAGCAGTTT GGTATAGCAATAGCAGCACC AGCAATATTTGTTATCTGACC CTGGAACACATGCTTGGCAA AAAAGATTATGTGTTCATCTA TGAACGTCGCGTGGAAGAAA TGAGCGAAGAAGAGATGCAC TTTTTTACCGAACTGATGATG GAATGTATGGAAAGCGCAGT TGAACATCTGGATGGCACCA TTGGTGAAGTTCTGGATGAA GTTCAGGCACGTCATCCGGA ACTGTGTGAAAGCGAAATGC GTGCAGTTTAA (SEQ ID NO: 103) | |
| acyl carrier protein | lbkT *Lachnospiraceae bacterium* | ATGGCCGACATCAAAATGTT CGATGAAATTCGTGATATCCT GCTGAATTATGCCGAAGTTG GTGCAGAAGAAATTAACACC GAAACCGATATCATTGAAGA ACTGGGCTTAGATAGCTTTA GCTTCATTAGCATGCTGGGTG AAGTTGAAGAAACCTTTGAT ATTAGCATCAGCGAGGAAGA AATGGAAGAAGCATTTCATC TTTTTACCCCTGCGGACATCA TCAAATTTGTTGCAAAAAAA GCAGCCTAA (SEQ ID NO: 105) | MADIKMFDEIRDILLNYA EVGAEEINTETDIIEELGL DSFSFISMLGEVEETFDISI SEEEMEEAFHLFTPADIIK FVAKKAA (SEQ ID NO: 106) |
| long-chian acyl-CoA synthetase | lbkA *Lachnospiraceae bacterium* | ATGACCCTGCAAGAAAAAAT CGATCGCAACATTACCGATTT TCGTAGCTTTCTGCGTGAACT GGCAGATAAATATGGTGATA CACCGGCAGTTCGTGAATAT CATGGTAAAGAACTGGTGGA TCGCAATTACCTGGAACTGA AACGTGATGCAGATGCAGTT AGCCGTTTTCTGCTGGCACAG GGTGCCGAAGAACGTATGCA TATTGCAGCAGTTGGTGCAA CCAGCTATCAGTATATTGCCG CATATTTTGGCACCGTTGATA CCGCAAATGTTATTGTTCCGA CCGAAGCACAGCTGAGCACC GAAACACAGTGTGAACTGTT TCACATGGCAGATGTTACCG GTCTGTTTTTCGATAAACATT TTGAAGATGCGATCCCGGAA ATCCATGAAAAATGTCCGGA TATCAAACTGTTCATTTGTCT GACCGATGGTGTTGAAAGCC ATGATCTGGGTGATATTCATA TCCATAGCATCAACGAGATC GAGAAAGAATATGCAGAAGG CGAAGAAATTATTGTGCCGC TGGAACATGATACCTTTAGC ACCATTCTGTTTACCAGCGGT ACAACCAGCGCACGTCCGAA AGCAGTTATGCTGTGTCATG GTGGTATTATCGACAACATTT TTAGCGGTGAACTGGAACAG CGTGATAGCACCAATAAAGT TAAACTGATTGCACTGCCGA TTCATCATGCACTGAGCTTTA ATACCGATATCTGTATGGGTT TTCGTAATGGCGATACCGTGT TTGTTAATGATAGCATGCTGC ATATCGCCAAGAATTTCAAA GTTGCAAAACCGTATACCGC AATTCTGGTGCCGATGATCTT TGAAAACTTCTACCACAAAA TCATGAAAGCCCATGAAGTT CATCCGGAAGTTGATCTGAA | MTLQEKIDRNITDFRSFLR ELADKYGDTPAVREYHG KELVDRNYLELKRDADA VSRFLLAQGAEERMHIAA VGATSYQYIAAYFGTVDT ANVIVPTEAQLSTETQCE LFHMADVTGLFFDKHFE DAIPEIHEKCPDIKLFICLT DGVESHDLGDIHIHSINEI EKEYAEGEEIIVPLEHDTF STILFTSGTTSARPKAVML CHGGIIDNIFSGELEQRDS TNKVKLIALPIHHALSFNT DICMGFRNGDTVFVNDS MLHIAKNFKVAKPYTAIL VPMIFENFYHKIMKAHEV HPEVDLKAMARDVFGGE VEVFYCGGAHLRAEIAD AFAEWGMPVFEGYGMTE CSPRVAANMPWRYRRDS IGRVVDNAHVRIKDTELQ VKSPSVMLGYYKDPEAT KAAFTEDGWLKSGDIGYI DEDGFIFLQGRIKNLIILSN GENVSPEEIETKLYDCTFI KECLVYEENGQITAEVFP DAEYAEMHKVTDVEKEI SAAIKAVNKSMPTTKSVR SVKFRYEPFERTATNKIK RTGRGKKAA (SEQ ID NO: 108) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | AGCAATGGCACGTGATGTTT TTGGTGGTGAAGTTGAAGTG TTTTATTGTGGTGGTGCACAT CTGCGTGCAGAAATTGCAGA TGCCTTTGCAGAATGGGGTA TGCCGGTTTTTGAAGGTTATG GTATGACCGAATGTAGTCCG CGTGTTGCAGCAAATATGCC GTGGCGTTATCGTCGTGATA GTATTGGTCGTGTTGTTGATA ATGCCCATGTGCGTATTAAA GATACCGAACTGCAGGTTAA AAGCCCGAGCGTTATGCTGG GTTATTACAAAGATCCGGAA GCAACCAAAGCAGCATTTAC CGAAGATGGTTGGCTGAAAA GCGGTGATATTGGCTATATTG ATGAAGATGGCTTTATCTTTC TGCAGGGACGTATCAAAAAC CTGATTATTCTGAGCAATGGC GAAAATGTTAGTCCGGAAGA AATTGAAACCAAACTGTATG ATTGCACCTTTATCAAAGAAT GCCTGGTGTATGAAGAAAAT GGTCAGATTACAGCCGAAGT TTTTCCGGATGCAGAATATGC CGAAATGCATAAAGTTACCG ATGTGGAAAAAGAAATCAGC GCAGCAATTAAAGCCGTGAA TAAAAGCATGCCGACCACCA AATCAGTTCGTAGCGTTAAA TTTCGCTATGAACCGTTTGAA CGTACCGCGACCAATAAAAT CAAACGTACCGGTCGTGGTA AAAAAGCAGCATAA (SEQ ID NO: 107) | |
| peptide synthetase | bsaC Blautia sp. | ATGCGTACCCGTAAAGGCCA TAAAGTTTATCCGCTGACCGT TGCACAGAAATTCCATCTGT ATTATCTGCCGTTTTGTCCGA GCGCAGCAGTTCTGAATATT GGCACCAGCGTTACCATTGA AATTGAGATTGATTGGGATC TGCTGGCCAAAAGCATTAAC AAAGCCTATGCACGTAGCGA AGGTATGCGTATTCGTTTTGC CAAAGATAAAGAAGGCAACT GGTATCAGTATGTTGCAGAT CCGGAAGAAATGAAAATCGA ATTTGCCGATTTTAGCAAGG GCACCATGGAAGAGGCAGAA AGCACCATGCAGCAGTGGAC CACCGTTCCGTTTAAAATGG AAGATAGCCAGATGAGCCGT ATTGTGATGATTCAGATGCC GGATGGTTTTAACGGTATCTA TTTTCTGGTGCATCACATGAT TGCCGATGCACAGAGCCTGA TTTGTTTTATGAAAGATATCA TCGAACTGTACTGCAACGAG AAATATGAAGGTGTTCCGTA TCCGAAAGATATGGCCAGCT ATATTGATCAGCTGAAAAAA GATCTGGATTACGAAGCAGG TAGCAAAGCACAGCTGCGTG ATATTGAATTTTTCCAGCGCG AAATTGAAAAAGGCGAACCG ATTTATAACGGTATTCATGGC ACCGATAAACTGGAAGCAGC ACGTGCAATGTTTAAAGATC CGAAACTGCGTACCGCATTT AATGCAAGTGATGATACCAA AAGCGCACTGGATATTTTTCA TCTGGAAGCCGATCCGACCA | MRTRKGHKVYPLTVAQK FHLYYLPFCPSAAVLNIG TSVTIEIEIDWDLLAKSIN KAYARSEGMRIRFAKDK EGNWYQYVADPEEMKIE FADFSKGTMEEAESTMQ QWTTVPFKMEDSQMSRI VMIQMPDGFNGIYFLVHH MIADAQSLICFMKDIIELY CNEKYEGVPYPKDMASY IDQLKKDLDYEAGSKAQ LRDIEFFQREIEKGEPIYN GIHGTDKLEAARAMFKD PKLRTAFNASDDTKSALD IFHLEADPTKRLMDFCEK YHVSLACLLLMGLRTYF QKMNGFEDVSINNAIARR ATLREKKSGGTRIHSFPIR TVFSEDMKFIDGVYAIRD KQNEIFRHANYDPTAYFA YRSKIYPQPHAGLTYEPIS LTYQPMTLQENGLTELG DIRYKTKWYPNGTCPQG MYLTVMHRPEDNGLDFN PEHQIKAVSREELEYLYY YLCKIMFKGTENPDLTIG EIIKLI (SEQ ID NO: 110) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | AACGTCTGATGGATTTTTGTG AGAAATATCATGTTAGCCTG GCATGTCTGCTGCTGATGGGT CTGCGTACCTATTTTCAGAAA ATGAACGGTTTTGAGGACGT GAGCATTAATAACGCGATTG CCCGTCGTGCAACCCTGCGT GAGAAAAAAGCGGTGGCAC CCGTATTCATAGCTTTCCGAT TCGTACCGTTTTTAGCGAGGA TATGAAATTTATCGATGGCGT GTATGCCATTCGCGATAAAC AGAATGAAATTTTCGCCAC GCAAACTATGATCCGACCGC ATATTTTGCATATCGCAGCAA AATCTATCCGCAGCCGCATG CCGGTCTGACCTATGAACCG ATTAGCCTGACCTATCAGCC GATGACACTGCAAGAAAATG GTCTGACCGAACTGGGTGAT ATTCGCTATAAAACCAAATG GTATCCGAATGGTACATGTC CGCAGGGTATGTATCTGACC GTTATGCATCGTCCGGAAGA TAACGGTCTGGATTTTAACTT TGAACACCAGATTAAAGCCG TGAGCCGTGAAGAACTGGAA TATCTGTACTATTACCTGTGC AAAATCATGTTCAAAGGCAC CGAAAATCCTGATCTGACCA TTGGCGAAATTATCAAGCTG ATCTAA (SEQ ID NO: 109) | |
| acyl carrier protein | bsaT Blautia sp. | ATGTTCGAAAAACTGGTGGA TATCATCTGCAGCTATGTGGA AGTGGAAAAGATAATATTC GTCCGGAAAGCCGCTTTATG GAAGATCTGGGTTTTACCAG CTATGACTTTATGAGCATGCT GGGCGAAATCGAAGATGAAT TTGATGTTGAAGTTGAACAG GCCGATGCCATGAATATTCG TACCGTTCAAGAAGCAGCAG ACTATCTGGAAAAACTGACC GCAGGTAATTAA (SEQ ID NO: 111) | MFEKLVDIICSYVEVEKD NIRPESRFMEDLGFTSYDF MSMLGEIEDEFDVEVEQA DAMNIRTVQEAADYLEK LTAGN (SEQ ID NO: 112) |
| AMP-binding protein | bsaA Blautia sp. | ATGCTGTGTAGCACCGTTCGT CAGATTCTGGTTAATACCGA ACAGAAATATGGTCCGGAAG ATGCCATTCGCTATAAAATC AGCAAAAACGAGATCGAGAG CAAAAACCTATACACAGCTGC GTGAAGATAGCGAAAGCTTT AGCTGTGTTCTGCGTGATCTG GGTGAACAGGGTAAACATAT TGCAGTTATTGGTACAACCA GCTATCCGTGGCTGACCGCA TATTTTGGCACCGTTAATAGC GGTAGCGTTGTTGTTCCGCTG GATGTTAATCTGCCTGCCGA AGATGTTTGTGATCTGATTCA TCGTAGCGATAGCACCGTGC TGGTTTATGATGAAGCACGT AAAGATGTTGCAGCCATTGC AAAAGAACGTTGTCCGCAGC TGAAAATTCTGATTAGCATG CAGCAGCAGGATCATAATGA ACAGGCCTATGCATTTTGGA AACTGCTGGAAGAACATCGT GGTAGCTTTGATTATATGCCT GATCCTGATCAGCTGTGCAC | MLCSTVRQILVNTEQKYG PEDAIRYKISKNEIESKTY TQLREDSESFSCVLRDLG EQGKHIAVIGTTSYPWLT AYFGTVNSGSVVVPLDV NLPAEDVCDLIHRSDSTV LVYDEARKDVAAIAKER CPQLKILISMQQQDHNEQ AYAFWKLLEEHRGSFDY MPDPDQLCTIMFTSGTTG KSKGVMLTHRNVAENAT CLDMKIPERIVIMTVLPIH HAYCLSMDILKGVSLGA VICINDSLMRVAKNIKLF KPEMILMVPLMIETMAK KLEEAALLPAKIVKNQVF GKQFHTICSGGAYLDPSY IDLFAKYDIIIQQGYGMTE CSPVISTTQKWNIRKDAV GQLLPNCQAKTVDGELW VKGSSVMQGYYKMPEET AETLEDGWLKTGDLGYV DEDGFVYLTGRKKNLIIT KNGENVSPEELENALS TN REVGEVEVREHNGVIEAE |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | CATTATGTTTACAAGCGGCA<br>CCACCGGTAAAAGCAAAGGT<br>GTTATGCTGACCCATCGTAAT<br>GTTGCAGAAAATGCAACCTG<br>TCTGGATATGAAAATTCCGG<br>AACGTATTGTGATTATGACC<br>GTTCTGCCGATTCATCATGCA<br>TATTGTCTGAGCATGGATATT<br>CTGAAAGGTGTGAGCCTGGG<br>TGCCGTTATTTGTATTAATGA<br>TAGCCTGATGCGTGTGGCCA<br>AAAACATCAAACTGTTTAAA<br>CCGGAAATGATTCTGATGGT<br>TCCGCTGATGATTGAAACCA<br>TGGCAAAAAAACTGGAAGAA<br>GCAGCACTGCTGCCTGCCAA<br>AATTGTTAAAAATCAGGTGT<br>TTGGCAAACAGTTCCATACC<br>ATTTGTAGCGGTGGTGCATAT<br>CTGGACCCGAGCTATATTGA<br>TCTTTTCGCCAAATATGACAT<br>CATCATCCAGCAAGGTTATG<br>GTATGACCGAATGTAGTCCG<br>GTTATTAGCACCACACAGAA<br>ATGGAATATTCGCAAAGATG<br>CAGTTGGTCAGCTGCTGCCG<br>AATTGTCAGGCAAAAACCGT<br>TGATGGTGAACTGTGGGTTA<br>AAGGTAGCAGCGTTATGCAG<br>GGTTATTACAAAATGCCGGA<br>AGAAACCGCAGAAACCCTGG<br>AAGATGGTTGGCTGAAAACA<br>GGCGATCTGGGTTATGTTGAT<br>GAAGATGGCTTTGTTTATCTG<br>ACCGGTCGCAAAAAAAACCT<br>GATCATTACCAAAAATGGCG<br>AGAATGTTTCACCGGAAGAA<br>CTGGAAAATGCACTGAGCAC<br>CAATCGTCTGGTTGGTGAAG<br>TTCTGGTTCGTGAACATAACG<br>GTGTTATTGAAGCAGAAATC<br>TATCCGGATCAGGACTACGT<br>TAAAAAGAAACGCATCAAAG<br>ATGTTAAGGCAAGCCTGCAA<br>GAGGTGATCGATGAATATAA<br>TCGTACCGCAGCTCCGCAGA<br>AAAAAATCTATAGTCTGATT<br>GTTCGCGATACCGAGTTTGA<br>AAAAACCACCACACGTAAAA<br>TCAAGCGCTTTTAA (SEQ ID<br>NO: 113) | IYPDQDYVKKKRIKDVK<br>ASLQEVIDEYNRTAAPQK<br>KIYSLIVRDTEFEKTTTRK<br>IKRF (SEQ ID NO: 114) |
| chromosome<br>condensation<br>protein | bweC *Blautia*<br>*wexlerae* | ATGACCAACTATTATCCGCTG<br>ACCGCAGCACAGAAAATGCA<br>TCATAATTGGATCATGGATTA<br>TGGCACCCAGCAGGTTAGCG<br>GTGTTAGCGTTGTTGCAAGC<br>GTTCAGGCAGAACTGGATTT<br>TGGTCTGCTGAAAAAATGCA<br>TTCAGATGGAAACCGAACGT<br>AGCGGTTGTACCCGTATTCGT<br>TTTACCAAACCGGATAAAGA<br>TGGTAACGTTCAGCAGTATCT<br>GGTTAAACAAGATCCGCGTG<br>ATATCGGCTTTAAAGATCTG<br>AGCGGTATGGGTAGCCTGGC<br>AAAAGCAGATGAACTGATGC<br>AGCAGTGGGCCTATGAAACC<br>TTTGATGGTGATGATATTCCG<br>ATGTGCGAATTCACCATGCT<br>GAAACTGCCGGAAGGTTATA<br>ATGGTTTTTTTGTGCACATGG<br>ATCACCGCCTGATTGATAGCT<br>GTGGTCTGGTTGTTATGATTG<br>GTGATCTTTTTCAGCTGTATA | MTNYYPLTAAQKMHHN<br>WIMDYGTQQVSGVSVVA<br>SVQAELDFGLLKKCIQME<br>TERSGCTRIRFTKPDKDG<br>NVQQYLVKQDPRDIGFK<br>DLSGMGSLAKADELMQQ<br>WAYETFDGDDIPMCEFT<br>MLKLPEGYNGFFVHMDH<br>RLIDSCGLVVMIGDLFQL<br>YTYYKYGTAYPQKLADF<br>ETVLKKDLAKAGNEKRF<br>AKDKKFWDDQLDALGEP<br>LYSDIQGPSVLEEARKRH<br>GNPKLRSSDIEMKDLFVA<br>VKDYYLEPGPTKNLIDFC<br>MNHQLSMTNLLLGIRTY<br>LSKVNNGQEDITIQNFISR<br>RSTHDEWTSGGSRTIMFP<br>CRTVIAPETDFLSAAYEIQ<br>NMQNRIYMHSNYDPAFI<br>MDEMRKRYNTPEHTGYE<br>SCYLTYQPMTVKVENEM<br>LGTIRQHAKWFANGAAT |

TABLE 1-continued

Non-limiting examples of biosynthetic enzymes from human gut microbiome-derived bacterium.

| Enzyme | Gene | Source | Nucleotide Sequence | Amino Acid Sequence |
|---|---|---|---|---|
| | | | CCTACTACAAATATGGCACC GCATATCCGCAGAAACTGGC AGATTTTGAAACCGTCCTGA AAAAGATCTGGCCAAAGCA GGTAATGAAAAACGCTTTGC CAAAGACAAAAAATTCTGGG ATGATCAGCTGGATGCACTG GGTGAACCGCTGTATAGCGA TATTCAGGGTCCGAGCGTTCT GGAAGAGGCACGTAAACGTC ATGGTAATCCGAAACTGCGT AGCAGCGATATTGAAATGAA AGACCTGTTTGTTGCCGTGAA AGATTATTATCTGGAACCGG GTCCGACCAAAAATCTGATT GATTTTTGTATGAACCATCAG CTGAGCATGACCAATCTGCT GCTGCTGGGTATTCGTACCTA TCTGAGCAAAGTTAATAACG GCCAAGAAGATATTACCATC CAGAACTTTATTAGCCGTCGT AGCACCCATGATGAATGGAC CAGCGGTGGTAGCCGTACCA TTATGTTTCCGTGTCGTACCG TTATTGCACCGGAAACCGAT TTTCTGAGCGCAGCGTATGA AATTCAGAATATGCAGAACC GCATCTACATGCACAGTAAT TATGATCCGGCATTTATCATG GATGAAATGCGCAAACGTTA TAACACACCGGAACACACAG GTTATGAAAGCTGTTATCTGA CCTATCAGCCGATGACCGTT AAAGTGGAAAATGAAATGCT GGGCACCATTCGTCAGCATG CAAAATGGTTTGCAAATGGT GCAGCAACCAAAAAAATGTA TCTGACCGTTAGCCATACCG AAGATGGTGGTATGAATTTC AGCTATCATTATCAGACCGC ACATCTGGAAGAACATGATA TGGAACTGCTGTACTATTATA TGATGCGCATTCTGTTTAAAG GCATTGCCGAACCGGATATG AGCATTGGTGAAATCATGGA ACTGGTGTAA (SEQ ID NO: 115) | KKMYLTVSHTEDGGMNF SYHYQTAHLEEHDMELL YYYMMRILFKGIAEPDMS IGEIMELV (SEQ ID NO: 116) |
| acyl carrier protein | bweT | *Blautia wexlerae* | ATGAATCAAGAGATGGAATT CAAGAACATCGTTGCCCAGT ATAGCAAAGTTGCACCGGAA GAAATGAATAACGAAATGCG TTTTCGTGAAGATCTGGGTTT TAGCAGCCTGGATTTTATGA GCTTTCTGGGTGAACTGGAA GATACCTTTGATCTGGAACTG GATGAAAGCGAAGTGCTGAA AATTACCACACTGGGTGAAG CACTGAATCTGCTGGAAGAA CTGCAGTAA (SEQ ID NO: 117) | MNQEMEFKNIVAQYSKV APEEMNNEMRFREDLGF SSLDFMSFLGELEDTFDL ELDESEVLKITTLGEALNL LEELQ (SEQ ID NO: 118) |
| AMP-binding protein | bweA | *Blautia wexlerae* | ATGCTGATTCGCAACATTCTG GAAGAAAGCGTGCGTAAATT TGATGAAGTTAAAGCCGTTA AATGGCTGAAAAAGAAAGAA ATCATGGAACGCAGCTATGG CGAACTGATGGAAAATGTTG TTAGCACCCGTAAAGGTCTG CTGGCAGAAGGTTTTGAAGG TAAACATATTGCACTGATTG GCACCAGCAGCGTTGAATGG ATGGAAAGCTATCTGGGTAT TATTACCGGTTGTACCACCGC AGTTCCGCTGGATGCAGCAC TGCCGTGTGAAGATCTGATT | MLIRNILEESVRKFDEVK AVKWLKKKEIMERSYGE LMENVVSTRKGLLAEGF EGKHIALIGTSSVEWMES YLGIITGCTTAVPLDAALP CEDLIDLLNRSDSAALFLS PKLRPYLDAFLGNCPKLQ KVWMLQEEVEDAPAKV YGIGELRNAGKSASADSV CPDAEDIATIIFTSGTTGK SKGVMLTQNNLASNVEA VKITAEPGTAVLSVLPIHH AFCLVMDWLKGFSLGAT LCINDSLLHMVRNMSIFK |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | GATCTGCTGAATCGTAGCGA TAGCGCAGCACTGTTTCTGA GCCCGAAACTGCGTCCGTAT CTGGATGCATTTCTGGGTAAT TGTCCTAAACTGCAGAAAGT TTGGATGCTGCAAGAAGAAG TTGAGGACGCACCGGCAAAA GTTTATGGTATTGGTGAACTG CGTAATGCAGGTAAAAGCGC AAGCGCAGATAGCGTTTGTC CGGATGCAGAAGATATTGCA ACCATTATCTTTACCAGCGGC ACCACCGGTAAAAGCAAAGG TGTTATGCTGACCCAGAATA ATCTGGCAAGCAATGTTGAA GCAGTGAAAATTACCGCAGA ACCGGGTACAGCAGTTCTGA GCGTTCTGCCGATTCATCATG CATTTTGTCTGGTTATGGATT GGCTGAAAGGTTTTAGCCTG GGTGCAACCCTGTGTATTAAT GATAGCCTGCTGCACATGGT TCGTAACATGAGCATCTTTAA ACCGGATATCATGCTGATGG TTCCGATGATGATTGAAACC ATCTATAAACGTCTGGCAGC AGCAGATCCGAGCATTCCGA AAGCCGTTCTGGCAGAAAAA GTTTTTGGTGGTAAACTGCGC ATTATTTTCACCGGTGGCGCA CATCTGGACCCGTATTATATC GATCGTTTTGTTGAATATGGT GTGGAAGTGCTGGAAGGTTA TGGTATGAGCGAATGTAGTC CGGTGATTAGCAATAATACG CTGGAAAACCATAAAAAAGG CAGCATTGGTAAACCTCTGG AAAATGCCGAAATTCGCTTT GAAAATGGTGAGATTCTGGT TAAAGGTAGCAGCGTGATGA AAGGCTATTATCAGATGCCG GATGAAACCGCAGAAACCCT GAAAGATGGTTGGCTGCATA CCGGTGATAAAGGTTATATG GATGAAGATGGCTACCTGTT TATTAACGGTCGTGTGAAAA ATCTGATCATTCTGAGCAATG GCGAAAATGTTAGTCCGGAA GAAATCGAAAATAAACTGGC ACTGAATCCGCTGGTTGGTG AAGTTATTGTTACAGGTGAA GATAACGGTCTGACCGCACG TATTTATCCGGAACAGGCAG TTGTTGAAGCCAAAGCACTG GATGCCGAAGCAATTCAGGC ACAGCTGCAGGCCTTTCTGG ATGAATATAATCGTAATCAG CCGACCTATCGTCGCATTACC GGTCTGGTTGTTCGTAAAAAT CCGTTTATTCGTAACACCACC AAGAAAATTCGTCGTCAGGA TGTGCTGATTGATGAACCGCT GGAATAA (SEQ ID NO: 119) | PDIMLMVPMMIETIYKRL AAADPSIPKAVLAEKVFG GKLRIIFTGGAHLDPYYID RFVEYGVEVLEGYGMSE CSPVISNNTLENHKKGSIG KPLENAEIRFENGEILVKG SSVMKGYYQMPDETAET LKDGWLHTGDKGYMDE DGYLFINGRVKNLIILSNG ENVSPEEIENKLALNPLV GEVIVTGEDNGLTARIYP EQAVVEAKALDAEAIQA QLQAFLDEYNRNQPTYR RITGLVVRKNPFIRNTTK KIRRQDVLIDEPLE (SEQ ID NO: 120) |
| chromosome condensation protein | lblC Lachnospiraceae bacterium | ATGCGCAAAGAATATCCGCT GACCGCAGCACAGAATATGC ATTATCAGTGGATCAAAGAG TACAAGACCCAGCAGGTTAG CGGTGTTAGCATTGTTGCAA GCCTGAAAGCAGAACTGGAT TTTGGTCTGCTGAAAAAATGT ATCCAGCTTGAGATGGAACG TTATGGTTGTCTGCGTCTGCG TTTTACCAAACCGGATGAAA AGGGTGAGATCAAACAGTAC | MRKEYPLTAAQNMHYQ WIKEYKTQQVSGVSIVAS LKAELDFGLLKKCIQLEM ERYGCLRLRFTKPDEKGE IKQYLIKHDSRDIPLKDM TGMTLAEADDMMQHWA YETLDGDNRPMCEIMMV KLPEGYNGFFIHMDHRLI DSCGLVVMVNDLMQLYT HYRFGAEYPADLADFEK VLESDLQKAGNEKRFAR |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | CTGATCAAACATGATAGCCG TGATATTCCGCTGAAAGATA TGACCGGTATGACCCTGGCC GAAGCAGATGACATGATGCA GCATTGGGCCTATGAAACCC TGGATGGTGATAATCGTCCG ATGTGTGAAATTATGATGGTT AAACTGCCGGAAGGCTATAA CGGCTTTTTTATCCACATGGA TCATCGTCTGATTGATAGCTG TGGTCTGGTTGTTATGGTTAA TGATCTGATGCAGCTGTATAC CCATTATCGTTTTGGTGCCGA ATATCCGGCAGATCTGGCAG ATTTTGAAAAAGTTCTGGAA AGCGATCTGCAGAAAGCCGG TAATGAAAAACGCTTTGCAC GCGATAAAAAGTTTTGGGAT GATCAGCTGGATGCACTGGG TGAACCGCTGTATAGCGATA TTCAGGGTCCGAGCGTTCTG GAAGAAGCACGTAAAAAACA CAAGAACAAAAAACTGCGTG CAGCCGATATTGAACGCAAA GAACTGTTTGTTGCCGTGAA AGATTATGTTCTGGAACCGG AACCGACCAAAGGTCTGATG GATTTTTGTATGAATCATCAG CTGAGCATGACCAATCTGCT GCTGCTGGGTATTCGTACCTA TCTGAGCAAAGTTAATAACG GCCAAGAGGATATTACCATC GAAAACTTTATTAGCCGTCGT AGCACCCATGATGAATGGAC CAGCGGTGGTAGCCGTACCA TTATGTTTCCGTGTCGTACCG TTATTCCTGCCGATATGGATT TTATGAGCGCAGCGTATGAA ATTCAGAATGTGCAGAATCG CATCTACATGCACAGCAATT ATGATCCGGCACTGATTCGT GAAGAAATGAAGAAACGTTA CAAAACACCGGATGATACCA CCTATGAAAGCTGTTATCTGA CCTATCAGCCGATGCCGGTTC ACATGGATAATCCGTTTCTGA ATGGTATTCAGATGCATAGC AAATGGTTTGCAAATGGTGC AGCCACCAAAAAGATGTATC TGACCGTTAGCCATACCGAT AATGGTGGTATGAACTTCAG CTATCATTATCAAACCGCAC GTCTGACCGAAAAAGATATG GAACTGCTGTATTATTACATG ATGCGTATCCTGTTTATGGGC ATTAGCAATCCGGATATGAA AATCGGCGATATTATGGAAC AGGTGTAA (SEQ ID NO: 121) | DKKFWDDQLDALGEPLY SDIQGPSVLEEARKKHKN KKLRAADIERKELFVAVK DYVLEPEPTKGLMDFCM NHQLSMTNLLLLGIRTYL SKVNNGQEDITIENFISRR STHDEWTSGGSRTIMFPC RTVIPADMDFMSAAYEIQ NVQNRIYMHSNYDPALIR EEMKKRYKTPDDTTYES CYLTYQPMPVHMDNPFL NGIQMHSKWFANGAATK KMYLTVSHTDNGGMNFS YHYQTARLTEKDMELLY YMMRILFMGISNPDMKI GDIMEQV (SEQ ID NO: 122) |
| acyl carrier protein | lblT Lachnospiraceae bacterium | ATGAATCGTGCCGAAGAGTT CAAAAACATTGTTGCACAGT ATAGCAGCGTTGCAGCCGAA GATATGACCGATGAAATGAG CCTGCGTGAAGATCTGGGTC TGAGCAGCCTGGATTTTATG ACCTTTCTGGGTGAAATCGA GGATACCTTTGATGTTGAACT GGATCTGGATCGTGCAGTTC AGATTCGTACCGTTGGTGAA GCAATTAGCATGATGAATGC ACTGGTTACCGCATAA (SEQ ID NO: 123) | MNRAEEFKNIVAQYSSV AAEDMTDEMSLREDLGL SSLDFMTFLGEIEDTFDVE LDLDRAVQIRTVGEAISM MNALVTA (SEQ ID NO: 124) |

TABLE 1-continued

Non-limiting examples of biosynthetic enzymes from human gut microbiome-derived bacterium.

| Enzyme | Gene | Source | Nucleotide Sequence | Amino Acid Sequence |
|---|---|---|---|---|
| AMP-binding protein | lblA | *Lachnospiraceae bacterium* | ATGAACACCATTCGCGAAAT TTGGGATAGCGCACTGAATA ACTATAGCGAACTGCCTGCC GTTCGTTGGCTGGAAAAAAA AGATATCATTGAACGTAGCT ATCGCGAGCTGAACAACGAT ATTGAAGAAATTCGTAAAGG CCTGAAAGCCGAAGGTCTGG ATGGTGTGCATATTAGCCTG ATTGGCACCGCAAGCATTAG CTGGATTGGTACATATCTGG GTATTACCACCGGTAATAAT GTTGCAGTTCCGCTGGATGC AGGTCTGCCTGCAGAAGATC TGATTGAACTGCTGAATGAT AGTGATGCAGAAGCACTGTT TCTGGCACCGAAAGGTAAAG CACTGGCAGAAGCAGTTAAA GCAAGCTGTCCGAAAATCCG TAAAATTTGGCTGCTGCAAG AAGAACCGGAAGAAGGTTTT AGCACCCTGGCAGATCTGAA AGATATGAGCAAAGGTCGTC AGGATGTTGAAGGTCGTAAA GCAGAAGATATTGCGACCCT GATTTATACCAGCGGTACAA CCGGTAAAAGCAAAGGTGTT ATGCTGACCCAGAGCAATCT GAGCCAGAATGTTGAAAGCG TTCCGTATAGCGCAGAACCG GGTTGTGTTCTGCTGAGCGTT CTGCCGGTTCATCATGCATTT TGTCTGGTTATGGATTGGCTG AAAGGTTTTTCACTGGGTGC AACCGTTTGTATCAACGATA GCTTTATGCATATCATCCGCA ACATGAGCATCTTTAAACCG GATGTGATGCTGATGGTTCC GCTGATGATTGAAACCATCT ATAAACGTCTGAGCGCAGTT GATCCGGCACTGCCGAAAGA AGCCGTTGCAGCAAACGTTT TTGGTGGTAATCTGAAAATC ATCTTTACAGGCGGTGCACA TCTGGACCCGTTTTATATCGA AAAACTGGCCGAATATGGTG TGAAAGTTCTGGAAGGTTAT GGTATGAGCGAATGTAGTCC GGTTATTAGCAGCAATACAC CGGAAGATCACAAAATTGGT AGCATTGGTAAACCGCTGCC GAATGTTAAAGTTCGTTTTGA AGATGGTGAAATTCAGGTTC AGGGTAGCAGCGTTATGAAA GGCTATTACAAAATGCCTGC CGAAACCGAAGAAACCCTGA AAGATGGTTGGCTGCATACC GGTGATAAAGGTTATCTGGA TGAAGATGGCTTTCTGTTTAT TAACGGTCGCGTGAAAAATC TGATTATTCTGAGCAATGGC GAAAACATCAGTCCGGAAGA AATTGAAAATAAGCTGGGCA TTAATCCGCTGGTTGGTGAA GTTATTGTTACCGGTGAAAAT AATGGTCTGACCGCACGTAT TTATCCGGATCAGGATGTGG TTAAAGCCACCGGTCTGGCC GAAGATGCCGTTAAAGCAGC ACTGGATAATATCCTGAAAG AGTATAATCAGAAACAGCCG ACCTATCGTCAGATTATTGCA | MNTIREIWDSALNNYSEL PAVRWLEKKDIIERSYRE LNNDIEEIRKGLKAEGLD GVHISLIGTASISWIGTYL GITTGNNVAVPLDAGLPA EDLIELLNDSDAEALFLAP KGKALAEAVKASCPKIRK IWLLQEEPEEGFSTLADL KDMSKGRQDVEGRKAED IATLIYTSGTTGKSKGVM LTQSNLSQNVESVPYSAE PGCVLLSVLPVHHAFCLV MDWLKGFSLGATVCIND SFMHIIRNMSIFKPDVML MVPLMIETIYKRLSAVDP ALPKEAVAANVFGGNLKI IFTGGAHLDPFYIEKLAEY GVKVLEGYGMSECSPVIS SNTPEDHKIGSIGKPLPNV KVRFEDGEIQVQGSSVM KGYYKMPAETEETLKDG WLHTGDKGYLDEDGFLFI NGRVKNLIILSNGENISPE EIENKLGINPLVGEVIVTG ENNGLTARIYPDQDVVK ATGLAEDAVKAALDNIL KEYNQKQPTYRQIIALVV RKNPFHRNATGKIVRAD AEIDE (SEQ ID NO: 126) |

TABLE 1-continued

Non-limiting examples of biosynthetic enzymes from human gut microbiome-derived bacterium.

| Enzyme | Gene | Source | Nucleotide Sequence | Amino Acid Sequence |
| --- | --- | --- | --- | --- |
| | | | CTGGTTGTTCGCAAAAATCC<br>GTTTCATCGTAATGCAACCG<br>GCAAAATTGTTCGTGCAGAT<br>GCAGAAATTGATGAATAA<br>(SEQ ID NO: 125) | |
| putative uncharacterized protein | rscC | *Ruminococcus sp.* | ATGAACAGCGTTAACAAACC<br>GGTGTATCCGCTGATTCCGCC<br>TCAAGAAATGATTCAGTTTAT<br>GCTGAAATACAGCTTTTTTCA<br>TAAACAGGTGACCCAGATTC<br>CGGATAGCATTATTGTTAGCC<br>AGAAAATCGACTTCGATGTT<br>ATGACCGAAGCCTTTAACAT<br>TGAAATCGAACGTAATGATT<br>GTCTGCGCCTGGTTTTTTTCA<br>AACAGAATGGCAACATCATG<br>CAGTATTTTCGTGATCCGTAT<br>CGTATTGGTAGCGTTCCGGTT<br>TATAACTTTAAATCCGATGA<br>AGAACGCGAGAAAGTTCTGA<br>CCGCAGATGCACAGAAACCG<br>ATTAAAATGCTGAAAGGCGA<br>AATCTTCCGCCTGAAATACTT<br>TACCACCTATGATGGTCGTTA<br>TGGCGTGTATATCAACATTCA<br>TCATCTGGTGATGGATAACG<br>CAGCAGTTTTTGCCTTTTTCA<br>ATGACCTGTTTGCCGTGTATG<br>ATCATCTGAAAAATGGTAAA<br>CCGATGCCGAAACCGCTGGG<br>TAGCTATGAAGATCGTATTA<br>AACGTGAACTGGCCTACGTT<br>GAAGATAAAAGCAATCTGGA<br>AAAAGAAAAGAGGCCTACA<br>CCGAATATATCACCCGTAAT<br>GGTGAACCGGTTTATCTGGG<br>TGTTGAAGGTCCGAAACTGC<br>TGGAAGCAGAACGCAAAAAA<br>AAGAAAGATCCGAGTATTAA<br>TGCACCGAGCCTGTTTGATCC<br>GATTCATGATAAAGCAGAAC<br>TGACCAAAACCACCTTTAGT<br>CCGGAACTGAGCGAAAAATT<br>CTTTAGCTTTTGCGAGAACAA<br>TAACGTGAGTCCGGAATGTC<br>TGGTTCAGCTGGCACTGCGT<br>ATGCATCTGAGCAAAATTAA<br>TAATGGTCACCTGGACACCT<br>ATTTCATTTGTCTGTGTACCC<br>GTCGTCGTACCCTGACCGAA<br>AAACGTAGCGGTGGCACCGT<br>TACCGCACCGCTGCCGTGGC<br>GTGTTCATCTGGAAGAGGAT<br>GATACCTTTATGAGCGCACT<br>GGATAAAATGGCAGATGCCC<br>AGGTTTGGGCATTTCGTCACA<br>TGGATTATCCGTATCTGGAAT<br>ATCGTGATCTGCAGCGTGAA<br>CTGTTTAACTATAGCGCAGC<br>AGCAGGTAGCAGCACCATGA<br>TGTTTAGCTGGATGCCGATTA<br>ACGAAAAAAGCATTAATGGC<br>TGGGAGTATGAGTATGTTGG<br>TTATGGTCTGGGTCGCTATAT<br>TATGGTTCTGTATACCTTTGC<br>AATGAAAGATGCACATAGCG<br>GCTGTCTGAAAATTAGCTGTC<br>TGCATCGTACCAAATTTGTGA<br>GCGTGGAAGATATTAAAGCA<br>CTGCATAATGGCACCAAAAA<br>GGTTCTGGAAATTGCACTGA<br>ATGAACCGGATATCAGCATT<br>AAAGATCTGCTGGAAAAGAT<br>GTAA (SEQ ID NO: 127) | MNSVNKPVYPLIPPQEMI<br>QFMLKYSFFHKQVTQIPD<br>SIIVSQKIDFDVMTEAFNI<br>EIERNDCLRLVFFKQNGN<br>IMQYFRDPYRIGSVPVYN<br>FKSDEEREKVLTADAQKP<br>IKMLKGEIFRLKYFTTYD<br>GRYGVYINIHHLVMDNA<br>AVFAFFNDLFAVYDHLK<br>NGKPMPKPLGSYEDRIKR<br>ELAYVEDKSNLEKEKEA<br>YTEYITRNGEPVYLGVEG<br>PKLLEAERKKKKDPSINA<br>PSLFDPIHDKAELTKTTFS<br>PELSEKFFSFCENNNVSPE<br>CLVQLALRMHLSKINNG<br>HLDTYFICLCTRRRTLTE<br>KRSGGTVTAPLPWRVHL<br>EEDDTFMSALDKMADAQ<br>VWAFRHMDYPYLEYRDL<br>QRELFNYSAAAGSSTMM<br>FSWMPINEKSINGWEYEY<br>VGYGLGRYIMVLYTFAM<br>KDAHSGCLKISCLHRTKF<br>VSVEDIKALHNGTKKVLE<br>IALNEPDISIKDLLEKM<br>(SEQ ID NO: 128) |

TABLE 1-continued

Non-limiting examples of biosynthetic enzymes from human gut microbiome-derived bacterium.

| Enzyme | Gene | Source | Nucleotide Sequence | Amino Acid Sequence |
|---|---|---|---|---|
| acyl carrier protein | rscT | *Ruminococcus sp.* | ATGCTGGAAACCTTTCGCAA CATCATTTGCAACTATGTGGA TATCGATCCGGAAGATATTA CCGAAGATAGCAAACTGCGT AGCGATATTGAACTGAACAG CTTTGATATGGTTAATGTTGC CGTGGATCTGGAAAATCAGT ATGGCGTTAAAATCGATAGC AAAAAATTCGGTGGTCTGAA AACCGTTGGTGATCTGATGA GCTATATCGAGAGCATCAAA TAA (SEQ ID NO: 129) | MLETFRNIICNYVDIDPED ITEDSKLRSDIELNSFDMV NVAVDLENQYGVKIDSK KFGGLKTVGDLMSYIESI K (SEQ ID NO: 130) |
| putative uncharacterized protein | rscA | *Ruminococcus sp.* | ATGAAGAAATTTGATGCACC GAGCGTTCGTGAACTGCTGG ATACCGGTGCAGAAAAATTT GGTGATGCAACCTTCATCAA ATTCATTCGCGACGGCAAAA TTGAAGAACGCAGCTTCAAA AAAGTTCGTAGCGATAGCCT GGCAGTTTGTCGTTGGATTCG TAGCCTGAGCGATAAACGTA TGCATATTGCCATTATTGGCA AGAGCAACTATGAGTATATT ACCTGTCTGAGCGGTATTCTG ATTAGCGGTAATGTTGCAGTT CCGTTTGCACCGGATATTAGC GTTGAAGAAGCCGCAGAACT GTTTAAACGTGCAGATATTG AAATGCTGCTGTATGAAGAT GAATTTACCGAAAACGCCGA GAAACTGAAAGAACTGTGTC CGTTTCTGCGTTTTAGCGTGA ATTTAGGTAATGGCGAAGAA TTCAACCGCATCTATACCGAT TATAGCGAAAATAGCGAATA TGCAGCACTGTCTGATATCAC CGTTGATAAAAATGCCTGCT GCGTGATTATCTTTACCAGCG GTACAACCGGTATCAAAAAA GGTGTTGAACTGAGCACCCT GGCACTGGTTGGCAATATTA TGTATCATGATTATTGCACCG ACATCTTTCTGCCGAATGATG TTAGCCTGAGTGTTCTGCCGA TGTATCACATTTATTGTTTCA GCGGTGACTATATCAAGAAC CTGAAAGATGGTCTGCAGGT TTGTCTGAATGGTAGCATGAT GGATCTGATTCACAACCTGA AAATCTTTGAACCGAAAGTT GTTCGTGTGGTTCCGATGATT GCACAGAGCCTGCTGCAGCG TGTTAAAGTTATTCTGGCAAA AGAACCGGAAACCAGCGTTA AAGATGCAGTTGCACAGGTT TTTGGTCGCAACATTAAATG GCTGATTAGTGGTGGTGCAT ATCTGAATCCGGAACTGATT GATGAATATGAGAAACTGGG TATTTTCCTGCGTCAAGGTTA TGGTATGACCGAAGCAGGTT GTCGTATTAGCGTGCCGGAT AATACCGCAAGCCGTGAAAG CGTTGGTCGTGTTACCGATGT TTGTACCGTTCGTATTCAGAA TGGTGAAATTCAGGTTAATA CCCCGACCGTTATGCTGGGTT ATTACAAAATGCCGGAAGAA ACCAAAGAAATGTTTACCGA AGATGGTTGGCTGAAAACCG GTGATATTGGTGAACTGACC GAAGATAACCAGCTGTTTAT TACCGGTCGTGTGAAAAACC | MKKFDAPSVRELLDTGA EKFGDATFIKFIRDGKIEE RSFKKVRSDSLAVCRWIR SLSDKRMHIAIIGKSNYEY ITCLSGILISGNVAVPFAP DISVEEAAELFKRADIEM LLYEDEFTENAEKLKELC PFLRFSVNEGNGEEFNRIY TDYSENSEYAALSDITVD KNACCVIIFTSGTTGIKKG VELSTLALVGNIMYHDY CTDIFLPNDVSLSVLPMY HIYCFSGDYIKNLKDGLQ VCLNGSMMDLIHNLKIFE PKVVRVVPMIAQSLLQRV KVILAKEPETSVKDAVAQ VFGRNIKWLISGGAYLNP ELIDEYEKLGIFLRQGYG MTEAGCRISVPDNTASRE SVGRVTDVCTVRIQNGEI QVNTPTVMLGYYKMPEE TKEMFTEDGWLKTGDIG ELTEDNQLFITGRVKNLII LSNGENVSPEAIEKKFAD NREVSEVEVYGEKDRIIA EIYPDYEYAKLEGIDDIQG ELEKTVDRMNKTAKAAH IISEVRVRTEPLEKTGSGK IKRKATVL (SEQ ID NO: 132) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | TGATTATTCTGAGCAATGGC<br>GAAAATGTTAGTCCGGAAGC<br>CATTGAAAAAAAGTTTGCAG<br>ATAATCGTCTGGTGAGCGAA<br>GTTCTGGTTTATGGTGAAAA<br>AGATCGCATTATCGCCGAAA<br>TCTATCCGGATTATGAGTATG<br>CAAAACTGGAAGGCATTGAT<br>GATATTCAGGGTGAACTGGA<br>AAAAACCGTGGATCGTATGA<br>ATAAAACCGCAAAAGCAGCA<br>CATATTATCAGCGAAGTGCG<br>TGTTCGTACCGAACCGTTAG<br>AAAAAACAGGTAGCGGTAAA<br>ATCAAACGTAAAGCAACCGT<br>TCTGTAA (SEQ ID NO: 131) | |
| condensation<br>domain protein | cslC Clostridium sp. | ATGATGATGAAACAGTATCC<br>GCTGACCGCAGCACAGAAAA<br>TGCATGATGATTGGATCAAA<br>AAGTACAAACCCAGCAGGT<br>TAGCGGTGTTAGCGTTGTTGC<br>AAGCCTGAAAGCAGAACTGG<br>ATTTTGGTCTGCTGAAAAAAT<br>GTATCCAACTGGAATATGAA<br>CGCTATGGTTGTATGCGTATT<br>CGTTTTACCAAACGCGATAA<br>AAATGGTGACGTTAAACAGT<br>ACCTGACCGAAAAAGAAACC<br>CGTGATATTCCGCTGAAAGA<br>TCTGAGCGGTATGCACATGG<br>AAGAGGCAGATAATCTGATG<br>CAGCAGTGGGCCTATGAAAC<br>CTTTGATGGTGATGATATCCC<br>GCTGTGTGATATTGTTATGGT<br>TAAACTGCCGGATGGCTATA<br>ACGGCTTTTTTATCCACATGG<br>ATCATCGTCTGATTGATAGCT<br>GTGGTCTGGTTGTGATGATTA<br>ATGATCTTATGCAGCTGTACA<br>CCCACTACAAATTTAACACC<br>CCGTATCCGCAGAAACTGGC<br>AGATTTTGAAGAAGTGCTGG<br>TTAAAGACCTGAATCGTGCC<br>AATAATGAAAAACGCTTTGC<br>CAAAGACAAAAAATTCTGGG<br>ATGATCAGCTGGATGCATGG<br>GGTGAACCGCTGTATAGCGA<br>TATTCAAGGTCTGGATGTTCT<br>GGAAGCAAGCCGTAAACTGC<br>ATCGTAATAAAACCCTGCGT<br>GCAGCAGATATTGAACTGGA<br>TCAGCTGTTTGTTGCCGTGAA<br>AGATTATCAACTGGAACCGG<br>AACCGACCAAAAACCTGATT<br>GATTTTTGTATGAATCATCAG<br>CTGAGCATGACCAATCTGCT<br>GCTGCTGGGTATTCGTACCTA<br>TCTGAGCAAAATGAATCATG<br>GCCAAGAAGATATCACCATC<br>GAAAACTTTATTAGCCGTCGT<br>AGCACCCATGATGAATGGAC<br>CAGCGGTGGTAGCCGTACCA<br>TTATGTTTCCGTGTCGTACCG<br>TTATTAGCGCAGATACCGATT<br>TTCTGAGCGCAGCGTATGAA<br>ATTCAGAATATGCAGAACCG<br>CATCTACATGCACAGCAATT<br>ATGATCCGGCACTGATTCGT<br>GAAGAAATGCAGAAACGTTA<br>TCATACCCCGAAAAACACCG<br>CTTATGAAAGCTGTTATCTGA<br>CCTATCAGCCGATGCCGGTG<br>AAACTGGATAATCCGCATCT<br>GGTTCAGATTCCGCAGCATG | MMMKQYPLTAAQKMHD<br>DWIKKYKTQQVSGVSVV<br>ASLKAELDFGLLKKCIQL<br>EYERYGCMRIRFTKRDK<br>NGDVKQYLTEKETRDIPL<br>KDLSGMHMEEADNLMQ<br>QWAYETFDGDDIPLCDIV<br>MVKLPDGYNGFFIHMDH<br>RLIDSCGLVVMINDLMQL<br>YTHYKFNTPYPQKLADFE<br>EVLVKDLNRANNEKRFA<br>KDKKFWDDQLDAWGEP<br>LYSDIQGLDVLEASRKLH<br>RNKTLRAADIELDQLFVA<br>VKDYQLEPEPTKNLIDFC<br>MNHQLSMTNLLLLGIRTY<br>LSKMNHGQEDITIENFISR<br>RSTHDEWTSGGSRTIMFP<br>CRTVISADTDFLSAAYEIQ<br>NMQNRIYMHSNYDPALI<br>REEMQKRYHTPKNTAYE<br>SCYLTYQPMPVKLDNPH<br>LVQIPQHAKWFANGAAT<br>KKMYLTVSHTDNGGMNF<br>SYHYQTAHLAEHDMELL<br>YYYMMRILFKGIAEPDMS<br>IGEIMEQV (SEQ ID NO:<br>134) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | CAAAATGGTTTGCAAATGGT GCAGCAACCAAAAAGATGTA TCTGACCGTTAGCCATACCG ATAATGGTGGTATGAACTTC AGCTATCATTACCAGACCGC ACATCTGGCAGAACATGATA TGGAACTGCTGTATTATTACA TGATGCGCATTCTGTTTAAAG GCATTGCCGAACCGGATATG AGCATTGGTGAAATTATGGA ACAGGTGTAA (SEQ ID NO: 133) | |
| alpha/beta hydrolase | cslT Clostridium sp. | ATGACCCAAGAGATGCAGTT CAAAAAAATCATTGCCCAGT ATTGCGACGTGAAACCGGAA GAAATGACCAACGATATGAA ATTTCGTGAAGATCTGGGTTT TAGCAGCCTGGATTTTATGA GCTTTCTGGGCGAAATTGAA GATACCTTTGATATCGAACTG GAAGAGGATGATGCACTGCA TGTTTTTACCATTGTTGAAGC ACTGGATCTGCTGGAACGTC TGCAGCAAGAAACCGTTTAA (SEQ ID NO: 135) | MTQEMQFKKIIAQYCDV KPEEMTNDMKFREDLGF SSLDFMSFLGEIEDTFDIE LEEDDALHVFTIVEALDL LERLQQETV (SEQ ID NO: 136) |
| AMP-binding protein | cslA Clostridium sp. | ATGCTGATTCGCGATATTCTG GAAGAAAGCGAGAAAAAATT CAGCGAAATCAAAGCCGTTA AGTGGCTGAAAAAGAAAGAA ATTCGTGATCGTAGCTATCGC GAACTGATGGAAAATGCAAA AAGCGTTCGTAAAGGTCTGT GCGAAGAAAGTTTTCAGGGT AAACATATTGCACTGATTGG TAGCAGCAGCGTTGAATGGA TTGAAGCATATCTGGGTATTA TTACCGGTCAGGCAGTTGCA GTTCCGCTGGATGCAGGTCT GCCTGCAGAAGATCTGATTG ATCTGCTGAATCGTAGTGAT GCAGAAGCACTGTTTCTGAG CCCGAAAATTCAGACCCTGA GCGAACGTATCCTGGAAGAA TGTCCGAAACTGAAGGAAAAT CTGGATTCTGCAAGAAGAAA ACATCGAAACCAACCAGAAA AAAGTTGCAAGCGTTGCAGA ACTGATGATGAGCGGTATTA ATGGCACCGATGATTTTGCA GCACCTGATCCGGAAGATAT TGCAACCATTATCTTTACCAG CGGCACCACCGGTAAAAGCA AAGGTGTTATGCTGACCCAG CGTAATCTGGCAGAAAATGT TAAAAGCGTGAACTATACCG CAGAACCGGGTACCGATTGTT CTGAGCGTTCTGCCGATTCAT CATGCATTTTGTCTGGTTATG GATTGGCTGAAAGGTTTTAG CTTTGGTGCAACCGTTTGCAT TAATGATAGCCTGCTGCACA TGGTGAAAAATATGGGTGTT TTTCATCCGGACATTATGCTG ATGGTTCCGCTGATGGTGGA AACCATCTATAAACGTCTGA GCGCAATGAATCCGCTGATT CCGAAAAAAATCGTTGCAGC AAAAGCCTTTGGTGGCAAAC TGAAAACCATTTTTACAGGT GGCGCACATCTGGACCCGTT TTATATCGAAAAATTTGCCG AATATGGCGTGAACATCTAT GAAGGTTATGGTATGAGCGA | MLIRDILEESEKKFSEIKA VKWLKKKEIRDRSYREL MENAKSVRKGLCEESFQ GKHIALIGSSSVEWIEAYL GIITGQAVAVPLDAGLPA EDLIDLLNRSDAEALFESP KIQTESERILEECPKEKKI WILQEENIETNQKKVASV AELMMSGINGTDDFAAP DPEDIATIIFTSGTTGKSK GVMLTQRNLAENVKSVN YTAEPGTIVLSVLPIHHAF CLVMDWLKGFSFGATVC INDSLLHMVKNMGVFHP DIMLMVPLMVETIYKRLS AMNPLIPKKIVAAKAFGG KLKTIFTGGAHLDPFYIEK FAEYGVNIYEGYGMSECS PVISSNVPEDHKTGSIGRP LSNVEISFEDGEILVRGSS VMKGYYQMPEETAEALR GGWLHTGDKGYLDKDG FLFINGRIKNLIILSNGENI SPEEIENKLALGKLVGEVI VTGENNGLIARIYPDQDA VSAKRMNEEAIRSELQAF IDSYNNTQPTYRRITGLVI RKYPFIKSATKKIKRQEV LIDEAP (SEQ ID NO: 138) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | ATGCAGTCCGGTTATTAGCA GCAATGTGCCGGAAGATCAT AAAACCGGTAGCATTGGTCG TCCGCTGAGCAATGTTGAAA TTAGCTTTGAAGATGGCGAA ATTCTGGTTCGTGGTAGCAGT GTTATGAAAGGCTATTATCA GATGCCTGAAGAAACAGCCG AAGCACTGCGTGGTGGTTGG CTGCATACCGGTGATAAAGG TTATCTGGATAAAGATGGCTT CCTGTTTATTAACGGTCGCAT CAAAAACCTGATTATTCTGA GTAACGGCGAAAACATTAGT CCGGAAGAAATCGAAAATAA ACTGGCACTGGGTAAACTGG TTGGTGAAGTTATTGTTACCG GTGAAAATAATGGTCTGATC GCACGTATTTATCCGGATCA AGATGCAGTTAGCGCAAAAC GTATGAATGAAGAAGCAATT CGTAGCGAACTGCAGGCATT TATTGATAGCTATAACAATA CCCAGCCGACCTATCGTCGT ATTACAGGTCTGGTGATTCGT AAATATCCGTTTATCAAAAG CGCCACCAAAAAGATCAAAC GTCAAGAGGTGCTGATTGAT GAAGCACCGTAA (SEQ ID NO: 137) | |
| lichenysin synthetase A | ccaC Clostridium sp. | ATGAAGAACTATTATCCGCT GACCGCAGCACAGAAAATGC ATTATAACTGGATCAAGAAG TACAAAACCCAGCAGGTTAG CGGTGTTAGCGTTGTTGCAA GCCTGAAAGCAGCACTGGAT TTTGGTCTGCTGAAAAAATGT ATTCAGCTGGAATTTGAACG CTATGGTTGTATGCGTCTGCG TTTTACCAAACCGGATGAAA ATTGTGATGTGATGCAGTAT ATTGCCAGCAATGATAGCCG TGATATTCCGATTAAAGATCT GAGCAATATGCGTATGGCAG ATGCAGATAAACTGATGCAG CAGTGGGCCTATGAAACCAT GGATGGTAATGATATCCCGA TGTGTGATGTTACCATGCTGA AACTGCCGGATGGTTATAAT GGCTTTTTTATCCACATGGAT CACCGCCTGATTGATAGCTGT GGTCTGATTGTTATGATCAAC GATCTGATGCAACTGTATAC CCATTATCGTTTTGGTAGCGA TTTTCCGAAAGATCTGGCAG ATTTTGAAACCGTTCTGAGCA AAGACCTGGAAAAAGCAGCA AACAAAAAACGCTTCCTGAA AGACAAAAAATTCTGGGATG ATCAGCTGGATATTCTGGGT GAACCGCTGTATAGCGATAT TCAGGGTCCTGCAATTCTGG AAGAAAGCCGTAAACTGCAT AACGATAAAAATCTGCGTGC AGCCGATATCGAACTGAAAA ACCTGTTTGTTGCCGTGAAAG ATTATTACCTGGAACCGGAA CCGACCAAGAATCTGCTGGA TTTTTGTACCAATCATCAGCT GAGCATGACCAATCTGCTGC TGCTGGGTATTCGTACCTATC TGAGTAAAGTTAATGATGGC CAAGAGGATATCACCATCCA GAACTTTATTAGCCGTCGTAG | MKNYYPLTAAQKMHYN WIKKYKTQQVSGVSVVA SLKAALDFGLLKKCIQLE FERYGCMRLRFTKPDENC DVMQYIASNDSRDIPIKD LSNMRMADADKLMQQW AYETMDGNDIPMCDVTM LKLPDGYNGFFIHMDHRL IDSCGLIVMINDLMQLYT HYRFGSDFPKDLADFETV LSKDLEKAANKKRFLKD KKFWDDQLDILGEPLYSD IQGPAILEESRKLHNDKN LRAADIELKNLFVAVKDY YLEPEPTKNLLDFCTNHQ LSMTNLLLLGIRTYLSKV NDGQEDITIQNFISRRSTH DEWTSGGSRTIMFPCRTV ISADTDFLTAAHEIQDIQN RIYMHSNYDPALIEEEMR RRYKTPENTSYESCYLTY QPMTVKMDNPHLENIPQ HSKWFANGAATKKMYL TVSHTDNGGTNFSYHYQ TANLKEHDMELLYYYM MRILFKGIAEPDMTIGEIIE QV (SEQ ID NO: 140) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | CACCCATGATGAATGGACCA GCGGTGGTAGCCGTACCATT ATGTTTCCGTGTCGTACCGTT ATTAGCGCAGATACCGATTTT CTGACAGCAGCCCATGAAAT TCAGGATATTCAGAACCGCA TTTACATGCACAGCAATTATG ATCCGGCACTGATTGAAGAA GAAATGCGTCGTCGTTATAA AACACCGGAAAACACCAGCT ATGAAAGCTGTTATCTGACCT ATCAGCCGATGACCGTGAAA ATGGATAATCCGCATCTGGA AAATATTCCGCAGCATAGCA AATGGTTTGCAAATGGTGCA GCCACCAAAAAGATGTATCT GACCGTTAGCCATACCGATA ATGGTGGCACCAATTTTAGCT ATCATTATCAGACCGCCAAC CTGAAAGAACATGATATGGA ACTGCTGTATTACTATATGAT GCGCATTCTGTTTAAAGGCAT TGCAGAACCGGATATGACCA TTGGCGAAATTATTGAACAG GTGTAA (SEQ ID NO: 139) | |
| acyl carrier protein | ccaT Clostridium sp. | ATGACCAAAGAGATGCAGTT CAAAAACATTGTTGCCCAGT ATTGCGAAGTGAAACCGGAA GATATGAATGGTGATATGCG TTTTCGTGAAGATCTGGGTTT TAGCAGCCTGGATTTTATGA GCTTTCTGGGTGAACTGGAA GATACCTTTGATGTTGAGCTG GAAGATGAAGAAGCACTGAA AATTCGTAATGTTAGCGAAG CACTGGAACTGCTGAATACC CTGGTTTAA (SEQ ID NO: 141) | MTKEMQFKNIVAQYCEV KPEDMNGDMRFREDLGF SSLDFMSFLGELEDTFDV ELEDEEALKIRNVSEALE LLNTLV (SEQ ID NO: 142) |
| AMP-binding protein | ccaA Clostridium sp. | ATGGAAAAACTGATCCGCGA CATTATTGAAGAAAGCGCAT GTCGTTTTGCAGAACTGACC GCAGTTAAATGGCTGAAAAA GAAAGAAATCTTCGAGATCA ATTACGCCAGCCTGAATGAA AACATTACCGCAATTCGTAA AGCCCTGCTGAAAGAAGGTT TTCTGAAAAAACATATTGCC CTGATTGGCACCAGCAGCGT TGAATGGATTGAAAGCTATC TGGGTATTATTACCGGTGGTT GTGTTGCAGTTCCGCTGGATG CAGGTCTGCCGGATAAAGAT CTGACCGATCTGATTAATCGT AGCGATAGCGAAGCACTGTT TCTGAGCCCGAAAAATCTGA GCCTGCTGAGCAGCATTCTG GCAGATTGTCCGAAACTGAA AAACATCTGGATTCTGAACA GCGATAATAACGACACCGAA AAAAACAGCATCCTGAACAA AATTAGCGCCTTTGCCAATA ACAGCATCAACAATAGCAAT ACCGTTAGCTTTGTGAGCGAT CTGAAAAATGTTGTTCGCAC GAGCGATAATGATGCAGATC GTCCGGCACCGGATGATACC GCAACCATTATCTTTACCAGC GGTACAACCGGTAAAAGCAA AGGTGTTATGCTGACCCATA ATAATCTGGCAAGCAATGTT CAGAGCGTGAACTATTACAC CGAAAGCGGCACCGTGATGC TGAGCGTTCTGCCGGTTCATC ATGTTTATTGTCTGGTTATGG | MEKLIRDIIEESACRFAEL TAVKWLKKKEIFEINYAS LNENITAIRKALLKEGFLK KHIALIGTSSVEWIESYLG IITGGCVAVPLDAGLPDK DLTDLINRSDSEALFLSPK NLSLLSSILADCPKLKNIW ILNSDNNDTEKNSILNKIS AFANNSINNSNTVSFVSD LKNVVRTSDNDADRPAP DDTATIIFTSGTTGKSKGV MLTHNNLASNVQSVNYY TESGTVMLSVLPVHHVY CLVMDWLKGFSLGATICI NDSLMHMMRNIGVFKPE VILMVPMMVETIYKRLA AADPSIPPNILANKIFGGN LHIIFMGGAHLDPFYIDKF AEYGIDIYEGYGMSECSP VISSNLPGCHKTGSIGRPL SNAEISFDNGEILVRGTSV MKGYYNMPKETAETLRD GWLHTGDKGYIDEDGFL FINGRVKNLIILSNGENISP EEIENKLALDDLVGEVIV TGEKNGLTARIYPEQELVI AANMTEDEVRKNLQAFI DKYNSEQPTYRRITGLVI RKNPFIRSSTKKIKRQEAL IDEPMI (SEQ ID NO: 144) |

TABLE 1-continued

Non-limiting examples of biosynthetic enzymes from human gut microbiome-derived bacterium.

| Enzyme | Gene Source | Nucleotide Sequence | Amino Acid Sequence |
|---|---|---|---|
| | | ATTGGCTGAAAGGTTTTAGC<br>CTGGGTGCAACCATTTGTATT<br>AATGATAGCCTGATGCACAT<br>GATGCGCAATATTGGTGTTTT<br>TAAACCGGAAGTGATTCTGA<br>TGGTTCCGATGATGGTTGAA<br>ACCATCTATAAACGTCTGGC<br>AGCAGCAGATCCGAGCATTC<br>CGCCTAATATTCTGGCCAATA<br>AAATCTTTGGTGGCAACCTG<br>CATATCATCTTTATGGGTGGT<br>GCACATCTGGACCCGTTTTAT<br>ATCGATAAATTTGCCGAATA<br>TGGCATCGACATCTATGAAG<br>GTTATGGTATGAGCGAATGT<br>AGTCCGGTTATTAGCAGCAA<br>TCTGCCTGGTTGTCATAAAAC<br>CGGTAGCATTGGTCGTCCGCT<br>GAGCAATGCAGAAATTAGCT<br>TTGATAATGGCGAAATTCTG<br>GTTCGTGGTACAAGCGTTAT<br>GAAAGGCTATTATAACATGC<br>CGAAAGAAACCGCAGAAACC<br>CTGCGTGATGGTTGGCTGCAT<br>ACCGGTGATAAAGGTTATAT<br>TGATGAAGATGGCTTCCTGTT<br>TATTAACGGTCGCGTTAAAA<br>ACCTGATTATTCTGTCCAATG<br>GCGAGAACATTAGTCCGGAA<br>GAAATTGAAAATAAACTGGC<br>CCTGGATGATCTGGTTGGTG<br>AAGTTATTGTGACCGGTGAA<br>AAAAATGGTCTGACCGCACG<br>TATTTATCCGGAACAAGAAC<br>TGGTTATTGCAGCCAATATG<br>ACCGAAGATGAAGTGCGTAA<br>AAATCTGCAGGCCTTTATCG<br>ACAAATATAACAGCGAACAG<br>CCGACCTATCGTCGCATTACC<br>GGTCTGGTGATTCGCAAAAA<br>TCCGTTTATTCGTAGCAGCAC<br>CAAAAAGATCAAACGTCAAG<br>AGGCACTGATCGATGAACCG<br>ATGATTTAA (SEQ ID NO: 143) | |

TABLE 2

Non-limiting examples of vector components.

| Vector component | Sequence |
|---|---|
| P(T7) | cgcgaaattaatacgactcactatagggaattgtgagcggataacaatt (SEQ ID NO: 73) |
| RBS(1) | cccctctagaaataattttgtttaactttaagaaggagatatacc (SEQ ID NO: 74) |
| RBS(2) | tccctctagaaataattttgtttaactttaagaaggagatatacc (SEQ ID NO: 75) |
| RBS(3) | ccccactagaaataattttgtttaactttaagaaggagatatacc (SEQ ID NO: 76) |
| RBS(4) | accctctagaaataattttgtttaactttaagaaggagatatacc (SEQ ID NO: 77) |
| RBS(5) | acccactagaaataattttgtttaactttaagaaggagatatacc (SEQ ID NO: 78) |
| T(T7) | Caaagcccgaaaggaagctgagttggctgctgccaccgctgagcaataactagcataaccccttggggcctctaa<br>acgggtcttgaggggttttttgctgaaaggaggaactatatccggat (SEQ ID NO: 79) |
| pET28a backbone | TGGCGAATGGGACGCGCCCTGTAGCGGCGCATTAAGCGCGGCGGGTG<br>TGGTGGTTACGCGCAGCGTGACCGCTACACTTGCCAGCGCCCTAGCG<br>CCCGCTCCTTTCGCTTTCTTCCCTTCCTTTCTCGCCACGTTCGCCGGCT<br>TTCCCCGTCAAGCTCTAAATCGGGGGCTCCCTTTAGGGTTCCGATTTA<br>GTGCTTTACGGCACCTCGACCCCAAAAAACTTGATTAGGGTGATGGTT<br>CACGTAGTGGGCCATCGCCCTGATAGACGGTTTTTCGCCCTTTGACGT |

TABLE 2-continued

Non-limiting examples of vector components.

| Vector component | Sequence |
| --- | --- |
| | TGGAGTCCACGTTCTTTAATAGTGGACTCTTGTTCCAAACTGGAACAA
CACTCAACCCTATCTCGGTCTATTCTTTTGATTTATAAGGGATTTTGCC
GATTTCGGCCTATTGGTTAAAAAATGAGCTGATTTAACAAAAATTTAA
CGCGAATTTTAACAAAATATTAACGTTTACAATTTCAGGTGGCACTTT
TCGGGGAAATGTGCGCGGAACCCCTATTTGTTTATTTTTCTAAATACA
TTCAAATATGTATCCGCTCATGAATTAATTCTTAGAAAAACTCATCGA
GCATCAAATGAAACTGCAATTTATTCATATCAGGATTATCAATACCAT
ATTTTTGAAAAAGCCGTTTCTGTAATGAAGGAGAAAACTCACCGAGG
CAGTTCCATAGGATGGCAAGATCCTGGTATCGGTCTGCGATTCCGACT
CGTCCAACATCAATACAACCTATTAATTTCCCCTCGTCAAAAATAAGG
TTATCAAGTGAGAAATCACCATGAGTGACGACTGAATCCGGTGAGAA
TGGCAAAAGTTTATGCATTTCTTTCCAGACTTGTTCAACAGGCCAGCC
ATTACGCTCGTCATCAAAATCACTCGCATCAACCAAACCGTTATTCAT
TCGTGATTGCGCCTGAGCGAGACGAAATACGCGATCGCTGTTAAAAG
GACAATTACAAACAGGAATCGAATGCAACCGGCGCAGGAACACTGCC
AGCGCATCAACAATATTTTCACCTGAATCAGGATATTCTTCTAATACC
TGGAATGCTGTTTTCCCGGGGATCGCAGTGGTGAGTAACCATGCATCA
TCAGGAGTACGGATAAAATGCTTGATGGTCGGAAGAGGCATAAATTC
CGTCAGCCAGTTTAGTCTGACCATCTCATCTGTAACATCATTGGCAAC
GCTACCTTTGCCATGTTTCAGAAACAACTCTGGCGCATCGGGCTTCCC
ATACAATCGATAGATTGTCGCACCTGATTGCCCGACATTATCGCGAGC
CCATTTATACCCATATAAATCAGCATCCATGTTGGAATTTAATCGCGG
CCTAGAGCAAGACGTTTCCCGTTGAATATGGCTCATAACACCCCTTGT
ATTACTGTTTATGTAAGCAGACAGTTTTATTGTTCATGACCAAAATCC
CTTAACGTGAGTTTTCGTTCCACTGAGCGTCAGACCCCGTAGAAAAGA
TCAAAGGATCTTCTTGAGATCCTTTTTTTCTGCGCGTAATCTGCTGCTT
GCAAACAAAAAAACCACCGCTACCAGCGGTGGTTTGTTTGCCGGATC
AAGAGCTACCAACTCTTTTTCCGAAGGTAACTGGCTTCAGCAGAGCG
CAGATACCAAATACTGTCCTTCTAGTGTAGCCGTAGTTAGGCCACCAC
TTCAAGAACTCTGTAGCACCGCCTACATACCTCGCTCTGCTAATCCTG
TTACCAGTGGCTGCTGCCAGTGGCGATAAGTCGTGTCTTACCGGGTTG
GACTCAAGACGATAGTTACCGGATAAGGCGCAGCGGTCGGGCTGAAC
GGGGGGTTCGTGCACACAGCCCAGCTTGGAGCGAACGACCTACACCG
AACTGAGATACCTACAGCGTGAGCTATGAGAAAGCGCCACGCTTCCC
GAAGGGAGAAAGGCGGACAGGTATCCGGTAAGCGGCAGGGTCGGAA
CAGGAGAGCGCACGAGGGAGCTTCCAGGGGGAAACGCCTGGTATCTT
TATAGTCCTGTCGGGTTTCGCCACCTCTGACTTGAGCGTCGATTTTTGT
GATGCTCGTCAGGGGGGCGGAGCCTATGGAAAAACGCCAGCAACGC
GGCCTTTTTACGGTTCCTGGCCTTTTGCTGGCCTTTTGCTCACATGTTC
TTTCCTGCGTTATCCCCTGATTCTGTGGATAACCGTATTACCGCCTTTG
AGTGAGCTGATACCGCTCGCCGCAGCCGAACGACCGAGCGCAGCGAG
TCAGTGAGCGAGGAAGCGGAAGAGCGCCTGATGCGGTATTTTCTCCT
TACGCATCTGTGCGGTATTTCACACCGCATATATGGTGCACTCTCAGT
ACAATCTGCTCTGATGCCGCATAGTTAAGCCAGTATACACTCCGCTAT
CGCTACGTGACTGGGTCATGGCTGCGCCCCGACACCCGCCAACACCC
GCTGACGCGCCCTGACGGGCTTGTCTGCTCCCGGCATCCGCTTACAGA
CAAGCTGTGACCGTCTCCGGGAGCTGCATGTGTCAGAGGTTTTCACCG
TCATCACCGAAACGCGCGAGGCAGCTGCGGTAAAGCTCATCAGCGTG
GTCGTGAAGCGATTCACAGATGTCTGCCTGTTCATCCGCGTCCAGCTC
GTTGAGTTTCTCCAGAAGCGTTAATGTCTGGCTTCTGATAAAGCGGGC
CATGTTAAGGGCGGTTTTTTCCTGTTTGGTCACTGATGCCTCCGTGTA
AGGGGGATTTCTGTTCATGGGGGTAATGATACCGATGAAACGAGAGA
GGATGCTCACGATACGGGTTACTGATGATGAACATGCCCGGTTACTG
GAACGTTGTGAGGGTAAACAACTGGCGGTATGGATGCGGCGGGACCA
GAGAAAAATCACTCAGGGTCAATGCCAGCGCTTCGTTAATACAGATG
TAGGTGTTCCACAGGGTAGCCAGCAGCATCCTGCGATGCAGATCCGG
AACATAATGGTGCAGGGCGCTGACTTCCGCGTTTCCAGACTTTACGAA
ACACGGAAACCGAAGACCATTCATGTTGTTGCTCAGGTCGCAGACGT
TTTGCAGCAGCAGTCGCTTCACGTTCGCTCGCGTATCGGTGATTCATT
CTGCTAACCAGTAAGGCAACCCCGCCAGCCTAGCCGGGTCCTCAACG
ACAGGAGCACGATCATGCGCACCCGTGGGGCCGCCATGCCGGCGATA
ATGGCCTGCTTCTCGCCGAAACGTTTGGTGGCGGGACCAGTGACGAA
GGCTTGAGCGAGGGCGTGCAAGATTCCGAATACCGCAAGCGACAGGC
CGATCATCGTCGCGCTCCAGCGAAAGCGGTCCTCGCCGAAAATGACC
CAGAGCGCTGCCGGCACCTGTCCTACGAGTTGCATGATAAAGAAGAC
AGTCATAAGTGCGGCGACGATAGTCATGCCCCGCGCCCACCGGAAGG
AGCTGACTGGGTTGAAGGCTCTCAAGGGCATCGGTCGAGATCCCGGT
GCCTAATGAGTGAGCTAACTTACATTAATTGCGTTGCGCTCACTGCCC
GCTTTCCAGTCGGGAAACCTGTCGTGCCAGCTGCATTAATGAATCGGC
CAACGCGCGGGGAGAGGCGGTTTGCGTATTGGGCGCCAGGGTGGTTT
TTCTTTTCACCAGTGAGACGGGCAACAGCTGATTGCCCTTCACCGCCT
GGCCCTGAGAGAGTTGCAGCAAGCGGTCCACGCTGGTTTGCCCCAGC
AGGCGAAAATCCTGTTTGATGGTGGTTAACGGCGGGATATAACATGA
GCTGTCTTCGGTATCGTCGTATCCCACTACCGAGATATCCGCACCAAC
GCGCAGCCCGGACTCGGTAATGGCGCGCATTGCGCCCAGCGCCATCT
GATCGTTGGCAACCAGCATCGCAGTGGGAACGATGCCCTCATTCAGC |

TABLE 2-continued

Non-limiting examples of vector components.

| Vector component | Sequence |
|---|---|
| | ATTTGCATGGTTTGTTGAAAACCGGACATGGCACTCCAGTCGCCTTCC<br>CGTTCCGCTATCGGCTGAATTTGATTGCGAGTGAGATATTTATGCCAG<br>CCAGCCAGACGCAGACGCGCCGAGACAGAACTTAATGGGCCCGCTAA<br>CAGCGCGATTTGCTGGTGACCCAATGCGACCAGATGCTCCACGCCCA<br>GTCGCGTACCGTCTTCATGGGAGAAAATAATACTGTTGATGGGTGTCT<br>GGTCAGAGACATCAAGAAATAACGCCGGAACATTAGTGCAGGCAGCT<br>TCCACAGCAATGGCATCCTGGTCATCCAGCGGATAGTTAATGATCAG<br>CCCACTGACGCGTTGCGCGAGAAGATTGTGCACCGCCGCTTTACAGG<br>CTTCGACGCCGCTTCGTTCTACCATCGACACCACCACGCTGGCACCCA<br>GTTGATCGGCGCGAGATTTAATCGCCGCGACAATTTGCGACGGCGCG<br>TGCAGGGCCAGACTGGAGGTGGCAACGCCAATCAGCAACGACTGTTT<br>GCCCGCCAGTTGTTGTGCCACGCGGTTGGGAATGTAATTCAGCTCCGC<br>CATCGCCGCTTCCACTTTTTCCCGCGTTTTCGCAGAAACGTGGCTGGC<br>CTGGTTCACCACGCGGGAAACGGTCTGATAAGAGACACCGGCATACT<br>CTGCGACATCGTATAACGTTACTGGTTTCACATTCACCACCCTGAATT<br>GACTCTCTTCCGGGCGCTATCATGCCATACCGCGAAAGGTTTTGCGCC<br>ATTCGATGGTGTCCGGGATCTCGACGCTCTCCCTTATGCGACTCCTGC<br>ATTAGGAAGCAGCCCAGTAGTAGGTTGAGGCCGTTGAGCACCGCCGC<br>CGCAAGGAATGGTGCATGCAAGGAGATGGCGCCCAACAGTCCCCCGG<br>CCACGGGGCCTGCCACCATACCCACGCCGAAACAAGCGCTCATGAGC<br>CCGAAGTGGCGAGCCCGATCTTCCCCATCGGTGATGTCGGCGATATA<br>GGCGCCAGCAACCGCACCTGTGGCGCCGGTGATGCCGGCCACGATGC<br>GTCCGGCGTAGAGGATCGAGATCTCGATCC (SEQ ID NO: 80) |
| T7 RNAP | ATGAACACGATTAACATCGCTAAGAACGACTTCTCTGACATCGAACT<br>GGCTGCTATCCCGTTCAACACTCTGGCTGACCATTACGGTGAGCGTTT<br>AGCTCGCGAACAGTTGGCCCTTGAGCATGAGTCTTACGAGATGGGTG<br>AAGCACGCTTCCGCAAGATGTTTGAGCGTCAACTTAAAGCTGGTGAG<br>GTTGCGGATAACGCTGCCGCCAAGCCTCTCATCACTACCCTACTCCCT<br>AAGATGATTGCACGCATCAACGACTGGTTTGAGGAAGTGAAAGCTAA<br>GCGCGGCAAGCGCCCGACAGCCTTCCAGTTCCTGCAAGAAATCAAGC<br>CGGAAGCCGTAGCGTACATCACCATTAAGACCACTCTGGCTTGCCTA<br>ACCAGTGCTGACAATACAACCGTTCAGGCTGTAGCAAGCGCAATCGG<br>TCGGGCCATTGAGGACGAGGCTCGCTTCGGTCGTATCCGTGACCTTGA<br>AGCTAAGCACTTCAAGAAAAACGTTGAGGAACAACTCAACAAGCGCG<br>TAGGGCACGTCTACAAGAAAGCATTTATGCAAGTTGTCGAGGCTGAC<br>ATGCTCTCTAAGGGTCTACTCGGTGGCGAGGCGTGGTCTTCGTGGCAT<br>AAGGAAGACTCTATTCATGTAGGAGTACGCTGCATCGAGATGCTCAT<br>TGAGTCAACCGGAATGGTTAGCTTACACCGCCAAAATGCTGGCGTAG<br>TAGGTCAAGACTCTGAGACTATCGAACTCGCACCTGAATACGCTGAG<br>GCTATCGCAACCCGTGCAGGTGCGCTGGCTGGCATCTCTCCGATGTTC<br>CAACCTTGCGTAGTTCCTCCTAAGCCGTGGACTGGCATTACTGGTGGT<br>GGCTATTGGGCTAACGGTCGTCGTCCTCTGGCGCTGGTGCGTACTCAC<br>AGTAAGAAAGCACTGATGCGCTACGAAGACGTTTACATGCCTGAGGT<br>GTACAAAGCGATTAACATTGCGCAAAACACCGCATGGAAAATCAACA<br>AGAAAGTCCTAGCGGTCGCCAACGTAATCACCAAGTGGAAGCATTGT<br>CCGGTCGAGGACATCCCTGCGATTGAGCGTGAAGAACTCCCGATGAA<br>ACCGGAAGACATCGACATGAATCCTGAGGCTCTCACCGCGTGGAAAC<br>GTGCTGCCGCTGCTGTGTACCGCAAGGACAAGGCTCGCAAGTCTCGC<br>CGTATCAGCCTTGAGTTCATGCTTGAGCAAGCCAATAAGTTTGCTAAC<br>CATAAGGCCATCTGGTTCCCTTACAACATGGACTGGCGCGGTCGTGTT<br>TACGCTGTGTCAATGTTCAACCCGCAAGGTAACGATATGACCAAAGG<br>ACTGCTTACGCTGGCGAAAGGTAAACCAATCGGTAAGGAAGGTTACT<br>ACTGGCTGAAAATCCACGGTGCAAACTGTGCGGGTGTCGATAAGGTT<br>CCGTTCCCTGAGCGCATCAAGTTCATTGAGGAAAACCACGAGAACAT<br>CATGGCTTGCGCTAAGTCTCCACTGGAGAACACTTGGTGGGCTGAGC<br>AAGATTCTCCGTTCTGCTTCCTTGCGTTCTGCTTTGAGTACGCTGGGGT<br>ACAGCACCACGGCCTGAGCTATAACTGCTCCCTTCCGCTGGCGTTTGA<br>CGGGTCTTGCTCTGGCATCCAGCACTTCTCCGCGATGCTCCGAGATGA<br>GGTAGGTGGTCGCGCGGTTAACTTGCTTCCTAGTGAAACCGTTCAGGA<br>CATCTACGGGATTGTTGCTAAGAAAGTCAACGAGATTCTACAAGCAG<br>ACGCAATCAATGGGACCGATAACGAAGTAGTTACCGTGACCGATGAG<br>AACACTGGTGAAATCTCTGAGAAAGTCAAGCTGGGCACTAAGGCACT<br>GGCTGGTCAATGGCTGGCTTACGGTGTTACTCGCAGTGTGACTAAGCG<br>TTCAGTCATGACGCTGGCTTACGGGTCCAAAGAGTTCGGCTTCCGTCA<br>ACAAGTGCTGGAAGATACCATTCAGCCAGCTATTGATTCCGGCAAGG<br>GTCTGATGTTCACTCAGCCGAATCAGGCTGCTGGATACATGGCTAAGC<br>TGATTTGGGAATCTGTGAGCGTGACGGTGGTAGCTGCGGTTGAAGCA<br>ATGAACTGGCTTAAGTCTGCTGCTAAGCTGCTGGCTGCTGAGGTCAAA<br>GATAAGAAGACTGGAGAGATTCTTCGCAAGCGTTGCGCTGTGCATTG<br>GGTAACTCCTGATGGTTTCCCTGTGTGGCAGGAATACAAGAAGCCTAT<br>TCAGACGCGCTTGAACCTGATGTTCCTCGGTCAGTTCCGCTTACAGCC<br>TACCATTAACACCAACAAAGATAGCGAGATTGATGCACACAAACAGG<br>AGTCTGGTATCGCTCCTAACTTTGTACACAGCCAAGACGGTAGCCACC<br>TTCGTAAGACTGTAGTGTGGGCACACGAGAAGTACGGAATCGAATCT<br>TTTGCACTGATTCACGACTCCTTCGGTACCATTCCGGCTGACGCTGCG |

TABLE 2-continued

Non-limiting examples of vector components.

| Vector component | Sequence |
|---|---|
|  | AACCTGTTCAAAGCAGTGCGCGAAACTATGGTTGACACATATGAGTC<br>TTGTGATGTACTGGCTGATTTCTACGACCAGTTCGCTGACCAGTTGCA<br>CGAGTCTCAATTGGACAAAATGCCAGCACTTCCGGCTAAAGGTAACT<br>TGAACCTCCGTGACATCTTAGAGTCGGACTTCGCGTTCGCGTAA (SEQ ID NO: 81) |
| lacI | ATGATAGCGCCCGGAAGAGAGTCAATTCAGGGTGGTGAATGTGAAAC<br>CAGTAACGTTATACGATGTCGCAGAGTATGCCGGTGTCTCTTATCAGA<br>CCGTTTCCCGCGTGGTGAACCAGGCCAGCCACGTTTCTGCGAAAACG<br>CGGGAAAAAGTGGAAGCGGCGATGGCGGAGCTGAATTACATTCCCAA<br>CCGCGTGGCACAACAACTGGCGGGCAAACAGTCGTTGCTGATTGGCG<br>TTGCCACCTCCAGTCTGGCCCTGCACGCGCCGTCGCAAATTGTCGCGG<br>CGATTAAATCTCGCGCCGATCAACTGGGTGCCAGCGTGGTGGTGTCG<br>ATGGTAGAACGAAGCGGCGTCGAAGCCTGTAAAGCGGCGGTGCACA<br>ATCTTCTCGCGCAACGCGTCAGTGGGCTGATCATTAACTATCCGCTGG<br>ATGACCAGGATGCCATTGCTGTGGAAGCTGCCTGCACTAATGTTCCGG<br>CGTTATTTCTTGATGTCTCTGACCAGACACCCATCAACAGTATTATTTT<br>CTCCCATGAAGACGGTACGCGACTGGGCGTGGAGCATCTGGTCGCAT<br>TGGGTCACCAGCAAATCGCGCTGTTAGCGGGCCCATTAAGTTCTGTCT<br>CGGCGCGTCTGCGTCTGGCTGGCTGGCATAAATATCTCACTCGCAATC<br>AAATTCAGCCGATAGCGGAACGGGAAGGCGACTGGAGTGCCATGTCC<br>GGTTTTCAACAAACCATGCAAATGCTGAATGAGGGCATCGTTCCCACT<br>GCGATGCTGGTTGCCAACGATCAGATGGCGCTGGGCGCAATGCGCGC<br>CATTACCGAGTCCGGGCTGCGCGTTGGTGCGGATATCTCGGTAGTGG<br>GATACGACGATACCGAAGACAGCTCATGTTATATCCCGCCGTTAACC<br>ACCATCAAACAGGATTTTCGCCTGCTGGGGCAAACCAGCGTGGACCG<br>CTTGCTGCAACTCTCTCAGGGCCAGGCGGTGAAGGGCAATCAGCTGT<br>TGCCCGTCTCACTGGTGAAAAGAAAAACCACCCTGGCGCCCAATACG<br>CAAACCGCCTCTCCCCGCGCGTTGGCCGATTCATTAATGCAGCTGGCA<br>CGACAGGTTTCCCGACTGGAAAGCGGGCAGTGA (SEQ ID NO: 83) |

Reagents and Chemicals

Commercially available reagents and chemicals were used. Fatty acid and amine substrates for the panel assay are listed separately (Table 3). Fatty acid substrates are prepared as 50 mM stock solutions in ethanol, neutralized with sodium hydroxide solution, stored at −80° C. prior to use. Amine substrates are prepared as 50 mM stock solutions in water (with pH adjusted to increase solubility), stored at −80° C. prior to use. IPTG was prepared as 1 M stock solution and stored at −20° C. CoA solution was freshly prepared from powder. PCR primers are ordered from Integrated DNA Technologies.

TABLE 3

Non-limiting examples of amines and fatty acids.

|  | Amines | Fatty Acids |
|---|---|---|
| phenylalanine | tyramine | acetic acid |
| tryptophan | histamine | propionic acid |
| tyrosine | serotonin | butyric acid |
| histidine | dopamine | valeric acid |
| lysine | epinephrine | hexanoic acid |
| glycine | norepinephrine | octanoic acid |
| alanine | γ-aminobutryic acid (GABA) | capric acid |
| valine | aminovaleric acid | lauric acid |
| leucine | ethanolamine | myristic acid |
| isoleucine | cadaverine | pentadecanoic acid |
| methionine | putrescine | palmitic acid |
| proline | spermine | stearic acid |
| serine | spermidine | arachidic acid |
| threonine | agmatine | iso-pentadecanoic acid |
| cysteine | propylamine | palmitoleic acid |
| asparagine | butylamine | oleic acid |
| glutamine | dimethylamine | vaccenic acid |
| aspartic acid | pyrollidine | linoleic acid |
| glutamic acid | piperidine | γ-linolenic acid |
| arginine | homocysteine | α-linolenic acid |
| ornithine | cysteamine | dihomo-γ-linolenic acid |
| β-alanine | homocysteamine | arachidonic acid |
| L-DOPA | taurine | eicosapentaenoic acid |
| creatine | hypotaurine | docosapentaenoic acid |
| citrulline | glutathione | docosahexaenoic acid |

TABLE 3-continued

Non-limiting examples of amines and fatty acids.

| | Amines | Fatty Acids |
|---|---|---|
| phenylacetylglutamine | vanillylamide | 8-methyl-6-nonenoic acid |
| phenylethylamine | melatonin | octynoic acid |
| tryptamine | 3-iodothyronamine | myristic acid alkyne |
| octopamine | | palmitic acid alkyne |

Computational Detection of Clostridia NRPS Pathways

Genome datasets from the human gut was searched on the genome browser of the JGI-IMG database querying "Gastrointestinal tract" as the Sample Body Site and "Human" as a keyword. The metadata from search result was used to locate and download the sequencing data from either JGI GOLD or NCBI GenBank database. The resulting datasets were run on antiSMASH 3.0 using default parameters with ClusterFinder-based border prediction, but excluding putative pathways detected by ClusterFinder (low-confidence).[22] The antiSMASH-detected pathways were blastn searched on the metagenomic reads of 148 fecal samples from HMP that passed QC assessment, retaining pathways that had at least two hits with e-value<1×10$^{-5}$ from the metagenomic reads spanning different stretches of the pathway. These were blastn searched, using the same cutoff filter as the previous step, on the mRNA reads from fecal samples of eight healthy subjects. The remaining pathways were run on BiG-SCAPE[33] to generate a similarity network matrix file with a distance cutoff of 0.75 and visualized using Cytoscape. For analyzing prevalence, all three biosynthetic proteins from the eight NRPS pathways were combined as a single query and submitted on MetaQuery with default parameters, except with a minimum percent identity of 80.

Detection of Homologous Pathways in Non-Redundant Sequence Database

E. rectale condensation protein and adenylation protein was each used as a query for blastp search with default parameters. Upon removing hits that were different in protein size (>800 or <200 amino acids) from the top 1000 hits, the hit table from each was cross-examined using Python script for their co-occurrence in the same pathway based on proximity in NCBI accession number.

Phylogenetic Tree Construction

For pathway phylogeny, MUSCLE alignment was performed on the adenylation protein sequences using MacVector version 16. The tree was constructed from the alignment using *Paraeggerthella hongkongensis* adenylation protein (accession: WP_123191107) as an outgroup for rooting (Method: Neighbor Joining Method, Distance: Uncorrected, Best Tree Mode). For taxonomical phylogeny, NCBI taxon ID extracted from the GenBank annotation of each pathway was collected, which was submitted to phyloT for tree construction (https://phylot.biobyte.de/). The trees are visualized using iTOL.[63]

E. coli In Vivo Heterologous Expression

Overnight culture of pathway-harboring *E coli* in LB broth at 37° C. overnight (230 rpm) was diluted to fresh media the next morning. Multiple fermentation and extraction conditions were attempted. For IPTG induction, the culture was induced at either early, middle, or late log phase (OD600=0.2, 0.5, 0.8) and at final concentration of 0.2 or 0.5 mM IPTG. After induction, culture media was grown in LB or M9 minimal media. The induced culture was grown at 25 or 30° C. and extracted after 8, 16, or 40 hr. The culture was extracted with equal volume of methanol, mixed on the vortex, spun down to remove particulates, and subjected to analytical LCMS run. The condition with highest clone-specific compound production relative to background was defined as the best condition for subsequent in vivo production studies (OD600=0.8; 0.2 mM IPTG; LB after induction; 25° C.; 16 hr).

Analytical LCMS Run

Analytical LCMS was conducted using an Agilent 6130 quadrupole MS on a C18 reverse phase column (Phenomenex Luna 5 m C18(2), 100×4.6 mm) with 1.0 mL/min flow rate and a gradient system of 90%:10% to 0%:100% water:acetonitrile with 0.1% formic acid for 15 min, followed by 2 min isocratic run at 100% acetonitrile (wash) and then 3 min at 90%:10% water:acetonitrile (re-equilibration).

Single-Gene Knockout Pathway Characterization

PCR fragment with flanking BsaI site was made using primer pair ereCko-F/ereCko-R, ereAko-F/ereAko-R, or ereTko-F/ereTko-R, which was then digested and ligated to generate a *E. rectale* pathway construct with the condensation, adenylation, or thiolation gene knockout, respectively. For pathway consisting of just the three biosynthetic genes, the primer pair ereC-F/ereA-R was used to amplify the appropriate fragment that was then cloned into pET28a. Each construct was transformed, cultured with the best condition (OD600=0.8; 0.2 mM IPTG; LB after induction; 25° C.; 16 hr), and analyzed like the wildtype pathway.

E. coli In Vivo Substrate Feeding Assay

Native *E. rectale* pathway-harboring *E. coli* was cultured with the best condition and as previously, except either octanoic acid (neutralized with sodium hydroxide) or tryptamine was added into the culture at a final concentration of 5 mM during IPTG induction. The extracts are analyzed as previously.

E. coli In Vivo Compound Characterization

Large-scale fermentation of pathway-harboring *E. coli* (16 L) was conducted using the best condition. Culture was extracted with equal volume of ethyl acetate, and the organic layer was dried in vacuo. The extract was run on preparatory C18 reverse phase column (Phenomenex Luna 5 m C18(2), 250×21.2 mm) with a gradient system of 90%:10% to 0%:100% water:acetonitrile with 0.1% acetic acid in 20 min at 10 mL/min. Major compound eluted with the 20%:80% water:acetonitrile fraction. Compound was then purified with a semi-prep C18 column (Phenomenex Luna 5 m C18(2), 250×10 mm) with a gradient system of 70%:30% to 0%:100% water:methanol with 0.1% acetic acid in 30 min at 5 mL/min. The major compound eluted in the 45%:65% water:methanol fraction as a white powder (0.1 mg). HRMS acquired on Agilent 6530 Q-TOF and 1-D and 2-D NMR spectra collected on Bruker Avance II 600 were used to determine chemical structure (FIG. 5). The compound identify was further confirmed by having an authentic standard chemically synthesized by KareBay Biochem and was found to be spectroscopically identical.

Protein Expression Plasmid Construction

Individual biosynthetic gene was PCR amplified from the synthesized construct using the primer set containing the gene name (nomenclature of "pathway source strain name abbreviation, followed by "NRPS domain type" (C, T, A). The amplified gene was cloned into pET28a and transformed into E. coli BL21(DE3). The exception was C. eutactus condensation protein, whose construct was sent to ABclonal Technology for custom protein expression and purification.

Protein Purification

Except the C. eutactus condensation protein construct, the construct-harboring E. coli was grown in LB at 25° C. (230 rpm) to OD=0.5, induced with IPTG at 0.5 mM final concentration, and grown at 16° C. (230 rpm) for 18 hr. The cells were pelleted at 4000 g for 20 min, resuspended in 10 mL Lysis Buffer (300 mM NaCl, 10 mM Imidazole, 50 mM Tris, pH 8.0) with EDTA-free Protease Inhibitors, and lysed using Q500 Qsonica sonicator with ⅛" stepped microtip probe (45% amplitude, 5 min continuous). Upon centrifuging the lysed cells at 14,000 g for 20 min, the supernatant was added to pre-equilibrated Ni-NTA resin and rotated at 4° C. for 16 hr. The beads were spun down at 1000 g for 1 min, resuspended in 10 mL Wash Buffer (300 mM NaCl, 20 mM Imidazole, 50 mM Tris, pH 8.0). Upon transferring to a new tube, the beads were washed three times with 10 mL Wash Buffer. In a new tube, the beads were eluted with 2 mL of Elution Buffer (300 mM NaCl, 20 mM Imidazole, 250 mM Tris, pH 8.0) and dialyzed using Slide-A-Lyzer (3.5K MWCO) against Dialysis Buffer (50 mM NaCl, 1 mM TCEP, 10% (v/v) glycerol). Protein purity was confirmed by 16% Tricine protein gel with SimplyBlue SafeStain.

In Vitro Reconstitution

Reaction mixture was set up in 100 µL volume with 100 mM Tris, 10 mM $MgCl_2$, 1 mM TCEP, 0.1 µM Sfp Synthase (New England Biolabs), 0.1 mM CoA, 5 mM ATP, 1 mM of each substrate (fatty acid, amine), and 1 M of each biosynthetic protein (condensation, thiolation, adenylation) and proceeded at 23° C.

Pyrophosphate Measurement for Adenylation Activity

Enzchek Pyrohospate Assay Kit (Molecular Probes) was used for pyrophosphate detection as similarly done if previous studies.[64] After a 2 hr reaction with adenylation and thiolation protein (no condensation), 10 µL of reaction sample was mixed with the kit solution containing MESG, phosphorylase, and pyrophosphatase in a 100 µL mixture following manufacturer protocol, incubated for 60 min at room temperature, spun down at 4000 g for 1 min to remove particulates, and transferred into Half Area 96 well UV microplate (Corning) for measurement of absorbance at 360 nm using BioTek Epoch Microplate Spectrophotometer, normalized to no adenylation enzyme control.

MS-Based Measurement for Adenylation and Condensation Activity

For adenylation activity, adenylation and thiolation proteins (no condensation) were added with the query fatty acid substrate(s) and tryptamine as a UV-active chromophore. For condensation activity, a pair of reaction with all three biosynthetic proteins and all but without the condensation protein was set up with the query amine substrate(s) and the fatty acid that yielded the highest adenylation activity. The reaction was mixed with equal volume of methanol, spun down at 21,000 g for 1 min, and analyzed with the same analytical LCMS run as described previously. The product appeared as the major peak on the extracted-ion chromatogram (EIC) of the corresponding m/z in either positive or negative mode, without appearing on both the no substrate control and no enzyme control. The peak, either from absorbance at 280 nm for adenylation activity or MS EIC for condensation activity, was integrated using the software Mestrelab MNova 10.0. For condensation activity, the reaction sample with and without condensation protein was run one after the other, and the ratio of the two peak areas was calculated.

Substrate Panel Assay

For the panel assays (Table 3), the fatty acid substrates were subpooled into five: Subpool Fa=F1, 6, 10, 13, 17, 20, 21; Fb=F2, 9, 11, 16, 22, 24; Fc=F3, 5, 7, 12, 14, 18; FD=Fd, 8, 15, 19, 23, 25. The amine substrates were subpooled into six: Subpool Aa=A9, 27, 28, 29, 30, 31, 32, 33, 34; Ab=A1, 2, 3, 4, 12, 16, 17, 20, 23; Ac=5, 11, 14, 21, 35, 37, 39, 42, 43; Ad=A6, 7, 8, 10, 13, 15, 18, 19, 38; Ae=22, 24, 25, 26, 40, 41, 47, 51, 53; Af=36, 44, 45, 46, 48, 49, 50, 52. First, reaction sample with C. eutactus proteins was analyzed over the course of ten different time points (FIG. 11). The reaction time that provided the largest difference between the highest activity and the rest was defined as the best time point (δ0 min for fatty acid and 120 min for amine panel) for collecting data in the determination of preferred product. Upon data collection with the same subpools, the experiments were conducted with a separate subpool consisting of the highest activity substrate from each subpool to confirm that the rank order of the substrate remained the same. The identities of the preferred products were further confirmed by having authentic standards chemically synthesized by KareBay Biochem (with the exception of oleoyl dopamine, which was purchased from Cayman Chemical) and conducting side-by-side analytical LCMS runs (FIG. 6).

REFERENCES SECTION 1

1 Arafat, E. S., Trimble, J. W., Andersen, R. N., Dass, C. & Desiderio, D. M. Identification of fatty acid amides in human plasma. *Life sciences* 45, 1679-1687 (1989).

2 Ezzili, C., Otrubova, K. & Boger, D. L. Fatty acid amide signaling molecules. *Bioorganic & medicinal chemistry letters* 20, 5959-5968, doi: 10.1016/j.bmcl.2010.08.048 (2010).

3 Devane, W. A. et al. Isolation and structure of a brain constituent that binds to the cannabinoid receptor. *Science* 258, 1946-1949 (1992).

4 Cravatt, B. F. et al. Molecular characterization of an enzyme that degrades neuromodulatory fatty-acid amides. *Nature* 384, 83-87, doi: 10.1038/384083a0 (1996).

5 Eisenstein, T. K., Meissler, J. J., Wilson, Q., Gaughan, J. P. & Adler, M. W. Anandamide and Delta9-tetrahydrocannabinol directly inhibit cells of the immune system via CB2 receptors. *Journal of neuroimmunology* 189, 17-22, doi: 10.1016/j.jneuroim.2007.06.001 (2007).

6 Osei-Hyiaman, D. et al. Endocannabinoid activation at hepatic CB1 receptors stimulates fatty acid synthesis and contributes to diet-induced obesity. *The Journal of clinical investigation* 115, 1298-1305, doi: 10.1172/JCI23057 (2005).

7 Chu, C. J. et al. N-oleoyldopamine, a novel endogenous capsaicin-like lipid that produces hyperalgesia. *The Journal of biological chemistry* 278, 13633-13639, doi: 10.1074/jbc.M211231200 (2003).

8 Ross, H. R., Gilmore, A. J. & Connor, M. Inhibition of human recombinant T-type calcium channels by the endocannabinoid N-arachidonoyl dopamine. *British journal of pharmacology* 156, 740-750, doi: 10.1111/j.1476-5381.2008.00072.x (2009).

9 Chu, Z. L. et al. N-oleoyldopamine enhances glucose homeostasis through the activation of GPR119. *Molecular endocrinology* 24, 161-170, doi: 10.1210/me.2009-0239 (2010).

10 Sergeeva, O. A. et al. N-oleoyldopamine modulates activity of midbrain dopaminergic neurons through multiple mechanisms. *Neuropharmacology* 119, 111-122, doi: 10.1016/j.neuropharm.2017.04.011 (2017).

11 Przegalinski, E., Filip, M., Zajac, D. & Pokorski, M. N-oleoyl-dopamine increases locomotor activity in the rat. *International journal of immunopathology and pharmacology* 19, 897-904, doi: 10.1177/039463200601900419 (2006).

12 Wang, Y. et al. Docosahexaenoyl serotonin emerges as most potent inhibitor of IL-17 and CCL-20 released by blood mononuclear cells from a series of N-acyl serotonins identified in human intestinal tissue. *Biochimica et biophysica acta. Molecular and cell biology of lipids* 1862, 823-831, doi: 10.1016/j.bbalip.2017.05.008 (2017).

13 Huang, S. M. et al. Identification of a new class of molecules, the arachidonyl amino acids, and characterization of one member that inhibits pain. *The Journal of biological chemistry* 276, 42639-42644, doi: 10.1074/jbc.M107351200 (2001).

14 Milman, G. et al. N-arachidonoyl L-serine, an endocannabinoid-like brain constituent with vasodilatory properties. *Proceedings of the National Academy of Sciences of the United States of America* 103, 2428-2433, doi: 10.1073/pnas.0510676103 (2006).

15 Mazmanian, S. K., Round, J. L. & Kasper, D. L. A microbial symbiosis factor prevents intestinal inflammatory disease. *Nature* 453, 620-625, doi: 10.1038/nature07008 (2008).

16 Schulz, S., Green, C. K., Yuen, P. S. & Garbers, D. L. Guanylyl cyclase is a heat-stable enterotoxin receptor. *Cell* 63, 941-948 (1990).

17 Cuevas-Ramos, G. et al. *Escherichia coli* induces DNA damage in vivo and triggers genomic instability in mammalian cells. *Proceedings of the National Academy of Sciences of the United States of America* 107, 11537-11542, doi: 10.1073/pnas.1001261107 (2010).

18 Nougayrede, J. P. et al. *Escherichia coli* induces DNA double-strand breaks in eukaryotic cells. *Science* 313, 848-851, doi: 10.1126/science. 1127059 (2006).

19 Schneditz, G. et al. Enterotoxicity of a nonribosomal peptide causes antibiotic-associated colitis. *Proceedings of the National Academy of Sciences of the United States of America* 111, 13181-13186, doi: 10.1073/pnas.1403274111 (2014).

20 Human Microbiome Project, C. Structure, function and diversity of the healthy human microbiome. *Nature* 486, 207-214, doi: 10.1038/nature11234 (2012).

21 Cohen, L. J. et al. Commensal bacteria make GPCR ligands that mimic human signalling molecules. *Nature* 549, 48-53, doi: 10.1038/nature23874 (2017).

22 Weber, T. et al. antiSMASH 3.0—a comprehensive resource for the genome mining of biosynthetic gene clusters. *Nucleic acids research* 43, W237-243, doi: 10.1093/nar/gkv437 (2015).

23 Donia, M. S. et al. A systematic analysis of biosynthetic gene clusters in the human microbiome reveals a common family of antibiotics. *Cell* 158, 1402-1414, doi: 10.1016/j.cell.2014.08.032 (2014).

24 Guo, C. J. et al. Discovery of Reactive Microbiota-Derived Metabolites that Inhibit Host Proteases. *Cell* 168, 517-526 e518, doi: 10.1016/j.cell.2016.12.021 (2017).

25 Macdonald, I. A., Bokkenheuser, V. D., Winter, J., McLernon, A. M. & Mosbach, E. H. Degradation of steroids in the human gut. *Journal of lipid research* 24, 675-700 (1983).

26 Brotherton, C. A. & Balskus, E. P. A prodrug resistance mechanism is involved in colibactin biosynthesis and cytotoxicity. *Journal of the American Chemical Society* 135, 3359-3362, doi: 10.1021/ja312154m (2013).

27 Fischbach, M. A. & Walsh, C. T. Assembly-line enzymology for polyketide and nonribosomal Peptide antibiotics: logic, machinery, and mechanisms. *Chemical reviews* 106, 3468-3496, doi: 10.1021/cr0503097 (2006).

28 Pfeifer, B. A., Admiraal, S. J., Gramajo, H., Cane, D. E. & Khosla, C. Biosynthesis of complex polyketides in a metabolically engineered strain of *E. coli. Science* 291, 1790-1792, doi: 10.1126/science.1058092 (2001).

29 Roche, E. D. & Walsh, C. T. Dissection of the EntF condensation domain boundary and active site residues in nonribosomal peptide synthesis. *Biochemistry* 42, 1334-1344, doi: 10.1021/bi026867m (2003).

30 Mori, S. et al. Activation and Loading of the Starter Unit during Thiocoraline Biosynthesis. *Biochemistry* 56, 4457-4467, doi: 10.1021/acs.biochem.7b00661 (2017).

31 Stachelhaus, T., Mootz, H. D., Bergendahl, V. & Marahiel, M. A. Peptide bond formation in nonribosomal peptide biosynthesis. Catalytic role of the condensation domain. *The Journal of biological chemistry* 273, 22773-22781 (1998).

32 Franzosa, E. A. et al. Relating the metatranscriptome and metagenome of the human gut. *Proceedings of the National Academy of Sciences of the United States of America* 111, E2329-2338, doi: 10.1073/pnas.1319284111 (2014).

33 Navarro-Muñoz, J. et al. A computational framework for systematic exploration of biosynthetic diversity from large-scale genomic data. *bioRxiv* (2018).

34 Raymond, K. N., Dertz, E. A. & Kim, S. S. Enterobactin: an archetype for microbial iron transport. *Proceedings of the National Academy of Sciences of the United States of America* 100, 3584-3588, doi: 10.1073/pnas.0630018100 (2003).

35 Nayfach, S., Fischbach, M. A. & Pollard, K. S. MetaQuery: a web server for rapid annotation and quantitative analysis of specific genes in the human gut microbiome. *Bioinformatics* 31, 3368-3370, doi: 10.1093/bioinformatics/btv382 (2015).

36 Frolov, A., Cho, T. H., Billheimer, J. T. & Schroeder, F. Sterol carrier protein-2, a new fatty acyl coenzyme A-binding protein. *The Journal of biological chemistry* 271, 31878-31884 (1996).

37 McKinney, M. K. & Cravatt, B. F. Structure and function of fatty acid amide hydrolase. *Annual review of biochemistry* 74, 411-432, doi: 10.1146/annurev.biochem.74.082803.133450 (2005).

38 Pugin, B. et al. A wide diversity of bacteria from the human gut produces and degrades biogenic amines. *Microbial ecology in health and disease* 28, 1353881, doi: 10.1080/16512235.2017.1353881 (2017).

39 Stachelhaus, T., Mootz, H. D. & Marahiel, M. A. The specificity-conferring code of adenylation domains in nonribosomal peptide synthetases. *Chemistry & biology* 6, 493-505, doi: 10.1016/S1074-5521(99)80082-9 (1999).

40 Gulick, A. M. Conformational dynamics in the Acyl-CoA synthetases, adenylation domains of nonribosomal peptide synthetases, and firefly luciferase. *ACS chemical biology* 4, 811-827, doi: 10.1021/cb900156h (2009).

41 Chu, J. et al. Discovery of MRSA active antibiotics using primary sequence from the human microbiome. *Nature chemical biology* 12, 1004-1006, doi: 10.1038/nchembio.2207 (2016).

42 Farrell, E. K. & Merkler, D. J. Biosynthesis, degradation and pharmacological importance of the fatty acid amides. *Drug discovery today* 13, 558-568, doi: 10.1016/j.drudis.2008.02.006 (2008).

43 Hill, M. J. *Microbial Metabolism In The Digestive Tract*. (CRC Press, 2018).

44 Abdelmagid, S. A. et al. Comprehensive profiling of plasma fatty acid concentrations in young healthy Canadian adults. *PloS one* 10, e0116195, doi: 10.1371/journal.pone.0116195 (2015).

45 Chan, M., Himes, R. H. & Akagi, J. M. Fatty acid composition of thermophilic, mesophilic, and psychrophilic clostridia. *Journal of bacteriology* 106, 876-881 (1971).

46 Vernocchi, P., Del Chierico, F. & Putignani, L. Gut Microbiota Profiling: Metabolomics Based Approach to Unravel Compounds Affecting Human Health. *Frontiers in microbiology* 7, 1144, doi: 10.3389/fmicb.2016.01144 (2016).

47 Lyte, M. & Freestone, P. P. E. *Microbial Endocrinology: Interkingdom Signaling in Infectious Disease and Health*. (Springer New York, 2010).

48 Schwarzer, D., Mootz, H. D. & Marahiel, M. A. Exploring the impact of different thioesterase domains for the design of hybrid peptide synthetases. *Chemistry & biology* 8, 997-1010 (2001).

49 Yeh, E., Lin, H., Clugston, S. L., Kohli, R. M. & Walsh, C. T. Enhanced macrocyclizing activity of the thioesterase from tyrocidine synthetase in presence of nonionic detergent. *Chemistry & biology* 11, 1573-1582, doi: 10.1016/j.chembiol.2004.09.003 (2004).

50 Keating, T. A., Miller, D. A. & Walsh, C. T. Expression, purification, and characterization of HMWP2, a 229 kDa, six domain protein subunit of Yersiniabactin synthetase. *Biochemistry* 39, 4729-4739 (2000).

51 Campbell, J. W. & Cronan, J. E., Jr. Bacterial fatty acid biosynthesis: targets for antibacterial drug discovery. *Annual review of microbiology* 55, 305-332, doi: 10.1146/annurev.micro.55.1.305 (2001).

52 Hahn, M. & Stachelhaus, T. Selective interaction between nonribosomal peptide synthetases is facilitated by short communication-mediating domains. *Proceedings of the National Academy of Sciences of the United States of America* 101, 15585-15590, doi: 10.1073/pnas.0404932101 (2004).

53 Ziemert, N., Alanjary, M. & Weber, T. The evolution of genome mining in microbes—a review. *Natural product reports* 33, 988-1005, doi: 10.1039/c6np00025h (2016).

54 Zhang, H., Wang, Y. & Pfeifer, B. A. Bacterial hosts for natural product production. *Molecular pharmaceutics* 5, 212-225, doi: 10.1021/mp7001329 (2008).

55 Dixit, S. & Das, M. Fatty acid composition including trans-fatty acids in edible oils and fats: probable intake in Indian population. *Journal of food science* 77, T188-199, doi: 10.1111/j.1750-3841.2012.02875.x (2012).

56 Kokatnur, M. G., Oalmann, M. C., Johnson, W. D., Malcom, G. T. & Strong, J. P. Fatty acid composition of human adipose tissue from two anatomical sites in a biracial community. *The American journal of clinical nutrition* 32, 2198-2205, doi: 10.1093/ajcn/32.11.2198 (1979).

57 Donia, M. S. & Fischbach, M. A. HUMAN MICROBIOTA. Small molecules from the human microbiota. *Science* 349, 1254766, doi: 10.1126/science.1254766 (2015).

58 McCutcheon, J. P. & von Dohlen, C. D. An interdependent metabolic patchwork in the nested symbiosis of mealybugs. *Current biology: CB* 21, 1366-1372, doi: 10.1016/j.cub.2011.06.051 (2011).

59 Ridaura, V. & Belkaid, Y. Gut microbiota: the link to your second brain. *Cell* 161, 193-194, doi: 10.1016/j.cell.2015.03.033 (2015).

60 Mittal, R. et al. Neurotransmitters: The Critical Modulators Regulating Gut-Brain Axis. *Journal of cellular physiology* 232, 2359-2372, doi: 10.1002/jcp.25518 (2017).

61 Pacher, P., Batkai, S. & Kunos, G. The endocannabinoid system as an emerging target of pharmacotherapy. *Pharmacological reviews* 58, 389-462, doi: 10.1124/pr.58.3.2 (2006).

62 Sharma, R. C. & Schimke, R. T. Preparation of electrocompetent *E. coli* using salt-free growth medium. *BioTechniques* 20, 42-44, doi: 10.2144/96201bm08 (1996).

63 Letunic, I. & Bork, P. Interactive tree of life (iTOL) v3: an online tool for the display and annotation of phylogenetic and other trees. *Nucleic acids research* 44, W242-245, doi: 10.1093/nar/gkw290 (2016).

64 Duckworth, B. P., Wilson, D. J. & Aldrich, C. C. Measurement of Nonribosomal Peptide Synthetase Adenylation Domain Activity Using a Continuous Hydroxylamine Release Assay. *Methods in molecular biology* 1401, 53-61, doi: 10.1007/978-1-4939-3375-4_3 (2016).

Example 2

Clostridia NRPS-Like Pathways Identified from Human Gut Sequencing Data

This work began with a broad survey of biosynthetic pathways present in human gut microbiome genomic datasets (FIG. 1a). Metadata from the Joint Genome Institute (JGI) was used to identify 1042 bacterial genomes associated with the human gastrointestinal tract. From these genomes, 3531 putative biosynthetic pathways were identified using antiSMASH, which recognizes protein domains from known natural product pathways (FIG. 15a)[15,45]. This set was further reduced to those that are present and actively transcribed in healthy human subjects[46]. This reduced the number of pathways to 2013 that were found in at least one metagenomic sample. This was further narrowed by examining their presence in RNA sequencing datasets from the stool samples of eight healthy subjects from the HMP (FIG. 15c)[47].

The 336 transcribed pathways were organized using the software BiG-SCAPE which uses network-similarity algorithms to group the pathways into families[48]. The groups were then manually inspected to disregard the known families[8,40,49]. Eight pathways of particular interest, specific to Clostridia that are prevalent in the human gut, were identified (FIG. 15a)[50]. A MetaQuery analysis showed that at least one pathway appears in 1730 of the 2271 publicly available human gut metagenomes[51]. When the search was performed with the NCBI nonredundant (nr) database, not requiring presence in human gut samples, 148 unique homologous pathways spanning diverse Clostridia were identified.

The Clostridia-derived gene clusters encode three conserved biosynthetic genes (FIG. 15d). Intriguingly, each shows sequence similarity to the C, T, and A domains of a NRPS minimal module (FIGS. 16a and 17-19). Neither of the proteins corresponding to the C and A domains show sequence homology to biosynthetic enzymes known to make FAAs. The closest homologue to the A protein is a fatty acyl-CoA ligase from *B. subtilis* (UniProt #: O07610). Meanwhile, the closest homologue to the C protein is a condensation domain of surfactin NRPS from *B. subtilis* (UniProt #: P27206). This condensation subtype forms its own clade in the phylogenetic tree of known NRPS condensation domains, and is known to conjugate long chain fatty acyl-CoA with thiotemplated α-amino acid[52]. The tandem action of C and A domains are both necessary for and exclusive to NRPS production and thus their co-localization is used as a search strategy to identify NRPS pathways. In rare occasions, the C, T, A functions appear as independent proteins. However, to the inventors' knowledge, this is the first example where all three functions are co-located as independent proteins without a termination domain. This suggests that although the most closely related known homologs of these pathways are NRPSs, they are likely not canonical NRPSs.

Figure 20A:
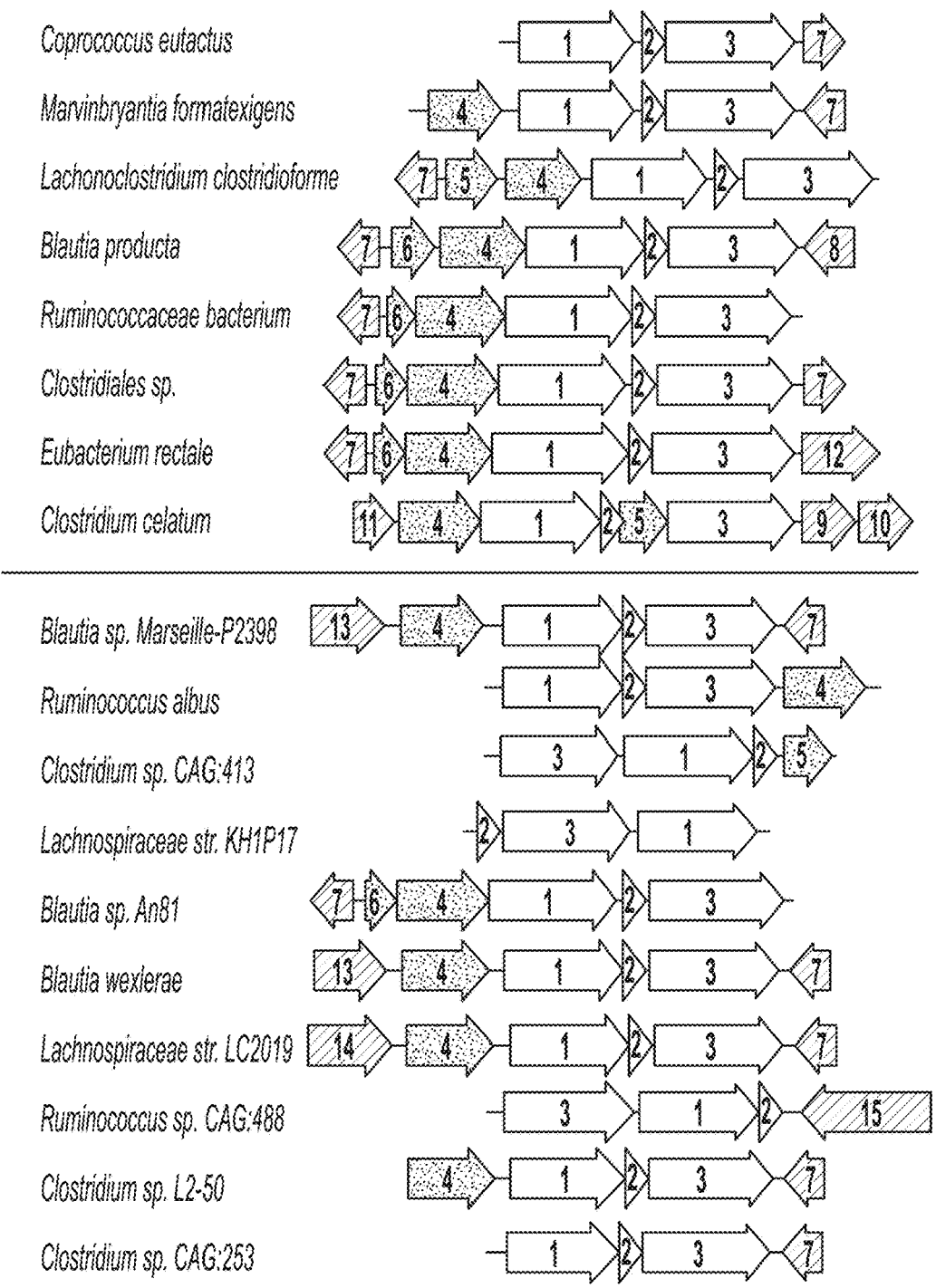

These three biosynthetic genes are the only genes conserved across all Clostridia-derived pathways. However, some pathways also contained genes encoding a sterol transfer protein, an alpha/beta-hydrolase protein, or a PPTase (FIG. 15a and Table 1). In addition, some pathways consisted of a TetR-like transcriptional regulator (FIG. 20). These generally constitute the genes that make up the pathways with boundaries predicted by antiSMASH. Other genes close to the predicted gene cluster boundaries were manually inspected and found to be putative housekeeping genes (e.g., cell wall glycosyltransferase) that are not conserved across any of the other pathways.

Mechanism Elucidated for Clostridia FAA Biosynthesis

Figure 21A:
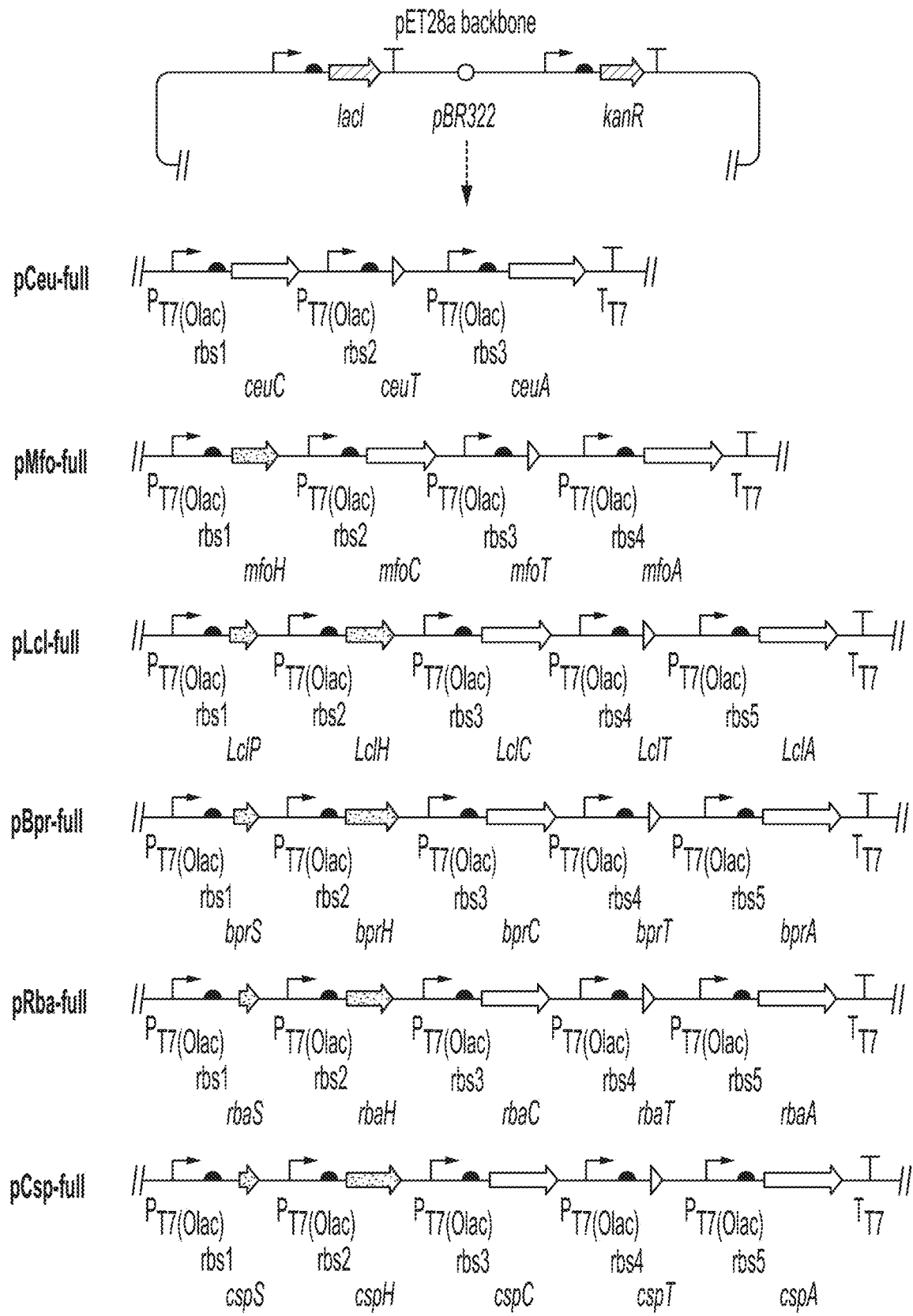
FIGS. 21A-21B show expression vector design. Cloning into pET28a (Novagen) for constructs containing a, redesigned pathways and b, single gene expression for protein purification.
Figure 21A:
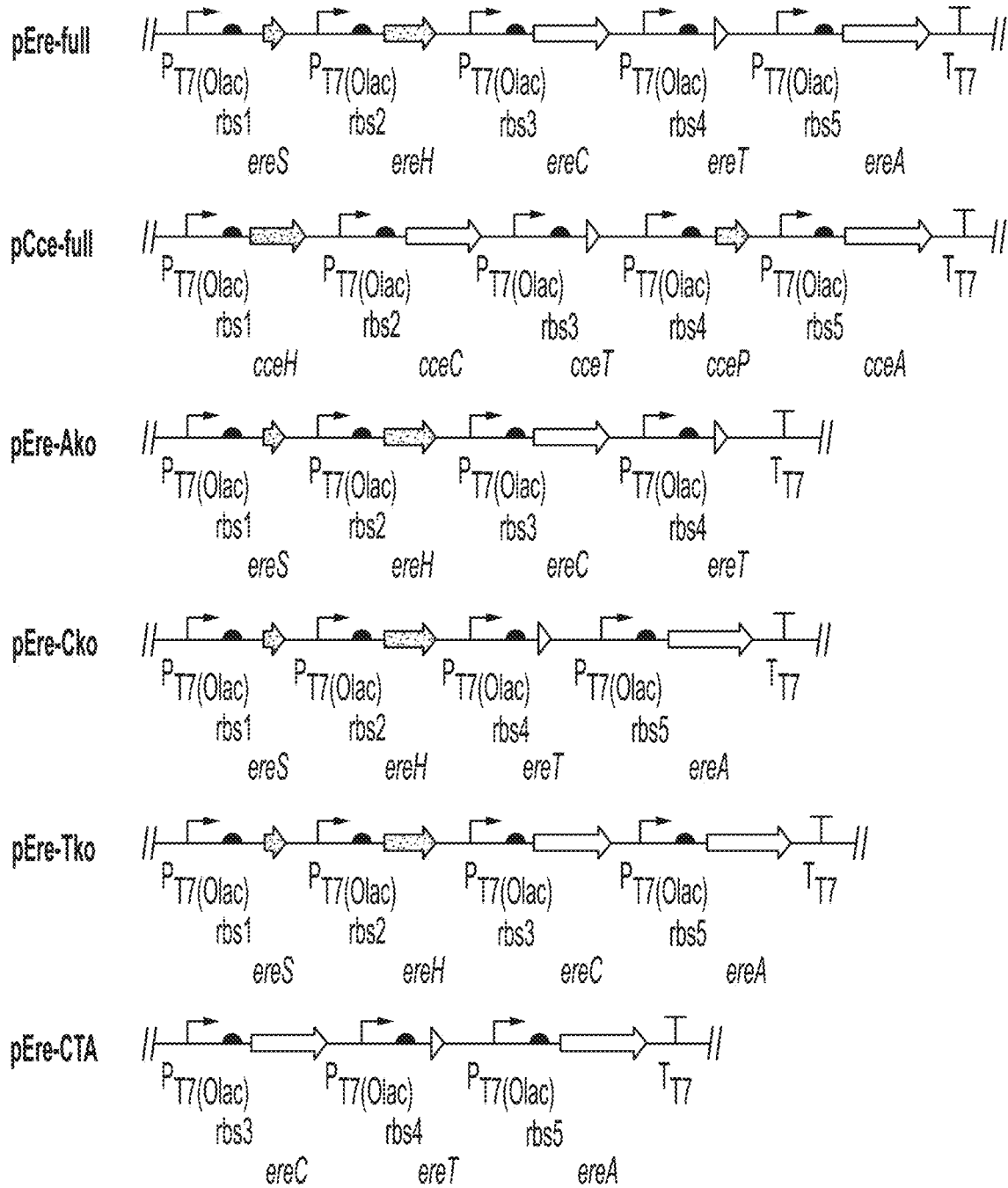

Some of the strains in which the pathways are found have not been isolated or are not available from a strain bank. Therefore, the pathways were reconstituted in *E. coli* containing a genome-encoded IPTG-inducible T7 RNA polymerase (RNAP). Initially focusing on the eight human gut Clostridia-derived pathways, the C, T, and A genes were codon optimized and placed under the control of strong T7 promoters and ribosome binding sites (RBSs) (FIG. 21, Tables 1 and 2). Sfp, a promiscuous PPTase from *Bacillus subtilis*, was placed under inducible control in the genome to ensure PPTation of T domain for proper NRPS activity. When the genes were expressed in *E. coli*, only a compound for the *E. rectale* pathway was able to be obtained, despite numerous attempts to optimize the fermentation and extraction conditions. The major compound was determined to be palmitoeyl putrescine by 1- and 2-D NMR, formed by palmitoleic acid and putrescene (FIGS. 5 and 16b). Considering that putrescine is highly produced in *E. coli* compared to Clostridia, it was questioned whether these are the actual substrates of this pathway.

To investigate the mechanism, variants of the *E. rectale* pathway were constructed where each gene was individually removed and the impact on pamitoeyl putrescine production was tested (FIGS. 6a and 16b). Removing either the A, T, or Sfp PPTase gene eliminated production, thereby confirming the thiotemplated reaction of A and T in FAA production. In contrast, deleting the C gene had no effect, thus indicating it is not participating in palmitoeyl putrescine production. Moreover, feeding the culture broth with either octanoic acid or tryptamine led to the production of octanoyl putrescine or palmitoleoyl tryptamine, respectively (FIG. 6b). The pathway is therefore capable of incorporating an exogenous fatty acid or amine.

Figure 16D:
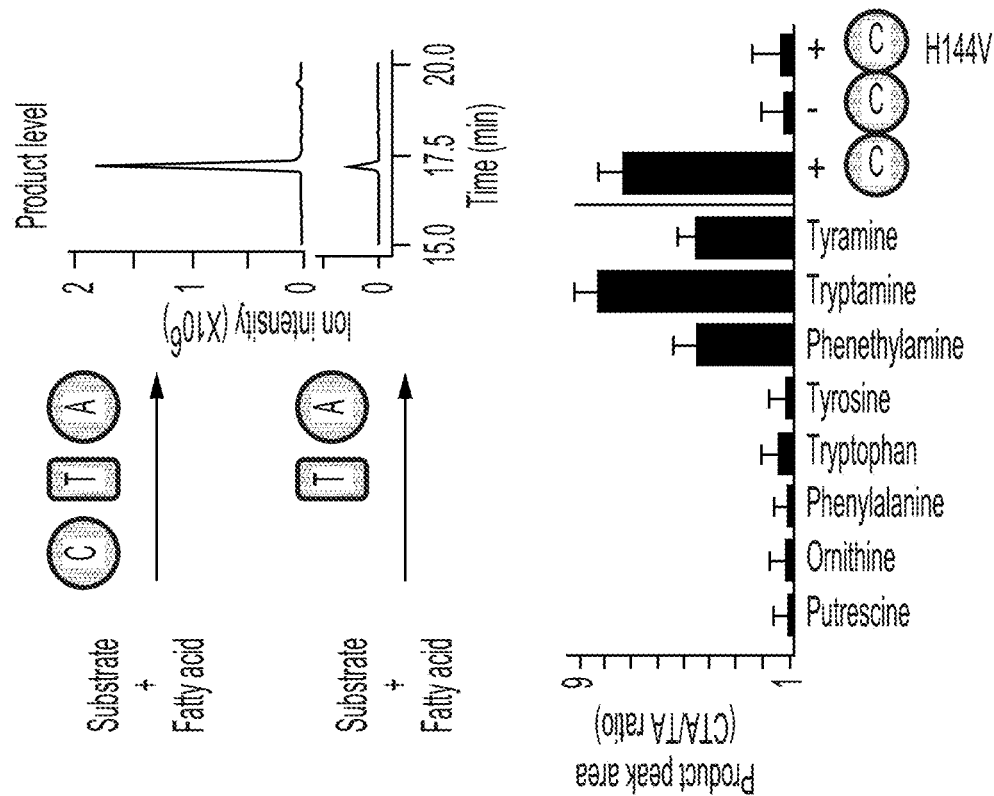
Figure 16C:
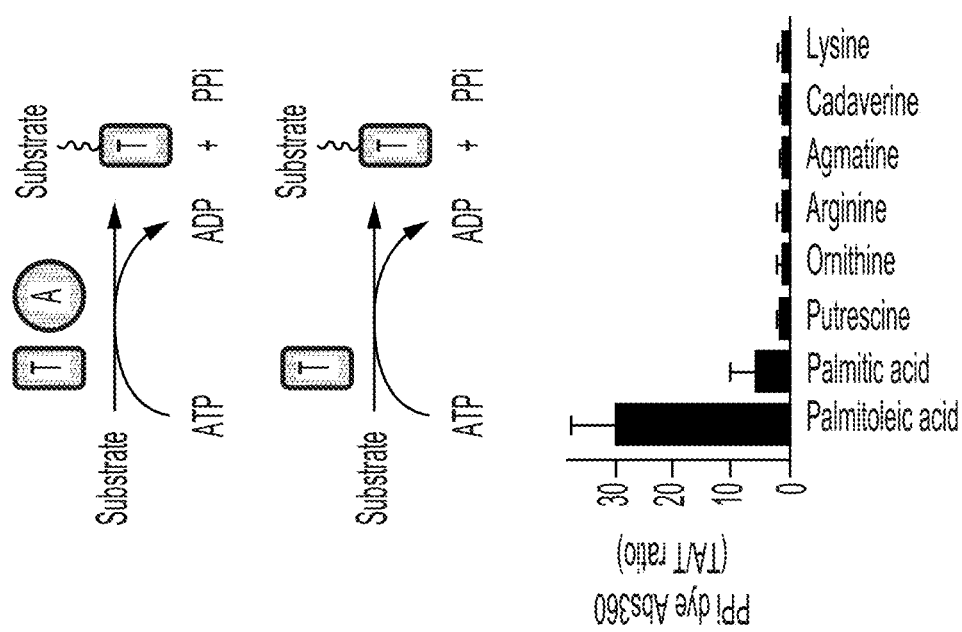
Figure 18:
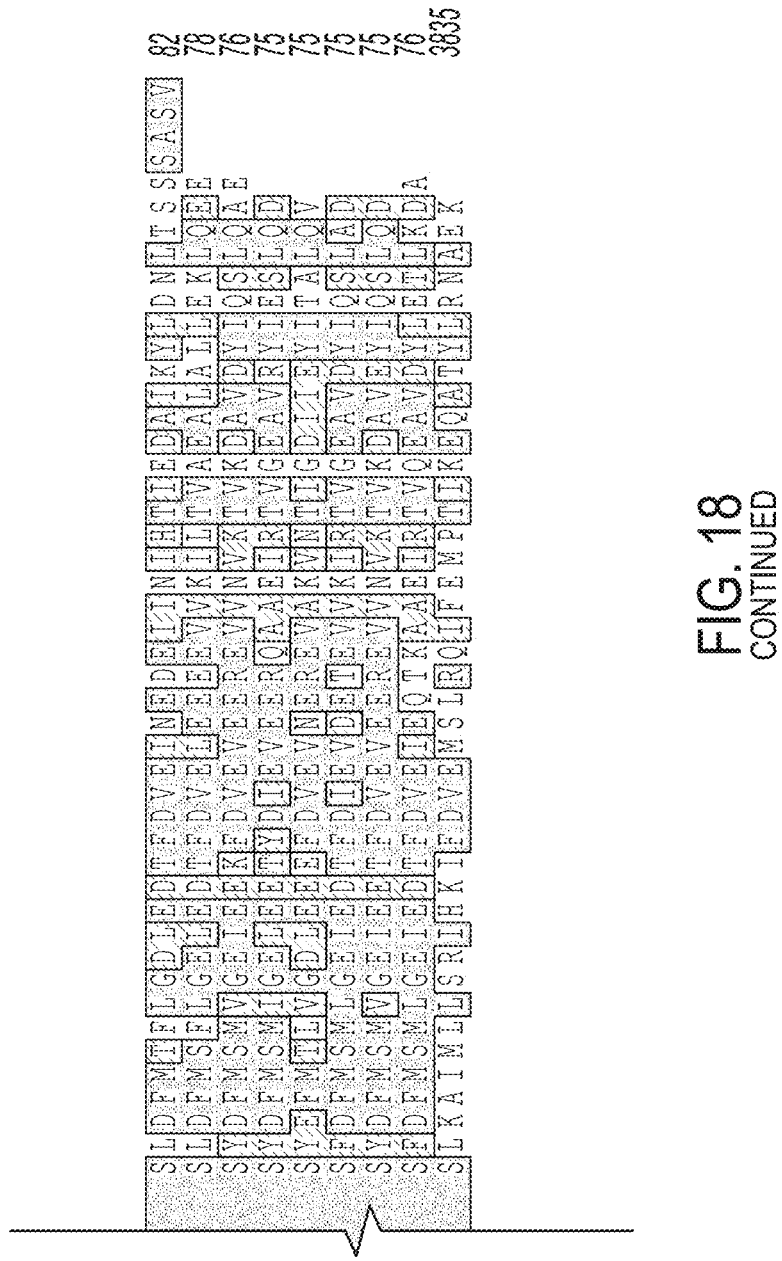
FIG. 18 shows thiolation domain protein sequence alignment. MUSCLE alignment of the eight thiolation-like PP-binding domain (Pfam: PF00550) containing proteins from the eight HMP-derived Clostridia pathways, along with the closest NRPS homolog in the NCBI nr database (NCBI Accession: WP_104149350).
Figure 21B:
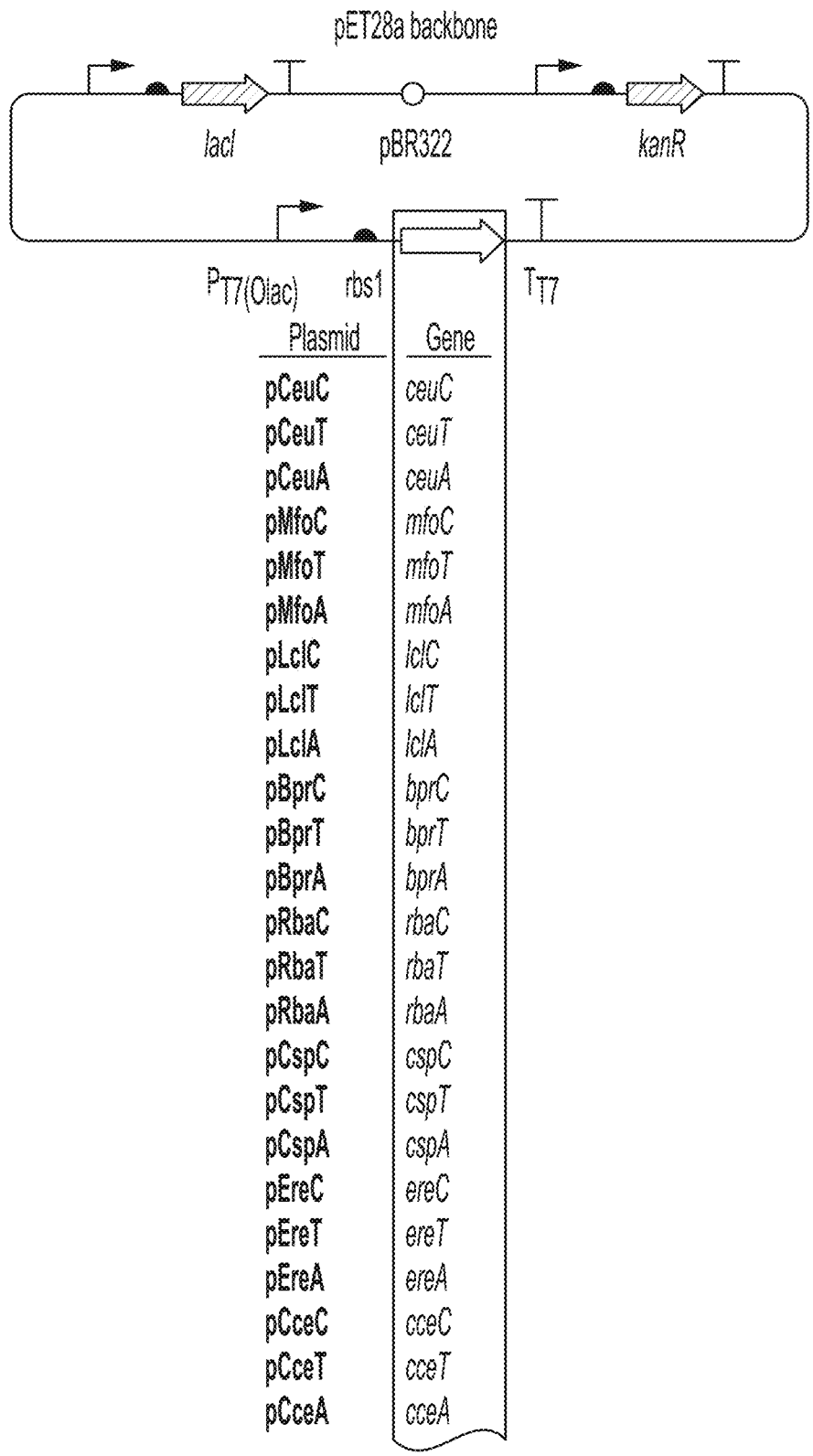
Figures 22A, 22B:
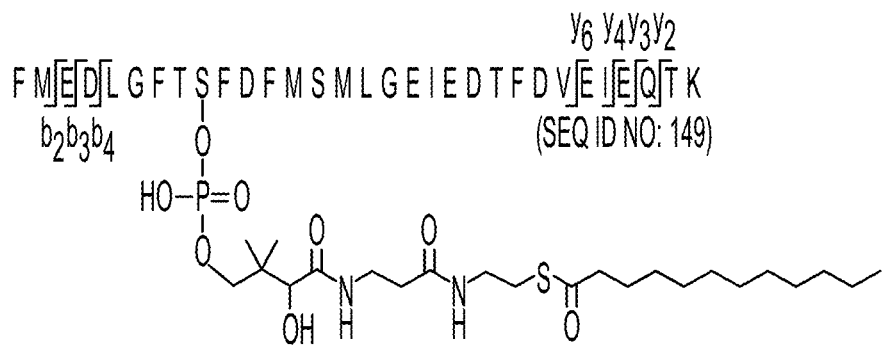
FIGS. 22A-22B show LC-MS detection of thiotemplated peptide. a, LC-MS detection of phosphopantetheinylated peptide conjugated with lauric acid. The peptide was generated by tryptic digestion of the *E. rectale* T protein upon reaction with the *E. rectale* A protein, Sfp, and lauric acid for substrate loading, and confirmed to be absent in the negative control reaction mixture without ATP. b, Summary of ions observed by MS/MS-based fragmentation of the peptide extending from the amino (b ions) and carboxyl (y ions) termini.
Figure 23:
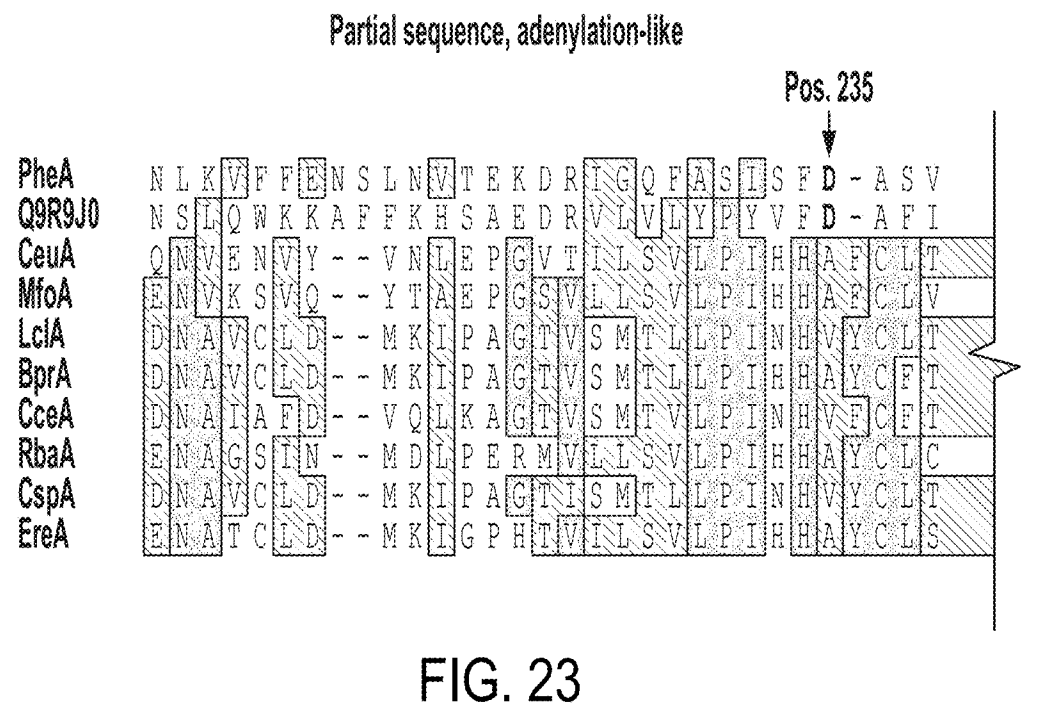
Figure 23:
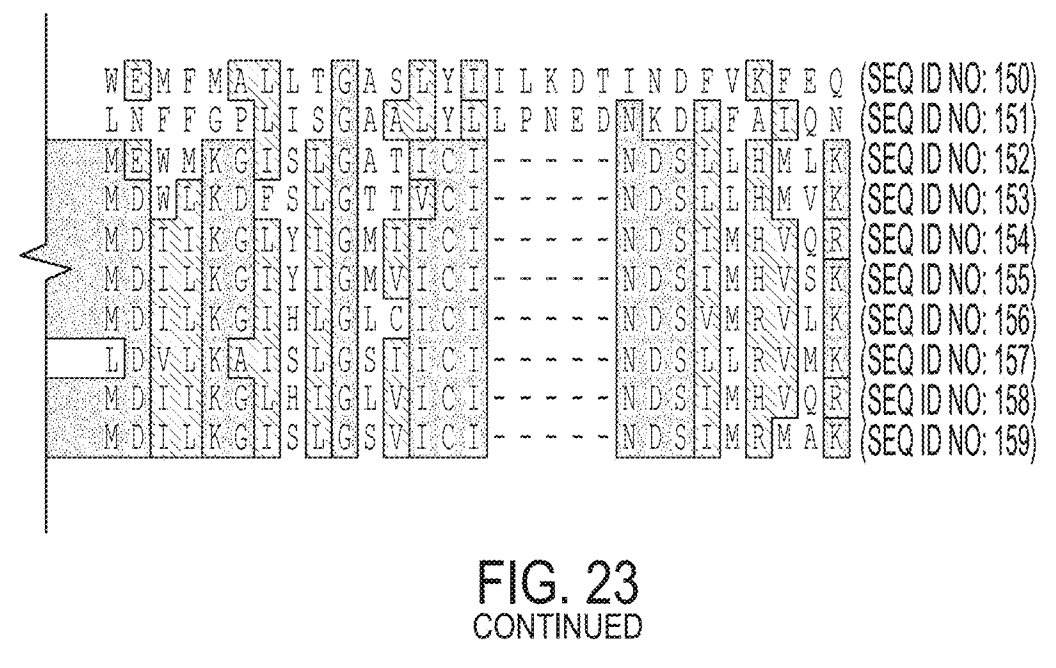

Each enzyme from the *E. rectale* pathway was then purified and reconstituted in vitro (FIG. 21b). The reaction is based on previously-studied NRPS in vitro systems, which include Sfp and Coenzyme A (CoA), TCEP as reducing agent, and ATP. First, the loading of the substrate onto T was measured by monitoring the ATP consumption using a phosphate assay based on a dye that quantifies PPi. PPi was measured in the presence and absence of the protein A, and this ratio was used to identify substrates (FIG. 16c). These data demonstrate that fatty acids are strongly preferred, with no observed incorporation of putrescine or any amino acid substrates that may further be processed to form a putrescine moiety. This was further confirmed by the detection of fatty acid thiotemplated T protein fragment using LC-MS/MS (FIG. 22). This is consistent with the protein sequence alignment showing that the Clostridia-derived A domain lacks the corresponding aspartic acid residue of a canonical NRPS A domain that interacts with the α-amino group (FIG. 23). Therefore, the A protein in this pathway is not a NRPS adenylation protein, but a fatty acyl-CoA ligase that tethers a fatty acid (instead of α-amino acid) onto the T protein.

Figure 24:
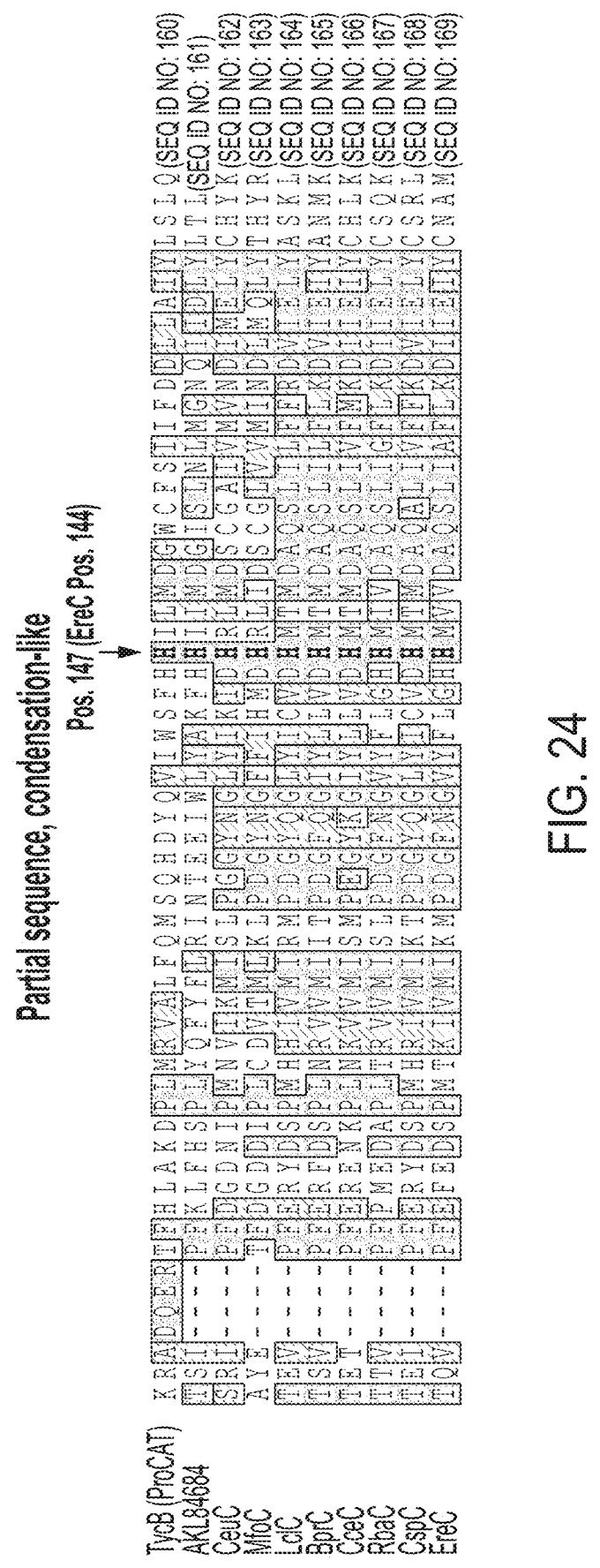

Deleting the C gene had no effect on the production of palmitoeyl putrescine in *E. coli*. This could be due to palmitoeyl putrescine being a shunt product that forms because *E. coli* lacks the appropriate substrate. To determine the substrate, a LC-MS assay was developed to measure the relative FAA product concentration formed by the in vitro reaction because condensation domains that utilize thiotemplated substrates catalyze ligation without ATP consumption. Different FAAs ionize at varying intensities, so ion abundance cannot be used for side-by-side comparisons of different amines. Instead, the fact that there is some background incorporation of amines (e.g., putrescine) was used, and the ratio of the LC-MS peaks in the presence and absence of the C protein was reported. Different amines are preferred, with tryptamine having 8-fold higher enzymatic incorporation (FIG. 16d). Catalytic incorporation was confirmed by mutating the histidine residue essential for the NRPS condensation reaction, which eliminated activity (FIGS. 16d and 24).

A mechanism can be inferred from the in vivo heterologous expression data and in vitro reconstruction. The T protein serves as an acyl carrier protein, the A protein is a fatty acyl-acyl carrier protein synthetase (fatty acyl-CoA ligase), and the C protein is a N-fatty acyltransferase (FIG. 16a). Upon Sfp-dependent activation of T with the PPT arm, A selects an exogenous fatty acid substrate and tethers it onto T. C then selects an exogenous amine and conjugates it onto the thiotemplated fatty acid (fatty acyl-T) to form the FAA product. The chemical mechanism differs from canonical NRPS systems in that the amine substrate is not selected by the A enzyme, and the C enzyme joins activated fatty acid with a free amine, thereby resembling N-acyltransferase systems characterized to generate FAAs in humans and bacteria. However, where canonical N-acyltransferase systems rely on endogenously available fatty acyl-CoA as substrates, this pathway has a mechanism to scavenge fatty acid that is available in the environment.

Figures 15B, 15C:
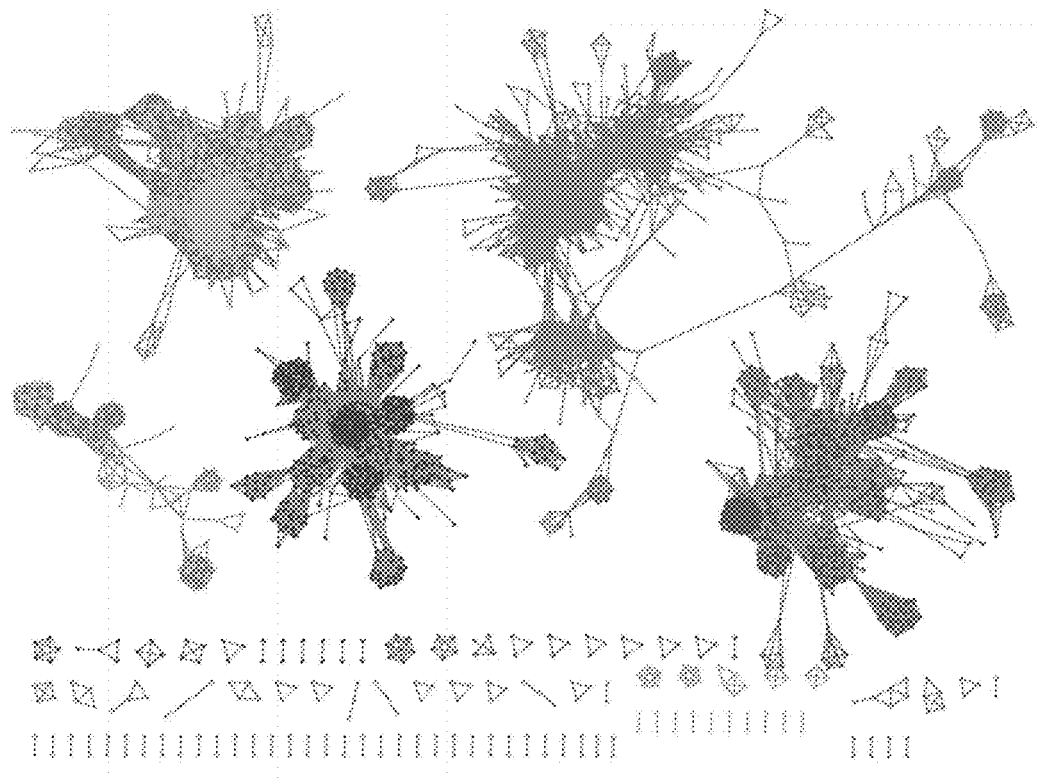

In addition to the three biosynthetic genes, most pathways also contained some combination of three additional conserved genes (genes labeled "Saccharide" in FIG. 15c). Excluding these genes has no effect on FAA production in Sfp-harboring *E. coli* (FIG. 6a). One gene has predicted homology with sterol transporters; thus, it is likely facilitating the transport of exogenous fatty acids from the human gut lumen to the bacterial cytoplasm in order to increase in vivo substrate availability of the A protein. The second gene encodes for serine aminopeptidase-like alpha/beta-hydrolase that could either serve to cleave human endogenous FAAs to generate free substrates for the Clostridia pathway or degrade the FAA pathway product as a negative regulatory mechanism much like human FAA hydrolases. The third gene is homologous to Sfp-like PPTase involved in the functionalization of the T protein with a PPT arm. This pathway-specific PPTase gene is likely necessary for FAA production in the native strain, but it is dispensable in the *E. coli* system because the *E. coli* strain harbors the *B. subtilis*-derived Sfp.

Preferred FAA Products Characterized by In Vitro Substrate Screening

The human gut lumen consists of fatty acids and amines from different sources that could be used by the enzymes to build FAAs. The in vitro system was expanded to determine the substrate specificities of the pathways. Rather than test all combinations, two assays were developed to test fatty acid and amine incorporation separately, where the other substrate is held constant. For the fatty acid screening to test adenylation activity, tryptamine is added to all the fatty acid reactions along with the purified T and A proteins and FAA formation is measured based on the UV absorbance (280 nm) of its indole chromophore. The reaction contained no C protein, thereby measuring FAA product as it is non-enzymatically released from the fatty acyl-T produced by the T and A proteins. The incorporation is presented as the ratio of the UV absorbance peak of the fatty acyl-tryptamine product with T and A proteins relative to that obtained from the control containing only T (FIG. 25*a*). To screen for amine specificity, the same assay is used as for FIG. 16*d*, and for each pathway, the fatty acid found to be the most active in the fatty acid screening was chosen to be held constant (FIG. 25*b*).

Figure 25C:
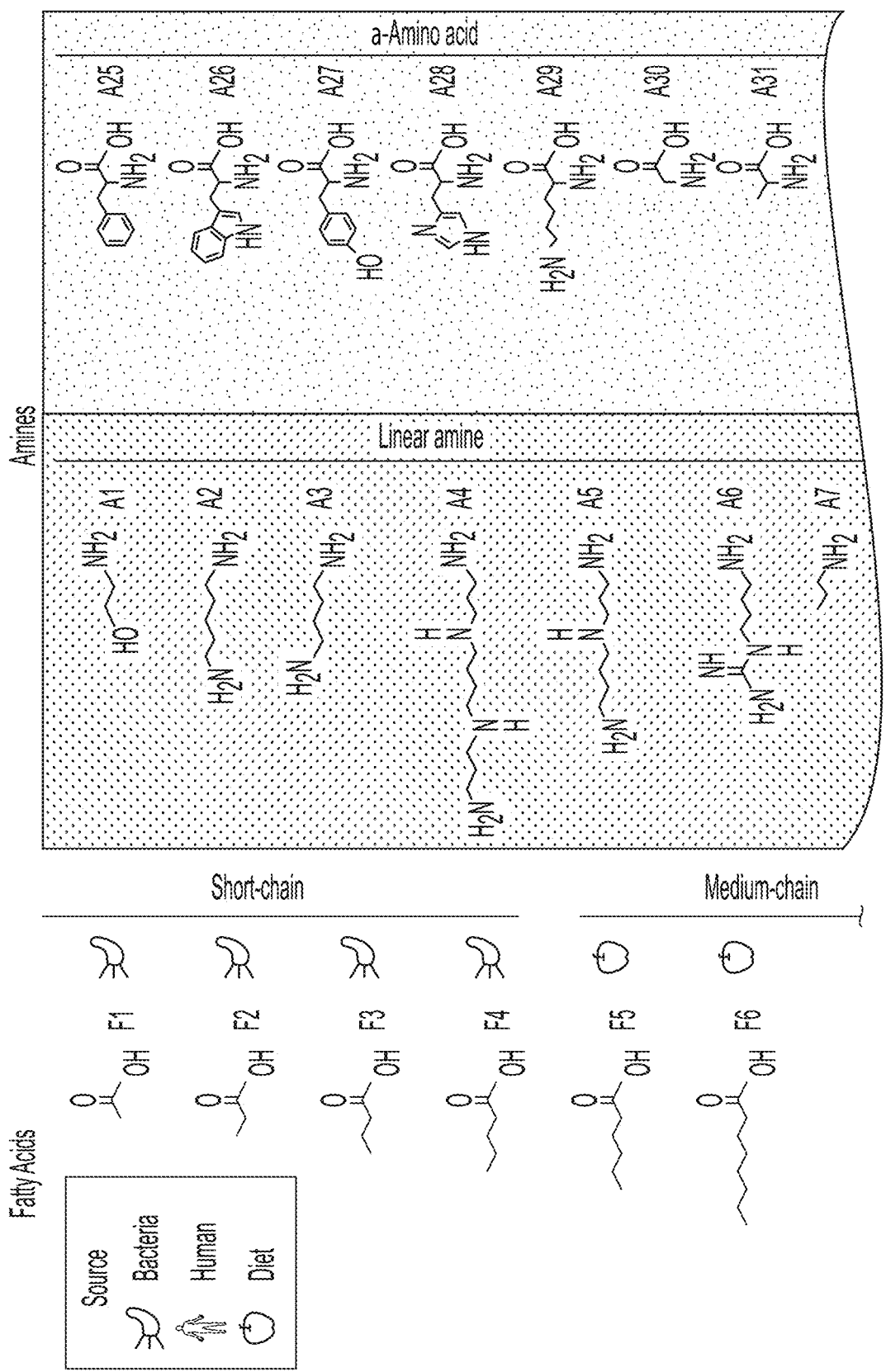

A panel of 25 fatty acids and 53 amines was collected, representative of biogenic sources present in the human gut, including bacteria, human cells, and diet (FIG. 25*c*, Table 3). This list includes all of the amines and fatty acids that identified from literature that are abundant in the human body and, for fatty acids, where the amine moiety is exposed for amide bond formation (e.g., excluding choline). The fatty acids and amines that constitute known mammalian FAAs are included in this panel. Some esoteric fatty acids were not included that are low in abundance or not commercially available (e.g., trans fatty acids, cyclopropane fatty acids).

Figure 25D:
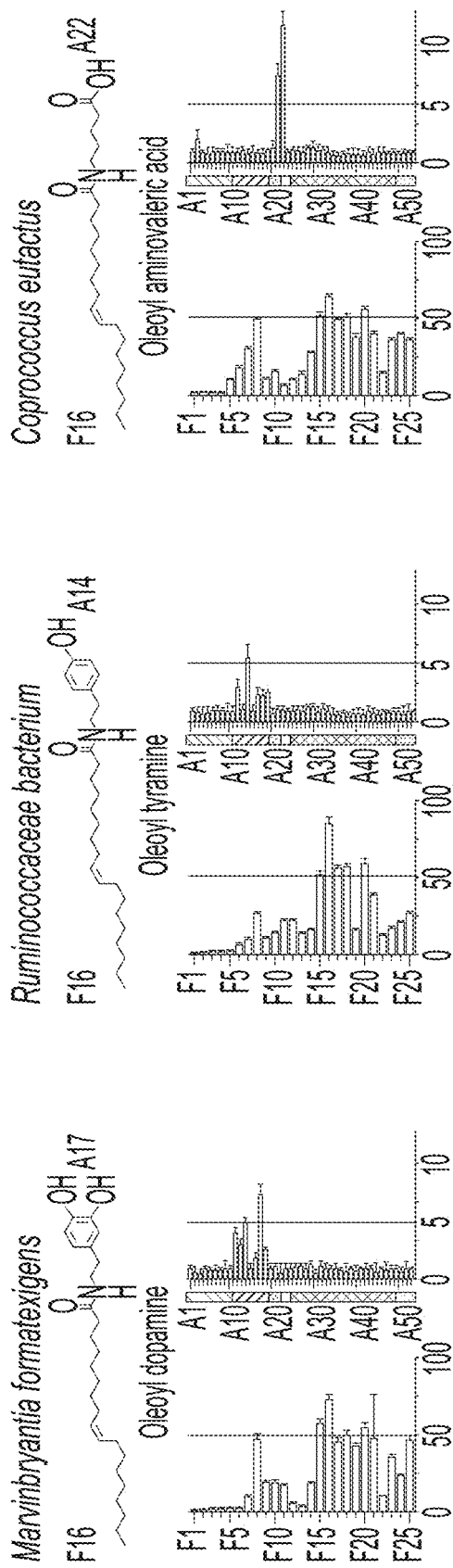
Figure 26:
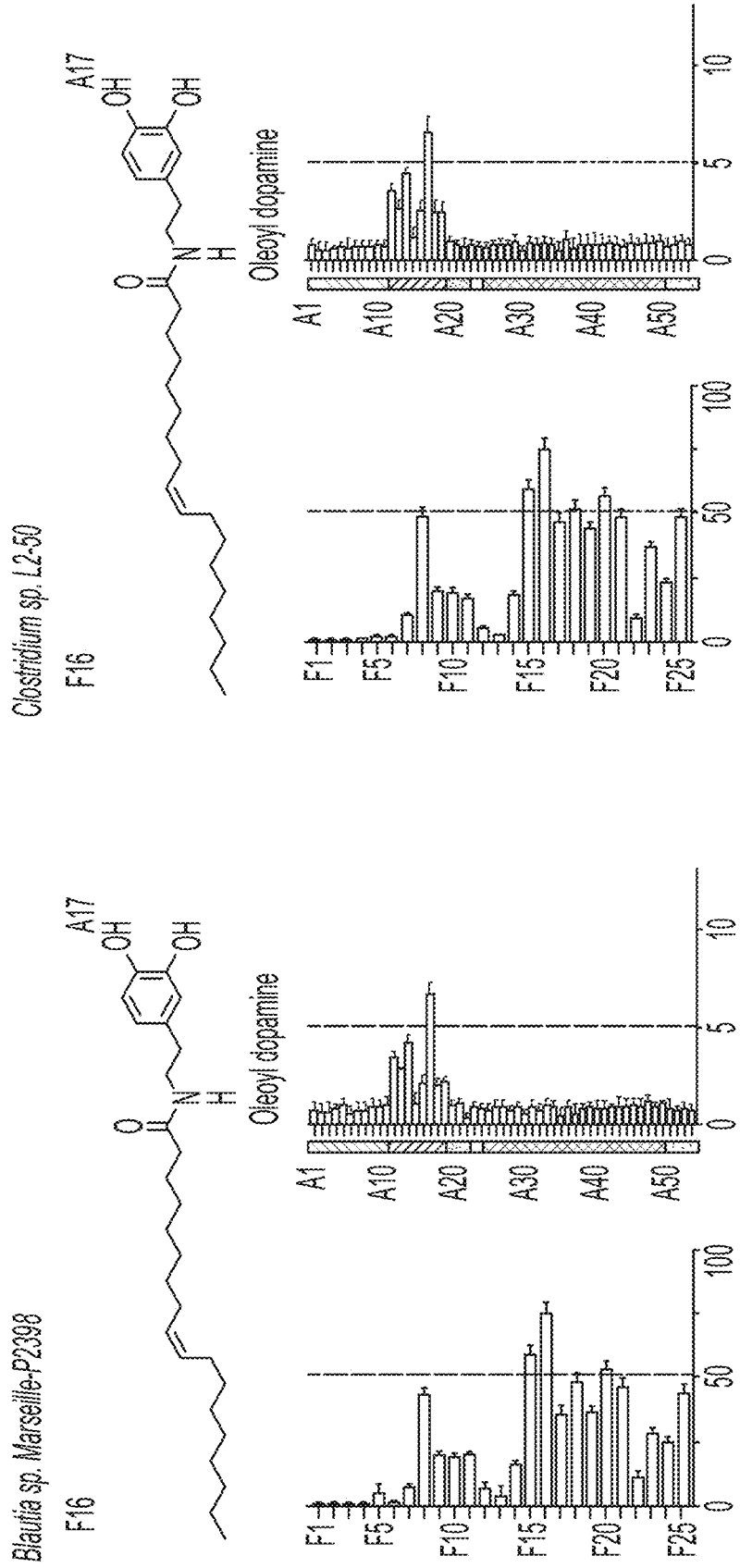
FIG. 26 shows in vitro substrate screening for pathways producing same major compounds. Six Clostridia-derived pathways encoding for major FAA compounds, each bar graph labeled with the major compound based on fatty acid and amine substrate with highest activity level in the panel assay. Bar graphs represent adenylation and condensation activity from the substrate panel assay. The data was taken in triplicate per day. The reported data is the average of the mean triplicate normalized values conducted on three different days, with the error bar being the s.d. of the three mean triplicate values.
Figure 26:
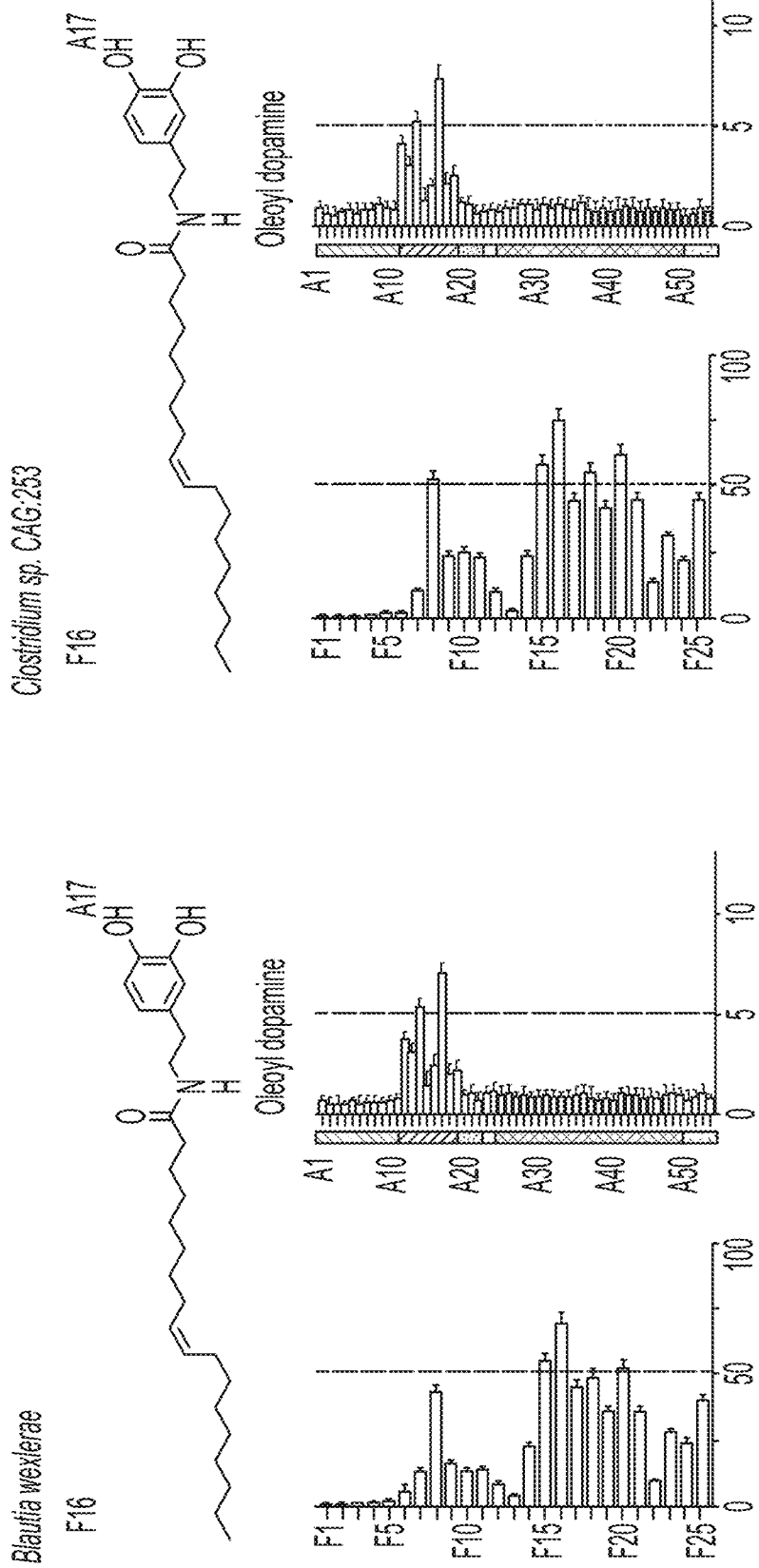
Figure 26:
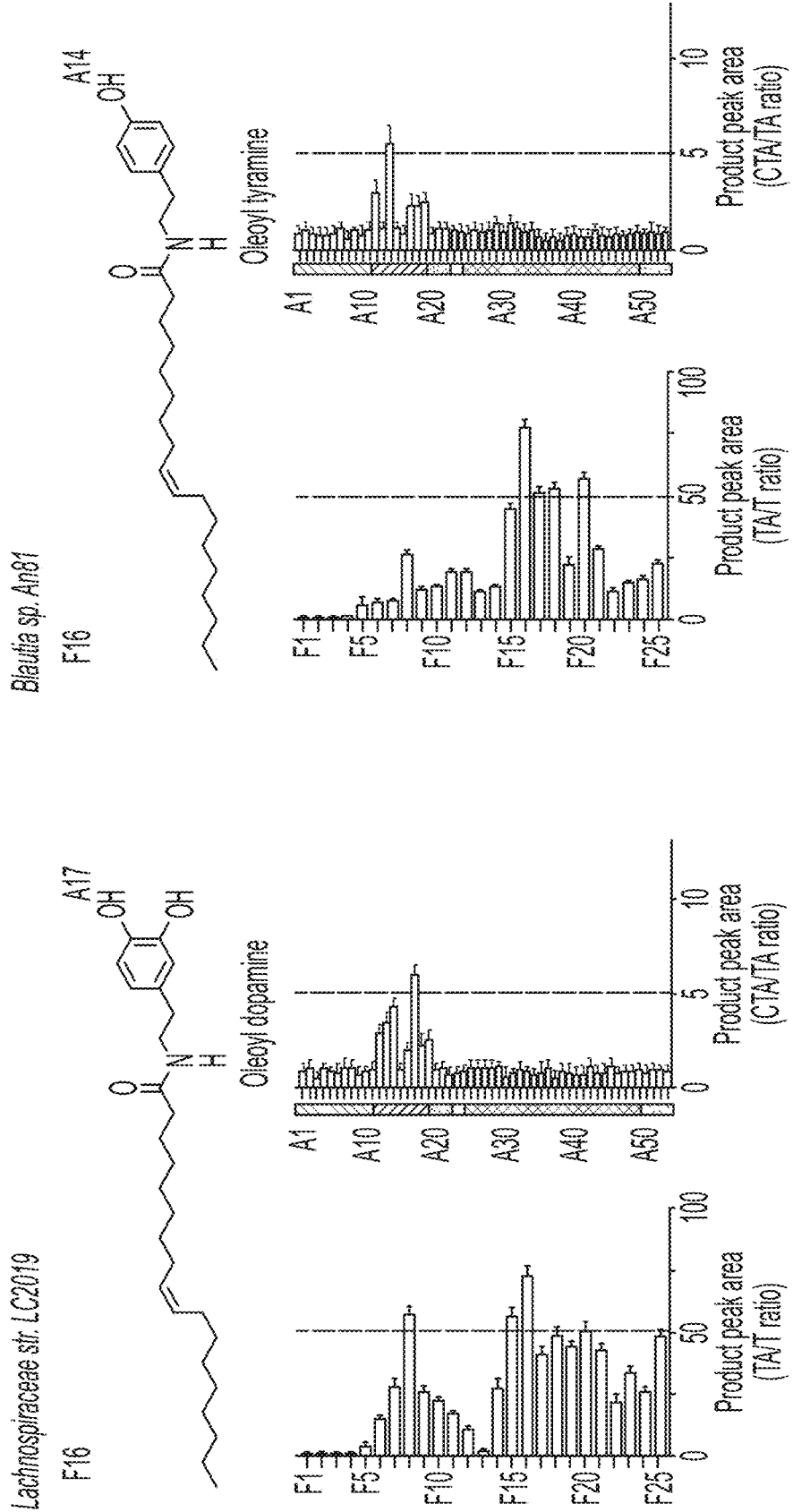
Figure 27A:
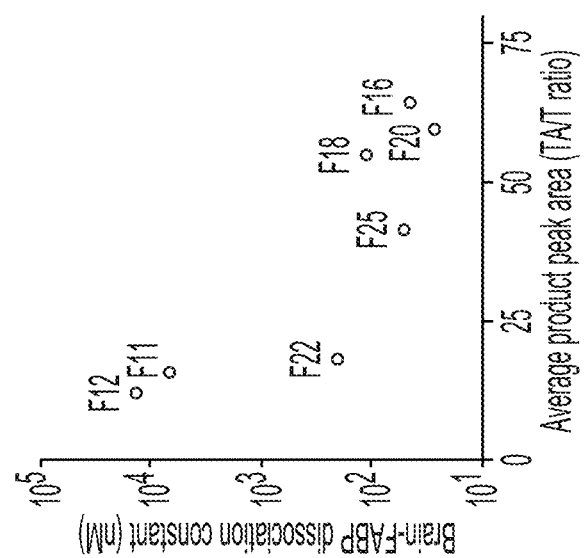
FIGS. 27A-27B show fatty acid specificity profile. a, Overall average of product peak area of the eighteen Clostridia A domain proteins on the following fatty acid substrates (from left to right data point): stearic acid (F12), palmitic acid (F11), arachidonic acid (F22), docosahexaenoic acid (F25), linoleic acid (F18), α-linolenic acid (F20), and oleic acid (F16). This is correlated with the dissociation constant of human brain fatty acid binding protein measured by isothermal titration calorimetry (TIC), as reported previously (Hanhoff, T., et al., Mol. Cell. Biochem. 239, 45-54 (2002)). Spearman correlation test (calculated using PRISM version 7): r=−0.9319, P(two-tailed)=0.0048. b, Substrate specificity profile of the Clostridia adenylation protein by the length of fatty acid substrate structure. The reported value of product peak is the overall average from the eighteen Clostridia A domain proteins. The structure length is calculated by importing the structure from PubChem onto Chem3D version 15 (in the U-bent configuration for unsaturated fatty acids) and measuring the distance from the carboxylic acid carbon to the most distal carbon.
Figure 27B:
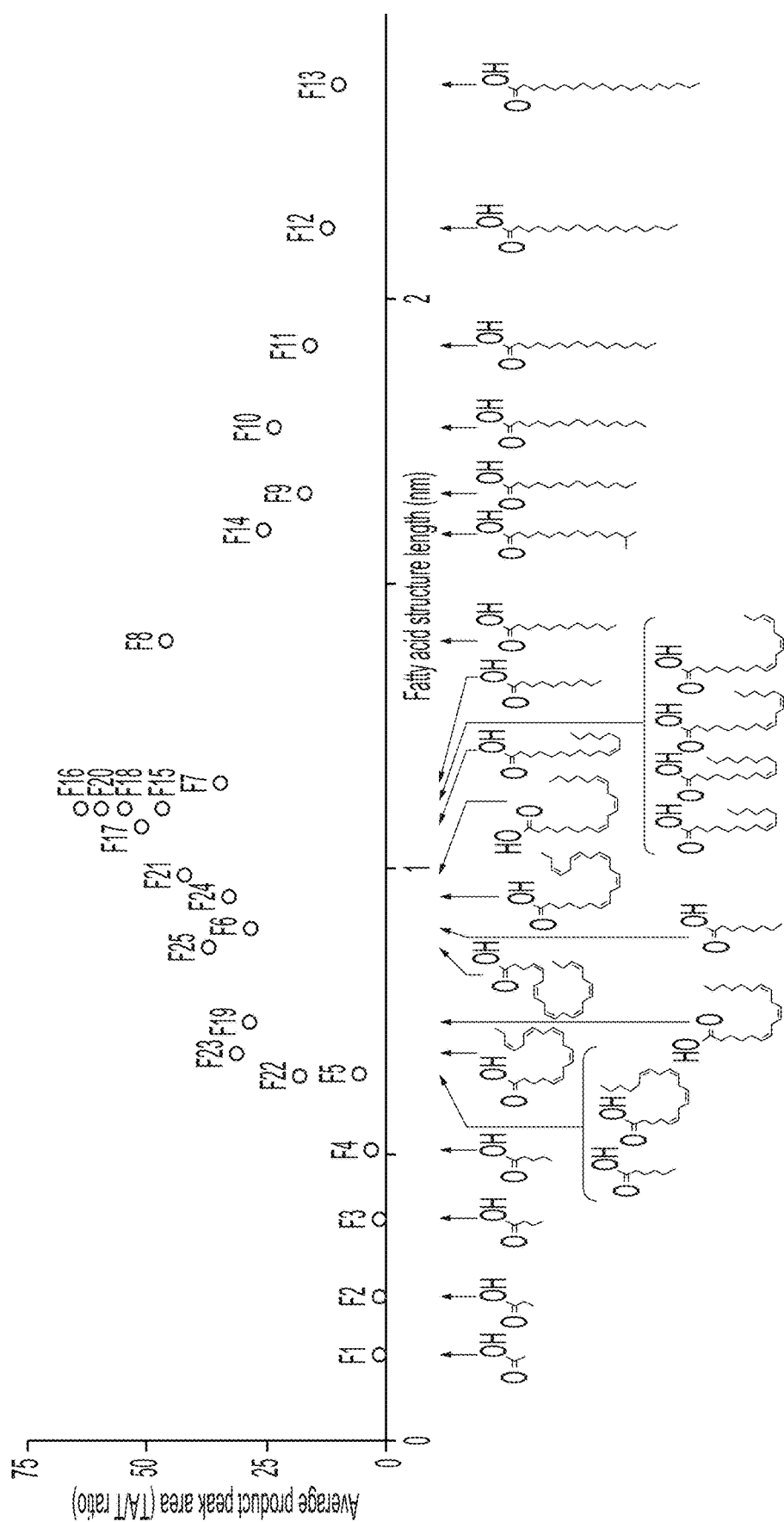

The enzymes associated with each of eighteen pathways (eight from HMP gut metagenome plus ten from the nr database) were screened against the fatty acid and amide panels. The A protein showed a broad range of substrate specificity that is similar amongst the homologues (FIGS. 25*d* and 26). The fatty acid specificity profile of Clostridia A domains resembles human fatty acid binding proteins (FABPs), which also bind a broad range of fatty acids. The correlation is particularly strong with the binding profile of human brain-FABP measured by isothermal titration calorimetry (ITC) (FIG. 27).

Figure 28A:
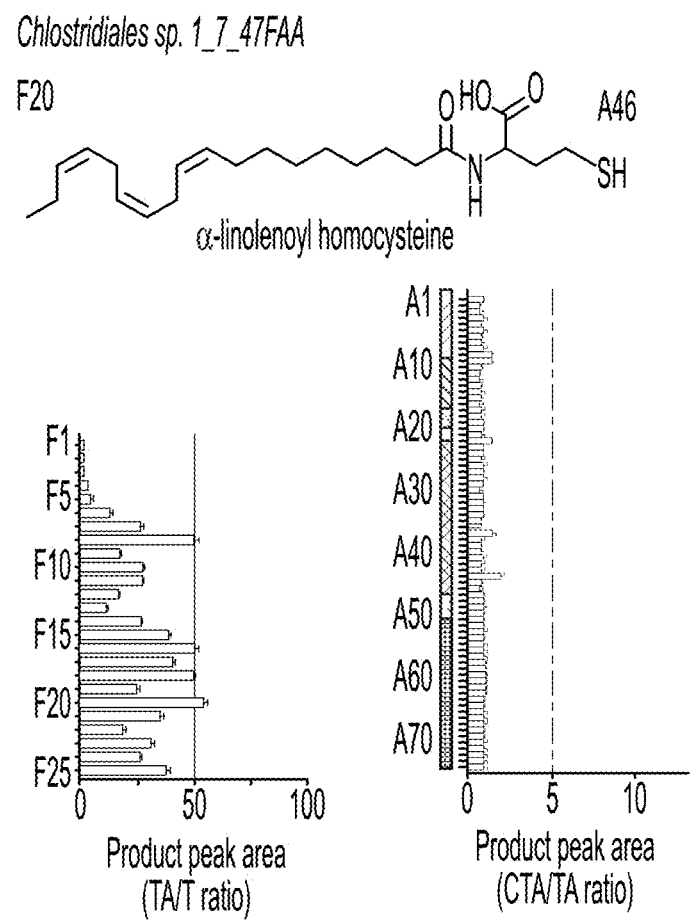

In contrast, considering amine incorporation, the C protein has a much narrower substrate specificity (FIGS. 25*d* and 26). Since the A protein is incapable of loading decarboxylated amines and the pathway lacks a separate release domain, the C protein has taken the place to select for specific amines and compete with the nonenzymatic release of the tethered substrate. The substrates of the C proteins show diversity in structure, ranging from straight-chain amines to arylamines. All amine substrates that are present in the major products are human neurotransmitters made by decarboxylation of proteinogenic α-amino acids, including dopamine, tyramine, tryptamine, and aminovaleric acid (GABA analog). For 6 out of the 18 pathways, no major amine substrate was detected (FIG. 28*a*). An expanded panel of 24 additional amine substrates, including D-amino acids, were screened for these pathways, but none provided enzymatic product formation (FIG. 28*b* and Table 3).

Figure 29:
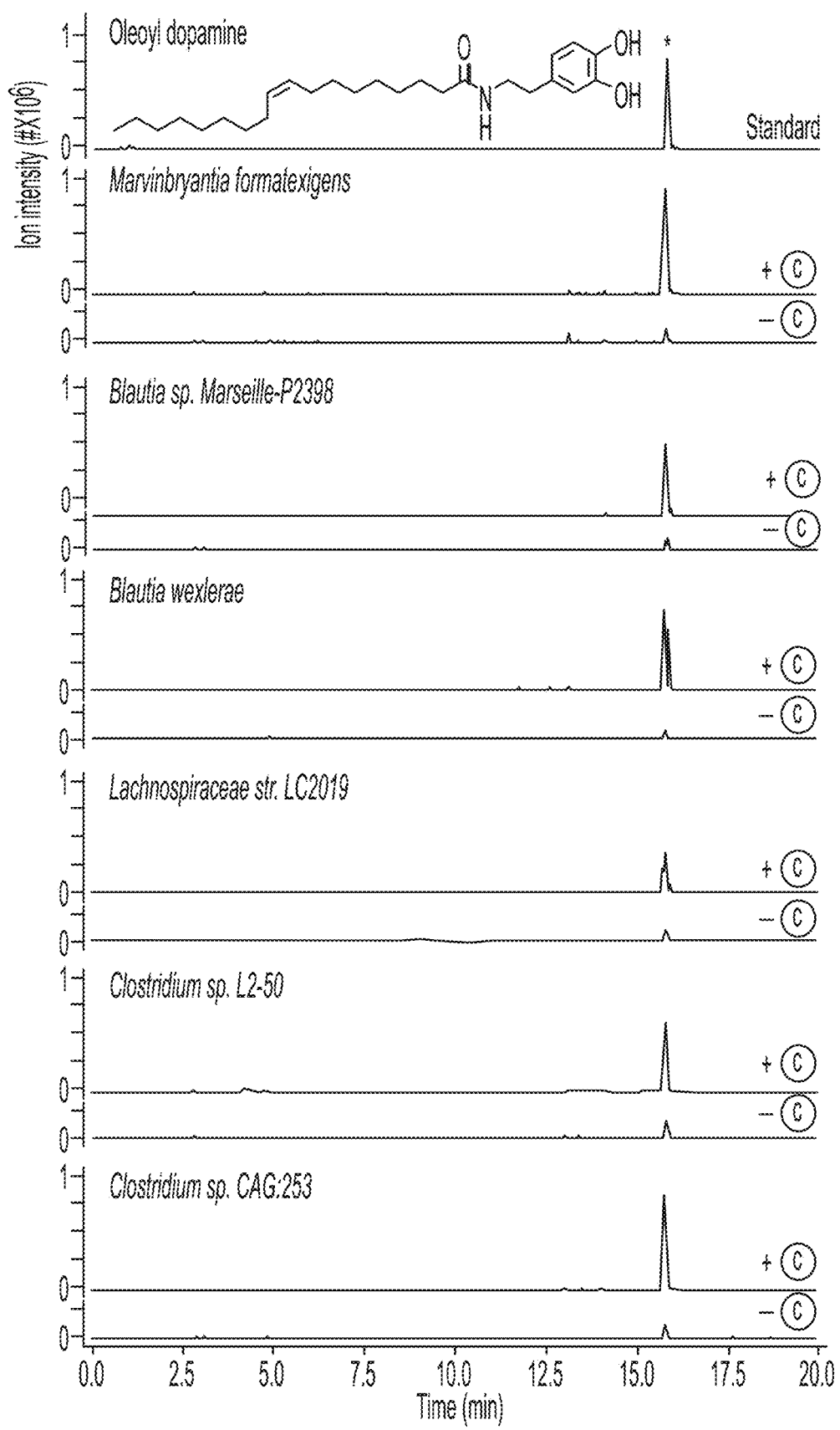
FIG. 29 shows a comparison of major compounds with chemically synthesized standards. MS chromatogram of the in vitro reaction containing the specific pair of substrates yielding the highest enzyme activity, with EIC ESI+ corresponding to m/z of the expected FAA product (oleoyl dopamine: theoretical=418.3316, experimental=418.2784); (oleoyl tyramine: theoretical=402.3367, experimental=402.2901); (oleoyl aminovaleric acid: theoretical=382.3316, experimental=382.2176); (α-linolenoyl phenylethylamine: theoretical=382.3104, experimental=382.2031) (caproyl tryptamine: theoretical 315.2431, experimental=315.2239) (lauroyl tryptamine: theoretical=343.2744, experimental=343.2381). The samples are injected alongside a chemically synthesized and structurally verified standard. The * denotes peak corresponding to the shown compound.

The major products of each pathway can be deduced from the in vitro screens by pairing the most active fatty acid with the most active amine (FIGS. 25*d* and 26). A cutoff was applied to the two panels to identify minor products, which may be physiologically relevant depending on substrate availability. After being deduced based on the panel screen, each of these products was confirmed by adding the pair of substrates and confirming that the pathway produces the FAA product (FIG. 29). Intriguingly, oleoyl dopamine is known human GPCR-targeting FAA and this is the major product for the *M. formatexigens*, B. sp. *Marseille*-P2398, *B. wexlerae*, L. str. LC2019, C. sp. L2-50, and C. sp. CAG:253 pathways. The other major products are oleoyl tyramine, oleoyl aminovaleric acid, α-linolenoyl phenylethylamine, caproyl tryptamine, and lauroyl tryptamine for the *R. bacterium* and B. sp. An81 pathways, *C. eutactus* pathway, *R. albus* pathway, R. sp. CAG:488 pathway, and *E. rectale* pathway, respectively (FIG. 19*d*).

FAA Targeting of Human GPCRs

Figure 31A:
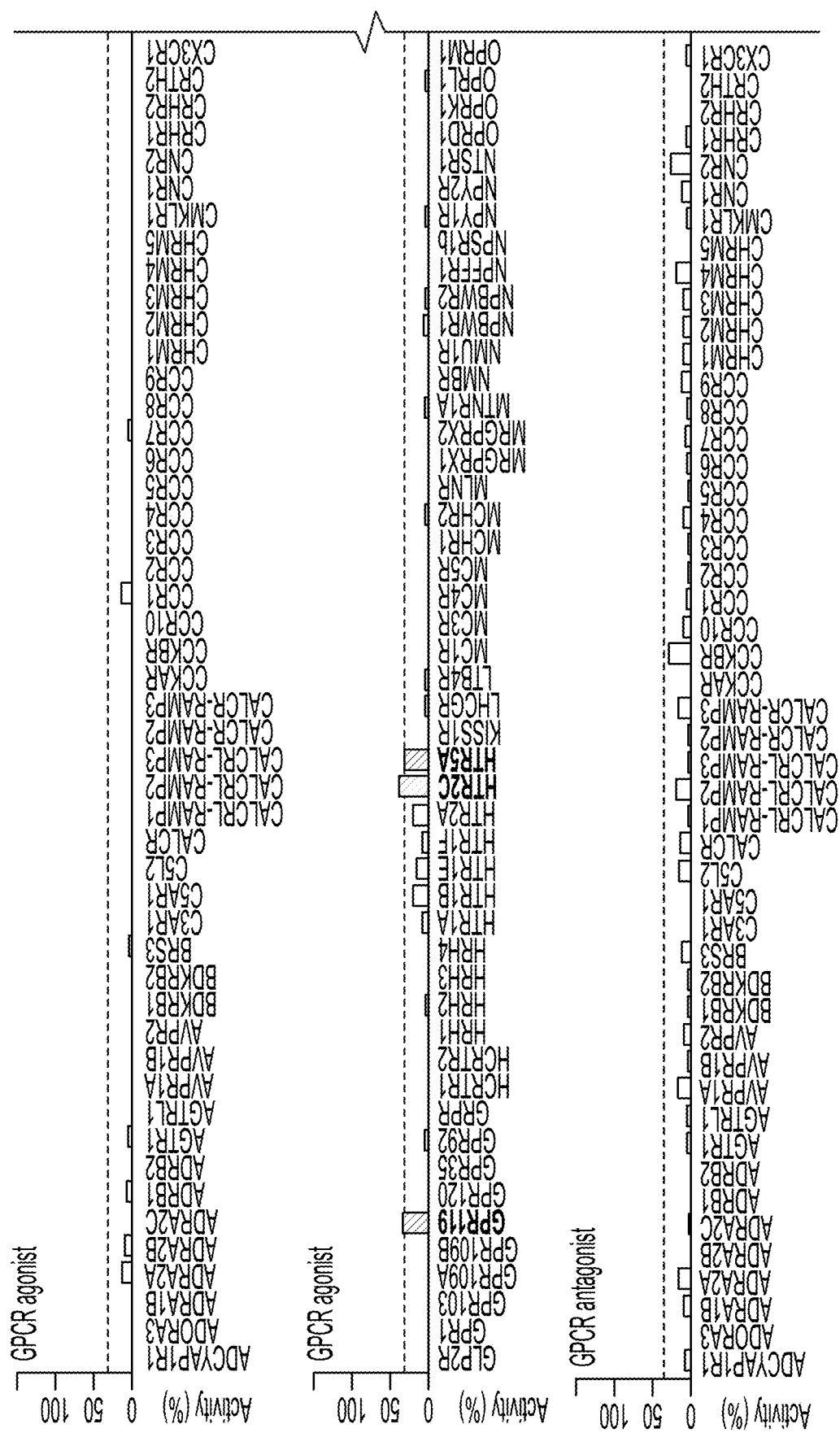
Figure 31A:
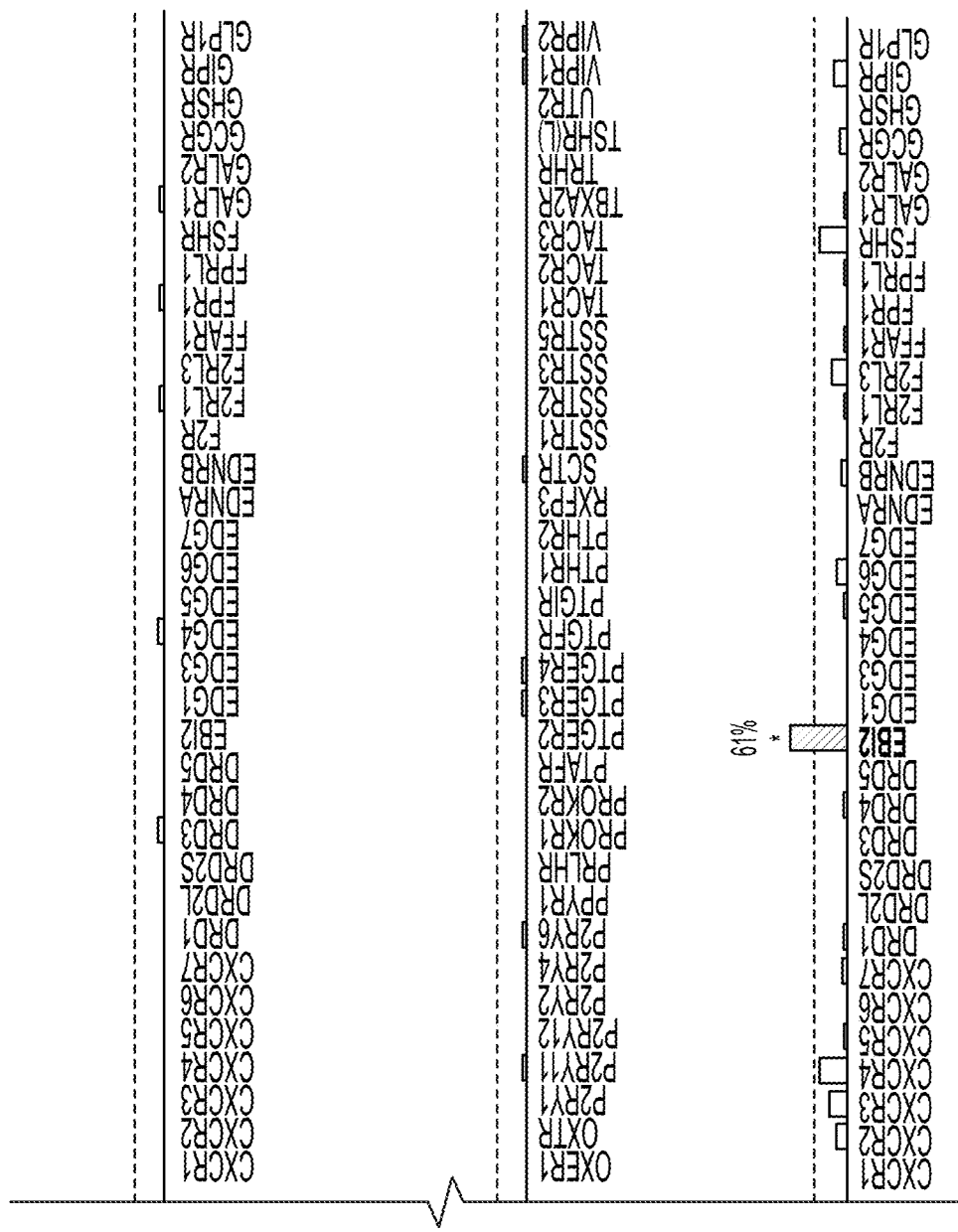
Figure 31A:
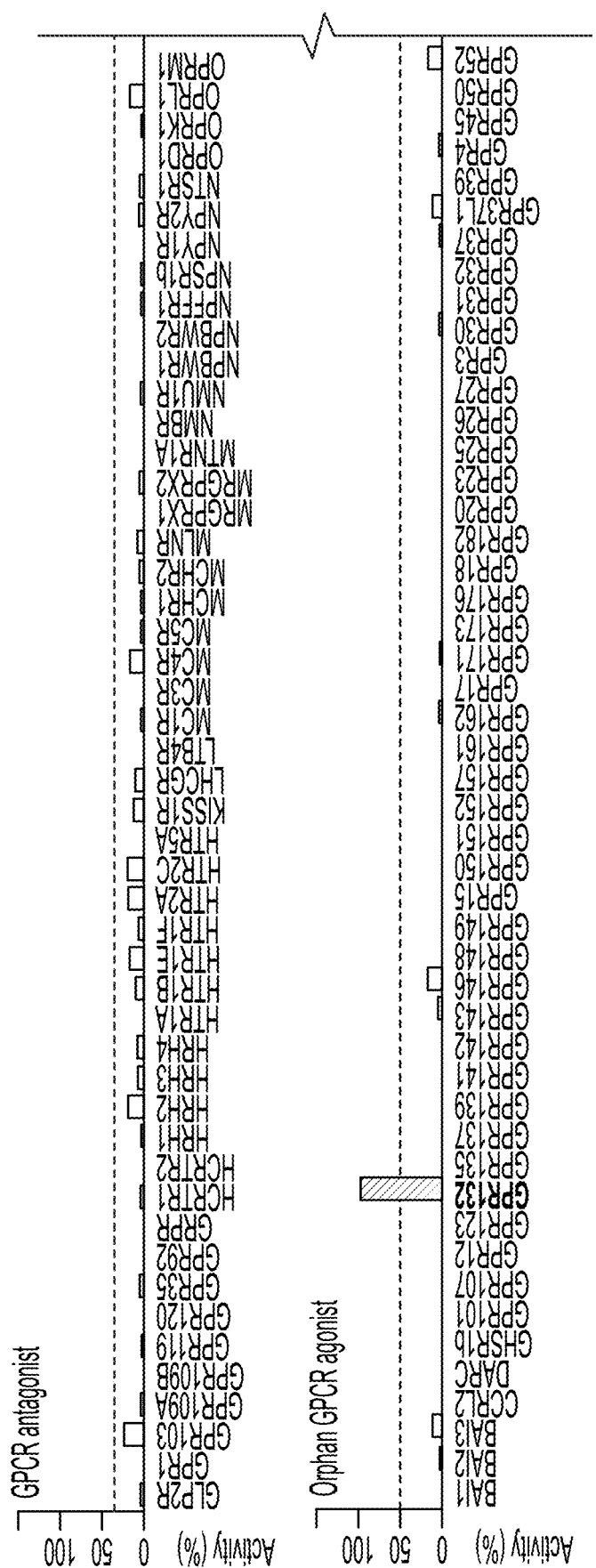
Figure 31A:
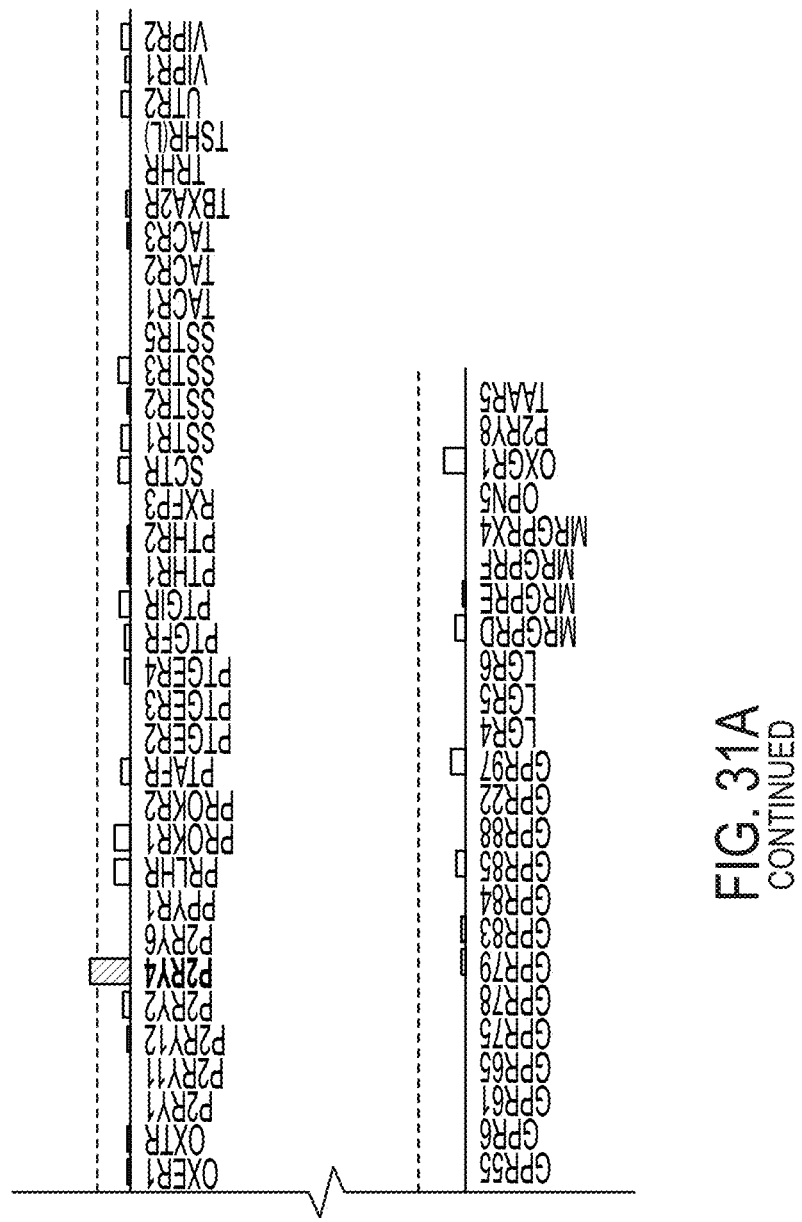
Figure 31H:
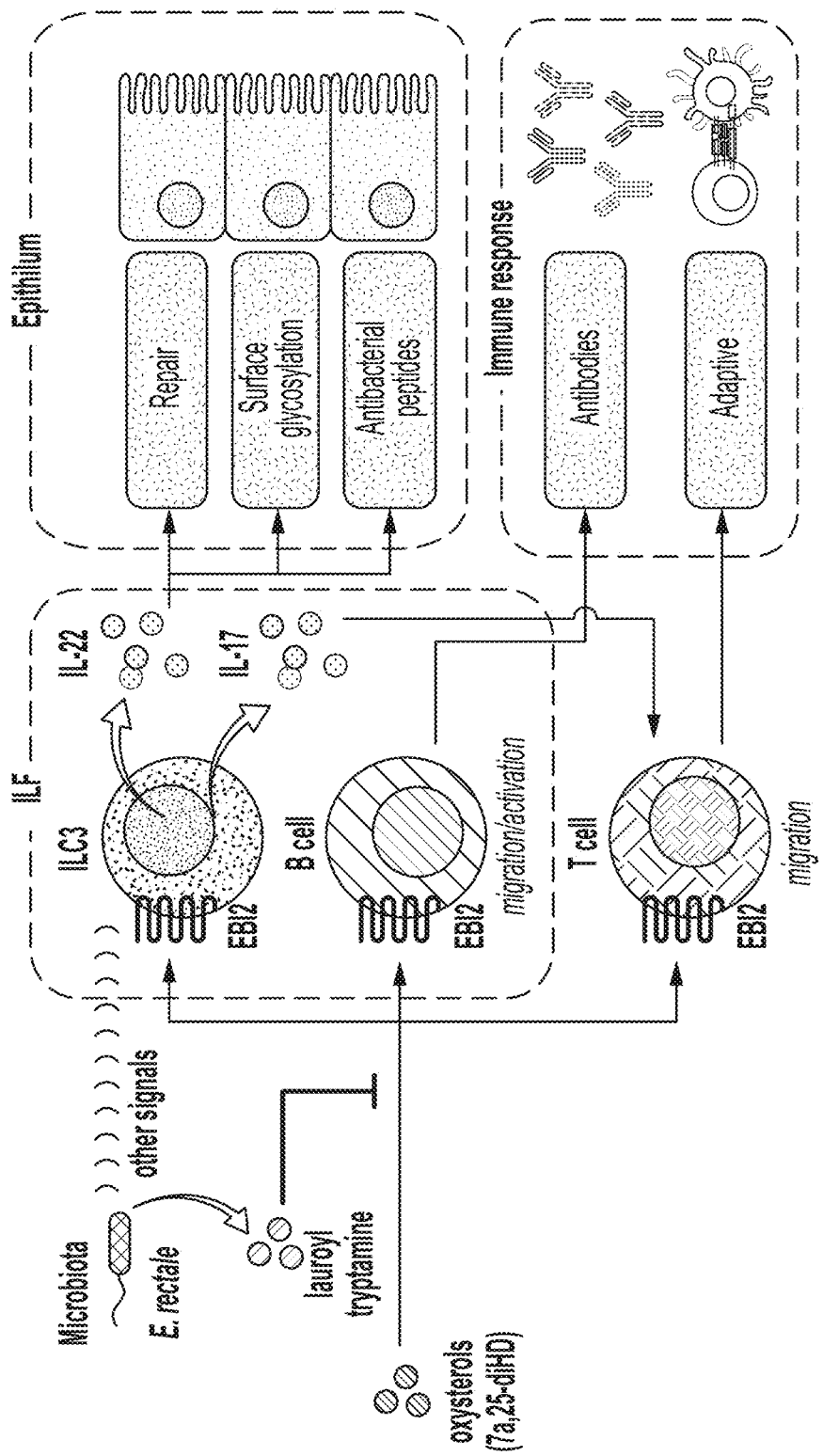
Figure 32:
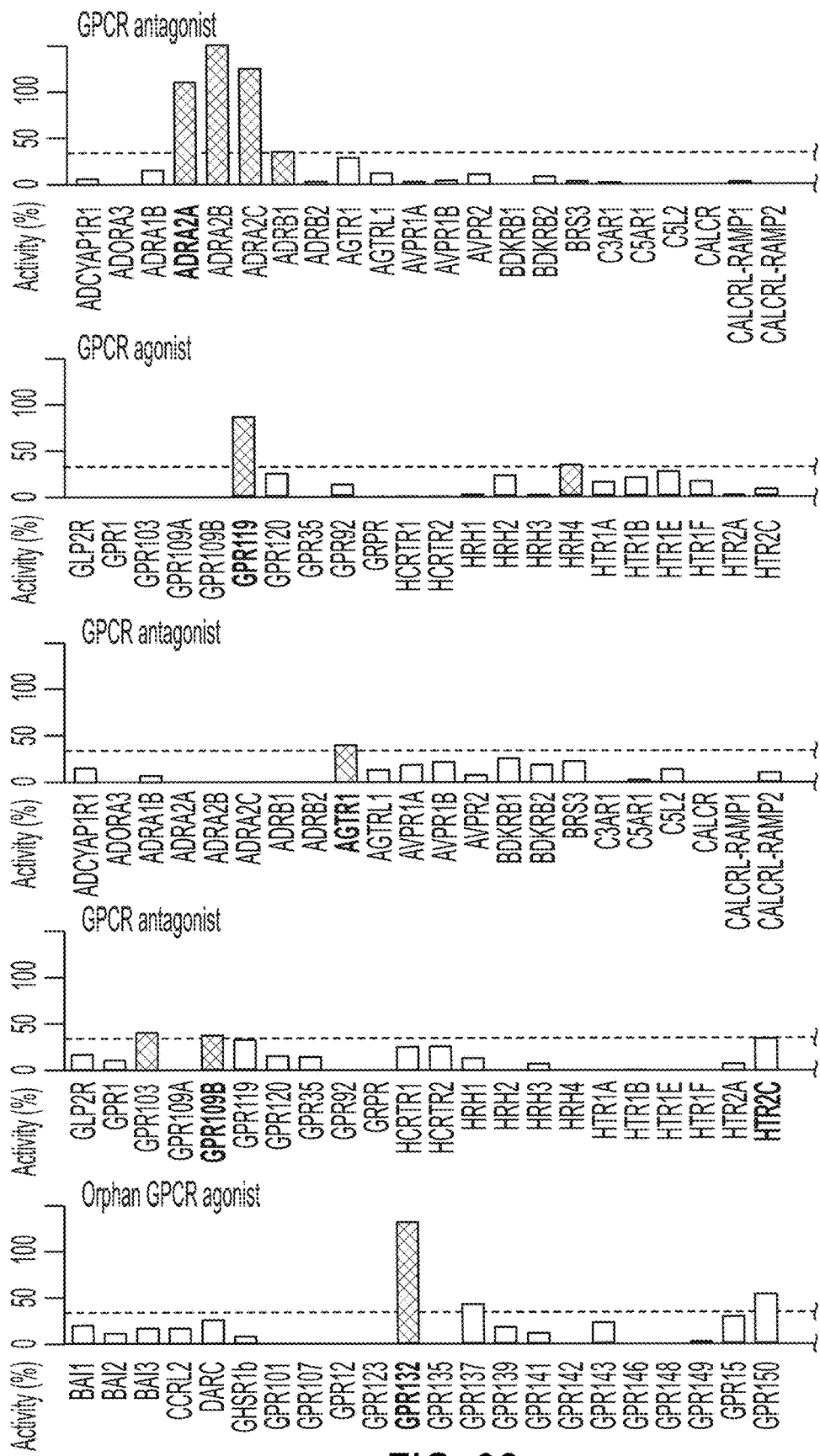
FIG. 32 shows GPCR activity assay of oleoyl dopamine. Cell-based β-arrestin reporter assay (DiscoveRx) with a panel of 168 GPCRs with known ligands in agonist mode and antagonist mode, and also 73 orphan GPCRs in agonist mode at 10 uM. Agonist mode measures % activity of target GPCR by the compound, relative to the baseline value (0% activity) and maximum value with a known ligand, or twofold increase over baseline for orphan GPCR (100% activation). Antagonist mode measures % inhibition of target GPCR by the compound in the presence of a known ligand, relative to the value at the EC80 (0% inhibition) and basal value (100% inhibition). GPCR targets with activity/inhibition higher than the empirical threshold provided by DiscoveRx (30%, 35%, or 50% for GPCR agonist, GPCR antagonist, or orphan GPCR agonist, respectively; plotted as dotted line) suggest that the interaction is potentially significant.
Figure 32:
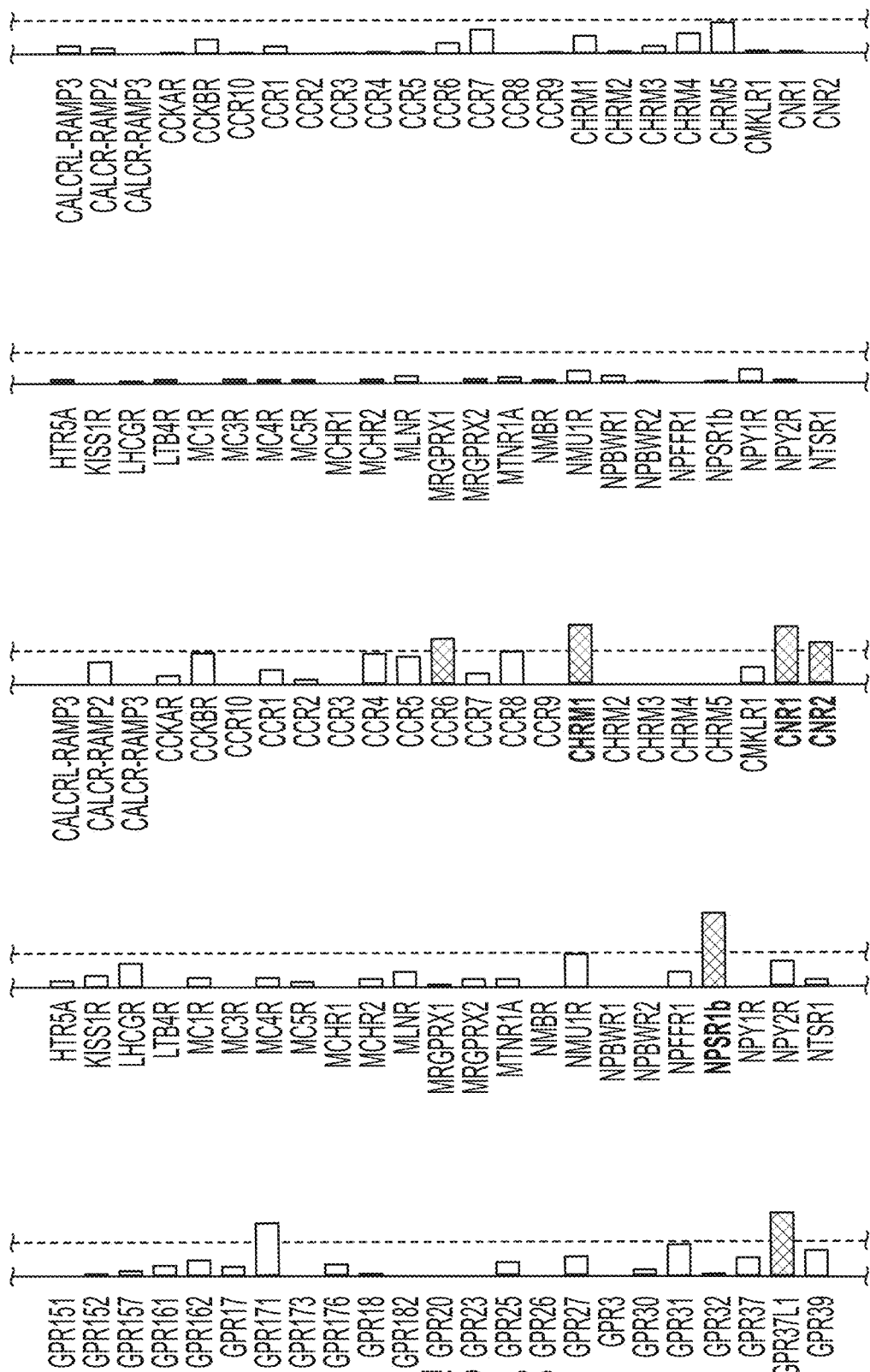
Figure 32:
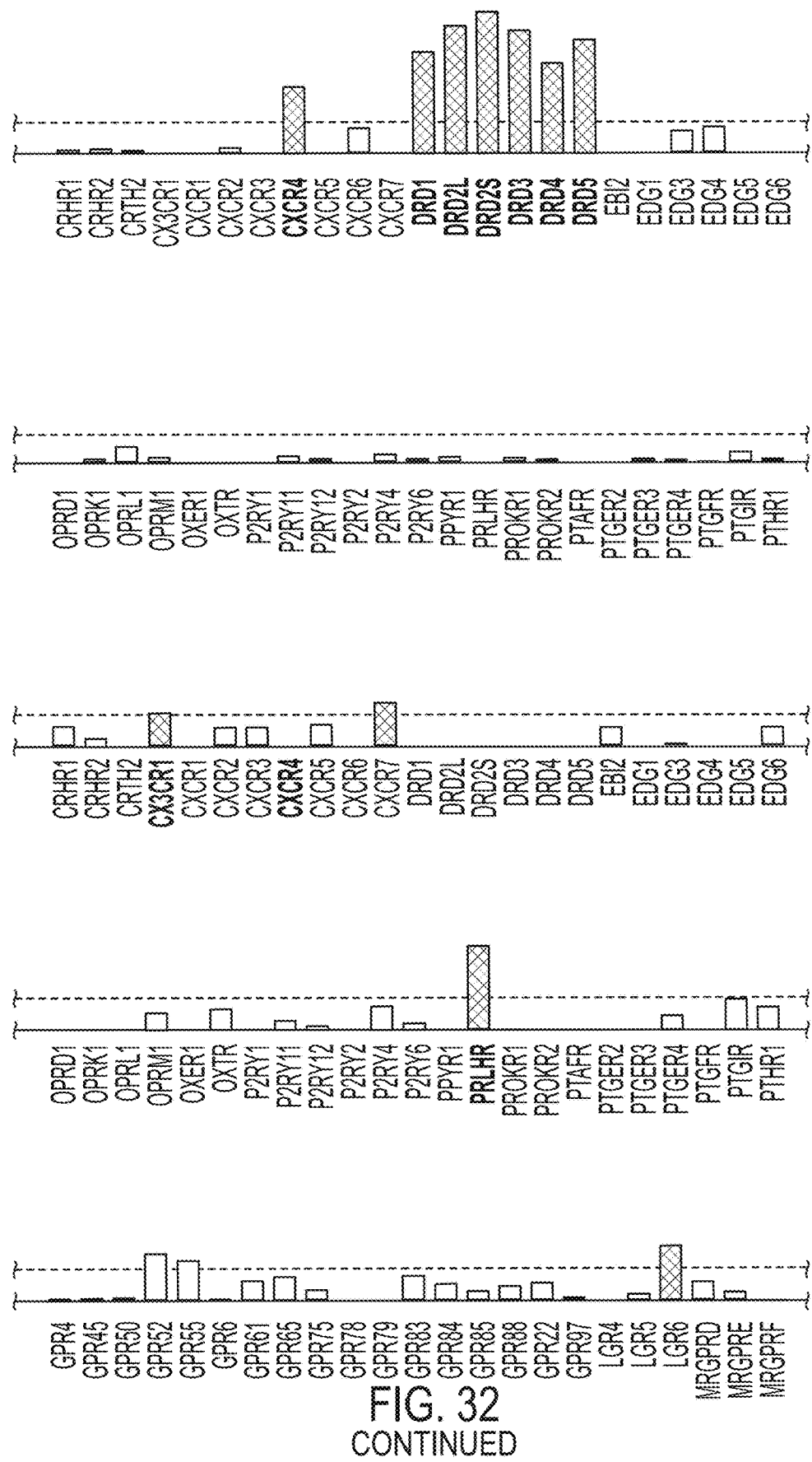
Figure 32:
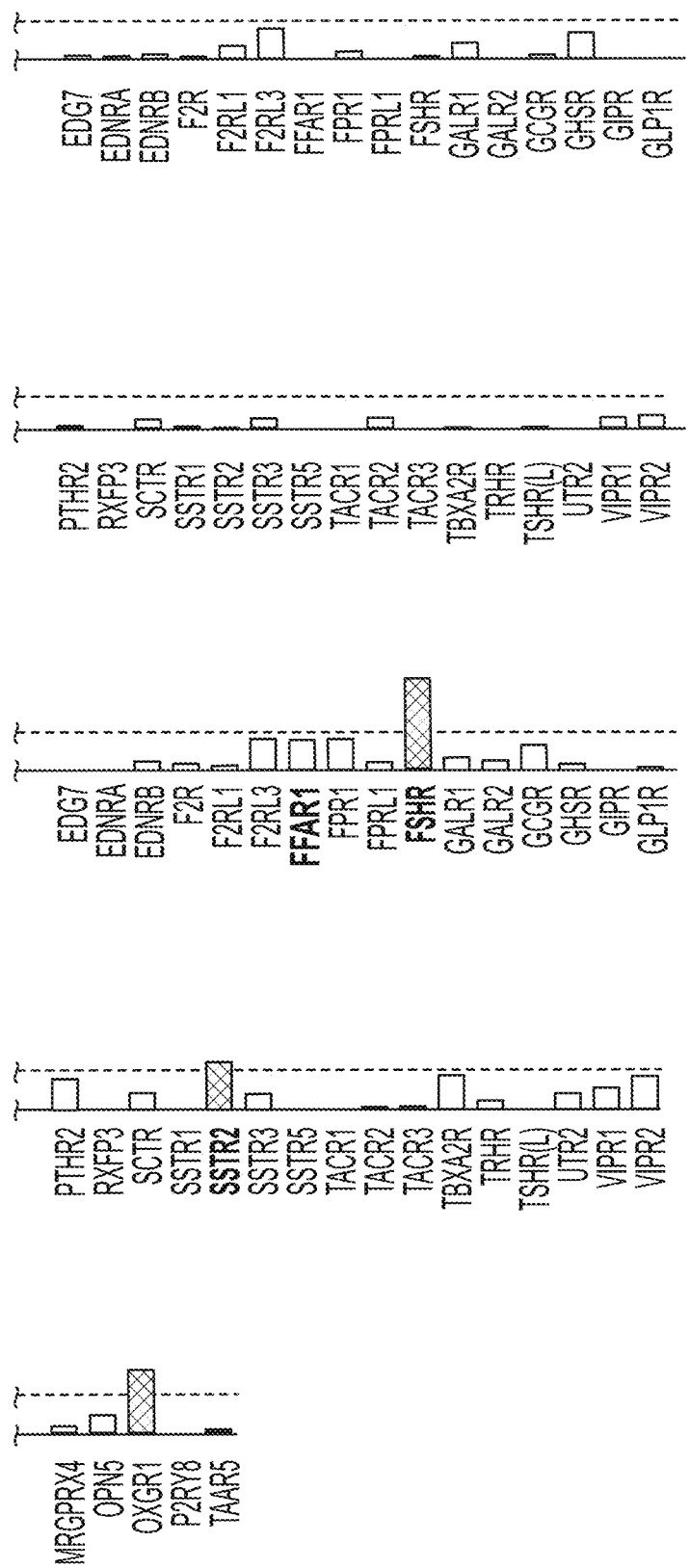
Figure 33:
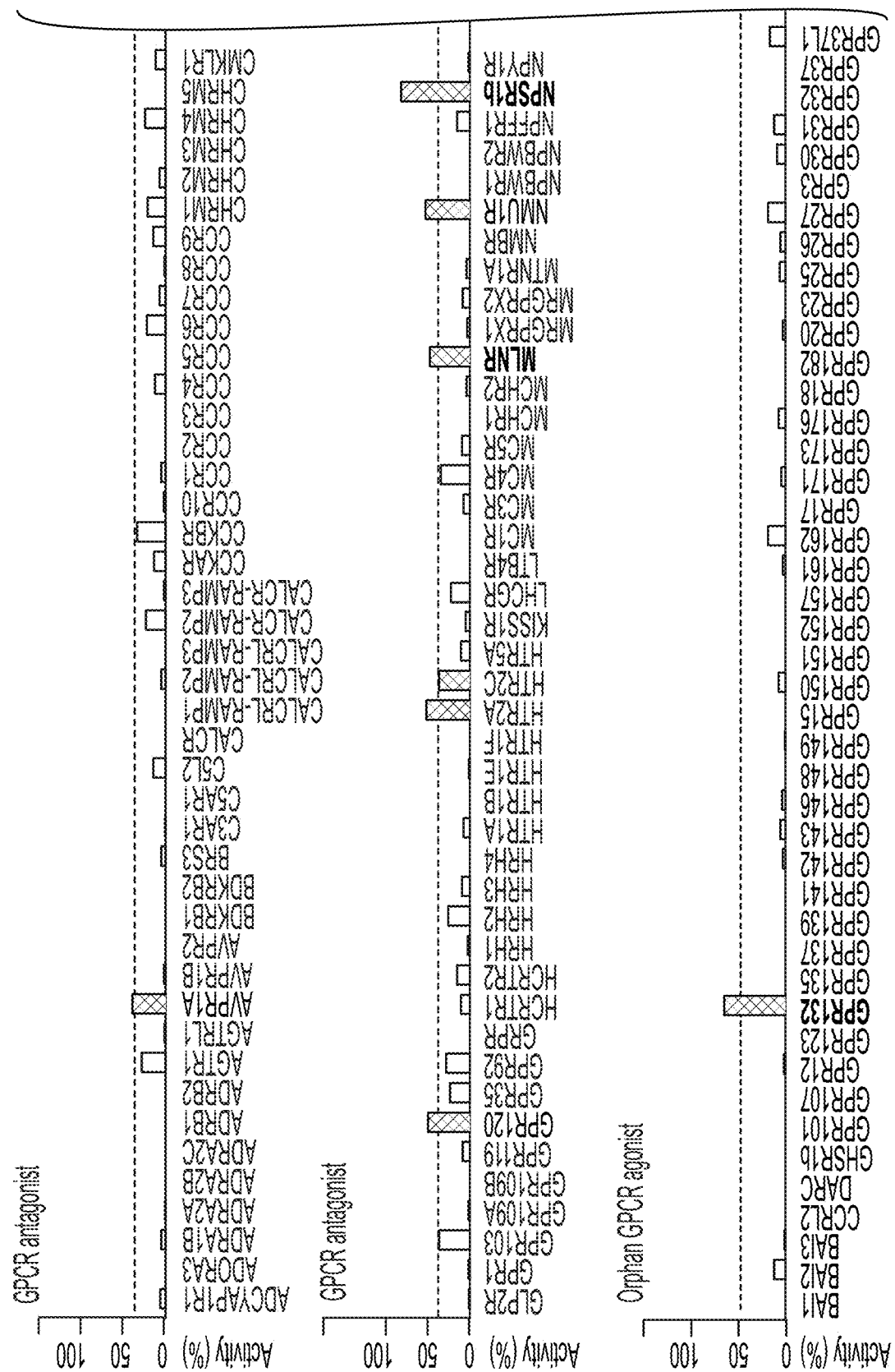
FIG. 33 shows a GPCR activity assay of oleoyl tyramine. Cell-based β-arrestin reporter assay (DiscoveRx) with a panel of 168 GPCRs with known ligands in agonist mode and antagonist mode, and also 73 orphan GPCRs in agonist mode at 10 uM. Agonist mode measures % activity of target GPCR by the compound, relative to the baseline value (0% activity) and maximum value with a known ligand, or twofold increase over baseline for orphan GPCR (100% activation). Antagonist mode measures % inhibition of target GPCR by the compound in the presence of a known ligand, relative to the value at the EC80 (0% inhibition) and basal value (100% inhibition). GPCR targets with activity/inhibition higher than the empirical threshold provided by DiscoveRx (30%, 35%, or 50% for GPCR agonist, GPCR antagonist, or orphan GPCR agonist, respectively; plotted as dotted line) suggest that the interaction is potentially significant.
Figure 33:
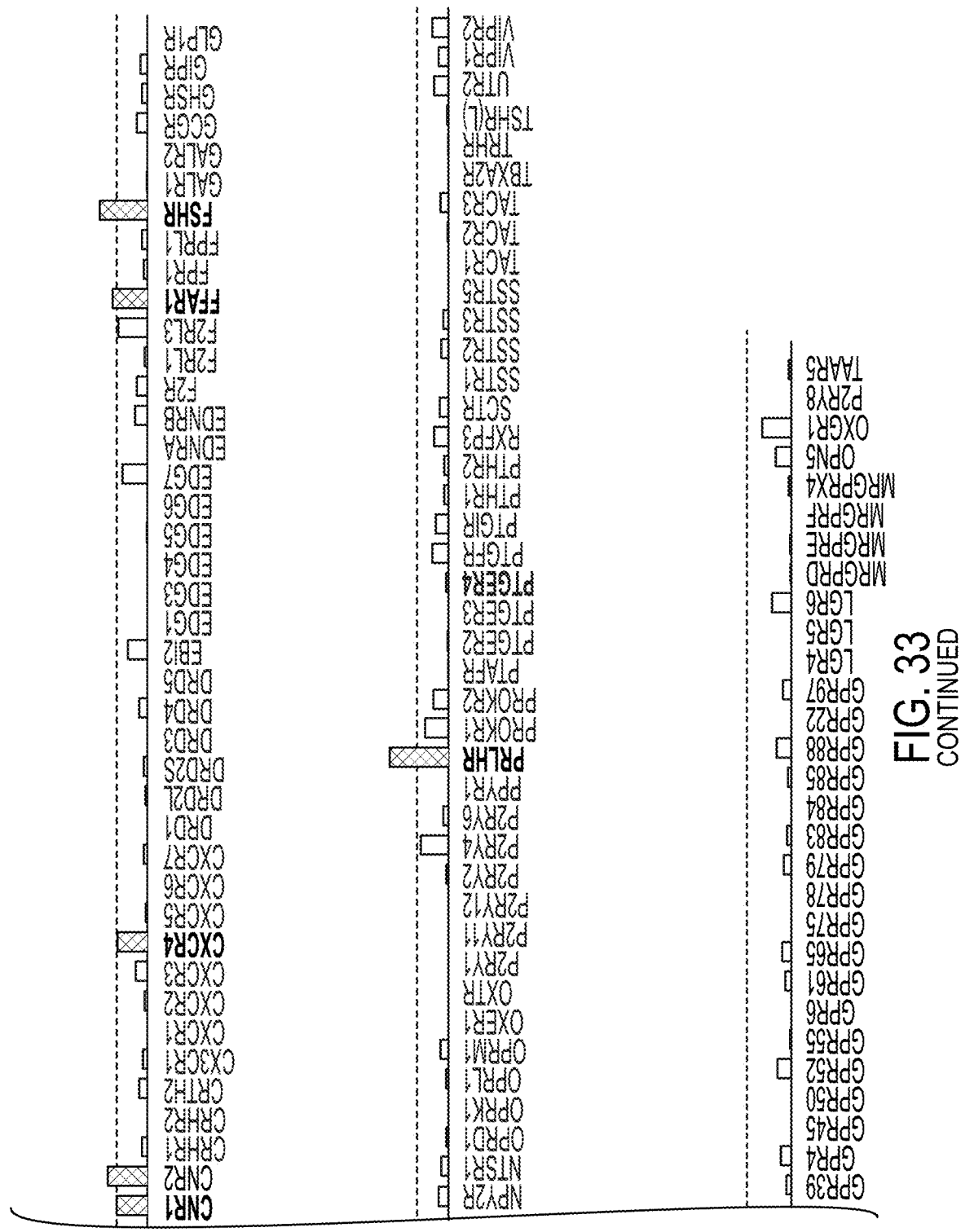
Figure 33:
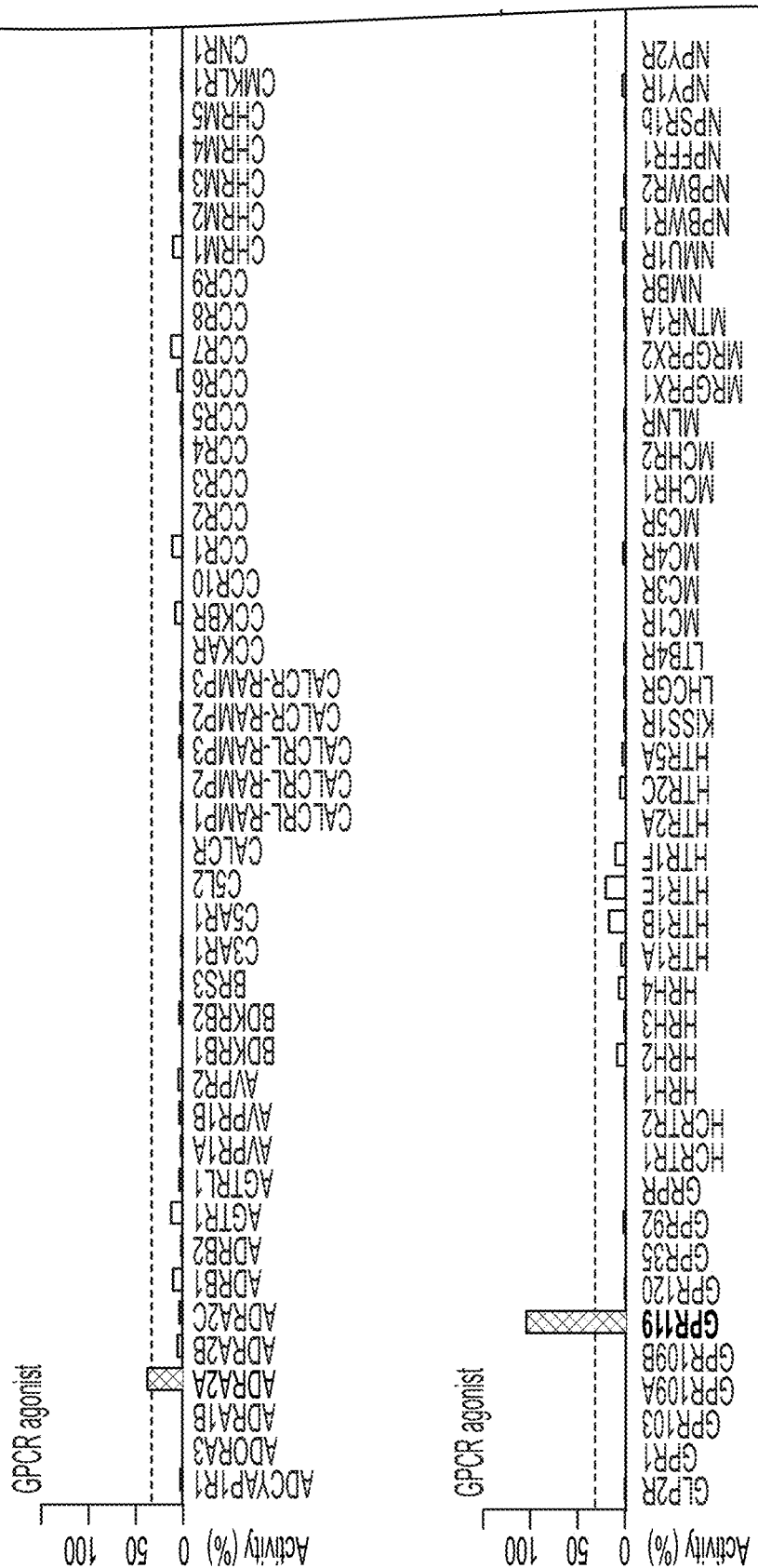
Figure 33:
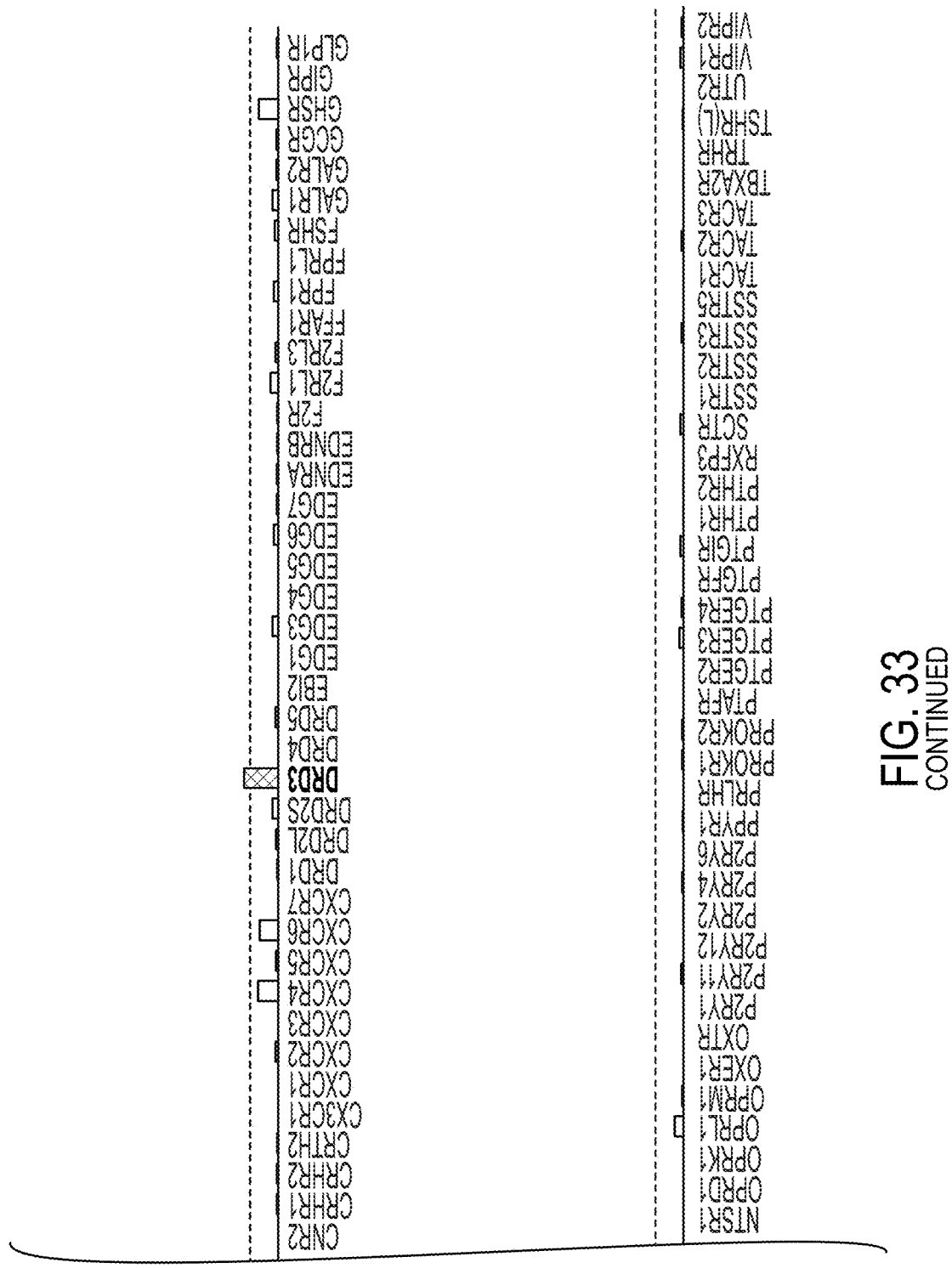
Figure 34:
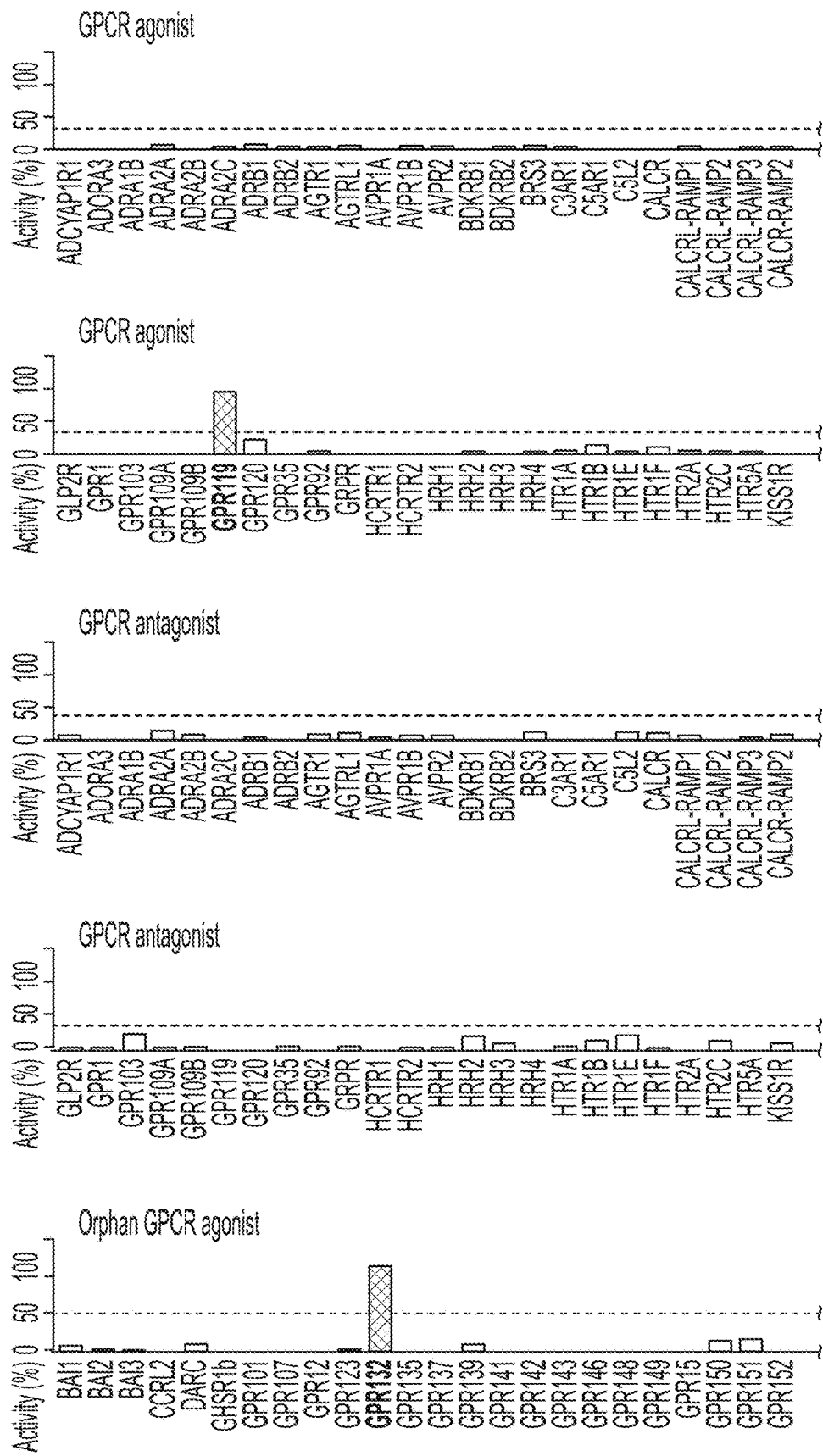
FIG. 34 shows a GPCR activity assay of oleoyl aminovaleric acid. Cell-based β-arrestin reporter assay (DiscoveRx) with a panel of 168 GPCRs with known ligands in agonist mode and antagonist mode, and also 73 orphan GPCRs in agonist mode at 10 uM. Agonist mode measures % activity of target GPCR by the compound, relative to the baseline value (0% activity) and maximum value with a known ligand, or twofold increase over baseline for orphan GPCR (100% activation). Antagonist mode measures % inhibition of target GPCR by the compound in the presence of a known ligand, relative to the value at the EC80 (0% inhibition) and basal value (100% inhibition). GPCR targets with activity/inhibition higher than the empirical threshold provided by DiscoveRx (30%, 35%, or 50% for GPCR agonist, GPCR antagonist, or orphan GPCR agonist, respectively; plotted as dotted line) suggest that the interaction is potentially significant.
Figure 34:
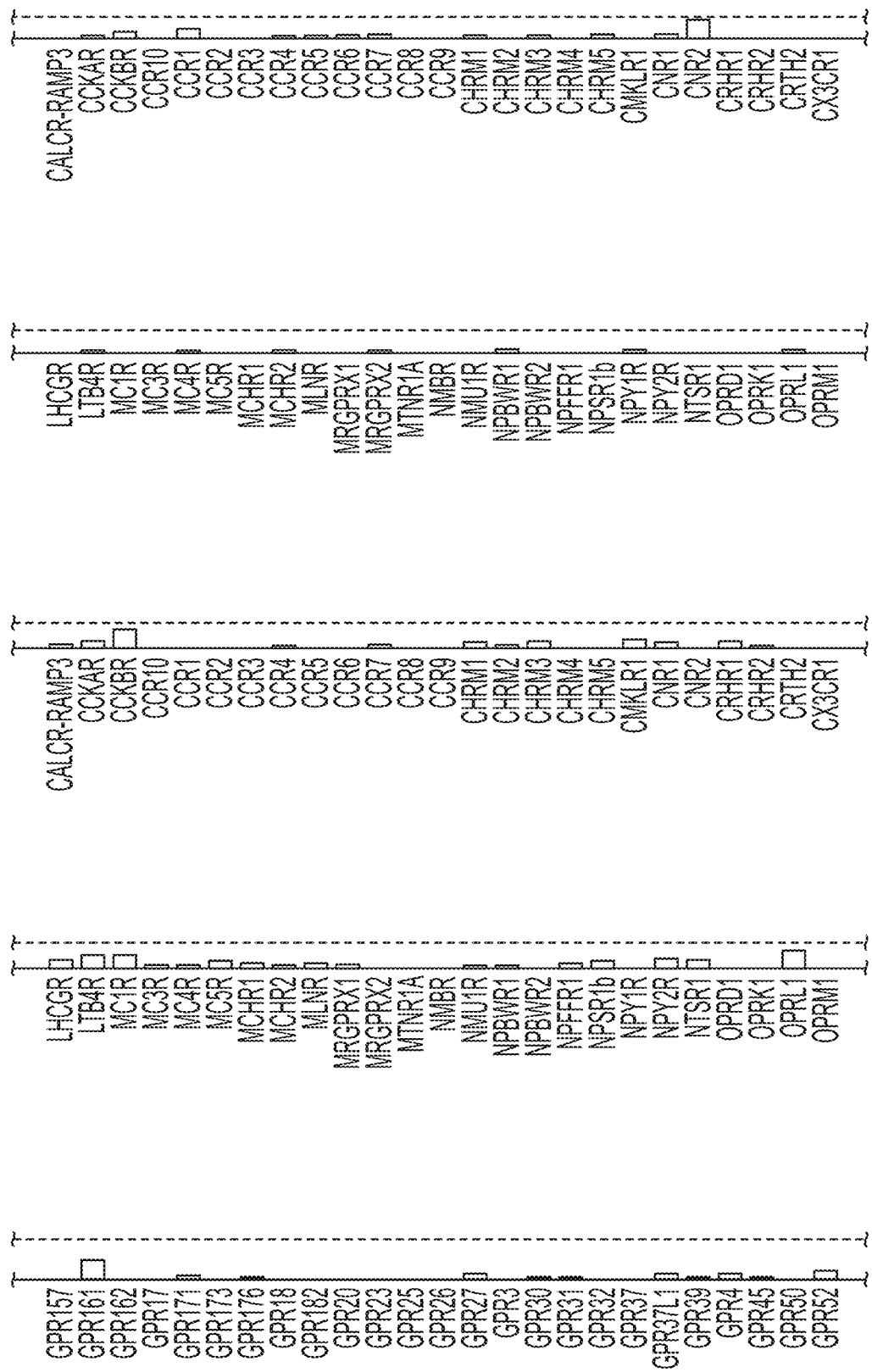
Figure 34:
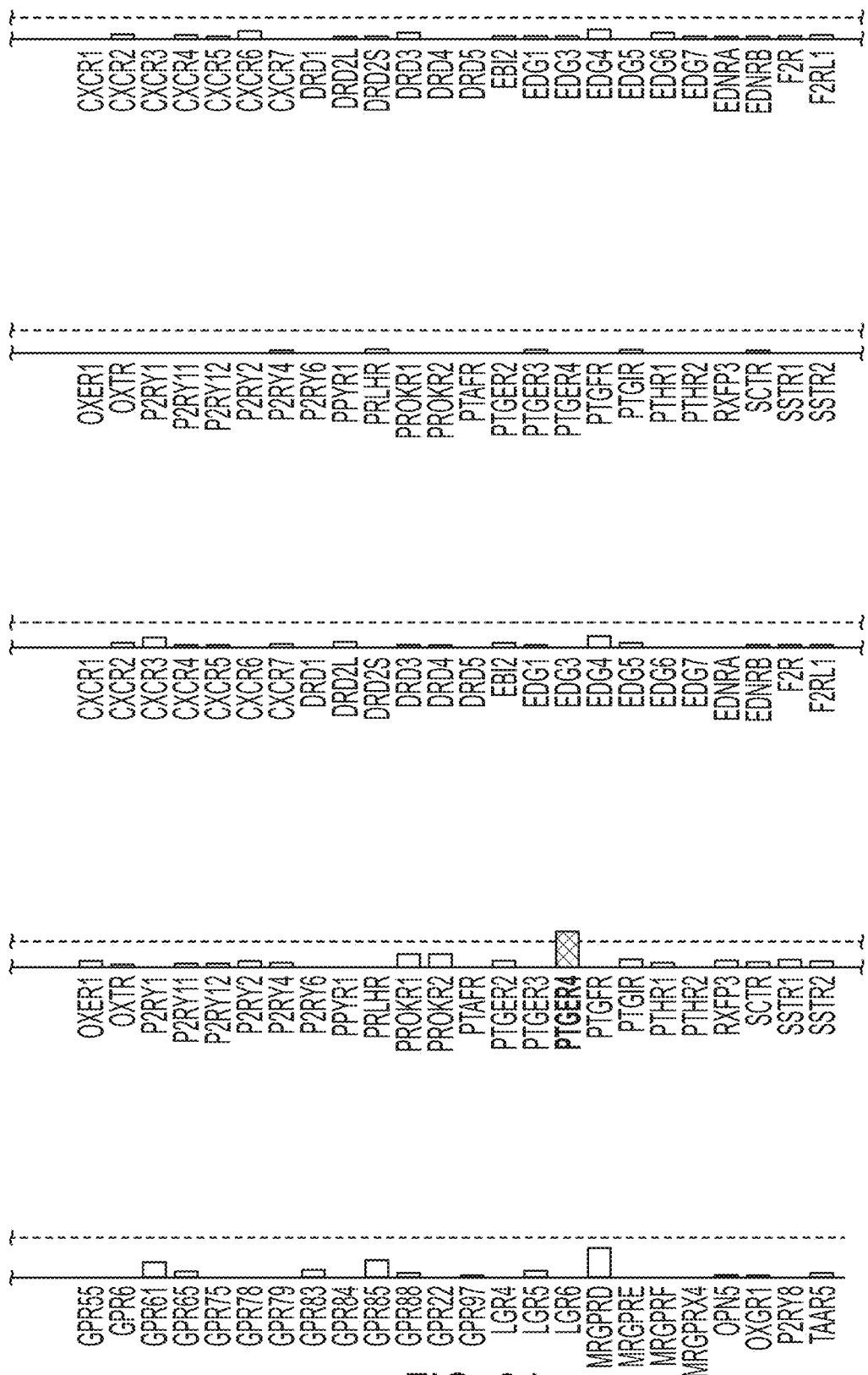

FAAs are known to modulate diverse biological functions by interacting with human GPCRs. The products of the FAA screen are either known GPCR ligands or appear to structurally mimic these molecules (FIG. 30). The FAAs were analyzed for activity against a panel of known and orphan human GPCRs using the DiscoverX platform. The major compound from the four human gut metagenome-derived pathways (oleoyl dopamine, oleoyl tyramine, oleoyl aminovaleric acid, and lauroyl tryptamine) were chemically synthesized and screened at 10 uM on a panel of 168 known GPCRs covering 60 distinct receptors in both agonist and antagonist mode and 73 orphan GPCRs in agonist mode. For the four FAAs tested, several GPCR hits were activated or inhibited at above an empirical threshold value provided by DiscoverX, indicating that the interaction is potentially significant. The results of the screen for lauryl tryptamine are shown in FIG. 31*a* and the other compounds are shown in FIGS. 32, 33, and 34.

The four Clostridia FAAs were found to interact with a subset of GPCRs, with some overlapping activities. The glucose homeostasis receptor GPR119 and orphan GPR132 were activated by all of the FAAs tested. While the activity of GPR132 is high for the FAAs tested, GPR119 activity is notably higher for the three with the oleic acid moiety. GPR119 and GPR132 agonist activity have previously been reported for known FAAs, including gut commensal-derived commendamide and oleoyl serinol[13]. This suggests that GPR119 and GPR132 are promiscuous for diverse human and bacterial FAAs.

Oleoyl dopamine was found to interact with the most GPCRs, including the previously reported receptors (CNR1, DRD2s, GPR119) and those associated with inflammatory bowel disease (IBD) and inflammation. Oleoyl tyramine differs from oleoyl dopamine by only a single hydroxyl group and it shares activity on NPSR1b and PRLHR, which have been associated with IBD and colorectal cancer. Lauroyl tryptamine was also found to activate known monoamine receptors, specifically serotonin receptors (HTRs). Specific to this compound was the inhibition of EBI2/GPR183, associated with IBD, and P2RY4. Finally, oleoyl aminovaleric acid is structurally similar to the known human FAAs, arachidonyl and oleoyl GABA. Inhibition was observed for PTGER4, associated with IBD, and has been previously reported to be a target for a gut commensal FAA, acyloxyacyl glutamine[13].

Lauroyl Tryptamine as EBI2 Inhibitor

Lauroyl tryptamine was selected to further validate its GPCR targets. The concentration-response curves were determined for the top three hits with activity/inhibition surpassing the empirical threshold: EBI2 antagonist (against 7a,25-diHC), P2RY4 antagonist (against UTP), and GPR132 agonist (FIGS. 31b, c, and d). The concentration-response curve of lauric acid and tryptamine on these GPCRs were also obtained to determine whether the effect can be achieved from the fatty acid or amine substituents alone. Titrations were performed with lauroyl tryptamine concentrations from 0.005 to 100 µM. The 50% inhibitory concentration (IC50) against EBI2 is 0.98 µM in the presence of 0.232 uM 7α,25-diHC (FIG. 31b). Neither lauric acid nor tryptamine showed inhibition on EBI2. The activity is slightly more potent than the previously reported human microbiome-derived fatty acid amide GPCR modulators, including commendamine (GPR132 agonist at 11.8 µM) and oleoyl serinol (GPR119 agonist at 7 µM)[12,13].

In contrast to EBI2, lauroyl tryptamine shows modest concentration-dependent inhibition on P2RY4 at the highest tested concentration. Although lauroyl tryptamine exhibited activity on GPR132 with EC50 of 1.45 µM, free lauric acid also showed activity on GPR132 with EC50 of 25.2 µM. Therefore, the hits against P2RY4 and GPR132 may have been false positives.

FAA Production by *Eubacterium rectale*

Figure 35:
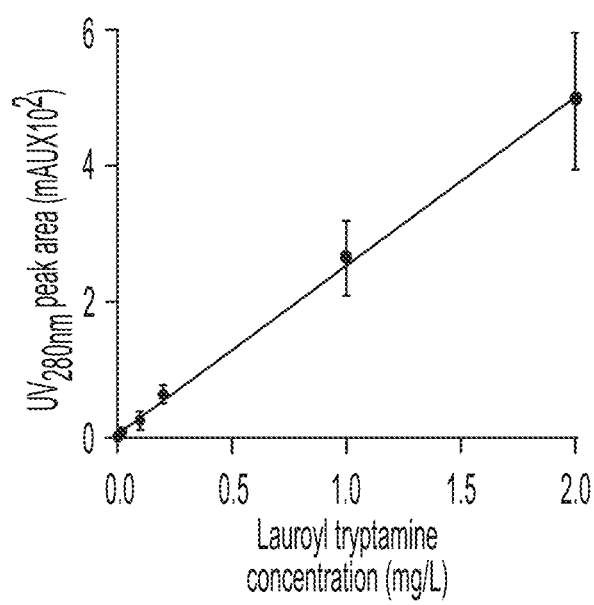
FIG. 35 shows a lauroyl tryptamine concentration standard curve. Standard curve of 280 nm absorbance (0.5 nm tolerance) peak area by injection of the chemically synthesized lauroyl tryptamine standard spanning nine concentration points in triplicates from 100 μg to 1 pg.
Figure 36:
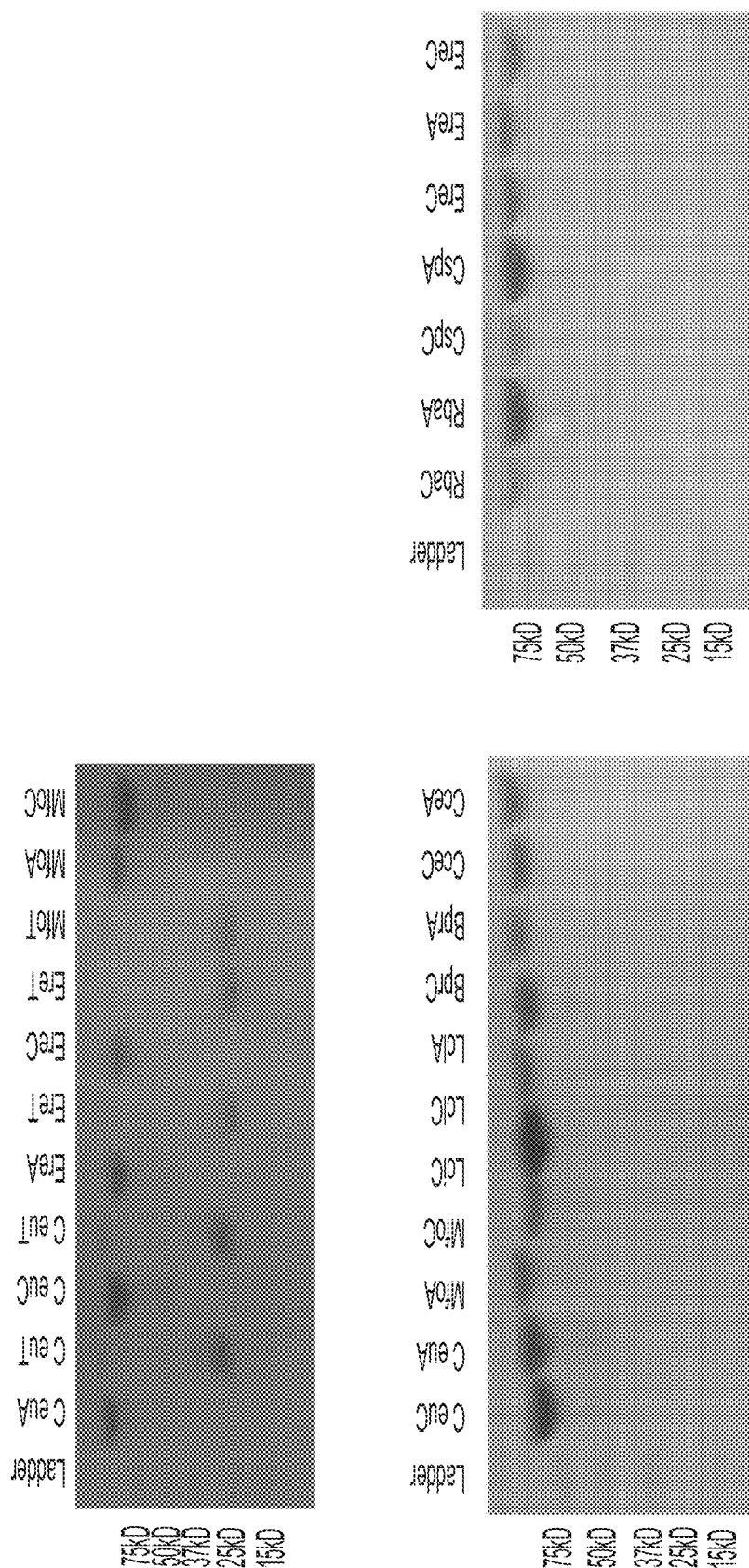
FIG. 36 shows a purified biosynthetic protein gel. Purified biosynthetic enzymes (C, T, A proteins) ran on 16% Tricine protein gel and stained with SimplyBlue SafeStain (Thermo Fisher Scientific) to check purity. Ladder=Precision Plus Protein Ladder (Bio-Rad).

Experiments were performed to determine whether the FAAs identified through the in vitro screen are produced by the gut commensal strain containing the native gene cluster. Doing so is not always possible because the pathways are obtained from metagenomic data and the original species can be unobtainable. However, two native Clostridia strains were identified in a public repository (Leibniz Institute DSMZ), *M. formatexigens* (DSM 14469) and *E. rectale* (DSM 17629), and tested these for the production of the FAAs identified in vitro. These strains were cultivated under different laboratory conditions, initially without fed substrates. LC-MS analysis of extract from *E. rectale* grown in RCM media revealed the presence of lauroyl tryptamine (titer of 0.04 mg/L), the major compound identified from the in vitro expression of the *E. rectale*-derived pathway (FIGS. 31e and 35). Although extracellular lauric acid is toxic to certain Clostridia strains, some Clostridia has been reported to endogenously produce lauric acid[66]. None of the minor compounds from the in vitro study were detected from the *E. rectale* culture extract; however, supplementation of the media with alternative substrates led to the minor products being produced (FIG. 31f). The titer increased to 0.2 mg/L when the substrates were added to the media. FAA production was not detected for *M. formatexigens* under the conditions tested.

The culture conditions may not be reflective of the environmental niche occupied by the bacteria in the human gut. Directly measuring the production of a FAA in this environment would be difficult. Instead, we analyzed published metatranscriptomic data obtained from human isolates[47]. The reads from RNA-sequencing datasets from the stool samples of eight healthy subjects were searched with the *E. rectale* pathway as the query sequence. Transcriptional reads across the FAA pathway were detected in three out of the eight human samples (subX319146421, subX311245214, subX316701492). Transcription was further analyzed for subject subX316701492 by mapping the reads to a 80 kb region of the *E. rectale* genome centered on the FAA pathway (FIG. 31g). The mean coverage of the 80 kb segment was 0.8 (SD=3.3), while the mean coverage of the FAA pathway by itself was 1.5 (SD=1.1). The pathway expression level is comparable to that of surrounding housekeeping genes (e.g. sugar biosynthesis, cell wall biogenesis), thus confirming transcription of the FAA pathway in the host.

Strains, Plasmids, and Media.

*E. coli* DH10B (C3019, New England Biolabs, Ipswich, Mass.) was used for routine cloning. *E. coli* BAP1 containing T7 DNA polymerase and Sfp phosphopantetheinyl transferase was used for heterologous expression of engineered pathways[55]. *E. coli* BL21(DE3) (CMC0016, Millipore Sigma, St. Louis, Mo.) was used for protein expression and pathway expression in the absence of Sfp. Vector pET28a (69864, Millipore Sigma) was used as backbone for all pathway and protein expression constructs (FIG. 21). LB media (L3152, Millipore Sigma) was used for routine cloning and in vivo compound production. M9 minimal media, consisting of M9 Minimal Salts (M6030, Millipore Sigma), 2 mM $MgSO_4$ (230391, Millipore Sigma), 100 uM $CaCl_2$ (97062, VWR, Radnor, Pa.), 0.4% glucose (BDH9230, VWR), was used as an alternative media for in vivo compound production. LB+1.5% agar (214010, BD, Franklin Lakes, N.J.) was used for growth on solid media. Kanamycin (K4000, Millipore Sigma) was used for selection at 30 ug/ml. IPTG (12481, Gold Biotechnology, St. Louis, Mo.) was used at final concentrations of 0.1-1.0 mM IPTG for induction of T7-driven expression. *Marvinbryantia formatexigens* DSM 14469 and *Eubacterium rectale* DSM 17629 were acquired from Leibniz Institute DSMZ (Braunschweig, Germany).

Pathway Design and Gene Synthesis.

Pathways including the biosynthetic and accessory genes were re-designed such that each gene was codon optimized for *E. coli* without Type IIS restriction sites (GeneArt CodonOptimizer, Thermo Fisher Scientific, Waltham, Mass.), placed under T7 promoter (with lacO operator) and RBS parts from pET28a, and arranged in the same direction in the order that they appear natively (FIG. 21 and Tables 1-2). The re-designed pathways were synthesized by either Thermo Fisher Scientific or Gen9 (Cambridge, Mass.) with flanking BsaI (R733, New England BioLabs) sites. The synthesized pathways, either as purified fragment or cloned in default vector, were cloned into pET28a using Golden Gate assembly and transformed into *E. coli* BAP1.

Reagents and Chemicals.

Fatty acid and amine substrates for the panel assay are summarized in Table 3. Fatty acid substrates were prepared as 50 mM stock solutions in ethanol neutralized with sodium hydroxide solution, and stored at −80° C. prior to use. Amine substrates were prepared as 50 mM stock solutions in water, and stored at −80° C. prior to use.

Computational Detection of Clostridia NRPS Pathways.

Genome datasets from the human gut were searched on the genome browser of the JGI-IMG database querying "Gastrointestinal tract" as the Sample Body Site and "Human" as a keyword. The metadata from search result was used to locate and download the sequencing data from either JGI GOLD or NCBI GenBank database. The resulting datasets were run on antiSMASH 3.0 using default parameters with ClusterFinder-based border prediction, but excluding putative pathways detected by ClusterFinder (low-confidence). The antiSMASH-detected pathways were blastn searched on the metagenomic reads of 148 fecal samples from HMP that passed QC assessment, retaining pathways that had at least two hits with e-value<1×10$^{-5}$ from the metagenomic reads spanning different stretches of the pathway. These were blastn searched, using the same cutoff filter as the previous step, on the mRNA reads from fecal samples of eight healthy subjects. The remaining pathways were run on BiG-SCAPE to generate a similarity network matrix file with a distance cutoff of 0.75 and visualized using Cytoscape[48]. For 16S rRNA-based phylogenic tree, 16S rRNA sequences of the strains were collected from NCBI database. The tree was constructed from the sequences using MacVector version 16 (Method: MUSCLE alignment, Neighbor Joining Method, Distance: Uncorrected, Best Tree Mode).

MetaQuery Search.

For analyzing prevalence, the condensation domain protein sequence for each of the pathways was used as the query for MetaQuery search with default parameters, except with a minimum percent identity of 98[51].

Pathway Homology Search.

E. rectale condensation protein (NCBI: WP_015516887) and adenylation protein (NCBI: WP_015516889) were each used as a query for blastp search with default parameters. Upon removing hits that were different in protein size (>800 or <200 amino acids) from the top 1,000 hits, the hit table from each was cross-examined using Python script for their co-occurrence in the same pathway based on proximity in NCBI accession number.

Biosynthetic Enzyme Homology Search.

The E. rectale biosynthetic protein sequences EreC and EreA were individually blastp searched on UniProt (EMBL-EBI, United Kingdom) using default parameters and "UniProtKB/Swiss-Prot" of characterized proteins as the target database.

Heterologous Expression of Clusters in E. coli.

To test for in vivo compound production under a comprehensive set of fermentation conditions, a total of 24 cultures were set up that each make up the possible combinations of the following four parameters: timing of IPTG induction, IPTG concentration, culture media, and pathway expression temperature. Overnight cultures of pathway-harboring E. coli in LB broth at 230 rpm and 37° C. (MS012NF, Multitron Standard, INFORS HT, Bottmingen, Switzerland) were diluted 200-fold the next morning to 4 mL fresh LB media in partially unscrewed 50 mL Conical tube (352098, Thermo Fisher Scientific). Upon growth to one of three IPTG induction times (corresponding to $OD_{600}$=0.2, 0.5, and 0.8, respectively), the culture was pelleted at 4,000 g and 4° C. for 3 min (75004537, Multifuge X3 FR, Thermo Fisher Scientific). The pellet was resuspended in 4 mL of one of two fresh culture media (LB or M9) at one of two IPTG concentrations (0.2 or 0.5 mM) for induction. The culture was grown with shaking (230 rpm) at one of two temperatures (25 or 30° C.). To monitor compound production over time, 1 mL sample was removed from each of 24 cultures after three different timepoints (8, 16, or 40 hr). Each sample was immediately extracted with 1 mL of methanol (BJLC230, VWR), mixed with the vortexer at maximum speed for 30 sec (SI-0236, Vortex-Genie 2, Scientific Industries, Bohemia, N.Y.), and pelleted at 20,000 g at room temperature for 1 min (022620401, Centrifuge 5424, Eppendorf, Hamburg, Germany). A 100 uL aliquot of the supernatant was injected for analytical LC-MS run (below). Clone-specific compound production was identified by visual inspection of clone-specific peaks in the chromatograph of electrospray ionization (ESI)+ total ion current (TIC), ESI-TIC, and diode array detector (DAD) total wavelength using software ChemStation (version 1.9, Agilent) and MestReNova (version 10, Mestrelab Research, Compostela, Spain).

For side-by-side compound production comparison of E. rectale pathway with gene-knockout variants or with fed substrate, each LCMS analytical sample was prepared following the same protocol, but only with a single fermentation condition and at a single extraction time point. In brief, the freshly inoculated 4 mL culture from overnight was grown to $OD_{600}$=0.8. The pelleted culture was resuspended in fresh LB containing 0.2 mM IPTG. For substrate feeding assay, the IPTG-containing LB also included 5 mM octanoic acid (neutralized with sodium hydroxide) or tryptamine. The culture was grown with shaking at 25° C. and extracted after 16 hr. The presence of expected product (i.e. palmitoleoyl putrescine, octanoyl putrescine, palmitoleoyl tryptamine) was identified by inspection of a clone-specific peak in the ESI+ extracted ion chromatograph (EIC) corresponding to the mass-to-charge ratio (m/z, 0.3 Da tolerance) of the protonated ion.

Analytical LC-MS.

Analytical LCMS was conducted using an Agilent (Agilent, Santa Clara, Calif.) 1260 Infinity system with 6130 quadrupole MS, binary pump (G1312B), and DAD (G1315D). The sample was run on a C18 reverse phase column [Luna 5 um C18(2), 100×4.6 mm] (00D-4252-E0, Phenomenex, Torrance, Calif.) with 1.0 mL/min flow rate and a gradient system of 90%:10% to 0%:100% water (WX0001, Millipore Sigma): acetonitrile (BJLC015, VWR) with 0.1% formic acid (5330020050, Millipore Sigma) for 15 min, followed by 2 min isocratic run at 100% acetonitrile (wash) and then 3 min at 90%:10% water:acetonitrile (re-equilibration).

E. coli In Vivo Compound Characterization.

Large-scale fermentation of pathway-harboring E. coli (16 L) was conducted. Overnight culture was diluted 200-fold to 1 L fresh LB in 4 L Erlenmeyer flasks (10545-845, VWR), and grown at 200 rpm and 30° C. (Multitron Standard). At $OD_{600}$ of around 0.4, the temperature was lowered to 25° C. The culture at $OD_{600}$=0.8 and 25° C. was then added with IPTG at a final concentration of 0.2 mM and grown with shaking at 25° C. for 16 hr. The 16 L culture was extracted with equal volume of ethyl acetate (JT9282, VWR), 1 L at a time in separatory funnel (4301-2000, Thermo Fisher Scientific). The organic layer was concentrated in vacuo using rotary evaporator (11100C2102, Rotavapor R-100, Buchi, Flawil, Switzerland), transferred to glass vial (66030-678, VWR), and dried using SpeedVac concentrator (SPD2010-230, Savant SpeedVac, Thermo Fisher Scientific). Preparatory LCMS was conducted using an Agilent (Agilent, Santa Clara, Calif.) 1260 Infinity system with quaternary pump (G1311B), DAD (G1315D), and fraction collector (G1364B). The extract resuspended in 5 mL acetonitrile was run on preparatory C18 reverse phase column [Luna 5 um C18(2), 250×21.2 mm] (00G-4252-P0-AX, Phenomenex) and a gradient system of 90%:10% to 0%:100% water:acetonitrile with 0.1% acetic acid (A11350, Thermo Fisher Scientific) in 20 min at 10 mL/min. Major compound eluted with the 20%:80% water:acetonitrile fractions, which were pooled and dried in vacuo. Upon resuspension in 2 mL acetonitrile, the compound was then purified over the course of ten injections (200 uL at a time) on a semi-prep C18 column [Luna 5 um C18(2), 250×10 mm] (00G-4252-N0, Phenomenex) and a gradient system of 70%:30% to 0%:100% water:methanol with 0.1% acetic acid in 30 min at 5 mL/min. The major compound eluted in the 45%:65% water:methanol fraction as a white powder (0.1 mg). HRMS acquired on 6530 Q-TOF (Agilent) and 1-D and 2-D NMR spectra in chloroform-d (151823, Millipore Sigma) collected on Avance II 600 (Bruker, Billerica, Mass.) were used to determine chemical structure (FIG. 5). The compound identity was further confirmed by having a standard chemically synthesized by KareBay Biochem (Monmouth Junction, N.J.) and was found to be spectroscopically identical.

Protein Expression and Purification.

The individual genes were cloned into the pET28a plasmid system shown in FIG. 21 and Tables 1-2. The plasmids were transformed into *E. coli* BL21(DE3). Overnight *E. coli* cultures containing the plasmids were diluted 200-fold to 1 L fresh LB in 4 L Erlenmeyber flask (10545-845, VWR) and grown at 200 rpm and 25° C. (Multitron Standard). At $OD_{600}$=0.35, the temperature was lowered to 16° C. The culture at $OD_{600}$=0.5 and 16° C. was then added with IPTG at a final concentration of 0.5 mM and grown with shaking at 16° C. for 18 hr. The culture was transferred to centrifuge bottles (75007300, Thermo Fisher Scientific) and pelleted at 4,000 g and 4° C. for 20 min (75004537, Multifuge X3 FR, Thermo Fisher Scientific). As a wash step, the pellet was resuspended in 200 mL Lysis Buffer, consisting of 200 mM NaCl (AB01915, American Bioanalytical, Canton, Mass.), 10 mM imidazole (15513, Millipore Sigma), 50 mM Tris (AB02000, American Bioanalytical) pH 8.0, and EDTA-free protease inhibitor cocktail (5056489001, Millipore Sigma). Upon pelleting again at 4,000 g 4° C. for 20 min, it was resuspended in 10 mL Lysis Buffer, transferred to 50 mL Conical tube (352098, Thermo Fisher Scientific), and lysed using a sonicator (Q125, Qsonica, Newtown Conn.) with 1/8" stepped microtip probe (4422, Qsonica) at 45% amplitude for 5 min continuously on ice.

Upon centrifuging the lysed cells at 14,000 g for 20 min (75004520, Sorvall Legend XTR Thermo Fisher Scientific), the supernatent was transferred to a new 50 mL Conical tube, mixed with 1 mL of pre-equilibrated Ni-NTA resin (88221, Thermo Fisher Scientific), and rotated using Tube Rotator at 20 rpm and 4° C. for 16 hr (1205R81, Scilogex, Rocky Kill, Conn.). The bead slurry was spun down at 1,000 g and 4° C. for 1 min (Multifuge X3 FR), and resuspended in 10 mL Wash Buffer, containing 200 mM NaCl, 20 mM Imidazole, and 50 mM Tris, pH 8.0. Upon transferring to a new 15 mL Conical tube (352097, Millipore Sigma), the bead slurry was washed twice with 10 mL Wash Buffer by spinning down at 1,000 g and 4° C. for 1 min. The bead slurry was then resuspended in 2 mL Wash Buffer, transferred to new 2 mL microcentrifuge tubes (022600044, Eppendorf), and spun down at 5000 g and 4° C. for 1 min (Centrifuge 5424R, Eppendorf). The bead slurry was added with 2 mL of Elution Buffer, consisting of 200 mM NaCl, 250 mM imidazole, and 50 mM Tris, ph 8.0, and spun down at 20,000 g and 4° C. for 1 min. The supernatant containing the purified protein was dialyzed using Slide-A-Lyzer, 3.5K MWCO (δ6333, Thermo Fisher), in 500 uL aliquot per cassette. Each cassette was submerged at 4° C. for 6 hr in 14 mL of Dialysis Buffer, consisting of 50 mM NaCl, 1 mM TCEP (TCEP, Gold Biotechnology), and 10% glycerol (AB00751, American Bioanalytical). The buffer was discarded, changed to a fresh Dialysis Buffer, and left at 4° C. for another 16 hr. The dialyzed protein sample was pooled from the cassettes, distributed in 20 uL aliquots for single freeze-cycle use, and frozen for storage at −20° C. Protein purity was confirmed by the presence of a single band corresponding to the expected size on Novex 16% Tricine protein gel (EC66952BOX, Thermo Fisher) in Tricine running buffer (LC1675, Thermo Scientific) stained with SimplyBlue SafeStain (LC6060, Thermo Fisher) alongside with Precision Plus Protein ladder (1610374, Bio-Rad Laboratories, Hercules, Calif.) (Supplementary FIG. 20). The protein sample was quantified by Bradford Assay following manufacturer protocol using Coomassie Plus (23236, Thermo Fisher). In brief, protein standards were prepared with bovine serine albumin at concentrations of 0; 25; 125; 250; 500; 750; 1,000; 1,500; 2,000 ug/mL. A 3.3 uL sample of each standard or protein sample (in triplicates) was pipetted into microplate wells (CLS3894, Millipore), added with 100 uL of the Coomassie reagent, and mixed in plate shaker at 900 rpm for 30 sec (I10103P, Multitron Pro, INFORS HT). After incubation at room temperature for 10 min, the plate was spun down at 4,000 g for 1 min (Multifuge X3 FR) to remove particulates. Upon transferring the supernatant into half-area microplate wells (CLS3679, Millipore Sigma), absorbance of each well at 595 nm was read using Synergy H1 Microplate Spectrophotometer (8041000, BioTek, Winooski, Vt.). The mean of the triplicate absorbance of the samples/standards was subtracted by the mean triplicate absorbance of blank water. The mean value of BSA standards was plotted using Prism (version 7, GraphPad, San Diego, Calif.) to prepare a standard curve and used to determine protein concentration from mean absorbance value. The exception to the above purification strategy was for the condensation protein from *C. eutactus*, where a presence of stronger and broader Coomassie band was detected on the protein gel at >250 kDa, suggesting aggregation. The pCeuC construct was thus sent to ABclonal Technology (Woburn, Mass.) for custom protein expression, purification, and quantification.

ATP Consumption (PPi) Assay.

The EnzChek Pyrophospate Assay Kit (E6646, Thermo Fisher) was used for pyrophosphate detection to measure adenylation activity. A pair of 100 μL in vitro reaction samples were prepared, one with *E. rectale* adenylation and thiolation proteins (no condensation) and the other with thiolation protein only, each protein at 1 μM final concentration. The protein(s) were added with query substrate at 1 mM final concentration (palmitoleic acid, palmitic acid, putrescine, ornithine, arginine, agmatine, cadaverine, or lysine) in an in vitro reaction mix, consisting of 100 mM Tris, 10 mM $MgCl_2$ (JT2448, VWR), 1 mM TCEP, 0.1 uM Sfp Synthase (P9302, New England Biolabs), 0.1 mM Coenzyme A (951-50, Lee Biosolutions, Maryland Heights, Mo.), and 5 mM ATP (A-081, Gold Biotechnology). After 60 min incubation at 23° C., 10 uL of each reaction sample was mixed with kit solution containing 0.2 mM MESG dye, 1 U $mL^{-1}$ purine nucleoside phosphorylase, 0.03 U $mL^{-1}$ inorganic pyrophosphatase, and 1× reaction buffer in 100 μL total volume. Upon transferring into microplate wells (CLS3894, Millipore Sigma), the sample was mixed in plate shaker at 900 rpm for 30 sec (I10103P, Multitron Pro, INFORS HT). After incubation at room temperature for 60 min, the plate was spun down at 4,000 g for 1 min (Multifuge X3 FR) to remove particulates. Upon transferring the supernatant into half-area microplate wells (CLS3679, Millipore Sigma), absorbance of each well at 360 nm was read using Synergy H1 Microplate Spectrophotometer (8041000, BioTek, Winooski, Vt.). Absorbance from each sample was subtracted by the mean triplicate absorbance of blank water. The absorbance from reaction with adenylation and thiolation proteins was normalized to thiolation protein only control. The data was taken in triplicate per day, and the average of the mean triplicate normalized absorbance conducted on three different days was reported.

LC-MS Detection of T Protein Intermediate Peptide.

A pair of 1000 μL in vitro reaction samples were prepared with 1 μM final concentration of the *E. rectale* adenylation protein, 1 μM of the thiolation protein, and 1 mM lauric acid in an in vitro reaction mix consisting of 100 mM Tris, 10 mM $MgCl_2$, 1 mM TCEP, 0.1 uM Sfp, and 0.1 mM Coenzyme A. ATP at 5 mM final concentration was added to only one of the sample. After 60 min incubation at 23° C., the proteins in the reaction mixtures were denatured and digested with trypsin (V511A, Promega, Madison, Wis.) following manufacturer's protocol, but at pH 7.0 to prevent base-catalyzed hydrolysis of the thiotemplated substrate. In brief, the mixtures were incubated at 90° C. for 20 min in 6M guanidine HCL (G3272, Sigma-Aldrich) and IM DTT (D9779, Sigma-Aldrich) in Tris-HCl (50 mM pH 7.0) before cooling to room temperature. Upon 6-fold dilution of the solution with Tris-HCl (50 mM pH 7.0) and $CaCl_2$ (1 mM) down to 0.96 M of guanidine HCl, the protein solutions were added with trypsin to a final protease:protein ratio of 1:50 (w/w) for 24 hr at 37° C. The resulting mixtures were cleaned using a C-18 Sep-Pak column (WAT0519, Waters, Milford, Mass.). For peptide analysis, the samples were injected on Agilent 6530 qTOF MS in ESI+ mode coupled to Agilent 1290 Infinity UHPLC system. The samples were run on AdvanceBio Peptide Mapping column [C18, 2.7 um, 120 Å, 150×2.1 mm] (δ53750-902, Agilent) with a 0.2 mL/min flow rate and a gradient system of 97%:3% to 35%:65% water:acetonitrile with 0.1% formic acid for 75 min. Sequences for peptides were identified using Agilent MassHunter BioConfirm (version 8) with a mass tolerance of 0.25 Da, MS and $MS^E$ mass match tolerance of 30.0 ppm and trypsin digest with 0 missed cleavages.

MS-Based Measurement for Condensation Activity.

A pair of 100 μL in vitro reaction samples were prepared, one with *E. rectale* condensation, adenylation, and thiolation proteins and the other with adenylation and thiolation proteins only, each protein at 1 μM final concentration. The proteins were added with query amine at 1 mM final concentration (putrescine, ornithine, phenylalanine, tryptophan, tyrosine, phenylethylamine, tryptamine, or tyramine) and 1 mM of fatty acid (palmitoleic acid) in an in vitro reaction mix (above). After 90 min incubation at 23° C., each sample was extracted with 1 mL of methanol, mixed with the vortexter at maximum speed for 30 sec (SI-0236, Vortex-Genie 2), pelleted at 20,000 g and room temperature for 1 min. A 100 ul of the supernatant was injected for analytical LC-MS run (above). Using MestReNova (version 10), the presence of FAA product was identified by inspection of a clone-specific peak in the ESI+ and ESI-extracted ion chromatograph (EIC) corresponding to the mass-to-charge ratio (m/z, 0.3 Da tolerance) of the protonated or deprotonated ion. Automated trace baseline correction, peak detection, and peak integration were applied by MestReNova. The peak area (ESI+ or ESI− depending on the amine substrate) from reaction with condensation, adenylation and thiolation proteins was normalized to adenylation and thiolation proteins only control. The data was taken in triplicate per day, and the average of the mean triplicate normalized peak area conducted on three different days was reported.

Substrate Panel Assay.

Figure 25D:
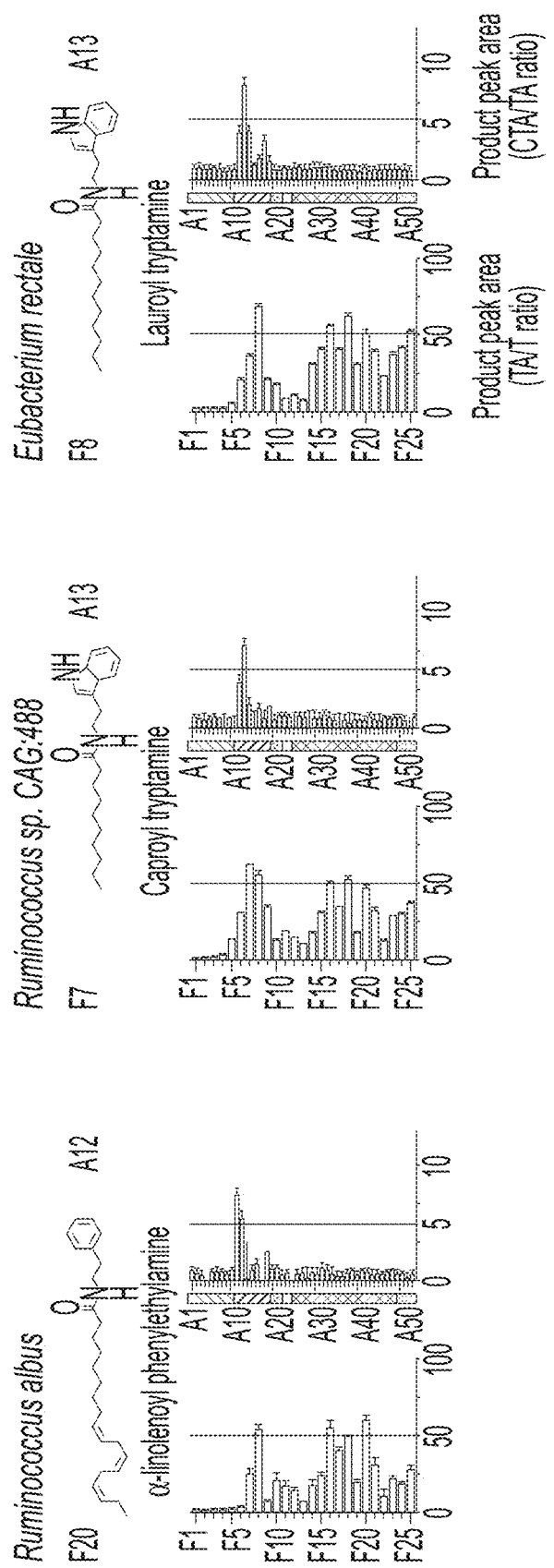
Figure 28A:
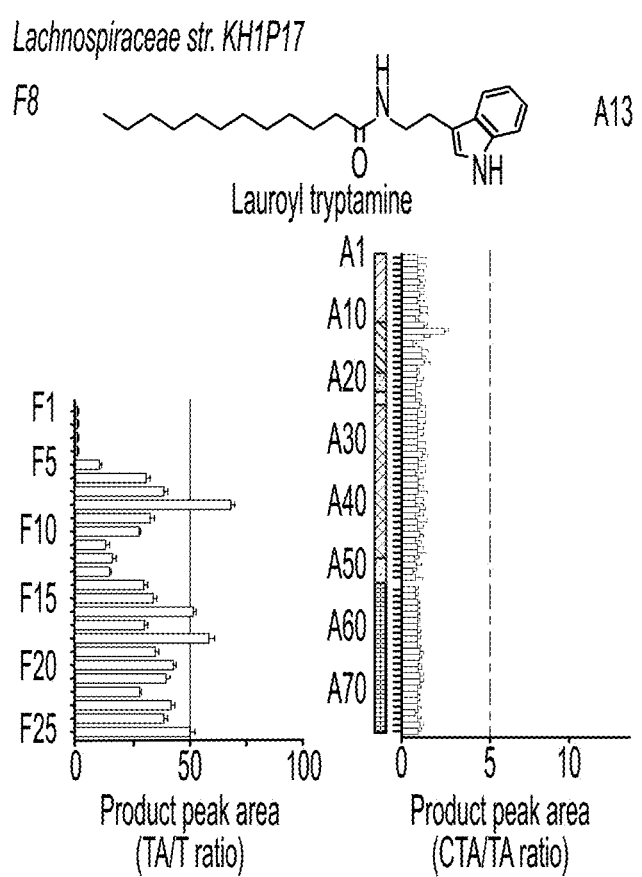

Adenylation and condensation activities from the eight HMP-derived pathways were measured on a panel of 25 fatty acids and 53 amines, respectively. Fatty acids were mixed with equimolar amounts to prepare five subpools, such that no two compounds sharing the same mass are in the same subpool: subpool Fa=F1, 6, 10, 13, 17, 20, 21; Fb=F2, 9, 11, 16, 22, 24; Fc=F3, 5, 7, 12, 14, 18; FD=Fd, 8, 15, 19, 23, 25 (FIG. 25 and Table 3). Amines were similarly mixed to prepare six subpools: subpool Aa=A9, 27, 28, 29, 30, 31, 32, 33, 34; Ab=A1, 2, 3, 4, 12, 16, 17, 20, 23; Ac=5, 11, 14, 21, 35, 37, 39, 42, 43; Ad=A6, 7, 8, 10, 13, 15, 18, 19, 38; Ae=22, 24, 25, 26, 40, 41, 47, 51, 53; Af=36, 44, 45, 46, 48, 49, 50, 52 (FIG. 25 and Table 3). For the additional panel of amines that were tested on the *L. clostridioforme, B. producta, C.* sp. 1_7_47FAA, *C. celatum, C.* sp. CAG: 413, and *L. str.* KH1P17 pathways, they were prepared as the following subpools: subpool Ag=54, 55, 56, 57, 58, 59, 60, 62; Ah=61, 63, 64, 65, 66, 67, 68, 70; Ai=69, 71, 72, 73, 74, 75, 76, 77 (FIG. 28 and Table 3).

For MS-based measurement of adenylation activity, a pair of 100 μL in vitro reaction samples were prepared, one with adenylation and thiolation proteins (no condensation) and the other with thiolation protein only, each protein at 1 μM final concentration. The protein(s) were added with one of the fatty acid subpool (Fa, Fb, Fc, or Fd) at a final concentration of 1 mM total fatty acid and tryptamine at a final concentration of 10 mM in an in vitro reaction mix (above). After 60 min incubation at 23° C., each sample was extracted with 1 mL of methanol, mixed with the vortexter at maximum speed for 30 sec (SI-0236, Vortex-Genie 2), and pelleted at 20,000 g and room temperature for 1 min. A 100 uL of the supernatant was injected for analytical LC-MS run (above). Using MestReNova (version 10), the presence of fatty acyl tryptamine product from each fatty acid substrate was identified by inspection of a clone-specific peak in the ESI+ extracted ion chromatograph (EIC) corresponding to the mass-to-charge ratio (m/z, 0.3 Da tolerance) of the protonated ion. The corresponding peak at the same retention time was identified on the DAD chromatogram at 280 nm (0.5 nm tolerance). Automated trace baseline correction, peak detection, and peak integration were applied by MestReNova. The DAD chromatogram peak area from reaction with adenylation and thiolation proteins was normalized to thiolation protein only control. The data was taken in triplicate per day, and the average of the mean triplicate normalized peak area conducted on three different days was reported.

The MS-based measurement of condensation activity follows similar steps as described (above). A pair of 100 μL in vitro reactions were prepared, one with condensation, adenylation, and thiolation proteins and the other with adenylation and thiolation protein only, each protein at 1 μM final concentration. The proteins were added with one of the amine subpool (Aa, Ab, Ac, Ad, Ae, Af, Ag, Ah, or Ai) at a final concentration of 1 mM total amine and fatty acid that provided highest adenylation activity (oleic acid for *C. eutactus, M. formatexigens, R. bacterium, B.* sp. *Marseille-P2398, B. wexlerae, L. str.* LC2019, *C.* sp. L2-50, *C.* sp. CAG:253, and *B.* sp. An81 pathways; α-linolenic acid for *R. albus, L. clostridioforme, B. producta, C. celatum*, and *C.* sp. 1_7_47AA pathways; lauric acid for *C. eutactus, C.* sp. CAG:413, and *L. str.* KH1P17 pathways; capric acid for *R.* sp. CAG:488 pathway) at a final concentration of 1 mM in an in vitro reaction mix (above). After 90 min incubation at 23° C., each sample was extracted with methanol and prepped for 100 uL analytical LC-MS run as described (above). Using MestReNova (version 10), the presence of FAA product for each amine substrate was identified by inspection of a clone-specific peak in the ESI+ and ESI− extracted ion chromatograph (EIC) corresponding to the mass-to-charge ratio (m/z, 0.3 Da tolerance) of the protonated or deprotonated ion. Automated trace baseline correction, peak detection, and peak integration were applied by MestReNova. The peak area (ESI+ or ESI− depending on the amine substrate) from reaction with condensation, adenylation and thiolation proteins was normalized to adenylation and thiolation proteins only control. The data was taken in triplicate per day, and the average of the mean triplicate normalized peak area conducted on three different days was reported.

With 1 mM each of lauric acid and tryptamine as substrates, and 1 μM each of the biosynthetic proteins from the *E. rectale* system, the reaction reached steady state at 18% conversion of lauric acid and 15% conversion of tryptamine after 8 hours at 23° C.

The identities of the major product determined from the in vitro assay (oleoyl dopamine, oleoyl tyramine, lauroyl tryptamine, oleoyl aminovaleric acid, α-linolenoyl phenylethylamine, and caproyl tryptamine) and α-linolenoyl homocysteine were confirmed for each by setting up an in vitro reaction with the specific pair of substrates. The resultant FAA product was analyzed by injecting the sample for analytical LC-MS alongside with a structurally verified standard, obtained either by purchasing from Cayman Chemical (Ann Arbor, Mich.; oleoyl dopamine, 10115), or having them chemically synthesized by KareBay Biochem (Monmouth Junction, N.J.).

The reaction time used in the adenylation and condensation activity assays was based on the time course of ten different time points. In brief, the MS-based measurements of adenylation and condensation activity were conducted as described above with *C. eutactus* proteins. However, a pair of 1,200 μL in vitro reactions were prepared, and instead of a single timepoint, a 100 μL aliquot was collected after 10, 20, 30, 45, 60, 90, 120, 240, 480, and 960 min of incubation at 23° C., extracted, and injected for analytical LC-MS run. The data was taken in triplicate per day. The time course graph was plotted for the average of the mean triplicate normalized peak area run on three different days and shows that the 60 min and 90 min timepoint for adenylation and condensation activity assay, respectively, resulted in the largest difference between the highest activity and the rest (FIG. 11).

Native Clostridia Strain Compound Characterization.

*Marvinbryantia formatexigens* DSM 14469 and *Eubacterium rectale* DSM 17629 were grown in an anaerobic chamber (1200001, Coy Laboratory Products, Grass Lack, Mich.) with an incubator (δ100000, Coy Laboratory Products). The strains were inoculated in one of the following 10 pre-reduced liquid media: RCM (BD218081, Becton Dickinson, Franklin Lakes, N.J.), BHI (M210, HiMedia, Mumbai, India), GAM (M1801, HiMedia), TSB (BD211825, Becton Dickinson), Casman (M766, HiMedia), WCABB (M863, HiMedia), Columbia (BD294420, Becton Dickinson), ABB (M1636, HiMedia), YCFAC (AS-680, Anaerobe Systems, Morgan Hill, Calif.), PYEG (AG24H, Hardy Diagnostics, Santa Maria, Calif.). Media without reducing agent L-cysteine in the ingredients were supplemented with L-cysteine at a final concentration of 0.05% (w/v). Each culture was grown as 2 mL volume in 14 mL Falcon culture tube (352059, Corning) at 37° C. for 2 days. The culture was extracted in the chamber with 2 mL of methanol and mixed by vigorous shaking (BJLC230, VWR). Upon taking the sample out from the chamber, the mixture was pelleted at 20,000 g for 1 min (022620401, Centrifuge 5424). A 100 uL aliquot of the supernatant was injected for analytical LC-MS run, as previously described. The presence of lauroyl tryptamine in *E. rectale* and oleoyl dopamine in *M. formatexigens* was checked by running alongside the synthesized standard and inspecting the ESI+ EIC corresponding to the m/z (0.3 Da tolerance) of the protonated ion.

For *E. rectale* feeding experiment, 20 μL of the 2-day *E. rectale* culture in RCM was inoculated in 2 mL of fresh RCM with 0.2 mM of tryptamine and 0.1 mM of the fatty acid substrate (lauric acid, linoleic acid, oleic acid, docosahexaenoic acid, or α-linolenic acid), and grown for an additional 2 days at 37° C. The culture was extracted and analyzed by LC-MS in the same way as above, with methanol extraction and injection of a 100 uL aliquot. Standards for linoleoyl, oleoyl, docosahexaenoyl, and α-linolenoyl tryptamine were made by adding the appropriate substrates in the in vitro system with purified *E. rectale* enzymes, and were run alongside to confirm presence in the *E. rectale* extracts (ESI+ EIC).

For product yield measurements, a standard curve for fatty acyl tryptamine was constructed based on the peak area of the DAD chromatogram at 280 nm (0.5 nm tolerance) with 100 μg, 10 μg, 1 μg, 100 ng, 10 ng, 1 ng, 100 pg, 10 pg, and 1 pg injections (in triplicates) of the chemically synthesized lauroyl tryptamine standard. Automated trace baseline correction, peak detection, and peak integration were applied by MestReNova.

Metatranscriptomics.

The *E. rectale* FAA pathway was first used as a query sequence for blastn search with default parameters on NCBI SRA datasets. A 80 kb region of the *E. rectale* genome centered at the FAA pathway was obtained from the NCBI nr database (accession: FP929042, region 2065556-2145556). The metatranscriptomic reads file (fastq) from subject subX316701492 was obtained from the NCBI Sequence Read Archive (SRA) database (accession: SRX247340). Upon loading the files to Geneious Prime (version 11), the reads were mapped onto the 80 kb region as the reference sequence (Geneious Mapper, Medium-Low Sensitivity/Fast).

Chemical Synthesis.

The FAA products lauroyl tryptamine, oleoyl tyramine, oleoyl aminovaleric acid, α-linolenoyl phenylethylamine, caproyl tryptamine, α-linolenoyl homocysteine, and palmitoeyl putrescine were chemically synthesized by KareBay Biochem (Monmouth Junction, N.J.). Oleoyl dopamine was acquired from Cayman Chemical (Ann Arbor, Mich.).

GPCR Screening.

The four human gut metagenome-derived major products (oleoyl dopamine, oleoyl tyramine, lauroyl tryptamine, oleoyl aminovaleric acid) were obtained from commercial source or chemical synthesis and confirmed to be identical to in vitro products. They were sent to DiscoverX (Fremont, Calif.) for a cell-based assay on a panel of 168 GPCRs with known ligands (gpcrMAX) in both agonist and antagonist mode, as well as 73 orphan GPCRs (orphanMAX) in agonist mode. Chemiluminescence indicating β-arrestin recruitment was used as output to measure agonist and antagonist activity of each compound on each GPCR at 10 micromolar concentration. Agonist mode measures % activity relative to the baseline value (0% activity) and maximum value activated by a known ligand (100% activation). For orphan GPCR, twofold increase in value over baseline is set as 100% activation. Antagonist mode measures % inhibition of target GPCR by the compound in the presence of a known ligand, relative to the value at the EC80 of the known ligand (0% inhibition) and basal value (100% inhibition). DiscoverX provides an empirical threshold value of 30%, 35%, or 50% for GPCR agonist, GPCR antagonist, or orphan GPCR agonist, respectively, where activity/inhibition higher than the threshold indicate that the interaction is potentially significant.

Concentration-Response Curve.

Lauroyl tryptamine, tryptamine, and lauric acid were sent to DiscoverX for a cell-based assay on EBI2 antagonist mode, P2RY4 antagonist mode, and GPR132 agonist mode. The experimental setup and output are the same as the panel assay, except % inhibition/activity was measured on ten concentration points (100, 33, 11, 3.7, 1.2, 0.41, 0.14, 0.046, 0.015, 0.0051 µM) to plot the concentration-response curve and determine IC50 or EC50.

REFERENCES SECTION 2

(Below references refer to reference numbers included only in Example 2)

1 Wilson, M. R., Zha, L. & Balskus, E. P. Natural product discovery from the human microbiome. *The Journal of biological chemistry* 292, 8546-8552, doi: 10.1074/jbc.R116.762906 (2017).
2 Lee, W. J. & Hase, K. Gut microbiota-generated metabolites in animal health and disease. *Nature chemical biology* 10, 416-424, doi: 10.1038/nchembio. 1535 (2014).
3 Donia, M. S. & Fischbach, M. A. HUMAN MICROBIOTA. Small molecules from the human microbiota. *Science* 349, 1254766, doi: 10.1126/science.1254766 (2015).
4 Sharon, G. et al. Specialized metabolites from the microbiome in health and disease. *Cell metabolism* 20, 719-730, doi: 10.1016/j.cmet.2014.10.016 (2014).
5 Chen, H. et al. A Forward Chemical Genetic Screen Reveals Gut Microbiota Metabolites That Modulate Host Physiology. *Cell*, doi: 10.1016/j.cell.2019.03.036 (2019).
6 Wang, Z. et al. Gut flora metabolism of phosphatidylcholine promotes cardiovascular disease. *Nature* 472, 57-63, doi: 10.1038/nature09922 (2011).
7 Ridlon, J. M., Kang, D. J. & Hylemon, P. B. Bile salt biotransformations by human intestinal bacteria. *Journal of lipid research* 47, 241-259, doi: 10.1194/jlr.R500013-JLR200 (2006).
8 Guo, C. J. et al. Discovery of Reactive Microbiota-Derived Metabolites that Inhibit Host Proteases. *Cell* 168, 517-526 e518, doi: 10.1016/j.cell.2016.12.021 (2017).
9 Wieland Brown, L. C. et al. Production of alpha-galactosylceramide by a prominent member of the human gut microbiota. *PLoS biology* 11, e1001610, doi: 10.1371/journal.pbio.1001610 (2013).
10 Ozaki, H. et al. Molecular structure of the toxin domain of heat-stable enterotoxin produced by a pathogenic strain of *Escherichia coli*. A putative binding site for a binding protein on rat intestinal epithelial cell membranes. *The Journal of biological chemistry* 266, 5934-5941 (1991).
11 Round, J. L. et al. The Toll-like receptor 2 pathway establishes colonization by a commensal of the human microbiota. *Science* 332, 974-977, doi: 10.1126/science.1206095 (2011).
12 Cohen, L. J. et al. Functional metagenomic discovery of bacterial effectors in the human microbiome and isolation of commendamide, a GPCR G2A/132 agonist. *Proceedings of the National Academy of Sciences of the United States of America* 112, E4825-4834, doi: 10.1073/pnas.1508737112 (2015).
13 Cohen, L. J. et al. Commensal bacteria make GPCR ligands that mimic human signalling molecules. *Nature* 549, 48-53, doi: 10.1038/nature23874 (2017).
14 Donia, M. S. et al. A systematic analysis of biosynthetic gene clusters in the human microbiome reveals a common family of antibiotics. *Cell* 158, 1402-1414, doi: 10.1016/j.cell.2014.08.032 (2014).
15 Blin, K. et al. antiSMASH 4.0—improvements in chemistry prediction and gene cluster boundary identification. *Nucleic acids research* 45, W36-W41, doi: 10.1093/nar/gkx319 (2017).
16 Magnusdottir, S. & Thiele, I. Modeling metabolism of the human gut microbiome. *Current opinion in biotechnology* 51, 90-96, doi: 10.1016/j.copbio.2017.12.005 (2018).
17 Sonnenburg, J. L. & Backhed, F. Diet-microbiota interactions as moderators of human metabolism. *Nature* 535, 56-64, doi: 10.1038/nature18846 (2016).
18 Brotherton, C. A. & Balskus, E. P. A prodrug resistance mechanism is involved in colibactin biosynthesis and cytotoxicity. *Journal of the American Chemical Society* 135, 3359-3362, doi: 10.1021/ja312154m (2013).
19 Arafat, E. S., Trimble, J. W., Andersen, R. N., Dass, C. & Desiderio, D. M. Identification of fatty acid amides in human plasma. *Life sciences* 45, 1679-1687 (1989).
Ezzili, C., Otrubova, K. & Boger, D. L. Fatty acid amide signaling molecules. *Bioorganic & medicinal chemistry letters* 20, 5959-5968, doi: 10.1016/j.bmcl.2010.08.048 (2010).
21 Devane, W. A. et al. Isolation and structure of a brain constituent that binds to the cannabinoid receptor. *Science* 258, 1946-1949 (1992).
22 Eisenstein, T. K., Meissler, J. J., Wilson, Q., Gaughan, J. P. & Adler, M. W. Anandamide and Delta9-tetrahydrocannabinol directly inhibit cells of the immune system via CB2 receptors. *Journal of neuroimmunology* 189, 17-22, doi: 10.1016/j.jneuroim.2007.06.001 (2007).
23 Osei-Hyiaman, D. et al. Endocannabinoid activation at hepatic CB1 receptors stimulates fatty acid synthesis and contributes to diet-induced obesity. *The Journal of clinical investigation* 115, 1298-1305, doi: 10.1172/JCI23057 (2005).
24 Caterina, M. J. et al. The capsaicin receptor: a heat-activated ion channel in the pain pathway. *Nature* 389, 816-824, doi: 10.1038/39807 (1997).
25 Chu, C. J. et al. N-oleoyldopamine, a novel endogenous capsaicin-like lipid that produces hyperalgesia. *The Journal of biological chemistry* 278, 13633-13639, doi: 10.1074/jbc.M211231200 (2003).
26 Przegalinski, E., Filip, M., Zajac, D. & Pokorski, M. N-oleoyl-dopamine increases locomotor activity in the rat. *International journal of immunopathology and pharmacology* 19, 897-904, doi: 10.1177/039463200601900419 (2006).
27 Chu, Z. L. et al. N-oleoyldopamine enhances glucose homeostasis through the activation of GPR119. *Molecular endocrinology* 24, 161-170, doi: 10.1210/me.2009-0239 (2010).
28 Ross, H. R., Gilmore, A. J. & Connor, M. Inhibition of human recombinant T-type calcium channels by the endocannabinoid N-arachidonoyl dopamine. *British journal of pharmacology* 156, 740-750, doi: 10.1111/j.1476-5381.2008.00072.x (2009).
29 Sergeeva, O. A. et al. N-oleoyldopamine modulates activity of midbrain dopaminergic neurons through multiple mechanisms. *Neuropharmacology* 119, 111-122, doi: 10.1016/j.neuropharm.2017.04.011 (2017).
30 Raboune, S. et al. Novel endogenous N-acyl amides activate TRPV1-4 receptors, BV-2 microglia, and are 30 regulated in brain in an acute model of inflammation. *Frontiers in cellular neuroscience* 8, 195, doi: 10.3389/fncel.2014.00195 (2014).
31 Huang, S. M. et al. Identification of a new class of molecules, the arachidonyl amino acids, and characterization of one member that inhibits pain. *The Journal of biological chemistry* 276, 42639-42644, doi: 10.1074/jbc.M107351200 (2001).
32 Oh, D. Y. et al. Identification of farnesyl pyrophosphate and N-arachidonylglycine as endogenous ligands for GPR92. *The Journal of biological chemistry* 283, 21054-21064, doi: 10.1074/jbc.M708908200 (2008).
33 Sasso, O. et al. Endogenous N-acyl taurines regulate skin wound healing. *Proceedings of the National Academy of Sciences of the United States of America* 113, E4397-4406, doi: 10.1073/pnas. 1605578113 (2016).
34 Hannedouche, S. & Roy, M. Ligand for G-protein coupled receptor GPR72 and uses thereof. United States patent (2008).
35 Milman, G. et al. N-arachidonoyl L-serine, an endocannabinoid-like brain constituent with vasodilatory properties. *Proceedings of the National Academy of Sciences of the United States of America* 103, 2428-2433, doi: 10.1073/pnas.0510676103 (2006).
36 Zhang, X., Maor, Y., Wang, J. F., Kunos, G. & Groopman, J. E. Endocannabinoid-like N-arachidonoyl serine is a novel pro-angiogenic mediator. *British journal of pharmacology* 160, 1583-1594, doi: 10.1111/j.1476-5381.2010.00841.x (2010).
37 Camilleri, M. Review article: tegaserod. *Aliment Pharmacol Ther* 15, 277-289, doi: 10.1046/j.1365-2036.2001.00925.x (2001).
38 Farrell, E. K. & Merkler, D. J. Biosynthesis, degradation and pharmacological importance of the fatty acid amides. *Drug discovery today* 13, 558-568, doi: 10.1016/j.drudis.2008.02.006 (2008).
39 Sussmuth, R. D. & Mainz, A. Nonribosomal Peptide Synthesis-Principles and Prospects. *Angewandte Chemie* 56, 3770-3821, doi: 10.1002/anie.201609079 (2017).
40 Raymond, K. N., Dertz, E. A. & Kim, S. S. Enterobactin: an archetype for microbial iron transport. *Proceedings of the National Academy of Sciences of the United States of America* 100, 3584-3588, doi: 10.1073/pnas.0630018100 (2003).
41 Schneditz, G. et al. Enterotoxicity of a nonribosomal peptide causes antibiotic-associated colitis. *Proceedings of the National Academy of Sciences of the United States of America* 111, 13181-13186, doi: 10.1073/pnas.1403274111 (2014).
42 Fischbach, M. A. & Walsh, C. T. Assembly-line enzymology for polyketide and nonribosomal Peptide antibiotics: logic, machinery, and mechanisms. *Chemical reviews* 106, 3468-3496, doi: 10.1021/cr0503097 (2006).
43 Roche, E. D. & Walsh, C. T. Dissection of the EntF condensation domain boundary and active site residues in nonribosomal peptide synthesis. *Biochemistry* 42, 1334-1344, doi: 10.1021/bi026867m (2003).
44 Mori, S. et al. Activation and Loading of the Starter Unit during Thiocoraline Biosynthesis. *Biochemistry* 56, 4457-4467, doi: 10.1021/acs.biochem.7b00661 (2017).
45 Weber, T. et al. antiSMASH 3.0—a comprehensive resource for the genome mining of biosynthetic gene clusters. *Nucleic acids research* 43, W237-243, doi: 10.1093/nar/gkv437 (2015).
46 Human Microbiome Project, C. Structure, function and diversity of the healthy human microbiome. *Nature* 486, 207-214, doi: 10.1038/nature11234 (2012).
47 Franzosa, E. A. et al. Relating the metatranscriptome and metagenome of the human gut. *Proceedings of the National Academy of Sciences of the United States of America* 111, E2329-2338, doi: 10.1073/pnas.1319284111 (2014).
48 Navarro-Muñoz, J. et al. A computational framework for systematic exploration of biosynthetic diversity from large-scale genomic data. *bioRxiv* (2018).
49 Mazmanian, S. K., Round, J. L. & Kasper, D. L. A microbial symbiosis factor prevents intestinal inflammatory disease. *Nature* 453, 620-625, doi: 10.1038/nature07008 (2008).
50 Almeida, A. et al. A new genomic blueprint of the human gut microbiota. *Nature* 568, 499-504, doi: 10.1038/s41586-019-0965-1 (2019).
51 Nayfach, S., Fischbach, M. A. & Pollard, K. S. MetaQuery: a web server for rapid annotation and quantitative analysis of specific genes in the human gut microbiome. *Bioinformatics* 31, 3368-3370, doi: 10.1093/bioinformatics/btv382 (2015).
52 Rausch, C., Hoof, I., Weber, T., Wohlleben, W. & Huson, D. H. Phylogenetic analysis of condensation domains in NRPS sheds light on their functional evolution. *BMC Evol Biol* 7, 78, doi: 10.1186/1471-2148-7-78 (2007).
53 Medema, M. H. et al. antiSMASH: rapid identification, annotation and analysis of secondary metabolite biosynthesis gene clusters in bacterial and fungal genome sequences. *Nucleic acids research* 39, W339-346, doi: 10.1093/nar/gkr466 (2011).
54 Keating, T. A., Marshall, C. G. & Walsh, C. T. Vibriobactin biosynthesis in *Vibrio cholerae*: VibH is an amide synthase homologous to nonribosomal peptide synthetase condensation domains. *Biochemistry* 39, 15513-15521 (2000).
55 Pfeifer, B. A., Admiraal, S. J., Gramajo, H., Cane, D. E. & Khosla, C. Biosynthesis of complex polyketides in a metabolically engineered strain of *E. coli*. *Science* 291, 1790-1792, doi: 10.1126/science.1058092 (2001).
56 Pugin, B. et al. A wide diversity of bacteria from the human gut produces and degrades biogenic amines. *Microbial ecology in health and disease* 28, 1353881, doi: 10.1080/16512235.2017.1353881 (2017).
57 Hansen, D. B., Bumpus, S. B., Aron, Z. D., Kelleher, N. L. & Walsh, C. T. The loading module of mycosubtilin: an adenylation domain with fatty acid selectivity. *Journal of the American Chemical Society* 129, 6366-6367, doi: 10.1021/ja070890j (2007).
58 Stachelhaus, T., Mootz, H. D. & Marahiel, M. A. The specificity-conferring code of adenylation domains in nonribosomal peptide synthetases. *Chemistry & biology* 6, 493-505, doi: 10.1016/S1074-5521(99)80082-9 (1999).
59 Stachelhaus, T., Mootz, H. D., Bergendahl, V. & Marahiel, M. A. Peptide bond formation in nonribosomal peptide biosynthesis. Catalytic role of the condensation domain. *The Journal of biological chemistry* 273, 22773-22781 (1998).
60 Brady, S. F. & Clardy, J. Palmitoylputrescine, an antibiotic isolated from the heterologous expression of DNA extracted from bromeliad tank water. *Journal of natural products* 67, 1283-1286, doi: 10.1021/np0499766 (2004).
61 Frolov, A., Cho, T. H., Billheimer, J. T. & Schroeder, F. Sterol carrier protein-2, a new fatty acyl coenzyme A-binding protein. *The Journal of biological chemistry* 271, 31878-31884 (1996).
62 McKinney, M. K. & Cravatt, B. F. Structure and function of fatty acid amide hydrolase. *Annual review of biochem-* istry 74, 411-432, doi: 10.1146/annurev.biochem.74.082803.133450 (2005).
63 Quadri, L. E. et al. Characterization of Sfp, a *Bacillus subtilis* phosphopantetheinyl transferase for peptidyl carrier protein domains in peptide synthetases. *Biochemistry* 37, 1585-1595, doi: 10.1021/bi9719861 (1998).
64 Hill, M. J. *Microbial Metabolism In The Digestive Tract*. (CRC Press, 2018).
65 Abdelmagid, S. A. et al. Comprehensive profiling of plasma fatty acid concentrations in young healthy Canadian adults. *PloS one* 10, e0116195, doi: 10.1371/journal.pone.0116195 (2015).
66 Chan, M., Himes, R. H. & Akagi, J. M. Fatty acid composition of thermophilic, mesophilic, and psychrophilic clostridia. *Journal of bacteriology* 106, 876-881 (1971).
67 Vernocchi, P., Del Chierico, F. & Putignani, L. Gut Microbiota Profiling: Metabolomics Based Approach to Unravel Compounds Affecting Human Health. *Frontiers in microbiology* 7, 1144, doi: 10.3389/fmicb.2016.01144 (2016).
68 Lyte, M. & Freestone, P. P. E. *Microbial Endocrinology: Interkingdom Signaling in Infectious Disease and Health*. (Springer New York, 2010).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method of producing fatty acid amides, the method comprising: contacting a composition, comprising one or more exogenous fatty acids and one or more amines, with a set of biosynthetic enzymes which are human gut microbiome-derived clostridia biosynthetic enzymes in an effective amount to produce a fatty acid amide, wherein the set of biosynthetic enzymes are recombinant proteins expressed from one or more vectors comprising a single operon, wherein the operon comprises genes encoding at least a fatty acyl transferase, an acyl carrier protein (ACP), and a fatty acyl-ACP synthetase.

2. The method of claim 1, wherein the method is performed in vitro.

3. The method of claim 1, wherein the composition is a culture broth.

4. The method of claim 1, wherein the set of biosynthetic enzymes are isolated from human gut microbiome-derived clostridia.

5. The method of claim 1, wherein the biosynthetic enzymes comprise a hydrolase.

6. The method of claim 1, wherein the biosynthetic enzymes comprise a lipid transfer protein.

7. The method of claim 1, wherein the biosynthetic enzymes comprise a glycosyltransferase.

8. The method of claim 1, wherein the set of biosynthetic enzymes are synthetic proteins.

9. The method of claim 1, wherein the set of biosynthetic enzymes are recombinant proteins expressed from a plurality of vectors comprising a first vector, a second vector, and a third vector, wherein each of the plurality of vectors comprises a gene in a single operon and under the control of a regulatory element.

10. The method of claim 1, wherein the one or more exogenous fatty acids are selected from a group consisting of acetic acid, propionic acid, butyric acid, valeric acid, hexanoic acid, octanoic acid, capric acid, lauric acid, myristic acid, pentadecanoic acid, palmitic acid, stearic acid, arachidic acid, iso-pentadecanoic acid, palmitoleic acid, oleic acid, vaccenic acid, linoleic acid, γ-linolenic acid, α-linolenic acid, dihomo-γ-linolenic acid, arachidonic acid, eicosapentaenoic acid, docosapentaenoic acid, docosahexaenoic acid, 8-methyl-6-nonenoic acid, octynoic acid, myristic acid alkyne, and palmitic acid alkyne.

11. The method of claim 1, wherein the one or more exogenous amines are selected from a group consisting of phenylalanine, tryptophan, tyrosine, histidine, lysine, glycine, alanine, valine, leucine, isoleucine, methionine, proline, serine, threonine, cysteine, asparagine, glutamine, aspartic acid, glutamic acid, arginine, ornithine, β-alanine, L-DOPA, creatine, citrulline, phenylacetylglutamine, phenylethylamine, tryptamine, tyramine, histamine, serotonin, dopamine, epinephrine, norepinephrine, γ-aminobutryic acid (GABA), aminovaleric acid, ethanolamine, cadaverine, putrescine, spermine, spermidine, agmatine, propylamine, butylamine, dimethylamine, pyrollidine, piperidine, homocysteine, cysteamine, homocysteamine, taurine, hypotaurine, glutathione, octopamine, 3-iodothyronamine, melatonin, and vanillylamide.

12. A method of producing a fatty acid amide, the method comprising (i) administering to a host a plurality of vectors comprising a first vector, a second vector, and a third vector, wherein each of the plurality of vectors comprises a human gut microbiome-derived bacterium gene under the control of a regulatory element; and
wherein the gene on the first vector, the second vector and the third vector encode a fatty acyl transferase, an acyl carrier protein, and fatty acyl-ACP synthetase, respectively; and
(ii) contacting the host with a composition in an effective amount to produce a fatty acid amide in the host.

13. A method of producing a fatty acid amide, the method comprising
(i) administering to a host a vector comprising genes, wherein each of the genes is under the control of a regulatory element, wherein each of the genes is derived from a human gut microbiome-derived bacterium, and wherein the genes encode a fatty acyl transferase, an acyl carrier protein, and fatty acyl-ACP synthetase; and
(ii) contacting the host with a composition in an effective amount to produce a fatty acid amide in the host.

14. The method of claim 13, wherein the regulatory element is an inducible promoter.

15. The method of claim 13, wherein the regulatory element is a constitutive promoter.

16. The method of claim 13, wherein the regulatory element is a repressible promoter.

17. The method of claim 13, wherein the regulatory element is a T7 promoter.

18. The method of claim 17, wherein the vector further encodes a T7 RNA polymerase.

19. The method of claim 13, wherein the vector further comprises a ribosomal binding site.

20. The method of claim 13, wherein the genes are codon-optimized.

21. The method of claim 13, wherein the genes are open reading frames.

22. The method of claim 13, wherein the host is *E. coli*.

23. The method of claim 13, wherein the gut microbiome-derived bacterium is from Clostridia.

24. The method of claim 22, wherein the genes are codon-optimized for production in *E. coli*.

25. The method of claim 13, wherein the fatty acid amide is palmitoleyl-putrescine, oleoyl aminovaleric acid, α-linolenoyl aminovaleric acid, oleoyl γ-aminobutyric acid, oleoyl dopamine, oleoyl tyramine, palmitoleoyl dopamine, α-linolenoyl tyramine, oleoyl phenethylamine, lauroyl tyrptamine, lineoleoyl tryptamine, lauroyl tyramine, α-linolenoyl homocysteine, oleoyl homocysteine, α-linolenoyl cysteine, linoleoyl homocysteine, oleoyl-aminopentanoic acid, or α-linolenoyl homocysteamine.

26. The method of claim 13, wherein the genes further comprise a gene encoding Sfp 4'-phosphopantetheinyl transferase.

27. The method of claim 13, wherein the genes are in a single operon.

28. The method of claim 13, wherein in (ii), the composition does not comprise an exogenous fatty acid.

29. The method of claim 13, wherein in (ii), the composition does not comprise an exogenous amine.

30. The method of claim 13, wherein in (ii), the composition comprises one or more exogenous fatty acids selected from a group consisting of acetic acid, propionic acid, butyric acid, valeric acid, hexanoic acid, octanoic acid, capric acid, lauric acid, myristic acid, pentadecanoic acid, palmitic acid, stearic acid, arachidic acid, iso-pentadecanoic acid, palmitoleic acid, oleic acid, vaccenic acid, linoleic acid, γ-linolenic acid, α-linolenic acid, dihomo-γ-linolenic acid, arachidonic acid, eicosapentaenoic acid, docosapentaenoic acid, docosahexaenoic acid, 8-methyl-6-nonenoic acid, octynoic acid, myristic acid alkyne, and palmitic acid alkyne.

31. The method of claim 13, wherein in (ii), the composition comprises one or more exogenous amines selected from a group consisting of phenylalanine, tryptophan, tyrosine, histidine, lysine, glycine, alanine, valine, leucine, isoleucine, methionine, proline, serine, threonine, cysteine, asparagine, glutamine, aspartic acid, glutamic acid, arginine, ornithine, β-alanine, L-DOPA, creatine, citrulline, phenylacetylglutamine, phenylethylamine, tryptamine, tyramine, histamine, serotonin, dopamine, epinephrine, norepinephrine, γ-aminobutryic acid (GABA), aminovaleric acid, ethanolamine, cadaverine, putrescine, spermine, spermidine, agmatine, propylamine, butylamine, dimethylamine, pyrollidine, piperidine, homocysteine, cysteamine, homocysteamine, taurine, hypotaurine, glutathione, octopamine, 3-iodothyronamine, melatonin, and vanillylamide.

* * * * *

SEQUENCE LISTING

```
<160> NUMBER OF SEQ ID NOS: 169

<210> SEQ ID NO 1
<211> LENGTH: 249
<212> TYPE: DNA
<213> ORGANISM: C. eutactus

<400> SEQUENCE: 1
atgaacaaca acatcacctt tctgaacatc gttgccgaat attgtaatac accggcagat    60
gaaattacca acgatatgcg ctttattgaa gatctgggtt ttagcagcct ggactttatg   120
acctttctgg gtgatctgga agatacctt gatgtggaaa tcaacgaaga tgagatcatc    180
aacatccaca ccattgaaga tgccatcaaa tatctggata atctgaccag cagcagcgca   240
agcgtttaa                                                           249

<210> SEQ ID NO 2
<211> LENGTH: 237
<212> TYPE: DNA
<213> ORGANISM: M. formatexigens

<400> SEQUENCE: 2
atgacccaag agatgcagtt taaaaccatt gcagcacagt attgtggtgt gaaaccggaa    60
gatatgacca atgatatgcg ttttcgtgaa gatctgggtt ttagcagcct ggattttatg   120
agctttctgg gtgaactgga agatacctt gatgttgagc tggaagaaga gaggttgtt    180 aaaattctga ccgttgcaga agcactggca ctgctggaaa aactgcaaga agaataa      237

<210> SEQ ID NO 3
<211> LENGTH: 231
<212> TYPE: DNA
<213> ORGANISM: Lachnoclostridium clostridioforme

<400> SEQUENCE: 3
atgttcgagg aactgaaaga aatcatctgc gaatatgttg atgttgcacc ggaaaccatt    60
aaagaaaaca gccgctttat tgaagatctg ggctttaaca gctatgattt catgagcatg   120
gtgggcgaaa tcgaagaaaa atttgatgtg gaagtggaag aacgcgaagt ggttaatgtt   180
aaaaccgtta agatgccgt ggattatatt cagagtctgc aggcagaata a             231

<210> SEQ ID NO 4
<211> LENGTH: 228
<212> TYPE: DNA
<213> ORGANISM: B. producta

<400> SEQUENCE: 4
atgttcgaga aactgaaaga catgatctgc gaatatgtgg aagtggataa aaatgccgtt    60
accgaaaata gccgtttttgt tgaagatctg ggtttcacca gctatgattt tatgagcatg   120
attggcgaac tggaagaaac ctatgatatc gaagttgaag aacgtcaggc agcagaaatt   180
cgtaccgttg gtgaagcagt tcgttatatt gaaagcctgc aggattaa                228

<210> SEQ ID NO 5
<211> LENGTH: 228
<212> TYPE: DNA
```

<213> ORGANISM: C. celatum

<400> SEQUENCE: 5

```
atgctggaaa aactgcgtga actgctgagc gaatatgttg aagttgcacg tgaagatatt      60
accgtggaaa gcaaactggt tgaagatctg gtctgaaca gctatgaatt tatgaccctg      120
gttggtgatc tggaagagga atttgatgtg gaagttaatg aacgtgaagt ggccaaagtt    180
aataccattg gcgatatcat cgaatacatt accgcactgc aggtctaa                      228
```

<210> SEQ ID NO 6
<211> LENGTH: 228
<212> TYPE: DNA
<213> ORGANISM: R. bacterium

<400> SEQUENCE: 6

```
atgttcgaga aactggtgga aatcatctgc aattatgttg aagttgagcc ggaaaaaatc       60
accagcgata gccgttttat ggaagatctg ggttttacca gctttgactt tatgagcatg    120
ctgggcgaaa ttgaagatac ctttgatatc gaagtggata aaacggaagt ggtgaaaatt    180
cgtaccgttg gtgaagccgt tgattatatt cagagcctgg cagattaa                      228
```

<210> SEQ ID NO 7
<211> LENGTH: 228
<212> TYPE: DNA
<213> ORGANISM: Unknown
<220> FEATURE:
<223> OTHER INFORMATION: Clostridiales sp.

<400> SEQUENCE: 7

```
atgttcgagg aactgaaaga actgatctgc gaatatgttg atgttgatcc gagcgccatt       60
aaagaagaaa gccgttttat tgaagatctg ggcttcaaca gctatgactt tatgagcatg    120
gttggcgaaa tcgaagaaac ctttgatgtg gaagttgaag aacgtgaagt ggtgaatgtt    180
aaaaccgtta aagatgccgt ggaatatatc cagagcctgc aggattaa                      228
```

<210> SEQ ID NO 8
<211> LENGTH: 231
<212> TYPE: DNA
<213> ORGANISM: E. rectale

<400> SEQUENCE: 8

```
atgttcgatg aactggtgga aatcatctgc aattatgttg atgttcagcc tgccgatgtt       60
catgaagaaa gccgttttat ggaagatctg ggttttacca gctttgactt tatgagcatg    120
ctgggcgaaa ttgaagatac ctttgatgtg gaaatcgaac agaccaaagc agcagaaatt    180
cgtaccgttc aagaagcagt tgattatctg gaaaccctga agatgcccta a                  231
```

<210> SEQ ID NO 9
<211> LENGTH: 1392
<212> TYPE: DNA
<213> ORGANISM: C. eutactus

<400> SEQUENCE: 9

```
atgcctcgta atactatcc gctgacaccg agccagaaaa ttcattttaa accgatcatt       60
gaattcggca cccagcaggt tgcaaatatt agcatttgta tgaccctgca ggcaccgctg    120
gattttggtc tgctgaaaaa atgtattcag ctggaatatg aacgctatga atgtctgcgt    180
attcgcttta ccaaagtgga tcagaatggt gaagttcgtc agtatgttgt tagccgtgat    240
gatcgcgata tcgattatga aaatctgagc tggctgagcg gtgatgatgc atatcatcgt    300
```

```
atggaagaat ggtcaagaat tccgtttgat ggcgataata ttccgatgaa cgtgatcaaa    360
atgattagcc tgcctggtgg ttataatggc ctgtatatca aaattgatca ccgcctgatg    420
gatagctgtg gtgccattgt tatggtgaac gatattatgg aactgtactg ccactacaaa    480
tttggcaccc cgtatccgga agatatggca agctttaccg atatggttga acgcgatctg    540
aaaaaaagca ccgatgaaaa acgtgtgagc aaagatcgta tgtattggca gaatgtgctg    600
gaagaaaatg gcgaaccgat ttatagcgat attcagggtc agcgtattct gcaagaaagc    660
cgtcgtctgc ataatgataa agcctgcgt gcagcagatc aagaaattaa tgatctgagc    720
gttgccacca aaaactatca tctggatgca gaaccgacac aaaatctgct ggatttctgc    780
atgaataacc atatcagcat gaccaacctg attctgatgg gtattcgtac ctatctgagc    840
aaagcaaatg gtggtcagac cgatatttcc attcgtaatt atgtgagccg tcgtagcacc    900
catgcagaat gggttagcgg tggtagccgt gcaatggcat atccgtgtcg taccattatt    960
gatccggata ccgaatttct ggatgccgtt tttatgattc aggatgtgca gaatcatgtg   1020
tatcgccatt gcaactatga tccggaactg ctgagcgatc agatgaaaga aatgtttcat   1080 accccctccgc ataccaccta tgaaagcgtt ggtctgacct atcagccgct gccgattcgt   1140
ctgaaaaatc cgcatctgga aaacattagc gttcgtagca tgtggattcc gaatggtaca   1200
agcaaacaga aaatctatct gaccgttatg catagcgcaa atgatctggg tctgaatttc   1260
tattttcgtt atcagaccgc aagcctgagc gaacaggata ttgaactgtt ttattattat   1320
ctgatgaaaa tcatctttaa aggcattgcc gaaccggaaa tgaccgttgg tgaaattatt   1380
gaatgcattt aa                                                      1392

<210> SEQ ID NO 10
<211> LENGTH: 1386
<212> TYPE: DNA
<213> ORGANISM: M. formatexigens

<400> SEQUENCE: 10
atgcgcgaat attatccgct gaccgcagca cagaaaatgc attataactg gattcgtaaa     60
tatcgcaccc agcaggttag cggtgttagc gttgttgcaa gcctgaaaag tccgctggat    120
tttggtctgc tgaaaaaatg tattcagctg gaaccgaaac gttatggttg tatgcgtgtt    180
cgttttaccg caccggatga aaaaggtggt attaaacagt atattgtgga tcgcgatacc    240
cgtgatattc cgatgaaaga tctgagcggt atgagcatgg ccgaagcaga taatctgatg    300
cagcagtggg cctatgaaac ctttgatggt gatgatatcc cgctgtgtga tgttaccatg    360
ctgaaactgc cggatggtta taatggcttt tttatccaca tggatcaccg cctgattgat    420
agctgtggtc tggttgttat gattaatgat cttatgcagc tgtataccca ctatcgtttt    480
ggtagcgcat atccgcagga tctggcagat tatgaaaccg ttctggcaaa agacctgaaa    540
cgtgccaata tgaaaaaacg ctttgccaaa gacaaaaaat ctgggatga tcagctgaat    600 gcactgggtg aaccgctgta tagcgatatt cagggtccga gcgttctgga agcagcacgt    660
aaacgtcata aaaatccgat gctgcgtgca gcagatattg aactggataa cctgtttgtg    720
gaagtgaaag attatcgtct ggaaccggaa ccgaccaaaa atctgattga ttttttgcatg    780 aatcatcagc tgagcatgac caatctgctg ctgctgggta ttcgtaccta tctgagcaaa    840
gttaataacg gccaagaaga tatcaccatc gaaaactttta ttagccgtcg tagcacccat    900
gatgaatgga ccagcggtgg tagccgtacc attatgtttc cgtgtcgtac cgttattagt    960
```

```
ccggaaaccg attttctgag cgcagcgtat gaaattcaga atgttcagaa ccgcatctac    1020
atgcacagca attatgatcc ggcactgatt gaagaagaaa tgcgtcgtcg ttatcataca    1080
ccggaaaaca ccacctatga aagctgttat ctgacctatc agccgatgcc ggttcagatg    1140
gataatccgc atctggcagg tattagccag catgcaaaat ggtttgcaaa tggtgcagca    1200
accaaaaaga tgtatctgac cgttagtcat accccctgatg gtggtatgaa tttcagctat    1260
cattatcaga cagcccagct gtgtgaacat gatatggaac tgctgtatta ttacatgatg    1320
cggatcctgt ttaaaggtat tgcagaaccg gatatgagca ttggcgaaat catggaactg    1380
gtctaa                                                                1386
```

<210> SEQ ID NO 11
<211> LENGTH: 1407
<212> TYPE: DNA
<213> ORGANISM: Lachnoclostridium clostridioforme

<400> SEQUENCE: 11

```
atgaaaaccc gcaaaggcta taaagtttat ccgctgacca gcgcacagaa actgcacttt     60
tattgtctga atactgccc gaaaaaacag gtgctgaata ttggtagcag cctgaccatt    120
caggttgatc tggattggga tgttctgaaa gattgtattc gtgaagccat gcacgttgt     180 gataccatgc gtctgcgttt tacccatgat aaagaaggta acgtctatca gtatgtggtg    240
aaagaagaaa ccaaagagat cgagcacttt gattttaccg gttggaaaga gaggacgcc     300 gaaggtaaac tgcgtgaatg gaccgaagtt ccgtttgaac gttatgatag cccgatgcat    360
catattgtga tgattcgtat gccggatggt tatcagggtc tgtatatttg tgttgatcac    420
atgaccatgg atgcacagag cctgattctg tttttccgtg atgttattga actgtacgcc    480
agcaaactgt atgatgaagt tgatcatccg aaagaaatga gcagctatat caaacagctg    540
gaaaaagatc tggcctatga accggtagc cgtgcatgtg agaaagatcg tcagtttttt    600
caagaactga ttgcaagcag cgaaccgatt tttaccgata tttatggccc taaaaaactg    660
tccgatgaac gtaaagcaac ccgtaatccg aaattacgtg cagcaaccaa taccagcgat    720
aatgttgaag ccaacatcac caattttcat ctggaaggtg atagcagcgg tcgtctgctg    780 gattttttgtg aaaaatatgg tattagcatg acctgcctgc tgctgatggg tctgcgtacc    840
tatctgcaga aagaaaatga tcaggatgat gtgagcatta ccaccaccat tagccgtcgt    900
gcaaccctga gcgaaaaacg ttgtggtggt agccgtattc attgttttcc gtttcgtacc    960
attgttccgc gtgaaaatac cttttatgaa ggcctgctga aaatccgtga tgcccagaat    1020
cagtattttc gtcatgcaga ttatagcccg agcgagtatt taactatcg ccacgattac    1080 tacaaactga agatggtca gacctatgaa ccgctgagcc tgacctatca gccgctggca    1140
atgaaatatg atggtcctgg tctggataaa ctgggcgata tcaaatacaa aaccgcacgt    1200
tatagcaatg tgtttgcagc acatacccctg tatctgaccg ttagccatcg tgccgaagat    1260
aatggcctgg atttttggttt tgaatatcag accggtgttg ttacaccgga acgtctggaa    1320
tatatctatt attacctgtg ccgcattatc tttcgtggtg ttgaagatcc ggaacgtacc    1380
gttggtgaaa ttattgaaat ggtgtaa                                        1407
```

<210> SEQ ID NO 12
<211> LENGTH: 1401
<212> TYPE: DNA
<213> ORGANISM: B. producta

<400> SEQUENCE: 12

```
atgaaagaga aatttggcaa accgctgtat ccgctgaccg cagcacagaa actgcatttt    60
ttctatcaga aatactgccc gaaaaaacag gtgctgaata ttggcaccag cctgaccatt   120
cagcagagcc tggattttgg tgcactgaaa gaagcagttt atcaggccta tgcacgttgt   180
gaaagcatgc gtctgcgttt tacccaggat gaagatggtg gtgtttatca gtatattgcc   240
gatcgtgaag aacgcgatat cgaattttt gatttcaccg gttggcaaga atgtcacgcc   300
gaagataaaa tgaaagaatg gaccagcgtt ccgtttgaac gttttgatag tccgctgaat   360
cgtgtggtga tgattattac accggatggt tttcagggta tctatctgct ggttgatcac   420
atgaccatgg atgcacagag cctgattctg tttctgaaag atgtgattga gatctatgcc   480
aacatgaagt atgaaggcat ggaatatccg aaagaaatga aaagctatat cgaacagctg   540
aaaaaagatc tggaatatga agcagatagc cgtgccaaaa aacgtgatac agaattcttc   600
gagaaaatga tcagcagcag cgaaccgatt tttaacagca ttttggtcc gggtaaactg   660
aaagcagaac gcgaaaaaga aaaaaacccg gatattcgtg cagttaccaa tgttagcgat   720
aatgtggatg cgaacattat caccttcag ctggaagcag atccgagcaa tcgtctgatg   780
cagttttgcg aagaacatca tattagcatg gtttgcctgc tgatgatggg tctgcgtacc   840
tatctgcaga aagttaatgg taatgatgac gtgagcatta ataccaccgt tgcacgtcgt   900
gcgaccctga cgaaaaacg ttgtggtggc accgtattc attgttttcc gtttcgtacc   960
gttgtggaaa aaggcgatac ctttatggaa ggcctgaaaa aaatccgtga tggtcagaat  1020
cgtattttc gccatgcaaa ttatgatccg accgcctatt atgcctatcg caacaaatac  1080
tataaactgc gtccgggtca gacctatgaa ccgctgagcc tgacctatca gccgctgaca  1140
ctgaaaggta aaggtatgga acgtctgcag gatattcgct ataaaagcgc atggtatagc  1200
aatggtgcag cagcacatgc actgtatctg accgttatgc atcgtgcgga agataatggt  1260
atgaacttta actttgaaca ccagaccggt gttgtgcatt ttgaagatct gcagtatctg  1320
tactattatc tgtgccgcat tatctttaaa ggcgtggaaa atccggatat gaccgttggt  1380
gaaattctgg aaagcgtgta a                                             1401
```

<210> SEQ ID NO 13
<211> LENGTH: 1416
<212> TYPE: DNA
<213> ORGANISM: C. celatum

<400> SEQUENCE: 13

```
atgatcaaag agaaggacat caaactgtat ccgctgaccg cagcacagaa actgcacttt    60
tataccctga cctattgtcc gaaaaaacag gttctgaata ttggcaccag cctgaccatt   120
aaagaagata tcgattttga agttctgcgc gaagcagttt atcgtgccta tgaacgttgt   180
gaagcaatgc gtattcgttt tgttcatgat gaaagcggta acgtgatgca gtatgttgca   240
gaaaaagaaa cccgctatat cgagttttt gaattcagcc attggaaggt tgaagatgcc   300
gagaaaaaaa tgcgtgaatg gaccgaaaca ccgtttgaac gtgaaaacaa accgctgaat   360
aaagtggtga tgattagcat gccggaaggc tataaaggta tttatctgct ggttgatcac   420
atgaccatgg atgcacagag cctgattgtt tttatgaaag acatcatcga gatctattgc   480
cacctgaaat atgaaggtat tccgtatccg cgtgaaatgg caagctatat tgagcagatt   540
gaaaaagacc tgacgtatga actgggcaac aaagcaaaag aacgtgacga gaattcttc   600
aaagaactga tcgaatgcaa agagccgatc tttaacgata ttgaaggtaa agaacgtctg   660
```

| | |
|---|---|
| cgtctggaac gcctgcagcg tgatagcgaa aatctgcgta gcgtgattaa taccagcaat | 720 |
| aatgtggatg ccaacattac catctttaac ctggaagcac atccgagcca tctgctggaa | 780 |
| cgttttttgtg aagaaaacaa aattccgatg tgtgcctgc tgattatggg tctgcgtacc | 840 |
| tatctgcaga aattcaatga tgaagatgac gtgagcatca tgagcaccat tgcacgtcgt | 900 |
| gcgaccctga gcgaaaaact gagcggtggc acccgtgttc attgttttcc gtgtcgtacc | 960 |
| attgttaaac gcgatatgac ctttatgaa ggcctggaag aaatccgtaa agaacagaat | 1020 |
| aaactgttcc gccacagcaa ttatgatccg gttaaatgtc tggaatatcg tcgcatgttc | 1080 |
| tataataacc tgcctggtga aacctatgaa ccgctgagtc tgacctatca gccgctgacc | 1140 |
| aaaaatgatc tgaaacagcg tccgggtcag accgttagct ttgaaagcat tgattacaaa | 1200 |
| accaactggt atagcaatgg cgcatgtgcc catgcactgt atctgaccgt tatgcatcgt | 1260 |
| gcaagcgata atggtctgga ttttaacttt gaatatcaga ccggtcgtgt gaccacagaa | 1320 |
| aaactggaat acatgtacta ctacctgtgc aaaattctgt ttaccggcat cgagaacaaa | 1380 |
| gataaaaccg tgggtgaaat catcgaaatg gtgtaa | 1416 |

<210> SEQ ID NO 14
<211> LENGTH: 1404
<212> TYPE: DNA
<213> ORGANISM: R. bacterium

<400> SEQUENCE: 14

| | |
|---|---|
| atgcgcaaac ataaaggtta tccggtttat ccgctgaccg ttgcacagaa atttcacctg | 60 |
| ttttatctgc cgtattgtcc gagcgcagca gttatgaata ttggcacccg tctgaccatt | 120 |
| cagagcgaaa ttgattggga tctgctgaaa cagagcattt atcaggccta tgatcgttgt | 180 |
| gaaggtatgc gtgttcgttt cgcaaaagat aaagatggca cctattatca gtacgtggtg | 240 |
| gataaagaag aacgcgatat tgaatttgtg gattttagcc agggcacccct ggaagaggcc | 300 |
| gataagtta tgcagcagtg gaccaccgtt ccgtttccga tggaagatgc accgctgaca | 360 |
| cgtgttgtta tgattagcct gccggatggt tttaatggtg tttattttct gggccatcac | 420 |
| atgattgttg atgcacagag cctgattggt tttctgaaag atatcatcga actgtattgc | 480 |
| agccagaaat atgaaggtgt tccggcaccg aaagaaatgg caagctatat tgagcagatt | 540 |
| cagaaagatc tggcctatga agcaggtagc aaagcacagc tgcgtgatat ggaattttc | 600 |
| cagaaagaaa tcgaaagcag cgagccgatt tataacggta tgaaaggcac cgataaactg | 660 |
| gaagcagcac gtcagatgtt tcagaatccg aatctgcgta ccgcatttaa tgcaagcggt | 720 |
| gataccacct cagcactgga tattttttcat ctggaaggtg aaccgacaca gcgtctgatg | 780 |
| aatttttgtg aagaatatca tgttagcctg gtttgtctgc tgctgatggg tatgcgtacc | 840 |
| tattttcaga aagttaacgg tcatgatgac gtgagcatta taacgccat tgcacgtcgt | 900 |
| gcgaccctga agagaaaaaa tcaggcggt acacgtattc acagctttcc gtttcgtacc | 960 |
| tgtttttcac aggacatgaa attcatcgat gccatttatg ccattcgcga taaacagaac | 1020 |
| gaatatttc gccacgcaaa ttatgatccg accgcatatt ttgcatatcg cagcaaaacc | 1080 |
| tatccgcagc gcatgccgg tctgacctat gaaccgattt cactgaccta tcagccgctg | 1140 |
| acgctgaaag aaaaaggtct ggatcagctg gcgatattc gttataccac caaatggtat | 1200 |
| ccgaatggta tgacaccgca ggcagtttat ctgaccgtta tgcatcgtcc ggaagataat | 1260 |
| ggtctggatt tcaattttga acaccaggtg aaagcattta gccgtgaaga actggaatac | 1320 |
| ttctattatt acctgtgcaa aatcatgttc aaaggcatcg aaaatccgaa cctgaccatt | 1380 |

```
ggcgaaatta tcaaactggt gtaa                                              1404
```

<210> SEQ ID NO 15
<211> LENGTH: 1407
<212> TYPE: DNA
<213> ORGANISM: Unknown
<220> FEATURE:
<223> OTHER INFORMATION: Clostridiales sp.

<400> SEQUENCE: 15

```
atgaaaccc gcaaaggcta taaagcatat ccgctgaccg cagcacagaa actgcacttt         60
tattgtctga aatactgccc gaaaaaacag gtgctgaata ttggtagcag cctgaccatt       120
gaaagcgatc tggattggga tgttctgcgt cagtgtatta agaagccat gcacgttgc         180
gaaagcatgc gtctgcgttt tgccaaagat cgtgatggta catttatca gtatgtggtg       240
aaagaagaaa ccaaagagat cgagcacttt gattttaccg gttggcaaga ggaagatgcc     300
gataaaaaac tgcgtgaatg gaccgaaatt ccgtttgaac gttatgatag ccctatgcat     360
cgtatcgtga tgattaaaac accggatggt tatcagggtc tgtatatttg tgttgatcac     420
atgaccatgg atgcacaggc actgattgtt ttttttcaaag atgtgatcga gctgtattgc   480
agccgtctgt atgaagaagt taactatccg aaagaaatga gcagctatat cgccagctg     540
gaaaaagatc tggcctatga agcaggtagc cgtgcatgtc agcgtgatcg tgaatttttt     600
gaaaatctga ttgcaagcag cgaaccggtt tttgcagata tttatggtcc gggtaaactg     660
ctgaaagaac gtaaagaaag ccgcaacaaa aagctgcgtg cagcaaccaa taccagcgat     720
aatgttgaag ccaacatcac caatttttcat ctggaaggtg gtccgagcaa acgtctgctg   780
gatttttgtg aagaaaaagg cattagcatg acctgtctgc tgctgatggg tctgcgtacc     840
ttcctgcaga agaaaaatga tgaagatgat atcagcatca ccaccaccat tgcgcgtcgt     900
gcaaccctgt tagaaaaacg ttgtggtggt agccgtattc attgtttttcc gtttcgtacc   960
attgttccgc gtgaagatac ctttatggaa ggtctgctga aaatccgtga tgcacagaat    1020
cagtattttc gtcatgcagg ttatagcccg agcgaatatt tcaatttttcg ccacgattac  1080
tacaaactga agatggtca gacctatgaa ccgctgagcc tgacctatca gccgctggca    1140
atgaaatatg atggtcctgg tctggataaa ctgggcgata tcaaatacaa aaccgcacgt    1200
tatagcaatg gtgttgcagc acatacctg tatctgaccg ttagccatcg taccatggat     1260
aatggcctgg atttttggttt tgaatatcag accggtgttg tgacaccgga aaaactggaa    1320
tatatctact attatctgtg ccgcattatc tttcgtggtg ttgaagatcc ggaacgtacc    1380
gttggtgaaa ttatggaaat ggtgtaa                                          1407
```

<210> SEQ ID NO 16
<211> LENGTH: 1416
<212> TYPE: DNA
<213> ORGANISM: E. rectale

<400> SEQUENCE: 16

```
atgaaaccc gcaaaggcca taatgtttat ccgattaccg ttgcgcagaa attccatctg        60
tattatgcaa atattgccc gaatatggcc gtgctgaata ttggcaccag cctgaccatt     120
ggcaccgaac tggattggaa tgtgctgcgt gatagcatta actatgccta tgcacgtaat    180
gaagcaatgc gtattcgttt cacccgtgat aaagatggtg agtgctatca gtatattgcc  240
gatgtggatg aagatttttaa agaacgcacc gtggatttca agatttttac cgatgttacc    300
```

```
atggaagagg ccgaaaatga aatgcaaggt tggacccagg ttccgtttga atttgaagat      360
agcccgatga ccaaaatcgt gatgatcaaa atgccggatg gttttaacgg tgtgtatttt      420
ctgggtcatc acatggttgt tgatgcacag agcctgattg catttctgaa agatatcatc      480
gagatctact gcaacgcaat gtatgaaggt gttccgtttc ctaaagatat gtgcagctat      540
atcgagcagc tgaaaaaaga tctggcctat gaagcaggta gcaaagcaca gctgcgcgat      600
cgtgaatttt ttgaaaaact gattcgtcag agcgagccga tttataacgg tattgatggc      660
accgcaaaac tggatgcagc acgtgaactg atgcatgata taaaactgcg tagcgcattt      720
aacgccagtg atgatgtgac cagcgcactg gatattttc atctggaagc agaaccgacc      780
aaacgtctga tggattttg tgagaaatat catattagcc tggcatgtct gctgctgatg      840
ggtattcgta catttttcca gaaagaaaac ggctttgatg acgtgagcgt taataatgcc      900
attgcacgtc gtgcgaccct gaaagagaaa aaatcaggcg gtacacgtat tcacagcttt      960
ccgtttcgta cctgttttag caaagatgtg cgtttttattg atgccgtgta taccattcgc     1020
gataaacaga atgaactgtt tcgtcacgca aactataatc cgaccgaata tttcgccctg     1080
cgtagcaaaa cctatccgca gccgaaagcc ggtctgacct atgaaccgat gagcctgaca     1140
tatcagccga tgacactgaa agaaaaaggt ctgaatgatc tgggcgacat caaatacaaa     1200
accaaatggt atccgaatgg catgaccaca caggcaatgt atctgaccgt tatgcatcgt     1260
ccggaagata atggtctgga tttcagcttt gaacatcagg ttaaagcagt tagccgtaaa     1320
cagctggaat acatgtacta ttacctgtgc aagatcatgt ttaaaggtgc cgaaaatccg     1380
gaactgacga ttggtgaaat tatcaaactg gtgtaa                              1416

<210> SEQ ID NO 17
<211> LENGTH: 1560
<212> TYPE: DNA
<213> ORGANISM: C. eutactus

<400> SEQUENCE: 17
atggaagaga acattctgga aatcgtggaa aaagctgtc gcattcatcg tgatgttatc       60
gccgttaaat atctgagcca tcgtgagatt gttgagaaaa gctatggtga tatgtgggat      120
gatattcgta aaaccgcagt gattctgcgt aataatggtc tgtgtggcac ccatattgca      180
ctggttggta gcagcagcta tgaatggatt tgtgcatata tggccattct gtttaccggc      240
aataccgcag ttccgctgga tgcaaatctg agcgttagcg aactgcatga actgctgaat      300
cgtagcggta gcattgcact gttttgtggt gcaagccgta agatgttat taccgaactg      360 accgatgatt gtccggaaat gaatattgtg ttcaccatgg aaaaaaagt ggacatcgaa      420 catctggaag tgcagatag caatccgcag ctggcaattc tgagctttga acagctgcgt      480
aatgaaatta ccattccgga tgattttgca ttcgccgatc aggataaaga taaaatgtgt      540
accctgatgt ataccagcgg caccaccggt aaaagcaaag tgttatgct gagccagttt      600 aatctggcac agaatgttga aaacgtgtac gttaatctgg aaccgggtgt taccattctg      660
agcgtgctgc cgattcatca tgcattttgt ctgaccatgg aatggatgaa aggtattagc      720
ctgggtgcaa ccatttgcat taatgatagc ctgctgcaca tgctgaaaaa catgaaacgt      780
tttcagccgg ttggtatgct gatggttccg ctgatggtgg aaaccattta caaaaaactg      840
aaagatgtga atccgctgct gccgaaaaaa ctggttgcaa agaagcattt ggcggtaaa      900 ctggaatata tctttgcgg tggtgcatat ctggatccga tgtatgttac cgagttaa        960 aagtatggca tcgatatcct gcaaggttat ggtatgaccg aatgtagtcc ggttattgc     1020
```

```
agcaataatc accgttataa tcgtccgggt agcgttggta aactgctgga taattgtgca    1080
gttcgttttg tggatgaaga gattcaggtt aaaggcacca gcgttatgag cggttattat    1140
gatatgccga acgaaacagc cgaagcattt caggatggtt ggctgtgtac cggtgatctg    1200
ggttatctgg atagtgatgg ctttatgtat attaccggtc gcaaaaagaa cctgattatt    1260
ctggccaatg gcgaaaacat tagtccggaa gaactggaag gtaaactgag tattgaaccg    1320
ctgattagcg aaattgtgat tacaggtgat ggtaatcatc tgaccgcaca tatttatccg    1380
gatcaggatt tcgtggacaa aaaacacatg gatgcagcac gtaccagcga aaaactgcag    1440
aaaattatcg acaccttcaa caaaaatcag ccgacctata aacgtattag cgcactggat    1500
attcgcaaag aaccgtttga aaaagcagc accaaaaaga ttaaacgcaa cctggtgtaa    1560
```

<210> SEQ ID NO 18
<211> LENGTH: 1554
<212> TYPE: DNA
<213> ORGANISM: M. formatexigens

<400> SEQUENCE: 18

```
atgctgattc gcgatattat tgaagaaagc ggcaaaaaat acgcaggcat taccgcaatt      60
aaatggctga aaagaaaga aatcatggaa atgagctatc gcgaactgct ggaaaatgca     120
gcagccgttc gtcgtggtct gctggccgaa ggttttgccg gtgcacatct ggcactgatt     180
ggtagcagca gcgcagaatg ggttgaaagc tatctgggta ttattaccgg caataccgtt     240
gcagttccgc tggatgcaaa tctgcctggt gaagatctgg ttgatctgct gaatcgtagt     300
gatgcagcag gtctgtttct gagcaccaaa cagaaaggcc tgctgggtca gattctggat     360
gaatgtccga aactgaaaaa aatctggatg ctggaagatg ccgttgaacc gggtaatgca     420
agcggtgcag aagttaccag cctggcagat ctgaaagcag ccggtgcagg tagcgttgca     480
gatgcagatc gtccggatcc tgaaagcatt gcaaccatta tctttaccag cggcaccacc     540
ggtaaaagca aggtgttat gctgacccag aaaaacctgg ccgaaaatgt taaaagcgtt     600
cagtataccg cagaaccggg ttcagttctg ctgagcgttc tgccgattca tcatgcattt     660
tgtctggtta tggattggct gaaaggtttt agcctgggta caaccgtttg tattaatgat     720
agcctgctgc acatggtgaa aaatatgggt gtgtttcagc cgcaggtaat gctgatggtt     780
ccgctgatgg tggaaaccat ctataaacgt ctggcaggcg cagatgcaag cattccgaaa     840
caaatggttg ccaaagcagt ttttggtggt cgtctgcata ccattttac aggtggcgct     900 catctggatc cgtattatat cgatcgtttt gccgaatatg gtgtggaagt tctggaaggt     960
tatggtatga gcaatgtag tccggttatt agcagcaata caccggaaga tcataaaaaa    1020
ggtagcgtgg gtcgtccgct gccgaatgtt gaactgagct ttgataatgg tgaaattctg    1080
gttcgtggtt ccagcgttat gaaggttat tatcagatgc gcaagaaac cgcagatacc    1140 ctgaaagatg gttggctgca taccggtgat aaggttatc tggatgagga tggttttctg    1200
tttattaacg gtcgcgtgaa gaacctgatt attctgagca atggcgaaaa cattagtccg    1260
gaagaaatcg aaaataaact ggcactgggt gcactggttg gtgaagttat tgttaccggt    1320
gaaaataatg gtctgaccgc acgtatttat cctgatccgg atgttgttgc agcaaaaggt    1380
atggatgcag aagcagttca gaccgaactg caggcatttc tggatcagta caataaaacc    1440
cagccgagct atcgtcagat taccggtctg gttgttcgta aaaatccgtt tatcaaaagc    1500
gcgacccgta aaatcaaacg tcaagaggtt ctggtggatg aaccgtgtgc ataa          1554
```

<210> SEQ ID NO 19
<211> LENGTH: 1509
<212> TYPE: DNA
<213> ORGANISM: Lachnoclostridium clostridioforme

<400> SEQUENCE: 19

```
atggcagcag aaaccctgcg tgatgttatt cgtcatggtg ccgaagccta tggtgaacag      60
accgcatttc gttacaaagt gaaaaaagag atcatcgata aaagctacaa cgaggtgaat     120
ctggatagca tggcagttag ccgtgcagtt gaagcactgg gtatgaaagg taaacatatt     180
gccgttattg gcaccaccag ttatcagtgg attaccgcat attttggcat tgttaatagc     240
ggtagcgttg cagttccgat tgatgcacag tttccagccg aagcaatttg tgaactgctg     300
aatcgtgcag atgttgaaat gctggtttat gatgaactgc gtagtgatgt tgccggtgat     360
gttcgtgaaa atgtccggg tattcgccat gttgttagca tgcaggcaca agaaacagcg     420
ggtgatgtgc tgagcctgag ccgtctgatt gcagaaaatg caggtacgta tgaaaccgaa     480
ctgagcggta gccagctgtg taccattctg tttaccagcg caccaccgg tcgtagcaaa      540
ggtgttatgc tgagccatcg taatctgacc gataatgcag tttgtctgga tatgaaaatt     600
ccggcaggca ccgttagcat gaccctgctg ccgattaatc atgtttattg tctgaccatg     660
gacatcatca aggtctgta tattggcatg atcatctgca tcaacgatag cattatgcat      720
gtgcagcgta acatgaaact gttcaaaccg gaaattgttc tgctggttcc gctggttatt     780
gaaagcattt atggcaaact gaaagatgcc ggtagcctga ttccgaaaaa aatggttgca     840
aaagcagcct ttggtggtaa tctgcgtatt atttgtagcg gtggtgcata tctggatccg     900
gattatgttg atcgctttaa agaatatggc atcaccattc tgcaaggtta tggtatgacc     960
gaatgtagtc cggttattag caccaatctg gaatgggaaa acaaaaaagg tagcgtgggt    1020
aaactgctgc ctaattgtga agcaaaagtt gtggatgaag aaatttgggt tcgtggtagc    1080
agcgttatgc agggttatta caaaatgccg gaacgtaccg cagaaacact ggaagatggt    1140
tggctgaaaa ccggtgatct gggctatgta gatgaagata ctttgtgta tattaccggt    1200
cgccgtaaaa acctgattat tctggcaaat ggtgaaaacg ttagtccgga gaactggaa    1260
aatgaactga ccgttcaga actggttaaa gaaattctgg tgcgcgagaa agataaaatc    1320
attgaagccg aagttttccc ggattacgaa tacgcaaaaa agaaacacat caaagatatt    1380
cgtggcaccc tgcaagaact gattgatggt tttaacaaag atatgccggt gtacaaacgc    1440
atctatagtc tgattgttcg cgaaaccgaa tttgaaaaaa ccccgagcaa aaaaatcaaa    1500
cgcttttaa                                                            1509
```

<210> SEQ ID NO 20
<211> LENGTH: 1515
<212> TYPE: DNA
<213> ORGANISM: B. producta

<400> SEQUENCE: 20

```
atgagcggca aaatcaacac catgaaagat atcattgatt atgcagccga aacctatggt      60
gatgcaccgg caattcgtta taaagttcgt aaagaagtta tcacccgtac ctttcgtgat     120
ctgaaacgtg atagcgaagc attttgtcgt gcactggata gcatgggtat gctgggtaaa     180
catgttgcag ttattggtcc gaccacctat gaatggattc tggcatattt tggtgcagca     240
aatagcggtt gtgttattgt tccgctggat gcacagctgc ctgcagcaga tgttgtgaa     300
ctgctgaatc gtgcagatat tagcgttctg gtttatgatg aactgcgtcg tgatgttgca     360
```

| | |
|---|---|
| gaaatggcaa aagaaaaatg tccgcaggtt cgttttatgg ttagcatgca ggcagaaaaa | 420 |
| gataaagaac aggttctgag cctgaccagc ctgctgaaaa acatgcagg tagctttagc | 480 |
| tgtgaactgg atccggataa actgtgtgca attctgttta ccagcggcac caccggtaaa | 540 |
| agcaaaggtg ttatgctgac ccatcgtaat ctgaccgata atgcagtttg tctggatatg | 600 |
| aaaattccgg caggcaccgt tagcatgacc ctgctgccga ttcatcatgc atattgtttt | 660 |
| accatggata tcctgaaggg catctatatt ggtatggtga tttgcatcaa cgacagcatt | 720 |
| atgcatgtga gcaaaaacat gaaactgttt aagccggaaa ttgttctgct ggttccgatg | 780 |
| gttattgaga gcatttacaa aaagctgaaa gaaagcaccg tatcctgcc gaaaaaaatg | 840 |
| gttgcaaaag cagcatttgg tggcaacctg aaaaccattt gtagcggtgg tgcatatctg | 900 |
| cctccggaaa tggttggtgc atttgccgaa tatggtatta ccattctgca aggttatggt | 960 |
| atgaccgaat gtagtccggt tattagcacc aatctggaat gggatagcaa agaaggtagc | 1020 |
| gttggtcgtc tgctgcctaa ttgtgaagca aaagttgtgg atgaagaaat ttgggttcgt | 1080 |
| ggtagcagcg ttatgatggg ttattacaaa atgcctgcag aaaccgaaga ggcactggaa | 1140 |
| gatggttggc tgaaaaccgg tgatctgggt tatgttgatc aggatgattt tgttttttctg | 1200 |
| accggtcgca aaaagaacct gattattctg aaaaatggcg agaatgtgtc accggaagaa | 1260 |
| ctggaaaatg aaatcagccg tagtccgctg gtgaaagaaa ttattgttcg tgaaaccgaa | 1320 |
| agcgtgattg aagcagaaat ttttccggat tatgagtatg ccagcaaaaa acgtattcgt | 1380 |
| gatgtgcgtg aaaaactgca agaagtgatc gataaactta atcgtggtct gccaccgtac | 1440 |
| aaaaaaatcc atggtctgaa aattcgcgag gaagaatttg aaaaaacccc gagcaaaaag | 1500 |
| atcaagcgct attaa | 1515 |

<210> SEQ ID NO 21
<211> LENGTH: 1527
<212> TYPE: DNA
<213> ORGANISM: C. celatum

<400> SEQUENCE: 21

| | |
|---|---|
| atgaacaaca tcaaaaacat gcgcgacatc attgatttcg cagccaaaaa ctatggcgat | 60 |
| aatatcgcgt tcaagtataa aatcaacaaa aacgaagtgg atgaaaaaag ctataacgat | 120 |
| ctgaaaaacg atagcgaagc agttagcaat gcactgaaaa gcctgaatat gattggtaaa | 180 |
| catgttgcca ttgttggcca gaccagctat ccgtggattg ttagctattt tggtgttgtt | 240 |
| aatagcggtg tgttattgt tccgattgat gttcagctgc ctgcagatga tatttgcgaa | 300 |
| ctgattgaac gtagtgatgc cgaaattctg atctatgatg aaattcgtca tgatgtggcc | 360 |
| gaacgcatta agaaaaaag ccacaacgtg aagtacatca tcagcatgaa tgaaaaactg | 420 |
| aacaccgaat ttgcactgag cctgaatgaa ctgatggcag aaaatcgtag cagctttcat | 480 |
| atcgaaatcg acgaagaaaa actgtgcacc attctgttta ccagcggcac caccggtaaa | 540 |
| agcaaaggtg ttatgctgaa tcatcgtaac ctgaccgata atgccattgc attcgatgtg | 600 |
| cagctgaaag caggcaccgt tagcatgacc gttctgccga ttaatcatgt ttttttgcttc | 660 |
| accatggata tcctgaaagg tattcatctg ggtctgtgca tttgcattaa tgatagcgtt | 720 |
| atgcgcgtgc tgaaaaatct gaaactgttt aaaccgcagg ttatgtgtct ggtgccgatg | 780 |
| attattgaaa gcctgtataa caactgatc gacgagagca agatatctg caaagaagtt | 840 |
| gttgccaaag ttgccttagg tggtaatctg aaaaccattt atagtggtgg tgcatatctg | 900 |

```
aacccggaaa ttattgatgg catgaacgat tttggcatcg aagtgattca aggttatggt    960
atgaccgaat gtagtccggt tattagcacc aacaataact gcgaattcaa acgtgaaagc   1020
gtgggcaaac tgattagtaa ttgtgaagcc aaaatcattg atgaagagat tggggttcgt   1080
ggtagcagcg ttatgatggg ttattacaaa atgccgaaag aaaccgaaga ggcactggtt   1140
gatggttggc tgaaaaccgg tgatctgggt tatatcgatg aagataactt tgtgtttatc   1200
accggtcgca aaagaacct gattattctg agcaatggcg aaaatgttag tccggaagaa   1260
ctggaaaatg agctgagcaa agccgtctg atcaagaaa ttctggtgag cgagtacaag    1320
aacatcatta agcggaaat tctgccggat tatgagtatg ccaataacaa cggcattaac   1380
gatatcgaaa acgaaattcg caatctggtg acaaatata actgtgaact gccgacctat   1440
aaacgcattg gtatggttat tattcgcgat accgaattcg aaaaaccac gagcaaaaaa   1500
atcaaacgcg agtacaccaa agtgtaa                                       1527

<210> SEQ ID NO 22
<211> LENGTH: 1506
<212> TYPE: DNA
<213> ORGANISM: R. bacterium

<400> SEQUENCE: 22
atgaccagca ccattcgtga aattctggtt gaagcacagc agcgttttgg tccggaagtt     60
gcagttcgtt ataaagtggg taaaaaccag atcgaggaca aaacctataa tcagctgcgt    120
caggatagcg aaagctttag cagcgcactg gcagcactgg gtgaacaggg tagccatatt    180
gcagttattg gtccgaccag ctatcgttgg atggttacct atctgggtat tgttaatagc    240
ggtagcgttg ccgttccgct ggatgcaagc ctgcctgcag cagatgtttg ggaactgctg    300
gatcgtgcag atgttaccac actggttgca gatgcagcac gtaaagatgt tgcagaaggt    360
gcaaaagaac attgcccgaa actgaaacat gttgtgatta tgcagcaaga gaacatagc    420
gacgcagcac tgtttctgcc gcagctgctg gccgaacatc agaccgcatt tgattttgaa   480
ccgcagccgg atcagctgtg taccattatg tttaccagcg gcaccaccgg taaaagcaaa    540
ggtgttatgc tgacccatcg taatctggca gaaaatgcag gtagcattaa tatggatctg   600
ccggaacgta tggttctgct gagcgttctg ccgattcatc atgcatattg tctgtgtctg    660
gatgtgctga agcaattag cctgggtagt attatttgca ttaatgatag cctgctgcgc    720
gtgatgaaaa acattcagct gtttaaaccg gaaatgattc tgatggttcc gctgatgatt    780
gaaacgattg caaaaaagct ggaagataat accctgctgc ctccgaaact ggttaaaaat    840
gcagttttg gtaagcagct gacgaaaatt agcagcggtg gtgcatatct ggatccgagc    900
tatattgacc tgtttgagaa atatggcatc accattctgc aaggttatgg tatgaccgaa    960
tgtagtccgg ttattagcac cacacgtccg tggaacatta caaaaatgc cgttggtcag   1020
ctgatcgata ttgtgaagc aaaaaccgtt gatggtgaac tgtgggttcg tggtagcagc   1080
gttatgcagg gttattacaa atgccggaa gaaaccgcag caaccctgga agatggttgg   1140
ctgaaaaccg gtgatctggg ttatgttgat gaagatggct tgtttatct gaccggtcgc   1200
aaaaaaaaacc tgatcatcac caaaaatggc gaaaatgtta gtccggaaga actggaaaat   1260
aaactgggtg ttgaacgcct gattcaagaa gttctggttc gcgaaaacaa agcgttatt   1320
gaagcagaaa tcttcccgga ttatgagtac gccaaaaaaa agcacattaa agatgtgcgt   1380
gcagccctgc aagaaatcat tgatcagtat aatctgcagg caccgcctca caaaaaaatc   1440
tatagcctga ttgttcgtga aaccgagttt gaaaaaaccc cgagcaaaaa gatcaaacgc   1500
``` ttctaa                                                        1506

<210> SEQ ID NO 23
<211> LENGTH: 1509
<212> TYPE: DNA
<213> ORGANISM: Unknown
<220> FEATURE:
<223> OTHER INFORMATION: Clostridiales sp.

<400> SEQUENCE: 23
atgccggttg gcaccctgcg tgatattatt cgtcatggtg cagatgccta tggtagccag      60
accgcatttc gttataaagt gaaaaaagaa atcgtggacc gcacctatct ggatgttaat     120
cgtgatagca tggcagttag ccgtatgctg gaaagcatgg gtatggaagg taaacatatt     180
gcactgattg gcaccaccac ctatcagtgg attgttggtt attttggtat tgttggtagc     240
ggtagcgttg cagttccgat tgatgcacag ctgcctgcag atgcagtttg tgaactgctg     300
gaacgtgcag atgttgaaat gctgattttt gatgaaattc gtcgtgatgt tgccaaagcc     360
gttaaagaaa atgtccgag cgttcgttat attgttagca tgcaggccga agaagcaggc     420
gacggtattc agagcctgag catgctgatg gcactgcatg ccggtgaata tgaaaaagaa     480
ctgagcggtg atcagctggc aaccattctg tttaccagcg gcaccaccgg taaaagcaaa     540
ggtgttatgc tgagccatcg taatctggtt gataatgccg tttgtctgga tatgaaaatt     600
ccggcaggca ccattagcat gaccctgctg ccgattaatc atgtttattg tctgaccatg     660
gacatcatca aggtctgca tattggtctg gtgatttgca ttaacgatag cattatgcat     720
gtgcagcgca acatgaaact gtttaaaccg gaaattgttc tgctggttcc gctggttatt     780
gaaagcattt atggcaaact gaaagatgcc ggtagcctga ttccgaaaaa atggttgca     840
aaagcagcct ttggtggtaa tctgcgtatt atttgtagcg gtggtgcata tctggatccg     900
gattatgttg ataagttcaa agaatacggc atcaccattc tgcaaggtta tggtatgacc     960
gaatgtagtc cggttattag caccaatctg gaatgggaaa acaaaaaagg tagcgtgggt    1020
aaactgctgc ctaattgtga agcaaaagtt gtggatgaag aaatttgggt tcgtggtagc    1080
agcgttatgc agggttatta caaaatgccg gaacagaccg cagaaaccct ggaagatggt    1140
tggctgaaaa ccggtgatct gggctatgtt gatgaagatc gttttgtgta tattaccggt    1200
cgtcgcaaaa acctgattat tctggcaaat ggtgaaaacg ttagtccgga agaactggaa    1260
aatcagctga gccgtagcga actggtgaaa gaaattctgg tgcgtgaaaa agataaagtg    1320
atcgaagcag aaatcttccc ggattacgaa tacgccaaaa aaaagcatgt gaaagacgtt    1380
gaagggaaac tgcaagaact ggtggatgat ttcaataaag atatgccggt gtacaaacgc    1440
atctatagtc tgattgttcg cgaaaccgaa tttgaaaaaa ccccgagcaa aaaaatcaaa    1500
cgcttttaa                                                             1509

<210> SEQ ID NO 24
<211> LENGTH: 1515
<212> TYPE: DNA
<213> ORGANISM: E. rectale

<400> SEQUENCE: 24
atgctgtttc ataccattcc ggatattctg agctatgcca tgaagcctat ggtgcagat       60
gatgcaattc gttggaaaaa agcaaaaac gaaattgaga ccgcaccta tagcgaactg      120
aaaaatgata ccgatagctt tgccaacgcc attgaaaaac tgggtaaaaa aggtcagcat     180

| | | |
|---|---|---|
| atcgcagtta ttggtccgag cagctatgaa tggattgtta gctatctggc aattaccgaa | 240 | |
| agcggtagcg ttgcagttcc gattgatgca agcctgcctg cagcagatat ttgtgaactg | 300 | |
| ctggatcgtg caagcgttcg tatgctgatt tttgatgaag cacgtagtga tgttgcagaa | 360 | |
| gcagcagcaa aaagctgcca tgatattaat gtttacgtga gcatgaacag caccgaacat | 420 | |
| tgtccgcagg ttctgagctt taaaggtctg attgatgata tcgcggtag ctatgaaccg | 480 | |
| gcagttgccg aagatgcact gtgtaccatt atgtttacca gcggcaccac cggtaaaagc | 540 | |
| aaaggtgtga tgctgaccca gaataatctg cagaaaatg caacctgtct ggacatgaaa | 600 | |
| attggtccgc ataccgtgat tctgagcgtt ctgccgattc atcatgcata ttgtctgagc | 660 | |
| atggatatcc tgaaaggtat tagcctgggt agcgtgattt gtattaacga tagcattatg | 720 | |
| cgcatggcca aaaacattca gctgtttaca ccggatatga ttctgatggt tccgctgatg | 780 | |
| attgaaacct ttgcacgtaa actggaagaa gttcgcgcag caggtctgcc tgccgaaccg | 840 | |
| gtgcgcaaaa aaatgtttgg tgaacgtctg cataccattt gtagcggtgg tgcatatctg | 900 | |
| aacccggatt atgttgacct gtttgccgaa tttggtatta ccattctgca aggttatggt | 960 | |
| atgaccgaat gtagtccggt tattagcacc aatctgagct gggatattcg taaaaatagc | 1020 | |
| gtgggtaaac tgatgccgaa ttgtgaagcc aaaaccgttg atggtgaact gtttgttcgt | 1080 | |
| ggcaccagcg ttatgcaggg ttattacaaa atgccgaaag aaaccgaaga aaccctgagt | 1140 | |
| gatggttggc tgcataccgg tgatctgggt tatgttgatg aagatggtta tatctatctg | 1200 | |
| accggtcgtc gcaaaaatct gattattacc aaaaatggcg aaaacgtgag tccggaagaa | 1260 | |
| ctggaaaatg cactgagcgt taatcacctg atcaaagaaa ttattgtgcg cgaaagcgaa | 1320 | |
| ggtgttattg aagcagaaat ttttccggat cgtgaatatg cacagaatac cggcattgca | 1380 | |
| gatattcgtt cagcactgca ggcactgatc gatgaatata atgttaatgc ccctgcctac | 1440 | |
| aaacgcatct atagcattaa agttcgtgaa agcgaattcg aaaaaaccgc aagccgtaaa | 1500 | |
| atcaaacgca gctaa | 1515 | |

<210> SEQ ID NO 25
<211> LENGTH: 960
<212> TYPE: DNA
<213> ORGANISM: Lachnoclostridium clostridioforme

<400> SEQUENCE: 25

| | | |
|---|---|---|
| atgggtatta aaggctggat tctgggttta gcagcagccg gtgcagcggg tgaatatggt | 60 | |
| attgcacgtt atttctttca tcgtaccgtt gttcgtggta atgcaaaacg tgatcgtacc | 120 | |
| cgtaaaatgg caggcaccga ttgggatgca tatattccgg gtattcgtgc aagccgtgaa | 180 | |
| tggctggcag gtcagccgca agaagaagtg tatattacca gccgtgatgg tctgcgtctg | 240 | |
| catggcacct ttttttgttg tgaaggtagc ggtaaagccg ttgtttgttt tcatggttat | 300 | |
| accagcgaag gcctgaatga ttataccagt attgccaaat tctatctgag ccagggtttt | 360 | |
| agcctgatgg cagttgatga acgtgcacat ggtaaaagcg aaggcaccta tattggtttt | 420 | |
| ggttgtctgg atcgtaatga tgcaaaacag tggatggaat acatggttga acgtctgggt | 480 | |
| gaagattgtg aactgatgct gcatggtatt agcatgggtg cagcaaccgt tctgatgagc | 540 | |
| accggtctga atctgccgaa acaggttcgt gcagcagtta gcgattgtgc atttaccagc | 600 | |
| gcatgggaag ttttttagcca tgttctgcgt agcatgtatc acatgcctgc atttccggtt | 660 | |
| atgcagattg cagatcgtat ggcacgtagc gaagcaggtt atggtctgga tgaatgtaat | 720 | |
| gcacgtgaag aagttaaaaa agcccgtatt ccgatcctgt ttattcatgg tgatcgtgat | 780 | |

| | |
|---|---|
| acctttgttc cgtgtagcat ggtttatgaa ctgtatgaag catgtgcaag cccgaaagaa | 840 |
| ctgctggtga ttccgggtgc aagccatgcc gaagcatact ataaagaagc agatcgttac | 900 |
| gaacatgcca tcgaagaact gattgcccgt ttttttggca agaagagaaa caaagtctaa | 960 |

<210> SEQ ID NO 26
<211> LENGTH: 1020
<212> TYPE: DNA
<213> ORGANISM: B. producta

<400> SEQUENCE: 26

| | |
|---|---|
| atgaatggtt ggagcctgct gttaggtgcc ggtgcactgg cagcagccgg tgaatatggt | 60 |
| attgcaagct attttttccg tcgtaccatg ctgcgtcaga atgcagcaac caaacgtacc | 120 |
| atggatatgg caggtacaaa ttgggatctg tatattccgg aaatcggcaa aatgaaacag | 180 |
| tggatgctgg aacaagaacg cgaagatgtt tatattcgta gcggtgatgg tctgaaactg | 240 |
| catggcacct ttttccagg tcaaggtagc ggtaaactgg tgatttgttt tcatggttat | 300 |
| accagcaaag gcatgagcga ttatattggt ctgagcaact attatctgcc tcgtggttat | 360 |
| cagatgctgc tggttgatga acgtgcacat ggtgatagcg aaggcaccta tattggtttt | 420 |
| ggttgtctgg atcgtgaaga tgcactgctg tggattacct atgcagttaa acgttttggt | 480 |
| agcggttgtc agatttggct gcatggtaca agcatgggtg caagcaccgt tctgatggca | 540 |
| agcggtctga aattaccgcc tcaggttcgt ggtattgtta gcgattgtgc atttaccacc | 600 |
| gcatgggatg tttttgcaca tgttctgaaa gatcagtatc atctgcctgc atatccgatc | 660 |
| ctgaaactga gcgatagcat gtgtcgtaaa aaagcaggtt atggcctgaa acaatgtagc | 720 |
| gcaagcgaag aagttaaacg cgcaaaagtt ccgattctgt ttattcatgg tgatgccgat | 780 |
| acctttgttc cgtgtcgtat gtgctatgaa atctatgaaa attgcgccag caaaaaagac | 840 |
| atgctgattg ttcatggtgc aggtcatgtt gaagccttct ataaagaaca ggcactgtat | 900 |
| gaacagaaac tgaccgaatt tctggaaacc gcaggcgaag catgggcacc agcaggtaaa | 960 |
| agcatttatg ttagtgatgt taccggtgaa ggtagcaccg tgatagtgt tccggtttaa | 1020 |

<210> SEQ ID NO 27
<211> LENGTH: 990
<212> TYPE: DNA
<213> ORGANISM: C. celatum

<400> SEQUENCE: 27

| | |
|---|---|
| atgagcaaac gcctgtttat tggtgcaggt attattggtc tggcagcact gaccgaagtt | 60 |
| gttatggcac gttatctgct ggaacgtgtt ctgattcgta aaaacgttaa aaccgaacgc | 120 |
| acccagaaaa tgagcggtac aaattgggat aactatatcc cgtttatcaa agaacgtaaa | 180 |
| gcatggctga tgctgcaaga acgtgaagat gtgtatatta ccagtgatga tggtctgcgt | 240 |
| ctgcatggtg ttctggttcc gaatgaaaat agcaaaaaaa ccgtgatctg cttccatggc | 300 |
| tatagcagca aggtgcaac cagcgatttt gcagcaatta gcaaattcta caaagagaac | 360 |
| gactttaaca tcctgatggt tgatgcacgt gcccatggtg aaagtgatgg caaatatatc | 420 |
| ggttttggtt gtctggatcg tatggatgtt ctgaaatgga ttaactacgt ggtggaaaaa | 480 |
| tttggcgaag aatgtcagat tctgctgcat ggtattagca tgggtggtgc aaccgtggtt | 540 |
| atggcaagcg tctgcatcct gccgaataat gtgaaattta tcattagcga ttgcgccttt | 600 |
| accagtccgt gggaagtttt tagtgatgtg ctgaaaaaca tgtatcacat tccgcctttt | 660 |

```
ccggtgatta acattgttag caacatgtgc aaaaagatgg caggctacaa ctttaaagaa    720
tgcaacgccg atattgaagt tcgtcgtgcc accgttccga ttctgtttat tcatggtgca    780
aatgatacct tgttccgtg tcgtatgtgc cacgatattt atgataattg ccacagcgat    840
aaagaaatcc tgattgttaa agaagcaggt cacgcagaga gctattacaa agaaaccgaa    900
atctacgaag aaacatcaa aaaattcatc agcaaataca tcctggatga aattggcgca    960
ggcaataacg ataaacgcaa acgctattaa                                    990

<210> SEQ ID NO 28
<211> LENGTH: 939
<212> TYPE: DNA
<213> ORGANISM: R. bacterium

<400> SEQUENCE: 28
atgggcctgc tgaaaaaagc agcagttctg gcaggtctgg cagcagcagc cgaaggtctg     60
ggcaccgcat atttctatcg tcgtaccatg attcgtacca atgcaaaacc ggaacgtagc    120
gcaaaaatga gcggtattga ttggagccag tattatccgc gtatgcatga aaatcgtgat    180
tggctgctgc aacagccgca tgaagaagtt ggtattctga ccatgatggg tctgaaactg    240
catggcacct atttttccagg tccgggtaat aaagttgtga tttgctttca tggctatacc    300
agctatggta tgggtgaata tccgagcctg gcacgttgtt ttatgagccg tggttttggt    360
gcactgatta ttgatcagcg tagccatggt gaaagcgaag caaatatat cggttttggt    420 tgtatggatc gtctggatgc actggaatgg attcgttgga ccattgataa agttggtcag    480
gatgcacaga ttattctgca tggtggtagc atgggtggtg caaccgtttg tatggttagc    540
ggtctggatc tgcctccgca ggttaaaggt attattagcg atagcgcatt tacgagcccg    600
aaatatgttt ttacccatgt tctgcacagc atgtatcatc tgcctgcaac accgatgatt    660
ccgctggcag ataaagttaa taaacgcctg gcaggttatg gtctggatga ttgtaatgca    720
gcacgtgaag ttcgtaaagc aaaagttccg atgctgttta ttcatggcag caaagatacc    780
tttgttccgc cttatatgtg tgatgaactg tatgaaaatt gtgccgcacc gaaaaccaaa    840
ctgattgttg aaggtgcagg tcatgttgag agctattaca aaaacaccca agaatatgaa    900
gaggccctgg ataaattcat tggtggcatc atcaaataa                           939

<210> SEQ ID NO 29
<211> LENGTH: 993
<212> TYPE: DNA
<213> ORGANISM: Unknown
<220> FEATURE:
<223> OTHER INFORMATION: Clostridiales sp.

<400> SEQUENCE: 29
atgggtaaaa ttggtctgct gtttggtctg gcagcagccg gtgcagcggg tgaatatggt     60
attgcacgtt atttctttca tcgtaccgtt gttcgtggta atgcaaaacg tgaacgtacc    120
cagaaaatgg caggcaccga ttgggatgca atattccgg gtattcgtgc aagcaaagaa    180
tggctgagcg gtaaaccgca agaagatgtg tatattacca gtgatgatgg tctgcgtctg    240
catggcacct ttttccgtg tccgggtagc gatcgtgcag ttatttgttt tcatggttat    300
accagcgaag gcctgaatga tttttagcagc attgcccgtt tttatctgga cagggttt     360 aatctgatgg tggttgatga acgtgcacat ggtcgtagcg aaggcaccta tattggtttt    420
ggttgtctgg atcgtatgga tgcacgtctg tggattgaat atgtgattga acgtctgggt    480
caagattgtc aggttatgct gcatggtatt agcatgggtg gtgcaaccgt tctgatgacc    540
```

```
accggtctga gcctgcctcc gcaggttaaa gcagcagtta gcgattgtgg ttttaccagt    600
gcatgggaag ttttagcta tgtgctgaaa agcatgtatc acatgccacc gtttccgatt    660
atgcagattg cagatcgcat ggcacgtcaa gaggcaggtt atggtctgga tcagtgtaat    720
gcacgtgatg aagttaaaaa agcccgtatt ccgatcctgt ttattcatgg tgatgcagat    780
acctttgtgc cgtgtagcat ggtttatcag ctgtatggtg catgtcgtag cggtaaagaa    840
ctgctggtta ttagcggtgc agcacatgca gaagcatatt acaaagatac caaaagctat    900
gaacgcgcag ttaccgaact gattggtcgt accattgaac cgctgggtga tcgtcatgaa    960
ggtcgtgata gccgtgatga aaaaggtgaa taa                                 993

<210> SEQ ID NO 30
<211> LENGTH: 954
<212> TYPE: DNA
<213> ORGANISM: E. rectale

<400> SEQUENCE: 30
atgcgtatga atgggggtat tattgccggt gttttaggtg gtattgcagc agccgaagcc     60
ggtggtagcg catatttcta tcgtcgtacc atgatgcgtt acaacgcaaa aaagaacgc    120 accatgaaaa tgagcggtgt tgattgggaa agctattaca gctttatgaa accgcatggt    180
gaatggatgc gtcacagac ccatgaagat gttttggatta aaagtgatga tggtctgcgt    240
ctgcatgcaa cctatttttcc gggtattgat ggtggtaatc cggataaagc agtgatttgc    300
tttcatggtt ataccagcga agcaatgagc gattatagca gcattagcaa ctactacctg    360
aaaaaaggtt atagcatgct gctggttgat gcacgtgccc atggtcagag cgaaggcaaa    420
tttatcggtt ttggttgcaa agatcgttac gatgcactga atggattga ctggatgatc    480 aaaaagccg gtaatggtat tcgtattgtg ctgatgggta tagcatggg tggtgcaacc    540 gttctgatgg caagcggtct gaatctgccg gaacaggtta aggtattgt tagcgattgt    600 gcatttacca gtccgaaagc agttttttacc catgttctgc atagcatgta tcatctgcct    660
gcatttccga tgattcagat tgccgatttt gtgaatcgta aaatggcagg ttatggtctg    720
gatgaatgta atgcagcaaa agaagttcag aaagccaaac tgccgattct gtttattcat    780
ggcgataaag ataccttttgt tccgtgtagc atgtgtgatg aactgtatgc aagctgtgca    840
agccagaaaa caaaactgat tgttaaaggt gccggtcact gcgaatccta ttacaaaat    900 accaaagcct tgaggatgc cctggataaa tttctggaag tgttatgcg ttaa            954

<210> SEQ ID NO 31
<211> LENGTH: 618
<212> TYPE: DNA
<213> ORGANISM: Lachnoclostridium clostridioforme

<400> SEQUENCE: 31
atgatttatc tggccaccta tgaacctggt ggtagcctgt ataatcgtga acgtgaacat     60
attctgggtc gtagcctgct gaattttggt ctgatgaaag aatatggtcg tacctgggaa    120
gttgaacaag aaaccggtag caaaccgtgt ctgaaaggtg cagaagatgt ggaatttaac    180
attagtcata cccgtggtct ggttgttgt gcagttgcag atcgtgcact gggtgttgat    240
accgaacgta ttcgtccgtt taaagaaggt ctgatgcgtc gtgtttgtag cgaaagcgaa    300
cgtggttttg ttctggaagg tcgtagcgaa gcagcacgtc aagaacgttt ttttcgtctg    360 tggacctga aagaaagctt tgttaaagcc attggtcgcg gtctggcatt tccgctgggt    420
```

```
gatattacct ttagcctgga agaaggtgca gttaaaggta gcattcctgg ttggcgtttt    480
tatcagagcc gtgtgtatca gagctatatt atcagcgttt gtgccgcaga tgaaaaagca    540 gttttttgcat ttaccaccgg caaactgaaa gttgaaggta gtctggaaaa agcactgatg   600
ctgcagaaat tgtgtaa                                                    618

<210> SEQ ID NO 32
<211> LENGTH: 576
<212> TYPE: DNA
<213> ORGANISM: C. celatum

<400> SEQUENCE: 32
atgagcattc tgcagccgta caaatacaag atcttctata acaaatccc gctgaaaaag     60 ggcatcagca actggaaca gaacaaaatt atgcatgatg ccggtattaa cctgctggat    120
gaaaaactgg aagaaatctt caacgtgaaa aacgcacgtg aaaactattg tagcagcctg   180
aatggtaaac cgtatctgaa aaatagcagc atcaacttca acatcagcca ctgcaataac   240
attgtggtgg tgattatcag caataagaac gtgggcattg atatcgagga tatcaaagag   300
ttcaaaaaaa gcatcatccg caaagtgctg accaacaatg aactgattga tctgctgagc   360
gccaacaaca aaaagagta ttttttcaaa ctgtggaccc tgaaagagag ctttctgaaa   420
gccattggca ccggtctgag ctatggtatg cagaatattg aattcagcat caaagacaaa   480
aacattatct gcaacaagat cggcttcctg ttcaaacaag aaagcctgat ctttaacaac   540
aacaagtaca ttgtgagcat cacctgggaa gtgtaa                             576

<210> SEQ ID NO 33
<211> LENGTH: 495
<212> TYPE: DNA
<213> ORGANISM: B. producta

<400> SEQUENCE: 33
atgacctatc aagaactggt gagcgaaatt cgtggcattt ttatgcaggc agatgtgagc    60
ggtattaaag aacatattgc ctaccagttt aacattcgtg gtgaagccga aggtgcattc   120
tatgcagaag ttctggaagg caaactgtat atcgaaccgt atgagtatta tgatcgtgat   180
gttctgttta ccaccaccgc agatacccctg ctgagcattg caaccggcac catggatgca   240
gttgcagcat ttcccctggg caaactgcag gttgaaggta gctttgataa agcactgctg   300
ctgcagagtt ttagcaaaca ggcaggtcgt gaaaaaaaga aaatgaaagc cgaagaaaaa   360
cgccagcaga aagcagaaga aagaactg cagaaagccg ttgaaaaaga aagccagaaa   420
gttgtggaaa aagttgccca gaaaacggaa gaaaaaaccg ccaaaaaaac cgttcgtcgt   480
ctgctgaaaa aataa                                                   495

<210> SEQ ID NO 34
<211> LENGTH: 336
<212> TYPE: DNA
<213> ORGANISM: R. bacterium

<400> SEQUENCE: 34
atgacctatg ccgatatgtt tagcgaagtt aaaggtatgc tggcaggcgc agatgttagc    60
gatattcaag aacatctggc ctatcagttt aacattattg gtgaagccga aggcatcttt   120
tatgccgaag tgaaagaagg caaactgtat atcgaaccgt atgagtattt tgatcgcgac   180 gtgatgtttta tttgtaccgc agatacccctg tttaaactgg caaaaggtaa aaccgatccg   240
gttctggcat ttaccaccgg taaactgaaa gtggaaggca atattgataa agccctgaaa   300
```

```
ctgggtgatc tgctggcacg taaacgtaaa ggttaa                              336
```

```
<210> SEQ ID NO 35
<211> LENGTH: 318
<212> TYPE: DNA
<213> ORGANISM: Unknown
<220> FEATURE:
<223> OTHER INFORMATION: Clostridiales sp.

<400> SEQUENCE: 35
atgaccttcg agaaagttttt cgaaaccgtg aaagaaatct tcatgaaagc cgatgttagc     60
aaagtggatg aacatctggc atttcagttt aacattaccg gtgaaggtga aggcatcttt    120
tatgccgaag caaagatgg taaactgtat gtggaaccgt atgagtatta tgatcgtgat     180
gccattttta tctgtagcgc agatacctg ctgaaactgg cagcaggtaa actggatccg     240
gtttttgcat ttaccaccgg caaactgaaa gttgaaggta gcctggaaaa agcactgaaa    300
ctgcagaaat ttgtgtaa                                                  318
```

```
<210> SEQ ID NO 36
<211> LENGTH: 333
<212> TYPE: DNA
<213> ORGANISM: E. rectale

<400> SEQUENCE: 36
atgacctatg ccgatatgtt cagcaaagtg aaaggtctgt ttatggaaag tgatgtgagc     60
gatattagcg aacatctggc atttcagttt aacattaccg gtgaagccga aggtatcttt    120
tatgccgaag ttaaagatgg tgttctggca gttgaaccgt atgaatattt tgatcgtgat    180 gccatctta tctgtagcgc agaaaccctg tttaaactgg cagaaggtcg tattgatccg    240
attctggcct ttaccaccgg caaactgaaa gttgaaggca atattgataa agcccctgcgt    300 ctgaagcaga tcatcgatag caaaaaagcc taa                                 333
```

```
<210> SEQ ID NO 37
<211> LENGTH: 82
<212> TYPE: PRT
<213> ORGANISM: C. eutactus

<400> SEQUENCE: 37

Met Asn Asn Asn Ile Thr Phe Leu Asn Ile Val Ala Glu Tyr Cys Asn
1               5                   10                  15

Thr Pro Ala Asp Glu Ile Thr Asn Asp Met Arg Phe Ile Glu Asp Leu
            20                  25                  30

Gly Phe Ser Ser Leu Asp Phe Met Thr Phe Leu Gly Asp Leu Glu Asp
        35                  40                  45

Thr Phe Asp Val Glu Ile Asn Glu Asp Glu Ile Ile Asn Ile His Thr
    50                  55                  60

Ile Glu Asp Ala Ile Lys Tyr Leu Asp Asn Leu Thr Ser Ser Ser Ala
65                  70                  75                  80

Ser Val
```

```
<210> SEQ ID NO 38
<211> LENGTH: 78
<212> TYPE: PRT
<213> ORGANISM: M. formatexigens

<400> SEQUENCE: 38

Met Thr Gln Glu Met Gln Phe Lys Thr Ile Ala Ala Gln Tyr Cys Gly
```

```
                1               5                  10                 15
Val Lys Pro Glu Asp Met Thr Asn Asp Met Arg Phe Arg Glu Asp Leu
            20                  25                 30

Gly Phe Ser Ser Leu Asp Phe Met Ser Phe Leu Gly Glu Leu Glu Asp
            35                  40                 45

Thr Phe Asp Val Glu Leu Glu Glu Glu Val Val Lys Ile Leu Thr
        50                  55                 60

Val Ala Glu Ala Leu Ala Leu Leu Glu Lys Leu Gln Glu Glu
65                  70                  75

<210> SEQ ID NO 39
<211> LENGTH: 76
<212> TYPE: PRT
<213> ORGANISM: Lachnoclostridium clostridioforme

<400> SEQUENCE: 39

Met Phe Glu Glu Leu Lys Glu Ile Ile Cys Glu Tyr Val Asp Val Ala
1               5                   10                  15

Pro Glu Thr Ile Lys Glu Asn Ser Arg Phe Ile Glu Asp Leu Gly Phe
            20                  25                  30

Asn Ser Tyr Asp Phe Met Ser Met Val Gly Glu Ile Glu Glu Lys Phe
        35                  40                  45

Asp Val Glu Val Glu Glu Arg Glu Val Val Asn Val Lys Thr Val Lys
    50                  55                  60

Asp Ala Val Asp Tyr Ile Gln Ser Leu Gln Ala Glu
65                  70                  75

<210> SEQ ID NO 40
<211> LENGTH: 75
<212> TYPE: PRT
<213> ORGANISM: B. producta

<400> SEQUENCE: 40

Met Phe Glu Lys Leu Lys Asp Met Ile Cys Glu Tyr Val Glu Val Asp
1               5                   10                  15

Lys Asn Ala Val Thr Glu Asn Ser Arg Phe Val Glu Asp Leu Gly Phe
            20                  25                  30

Thr Ser Tyr Asp Phe Met Ser Met Ile Gly Glu Leu Glu Glu Thr Tyr
        35                  40                  45

Asp Ile Glu Val Glu Glu Arg Gln Ala Ala Glu Ile Arg Thr Val Gly
    50                  55                  60

Glu Ala Val Arg Tyr Ile Glu Ser Leu Gln Asp
65                  70                  75

<210> SEQ ID NO 41
<211> LENGTH: 75
<212> TYPE: PRT
<213> ORGANISM: C. celatum

<400> SEQUENCE: 41

Met Leu Glu Lys Leu Arg Glu Leu Leu Ser Glu Tyr Val Glu Val Ala
1               5                   10                  15

Arg Glu Asp Ile Thr Val Glu Ser Lys Leu Val Glu Asp Leu Gly Leu
            20                  25                  30

Asn Ser Tyr Glu Phe Met Thr Leu Val Gly Asp Leu Glu Glu Glu Phe
        35                  40                  45

Asp Val Glu Val Asn Glu Arg Glu Val Ala Lys Val Asn Thr Ile Gly
    50                  55                  60
```

Asp Ile Ile Glu Tyr Ile Thr Ala Leu Gln Val
65                  70                  75

<210> SEQ ID NO 42
<211> LENGTH: 75
<212> TYPE: PRT
<213> ORGANISM: R. bacterium

<400> SEQUENCE: 42

Met Phe Glu Lys Leu Val Glu Ile Ile Cys Asn Tyr Val Glu Val Glu
1               5                   10                  15

Pro Glu Lys Ile Thr Ser Asp Ser Arg Phe Met Glu Asp Leu Gly Phe
            20                  25                  30

Thr Ser Phe Asp Phe Met Ser Met Leu Gly Glu Ile Glu Asp Thr Phe
        35                  40                  45

Asp Ile Glu Val Asp Glu Thr Glu Val Val Lys Ile Arg Thr Val Gly
    50                  55                  60

Glu Ala Val Asp Tyr Ile Gln Ser Leu Ala Asp
65                  70                  75

<210> SEQ ID NO 43
<211> LENGTH: 75
<212> TYPE: PRT
<213> ORGANISM: Unknown
<220> FEATURE:
<223> OTHER INFORMATION: Clostridiales sp.

<400> SEQUENCE: 43

Met Phe Glu Glu Leu Lys Glu Leu Ile Cys Glu Tyr Val Asp Val Asp
1               5                   10                  15

Pro Ser Ala Ile Lys Glu Glu Ser Arg Phe Ile Glu Asp Leu Gly Phe
            20                  25                  30

Asn Ser Tyr Asp Phe Met Ser Met Val Gly Glu Ile Glu Glu Thr Phe
        35                  40                  45

Asp Val Glu Val Glu Glu Arg Glu Val Val Asn Val Lys Thr Val Lys
    50                  55                  60

Asp Ala Val Glu Tyr Ile Gln Ser Leu Gln Asp
65                  70                  75

<210> SEQ ID NO 44
<211> LENGTH: 76
<212> TYPE: PRT
<213> ORGANISM: E. rectale

<400> SEQUENCE: 44

Met Phe Asp Glu Leu Val Glu Ile Ile Cys Asn Tyr Val Asp Val Gln
1               5                   10                  15

Pro Ala Asp Val His Glu Glu Ser Arg Phe Met Glu Asp Leu Gly Phe
            20                  25                  30

Thr Ser Phe Asp Phe Met Ser Met Leu Gly Glu Ile Glu Asp Thr Phe
        35                  40                  45

Asp Val Glu Ile Glu Gln Thr Lys Ala Ala Glu Ile Arg Thr Val Gln
    50                  55                  60

Glu Ala Val Asp Tyr Leu Glu Thr Leu Lys Asp Ala
65                  70                  75

<210> SEQ ID NO 45
<211> LENGTH: 463
<212> TYPE: PRT

<213> ORGANISM: C. eutactus

<400> SEQUENCE: 45

```
Met Pro Arg Lys Tyr Tyr Pro Leu Thr Pro Ser Gln Lys Ile His Phe
1               5                   10                  15

Lys Pro Ile Ile Glu Phe Gly Thr Gln Gln Val Ala Asn Ile Ser Ile
            20                  25                  30

Cys Met Thr Leu Gln Ala Pro Leu Asp Phe Gly Leu Leu Lys Lys Cys
        35                  40                  45

Ile Gln Leu Glu Tyr Glu Arg Tyr Glu Cys Leu Arg Ile Arg Phe Thr
    50                  55                  60

Lys Val Asp Gln Asn Gly Glu Val Arg Gln Tyr Val Val Ser Arg Asp
65                  70                  75                  80

Asp Arg Asp Ile Asp Tyr Glu Asn Leu Ser Trp Leu Ser Gly Asp Asp
                85                  90                  95

Ala Tyr His Arg Met Glu Glu Trp Ser Arg Ile Pro Phe Asp Gly Asp
            100                 105                 110

Asn Ile Pro Met Asn Val Ile Lys Met Ile Ser Leu Pro Gly Gly Tyr
        115                 120                 125

Asn Gly Leu Tyr Ile Lys Ile Asp His Arg Leu Met Asp Ser Cys Gly
    130                 135                 140

Ala Ile Val Met Val Asn Asp Ile Met Glu Leu Tyr Cys His Tyr Lys
145                 150                 155                 160

Phe Gly Thr Pro Tyr Pro Glu Asp Met Ala Ser Phe Thr Asp Met Val
                165                 170                 175

Glu Arg Asp Leu Lys Lys Ser Thr Asp Glu Lys Arg Val Ser Lys Asp
            180                 185                 190

Arg Met Tyr Trp Gln Asn Val Leu Glu Glu Asn Gly Glu Pro Ile Tyr
        195                 200                 205

Ser Asp Ile Gln Gly Gln Arg Ile Leu Gln Glu Ser Arg Arg Leu His
    210                 215                 220

Asn Asp Lys Ser Leu Arg Ala Ala Asp Gln Glu Ile Asn Asp Leu Ser
225                 230                 235                 240

Val Ala Thr Lys Asn Tyr His Leu Asp Ala Glu Pro Thr Gln Asn Leu
                245                 250                 255

Leu Asp Phe Cys Met Asn Asn His Ile Ser Met Thr Asn Leu Ile Leu
            260                 265                 270

Met Gly Ile Arg Thr Tyr Leu Ser Lys Ala Asn Gly Gly Gln Thr Asp
        275                 280                 285

Ile Ser Ile Arg Asn Tyr Val Ser Arg Arg Ser Thr His Ala Glu Trp
    290                 295                 300

Val Ser Gly Gly Ser Arg Ala Met Ala Tyr Pro Cys Arg Thr Ile Ile
305                 310                 315                 320

Asp Pro Asp Thr Glu Phe Leu Asp Ala Val Phe Met Ile Gln Asp Val
                325                 330                 335

Gln Asn His Val Tyr Arg His Cys Asn Tyr Asp Pro Glu Leu Leu Ser
            340                 345                 350

Asp Gln Met Lys Glu Met Phe His Thr Pro Pro His Thr Thr Tyr Glu
        355                 360                 365

Ser Val Gly Leu Thr Tyr Gln Pro Leu Pro Ile Arg Leu Lys Asn Pro
    370                 375                 380

His Leu Glu Asn Ile Ser Val Arg Ser Met Trp Ile Pro Asn Gly Thr
385                 390                 395                 400
```

-continued

Ser Lys Gln Lys Ile Tyr Leu Thr Val Met His Ser Ala Asn Asp Leu
              405                 410                 415

Gly Leu Asn Phe Tyr Phe Arg Tyr Gln Thr Ala Ser Leu Ser Glu Gln
          420                 425                 430

Asp Ile Glu Leu Phe Tyr Tyr Leu Met Lys Ile Ile Phe Lys Gly
      435                 440                 445

Ile Ala Glu Pro Glu Met Thr Val Gly Glu Ile Ile Glu Cys Ile
450                 455                 460

<210> SEQ ID NO 46
<211> LENGTH: 461
<212> TYPE: PRT
<213> ORGANISM: M. formatexigens

<400> SEQUENCE: 46

Met Arg Glu Tyr Tyr Pro Leu Thr Ala Ala Gln Lys Met His Tyr Asn
1               5                   10                  15

Trp Ile Arg Lys Tyr Arg Thr Gln Gln Val Ser Gly Val Ser Val Val
            20                  25                  30

Ala Ser Leu Lys Ser Pro Leu Asp Phe Gly Leu Leu Lys Lys Cys Ile
        35                  40                  45

Gln Leu Glu Thr Glu Arg Tyr Gly Cys Met Arg Val Arg Phe Thr Ala
    50                  55                  60

Pro Asp Glu Lys Gly Gly Ile Lys Gln Tyr Ile Val Asp Arg Asp Thr
65                  70                  75                  80

Arg Asp Ile Pro Met Lys Asp Leu Ser Gly Met Ser Met Ala Glu Ala
                85                  90                  95

Asp Asn Leu Met Gln Gln Trp Ala Tyr Glu Thr Phe Asp Gly Asp Asp
            100                 105                 110

Ile Pro Leu Cys Asp Val Thr Met Leu Lys Leu Pro Gly Tyr Asn
        115                 120                 125

Gly Phe Phe Ile His Met Asp His Arg Leu Ile Asp Ser Cys Gly Leu
    130                 135                 140

Val Val Met Ile Asn Asp Leu Met Gln Leu Tyr Thr His Tyr Arg Phe
145                 150                 155                 160

Gly Ser Ala Tyr Pro Gln Asp Leu Ala Asp Tyr Glu Thr Val Leu Ala
                165                 170                 175

Lys Asp Leu Lys Arg Ala Asn Asn Glu Lys Arg Phe Ala Lys Asp Lys
            180                 185                 190

Lys Phe Trp Asp Asp Gln Leu Asn Ala Leu Gly Glu Pro Leu Tyr Ser
        195                 200                 205

Asp Ile Gln Gly Pro Ser Val Leu Glu Ala Ala Arg Lys Arg His Lys
    210                 215                 220

Asn Pro Met Leu Arg Ala Ala Asp Ile Glu Leu Asp Asn Leu Phe Val
225                 230                 235                 240

Glu Val Lys Asp Tyr Arg Leu Glu Pro Glu Pro Thr Lys Asn Leu Ile
                245                 250                 255

Asp Phe Cys Met Asn His Gln Leu Ser Met Thr Asn Leu Leu Leu Leu
            260                 265                 270

Gly Ile Arg Thr Tyr Leu Ser Lys Val Asn Asn Gly Gln Glu Asp Ile
        275                 280                 285

Thr Ile Glu Asn Phe Ile Ser Arg Arg Ser Thr His Asp Glu Trp Thr
    290                 295                 300

Ser Gly Gly Ser Arg Thr Ile Met Phe Pro Cys Arg Thr Val Ile Ser
305                 310                 315                 320

```
Pro Glu Thr Asp Phe Leu Ser Ala Ala Tyr Glu Ile Gln Asn Val Gln
            325                 330                 335

Asn Arg Ile Tyr Met His Ser Asn Tyr Asp Pro Ala Leu Ile Glu Glu
            340                 345                 350

Glu Met Arg Arg Tyr His Thr Pro Glu Asn Thr Thr Tyr Glu Ser
            355                 360                 365

Cys Tyr Leu Thr Tyr Gln Pro Met Pro Val Gln Met Asp Asn Pro His
            370                 375                 380

Leu Ala Gly Ile Ser Gln His Ala Lys Trp Phe Ala Asn Gly Ala Ala
385                 390                 395                 400

Thr Lys Lys Met Tyr Leu Thr Val Ser His Thr Pro Asp Gly Gly Met
            405                 410                 415

Asn Phe Ser Tyr His Tyr Gln Thr Ala Gln Leu Cys Glu His Asp Met
            420                 425                 430

Glu Leu Leu Tyr Tyr Tyr Met Met Arg Ile Leu Phe Lys Gly Ile Ala
            435                 440                 445

Glu Pro Asp Met Ser Ile Gly Glu Ile Met Glu Leu Val
            450                 455                 460

<210> SEQ ID NO 47
<211> LENGTH: 468
<212> TYPE: PRT
<213> ORGANISM: Lachnoclostridium clostridioforme

<400> SEQUENCE: 47

Met Lys Thr Arg Lys Gly Tyr Lys Val Tyr Pro Leu Thr Ser Ala Gln
1               5                   10                  15

Lys Leu His Phe Tyr Cys Leu Lys Tyr Cys Pro Lys Lys Gln Val Leu
            20                  25                  30

Asn Ile Gly Ser Ser Leu Thr Ile Gln Val Asp Leu Asp Trp Asp Val
        35                  40                  45

Leu Lys Asp Cys Ile Arg Glu Ala Ile Ala Arg Cys Asp Thr Met Arg
    50                  55                  60

Leu Arg Phe Thr His Asp Lys Glu Gly Asn Val Tyr Gln Tyr Val Val
65                  70                  75                  80

Lys Glu Glu Thr Lys Glu Ile Glu His Phe Asp Phe Thr Gly Trp Lys
                85                  90                  95

Glu Glu Asp Ala Glu Gly Lys Leu Arg Glu Trp Thr Glu Val Pro Phe
            100                 105                 110

Glu Arg Tyr Asp Ser Pro Met His His Ile Val Met Ile Arg Met Pro
            115                 120                 125

Asp Gly Tyr Gln Gly Leu Tyr Ile Cys Val Asp His Met Thr Met Asp
        130                 135                 140

Ala Gln Ser Leu Ile Leu Phe Phe Arg Asp Val Ile Glu Leu Tyr Ala
145                 150                 155                 160

Ser Lys Leu Tyr Asp Glu Val Asp His Pro Lys Glu Met Ser Ser Tyr
                165                 170                 175

Ile Lys Gln Leu Glu Lys Asp Leu Ala Tyr Glu Thr Gly Ser Arg Ala
            180                 185                 190

Cys Glu Lys Asp Arg Gln Phe Phe Gln Glu Leu Ile Ala Ser Ser Glu
            195                 200                 205

Pro Ile Phe Thr Asp Ile Tyr Gly Pro Lys Lys Leu Ser Asp Glu Arg
        210                 215                 220

Lys Ala Thr Arg Asn Pro Lys Leu Arg Ala Ala Thr Asn Thr Ser Asp
```

```
                    225                 230                 235                 240
            Asn Val Glu Ala Asn Ile Thr Asn Phe His Leu Glu Gly Asp Ser Ser
                            245                 250                 255
            Gly Arg Leu Leu Asp Phe Cys Glu Lys Tyr Gly Ile Ser Met Thr Cys
                            260                 265                 270
            Leu Leu Leu Met Gly Leu Arg Thr Tyr Leu Gln Lys Glu Asn Asp Gln
                            275                 280                 285
            Asp Asp Val Ser Ile Thr Thr Thr Ile Ser Arg Ala Thr Leu Ser
                290                 295                 300
            Glu Lys Arg Cys Gly Gly Ser Arg Ile His Cys Phe Pro Phe Arg Thr
            305                 310                 315                 320
            Ile Val Pro Arg Glu Asn Thr Phe Met Glu Gly Leu Leu Lys Ile Arg
                            325                 330                 335
            Asp Ala Gln Asn Gln Tyr Phe Arg His Ala Asp Tyr Ser Pro Ser Glu
                            340                 345                 350
            Tyr Phe Asn Tyr Arg His Asp Tyr Lys Leu Lys Asp Gly Gln Thr
                            355                 360                 365
            Tyr Glu Pro Leu Ser Leu Thr Tyr Gln Pro Leu Ala Met Lys Tyr Asp
                370                 375                 380
            Gly Pro Gly Leu Asp Lys Leu Gly Asp Ile Lys Tyr Lys Thr Ala Arg
            385                 390                 395                 400
            Tyr Ser Asn Gly Val Ala Ala His Thr Leu Tyr Leu Thr Val Ser His
                            405                 410                 415
            Arg Ala Glu Asp Asn Gly Leu Asp Phe Gly Phe Glu Tyr Gln Thr Gly
                            420                 425                 430
            Val Val Thr Pro Glu Arg Leu Glu Tyr Ile Tyr Tyr Leu Cys Arg
                            435                 440                 445
            Ile Ile Phe Arg Gly Val Glu Asp Pro Glu Arg Thr Val Gly Glu Ile
                            450                 455                 460
            Ile Glu Met Val
            465

<210> SEQ ID NO 48
<211> LENGTH: 466
<212> TYPE: PRT
<213> ORGANISM: B. producta

<400> SEQUENCE: 48

Met Lys Glu Lys Phe Gly Lys Pro Leu Tyr Pro Leu Thr Ala Ala Gln
            1               5                   10                  15
            Lys Leu His Phe Phe Tyr Gln Lys Tyr Cys Pro Lys Lys Gln Val Leu
                            20                  25                  30
            Asn Ile Gly Thr Ser Leu Thr Ile Gln Gln Ser Leu Asp Phe Gly Ala
                            35                  40                  45
            Leu Lys Glu Ala Val Tyr Gln Ala Tyr Ala Arg Cys Glu Ser Met Arg
                50                  55                  60
            Leu Arg Phe Thr Gln Asp Glu Asp Gly Gly Val Tyr Gln Tyr Ile Ala
            65                  70                  75                  80
            Asp Arg Glu Glu Arg Asp Ile Glu Phe Phe Asp Phe Thr Gly Trp Gln
                            85                  90                  95
            Glu Cys His Ala Glu Asp Lys Met Lys Glu Trp Thr Ser Val Pro Phe
                            100                 105                 110
            Glu Arg Phe Asp Ser Pro Leu Asn Arg Val Val Met Ile Ile Thr Pro
                            115                 120                 125
```

-continued

Asp Gly Phe Gln Gly Ile Tyr Leu Leu Val Asp His Met Thr Met Asp
    130                 135                 140

Ala Gln Ser Leu Ile Leu Phe Leu Lys Asp Val Ile Glu Ile Tyr Ala
145                 150                 155                 160

Asn Met Lys Tyr Glu Gly Met Glu Tyr Pro Lys Glu Met Lys Ser Tyr
                165                 170                 175

Ile Glu Gln Leu Lys Lys Asp Leu Glu Tyr Glu Ala Asp Ser Arg Ala
            180                 185                 190

Lys Lys Arg Asp Thr Glu Phe Phe Glu Lys Met Ile Ser Ser Ser Glu
            195                 200                 205

Pro Ile Phe Asn Ser Ile Phe Gly Pro Gly Lys Leu Lys Ala Glu Arg
    210                 215                 220

Glu Lys Glu Lys Asn Pro Asp Ile Arg Ala Val Thr Asn Val Ser Asp
225                 230                 235                 240

Asn Val Asp Ala Asn Ile Ile Thr Phe Gln Leu Glu Ala Asp Pro Ser
                245                 250                 255

Asn Arg Leu Met Gln Phe Cys Glu Glu His His Ile Ser Met Val Cys
            260                 265                 270

Leu Leu Met Met Gly Leu Arg Thr Tyr Leu Gln Lys Val Asn Gly Asn
            275                 280                 285

Asp Asp Val Ser Ile Asn Thr Thr Val Ala Arg Arg Ala Thr Leu Ser
    290                 295                 300

Glu Lys Arg Cys Gly Gly Thr Arg Ile His Cys Phe Pro Phe Arg Thr
305                 310                 315                 320

Val Val Glu Lys Gly Asp Thr Phe Met Glu Gly Leu Lys Lys Ile Arg
                325                 330                 335

Asp Gly Gln Asn Arg Ile Phe Arg His Ala Asn Tyr Asp Pro Thr Ala
            340                 345                 350

Tyr Tyr Ala Tyr Arg Asn Lys Tyr Tyr Lys Leu Arg Pro Gly Gln Thr
            355                 360                 365

Tyr Glu Pro Leu Ser Leu Thr Tyr Gln Pro Leu Thr Leu Lys Gly Lys
    370                 375                 380

Gly Met Glu Arg Leu Gln Asp Ile Arg Tyr Lys Ser Ala Trp Tyr Ser
385                 390                 395                 400

Asn Gly Ala Ala Ala His Ala Leu Tyr Leu Thr Val Met His Arg Ala
                405                 410                 415

Glu Asp Asn Gly Met Asn Phe Asn Phe Glu His Gln Thr Gly Val Val
            420                 425                 430

His Phe Glu Asp Leu Gln Tyr Leu Tyr Tyr Leu Cys Arg Ile Ile
            435                 440                 445

Phe Lys Gly Val Glu Asn Pro Asp Met Thr Val Gly Glu Ile Leu Glu
    450                 455                 460

Ser Val
465

<210> SEQ ID NO 49
<211> LENGTH: 471
<212> TYPE: PRT
<213> ORGANISM: C. celatum

<400> SEQUENCE: 49

Met Ile Lys Glu Lys Asp Ile Lys Leu Tyr Pro Leu Thr Ala Ala Gln
1               5                   10                  15

Lys Leu His Phe Tyr Thr Leu Thr Tyr Cys Pro Lys Lys Gln Val Leu
            20                  25                  30

```
Asn Ile Gly Thr Ser Leu Thr Ile Lys Glu Asp Ile Asp Phe Glu Val
         35                  40                  45

Leu Arg Glu Ala Val Tyr Arg Ala Tyr Glu Arg Cys Glu Ala Met Arg
 50                  55                  60

Ile Arg Phe Val His Asp Glu Ser Gly Asn Val Met Gln Tyr Val Ala
 65                  70                  75                  80

Glu Lys Glu Thr Arg Tyr Ile Glu Phe Phe Glu Phe Ser His Trp Lys
                 85                  90                  95

Val Glu Asp Ala Glu Lys Lys Met Arg Glu Trp Thr Glu Thr Pro Phe
                100                 105                 110

Glu Arg Glu Asn Lys Pro Leu Asn Lys Val Val Met Ile Ser Met Pro
                115                 120                 125

Glu Gly Tyr Lys Gly Ile Tyr Leu Leu Val Asp His Met Thr Met Asp
        130                 135                 140

Ala Gln Ser Leu Ile Val Phe Met Lys Asp Ile Ile Glu Ile Tyr Cys
145                 150                 155                 160

His Leu Lys Tyr Glu Gly Ile Pro Tyr Pro Arg Glu Met Ala Ser Tyr
                165                 170                 175

Ile Glu Gln Ile Glu Lys Asp Leu Thr Tyr Glu Leu Gly Asn Lys Ala
                180                 185                 190

Lys Glu Arg Asp Glu Lys Phe Phe Lys Glu Leu Ile Glu Cys Lys Glu
                195                 200                 205

Pro Ile Phe Asn Asp Ile Glu Gly Lys Glu Arg Leu Arg Leu Glu Arg
        210                 215                 220

Leu Gln Arg Asp Ser Glu Asn Leu Arg Ser Val Ile Asn Thr Ser Asn
225                 230                 235                 240

Asn Val Asp Ala Asn Ile Thr Ile Phe Asn Leu Glu Ala His Pro Ser
                245                 250                 255

His Leu Leu Glu Arg Phe Cys Glu Glu Asn Lys Ile Pro Met Val Cys
                260                 265                 270

Leu Leu Ile Met Gly Leu Arg Thr Tyr Leu Gln Lys Phe Asn Asp Glu
        275                 280                 285

Asp Asp Val Ser Ile Met Ser Thr Ile Ala Arg Arg Ala Thr Leu Ser
290                 295                 300

Glu Lys Leu Ser Gly Gly Thr Arg Val His Cys Phe Pro Cys Arg Thr
305                 310                 315                 320

Ile Val Lys Arg Asp Met Thr Phe Met Glu Gly Leu Glu Glu Ile Arg
                325                 330                 335

Lys Glu Gln Asn Lys Leu Phe Arg His Ser Asn Tyr Asp Pro Val Lys
                340                 345                 350

Cys Leu Glu Tyr Arg Arg Met Phe Tyr Asn Asn Leu Pro Gly Glu Thr
        355                 360                 365

Tyr Glu Pro Leu Ser Leu Thr Tyr Gln Pro Leu Thr Lys Asn Asp Leu
370                 375                 380

Lys Gln Arg Pro Gly Gln Thr Val Ser Phe Glu Ser Ile Asp Tyr Lys
385                 390                 395                 400

Thr Asn Trp Tyr Ser Asn Gly Ala Cys Ala His Ala Leu Tyr Leu Thr
                405                 410                 415

Val Met His Arg Ala Ser Asp Asn Gly Leu Asp Phe Asn Phe Glu Tyr
                420                 425                 430

Gln Thr Gly Arg Val Thr Thr Glu Lys Leu Glu Tyr Met Tyr Tyr Tyr
        435                 440                 445
```

```
Leu Cys Lys Ile Leu Phe Thr Gly Ile Glu Asn Lys Asp Lys Thr Val
    450                 455                 460

Gly Glu Ile Ile Glu Met Val
465                 470

<210> SEQ ID NO 50
<211> LENGTH: 467
<212> TYPE: PRT
<213> ORGANISM: R. bacterium

<400> SEQUENCE: 50

Met Arg Lys His Lys Gly Tyr Pro Val Tyr Pro Leu Thr Val Ala Gln
1               5                   10                  15

Lys Phe His Leu Phe Tyr Leu Pro Tyr Cys Pro Ser Ala Ala Val Met
                20                  25                  30

Asn Ile Gly Thr Arg Leu Thr Ile Gln Ser Glu Ile Asp Trp Asp Leu
            35                  40                  45

Leu Lys Gln Ser Ile Tyr Gln Ala Tyr Asp Arg Cys Glu Gly Met Arg
        50                  55                  60

Val Arg Phe Ala Lys Asp Lys Asp Gly Thr Tyr Tyr Gln Tyr Val Val
65                  70                  75                  80

Asp Lys Glu Glu Arg Asp Ile Glu Phe Val Asp Phe Ser Gln Gly Thr
                85                  90                  95

Leu Glu Glu Ala Asp Lys Val Met Gln Gln Trp Thr Thr Val Pro Phe
            100                 105                 110

Pro Met Glu Asp Ala Pro Leu Thr Arg Val Val Met Ile Ser Leu Pro
        115                 120                 125

Asp Gly Phe Asn Gly Val Tyr Phe Leu Gly His His Met Ile Val Asp
130                 135                 140

Ala Gln Ser Leu Ile Gly Phe Leu Lys Asp Ile Ile Glu Leu Tyr Cys
145                 150                 155                 160

Ser Gln Lys Tyr Glu Gly Val Pro Ala Pro Lys Glu Met Ala Ser Tyr
                165                 170                 175

Ile Glu Gln Ile Gln Lys Asp Leu Ala Tyr Glu Ala Gly Ser Lys Ala
            180                 185                 190

Gln Leu Arg Asp Met Glu Phe Phe Gln Lys Glu Ile Glu Ser Ser Glu
        195                 200                 205

Pro Ile Tyr Asn Gly Met Lys Gly Thr Asp Lys Leu Glu Ala Ala Arg
210                 215                 220

Gln Met Phe Gln Asn Pro Asn Leu Arg Thr Ala Phe Asn Ala Ser Gly
225                 230                 235                 240

Asp Thr Thr Ser Ala Leu Asp Ile Phe His Leu Glu Gly Glu Pro Thr
                245                 250                 255

Gln Arg Leu Met Asn Phe Cys Glu Glu Tyr His Val Ser Leu Val Cys
            260                 265                 270

Leu Leu Leu Met Gly Met Arg Thr Tyr Phe Gln Lys Val Asn Gly His
        275                 280                 285

Asp Asp Val Ser Ile Asn Asn Ala Ile Ala Arg Arg Ala Thr Leu Lys
290                 295                 300

Glu Lys Lys Ser Gly Gly Thr Arg Ile His Ser Phe Pro Phe Arg Thr
305                 310                 315                 320

Cys Phe Ser Gln Asp Met Lys Phe Ile Asp Ala Ile Tyr Ala Ile Arg
                325                 330                 335

Asp Lys Gln Asn Glu Tyr Phe Arg His Ala Asn Tyr Asp Pro Thr Ala
            340                 345                 350
```

```
Tyr Phe Ala Tyr Arg Ser Lys Thr Tyr Pro Gln Pro His Ala Gly Leu
            355                 360                 365

Thr Tyr Glu Pro Ile Ser Leu Thr Tyr Gln Pro Leu Thr Leu Lys Glu
        370                 375                 380

Lys Gly Leu Asp Gln Leu Gly Asp Ile Arg Tyr Thr Thr Lys Trp Tyr
385                 390                 395                 400

Pro Asn Gly Met Thr Pro Gln Ala Val Tyr Leu Thr Val Met His Arg
                405                 410                 415

Pro Glu Asp Asn Gly Leu Asp Phe Asn Phe Glu His Gln Val Lys Ala
            420                 425                 430

Phe Ser Arg Glu Glu Leu Glu Tyr Phe Tyr Tyr Leu Cys Lys Ile
        435                 440                 445

Met Phe Lys Gly Ile Glu Asn Pro Asn Leu Thr Ile Gly Glu Ile Ile
    450                 455                 460

Lys Leu Val
465

<210> SEQ ID NO 51
<211> LENGTH: 468
<212> TYPE: PRT
<213> ORGANISM: Unknown
<220> FEATURE:
<223> OTHER INFORMATION: Clostridiales sp.

<400> SEQUENCE: 51

Met Lys Thr Arg Lys Gly Tyr Lys Ala Tyr Pro Leu Thr Ala Ala Gln
1               5                   10                  15

Lys Leu His Phe Tyr Cys Leu Lys Tyr Cys Pro Lys Lys Gln Val Leu
            20                  25                  30

Asn Ile Gly Ser Ser Leu Thr Ile Glu Ser Asp Leu Asp Trp Asp Val
        35                  40                  45

Leu Arg Gln Cys Ile Lys Glu Ala Ile Ala Arg Cys Glu Ser Met Arg
    50                  55                  60

Leu Arg Phe Ala Lys Asp Arg Asp Gly Asn Ile Tyr Gln Tyr Val Val
65                  70                  75                  80

Lys Glu Glu Thr Lys Glu Ile Glu His Phe Asp Phe Thr Gly Trp Gln
                85                  90                  95

Glu Glu Asp Ala Asp Lys Lys Leu Arg Glu Trp Thr Gly Ile Pro Phe
            100                 105                 110

Glu Arg Tyr Asp Ser Pro Met His Arg Ile Val Met Ile Lys Thr Pro
        115                 120                 125

Asp Gly Tyr Gln Gly Leu Tyr Ile Cys Val Asp His Met Thr Met Asp
    130                 135                 140

Ala Gln Ala Leu Ile Val Phe Lys Asp Val Ile Glu Leu Tyr Cys
145                 150                 155                 160

Ser Arg Leu Tyr Glu Glu Val Asn Tyr Pro Lys Glu Met Ser Ser Tyr
                165                 170                 175

Ile Arg Gln Leu Glu Lys Asp Leu Ala Tyr Glu Ala Gly Ser Arg Ala
            180                 185                 190

Cys Gln Arg Asp Arg Glu Phe Phe Glu Asn Leu Ile Ala Ser Ser Glu
        195                 200                 205

Pro Val Phe Ala Asp Ile Tyr Gly Pro Gly Lys Leu Leu Lys Glu Arg
    210                 215                 220

Lys Glu Ser Arg Asn Lys Lys Leu Arg Ala Ala Thr Asn Thr Ser Asp
225                 230                 235                 240
```

```
Asn Val Glu Ala Asn Ile Thr Asn Phe His Leu Gly Gly Pro Ser
            245                 250                 255

Lys Arg Leu Leu Asp Phe Cys Glu Glu Lys Gly Ile Ser Met Thr Cys
        260                 265                 270

Leu Leu Leu Met Gly Leu Arg Thr Phe Leu Gln Lys Glu Asn Asp Glu
    275                 280                 285

Asp Asp Ile Ser Ile Thr Thr Thr Ile Ala Arg Arg Ala Thr Leu Leu
290                 295                 300

Glu Lys Arg Cys Gly Gly Ser Arg Ile His Cys Phe Pro Phe Arg Thr
305                 310                 315                 320

Ile Val Pro Arg Glu Asp Thr Phe Met Glu Gly Leu Leu Lys Ile Arg
                325                 330                 335

Asp Ala Gln Asn Gln Tyr Phe Arg His Ala Gly Tyr Ser Pro Ser Glu
            340                 345                 350

Tyr Phe Asn Phe Arg His Asp Tyr Tyr Lys Leu Lys Asp Gly Gln Thr
        355                 360                 365

Tyr Glu Pro Leu Ser Leu Thr Tyr Gln Pro Leu Ala Met Lys Tyr Asp
    370                 375                 380

Gly Pro Gly Leu Asp Lys Leu Gly Asp Ile Lys Tyr Lys Thr Ala Arg
385                 390                 395                 400

Tyr Ser Asn Gly Val Ala Ala His Thr Leu Tyr Leu Thr Val Ser His
                405                 410                 415

Arg Thr Met Asp Asn Gly Leu Asp Phe Gly Phe Glu Tyr Gln Thr Gly
            420                 425                 430

Val Val Thr Pro Glu Lys Leu Glu Tyr Ile Tyr Tyr Leu Cys Arg
        435                 440                 445

Ile Ile Phe Arg Gly Val Glu Asp Pro Glu Arg Thr Val Gly Glu Ile
    450                 455                 460

Met Glu Met Val
465

<210> SEQ ID NO 52
<211> LENGTH: 471
<212> TYPE: PRT
<213> ORGANISM: E. rectale

<400> SEQUENCE: 52

Met Lys Thr Arg Lys Gly His Asn Val Tyr Pro Ile Thr Val Ala Gln
1               5                   10                  15

Lys Phe His Leu Tyr Tyr Ala Lys Tyr Cys Pro Asn Met Ala Val Leu
            20                  25                  30

Asn Ile Gly Thr Ser Leu Thr Ile Gly Thr Glu Leu Asp Trp Asn Val
        35                  40                  45

Leu Arg Asp Ser Ile Asn Tyr Ala Tyr Ala Arg Asn Glu Ala Met Arg
    50                  55                  60

Ile Arg Phe Thr Arg Asp Lys Asp Gly Glu Cys Tyr Gln Tyr Ile Ala
65                  70                  75                  80

Asp Val Asp Glu Asp Phe Lys Glu Arg Thr Val Asp Phe Lys Asp Phe
                85                  90                  95

Thr Asp Val Thr Met Glu Glu Ala Glu Asn Glu Met Gln Gly Trp Thr
            100                 105                 110

Gln Val Pro Phe Glu Phe Glu Asp Ser Pro Met Thr Lys Ile Val Met
        115                 120                 125

Ile Lys Met Pro Asp Gly Phe Asn Gly Val Tyr Phe Leu Gly His His
```

```
                130                 135                 140
Met Val Val Asp Ala Gln Ser Leu Ile Ala Phe Leu Lys Asp Ile Ile
145                 150                 155                 160

Glu Ile Tyr Cys Asn Ala Met Tyr Glu Gly Val Pro Phe Pro Lys Asp
                165                 170                 175

Met Cys Ser Tyr Ile Glu Gln Leu Lys Lys Asp Leu Ala Tyr Glu Ala
            180                 185                 190

Gly Ser Lys Ala Gln Leu Arg Asp Arg Glu Phe Phe Glu Lys Leu Ile
        195                 200                 205

Arg Gln Ser Glu Pro Ile Tyr Asn Gly Ile Asp Gly Thr Ala Lys Leu
    210                 215                 220

Asp Ala Ala Arg Glu Leu Met His Asp Asn Lys Leu Arg Ser Ala Phe
225                 230                 235                 240

Asn Ala Ser Asp Asp Val Thr Ser Ala Leu Asp Ile Phe His Leu Glu
                245                 250                 255

Ala Glu Pro Thr Lys Arg Leu Met Asp Phe Cys Glu Lys Tyr His Ile
            260                 265                 270

Ser Leu Ala Cys Leu Leu Met Gly Ile Arg Thr Phe Phe Gln Lys
        275                 280                 285

Glu Asn Gly Phe Asp Asp Val Ser Val Asn Asn Ala Ile Ala Arg Arg
    290                 295                 300

Ala Thr Leu Lys Glu Lys Lys Ser Gly Gly Thr Arg Ile His Ser Phe
305                 310                 315                 320

Pro Phe Arg Thr Cys Phe Ser Lys Asp Val Arg Phe Ile Asp Ala Val
                325                 330                 335

Tyr Thr Ile Arg Asp Lys Gln Asn Glu Leu Phe Arg His Ala Asn Tyr
            340                 345                 350

Asn Pro Thr Glu Tyr Phe Ala Leu Arg Ser Lys Thr Tyr Pro Gln Pro
        355                 360                 365

Lys Ala Gly Leu Thr Tyr Glu Pro Met Ser Leu Thr Tyr Gln Pro Met
    370                 375                 380

Thr Leu Lys Glu Lys Gly Leu Asn Asp Leu Gly Asp Ile Lys Tyr Lys
385                 390                 395                 400

Thr Lys Trp Tyr Pro Asn Gly Met Thr Thr Gln Ala Met Tyr Leu Thr
                405                 410                 415

Val Met His Arg Pro Glu Asp Asn Gly Leu Asp Phe Ser Phe Glu His
            420                 425                 430

Gln Val Lys Ala Val Ser Arg Lys Gln Leu Glu Tyr Met Tyr Tyr Tyr
        435                 440                 445

Leu Cys Lys Ile Met Phe Lys Gly Ala Glu Asn Pro Glu Leu Thr Ile
    450                 455                 460

Gly Glu Ile Ile Lys Leu Val
465                 470

<210> SEQ ID NO 53
<211> LENGTH: 519
<212> TYPE: PRT
<213> ORGANISM: C. eutactus

<400> SEQUENCE: 53

Met Glu Glu Asn Ile Leu Glu Ile Val Glu Lys Ser Cys Arg Ile His
1               5                   10                  15

Arg Asp Val Ile Ala Val Lys Tyr Leu Ser His Arg Glu Ile Val Glu
            20                  25                  30
```

-continued

```
Lys Ser Tyr Gly Asp Met Trp Asp Ile Arg Lys Thr Ala Val Ile
         35                  40                  45

Leu Arg Asn Asn Gly Leu Cys Gly Thr His Ile Ala Leu Val Gly Ser
 50                  55                  60

Ser Ser Tyr Glu Trp Ile Cys Ala Tyr Met Ala Ile Leu Phe Thr Gly
 65                  70                  75                  80

Asn Thr Ala Val Pro Leu Asp Ala Asn Leu Ser Val Ser Glu Leu His
                 85                  90                  95

Glu Leu Leu Asn Arg Ser Gly Ser Ile Ala Leu Phe Cys Gly Ala Ser
            100                 105                 110

Arg Lys Asp Val Ile Thr Glu Leu Thr Asp Asp Cys Pro Glu Met Asn
            115                 120                 125

Ile Val Phe Thr Met Glu Lys Lys Val Asp Ile Glu His Leu Glu Gly
            130                 135                 140

Ala Asp Ser Asn Pro Gln Leu Ala Ile Leu Ser Phe Glu Gln Leu Arg
145                 150                 155                 160

Asn Glu Ile Thr Ile Pro Asp Asp Phe Ala Phe Ala Asp Gln Asp Lys
                165                 170                 175

Asp Lys Met Cys Thr Leu Met Tyr Thr Ser Gly Thr Thr Gly Lys Ser
            180                 185                 190

Lys Gly Val Met Leu Ser Gln Phe Asn Leu Ala Gln Asn Val Glu Asn
            195                 200                 205

Val Tyr Val Asn Leu Glu Pro Gly Val Thr Ile Leu Ser Val Leu Pro
            210                 215                 220

Ile His His Ala Phe Cys Leu Thr Met Glu Trp Met Lys Gly Ile Ser
225                 230                 235                 240

Leu Gly Ala Thr Ile Cys Ile Asn Asp Ser Leu Leu His Met Leu Lys
                245                 250                 255

Asn Met Lys Arg Phe Gln Pro Val Gly Met Leu Met Val Pro Leu Met
            260                 265                 270

Val Glu Thr Ile Tyr Lys Lys Leu Lys Asp Val Asn Pro Leu Leu Pro
            275                 280                 285

Lys Lys Leu Val Ala Lys Glu Ala Phe Gly Gly Lys Leu Glu Tyr Ile
            290                 295                 300

Phe Cys Gly Gly Ala Tyr Leu Asp Pro Met Tyr Val Thr Glu Phe Lys
305                 310                 315                 320

Lys Tyr Gly Ile Asp Ile Leu Gln Gly Tyr Gly Met Thr Glu Cys Ser
                325                 330                 335

Pro Val Ile Cys Ser Asn Asn His Arg Tyr Asn Arg Pro Gly Ser Val
            340                 345                 350

Gly Lys Leu Leu Asp Asn Cys Ala Val Arg Phe Val Asp Glu Glu Ile
            355                 360                 365

Gln Val Lys Gly Thr Ser Val Met Ser Gly Tyr Tyr Asp Met Pro Asn
            370                 375                 380

Glu Thr Ala Glu Ala Phe Gln Asp Gly Trp Leu Cys Thr Gly Asp Leu
385                 390                 395                 400

Gly Tyr Leu Asp Ser Asp Gly Phe Met Tyr Ile Thr Gly Arg Lys Lys
                405                 410                 415

Asn Leu Ile Ile Leu Ala Asn Gly Glu Asn Ile Ser Pro Glu Glu Leu
            420                 425                 430

Glu Gly Lys Leu Ser Ile Glu Pro Leu Ile Ser Glu Ile Val Ile Thr
            435                 440                 445

Gly Asp Gly Asn His Leu Thr Ala His Ile Tyr Pro Asp Gln Asp Phe
```

```
                    450                 455                 460
Val Asp Lys Lys His Met Asp Ala Ala Arg Thr Ser Glu Lys Leu Gln
465                 470                 475                 480

Lys Ile Ile Asp Thr Phe Asn Lys Asn Gln Pro Thr Tyr Lys Arg Ile
                485                 490                 495

Ser Ala Leu Asp Ile Arg Lys Glu Pro Phe Glu Lys Ser Ser Thr Lys
            500                 505                 510

Lys Ile Lys Arg Asn Leu Val
        515

<210> SEQ ID NO 54
<211> LENGTH: 517
<212> TYPE: PRT
<213> ORGANISM: M. formatexigens

<400> SEQUENCE: 54

Met Leu Ile Arg Asp Ile Ile Glu Glu Ser Gly Lys Lys Tyr Ala Gly
1               5                   10                  15

Ile Thr Ala Ile Lys Trp Leu Lys Lys Glu Ile Met Glu Met Ser
            20                  25                  30

Tyr Arg Glu Leu Leu Glu Asn Ala Ala Ala Val Arg Arg Gly Leu Leu
        35                  40                  45

Ala Glu Gly Phe Ala Gly Ala His Leu Ala Leu Ile Gly Ser Ser Ser
    50                  55                  60

Ala Glu Trp Val Glu Ser Tyr Leu Gly Ile Ile Thr Gly Asn Thr Val
65                  70                  75                  80

Ala Val Pro Leu Asp Ala Asn Leu Pro Gly Glu Asp Leu Val Asp Leu
                85                  90                  95

Leu Asn Arg Ser Asp Ala Ala Gly Leu Phe Leu Ser Thr Lys Gln Lys
            100                 105                 110

Gly Leu Leu Gly Gln Ile Leu Asp Glu Cys Pro Lys Leu Lys Lys Ile
        115                 120                 125

Trp Met Leu Glu Asp Ala Val Glu Pro Gly Asn Ala Ser Gly Ala Glu
    130                 135                 140

Val Thr Ser Leu Ala Asp Leu Lys Ala Ala Gly Ala Gly Ser Val Ala
145                 150                 155                 160

Asp Ala Asp Arg Pro Asp Pro Glu Ser Ile Ala Thr Ile Ile Phe Thr
                165                 170                 175

Ser Gly Thr Thr Gly Lys Ser Lys Gly Val Met Leu Thr Gln Lys Asn
            180                 185                 190

Leu Ala Glu Asn Val Lys Ser Val Gln Tyr Thr Ala Glu Pro Gly Ser
        195                 200                 205

Val Leu Leu Ser Val Leu Pro Ile His His Ala Phe Cys Leu Val Met
    210                 215                 220

Asp Trp Leu Lys Gly Phe Ser Leu Gly Thr Thr Val Cys Ile Asn Asp
225                 230                 235                 240

Ser Leu Leu His Met Val Lys Asn Met Gly Val Phe Gln Pro Gln Val
                245                 250                 255

Met Leu Met Val Pro Leu Met Val Glu Thr Ile Tyr Lys Arg Leu Ala
            260                 265                 270

Gly Ala Asp Ala Ser Ile Pro Lys Gln Met Val Ala Lys Ala Val Phe
        275                 280                 285

Gly Gly Arg Leu His Thr Ile Phe Thr Gly Gly Ala His Leu Asp Pro
    290                 295                 300
```

```
Tyr Tyr Ile Asp Arg Phe Ala Glu Tyr Gly Val Glu Val Leu Glu Gly
305                 310                 315                 320

Tyr Gly Met Ser Glu Cys Ser Pro Val Ile Ser Ser Asn Thr Pro Glu
            325                 330                 335

Asp His Lys Lys Gly Ser Val Gly Arg Pro Leu Pro Asn Val Glu Leu
            340                 345                 350

Ser Phe Asp Asn Gly Glu Ile Leu Val Arg Gly Ser Ser Val Met Lys
        355                 360                 365

Gly Tyr Tyr Gln Met Pro Gln Glu Thr Ala Asp Thr Leu Lys Asp Gly
    370                 375                 380

Trp Leu His Thr Gly Asp Lys Gly Tyr Leu Asp Glu Asp Gly Phe Leu
385                 390                 395                 400

Phe Ile Asn Gly Arg Val Lys Asn Leu Ile Ile Leu Ser Asn Gly Glu
                405                 410                 415

Asn Ile Ser Pro Glu Glu Ile Glu Asn Lys Leu Ala Leu Gly Ala Leu
                420                 425                 430

Val Gly Glu Val Ile Val Thr Gly Glu Asn Asn Gly Leu Thr Ala Arg
        435                 440                 445

Ile Tyr Pro Asp Pro Asp Val Val Ala Ala Lys Gly Met Asp Ala Glu
    450                 455                 460

Ala Val Gln Thr Glu Leu Gln Ala Phe Leu Asp Gln Tyr Asn Lys Thr
465                 470                 475                 480

Gln Pro Ser Tyr Arg Gln Ile Thr Gly Leu Val Val Arg Lys Asn Pro
                485                 490                 495

Phe Ile Lys Ser Ala Thr Arg Lys Ile Lys Arg Gln Glu Val Leu Val
                500                 505                 510

Asp Glu Pro Cys Ala
        515

<210> SEQ ID NO 55
<211> LENGTH: 502
<212> TYPE: PRT
<213> ORGANISM: Lachnoclostridium clostridioforme

<400> SEQUENCE: 55

Met Ala Ala Glu Thr Leu Arg Asp Val Ile Arg His Gly Ala Glu Ala
1               5                   10                  15

Tyr Gly Glu Gln Thr Ala Phe Arg Tyr Lys Val Lys Lys Glu Ile Ile
            20                  25                  30

Asp Lys Ser Tyr Asn Glu Val Asn Leu Asp Ser Met Ala Val Ser Arg
        35                  40                  45

Ala Val Glu Ala Leu Gly Met Lys Gly Lys His Ile Ala Val Ile Gly
    50                  55                  60

Thr Thr Ser Tyr Gln Trp Ile Thr Ala Tyr Phe Gly Ile Val Asn Ser
65                  70                  75                  80

Gly Ser Val Ala Val Pro Ile Asp Ala Gln Phe Pro Ala Glu Ala Ile
            85                  90                  95

Cys Glu Leu Leu Asn Arg Ala Asp Val Glu Met Leu Val Tyr Asp Glu
            100                 105                 110

Leu Arg Ser Asp Val Ala Gly Asp Val Arg Glu Lys Cys Pro Gly Ile
        115                 120                 125

Arg His Val Val Ser Met Gln Ala Gln Glu Thr Ala Gly Asp Val Leu
    130                 135                 140

Ser Leu Ser Arg Leu Ile Ala Glu Asn Ala Gly Thr Tyr Glu Thr Glu
145                 150                 155                 160
```

Leu Ser Gly Ser Gln Leu Cys Thr Ile Leu Phe Thr Ser Gly Thr Thr
                165                 170                 175

Gly Arg Ser Lys Gly Val Met Leu Ser His Arg Asn Leu Thr Asp Asn
            180                 185                 190

Ala Val Cys Leu Asp Met Lys Ile Pro Ala Gly Thr Val Ser Met Thr
        195                 200                 205

Leu Leu Pro Ile Asn His Val Tyr Cys Leu Thr Met Asp Ile Ile Lys
    210                 215                 220

Gly Leu Tyr Ile Gly Met Ile Ile Cys Ile Asn Asp Ser Ile Met His
225                 230                 235                 240

Val Gln Arg Asn Met Lys Leu Phe Lys Pro Glu Ile Val Leu Leu Val
                245                 250                 255

Pro Leu Val Ile Glu Ser Ile Tyr Gly Lys Leu Lys Asp Ala Gly Ser
            260                 265                 270

Leu Ile Pro Lys Lys Met Val Ala Lys Ala Phe Gly Gly Asn Leu
        275                 280                 285

Arg Ile Ile Cys Ser Gly Gly Ala Tyr Leu Asp Pro Asp Tyr Val Asp
    290                 295                 300

Arg Phe Lys Glu Tyr Gly Ile Thr Ile Leu Gln Gly Tyr Gly Met Thr
305                 310                 315                 320

Glu Cys Ser Pro Val Ile Ser Thr Asn Leu Glu Trp Glu Asn Lys Lys
                325                 330                 335

Gly Ser Val Gly Lys Leu Leu Pro Asn Cys Glu Ala Lys Val Val Asp
            340                 345                 350

Glu Glu Ile Trp Val Arg Gly Ser Ser Val Met Gln Gly Tyr Tyr Lys
        355                 360                 365

Met Pro Glu Arg Thr Ala Glu Thr Leu Glu Asp Gly Trp Leu Lys Thr
    370                 375                 380

Gly Asp Leu Gly Tyr Val Asp Glu Asp Asn Phe Val Tyr Ile Thr Gly
385                 390                 395                 400

Arg Arg Lys Asn Leu Ile Ile Leu Ala Asn Gly Glu Asn Val Ser Pro
                405                 410                 415

Glu Glu Leu Glu Asn Glu Leu Ser Arg Ser Glu Leu Val Lys Glu Ile
            420                 425                 430

Leu Val Arg Glu Lys Asp Lys Ile Ile Glu Ala Glu Val Phe Pro Asp
        435                 440                 445

Tyr Glu Tyr Ala Lys Lys Lys His Ile Lys Asp Ile Arg Gly Thr Leu
    450                 455                 460

Gln Glu Leu Ile Asp Gly Phe Asn Lys Asp Met Pro Val Tyr Lys Arg
465                 470                 475                 480

Ile Tyr Ser Leu Ile Val Arg Glu Thr Glu Phe Glu Lys Thr Pro Ser
                485                 490                 495

Lys Lys Ile Lys Arg Phe
            500

<210> SEQ ID NO 56
<211> LENGTH: 504
<212> TYPE: PRT
<213> ORGANISM: B. producta

<400> SEQUENCE: 56

Met Ser Gly Lys Ile Asn Thr Met Lys Asp Ile Ile Asp Tyr Ala Ala
1               5                   10                  15

Glu Thr Tyr Gly Asp Ala Pro Ala Ile Arg Tyr Lys Val Arg Lys Glu

```
                  20                  25                  30
Val Ile Thr Arg Thr Phe Arg Asp Leu Lys Arg Asp Ser Glu Ala Phe
             35                  40                  45
Cys Arg Ala Leu Asp Ser Met Gly Met Leu Gly Lys His Val Ala Val
         50                  55                  60
Ile Gly Pro Thr Thr Tyr Glu Trp Ile Leu Ala Tyr Phe Gly Ala Ala
65                  70                  75                  80
Asn Ser Gly Cys Val Ile Val Pro Leu Asp Ala Gln Leu Pro Ala Ala
                 85                  90                  95
Asp Val Cys Glu Leu Leu Asn Arg Ala Asp Ile Ser Val Leu Val Tyr
             100                 105                 110
Asp Glu Leu Arg Arg Asp Val Ala Glu Met Ala Lys Glu Lys Cys Pro
         115                 120                 125
Gln Val Arg Phe Met Val Ser Met Gln Ala Glu Lys Asp Lys Glu Gln
         130                 135                 140
Val Leu Ser Leu Thr Ser Leu Leu Lys Lys His Ala Gly Ser Phe Ser
145                 150                 155                 160
Cys Glu Leu Asp Pro Asp Lys Leu Cys Ala Ile Leu Phe Thr Ser Gly
                 165                 170                 175
Thr Thr Gly Lys Ser Lys Gly Val Met Leu Thr His Arg Asn Leu Thr
             180                 185                 190
Asp Asn Ala Val Cys Leu Asp Met Lys Ile Pro Ala Gly Thr Val Ser
         195                 200                 205
Met Thr Leu Leu Pro Ile His His Ala Tyr Cys Phe Thr Met Asp Ile
         210                 215                 220
Leu Lys Gly Ile Tyr Ile Gly Met Val Ile Cys Ile Asn Asp Ser Ile
225                 230                 235                 240
Met His Val Ser Lys Asn Met Lys Leu Phe Lys Pro Glu Ile Val Leu
                 245                 250                 255
Leu Val Pro Met Val Ile Glu Ser Ile Tyr Lys Lys Leu Lys Glu Ser
             260                 265                 270
Thr Gly Ile Leu Pro Lys Lys Met Val Ala Lys Ala Ala Phe Gly Gly
         275                 280                 285
Asn Leu Lys Thr Ile Cys Ser Gly Gly Ala Tyr Leu Pro Pro Glu Met
         290                 295                 300
Val Gly Ala Phe Ala Glu Tyr Gly Ile Thr Ile Leu Gln Gly Tyr Gly
305                 310                 315                 320
Met Thr Glu Cys Ser Pro Val Ile Ser Thr Asn Leu Glu Trp Asp Ser
                 325                 330                 335
Lys Glu Gly Ser Val Gly Arg Leu Leu Pro Asn Cys Glu Ala Lys Val
             340                 345                 350
Val Asp Glu Glu Ile Trp Val Arg Gly Ser Ser Val Met Met Gly Tyr
         355                 360                 365
Tyr Lys Met Pro Ala Glu Thr Glu Glu Ala Leu Glu Asp Gly Trp Leu
         370                 375                 380
Lys Thr Gly Asp Leu Gly Tyr Val Asp Gln Asp Asp Phe Val Phe Leu
385                 390                 395                 400
Thr Gly Arg Lys Lys Asn Leu Ile Ile Leu Lys Asn Gly Glu Asn Val
                 405                 410                 415
Ser Pro Glu Glu Leu Glu Asn Glu Ile Ser Arg Ser Pro Leu Val Lys
             420                 425                 430
Glu Ile Ile Val Arg Glu Thr Glu Ser Val Ile Glu Ala Glu Ile Phe
         435                 440                 445
```

```
Pro Asp Tyr Glu Tyr Ala Ser Lys Lys Arg Ile Arg Asp Val Arg Glu
    450                 455                 460

Lys Leu Gln Glu Val Ile Asp Asn Phe Asn Arg Gly Leu Pro Pro Tyr
465                 470                 475                 480

Lys Lys Ile His Gly Leu Lys Ile Arg Glu Glu Phe Glu Lys Thr
                485                 490                 495

Pro Ser Lys Lys Ile Lys Arg Tyr
            500

<210> SEQ ID NO 57
<211> LENGTH: 508
<212> TYPE: PRT
<213> ORGANISM: C. celatum

<400> SEQUENCE: 57

Met Asn Asn Ile Lys Asn Met Arg Asp Ile Ile Asp Phe Ala Ala Lys
1               5                   10                  15

Asn Tyr Gly Asp Asn Ile Ala Phe Lys Tyr Lys Ile Asn Lys Asn Glu
                20                  25                  30

Val Asp Glu Lys Ser Tyr Asn Asp Leu Lys Asn Asp Ser Glu Ala Val
            35                  40                  45

Ser Asn Ala Leu Lys Ser Leu Asn Met Ile Gly Lys His Val Ala Ile
50                  55                  60

Val Gly Gln Thr Ser Tyr Pro Trp Ile Val Ser Tyr Phe Gly Val Val
65                  70                  75                  80

Asn Ser Gly Gly Val Ile Val Pro Ile Asp Val Gln Leu Pro Ala Asp
                85                  90                  95

Asp Ile Cys Glu Leu Ile Glu Arg Ser Asp Ala Glu Ile Leu Ile Tyr
                100                 105                 110

Asp Glu Ile Arg His Asp Val Ala Glu Arg Ile Lys Glu Lys Ser His
            115                 120                 125

Asn Val Lys Tyr Ile Ile Ser Met Asn Glu Lys Leu Asn Thr Glu Phe
            130                 135                 140

Ala Leu Ser Leu Asn Glu Leu Met Ala Glu Asn Arg Ser Ser Phe His
145                 150                 155                 160

Ile Glu Ile Asp Glu Glu Lys Leu Cys Thr Ile Leu Phe Thr Ser Gly
                165                 170                 175

Thr Thr Gly Lys Ser Lys Gly Val Met Leu Asn His Arg Asn Leu Thr
            180                 185                 190

Asp Asn Ala Ile Ala Phe Asp Val Gln Leu Lys Ala Gly Thr Val Ser
            195                 200                 205

Met Thr Val Leu Pro Ile Asn His Val Phe Cys Phe Thr Met Asp Ile
210                 215                 220

Leu Lys Gly Ile His Leu Gly Leu Cys Ile Cys Ile Asn Asp Ser Val
225                 230                 235                 240

Met Arg Val Leu Lys Asn Leu Lys Leu Phe Lys Pro Gln Val Met Cys
                245                 250                 255

Leu Val Pro Met Ile Ile Glu Ser Leu Tyr Asn Lys Leu Ile Asp Glu
                260                 265                 270

Ser Lys Asp Ile Cys Lys Glu Val Ala Lys Val Ala Leu Gly Gly
            275                 280                 285

Asn Leu Lys Thr Ile Tyr Ser Gly Gly Ala Tyr Leu Asn Pro Glu Ile
            290                 295                 300

Ile Asp Gly Met Asn Asp Phe Gly Ile Glu Val Ile Gln Gly Tyr Gly
```

```
                305                 310                 315                 320
Met Thr Glu Cys Ser Pro Val Ile Ser Thr Asn Asn Asn Cys Glu Phe
                325                 330                 335
Lys Arg Glu Ser Val Gly Lys Leu Ile Ser Asn Cys Glu Ala Lys Ile
                340                 345                 350
Ile Asp Glu Glu Ile Trp Val Arg Gly Ser Ser Val Met Met Gly Tyr
                355                 360                 365
Tyr Lys Met Pro Lys Glu Thr Glu Ala Leu Val Asp Gly Trp Leu
                370                 375             380
Lys Thr Gly Asp Leu Gly Tyr Ile Asp Glu Asp Asn Phe Val Phe Ile
385                 390                 395                 400
Thr Gly Arg Lys Lys Asn Leu Ile Ile Leu Ser Asn Gly Glu Asn Val
                405                 410                 415
Ser Pro Glu Glu Leu Glu Asn Glu Leu Ser Lys Ser Arg Leu Ile Lys
                420                 425                 430
Glu Ile Leu Val Ser Glu Tyr Lys Asn Ile Ile Lys Ala Glu Ile Leu
                435                 440                 445
Pro Asp Tyr Glu Tyr Ala Asn Asn Asn Gly Ile Asn Asp Ile Glu Asn
                450                 455                 460
Glu Ile Arg Asn Leu Val Asp Lys Tyr Asn Cys Glu Leu Pro Thr Tyr
465                 470                 475                 480
Lys Arg Ile Gly Met Val Ile Ile Arg Asp Thr Glu Phe Glu Lys Thr
                485                 490                 495
Thr Ser Lys Lys Ile Lys Arg Glu Tyr Thr Lys Val
                500                 505

<210> SEQ ID NO 58
<211> LENGTH: 501
<212> TYPE: PRT
<213> ORGANISM: R. bacterium

<400> SEQUENCE: 58

Met Thr Ser Thr Ile Arg Glu Ile Leu Val Glu Ala Gln Gln Arg Phe
1               5                   10                  15
Gly Pro Glu Val Ala Val Arg Tyr Lys Val Gly Lys Asn Gln Ile Glu
                20                  25                  30
Asp Lys Thr Tyr Asn Gln Leu Arg Gln Asp Ser Glu Ser Phe Ser Ser
            35                  40                  45
Ala Leu Ala Ala Leu Gly Glu Gln Gly Ser His Ile Ala Val Ile Gly
        50                  55                  60
Pro Thr Ser Tyr Arg Trp Met Val Thr Tyr Leu Gly Ile Val Asn Ser
65                  70                  75                  80
Gly Ser Val Ala Val Pro Leu Asp Ala Ser Leu Pro Ala Ala Asp Val
                85                  90                  95
Trp Glu Leu Leu Asp Arg Ala Asp Val Thr Thr Leu Val Ala Asp Ala
                100                 105                 110
Ala Arg Lys Asp Val Ala Glu Gly Ala Lys Glu His Cys Pro Lys Leu
            115                 120                 125
Lys His Val Val Ile Met Gln Gln Glu Glu His Ser Asp Ala Ala Leu
        130                 135                 140
Phe Leu Pro Gln Leu Leu Ala Glu His Gln Thr Ala Phe Asp Phe Glu
145                 150                 155                 160
Pro Gln Pro Asp Gln Leu Cys Thr Ile Met Phe Thr Ser Gly Thr Thr
                165                 170                 175
```

```
Gly Lys Ser Lys Gly Val Met Leu Thr His Arg Asn Leu Ala Glu Asn
            180                 185                 190

Ala Gly Ser Ile Asn Met Asp Leu Pro Glu Arg Met Val Leu Leu Ser
        195                 200                 205

Val Leu Pro Ile His His Ala Tyr Cys Leu Cys Leu Asp Val Leu Lys
    210                 215                 220

Ala Ile Ser Leu Gly Ser Ile Ile Cys Ile Asn Asp Ser Leu Leu Arg
225                 230                 235                 240

Val Met Lys Asn Ile Gln Leu Phe Lys Pro Glu Met Ile Leu Met Val
                245                 250                 255

Pro Leu Met Ile Glu Thr Ile Ala Lys Lys Leu Glu Asp Asn Thr Leu
            260                 265                 270

Leu Pro Pro Lys Leu Val Lys Asn Ala Val Phe Gly Lys Gln Leu Thr
        275                 280                 285

Lys Ile Ser Ser Gly Gly Ala Tyr Leu Asp Pro Ser Tyr Ile Asp Leu
    290                 295                 300

Phe Glu Lys Tyr Gly Ile Thr Ile Leu Gln Gly Tyr Gly Met Thr Glu
305                 310                 315                 320

Cys Ser Pro Val Ile Ser Thr Thr Arg Pro Trp Asn Ile Asn Lys Asn
                325                 330                 335

Ala Val Gly Gln Leu Ile Asp Asn Cys Glu Ala Lys Thr Val Asp Gly
            340                 345                 350

Glu Leu Trp Val Arg Gly Ser Ser Val Met Gln Gly Tyr Tyr Lys Met
        355                 360                 365

Pro Glu Glu Thr Ala Ala Thr Leu Glu Asp Gly Trp Leu Lys Thr Gly
    370                 375                 380

Asp Leu Gly Tyr Val Asp Glu Asp Gly Phe Val Tyr Leu Thr Gly Arg
385                 390                 395                 400

Lys Lys Asn Leu Ile Ile Thr Lys Asn Gly Glu Asn Val Ser Pro Glu
                405                 410                 415

Glu Leu Glu Asn Lys Leu Gly Val Glu Arg Leu Ile Gln Glu Val Leu
            420                 425                 430

Val Arg Glu Asn Lys Ser Val Ile Glu Ala Glu Ile Phe Pro Asp Tyr
        435                 440                 445

Glu Tyr Ala Lys Lys Lys His Ile Lys Asp Val Arg Ala Ala Leu Gln
    450                 455                 460

Glu Ile Ile Asp Gln Tyr Asn Leu Gln Ala Pro His Lys Lys Ile
465                 470                 475                 480

Tyr Ser Leu Ile Val Arg Glu Thr Glu Phe Glu Lys Thr Pro Ser Lys
                485                 490                 495

Lys Ile Lys Arg Phe
            500

<210> SEQ ID NO 59
<211> LENGTH: 502
<212> TYPE: PRT
<213> ORGANISM: Unknown
<220> FEATURE:
<223> OTHER INFORMATION: Clostridiales sp.

<400> SEQUENCE: 59

Met Pro Val Gly Thr Leu Arg Asp Ile Ile Arg His Gly Ala Asp Ala
1               5                   10                  15

Tyr Gly Ser Gln Thr Ala Phe Arg Tyr Lys Val Lys Lys Glu Ile Val
            20                  25                  30
```

-continued

Asp Arg Thr Tyr Leu Asp Val Asn Arg Asp Ser Met Ala Val Ser Arg
         35                  40                  45

Met Leu Glu Ser Met Gly Met Glu Gly Lys His Ile Ala Leu Ile Gly
 50                  55                  60

Thr Thr Thr Tyr Gln Trp Ile Val Gly Tyr Phe Gly Ile Val Gly Ser
 65                  70                  75                  80

Gly Ser Val Ala Val Pro Ile Asp Ala Gln Leu Pro Ala Asp Ala Val
                 85                  90                  95

Cys Glu Leu Leu Glu Arg Ala Asp Val Glu Met Leu Ile Phe Asp Glu
            100                 105                 110

Ile Arg Arg Asp Val Ala Lys Ala Val Lys Glu Lys Cys Pro Ser Val
        115                 120                 125

Arg Tyr Ile Val Ser Met Gln Ala Glu Glu Ala Gly Asp Gly Ile Gln
    130                 135                 140

Ser Leu Ser Met Leu Met Ala Leu His Ala Gly Glu Tyr Glu Lys Glu
145                 150                 155                 160

Leu Ser Gly Asp Gln Leu Ala Thr Ile Leu Phe Thr Ser Gly Thr Thr
                165                 170                 175

Gly Lys Ser Lys Gly Val Met Leu Ser His Arg Asn Leu Val Asp Asn
            180                 185                 190

Ala Val Cys Leu Asp Met Lys Ile Pro Ala Gly Thr Ile Ser Met Thr
        195                 200                 205

Leu Leu Pro Ile Asn His Val Tyr Cys Leu Thr Met Asp Ile Ile Lys
    210                 215                 220

Gly Leu His Ile Gly Leu Val Ile Cys Ile Asn Asp Ser Ile Met His
225                 230                 235                 240

Val Gln Arg Asn Met Lys Leu Phe Lys Pro Glu Ile Val Leu Leu Val
                245                 250                 255

Pro Leu Val Ile Glu Ser Ile Tyr Gly Lys Leu Lys Asp Ala Gly Ser
            260                 265                 270

Leu Ile Pro Lys Lys Met Val Ala Lys Ala Ala Phe Gly Gly Asn Leu
        275                 280                 285

Arg Ile Ile Cys Ser Gly Gly Ala Tyr Leu Asp Pro Asp Tyr Val Asp
    290                 295                 300

Lys Phe Lys Glu Tyr Gly Ile Thr Ile Leu Gln Gly Tyr Gly Met Thr
305                 310                 315                 320

Glu Cys Ser Pro Val Ile Ser Thr Asn Leu Glu Trp Glu Asn Lys Lys
                325                 330                 335

Gly Ser Val Gly Lys Leu Leu Pro Asn Cys Glu Ala Lys Val Val Asp
            340                 345                 350

Glu Glu Ile Trp Val Arg Gly Ser Ser Val Met Gln Gly Tyr Tyr Lys
        355                 360                 365

Met Pro Glu Gln Thr Ala Glu Thr Leu Glu Asp Gly Trp Leu Lys Thr
    370                 375                 380

Gly Asp Leu Gly Tyr Val Asp Glu Asp Arg Phe Val Tyr Ile Thr Gly
385                 390                 395                 400

Arg Arg Lys Asn Leu Ile Ile Leu Ala Asn Gly Glu Asn Val Ser Pro
                405                 410                 415

Glu Glu Leu Glu Asn Gln Leu Ser Arg Ser Glu Leu Val Lys Glu Ile
            420                 425                 430

Leu Val Arg Glu Lys Asp Lys Val Ile Glu Ala Glu Ile Phe Pro Asp
        435                 440                 445

Tyr Glu Tyr Ala Lys Lys Lys His Val Lys Asp Val Glu Gly Lys Leu

```
            450                 455                 460
Gln Glu Leu Val Asp Asp Phe Asn Lys Asp Met Pro Val Tyr Lys Arg
465                 470                 475                 480

Ile Tyr Ser Leu Ile Val Arg Glu Thr Glu Phe Glu Lys Thr Pro Ser
                485                 490                 495

Lys Lys Ile Lys Arg Phe
                500

<210> SEQ ID NO 60
<211> LENGTH: 504
<212> TYPE: PRT
<213> ORGANISM: E. rectale

<400> SEQUENCE: 60

Met Leu Phe His Thr Ile Pro Asp Ile Leu Ser Tyr Ala Asn Glu Ala
1               5                   10                  15

Tyr Gly Ala Asp Asp Ala Ile Arg Trp Lys Lys Ser Lys Asn Glu Ile
                20                  25                  30

Glu Ser Arg Thr Tyr Ser Glu Leu Lys Asn Asp Thr Asp Ser Phe Ala
            35                  40                  45

Asn Ala Ile Glu Lys Leu Gly Lys Gly Gln His Ile Ala Val Ile
50                  55                  60

Gly Pro Ser Ser Tyr Glu Trp Ile Val Ser Tyr Leu Ala Ile Thr Glu
65              70                  75                  80

Ser Gly Ser Val Ala Val Pro Ile Asp Ala Ser Leu Pro Ala Ala Asp
                85                  90                  95

Ile Cys Glu Leu Leu Asp Arg Ala Ser Val Arg Met Leu Ile Phe Asp
            100                 105                 110

Glu Ala Arg Ser Asp Val Ala Glu Ala Ala Lys Ser Cys His Asp
            115                 120                 125

Ile Asn Val Tyr Val Ser Met Asn Ser Thr Glu His Cys Pro Gln Val
130                 135                 140

Leu Ser Phe Lys Gly Leu Ile Asp Asp Asn Arg Gly Ser Tyr Glu Pro
145                 150                 155                 160

Ala Val Ala Glu Asp Ala Leu Cys Thr Ile Met Phe Thr Ser Gly Thr
                165                 170                 175

Thr Gly Lys Ser Lys Gly Val Met Leu Thr Gln Asn Asn Leu Ala Glu
            180                 185                 190

Asn Ala Thr Cys Leu Asp Met Lys Ile Gly Pro His Thr Val Ile Leu
            195                 200                 205

Ser Val Leu Pro Ile His His Ala Tyr Cys Leu Ser Met Asp Ile Leu
        210                 215                 220

Lys Gly Ile Ser Leu Gly Ser Val Ile Cys Ile Asn Asp Ser Ile Met
225                 230                 235                 240

Arg Met Ala Lys Asn Ile Gln Leu Phe Thr Pro Asp Met Ile Leu Met
                245                 250                 255

Val Pro Leu Met Ile Glu Thr Phe Ala Arg Lys Leu Glu Glu Val Arg
            260                 265                 270

Ala Ala Gly Leu Pro Ala Glu Pro Val Arg Lys Lys Met Phe Gly Glu
        275                 280                 285

Arg Leu His Thr Ile Cys Ser Gly Gly Ala Tyr Leu Asn Pro Asp Tyr
    290                 295                 300

Val Asp Leu Phe Ala Glu Phe Gly Ile Thr Ile Leu Gln Gly Tyr Gly
305                 310                 315                 320
```

```
Met Thr Glu Cys Ser Pro Val Ile Ser Thr Asn Leu Ser Trp Asp Ile
                325                 330                 335

Arg Lys Asn Ser Val Gly Lys Leu Met Pro Asn Cys Glu Ala Lys Thr
            340                 345                 350

Val Asp Gly Glu Leu Phe Val Arg Gly Thr Ser Val Met Gln Gly Tyr
        355                 360                 365

Tyr Lys Met Pro Lys Glu Thr Glu Thr Leu Ser Asp Gly Trp Leu
    370                 375                 380

His Thr Gly Asp Leu Gly Tyr Val Asp Glu Asp Gly Tyr Ile Tyr Leu
385                 390                 395                 400

Thr Gly Arg Arg Lys Asn Leu Ile Ile Thr Lys Asn Gly Glu Asn Val
                405                 410                 415

Ser Pro Glu Glu Leu Glu Asn Ala Leu Ser Val Asn His Leu Ile Lys
            420                 425                 430

Glu Ile Ile Val Arg Glu Ser Glu Gly Val Ile Glu Ala Glu Ile Phe
        435                 440                 445

Pro Asp Arg Glu Tyr Ala Gln Asn Thr Gly Ile Ala Asp Ile Arg Ser
    450                 455                 460

Ala Leu Gln Ala Leu Ile Asp Glu Tyr Asn Val Asn Ala Pro Ala Tyr
465                 470                 475                 480

Lys Arg Ile Tyr Ser Ile Lys Val Arg Glu Ser Glu Phe Glu Lys Thr
                485                 490                 495

Ala Ser Arg Lys Ile Lys Arg Ser
            500

<210> SEQ ID NO 61
<211> LENGTH: 319
<212> TYPE: PRT
<213> ORGANISM: Lachnoclostridium clostridioforme

<400> SEQUENCE: 61

Met Gly Ile Lys Gly Trp Ile Leu Gly Leu Ala Ala Ala Gly Ala Ala
1               5                   10                  15

Gly Glu Tyr Gly Ile Ala Arg Tyr Phe Phe His Arg Thr Val Val Arg
            20                  25                  30

Gly Asn Ala Lys Arg Asp Arg Thr Arg Lys Met Ala Gly Thr Asp Trp
        35                  40                  45

Asp Ala Tyr Ile Pro Gly Ile Arg Ala Ser Arg Glu Trp Leu Ala Gly
    50                  55                  60

Gln Pro Gln Glu Glu Val Tyr Ile Thr Ser Arg Asp Gly Leu Arg Leu
65                  70                  75                  80

His Gly Thr Phe Phe Cys Cys Glu Gly Ser Gly Lys Ala Val Val Cys
                85                  90                  95

Phe His Gly Tyr Thr Ser Glu Gly Leu Asn Asp Tyr Thr Ser Ile Ala
            100                 105                 110

Lys Phe Tyr Leu Ser Gln Gly Phe Ser Leu Met Ala Val Asp Glu Arg
        115                 120                 125

Ala His Gly Lys Ser Glu Gly Thr Tyr Ile Gly Phe Gly Cys Leu Asp
    130                 135                 140

Arg Asn Asp Ala Lys Gln Trp Met Glu Tyr Met Val Glu Arg Leu Gly
145                 150                 155                 160

Glu Asp Cys Glu Leu Met Leu His Gly Ile Ser Met Gly Ala Ala Thr
                165                 170                 175

Val Leu Met Ser Thr Gly Leu Asn Leu Pro Lys Gln Val Arg Ala Ala
            180                 185                 190
```

```
Val Ser Asp Cys Ala Phe Thr Ser Ala Trp Glu Val Phe Ser His Val
        195                 200                 205

Leu Arg Ser Met Tyr His Met Pro Ala Phe Pro Val Met Gln Ile Ala
    210                 215                 220

Asp Arg Met Ala Arg Ser Glu Ala Gly Tyr Gly Leu Asp Glu Cys Asn
225                 230                 235                 240

Ala Arg Glu Glu Val Lys Lys Ala Arg Ile Pro Ile Leu Phe Ile His
                245                 250                 255

Gly Asp Arg Asp Thr Phe Val Pro Cys Ser Met Val Tyr Glu Leu Tyr
                260                 265                 270

Glu Ala Cys Ala Ser Pro Lys Glu Leu Leu Val Ile Pro Gly Ala Ser
                275                 280                 285

His Ala Glu Ala Tyr Tyr Lys Glu Ala Asp Arg Tyr Glu His Ala Ile
                290                 295                 300

Glu Glu Leu Ile Ala Arg Phe Phe Gly Lys Glu Glu Asn Lys Val
305                 310                 315

<210> SEQ ID NO 62
<211> LENGTH: 339
<212> TYPE: PRT
<213> ORGANISM: B. producta

<400> SEQUENCE: 62

Met Asn Gly Trp Ser Leu Leu Gly Ala Gly Leu Ala Leu Ala Ala Ala
1               5                   10                  15

Gly Glu Tyr Gly Ile Ala Ser Tyr Phe Phe Arg Arg Thr Met Leu Arg
                20                  25                  30

Gln Asn Ala Ala Thr Lys Arg Thr Met Asp Met Ala Gly Thr Asn Trp
            35                  40                  45

Asp Leu Tyr Ile Pro Glu Ile Gly Lys Met Lys Gln Trp Met Leu Glu
    50                  55                  60

Gln Glu Arg Glu Asp Val Tyr Ile Arg Ser Gly Asp Gly Leu Lys Leu
65                  70                  75                  80

His Gly Thr Tyr Phe Pro Gly Gln Gly Ser Gly Lys Leu Val Ile Cys
                85                  90                  95

Phe His Gly Tyr Thr Ser Lys Gly Met Ser Asp Tyr Ile Gly Leu Ser
                100                 105                 110

Asn Tyr Tyr Leu Pro Arg Gly Tyr Gln Met Leu Leu Val Asp Glu Arg
            115                 120                 125

Ala His Gly Asp Ser Glu Gly Thr Tyr Ile Gly Phe Gly Cys Leu Asp
    130                 135                 140

Arg Glu Asp Ala Leu Leu Trp Ile Thr Tyr Ala Val Lys Arg Phe Gly
145                 150                 155                 160

Ser Gly Cys Gln Ile Trp Leu His Gly Thr Ser Met Gly Ala Ser Thr
                165                 170                 175

Val Leu Met Ala Ser Gly Leu Lys Leu Pro Pro Gln Val Arg Gly Ile
                180                 185                 190

Val Ser Asp Cys Ala Phe Thr Thr Ala Trp Asp Val Phe Ala His Val
                195                 200                 205

Leu Lys Asp Gln Tyr His Leu Pro Ala Tyr Pro Ile Leu Lys Leu Ser
    210                 215                 220

Asp Ser Met Cys Arg Lys Lys Ala Gly Tyr Gly Leu Lys Gln Cys Ser
225                 230                 235                 240

Ala Ser Glu Glu Val Lys Arg Ala Lys Val Pro Ile Leu Phe Ile His
```

```
                        245                 250                 255
Gly Asp Ala Asp Thr Phe Val Pro Cys Arg Met Cys Tyr Glu Ile Tyr
            260                 265                 270
Glu Asn Cys Ala Ser Lys Lys Asp Met Leu Ile Val His Gly Ala Gly
        275                 280                 285
His Val Glu Ala Phe Tyr Lys Glu Gln Ala Leu Tyr Glu Gln Lys Leu
    290                 295                 300
Thr Glu Phe Leu Glu Thr Ala Gly Glu Ala Trp Ala Pro Ala Gly Lys
305                 310                 315                 320
Ser Ile Tyr Val Ser Asp Val Thr Gly Glu Gly Ser Thr Gly Asp Ser
                325                 330                 335
Val Pro Val

<210> SEQ ID NO 63
<211> LENGTH: 329
<212> TYPE: PRT
<213> ORGANISM: C. celatum

<400> SEQUENCE: 63

Met Ser Lys Arg Leu Phe Ile Gly Ala Gly Ile Ile Gly Leu Ala Ala
1               5                   10                  15
Leu Thr Glu Val Val Met Ala Arg Tyr Leu Leu Glu Arg Val Leu Ile
            20                  25                  30
Arg Lys Asn Val Lys Thr Glu Arg Thr Gln Lys Met Ser Gly Thr Asn
        35                  40                  45
Trp Asp Asn Tyr Ile Pro Phe Ile Lys Glu Arg Lys Ala Trp Leu Met
    50                  55                  60
Leu Gln Glu Arg Glu Asp Val Tyr Ile Thr Ser Asp Asp Gly Leu Arg
65                  70                  75                  80
Leu His Gly Val Leu Val Pro Asn Glu Asn Ser Lys Lys Thr Val Ile
                85                  90                  95
Cys Phe His Gly Tyr Ser Ser Lys Gly Ala Thr Ser Asp Phe Ala Ala
            100                 105                 110
Ile Ser Lys Phe Tyr Lys Glu Asn Asp Phe Asn Ile Leu Met Val Asp
        115                 120                 125
Ala Arg Ala His Gly Glu Ser Asp Gly Lys Tyr Ile Gly Phe Gly Cys
    130                 135                 140
Leu Asp Arg Met Asp Val Leu Lys Trp Ile Asn Tyr Val Val Glu Lys
145                 150                 155                 160
Phe Gly Glu Glu Cys Gln Ile Leu Leu His Gly Ile Ser Met Gly Gly
                165                 170                 175
Ala Thr Val Val Met Ala Ser Gly Leu His Leu Pro Asn Asn Val Lys
            180                 185                 190
Phe Ile Ile Ser Asp Cys Ala Phe Thr Ser Pro Trp Glu Val Phe Ser
        195                 200                 205
Asp Val Leu Lys Asn Met Tyr His Ile Pro Pro Phe Pro Val Ile Asn
    210                 215                 220
Ile Val Ser Asn Met Cys Lys Lys Met Ala Gly Tyr Asn Phe Lys Glu
225                 230                 235                 240
Cys Asn Ala Asp Ile Glu Val Arg Arg Ala Thr Val Pro Ile Leu Phe
                245                 250                 255
Ile His Gly Ala Asn Asp Thr Phe Val Pro Cys Arg Met Cys His Asp
            260                 265                 270
Ile Tyr Asp Asn Cys His Ser Asp Lys Glu Ile Leu Ile Val Lys Glu
```

```
            275                 280                 285
Ala Gly His Ala Glu Ser Tyr Tyr Lys Glu Thr Glu Ile Tyr Glu Glu
            290                 295                 300

Asn Ile Lys Lys Phe Ile Ser Lys Tyr Ile Leu Asp Glu Ile Gly Ala
305                 310                 315                 320

Gly Asn Asn Asp Lys Arg Lys Arg Tyr
                325

<210> SEQ ID NO 64
<211> LENGTH: 312
<212> TYPE: PRT
<213> ORGANISM: R. bacterium

<400> SEQUENCE: 64

Met Gly Leu Leu Lys Lys Ala Ala Val Leu Ala Gly Leu Ala Ala Ala
1               5                   10                  15

Ala Glu Gly Leu Gly Thr Ala Tyr Phe Tyr Arg Arg Thr Met Ile Arg
                20                  25                  30

Thr Asn Ala Lys Pro Glu Arg Ser Ala Lys Met Ser Gly Ile Asp Trp
            35                  40                  45

Ser Gln Tyr Tyr Pro Arg Met His Glu Asn Arg Asp Trp Leu Leu Gln
    50                  55                  60

Gln Pro His Glu Glu Val Gly Ile Leu Ser His Asp Gly Leu Lys Leu
65                  70                  75                  80

His Gly Thr Tyr Phe Pro Gly Pro Gly Asn Lys Val Val Ile Cys Phe
                85                  90                  95

His Gly Tyr Thr Ser Tyr Gly Met Gly Glu Tyr Pro Ser Leu Ala Arg
                100                 105                 110

Cys Phe Met Ser Arg Gly Phe Gly Ala Leu Ile Ile Asp Gln Arg Ser
            115                 120                 125

His Gly Glu Ser Glu Gly Lys Tyr Ile Gly Phe Gly Cys Met Asp Arg
    130                 135                 140

Leu Asp Ala Leu Glu Trp Ile Arg Trp Thr Ile Asp Lys Val Gly Gln
145                 150                 155                 160

Asp Ala Gln Ile Ile Leu His Gly Gly Ser Met Gly Gly Ala Thr Val
                165                 170                 175

Cys Met Val Ser Gly Leu Asp Leu Pro Pro Gln Val Lys Gly Ile Ile
            180                 185                 190

Ser Asp Ser Ala Phe Thr Ser Pro Lys Tyr Val Phe Thr His Val Leu
    195                 200                 205

His Ser Met Tyr His Leu Pro Ala Thr Pro Met Ile Pro Leu Ala Asp
    210                 215                 220

Lys Val Asn Lys Arg Leu Ala Gly Tyr Gly Leu Asp Asp Cys Asn Ala
225                 230                 235                 240

Ala Arg Glu Val Arg Lys Ala Lys Val Pro Met Leu Phe Ile His Gly
                245                 250                 255

Ser Lys Asp Thr Phe Val Pro Pro Tyr Met Cys Asp Glu Leu Tyr Glu
            260                 265                 270

Asn Cys Ala Ala Pro Lys Thr Lys Leu Ile Val Glu Gly Ala Gly His
        275                 280                 285

Val Glu Ser Tyr Tyr Lys Asn Thr Gln Glu Tyr Glu Glu Ala Leu Asp
    290                 295                 300

Lys Phe Ile Gly Gly Ile Ile Lys
305                 310
```

<210> SEQ ID NO 65
<211> LENGTH: 330
<212> TYPE: PRT
<213> ORGANISM: Unknown
<220> FEATURE:
<223> OTHER INFORMATION: Clostridiales sp.

<400> SEQUENCE: 65

Met Gly Lys Ile Gly Leu Leu Phe Gly Leu Ala Ala Ala Gly Ala Ala
1               5                   10                  15

Gly Glu Tyr Gly Ile Ala Arg Tyr Phe Phe His Arg Thr Val Val Arg
            20                  25                  30

Gly Asn Ala Lys Arg Glu Arg Thr Gln Lys Met Ala Gly Thr Asp Trp
        35                  40                  45

Asp Ala Tyr Ile Pro Gly Ile Arg Ala Ser Lys Glu Trp Leu Ser Gly
    50                  55                  60

Lys Pro Gln Glu Asp Val Tyr Ile Thr Ser Asp Asp Gly Leu Arg Leu
65                  70                  75                  80

His Gly Thr Phe Phe Pro Cys Pro Gly Ser Asp Arg Ala Val Ile Cys
                85                  90                  95

Phe His Gly Tyr Thr Ser Glu Gly Leu Asn Asp Phe Ser Ser Ile Ala
            100                 105                 110

Arg Phe Tyr Leu Glu Gln Gly Phe Asn Leu Met Val Val Asp Glu Arg
        115                 120                 125

Ala His Gly Arg Ser Glu Gly Thr Tyr Ile Gly Phe Gly Cys Leu Asp
    130                 135                 140

Arg Met Asp Ala Arg Leu Trp Ile Glu Tyr Val Ile Glu Arg Leu Gly
145                 150                 155                 160

Gln Asp Cys Gln Val Met Leu His Gly Ile Ser Met Gly Gly Ala Thr
                165                 170                 175

Val Leu Met Thr Thr Gly Leu Ser Leu Pro Pro Gln Val Lys Ala Ala
            180                 185                 190

Val Ser Asp Cys Gly Phe Thr Ser Ala Trp Glu Val Phe Ser Tyr Val
        195                 200                 205

Leu Lys Ser Met Tyr His Met Pro Pro Phe Pro Ile Met Gln Ile Ala
    210                 215                 220

Asp Arg Met Ala Arg Gln Glu Ala Gly Tyr Gly Leu Asp Gln Cys Asn
225                 230                 235                 240

Ala Arg Asp Glu Val Lys Lys Ala Arg Ile Pro Ile Leu Phe Ile His
                245                 250                 255

Gly Asp Ala Asp Thr Phe Val Pro Cys Ser Met Val Tyr Gln Leu Tyr
            260                 265                 270

Gly Ala Cys Arg Ser Gly Lys Glu Leu Leu Val Ile Ser Gly Ala Ala
        275                 280                 285

His Ala Glu Ala Tyr Tyr Lys Asp Thr Lys Ser Tyr Glu Arg Ala Val
    290                 295                 300

Thr Glu Leu Ile Gly Arg Thr Ile Glu Pro Leu Gly Asp Arg His Glu
305                 310                 315                 320

Gly Arg Asp Ser Arg Asp Glu Lys Gly Glu
                325                 330

<210> SEQ ID NO 66
<211> LENGTH: 317
<212> TYPE: PRT
<213> ORGANISM: E. rectale

<400> SEQUENCE: 66

```
Met Arg Met Lys Trp Gly Ile Ile Ala Gly Val Leu Gly Ile Ala
1               5                   10                  15

Ala Ala Glu Ala Gly Gly Ser Ala Tyr Phe Tyr Arg Arg Thr Met Met
            20                  25                  30

Arg Tyr Asn Ala Lys Lys Glu Arg Thr Met Lys Met Ser Gly Val Asp
                35                  40                  45

Trp Glu Ser Tyr Tyr Ser Phe Met Lys Pro His Gly Glu Trp Met Arg
        50                  55                  60

Ala Gln Thr His Glu Asp Val Trp Ile Lys Ser Asp Asp Gly Leu Arg
65                  70                  75                  80

Leu His Ala Thr Tyr Phe Pro Gly Ile Asp Gly Asn Pro Asp Lys
                85                  90                  95

Ala Val Ile Cys Phe His Gly Tyr Thr Ser Glu Ala Met Ser Asp Tyr
                100                 105                 110

Ser Ser Ile Ser Asn Tyr Tyr Leu Lys Lys Gly Tyr Ser Met Leu Leu
            115                 120                 125

Val Asp Ala Arg Ala His Gly Gln Ser Glu Gly Lys Phe Ile Gly Phe
        130                 135                 140

Gly Cys Lys Asp Arg Tyr Asp Ala Leu Lys Trp Ile Asp Trp Met Ile
145                 150                 155                 160

Lys Lys Ala Gly Asn Gly Ile Arg Ile Val Leu Met Gly Asn Ser Met
                165                 170                 175

Gly Gly Ala Thr Val Leu Met Ala Ser Gly Leu Asn Leu Pro Glu Gln
            180                 185                 190

Val Lys Gly Ile Val Ser Asp Cys Ala Phe Thr Ser Pro Lys Ala Val
        195                 200                 205

Phe Thr His Val Leu His Ser Met Tyr His Leu Pro Ala Phe Pro Met
    210                 215                 220

Ile Gln Ile Ala Asp Phe Val Asn Arg Lys Met Ala Gly Tyr Gly Leu
225                 230                 235                 240

Asp Glu Cys Asn Ala Ala Lys Glu Val Gln Lys Ala Lys Leu Pro Ile
                245                 250                 255

Leu Phe Ile His Gly Asp Lys Asp Thr Phe Val Pro Cys Ser Met Cys
                260                 265                 270

Asp Glu Leu Tyr Ala Ser Cys Ala Ser Gln Lys Thr Lys Leu Ile Val
            275                 280                 285

Lys Gly Ala Gly His Cys Glu Ser Tyr Tyr Lys Asn Thr Lys Ala Phe
        290                 295                 300

Glu Asp Ala Leu Asp Lys Phe Leu Glu Gly Val Met Arg
305                 310                 315
```

<210> SEQ ID NO 67
<211> LENGTH: 205
<212> TYPE: PRT
<213> ORGANISM: Lachnoclostridium clostridioforme

<400> SEQUENCE: 67

```
Met Ile Tyr Leu Ala Thr Tyr Glu Pro Gly Gly Ser Leu Tyr Asn Arg
1               5                   10                  15

Glu Arg Glu His Ile Leu Gly Arg Ser Leu Leu Asn Phe Gly Leu Met
            20                  25                  30

Lys Glu Tyr Gly Arg Thr Trp Glu Val Glu Gln Glu Thr Gly Ser Lys
        35                  40                  45
```

-continued

```
Pro Cys Leu Lys Gly Ala Glu Asp Val Glu Phe Asn Ile Ser His Thr
 50                  55                  60

Arg Gly Leu Val Val Cys Ala Val Ala Asp Arg Ala Leu Gly Val Asp
 65                  70                  75                  80

Thr Glu Arg Ile Arg Pro Phe Lys Gly Leu Met Arg Arg Val Cys
                 85                  90                  95

Ser Glu Ser Glu Arg Gly Phe Val Leu Glu Gly Arg Ser Glu Ala Ala
                100                 105                 110

Arg Gln Glu Arg Phe Phe Arg Leu Trp Thr Leu Lys Glu Ser Phe Val
                115                 120                 125

Lys Ala Ile Gly Arg Gly Leu Ala Phe Pro Leu Gly Asp Ile Thr Phe
130                 135                 140

Ser Leu Glu Glu Gly Ala Val Lys Gly Ser Ile Pro Gly Trp Arg Phe
145                 150                 155                 160

Tyr Gln Ser Arg Val Tyr Gln Ser Tyr Ile Ile Ser Val Cys Ala Ala
                165                 170                 175

Asp Glu Lys Ala Val Phe Ala Phe Thr Thr Gly Lys Leu Lys Val Glu
                180                 185                 190

Gly Ser Leu Glu Lys Ala Leu Met Leu Gln Lys Phe Val
                195                 200                 205

<210> SEQ ID NO 68
<211> LENGTH: 191
<212> TYPE: PRT
<213> ORGANISM: C. celatum

<400> SEQUENCE: 68

Met Ser Ile Leu Gln Pro Tyr Lys Tyr Lys Ile Phe Tyr Lys Gln Ile
 1               5                  10                  15

Pro Leu Lys Lys Gly Ile Ser Lys Leu Glu Gln Asn Lys Ile Met His
                20                  25                  30

Asp Ala Gly Ile Asn Leu Leu Asp Glu Lys Leu Glu Glu Ile Phe Asn
             35                  40                  45

Val Lys Asn Ala Arg Glu Asn Tyr Cys Ser Ser Leu Asn Gly Lys Pro
 50                  55                  60

Tyr Leu Lys Asn Ser Ser Ile Asn Phe Asn Ile Ser His Cys Asn Asn
 65                  70                  75                  80

Ile Val Val Val Ile Ser Asn Lys Asn Val Gly Ile Asp Ile Glu
                 85                  90                  95

Asp Ile Lys Glu Phe Lys Lys Ser Ile Ile Arg Lys Val Leu Thr Asn
                100                 105                 110

Asn Glu Leu Ile Asp Leu Leu Ser Ala Asn Asn Lys Lys Glu Tyr Phe
             115                 120                 125

Phe Lys Leu Trp Thr Leu Lys Glu Ser Phe Leu Lys Ala Ile Gly Thr
130                 135                 140

Gly Leu Ser Tyr Gly Met Gln Asn Ile Glu Phe Ser Ile Lys Asp Lys
145                 150                 155                 160

Asn Ile Ile Cys Asn Lys Ile Gly Phe Leu Phe Lys Gln Glu Ser Leu
                165                 170                 175

Ile Phe Asn Asn Asn Lys Tyr Ile Val Ser Ile Thr Trp Glu Val
                180                 185                 190

<210> SEQ ID NO 69
<211> LENGTH: 164
<212> TYPE: PRT
<213> ORGANISM: B. producta
```

<400> SEQUENCE: 69

Met Thr Tyr Gln Glu Leu Val Ser Glu Ile Arg Gly Ile Phe Met Gln
1               5                   10                  15

Ala Asp Val Ser Gly Ile Lys Glu His Ile Ala Tyr Gln Phe Asn Ile
                20                  25                  30

Arg Gly Glu Ala Glu Gly Ala Phe Tyr Ala Glu Val Leu Glu Gly Lys
            35                  40                  45

Leu Tyr Ile Glu Pro Tyr Glu Tyr Tyr Asp Arg Asp Val Leu Phe Thr
        50                  55                  60

Thr Thr Ala Asp Thr Leu Leu Ser Ile Ala Thr Gly Thr Met Asp Ala
65                  70                  75                  80

Val Ala Ala Phe Thr Leu Gly Lys Leu Gln Val Glu Gly Ser Phe Asp
                85                  90                  95

Lys Ala Leu Leu Leu Gln Ser Phe Ser Lys Gln Ala Gly Arg Glu Lys
            100                 105                 110

Lys Lys Met Lys Ala Glu Lys Arg Gln Gln Lys Ala Glu Glu Lys
        115                 120                 125

Glu Leu Gln Lys Ala Val Glu Lys Glu Ser Gln Lys Val Val Glu Lys
130                 135                 140

Val Ala Gln Lys Thr Glu Glu Lys Thr Ala Lys Lys Thr Val Arg Arg
145                 150                 155                 160

Leu Leu Lys Lys

<210> SEQ ID NO 70
<211> LENGTH: 111
<212> TYPE: PRT
<213> ORGANISM: R. bacterium

<400> SEQUENCE: 70

Met Thr Tyr Ala Asp Met Phe Ser Glu Val Lys Gly Met Leu Ala Gly
1               5                   10                  15

Ala Asp Val Ser Asp Ile Gln Glu His Leu Ala Tyr Gln Phe Asn Ile
                20                  25                  30

Ile Gly Glu Ala Glu Gly Ile Phe Tyr Ala Glu Val Lys Glu Gly Lys
            35                  40                  45

Leu Tyr Ile Glu Pro Tyr Glu Tyr Phe Asp Arg Asp Val Met Phe Ile
        50                  55                  60

Cys Thr Ala Asp Thr Leu Phe Lys Leu Ala Lys Gly Lys Thr Asp Pro
65                  70                  75                  80

Val Leu Ala Phe Thr Thr Gly Lys Leu Lys Val Glu Gly Asn Ile Asp
                85                  90                  95

Lys Ala Leu Lys Leu Gly Asp Leu Leu Ala Arg Lys Arg Lys Gly
            100                 105                 110

<210> SEQ ID NO 71
<211> LENGTH: 105
<212> TYPE: PRT
<213> ORGANISM: Unknown
<220> FEATURE:
<223> OTHER INFORMATION: Clostridiales sp.

<400> SEQUENCE: 71

Met Thr Phe Glu Lys Val Phe Glu Thr Val Lys Glu Ile Phe Met Lys
1               5                   10                  15

Ala Asp Val Ser Lys Val Asp Glu His Leu Ala Phe Gln Phe Asn Ile
                20                  25                  30

Thr Gly Glu Gly Glu Gly Ile Phe Tyr Ala Glu Ala Lys Asp Gly Lys
         35                  40                  45

Leu Tyr Val Glu Pro Tyr Glu Tyr Asp Arg Asp Ala Ile Phe Ile
 50                  55                  60

Cys Ser Ala Asp Thr Leu Leu Lys Leu Ala Ala Gly Lys Leu Asp Pro
 65                  70                  75                  80

Val Phe Ala Phe Thr Thr Gly Lys Leu Lys Val Glu Gly Ser Leu Glu
             85                  90                  95

Lys Ala Leu Lys Leu Gln Lys Phe Val
            100                 105

<210> SEQ ID NO 72
<211> LENGTH: 110
<212> TYPE: PRT
<213> ORGANISM: E. rectale

<400> SEQUENCE: 72

Met Thr Tyr Ala Asp Met Phe Ser Lys Val Lys Gly Leu Phe Met Glu
 1               5                  10                  15

Ser Asp Val Ser Asp Ile Ser Glu His Leu Ala Phe Gln Phe Asn Ile
             20                  25                  30

Thr Gly Glu Ala Glu Gly Ile Phe Tyr Ala Glu Val Lys Asp Gly Val
         35                  40                  45

Leu Ala Val Glu Pro Tyr Glu Tyr Phe Asp Arg Asp Ala Ile Phe Ile
 50                  55                  60

Cys Ser Ala Glu Thr Leu Phe Lys Leu Ala Glu Gly Arg Ile Asp Pro
 65                  70                  75                  80

Ile Leu Ala Phe Thr Thr Gly Lys Leu Lys Val Glu Gly Asn Ile Asp
             85                  90                  95

Lys Ala Leu Arg Leu Lys Gln Ile Ile Asp Ser Lys Lys Ala
            100                 105                 110

<210> SEQ ID NO 73
<211> LENGTH: 50
<212> TYPE: DNA
<213> ORGANISM: Artificial Sequence
<220> FEATURE:
<223> OTHER INFORMATION: Synthetic

<400> SEQUENCE: 73
cgcgaaatta atacgactca ctatagggga attgtgagcg gataacaatt         50

<210> SEQ ID NO 74
<211> LENGTH: 45
<212> TYPE: DNA
<213> ORGANISM: Artificial Sequence
<220> FEATURE:
<223> OTHER INFORMATION: Synthetic

<400> SEQUENCE: 74
cccctctaga aataattttg tttaacttta agaaggagat atacc              45

<210> SEQ ID NO 75
<211> LENGTH: 45
<212> TYPE: DNA
<213> ORGANISM: Artificial Sequence
<220> FEATURE:
<223> OTHER INFORMATION: Synthetic

<400> SEQUENCE: 75

```
tccctctaga aataattttg tttaacttta agaaggagat atacc              45

<210> SEQ ID NO 76
<211> LENGTH: 45
<212> TYPE: DNA
<213> ORGANISM: Artificial Sequence
<220> FEATURE:
<223> OTHER INFORMATION: Synthetic

<400> SEQUENCE: 76
ccccactaga aataattttg tttaacttta agaaggagat atacc              45

<210> SEQ ID NO 77
<211> LENGTH: 45
<212> TYPE: DNA
<213> ORGANISM: Artificial Sequence
<220> FEATURE:
<223> OTHER INFORMATION: Synthetic

<400> SEQUENCE: 77
accctctaga aataattttg tttaacttta agaaggagat atacc              45

<210> SEQ ID NO 78
<211> LENGTH: 45
<212> TYPE: DNA
<213> ORGANISM: Artificial Sequence
<220> FEATURE:
<223> OTHER INFORMATION: Synthetic

<400> SEQUENCE: 78
acccactaga aataattttg tttaacttta agaaggagat atacc              45

<210> SEQ ID NO 79
<211> LENGTH: 122
<212> TYPE: DNA
<213> ORGANISM: Artificial Sequence
<220> FEATURE:
<223> OTHER INFORMATION: Synthetic

<400> SEQUENCE: 79
caaagcccga aaggaagctg agttggctgc tgccaccgct gagcaataac tagcataacc    60
ccttggggcc tctaaacggg tcttgagggg ttttttgctg aaaggaggaa ctatatccgg   120
at                                                                 122

<210> SEQ ID NO 80
<211> LENGTH: 4975
<212> TYPE: DNA
<213> ORGANISM: Artificial Sequence
<220> FEATURE:
<223> OTHER INFORMATION: Synthetic

<400> SEQUENCE: 80
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta aatcggggc tccctttagg   180 gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aaccctatct cggtctattc   360
ttttgattta taagggattt tgccgatttc ggctattgg ttaaaaaatg agctgattta   420
acaaaaattt aacgcgaatt ttaacaaaat attaacgttt acaatttcag gtggcacttt   480
```

```
tcggggaaat gtgcgcggaa ccccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa agtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg ggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccgggttg gactcaagac gatagttacc ggataaggcg   1800
cagcggtcgg gctgaacggg gggttcgtgc acacagccca gcttggagcg aacgacctac   1860
accgaactga tacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gccttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac accgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
```

```
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggtttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcc         4975
```

<210> SEQ ID NO 81
<211> LENGTH: 2652
<212> TYPE: DNA
<213> ORGANISM: Artificial Sequence
<220> FEATURE:
<223> OTHER INFORMATION: Synthetic

<400> SEQUENCE: 81

```
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag acatccctg cgattgagcg tgaagaactc   1080
ccgatgaaac cggaagacat cgacatgaat cctgaggctc tcaccgcgtg aaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg tcgtgtttta cgctgtgtca atgttcaacc cgcaaggtaa cgatatgacc   1320
aaaggactgc ttacgctggc gaaaggtaaa ccaatcggta aggaaggtta ctactgctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg tgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcgttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
```

-continued

| | |
|---|---|
| attaacacca acaaagatag cgagattgat gcacacaaac aggagtctgg tatcgctcct | 2340 |
| aactttgtac acagccaaga cggtagccac cttcgtaaga ctgtagtgtg ggcacacgag | 2400 |
| aagtacggaa tcgaatcttt tgcactgatt cacgactcct tcggtaccat tccggctgac | 2460 |
| gctgcgaacc tgttcaaagc agtgcgcgaa actatggttg acacatatga gtcttgtgat | 2520 |
| gtactggctg atttctacga ccagttcgct gaccagttgc acgagtctca attggacaaa | 2580 |
| atgccagcac ttccggctaa aggtaacttg aacctccgtg acatcttaga gtcggacttc | 2640 |
| gcgttcgcgt aa | 2652 |

<210> SEQ ID NO 82
<211> LENGTH: 675
<212> TYPE: DNA
<213> ORGANISM: B. subtilis

<400> SEQUENCE: 82

| | |
|---|---|
| atgaagattt acggaattta tatggaccgc ccgctttcac aggaagaaaa tgaacggttc | 60 |
| atgactttca tatcacctga aaaacgggag aaatgccgga gattttatca taagaagat | 120 |
| gctcaccgca ccctgctggg agatgtgctc gttcgctcag tcataagcag gcagtatcag | 180 |
| ttggacaaat ccgatatccg ctttagcacg caggaatacg ggaagccgtg catccctgat | 240 |
| cttcccgacg ctcatttcaa catttctcac tccggccgct gggtcattgg tgcgtttgat | 300 |
| tcacagccga tcggcataga tatcgaaaaa acgaaaccga tcagccttga gatcgccaag | 360 |
| cgcttcttt caaaaacaga gtacagcgac cttttagcaa agacaaggaa cgagcagaca | 420 |
| gactattttt atcatctatg gtcaatgaaa gaaagcttta tcaaacagga aggcaaaggc | 480 |
| ttatcgcttc cgcttgattc cttttcagtg cgcctgcatc aggacggaca agtatccatt | 540 |
| gagcttccgg acagccattc cccatgctat atcaaaacgt atgaggtcga tcccggctac | 600 |
| aaaatggctg tatgcgccgc acaccctgat ttccccgagg atatcacaat ggtctcgtac | 660 |
| gaagagcttt tataa | 675 |

<210> SEQ ID NO 83
<211> LENGTH: 1123
<212> TYPE: DNA
<213> ORGANISM: E. coli

<400> SEQUENCE: 83

| | |
|---|---|
| atgatagcgc ccggaagaga gtcaattcag ggtggtgaat gtgaaaccag taacgttata | 60 |
| cgatgtcgca gagtatgccg gtgtctctta tcagaccgtt tccgcgtgg tgaaccaggc | 120 |
| cagccacgtt tctgcgaaaa cgcgggaaaa agtggaagcg gcgatggcgg agctgaatta | 180 |
| cattcccaac cgcgtggcac aacaactggc gggcaaacag tcgttgctga ttggcgttgc | 240 |
| cacctccagt ctggccctgc acgcgccgtc gcaaattgtc gcggcgatta atctcgcgc | 300 |
| cgatcaactg ggtgccagcg tggtggtgtc gatggtagaa cgaagcggcg tcgaagcctg | 360 |
| taaagcggcg gtgcacaatc ttctcgcgca acgcgtcagt gggctgatca ttaactatcc | 420 |
| gctggatgac caggatgcca ttgctgtgga agctgcctgc actaatgttc cggcgttatt | 480 |
| tcttgatgtc tctgaccaga cacccatcaa cagtattatt ttctcccatg aagacggtac | 540 |
| gcgactgggc gtggagcatc tggtcgcatt gggtcaccag caaatcgcgc tgttagcggg | 600 |
| cccattaagt tctgtctcgg cgcgtctgcg tctggctggc tggcataaat atctcactcg | 660 |
| caatcaaatt cagccgatag cggaacggga aggcgactgg agtgccatgt ccggttttca | 720 |
| acaaaccatg caaatgctga atgagggcat cgttcccact gcgatgctgg ttgccaacga | 780 |

```
tcagatggcg ctgggcgcaa tgcgcgccat taccgagtcc gggctgcgcg ttggtgcgga    840
tatctcggta gtgggatacg acgataccga agacagctca tgttatatcc cgccgttaac    900
caccatcaaa caggattttc gcctgctggg gcaaaccagc gtggaccgct tgctgcaact    960
ctctcagggc caggcggtga agggcaatca gctgttgccc gtctcactgg tgaaaagaaa   1020
aaccaccctg gcgcccaata cgcaaaccgc ctctccccgc gcgttggccg attcattaat   1080
gcagctggca cgacaggttt cccgactgga agcgggcag tga                      1123
```

<210> SEQ ID NO 84
<211> LENGTH: 224
<212> TYPE: PRT
<213> ORGANISM: B. subtilis

<400> SEQUENCE: 84

```
Met Lys Ile Tyr Gly Ile Tyr Met Asp Arg Pro Leu Ser Gln Glu Glu
 1               5                  10                  15

Asn Glu Arg Phe Met Thr Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Gly Ala Phe Asp Ser Gln Pro Ile Gly Ile Asp Ile Glu Lys Thr Lys
           100                 105                 110

Pro Ile Ser Leu Glu Ile Ala Lys Arg Phe Phe Ser Lys Thr Glu Tyr
       115                 120                 125

Ser Asp Leu Leu Ala Lys Asp Lys Asp Glu Gln Thr Asp Tyr Phe Tyr
   130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220
```

<210> SEQ ID NO 85
<211> LENGTH: 1389
<212> TYPE: DNA
<213> ORGANISM: Blautia sp.

<400> SEQUENCE: 85

```
atgaccaact attatccgct gaccgcagca cagaaaatgc atcataattg gatcatggat     60
tatggcaccc agcaggttag cggtgttagc gttgttgcaa gcgttcaggc agaactggat    120
tttggtctgc tgaaaaaatg cattcagatg gaaaccgaac gtagcggttg tacccgtatt    180
cgttttacca aaccggataa agatggtaac gttcagcagt atctggttaa caagatccg    240
```

```
cgtgatatcg gctttaaaga tctgagcggt atgggtagcc tggcaaaagc agatgaactg    300
atgcagcagt gggcctatga aacctttgat ggtgatgata ttccgatgtg cgaattcacc    360
atgctgaaac tgccggaagg ttataatggt ttttttgtgc acatggatca ccgcctgatt    420
gatagctgtg gtctggttgt tatgattggt gatctttttc agctgtatac ctactacaaa    480
tatggcaccg catatccgca agaactggca gattttgaaa ccgtcctgaa aaagatctg     540 gccaaagcag gtaatgaaaa acgctttgcc aaagacaaaa aattctggga tgatcagctg    600
gatgcactgg gtgaaccgct gtatagtgat gttcagggtc cgagcgttct ggaagaggca    660
cgtaaacgtc atggtaatcc gaaactgcgt agcagcgata ttgaaatgaa agacctgttt    720
gttgccgtga agattatta tctggaaccg gtccgaccaaaaatctgat tgattttgt       780 atgaaccatc agctgagcat gaccaatctg ctgctgctgg gtattcgtac ctatctgagc    840
aaagttaata acggccaaga agatattacc atccagaact ttattagccg tcgtagcacc    900
catgatgaat ggaccagcgg tggtagccgt accattatgt ttccgtgtcg taccgttatt    960
gcaccggaaa ccgattttct gagcgcagcg tatgaaattc agaatatgca gaaccgcatc   1020
tacatgcaca gtaattatga tccggcattt atcatggatg aaatgcgcaa acgttataac   1080
acaccggaac acacaggtta tgaaagctgt tatctgacct atcagccgat gaccgttaaa   1140
gtggaaaatg aaatgctggg caccattcgt cagcatgcaa atggtttgc aaatggtgca    1200 gcaaccaaaa aaatgtatct gaccgttagc cataccgaag atggtggtat gaatttcagc   1260
tatcattatc agaccgcaca tctggaagaa catgatatgg aactgctgta ctattatatg   1320
atgcgcattc tgtttaaagg cattgccgaa ccggatatga gcattggtga atcatggaa    1380 ctggtgtaa                                                          1389
```

<210> SEQ ID NO 86
<211> LENGTH: 462
<212> TYPE: PRT
<213> ORGANISM: Blautia sp.

<400> SEQUENCE: 86

Met Thr Asn Tyr Tyr Pro Leu Thr Ala Ala Gln Lys Met His His Asn
1               5                   10                  15

Trp Ile Met Asp Tyr Gly Thr Gln Gln Val Ser Gly Val Ser Val Val
                20                  25                  30

Ala Ser Val Gln Ala Glu Leu Asp Phe Gly Leu Leu Lys Lys Cys Ile
            35                  40                  45

Gln Met Glu Thr Glu Arg Ser Gly Cys Thr Arg Ile Arg Phe Thr Lys
        50                  55                  60

Pro Asp Lys Asp Gly Asn Val Gln Gln Tyr Leu Val Lys Gln Asp Pro
65                  70                  75                  80

Arg Asp Ile Gly Phe Lys Asp Leu Ser Gly Met Gly Ser Leu Ala Lys
                85                  90                  95

Ala Asp Glu Leu Met Gln Gln Trp Ala Tyr Glu Thr Phe Asp Gly Asp
            100                 105                 110

Asp Ile Pro Met Cys Glu Phe Thr Met Leu Lys Leu Pro Glu Gly Tyr
        115                 120                 125

Asn Gly Phe Phe Val His Met Asp His Arg Leu Ile Asp Ser Cys Gly
    130                 135                 140

Leu Val Val Met Ile Gly Asp Leu Phe Gln Leu Tyr Thr Tyr Tyr Lys
145                 150                 155                 160

Tyr Gly Thr Ala Tyr Pro Gln Glu Leu Ala Asp Phe Glu Thr Val Leu

```
                165                 170                 175
Lys Lys Asp Leu Ala Lys Ala Gly Asn Glu Lys Arg Phe Ala Lys Asp
            180                 185                 190

Lys Lys Phe Trp Asp Asp Gln Leu Asp Ala Leu Gly Glu Pro Leu Tyr
        195                 200                 205

Ser Asp Val Gln Gly Pro Ser Val Leu Glu Glu Ala Arg Lys Arg His
    210                 215                 220

Gly Asn Pro Lys Leu Arg Ser Ser Asp Ile Glu Met Lys Asp Leu Phe
225                 230                 235                 240

Val Ala Val Lys Asp Tyr Tyr Leu Glu Pro Gly Pro Thr Lys Asn Leu
                245                 250                 255

Ile Asp Phe Cys Met Asn His Gln Leu Ser Met Thr Asn Leu Leu Leu
            260                 265                 270

Leu Gly Ile Arg Thr Tyr Leu Ser Lys Val Asn Asn Gly Gln Glu Asp
        275                 280                 285

Ile Thr Ile Gln Asn Phe Ile Ser Arg Arg Ser Thr His Asp Glu Trp
    290                 295                 300

Thr Ser Gly Gly Ser Arg Thr Ile Met Phe Pro Cys Arg Thr Val Ile
305                 310                 315                 320

Ala Pro Glu Thr Asp Phe Leu Ser Ala Ala Tyr Glu Ile Gln Asn Met
                325                 330                 335

Gln Asn Arg Ile Tyr Met His Ser Asn Tyr Asp Pro Ala Phe Ile Met
            340                 345                 350

Asp Glu Met Arg Lys Arg Tyr Asn Thr Pro Glu His Thr Gly Tyr Glu
        355                 360                 365

Ser Cys Tyr Leu Thr Tyr Gln Pro Met Thr Val Lys Val Glu Asn Glu
    370                 375                 380

Met Leu Gly Thr Ile Arg Gln His Ala Lys Trp Phe Ala Asn Gly Ala
385                 390                 395                 400

Ala Thr Lys Lys Met Tyr Leu Thr Val Ser His Thr Glu Asp Gly Gly
                405                 410                 415

Met Asn Phe Ser Tyr His Tyr Gln Thr Ala His Leu Glu Glu His Asp
            420                 425                 430

Met Glu Leu Leu Tyr Tyr Tyr Met Met Arg Ile Leu Phe Lys Gly Ile
        435                 440                 445

Ala Glu Pro Asp Met Ser Ile Gly Glu Ile Met Glu Leu Val
    450                 455                 460

<210> SEQ ID NO 87
<211> LENGTH: 231
<212> TYPE: DNA
<213> ORGANISM: Blautia sp.

<400> SEQUENCE: 87
atgaatcaag agatggaatt caagaacatc gttgcccagt atagcaaagt tgcaagcgaa      60
gaaatgaata acgaaatgcg tttttcgtgaa gatctgggtt ttagcagcct ggattttatg    120
agctttctgg gtgaactgga agatacccttt gatctggaac tggatgaaag cgaagtgctg    180
aaaattacca cactgggtga agcactgaat ctgctggaag aactgcagta a              231

<210> SEQ ID NO 88
<211> LENGTH: 76
<212> TYPE: PRT
<213> ORGANISM: Blautia sp.

<400> SEQUENCE: 88
```

```
Met Asn Gln Glu Met Glu Phe Lys Asn Ile Val Ala Gln Tyr Ser Lys
1               5                   10                  15

Val Ala Ser Glu Glu Met Asn Asn Glu Met Arg Phe Arg Glu Asp Leu
            20                  25                  30

Gly Phe Ser Ser Leu Asp Phe Met Ser Phe Leu Gly Glu Leu Glu Asp
            35                  40                  45

Thr Phe Asp Leu Glu Leu Asp Glu Ser Glu Val Leu Lys Ile Thr Thr
        50                  55                  60

Leu Gly Glu Ala Leu Asn Leu Leu Glu Glu Leu Gln
65                  70                  75
```

```
<210> SEQ ID NO 89
<211> LENGTH: 1545
<212> TYPE: DNA
<213> ORGANISM: Blautia sp.

<400> SEQUENCE: 89
atgctgattc gcaacattct ggaagaaagc gtgcgtaaat ttgatgaagt taaagccgtt      60
aaatggctga aaagaaaga aatcatggaa cgcagctatg cgaactgat ggaaaatgtt      120
gttagcaccc gtaaaggtct gctggcagaa ggttttgaag taaacatat tgcactgatt      180
ggcaccagca gcgttgaatg gatggaaagc tatctgggta ttattaccgg ttgtaccacc      240
gcagttccgc tggatgcagc actgccgtgt gaagatctga ttgatctgct gaatcgtagc      300
gatagcgcag cactgtttct gagcccgaaa ctgaaaccgt atctggatgc atttctggaa      360
aattgtccga aactgcagaa agtttggatg ctgcaagaag aagttgagga cgcaccggca      420
aaagtttatg gtattggtga actgcgtaat gcaggtaaaa gcgcaagcgc agatagcgtt      480
tgtccggatg cagaagatat tgcaaccatt atctttacca gcggcaccac cggtaaaagc      540
aaaggtgtta tgctgaccca gaataatctg gcaagcaatg ttgaagcagt gaaaattacc      600
gcagaaccgg gtacagcagt tctgagcgtt ctgccgattc atcatgcatt ttgtctggtt      660
atggattggc tgaaaggttt tagcctgggt gcaaccctgt gtattaatga tagcctgctg      720
cacatggttc gtaacatgag catctttaaa ccggaaatta tgctgatggt gccgatgatg      780
attgaaacca tctataaacg tctggcagca gcagatccga gcattccgaa aaccgttctg      840
gcagaaaaag ttttttggtgg taaactgcgc attattttca ccggtggcgc acatctggac      900
ccgtattata tcgatcgttt tgcagaatat ggtgtcgaag ttctggaagg ttatggtatg      960
agcgaatgta gtccggtgat tagcaataat acgctggaaa acaacaaaaa aggcagcatt      1020
ggtaaaccac tggaaaatgc ggaaattcgc tttgaaaatg gtgagattct ggttaaaggt      1080
agcagcgtga tgaaggcta ttatcagatg ccggatgaaa ccgcagaaac cctgaaagat      1140
ggttggctgc ataccggtga taaggttat atggatgaag atggctacct gtttattaac      1200
ggtcgtgtga aaaatctgat cattctgagc aatggcgaaa atgttagtcc ggaagaaatc      1260
gaaaataaac tggcactgaa tccgctgatt ggtgaagtta ttgttacggg tgaagataac      1320
ggtctgaccg cacgtatttta tccggaacag gcagttgttg aagccaaagc actggatgcc      1380
gaagcaattc aggcacagct gcaggccttt ctggatgaat ataatcgtaa tcagccgacc      1440
tatcgtcgca ttaccggtct ggttgttcgt aaaaatccgt ttattcgtaa caccaccaag      1500
aaaattcgtc gtcaggatgt gctgattgat gaaccgctgg aataa                    1545

<210> SEQ ID NO 90
<211> LENGTH: 514
```

```
<212> TYPE: PRT
<213> ORGANISM: Blautia sp.

<400> SEQUENCE: 90
```

| | | | | | | | | | | | | | | |
|---|---|---|---|---|---|---|---|---|---|---|---|---|---|---|
|Met|Leu|Ile|Arg|Asn|Ile|Leu|Glu|Glu|Ser|Val|Arg|Lys|Phe|Asp|Glu
1| | | |5| | | | |10| | | | |15

Val Lys Ala Val Lys Trp Leu Lys Lys Glu Ile Met Glu Arg Ser
            20                  25                  30

Tyr Gly Glu Leu Met Glu Asn Val Val Ser Thr Arg Lys Gly Leu Leu
                35                  40                  45

Ala Glu Gly Phe Glu Gly Lys His Ile Ala Leu Ile Gly Thr Ser Ser
    50                  55                  60

Val Glu Trp Met Glu Ser Tyr Leu Gly Ile Ile Thr Gly Cys Thr Thr
65                  70                  75                  80

Ala Val Pro Leu Asp Ala Leu Pro Cys Glu Asp Leu Ile Asp Leu
                85                  90                  95

Leu Asn Arg Ser Asp Ser Ala Ala Leu Phe Leu Ser Pro Lys Leu Lys
                100                 105                 110

Pro Tyr Leu Asp Ala Phe Leu Glu Asn Cys Pro Lys Leu Gln Lys Val
            115                 120                 125

Trp Met Leu Gln Glu Glu Val Glu Asp Ala Pro Ala Lys Val Tyr Gly
        130                 135                 140

Ile Gly Glu Leu Arg Asn Ala Gly Lys Ser Ala Ser Ala Asp Ser Val
145                 150                 155                 160

Cys Pro Asp Ala Glu Asp Ile Ala Thr Ile Ile Phe Thr Ser Gly Thr
                165                 170                 175

Thr Gly Lys Ser Lys Gly Val Met Leu Thr Gln Asn Asn Leu Ala Ser
                180                 185                 190

Asn Val Glu Ala Val Lys Ile Thr Ala Glu Pro Gly Thr Ala Val Leu
            195                 200                 205

Ser Val Leu Pro Ile His His Ala Phe Cys Leu Val Met Asp Trp Leu
210                 215                 220

Lys Gly Phe Ser Leu Gly Ala Thr Leu Cys Ile Asn Asp Ser Leu Leu
225                 230                 235                 240

His Met Val Arg Asn Met Ser Ile Phe Lys Pro Glu Ile Met Leu Met
                245                 250                 255

Val Pro Met Met Ile Glu Thr Ile Tyr Lys Arg Leu Ala Ala Ala Asp
            260                 265                 270

Pro Ser Ile Pro Lys Thr Val Leu Ala Glu Lys Val Phe Gly Gly Lys
        275                 280                 285

Leu Arg Ile Ile Phe Thr Gly Gly Ala His Leu Asp Pro Tyr Tyr Ile
    290                 295                 300

Asp Arg Phe Ala Glu Tyr Gly Val Glu Val Leu Glu Gly Tyr Gly Met
305                 310                 315                 320

Ser Glu Cys Ser Pro Val Ile Ser Asn Asn Thr Leu Glu Asn Lys
                325                 330                 335

Lys Gly Ser Ile Gly Lys Pro Leu Glu Asn Ala Glu Ile Arg Phe Glu
                340                 345                 350

Asn Gly Glu Ile Leu Val Lys Gly Ser Ser Val Met Lys Gly Tyr Tyr
            355                 360                 365

Gln Met Pro Asp Glu Thr Ala Glu Thr Leu Lys Asp Gly Trp Leu His
        370                 375                 380

Thr Gly Asp Lys Gly Tyr Met Asp Glu Asp Gly Tyr Leu Phe Ile Asn
385                 390                 395                 400

Gly Arg Val Lys Asn Leu Ile Ile Leu Ser Asn Gly Glu Asn Val Ser
                405                 410                 415

Pro Glu Glu Ile Glu Asn Lys Leu Ala Leu Asn Pro Leu Ile Gly Glu
            420                 425                 430

Val Ile Val Thr Gly Glu Asp Asn Gly Leu Thr Ala Arg Ile Tyr Pro
                435                 440                 445

Glu Gln Ala Val Val Glu Ala Lys Ala Leu Asp Ala Glu Ala Ile Gln
            450                 455                 460

Ala Gln Leu Gln Ala Phe Leu Asp Glu Tyr Asn Arg Asn Gln Pro Thr
465                 470                 475                 480

Tyr Arg Arg Ile Thr Gly Leu Val Val Arg Lys Asn Pro Phe Ile Arg
                485                 490                 495

Asn Thr Thr Lys Lys Ile Arg Arg Gln Asp Val Leu Ile Asp Glu Pro
                500                 505                 510

Leu Glu

<210> SEQ ID NO 91
<211> LENGTH: 1389
<212> TYPE: DNA
<213> ORGANISM: Ruminococcus albus

<400> SEQUENCE: 91

| | | | | | |
|---|---|---|---|---|---|
| atggaaaaac | gctatgaact | gaccgcagca | cagaaaatgc | attatcgttg | gattaaagaa | 60 |
| tatggcaccc | agcaggttag | cggtctgagc | attgttgcag | catttggtgc | agaactggat | 120 |
| attggtctgc | tgaaaaaatg | tatcgagctg | gaaaaacagc | gttatagctg | tctgcgtctg | 180 |
| cgttttacca | accggatga | taatggtgag | atcaaacagt | atattgccga | atatcagccg | 240 |
| gaagaaatca | agaatacga | tctgcgtgat | atgaccctgc | cggaagcaga | tgacattatg | 300 |
| cagaattggg | cctatgaaac | ctttgatggt | gatgatattc | cgatgtgcga | atttcgtatt | 360 |
| gttatgctgc | tgaaggtta | taccggtttt | tttgttcaca | tggatcatcg | tctgaatgat | 420 |
| agcgttggtg | ttgcagttat | ggcaaccgat | attatgaacc | tgtacaagca | cttcaaattt | 480 |
| ggtgatgaag | aaccggcacc | gctggcagat | tttgaaaaag | ttctgattaa | cgacctggaa | 540 |
| aaagccagca | atgaaaaacg | tcatgcaaaa | gccaacgct | tctgggatga | agaattagat | 600 |
| gaactgggtg | aaccgctgta | tagcgatatt | cagggcacca | gcgttctgga | agaagcacgt | 660 |
| cgtaaacata | tgcaccgaa | tctgcgtgca | gccgatattg | aacgtaaaga | actgtttgtt | 720 |
| gccgtgaaag | attatcagct | ggaagttgat | agcatgcagc | gtgcaattaa | ctttttgcctg | 780 |
| cataatcaga | ttagcccgac | caatctgatt | ctgctggtta | ttcgtaccta | tctgagcaaa | 840 |
| gttaatggtg | ccaagaaga | tattaccgtc | gaaaactta | ttagccgtcg | tagcacccat | 900 |
| gatgagctga | ccagcggtgg | tagtcgtacc | ctgtgttttc | cgtgtcgtac | cgttattagc | 960 |
| ggtgatacca | cctttattga | tgcagcacgt | aaaattcaga | atcatcagaa | ccgcatctat | 1020 |
| atgttcagcg | gttatgatcc | ggaatttatt | cgcgacgaaa | tgaaaaagcg | ctataatacc | 1080 |
| cctgatgata | ccacgtatgt | ttcagtgtat | ctgacctatc | agcctccgat | gaccagccag | 1140 |
| gatctggacc | cgaatgcaca | gaaactgccg | ctgtatgtta | atggttttgc | aaatggtgca | 1200 |
| gccacgaaaa | agatgtacct | gaccgttagc | catctgccgg | atcgtaaact | gaatttcagc | 1260 |
| tatcattatc | agaccgcaca | tctgaccgag | aaagatgccg | aactgatgta | ttattacatg | 1320 |
| atgcgtattc | tgttccgtgg | cattgaagat | ccgggtcgta | ccattagcga | aattattgat | 1380 |
| atggtgtaa | | | | | | 1389 |

<210> SEQ ID NO 92
<211> LENGTH: 462
<212> TYPE: PRT
<213> ORGANISM: Ruminococcus albus

<400> SEQUENCE: 92

```
Met Glu Lys Arg Tyr Glu Leu Thr Ala Ala Gln Lys Met His Tyr Arg
1               5                   10                  15

Trp Ile Lys Glu Tyr Gly Thr Gln Val Ser Gly Leu Ser Ile Val
                20                  25                  30

Ala Ala Phe Gly Ala Glu Leu Asp Ile Gly Leu Leu Lys Lys Cys Ile
            35                  40                  45

Glu Leu Glu Lys Gln Arg Tyr Ser Cys Leu Arg Leu Arg Phe Thr Lys
    50                  55                  60

Pro Asp Asp Asn Gly Glu Ile Lys Gln Tyr Ile Ala Glu Tyr Gln Pro
65                  70                  75                  80

Glu Glu Ile Lys Glu Tyr Asp Leu Arg Asp Met Thr Leu Pro Glu Ala
                85                  90                  95

Asp Asp Ile Met Gln Asn Trp Ala Tyr Glu Thr Phe Asp Gly Asp Asp
            100                 105                 110

Ile Pro Met Cys Glu Phe Arg Ile Val Met Leu Pro Glu Gly Tyr Thr
    115                 120                 125

Gly Phe Phe Val His Met His Arg Leu Asn Asp Ser Val Gly Val
130                 135                 140

Ala Val Met Ala Thr Asp Ile Met Asn Leu Tyr Lys His Phe Lys Phe
145                 150                 155                 160

Gly Asp Glu Glu Pro Ala Pro Leu Ala Asp Phe Glu Lys Val Leu Ile
                165                 170                 175

Asn Asp Leu Glu Lys Ala Ser Asn Glu Lys Arg His Ala Lys Ala Lys
            180                 185                 190

Arg Phe Trp Asp Glu Glu Leu Asp Glu Leu Gly Glu Pro Leu Tyr Ser
    195                 200                 205

Asp Ile Gln Gly Thr Ser Val Leu Glu Glu Ala Arg Arg Lys His Asn
210                 215                 220

Ala Pro Asn Leu Arg Ala Ala Asp Ile Glu Arg Lys Glu Leu Phe Val
225                 230                 235                 240

Ala Val Lys Asp Tyr Gln Leu Glu Val Asp Ser Met Gln Arg Ala Ile
                245                 250                 255

Asn Phe Cys Leu His Asn Gln Ile Ser Pro Thr Asn Leu Ile Leu Leu
            260                 265                 270

Val Ile Arg Thr Tyr Leu Ser Lys Val Asn Gly Gly Gln Glu Asp Ile
    275                 280                 285

Thr Val Glu Asn Phe Ile Ser Arg Arg Ser Thr His Asp Glu Leu Thr
290                 295                 300

Ser Gly Gly Ser Arg Thr Leu Cys Phe Pro Cys Arg Thr Val Ile Ser
305                 310                 315                 320

Gly Asp Thr Thr Phe Ile Asp Ala Ala Arg Lys Ile Gln Asn His Gln
                325                 330                 335

Asn Arg Ile Tyr Met Phe Ser Gly Tyr Asp Pro Glu Phe Ile Arg Asp
            340                 345                 350

Glu Met Lys Lys Arg Tyr Asn Thr Pro Asp Thr Thr Tyr Val Ser
    355                 360                 365

Val Tyr Leu Thr Tyr Gln Pro Pro Met Thr Ser Gln Asp Leu Asp Pro
```

```
                     370                 375                 380

Asn Ala Gln Lys Leu Pro Leu Tyr Val Lys Trp Phe Ala Asn Gly Ala
385                 390                 395                 400

Ala Thr Lys Lys Met Tyr Leu Thr Val Ser His Leu Pro Asp Arg Lys
                405                 410                 415

Leu Asn Phe Ser Tyr His Tyr Gln Thr Ala His Leu Thr Glu Lys Asp
            420                 425                 430

Ala Glu Leu Met Tyr Tyr Met Met Arg Ile Leu Phe Arg Gly Ile
        435                 440                 445

Glu Asp Pro Gly Arg Thr Ile Ser Glu Ile Ile Asp Met Val
    450                 455                 460

<210> SEQ ID NO 93
<211> LENGTH: 240
<212> TYPE: DNA
<213> ORGANISM: Ruminococcus albus

<400> SEQUENCE: 93
atggaacaga gtttaaaga aatcgccagc cgttattgca aaggtgatgt tggtgaaatc      60
acaccggaaa tggcaattcg tgaagatctg gtctgagca gcctggatct gatgaccttt    120
ctgggtgatc tggaagatga atttgatatc gagtttgatt ttggtgccga tgaacagaaa    180
ctgggtaata ttcgtaccgt tggtgatgcc attggtctgc tgaatgaata tgttggttaa    240

<210> SEQ ID NO 94
<211> LENGTH: 79
<212> TYPE: PRT
<213> ORGANISM: Ruminococcus albus

<400> SEQUENCE: 94

Met Glu Gln Lys Phe Lys Glu Ile Ala Ser Arg Tyr Cys Lys Gly Asp
1               5                   10                  15

Val Gly Glu Ile Thr Pro Glu Met Ala Ile Arg Glu Asp Leu Gly Leu
            20                  25                  30

Ser Ser Leu Asp Leu Met Thr Phe Leu Gly Asp Leu Glu Asp Glu Phe
        35                  40                  45

Asp Ile Glu Phe Asp Phe Gly Ala Asp Glu Gln Lys Leu Gly Asn Ile
    50                  55                  60

Arg Thr Val Gly Asp Ala Ile Gly Leu Leu Asn Glu Tyr Val Gly
65                  70                  75

<210> SEQ ID NO 95
<211> LENGTH: 1533
<212> TYPE: DNA
<213> ORGANISM: Ruminococcus albus

<400> SEQUENCE: 95
atgaaaaaga ccattcacac cctgtggaat cgtagcgcaa aagattatgc cgatctgcct      60
gcagttcgtt ggctggttaa aaaagatatc aaagaaatca gctacaagca ggccgatgaa    120
gttattagcg gtctgcgtaa aggtgcctat gcactgggtt ttgaacatcg tcatattgca    180
ctggttggca ccaatagcgc agaatggatt gaagcatata tgagcgttgt taccagtacc    240
aataccgcag ttccgctgga tagcgcactg cctgcacatg atctgatcga tctgattgat    300
cgtagcgata gcgaaggtgt ttttctggac ccgaaatttg caagcctggc aaccgaaatc    360
aaagacaaat gcaaaaaagt gaaaaaaatc tggatgctga cgacgaagc cattgaaggc    420 accgaaagcc tgaaagacct gattgcagcc ggtgaaggtg cagatgaacc gagcgcaccg    480
```

```
gaagaggatg atattagcat gattgttttt accagcggca ccaccggtaa aagcaaaggt    540
gttatgctga cccagagcaa tctgtatacc aatattgaag ccatcctgta tgatatggac    600
cctggtctga tttttctgag cgttctgccg gttcatcatt gtttttgtct ggttatggat    660
tggctgaatg gttttgggat gggtgcagtt ctgtgtatta atgatagcct gatgcacatg    720
gttcgtaaca tgaccatttt taacccggat gtgatgctga tggttccgct gatggtggaa    780
accatctata aacgtctgcg taccttagat ccgagcattc cgcctgaagt tgtgagcgaa    840
aaagtgtttg gtaagaacct gaaatacatt tttacaggtg cgcacatct  ggaaccgtat    900 tatatcgaag agttcaacaa atatggcatc gatgtgtatg aaggttatgg tatgagcgaa    960
tgtagtccgg ttattagcag caacaaaatt ggtgatagca aaccgggtag cattggtcgt   1020
ccgctgccga atgttgaaat caaatttgtt gatggcgaaa ttctggttcg tagcaccagc   1080
gttatgaaag gctattacaa gatggaaaaa gaaaccgaag aaaccctgaa ggatggttgg   1140
ctgcataccg gtgataaagg ttatattgat gaagatggct tcctgtttat taacggtcgt   1200
gtgaaaaatc tgatcattct gagcaatggc gaaaacatta gtccggaaga aattgaaaat   1260
cgtctggcac tgaatgacct tattggtgaa attgttgtta ccggtgaaga taatctgctg   1320
accgcacgta ttttccaga tccggatatg accggtggta tgagtgatga agaaattcgt    1380
aatgccctgc aagaaatcct gaacgattat aacaaacagc agccgaccta taaacagctg   1440
agcaaactgg ttgttcgcaa atatccgttt ctgaaaaaca cgacccgtaa aatcattcgt   1500
gccgaagttt atcgtgatga acagggtgca taa                                1533
```

<210> SEQ ID NO 96
<211> LENGTH: 510
<212> TYPE: PRT
<213> ORGANISM: Ruminococcus albus

<400> SEQUENCE: 96

```
Met Lys Lys Thr Ile His Thr Leu Trp Asn Arg Ser Ala Lys Asp Tyr
1               5                   10                  15

Ala Asp Leu Pro Ala Val Arg Trp Leu Val Lys Lys Asp Ile Lys Glu
            20                  25                  30

Ile Ser Tyr Lys Gln Ala Asp Glu Val Ile Ser Gly Leu Arg Lys Gly
        35                  40                  45

Ala Tyr Ala Leu Gly Phe Glu His Arg His Ile Ala Leu Val Gly Thr
    50                  55                  60

Asn Ser Ala Glu Trp Ile Glu Ala Tyr Met Ser Val Val Thr Ser Thr
65                  70                  75                  80

Asn Thr Ala Val Pro Leu Asp Ser Ala Leu Pro Ala His Asp Leu Ile
                85                  90                  95

Asp Leu Ile Asp Arg Ser Asp Ser Glu Gly Val Phe Leu Asp Pro Lys
            100                 105                 110

Phe Ala Ser Leu Ala Thr Glu Ile Lys Asp Lys Cys Lys Lys Val Lys
        115                 120                 125

Lys Ile Trp Met Leu Ser Asp Glu Ala Ile Glu Gly Thr Glu Ser Leu
    130                 135                 140

Lys Asp Leu Ile Ala Ala Gly Glu Gly Ala Asp Glu Pro Ser Ala Pro
145                 150                 155                 160

Glu Glu Asp Asp Ile Ser Met Ile Val Phe Thr Ser Gly Thr Thr Gly
                165                 170                 175

Lys Ser Lys Gly Val Met Leu Thr Gln Ser Asn Leu Tyr Thr Asn Ile
```

```
                    180                 185                 190
Glu Ala Ile Leu Tyr Asp Met Asp Pro Gly Leu Ile Phe Leu Ser Val
                195                 200                 205

Leu Pro Val His His Cys Phe Cys Leu Val Met Asp Trp Leu Asn Gly
            210                 215                 220

Phe Trp Met Gly Ala Val Leu Cys Ile Asn Asp Ser Leu Met His Met
225                 230                 235                 240

Val Arg Asn Met Thr Ile Phe Asn Pro Asp Val Met Leu Met Val Pro
                245                 250                 255

Leu Met Val Glu Thr Ile Tyr Lys Arg Leu Arg Thr Leu Asp Pro Ser
            260                 265                 270

Ile Pro Pro Glu Val Val Ser Glu Lys Val Phe Gly Lys Asn Leu Lys
        275                 280                 285

Tyr Ile Phe Thr Gly Gly Ala His Leu Glu Pro Tyr Tyr Ile Glu Glu
    290                 295                 300

Phe Asn Lys Tyr Gly Ile Asp Val Tyr Glu Gly Tyr Gly Met Ser Glu
305                 310                 315                 320

Cys Ser Pro Val Ile Ser Ser Asn Lys Ile Gly Asp Ser Lys Pro Gly
                325                 330                 335

Ser Ile Gly Arg Pro Leu Pro Asn Val Glu Ile Lys Phe Val Asp Gly
            340                 345                 350

Glu Ile Leu Val Arg Ser Thr Ser Val Met Lys Gly Tyr Tyr Lys Met
        355                 360                 365

Glu Lys Glu Thr Glu Glu Thr Leu Lys Asp Gly Trp Leu His Thr Gly
    370                 375                 380

Asp Lys Gly Tyr Ile Asp Glu Asp Gly Phe Leu Phe Ile Asn Gly Arg
385                 390                 395                 400

Val Lys Asn Leu Ile Ile Leu Ser Asn Gly Glu Asn Ile Ser Pro Glu
                405                 410                 415

Glu Ile Glu Asn Arg Leu Ala Leu Asn Asp Leu Ile Gly Glu Ile Val
            420                 425                 430

Val Thr Gly Glu Asp Asn Leu Leu Thr Ala Arg Ile Phe Pro Asp Pro
        435                 440                 445

Asp Met Thr Gly Gly Met Ser Asp Glu Glu Ile Arg Asn Ala Leu Gln
    450                 455                 460

Glu Ile Leu Asn Asp Tyr Asn Lys Gln Gln Pro Thr Tyr Lys Gln Leu
465                 470                 475                 480

Ser Lys Leu Val Val Arg Lys Tyr Pro Phe Leu Lys Asn Thr Thr Arg
                485                 490                 495

Lys Ile Ile Arg Ala Glu Val Tyr Arg Asp Glu Gln Gly Ala
            500                 505                 510

<210> SEQ ID NO 97
<211> LENGTH: 1449
<212> TYPE: DNA
<213> ORGANISM: Clostridium sp.

<400> SEQUENCE: 97
atgctggaat atacccctgcc ggatggtcgt accgttgaaa gctatccgct gacaccggca      60
cagcagctga tgctgtatct gagcattcag tatggtaatc atgttccggt tctgaatatt     120
tgcaccggct attatttcca gggtgagttt gatagcaaag tgatgaaaga agcagttctg     180
gaagccattg atcgttgtga tgttatgcgt ctgcgttttg ccaaacatcc gctgtttaaa     240
gttgttcagt atctggcaga tgaagccggt attgaagttg aagaagagga tctgagcaat     300
```

```
atgccgtggg atgaagcaca tgaatttatc aaagaacgtg gccatagcct gattgatacc    360
tttgcagatg caccgctgca tcagattaaa atcattcatc tggaaaacga ctacaacggc    420
atctatctga aactgcatca tctgggtttt gatggctata gcagcaaaat gctgattagc    480
gatattatgg ccatttacct gagcaaaaaa tacggtaaac cgtatccgaa accgatgcgt    540
agctattttg aatgcctgga taaagaattt gcctatgcag aaagcgatcg ccatgatgaa    600
gatattgatt attgggttag caccattacc gatcgtccgg aagcaattta taccgattat    660
gttcgtccga gccgtctgat tgaacagcgt attcgtgaaa ataaaccgga tctgcgtatt    720
gcaagcgttc atgatggtga tgatccgagc agtaaaaccc tgcgttatag cctgagtaaa    780
gaaaccagcg ataaaatcat gagcctgtgt gcagaaaaag gtctgagcgt tccgtgtgtt    840
atgatgatgg gtctgcgttg tgcactgagc agctttaatg ataatgaaga agatgtgagc    900
ttcaaactga tggttaatcg tcgtgcaacc ctgctggaaa agaaaagcgg tggtatgcgt    960
atgcactttt ttagcatgcg tagcattgtt aaaccggaaa tgaccttcct ggaagccctg   1020
aaagttattg aacaggcaca gaatgaagtg tttgaacata gcaatctgag cagcctggaa   1080
gcgattgcag ttcgtcataa agcaatgggt aatgaaaccc acgatgtgta tgaaaagcatg  1140 agctttagct atcagccgta tgccggttcc cgtgtctgg atgaaaaaat gcgtgatagc    1200
agccgtggtt tttggtataa taacgatgca agcatgcaga tctgtacct gaccgttatg    1260 catcgtagca atgatgcagg tctggatttc aattatgaat accgcaccaa aaacaacccg   1320
attaatgaac tgggcatctt ccataacaaa ctgatcaaaa gcattctgct gggcacccgt   1380
aataccggca ttaccgttgg tgaaattctg gatgagatca agaagatga ggtcgatatt    1440 tacgcctaa                                                           1449
```

<210> SEQ ID NO 98
<211> LENGTH: 482
<212> TYPE: PRT
<213> ORGANISM: Clostridium sp.

<400> SEQUENCE: 98

Met Leu Glu Tyr Thr Leu Pro Asp Gly Arg Thr Val Glu Ser Tyr Pro
1               5                   10                  15

Leu Thr Pro Ala Gln Gln Leu Met Leu Tyr Leu Ser Ile Gln Tyr Gly
            20                  25                  30

Asn His Val Pro Val Leu Asn Ile Cys Thr Gly Tyr Tyr Phe Gln Gly
        35                  40                  45

Glu Phe Asp Ser Lys Val Met Lys Glu Ala Val Leu Glu Ala Ile Asp
    50                  55                  60

Arg Cys Asp Val Met Arg Leu Arg Phe Ala Lys His Pro Leu Phe Lys
65                  70                  75                  80

Val Val Gln Tyr Leu Ala Asp Glu Ala Gly Ile Glu Val Glu Glu Glu
                85                  90                  95

Asp Leu Ser Asn Met Pro Trp Asp Glu Ala His Glu Phe Ile Lys Glu
            100                 105                 110

Arg Gly His Ser Leu Ile Asp Thr Phe Ala Asp Ala Pro Leu His Gln
        115                 120                 125

Ile Lys Ile Ile His Leu Glu Asn Asp Tyr Asn Gly Ile Tyr Leu Lys
    130                 135                 140

Leu His His Leu Gly Phe Asp Gly Tyr Ser Ser Lys Met Leu Ile Ser
145                 150                 155                 160

Asp Ile Met Ala Ile Tyr Leu Ser Lys Lys Tyr Gly Lys Pro Tyr Pro
165 170 175

Lys Pro Met Arg Ser Tyr Phe Glu Cys Leu Asp Lys Glu Phe Ala Tyr
180 185 190

Ala Glu Ser Asp Arg His Asp Glu Asp Ile Asp Tyr Trp Val Ser Thr
195 200 205

Ile Thr Asp Arg Pro Glu Ala Ile Tyr Thr Asp Tyr Val Arg Pro Ser
210 215 220

Arg Leu Ile Glu Gln Arg Ile Arg Glu Asn Lys Pro Asp Leu Arg Ile
225 230 235 240

Ala Ser Val His Asp Gly Asp Pro Ser Ser Lys Thr Leu Arg Tyr
245 250 255

Ser Leu Ser Lys Glu Thr Ser Asp Lys Ile Met Ser Leu Cys Ala Glu
260 265 270

Lys Gly Leu Ser Val Pro Cys Val Met Met Met Gly Leu Arg Cys Ala
275 280 285

Leu Ser Ser Phe Asn Asp Asn Glu Glu Asp Val Ser Phe Lys Leu Met
290 295 300

Val Asn Arg Arg Ala Thr Leu Leu Glu Lys Lys Ser Gly Gly Met Arg
305 310 315 320

Met His Phe Phe Ser Met Arg Ser Ile Val Lys Pro Glu Met Thr Phe
325 330 335

Leu Glu Ala Leu Lys Val Ile Glu Gln Ala Gln Asn Glu Val Phe Glu
340 345 350

His Ser Asn Leu Ser Ser Leu Glu Ala Ile Ala Val Arg His Lys Ala
355 360 365

Met Gly Asn Glu Thr His Asp Val Tyr Glu Ser Met Ser Phe Ser Tyr
370 375 380

Gln Pro Tyr Met Pro Val Pro Cys Leu Asp Glu Lys Met Arg Asp Ser
385 390 395 400

Ser Arg Gly Phe Trp Tyr Asn Asn Asp Ala Ser Met Gln Asn Leu Tyr
405 410 415

Leu Thr Val Met His Arg Ser Asn Asp Ala Gly Leu Asp Phe Asn Tyr
420 425 430

Glu Tyr Arg Thr Lys Asn Asn Pro Ile Asn Glu Leu Gly Ile Phe His
435 440 445

Asn Lys Leu Ile Lys Ser Ile Leu Leu Gly Thr Arg Asn Thr Gly Ile
450 455 460

Thr Val Gly Glu Ile Leu Asp Glu Ile Lys Glu Asp Glu Val Asp Ile
465 470 475 480

Tyr Ala

<210> SEQ ID NO 99
<211> LENGTH: 222
<212> TYPE: DNA
<213> ORGANISM: Clostridium sp.

<400> SEQUENCE: 99

```
atgctggaaa aaatcgtgga catcatcctg aattatgtgg aaccggatga tgaaattaca      60
ccggatacac gtattaaaag cgaactgggt atgtcctcat tgatctggt ttgttttggt     120
gatgatctgt atgatgaatt cggcgttaaa attggtgccg atgattttcg tcgttgtgat     180
accgttggta aactggcagc atatattggt gcaaattgct aa                        222
```

<210> SEQ ID NO 100
<211> LENGTH: 73
<212> TYPE: PRT
<213> ORGANISM: Clostridium sp.

<400> SEQUENCE: 100

```
Met Leu Glu Lys Ile Val Asp Ile Ile Leu Asn Tyr Val Glu Pro Asp
1               5                   10                  15

Asp Glu Ile Thr Pro Asp Thr Arg Ile Lys Ser Glu Leu Gly Met Ser
            20                  25                  30

Ser Phe Asp Leu Val Cys Phe Gly Asp Asp Leu Tyr Asp Glu Phe Gly
        35                  40                  45

Val Lys Ile Gly Ala Asp Asp Phe Arg Arg Cys Asp Thr Val Gly Lys
    50                  55                  60

Leu Ala Ala Tyr Ile Gly Ala Asn Cys
65                  70
```

<210> SEQ ID NO 101
<211> LENGTH: 1575
<212> TYPE: DNA
<213> ORGANISM: Clostridium sp.

<400> SEQUENCE: 101

```
atggcaagcg aacagaatcg cctggaatat tatgcaaaag ttaataccgt tcgcgatctg     60
attgatctgg cagcagaacg ttatggtgat aaaccgttta ttaagtatct ggaaggtgat    120
cgcattaccg aaaaaagctt tagcgaactg cgtagcaata gcctggcact gagccgttat    180
attcgtagca tttgtccgcg tcgtatgcat attgcagtta ttggtcgtac cacctatgaa    240
tatatcaccg cactgaccgg tacactggtt agcggtaatg tttttgttcc gtttgcaccg    300
aacattagcg ttaatgaagc atgtgaactg tttgccgatg gtgatgttga agcactgttt    360
tatgaagccg attttgatga acgtgccaaa gaaatcgcaa aaaaatgtcc gcagctgaaa    420
accgttgtta atatgggtga tgcagaacat tttgccagca tctatgcaga atatggtgaa    480
ggtagcgaat atgcaaccct gagcgaagtt gaactggacc cggatgattg tgcagcaatt    540
atctatacca gcggcaccac cggtgttcgt aaaggtgtta tgctgagcag ccgtaatctg    600
attagcaatg ttacctatac cgaactggcg ttagatccga atgatgtgat gctgagcgtt    660
ctgccgatgc atcacatttt ttgtattagc tgcgattact tcaaaccgct gctggatggt    720
attaccgttt gtctgaatgg tgaaattagc aatattggtc gcagcctggc aacctttaaa    780
ccgaccacca tgcgtgcagt tccgatgatt tgtgataccc tgatcaaaaa agtgcacatg    840
ctgcataaaa agtatccgga actgaccgat cgtcaggcag ccgaactggt ttttggtgaa    900
aactttaaat ggattgcagt tggtggtgca gcattaggta aaggtctggt tgcagattat    960
gaaaaacatg gtattatgct gcgccaaggt tatggtatga ccgaagttag cccgaaaatt   1020
tcaaccgcag attttggtga tgaatgcaaa gatagcagcg gtaaaattct gcgtagtatt   1080
ggtgatgtgc gtattgttga tggcgaaatt caggttaaag gtagcagcgt tatgatgggc   1140
tattataaga aaccggaaga aaccgccaaa gtgtttaccg aagatggtta tctgaaaaca   1200
ggtgatctgg gtcgtattac cagcagcgat catatttatg tgaccggtcg tctgaaaaac   1260
ctgattattc tgagcaatgg cgaaaatgtt agtccggaaa tgctggaaaa caaattcgcc   1320
gatgaaaagg tgatcaaaga aattgtggtg tatggcgata aagatcgtat tgtggcagaa   1380
atttttccgg atgccgaata tgccagcgca gcaggtattg atgatattaa aggttacctg   1440
gaagcaaaag cacagcagct gaatgatagc gaacctgaag aacgtcgtat tgcagaaatt   1500
```

```
cgtctgcgcg ataaaccttt tgaaaaaacc accaccggca aaatcaaacg taccgcagtt    1560
aaaatcgagt attaa                                                     1575
```

<210> SEQ ID NO 102
<211> LENGTH: 524
<212> TYPE: PRT
<213> ORGANISM: Clostridium sp.

<400> SEQUENCE: 102

Met Ala Ser Glu Gln Asn Arg Leu Glu Tyr Tyr Ala Lys Val Asn Thr
1               5                   10                  15

Val Arg Asp Leu Ile Asp Leu Ala Ala Glu Arg Tyr Gly Asp Lys Pro
            20                  25                  30

Phe Ile Lys Tyr Leu Glu Gly Asp Arg Ile Thr Glu Lys Ser Phe Ser
        35                  40                  45

Glu Leu Arg Ser Asn Ser Leu Ala Leu Ser Arg Tyr Ile Arg Ser Ile
    50                  55                  60

Cys Pro Arg Arg Met His Ile Ala Val Ile Gly Arg Thr Thr Tyr Glu
65                  70                  75                  80

Tyr Ile Thr Ala Leu Thr Gly Thr Leu Val Ser Gly Asn Val Phe Val
                85                  90                  95

Pro Phe Ala Pro Asn Ile Ser Val Asn Glu Ala Cys Glu Leu Phe Ala
            100                 105                 110

Asp Gly Asp Val Glu Ala Leu Phe Tyr Glu Ala Asp Phe Asp Glu Arg
        115                 120                 125

Ala Lys Glu Ile Ala Lys Lys Cys Pro Gln Leu Lys Thr Val Val Asn
    130                 135                 140

Met Gly Asp Ala Glu His Phe Ala Ser Ile Tyr Ala Glu Tyr Gly Glu
145                 150                 155                 160

Gly Ser Glu Tyr Ala Thr Leu Ser Glu Val Glu Leu Asp Pro Asp Asp
                165                 170                 175

Cys Ala Ala Ile Ile Tyr Thr Ser Gly Thr Thr Gly Val Arg Lys Gly
            180                 185                 190

Val Met Leu Ser Ser Arg Asn Leu Ile Ser Asn Val Thr Tyr Thr Glu
        195                 200                 205

Leu Ala Leu Asp Pro Asn Asp Val Met Leu Ser Val Leu Pro Met His
    210                 215                 220

His Ile Phe Cys Ile Ser Cys Asp Tyr Phe Lys Pro Leu Leu Asp Gly
225                 230                 235                 240

Ile Thr Val Cys Leu Asn Gly Glu Ile Ser Asn Ile Gly Arg Ser Leu
                245                 250                 255

Ala Thr Phe Lys Pro Thr Thr Met Arg Ala Val Pro Met Ile Cys Asp
            260                 265                 270

Thr Leu Ile Lys Lys Val His Met Leu His Lys Lys Tyr Pro Glu Leu
        275                 280                 285

Thr Asp Arg Gln Ala Ala Glu Leu Val Phe Gly Glu Asn Phe Lys Trp
    290                 295                 300

Ile Ala Val Gly Gly Ala Ala Leu Gly Lys Gly Leu Val Ala Asp Tyr
305                 310                 315                 320

Glu Lys His Gly Ile Met Leu Arg Gln Gly Tyr Gly Met Thr Glu Val
                325                 330                 335

Ser Pro Lys Ile Ser Thr Ala Asp Phe Gly Asp Glu Cys Lys Asp Ser
            340                 345                 350

Ser Gly Lys Ile Leu Arg Ser Ile Gly Asp Val Arg Ile Val Asp Gly
        355                 360                 365

Glu Ile Gln Val Lys Gly Ser Ser Val Met Met Gly Tyr Tyr Lys Lys
    370                 375                 380

Pro Glu Glu Thr Ala Lys Val Phe Thr Glu Asp Gly Tyr Leu Lys Thr
385                 390                 395                 400

Gly Asp Leu Gly Arg Ile Thr Ser Ser Asp His Ile Tyr Val Thr Gly
                405                 410                 415

Arg Leu Lys Asn Leu Ile Ile Leu Ser Asn Gly Glu Asn Val Ser Pro
            420                 425                 430

Glu Met Leu Glu Asn Lys Phe Ala Asp Glu Lys Val Ile Lys Glu Ile
        435                 440                 445

Val Val Tyr Gly Asp Lys Asp Arg Ile Val Ala Glu Ile Phe Pro Asp
    450                 455                 460

Ala Glu Tyr Ala Ser Ala Gly Ile Asp Asp Ile Lys Gly Tyr Leu
465                 470                 475                 480

Glu Ala Lys Ala Gln Gln Leu Asn Asp Ser Pro Glu Glu Arg Arg
                485                 490                 495

Ile Ala Glu Ile Arg Leu Arg Asp Lys Pro Phe Glu Lys Thr Thr Thr
            500                 505                 510

Gly Lys Ile Lys Arg Thr Ala Val Lys Ile Glu Tyr
        515                 520

<210> SEQ ID NO 103
<211> LENGTH: 1446
<212> TYPE: DNA
<213> ORGANISM: Lachnospiraceae bacterium

<400> SEQUENCE: 103
atgaccgaac gtctgattaa tgtgttatg gttaaaacct ggcctctgac cgatgttcaa      60
ggtggtctgt ataaagtttt tgcacattat gccagcatcc aagaaatgaa tttaggtgtg    120
ggcttctact tcaagatgga tatgaatgaa gaactgatgc gtcagagcat gcgtgaagcc    180
attggttata tggaagcact gaatgttcgt tttggccagg atgaaaatgg tgagatgtat    240
cagtatatta acccggaacc gtggaacgaa gaaatgccgc tgtgggatct gagcgatctg    300
tcagaaaaag aagcaaaaga gtacctgacc aaagttacca gcgaaccgat tgattatctg    360
cacaaaaaca tgaccattgt gagcctggtt aaactgcgtg atggttttag cggtgtgtat    420
atcaatttca atcacatgct ggcagatggc tatagcatca atatgtttat gacctatctg    480
gccgtgatct atttcagcca tgcagcaggt aaagaaattg atctgcctcg taaaagcgac    540
tatatcaaaa tgatcgagaa agaactggaa tacaaaggta gcgaacgtga aaaagccgat    600
catgaatttt ggaatagcac cctggaagaa ggtgaaccga tttatacccc accgaccgca    660
gcaccgaata atgcacgtgt tcgtcagctg cgcgaaaaag gtgaaacccg ttattttgaa    720
aatacgatta gcccgaaagc cagcattgat agcgaaatta ttggtggtga acgtgccgaa    780
aaactggttg atgccattgc agaaaataaa ctgagcgaaa atgcactggc aaccctggca    840
ctgcgtagta ccctgagcct gctgaatcat cgtgaaaccg atattgcagc acgtgttatt    900
gttaatcgtc gcggtacaat taatgaacgt tatagcggtg gtaatcgcat gaccttttctg    960 acctggcgta gcattattga tgatgatatg ccggttcgtg atgccctgaa agaaatgatt   1020
gatagccaga aaaaaatctt tcgccacgcc gattataaca gcatgaaacg tctggcagaa   1080
cgtggtcagt attttggtaa tccgcctctg gcaacctatg aaagcgttac ctttacctat   1140

-continued

```
cagccgaata ccgttcagat tgatccgcgt ctgccggaaa tgaaagcagt ttggtatagc      1200
aatagcagca ccagcaatat tgttatctg accctggaac acatgcttgg caaaaaagat       1260
tatgtgttca tctatgaacg tcgcgtggaa gaaatgagcg aagaagagat gcactttttt      1320
accgaactga tgatggaatg tatggaaagc gcagttgaac atctggatgg caccattggt      1380
gaagttctgg atgaagttca ggcacgtcat ccggaactgt gtgaaagcga atgcgtgca       1440 gtttaa                                                                 1446
```

<210> SEQ ID NO 104
<211> LENGTH: 481
<212> TYPE: PRT
<213> ORGANISM: Lachnospiraceae bacterium

<400> SEQUENCE: 104

```
Met Thr Glu Arg Leu Ile Asn Gly Val Met Val Lys Thr Trp Pro Leu
1               5                   10                  15

Thr Asp Val Gln Gly Gly Leu Tyr Lys Val Phe Ala His Tyr Ala Ser
            20                  25                  30

Ile Gln Glu Met Asn Leu Gly Val Gly Phe Tyr Phe Lys Met Asp Met
        35                  40                  45

Asn Glu Glu Leu Met Arg Gln Ser Met Arg Glu Ala Ile Gly Tyr Met
    50                  55                  60

Glu Ala Leu Asn Val Arg Phe Gly Gln Asp Glu Asn Gly Glu Met Tyr
65                  70                  75                  80

Gln Tyr Ile Asn Pro Glu Pro Trp Asn Glu Glu Met Pro Leu Trp Asp
                85                  90                  95

Leu Ser Asp Leu Ser Glu Lys Glu Ala Lys Glu Tyr Leu Thr Lys Val
            100                 105                 110

Thr Ser Glu Pro Ile Asp Tyr Leu His Lys Asn Met Thr Ile Val Ser
        115                 120                 125

Leu Val Lys Leu Arg Asp Gly Phe Ser Gly Val Tyr Ile Asn Phe Asn
    130                 135                 140

His Met Leu Ala Asp Gly Tyr Ser Ile Asn Met Phe Met Thr Tyr Leu
145                 150                 155                 160

Ala Val Ile Tyr Phe Ser His Ala Ala Gly Lys Glu Ile Asp Leu Pro
                165                 170                 175

Arg Lys Ser Asp Tyr Ile Lys Met Ile Glu Lys Glu Leu Glu Tyr Lys
            180                 185                 190

Gly Ser Glu Arg Glu Lys Ala Asp His Glu Phe Trp Asn Ser Thr Leu
        195                 200                 205

Glu Glu Gly Glu Pro Ile Tyr Thr His Pro Thr Ala Ala Pro Asn Asn
    210                 215                 220

Ala Arg Val Arg Gln Leu Arg Glu Lys Gly Thr Arg Tyr Phe Glu
225                 230                 235                 240

Asn Thr Ile Ser Pro Lys Ala Ser Ile Asp Ser Glu Ile Ile Gly Gly
                245                 250                 255

Glu Arg Ala Glu Lys Leu Val Asp Ala Ile Ala Glu Asn Lys Leu Ser
            260                 265                 270

Glu Asn Ala Leu Ala Thr Leu Ala Leu Arg Ser Thr Leu Ser Leu Leu
        275                 280                 285

Asn His Arg Glu Thr Asp Ile Ala Ala Arg Val Ile Val Asn Arg Arg
    290                 295                 300

Gly Thr Ile Asn Glu Arg Tyr Ser Gly Gly Asn Arg Met Thr Phe Leu
305                 310                 315                 320
```

```
Thr Trp Arg Ser Ile Ile Asp Asp Met Pro Val Arg Asp Ala Leu
                325                 330                 335

Lys Glu Met Ile Asp Ser Gln Lys Lys Ile Phe Arg His Ala Asp Tyr
            340                 345                 350

Asn Ser Met Lys Arg Leu Ala Glu Arg Gly Gln Tyr Phe Gly Asn Pro
        355                 360                 365

Pro Leu Ala Thr Tyr Glu Ser Val Thr Phe Thr Tyr Gln Pro Asn Thr
    370                 375                 380

Val Gln Ile Asp Pro Arg Leu Pro Glu Met Lys Ala Val Trp Tyr Ser
385                 390                 395                 400

Asn Ser Ser Thr Ser Asn Ile Cys Tyr Leu Thr Leu Glu His Met Leu
                405                 410                 415

Gly Lys Lys Asp Tyr Val Phe Ile Tyr Glu Arg Arg Val Glu Glu Met
            420                 425                 430

Ser Glu Glu Glu Met His Phe Phe Thr Glu Leu Met Met Glu Cys Met
        435                 440                 445

Glu Ser Ala Val Glu His Leu Asp Gly Thr Ile Gly Glu Val Leu Asp
    450                 455                 460

Glu Val Gln Ala Arg His Pro Glu Leu Cys Glu Ser Glu Met Arg Ala
465                 470                 475                 480

Val

<210> SEQ ID NO 105
<211> LENGTH: 252
<212> TYPE: DNA
<213> ORGANISM: Lachnospiraceae bacterium

<400> SEQUENCE: 105
atggccgaca tcaaaatgtt cgatgaaatt cgtgatatcc tgctgaatta tgccgaagtt      60
ggtgcagaag aaattaacac cgaaaccgat atcattgaag aactgggctt agatagcttt     120
agcttcatta gcatgctggg tgaagttgaa gaaacctttg atattagcat cagcgaggaa     180
gaaatggaag aagcatttca tcttttttacc cctgcggaca tcatcaaatt tgttgcaaaa     240
aaagcagcct aa                                                         252

<210> SEQ ID NO 106
<211> LENGTH: 83
<212> TYPE: PRT
<213> ORGANISM: Lachnospiraceae bacterium

<400> SEQUENCE: 106

Met Ala Asp Ile Lys Met Phe Asp Glu Ile Arg Asp Ile Leu Leu Asn
1               5                   10                  15

Tyr Ala Glu Val Gly Ala Glu Glu Ile Asn Thr Glu Thr Asp Ile Ile
            20                  25                  30

Glu Glu Leu Gly Leu Asp Ser Phe Ser Phe Ile Ser Met Leu Gly Glu
        35                  40                  45

Val Glu Glu Thr Phe Asp Ile Ser Ile Ser Glu Glu Met Glu Glu
    50                  55                  60

Ala Phe His Leu Phe Thr Pro Ala Asp Ile Ile Lys Phe Val Ala Lys
65                  70                  75                  80

Lys Ala Ala

<210> SEQ ID NO 107
<211> LENGTH: 1599
```

<212> TYPE: DNA
<213> ORGANISM: Lachnospiraceae bacterium

<400> SEQUENCE: 107

```
atgaccctgc aagaaaaaat cgatcgcaac attaccgatt ttcgtagctt tctgcgtgaa      60
ctggcagata aatatggtga tacaccggca gttcgtgaat atcatggtaa agaactggtg     120
gatcgcaatt acctggaact gaaacgtgat gcagatgcag ttagccgttt tctgctggca     180
cagggtgccg aagaacgtat gcatattgca gcagttggtg caaccagcta tcagtatatt     240
gccgcatatt ttggcaccgt tgataccgca atgttattg ttccgaccga agcacagctg      300
agcaccgaaa cacagtgtga actgtttcac atggcagatg ttaccggtct gttttttcgat    360
aaacattttg aagatgcgat cccggaaatc catgaaaaat gtccggatat caaactgttc     420
atttgtctga ccgatggtgt tgaaagccat gatctgggtg atattcatat ccatagcatc     480
aacgagatcg agaaagaata tgcagaaggc gaagaaatta ttgtgccgct ggaacatgat     540
acctttagca ccattctgtt taccagcggt acaaccagcg cacgtccgaa agcagttatg     600
ctgtgtcatg gtggtattat cgacaacatt tttagcggtg aactggaaca gcgtgatagc     660
accaataaag ttaaactgat tgcactgccg attcatcatg cactgagctt taataccgat     720
atctgtatgg gttttcgtaa tggcgatacc gtgtttgtta atgatagcat gctgcatatc     780
gccaagaatt tcaaagttgc aaaaccgtat accgcaattc tggtgccgat gatctttgaa     840
aacttctacc acaaaatcat gaaagcccat gaagttcatc cggaagttga tctgaaagca     900
atggcacgtg atgtttttgg tggtgaagtt gaagtgtttt attgtggtgg tgcacatctg     960
cgtgcagaaa ttgcagatgc ctttgcagaa tggggtatgc cggttttga aggttatggt      1020
atgaccgaat gtagtccgcg tgttgcagca aatatgccgt ggcgttatcg tcgtgatagt     1080
attggtcgtg ttgttgataa tgcccatgtg cgtattaaag ataccgaact gcaggttaaa     1140
agcccgagcg ttatgctggg ttattacaaa gatccggaag caaccaaagc agcatttacc     1200
gaagatggtt ggctgaaaag cggtgatatt ggctatattg atgaagatgg ctttatcttt     1260
ctgcagggac gtatcaaaaa cctgattatt ctgagcaatg gcgaaaatgt tagtccggaa     1320
gaaattgaaa ccaaactgta tgattgcacc tttatcaaag aatgcctggt gtatgaagaa     1380
aatggtcaga ttacagccga agttttttccg gatgcagaat atgccgaaat gcataaagtt    1440
accgatgtgg aaaaagaaat cagcgcagca attaagccg tgaataaaag catgccgacc      1500
accaaatcag ttcgtagcgt taaatttcgc tatgaaccgt tgaacgtac cgcgaccaat      1560
aaaatcaaac gtaccggtcg tggtaaaaaa gcagcataa                            1599
```

<210> SEQ ID NO 108
<211> LENGTH: 532
<212> TYPE: PRT
<213> ORGANISM: Lachnospiraceae bacterium

<400> SEQUENCE: 108

```
Met Thr Leu Gln Glu Lys Ile Asp Arg Asn Ile Thr Asp Phe Arg Ser
  1               5                  10                  15

Phe Leu Arg Glu Leu Ala Asp Lys Tyr Gly Asp Thr Pro Ala Val Arg
             20                  25                  30

Glu Tyr His Gly Lys Glu Leu Val Asp Arg Asn Tyr Leu Glu Leu Lys
         35                  40                  45

Arg Asp Ala Asp Ala Val Ser Arg Phe Leu Leu Ala Gln Gly Ala Glu
     50                  55                  60
```

```
Glu Arg Met His Ile Ala Val Gly Ala Thr Ser Tyr Gln Tyr Ile
 65                  70                  75                  80

Ala Ala Tyr Phe Gly Thr Val Asp Thr Ala Asn Val Ile Val Pro Thr
                 85                  90                  95

Glu Ala Gln Leu Ser Thr Glu Thr Gln Cys Glu Leu Phe His Met Ala
            100                 105                 110

Asp Val Thr Gly Leu Phe Phe Asp Lys His Phe Glu Asp Ala Ile Pro
        115                 120                 125

Glu Ile His Glu Lys Cys Pro Asp Ile Lys Leu Phe Ile Cys Leu Thr
    130                 135                 140

Asp Gly Val Glu Ser His Asp Leu Gly Asp Ile His Ile His Ser Ile
145                 150                 155                 160

Asn Glu Ile Glu Lys Glu Tyr Ala Glu Gly Glu Ile Ile Val Pro
                165                 170                 175

Leu Glu His Asp Thr Phe Ser Thr Ile Leu Phe Thr Ser Gly Thr Thr
            180                 185                 190

Ser Ala Arg Pro Lys Ala Val Met Leu Cys His Gly Ile Ile Asp
        195                 200                 205

Asn Ile Phe Ser Gly Glu Leu Glu Gln Arg Asp Ser Thr Asn Lys Val
    210                 215                 220

Lys Leu Ile Ala Leu Pro Ile His His Ala Leu Ser Phe Asn Thr Asp
225                 230                 235                 240

Ile Cys Met Gly Phe Arg Asn Gly Asp Thr Val Phe Val Asn Asp Ser
                245                 250                 255

Met Leu His Ile Ala Lys Asn Phe Lys Val Ala Lys Pro Tyr Thr Ala
            260                 265                 270

Ile Leu Val Pro Met Ile Phe Glu Asn Phe Tyr His Lys Ile Met Lys
        275                 280                 285

Ala His Glu Val His Pro Glu Val Asp Leu Lys Ala Met Ala Arg Asp
    290                 295                 300

Val Phe Gly Gly Glu Val Glu Val Phe Tyr Cys Gly Gly Ala His Leu
305                 310                 315                 320

Arg Ala Glu Ile Ala Asp Ala Phe Ala Glu Trp Gly Met Pro Val Phe
                325                 330                 335

Glu Gly Tyr Gly Met Thr Glu Cys Ser Pro Arg Val Ala Ala Asn Met
            340                 345                 350

Pro Trp Arg Tyr Arg Arg Asp Ser Ile Gly Arg Val Val Asp Asn Ala
        355                 360                 365

His Val Arg Ile Lys Asp Thr Glu Leu Gln Val Lys Ser Pro Ser Val
    370                 375                 380

Met Leu Gly Tyr Tyr Lys Asp Pro Glu Ala Thr Lys Ala Ala Phe Thr
385                 390                 395                 400

Glu Asp Gly Trp Leu Lys Ser Gly Asp Ile Gly Tyr Ile Asp Glu Asp
                405                 410                 415

Gly Phe Ile Phe Leu Gln Gly Arg Ile Lys Asn Leu Ile Ile Leu Ser
            420                 425                 430

Asn Gly Glu Asn Val Ser Pro Glu Glu Ile Glu Thr Lys Leu Tyr Asp
        435                 440                 445

Cys Thr Phe Ile Lys Glu Cys Leu Val Tyr Glu Asn Gly Gln Ile
    450                 455                 460

Thr Ala Glu Val Phe Pro Asp Ala Glu Tyr Ala Glu Met His Lys Val
465                 470                 475                 480

Thr Asp Val Glu Lys Glu Ile Ser Ala Ala Ile Lys Ala Val Asn Lys
```

485                 490                 495
Ser Met Pro Thr Thr Lys Ser Val Arg Ser Val Lys Phe Arg Tyr Glu
              500                 505                 510

Pro Phe Glu Arg Thr Ala Thr Asn Lys Ile Lys Arg Thr Gly Arg Gly
              515                 520                 525

Lys Lys Ala Ala
        530

<210> SEQ ID NO 109
<211> LENGTH: 1404
<212> TYPE: DNA
<213> ORGANISM: Blautia sp.

<400> SEQUENCE: 109

| | | | | | |
|---|---|---|---|---|---|
| atgcgtaccc | gtaaaggcca | taaagtttat | ccgctgaccg | ttgcacagaa | attccatctg | 60 |
| tattatctgc | cgttttgtcc | gagcgcagca | gttctgaata | ttggcaccag | cgttaccatt | 120 |
| gaaattgaga | ttgattggga | tctgctggcc | aaaagcatta | caaagcccta | tgcacgtagc | 180 |
| gaaggtatgc | gtattcgttt | tgccaaagat | aaagaaggca | actggtatca | gtatgttgca | 240 |
| gatccggaag | aaatgaaaat | cgaatttgcc | gattttagca | aggcaccat | ggaagaggca | 300 |
| gaaagcacca | tgcagcagtg | gaccaccgtt | ccgtttaaaa | tggaagatag | ccagatgagc | 360 |
| cgtattgtga | tgattcagat | gccggatggt | tttaacggta | tctatttct | ggtgcatcac | 420 |
| atgattgccg | atgcacagag | cctgatttgt | tttatgaaag | atatcatcga | actgtactgc | 480 |
| aacgagaaat | atgaaggtgt | tccgtatccg | aaagatatgg | ccagctatat | tgatcagctg | 540 |
| aaaaaagatc | tggattacga | agcaggtagc | aaagcacagc | tgcgtgatat | tgaattttc | 600 |
| cagcgcgaaa | ttgaaaaagg | cgaaccgatt | ataacggta | ttcatggcac | cgataaactg | 660 |
| gaagcagcac | gtgcaatgtt | taaagatccg | aaactgcgta | ccgcatttaa | tgcaagtgat | 720 |
| gataccaaaa | gcgcactgga | tattttcat | ctggaagccg | atccgaccaa | acgtctgatg | 780 |
| gatttttgtg | agaaatatca | tgttagcctg | gcatgtctgc | tgctgatggg | tctgcgtacc | 840 |
| tattttcaga | aaatgaacgg | ttttgaggac | gtgagcatta | taacgcgat | gcccgtcgt | 900 |
| gcaaccctgc | gtgagaaaaa | aagcggtggc | accgtattc | atagctttcc | gattcgtacc | 960 |
| gttttagcg | aggatatgaa | atttatcgat | ggcgtgtatg | ccattcgcga | taaacagaat | 1020 |
| gaaatttttc | gccacgcaaa | ctatgatccg | accgcatatt | ttgcatatcg | cagcaaaatc | 1080 |
| tatccgcagc | cgcatgccgg | tctgacctat | gaaccgatta | gcctgaccta | tcagccgatg | 1140 |
| acactgcaag | aaaatggtct | gaccgaactg | ggtgatattc | gctataaaac | caatggtat | 1200 |
| ccgaatggta | catgtccgca | gggtatgtat | ctgaccgtta | tgcatcgtcc | ggaagataac | 1260 |
| ggtctggatt | ttaactttga | acaccagatt | aaagccgtga | gccgtgaaga | actggaatat | 1320 |
| ctgtactatt | acctgtgcaa | aatcatgttc | aaaggcaccg | aaaatcctga | tctgaccatt | 1380 |
| ggcgaaatta | tcaagctgat | ctaa | | | | 1404 |

<210> SEQ ID NO 110
<211> LENGTH: 467
<212> TYPE: PRT
<213> ORGANISM: Blautia sp.

<400> SEQUENCE: 110

Met Arg Thr Arg Lys Gly His Lys Val Tyr Pro Leu Thr Val Ala Gln
1               5                   10                  15

Lys Phe His Leu Tyr Tyr Leu Pro Phe Cys Pro Ser Ala Ala Val Leu

-continued

```
               20                  25                  30
Asn Ile Gly Thr Ser Val Thr Ile Glu Ile Glu Ile Asp Trp Asp Leu
            35                  40                  45
Leu Ala Lys Ser Ile Asn Lys Ala Tyr Ala Arg Ser Glu Gly Met Arg
        50                  55                  60
Ile Arg Phe Ala Lys Asp Lys Glu Gly Asn Trp Tyr Gln Tyr Val Ala
65                  70                  75                  80
Asp Pro Glu Glu Met Lys Ile Glu Phe Ala Asp Phe Ser Lys Gly Thr
                85                  90                  95
Met Glu Glu Ala Glu Ser Thr Met Gln Gln Trp Thr Thr Val Pro Phe
            100                 105                 110
Lys Met Glu Asp Ser Gln Met Ser Arg Ile Val Met Ile Gln Met Pro
        115                 120                 125
Asp Gly Phe Asn Gly Ile Tyr Phe Leu Val His His Met Ile Ala Asp
    130                 135                 140
Ala Gln Ser Leu Ile Cys Phe Met Lys Asp Ile Ile Glu Leu Tyr Cys
145                 150                 155                 160
Asn Glu Lys Tyr Glu Gly Val Pro Tyr Pro Lys Asp Met Ala Ser Tyr
                165                 170                 175
Ile Asp Gln Leu Lys Lys Asp Leu Asp Tyr Glu Ala Gly Ser Lys Ala
            180                 185                 190
Gln Leu Arg Asp Ile Glu Phe Phe Gln Arg Glu Ile Glu Lys Gly Glu
        195                 200                 205
Pro Ile Tyr Asn Gly Ile His Gly Thr Asp Lys Leu Glu Ala Ala Arg
    210                 215                 220
Ala Met Phe Lys Asp Pro Lys Leu Arg Thr Ala Phe Asn Ala Ser Asp
225                 230                 235                 240
Asp Thr Lys Ser Ala Leu Asp Ile Phe His Leu Glu Ala Asp Pro Thr
                245                 250                 255
Lys Arg Leu Met Asp Phe Cys Glu Lys Tyr His Val Ser Leu Ala Cys
            260                 265                 270
Leu Leu Leu Met Gly Leu Arg Thr Tyr Phe Gln Lys Met Asn Gly Phe
        275                 280                 285
Glu Asp Val Ser Ile Asn Asn Ala Ile Ala Arg Arg Ala Thr Leu Arg
    290                 295                 300
Glu Lys Lys Ser Gly Gly Thr Arg Ile His Ser Phe Pro Ile Arg Thr
305                 310                 315                 320
Val Phe Ser Glu Asp Met Lys Phe Ile Asp Gly Val Tyr Ala Ile Arg
                325                 330                 335
Asp Lys Gln Asn Glu Ile Phe Arg His Ala Asn Tyr Asp Pro Thr Ala
            340                 345                 350
Tyr Phe Ala Tyr Arg Ser Lys Ile Tyr Pro Gln Pro His Ala Gly Leu
        355                 360                 365
Thr Tyr Glu Pro Ile Ser Leu Thr Tyr Gln Pro Met Thr Leu Gln Glu
    370                 375                 380
Asn Gly Leu Thr Glu Leu Gly Asp Ile Arg Tyr Lys Thr Lys Trp Tyr
385                 390                 395                 400
Pro Asn Gly Thr Cys Pro Gln Gly Met Tyr Leu Thr Val Met His Arg
                405                 410                 415
Pro Glu Asp Asn Gly Leu Asp Phe Asn Phe Glu His Gln Ile Lys Ala
            420                 425                 430
Val Ser Arg Glu Glu Leu Glu Tyr Leu Tyr Tyr Leu Cys Lys Ile
        435                 440                 445
```

```
Met Phe Lys Gly Thr Glu Asn Pro Asp Leu Thr Ile Gly Glu Ile Ile
    450                 455                 460

Lys Leu Ile
465

<210> SEQ ID NO 111
<211> LENGTH: 234
<212> TYPE: DNA
<213> ORGANISM: Blautia sp.

<400> SEQUENCE: 111
atgttcgaaa aactggtgga tatcatctgc agctatgtgg aagtggaaaa agataatatt      60
cgtccggaaa gccgctttat ggaagatctg ggttttacca gctatgactt tatgagcatg     120
ctgggcgaaa tcgaagatga atttgatgtt gaagttgaac aggccgatgc catgaatatt     180
cgtaccgttc aagaagcagc agactatctg aaaaactga ccgcaggtaa ttaa            234

<210> SEQ ID NO 112
<211> LENGTH: 77
<212> TYPE: PRT
<213> ORGANISM: Blautia sp.

<400> SEQUENCE: 112

Met Phe Glu Lys Leu Val Asp Ile Ile Cys Ser Tyr Val Glu Val Glu
1               5                   10                  15

Lys Asp Asn Ile Arg Pro Glu Ser Arg Phe Met Glu Asp Leu Gly Phe
            20                  25                  30

Thr Ser Tyr Asp Phe Met Ser Met Leu Gly Glu Ile Glu Asp Glu Phe
        35                  40                  45

Asp Val Glu Val Glu Gln Ala Asp Ala Met Asn Ile Arg Thr Val Gln
    50                  55                  60

Glu Ala Ala Asp Tyr Leu Glu Lys Leu Thr Ala Gly Asn
65                  70                  75

<210> SEQ ID NO 113
<211> LENGTH: 1509
<212> TYPE: DNA
<213> ORGANISM: Blautia sp.

<400> SEQUENCE: 113
atgctgtgta gcaccgttcg tcagattctg gttaataccg aacagaaata tggtccggaa      60
gatgccattc gctataaaat cagcaaaaac gagatcgaga gcaaaaccta tacacagctg     120
cgtgaagata gcgaaagctt tagctgtgtt ctgcgtgatc tgggtgaaca gggtaaacat     180
attgcagtta ttggtacaac cagctatccg tggctgaccg catattttgg caccgttaat     240
agcggtagcg ttgttgttcc gctggatgtt aatctgcctg ccgaagatgt tgtgatctg      300 attcatcgta gcgatagcac cgtgctggtt tatgatgaag cacgtaaaga tgttgcagcc     360
attgcaaaag aacgttgtcc gcagctgaaa attctgatta gcatgcagca gcaggatcat     420
aatgaacagg cctatgcatt ttggaaactg ctggaagaac atcgtggtag ctttgattat     480
atgcctgatc ctgatcagct gtgcaccatt atgtttacaa gcggcaccac cggtaaaagc     540
aaaggtgtta tgctgaccca tcgtaatgtt gcagaaaatg caacctgtct ggatatgaaa     600
attccggaac gtattgtgat tatgaccgtt ctgccgattc atcatgcata ttgtctgagc     660
atggatattc tgaaaggtgt gagcctgggt gccgttattt gtattaatga tagcctgatg     720
cgtgtggcca aaaacatcaa actgtttaaa ccggaaatga ttctgatggt tccgctgatg     780
```

```
attgaaaccca tggcaaaaaa actggaagaa gcagcactgc tgcctgccaa aattgttaaa    840
aatcaggtgt ttggcaaaca gttccatacc atttgtagcg gtggtgcata tctggacccg    900
agctatattg atcttttcgc caaatatgac atcatcatcc agcaaggtta tggtatgacc    960
gaatgtagtc cggttattag caccacacag aaatggaata ttcgcaaaga tgcagttggt   1020
cagctgctgc cgaattgtca ggcaaaaacc gttgatggtg aactgtgggt taaaggtagc   1080
agcgttatgc agggttatta caaaatgccg gaagaaaccg cagaaaccct ggaagatggt   1140
tggctgaaaa caggcgatct gggttatgtt gatgaagatg ctttgttta tctgaccggt   1200 cgcaaaaaaa acctgatcat taccaaaaat ggcgagaatg tttcaccgga gaactggaa    1260 aatgcactga gcaccaatcg tctggttggt gaagttctgg ttcgtgaaca taacggtgtt   1320
attgaagcag aaatctatcc ggatcaggac tacgttaaaa agaaacgcat caaagatgtt   1380
aaggcaagcc tgcaagaggt gatcgatgaa tataatcgta ccgcagctcc gcagaaaaaa   1440
atctatagtc tgattgttcg cgataccgag tttgaaaaaa ccaccacacg taaaatcaag   1500
cgcttttaa                                                          1509

<210> SEQ ID NO 114
<211> LENGTH: 502
<212> TYPE: PRT
<213> ORGANISM: Blautia sp.

<400> SEQUENCE: 114

Met Leu Cys Ser Thr Val Arg Gln Ile Leu Val Asn Thr Glu Gln Lys
1               5                   10                  15

Tyr Gly Pro Glu Asp Ala Ile Arg Tyr Lys Ile Ser Lys Asn Glu Ile
            20                  25                  30

Glu Ser Lys Thr Tyr Thr Gln Leu Arg Glu Asp Ser Glu Ser Phe Ser
        35                  40                  45

Cys Val Leu Arg Asp Leu Gly Glu Gln Gly Lys His Ile Ala Val Ile
    50                  55                  60

Gly Thr Thr Ser Tyr Pro Trp Leu Thr Ala Tyr Phe Gly Thr Val Asn
65                  70                  75                  80

Ser Gly Ser Val Val Pro Leu Asp Val Asn Leu Pro Ala Glu Asp
            85                  90                  95

Val Cys Asp Leu Ile His Arg Ser Asp Ser Thr Val Leu Val Tyr Asp
            100                 105                 110

Glu Ala Arg Lys Asp Val Ala Ala Ile Ala Lys Glu Arg Cys Pro Gln
        115                 120                 125

Leu Lys Ile Leu Ile Ser Met Gln Gln Gln Asp His Asn Glu Gln Ala
    130                 135                 140

Tyr Ala Phe Trp Lys Leu Leu Glu Glu His Arg Gly Ser Phe Asp Tyr
145                 150                 155                 160

Met Pro Asp Pro Asp Gln Leu Cys Thr Ile Met Phe Thr Ser Gly Thr
            165                 170                 175

Thr Gly Lys Ser Lys Gly Val Met Leu Thr His Arg Asn Val Ala Glu
        180                 185                 190

Asn Ala Thr Cys Leu Asp Met Lys Ile Pro Glu Arg Ile Val Ile Met
    195                 200                 205

Thr Val Leu Pro Ile His His Ala Tyr Cys Leu Ser Met Asp Ile Leu
    210                 215                 220

Lys Gly Val Ser Leu Gly Ala Val Ile Cys Ile Asn Asp Ser Leu Met
225                 230                 235                 240
```

```
Arg Val Ala Lys Asn Ile Lys Leu Phe Lys Pro Glu Met Ile Leu Met
            245                 250                 255

Val Pro Leu Met Ile Glu Thr Met Ala Lys Lys Leu Glu Glu Ala Ala
        260                 265                 270

Leu Leu Pro Ala Lys Ile Val Lys Asn Gln Val Phe Gly Lys Gln Phe
    275                 280                 285

His Thr Ile Cys Ser Gly Gly Ala Tyr Leu Asp Pro Ser Tyr Ile Asp
290                 295                 300

Leu Phe Ala Lys Tyr Asp Ile Ile Gln Gln Gly Tyr Gly Met Thr
305                 310                 315                 320

Glu Cys Ser Pro Val Ile Ser Thr Thr Gln Lys Trp Asn Ile Arg Lys
                325                 330                 335

Asp Ala Val Gly Gln Leu Leu Pro Asn Cys Gln Ala Lys Thr Val Asp
            340                 345                 350

Gly Glu Leu Trp Val Lys Gly Ser Ser Val Met Gln Gly Tyr Tyr Lys
        355                 360                 365

Met Pro Glu Glu Thr Ala Glu Thr Leu Glu Asp Gly Trp Leu Lys Thr
    370                 375                 380

Gly Asp Leu Gly Tyr Val Asp Glu Asp Gly Phe Val Tyr Leu Thr Gly
385                 390                 395                 400

Arg Lys Lys Asn Leu Ile Ile Thr Lys Asn Gly Glu Asn Val Ser Pro
                405                 410                 415

Glu Glu Leu Glu Asn Ala Leu Ser Thr Asn Arg Leu Val Gly Glu Val
            420                 425                 430

Leu Val Arg Glu His Asn Gly Val Ile Glu Ala Glu Ile Tyr Pro Asp
        435                 440                 445

Gln Asp Tyr Val Lys Lys Arg Ile Lys Asp Val Lys Ala Ser Leu
    450                 455                 460

Gln Glu Val Ile Asp Glu Tyr Asn Arg Thr Ala Ala Pro Gln Lys Lys
465                 470                 475                 480

Ile Tyr Ser Leu Ile Val Arg Asp Thr Glu Phe Glu Lys Thr Thr Thr
                485                 490                 495

Arg Lys Ile Lys Arg Phe
            500

<210> SEQ ID NO 115
<211> LENGTH: 1389
<212> TYPE: DNA
<213> ORGANISM: Blautia wexlerae

<400> SEQUENCE: 115
atgaccaact attatccgct gaccgcagca cagaaaatgc atcataattg gatcatggat      60
tatggcaccc agcaggttag cggtgttagc gttgttgcaa gcgttcaggc agaactggat     120
tttggtctgc tgaaaaaatg cattcagatg gaaaccgaac gtagcggttg tacccgtatt     180
cgttttacca aaccggataa agatggtaac gttcagcagt atctggttaa caagatccg     240 cgtgatatcg gctttaaaga tctgagcggt atgggtagcc tggcaaaagc agatgaactg     300
atgcagcagt gggcctatga aacctttgat ggtgatgata ttccgatgtg cgaattcacc     360
atgctgaaac tgccggaagg ttataatggt ttttttgtgc acatggatca ccgcctgatt     420
gatagctgtg gtctggttgt tatgattggt gatcttttc agctgtatac ctactacaaa     480
tatggcaccg catatccgca gaaactggca gattttgaaa ccgtcctgaa aaagatctg     540 gccaaagcag gtaatgaaaa acgctttgcc aaagacaaaa aattctggga tgatcagctg     600
```

```
gatgcactgg gtgaaccgct gtatagcgat attcagggtc cgagcgttct ggaagaggca    660
cgtaaacgtc atggtaatcc gaaactgcgt agcagcgata ttgaaatgaa agacctgttt    720
gttgccgtga agattatta tctggaaccg ggtccgacca aaaatctgat tgattttgt     780 atgaaccatc agctgagcat gaccaatctg ctgctgctgg gtattcgtac ctatctgagc    840
aaagttaata acggccaaga agatattacc atccagaact ttattagccg tcgtagcacc    900
catgatgaat ggaccagcgg tggtagccgt accattatgt ttccgtgtcg taccgttatt    960
gcaccggaaa ccgattttct gagcgcagcg tatgaaattc agaatatgca gaaccgcatc   1020
tacatgcaca gtaattatga tccggcattt atcatggatg aaatgcgcaa acgttataac   1080
acaccggaac acacaggtta tgaaagctgt tatctgacct atcagccgat gaccgttaaa   1140
gtggaaaatg aaatgctggg caccattcgt cagcatgcaa atggtttgc aaatggtgca   1200 gcaaccaaaa aaatgtatct gaccgttagc cataccgaag atggtggtat gaatttcagc   1260
tatcattatc agaccgcaca tctggaagaa catgatatgg aactgctgta ctattatatg   1320
atgcgcattc tgtttaaagg cattgccgaa ccggatatga gcattggtga atcatggaa    1380 ctggtgtaa                                                          1389
```

<210> SEQ ID NO 116
<211> LENGTH: 462
<212> TYPE: PRT
<213> ORGANISM: Blautia wexlerae

<400> SEQUENCE: 116

```
Met Thr Asn Tyr Tyr Pro Leu Thr Ala Ala Gln Lys Met His His Asn
1               5                   10                  15

Trp Ile Met Asp Tyr Gly Thr Gln Gln Val Ser Gly Val Ser Val Val
            20                  25                  30

Ala Ser Val Gln Ala Glu Leu Asp Phe Gly Leu Leu Lys Lys Cys Ile
        35                  40                  45

Gln Met Glu Thr Glu Arg Ser Gly Cys Thr Arg Ile Arg Phe Thr Lys
    50                  55                  60

Pro Asp Lys Asp Gly Asn Val Gln Gln Tyr Leu Val Lys Gln Asp Pro
65                  70                  75                  80

Arg Asp Ile Gly Phe Lys Asp Leu Ser Gly Met Gly Ser Leu Ala Lys
                85                  90                  95

Ala Asp Glu Leu Met Gln Gln Trp Ala Tyr Glu Thr Phe Asp Gly Asp
            100                 105                 110

Asp Ile Pro Met Cys Glu Phe Thr Met Leu Lys Leu Pro Glu Gly Tyr
        115                 120                 125

Asn Gly Phe Phe Val His Met Asp His Arg Leu Ile Asp Ser Cys Gly
    130                 135                 140

Leu Val Val Met Ile Gly Asp Leu Phe Gln Leu Tyr Thr Tyr Tyr Lys
145                 150                 155                 160

Tyr Gly Thr Ala Tyr Pro Gln Lys Leu Ala Asp Phe Glu Thr Val Leu
                165                 170                 175

Lys Lys Asp Leu Ala Lys Ala Gly Asn Glu Lys Arg Phe Ala Lys Asp
            180                 185                 190

Lys Lys Phe Trp Asp Asp Gln Leu Asp Ala Leu Gly Glu Pro Leu Tyr
        195                 200                 205

Ser Asp Ile Gln Gly Pro Ser Val Leu Glu Glu Ala Arg Lys Arg His
    210                 215                 220
```

Gly Asn Pro Lys Leu Arg Ser Ser Asp Ile Glu Met Lys Asp Leu Phe
225                 230                 235                 240

Val Ala Val Lys Asp Tyr Tyr Leu Glu Pro Gly Pro Thr Lys Asn Leu
            245                 250                 255

Ile Asp Phe Cys Met Asn His Gln Leu Ser Met Thr Asn Leu Leu Leu
        260                 265                 270

Leu Gly Ile Arg Thr Tyr Leu Ser Lys Val Asn Asn Gly Gln Glu Asp
    275                 280                 285

Ile Thr Ile Gln Asn Phe Ile Ser Arg Arg Ser Thr His Asp Glu Trp
290                 295                 300

Thr Ser Gly Ser Arg Thr Ile Met Phe Pro Cys Arg Thr Val Ile
305                 310                 315                 320

Ala Pro Glu Thr Asp Phe Leu Ser Ala Ala Tyr Glu Ile Gln Asn Met
            325                 330                 335

Gln Asn Arg Ile Tyr Met His Ser Asn Tyr Asp Pro Ala Phe Ile Met
        340                 345                 350

Asp Glu Met Arg Lys Arg Tyr Asn Thr Pro Glu His Thr Gly Tyr Glu
    355                 360                 365

Ser Cys Tyr Leu Thr Tyr Gln Pro Met Thr Val Lys Val Glu Asn Glu
370                 375                 380

Met Leu Gly Thr Ile Arg Gln His Ala Lys Trp Phe Ala Asn Gly Ala
385                 390                 395                 400

Ala Thr Lys Lys Met Tyr Leu Thr Val Ser His Thr Glu Asp Gly Gly
            405                 410                 415

Met Asn Phe Ser Tyr His Tyr Gln Thr Ala His Leu Glu Glu His Asp
        420                 425                 430

Met Glu Leu Leu Tyr Tyr Tyr Met Met Arg Ile Leu Phe Lys Gly Ile
    435                 440                 445

Ala Glu Pro Asp Met Ser Ile Gly Glu Ile Met Glu Leu Val
450                 455                 460

<210> SEQ ID NO 117
<211> LENGTH: 231
<212> TYPE: DNA
<213> ORGANISM: Blautia wexlerae

<400> SEQUENCE: 117
atgaatcaag agatggaatt caagaacatc gttgcccagt atagcaaagt tgcaccggaa      60
gaaatgaata cgaaatgcg ttttcgtgaa gatctgggtt ttagcagcct ggatttatg      120 agctttctgg gtgaactgga agatacctt gatctggaac tggatgaaag cgaagtgctg      180
aaaattacca cactgggtga agcactgaat ctgctggaag aactgcagta a              231

<210> SEQ ID NO 118
<211> LENGTH: 76
<212> TYPE: PRT
<213> ORGANISM: Blautia wexlerae

<400> SEQUENCE: 118

Met Asn Gln Glu Met Glu Phe Lys Asn Ile Val Ala Gln Tyr Ser Lys
1               5                   10                  15

Val Ala Pro Glu Glu Met Asn Asn Glu Met Arg Phe Arg Glu Asp Leu
            20                  25                  30

Gly Phe Ser Ser Leu Asp Phe Met Ser Phe Leu Gly Glu Leu Glu Asp
        35                  40                  45

Thr Phe Asp Leu Glu Leu Asp Glu Ser Glu Val Leu Lys Ile Thr Thr

```
                    50                  55                  60
Leu Gly Glu Ala Leu Asn Leu Leu Glu Glu Leu Gln
65                  70                  75

<210> SEQ ID NO 119
<211> LENGTH: 1545
<212> TYPE: DNA
<213> ORGANISM: Blautia wexlerae

<400> SEQUENCE: 119
atgctgattc gcaacattct ggaagaaagc gtgcgtaaat ttgatgaagt taaagccgtt      60
aaatggctga aaagaaagaa atcatggaaa cgcagctatg cgaactgatg gaaaatgtt    120 gttagcaccc gtaaaggtct gctggcagaa ggttttgaag gtaaacatat tgcactgatt    180
ggcaccagca gcgttgaatg gatggaaagc tatctgggta ttattaccgg ttgtaccacc    240
gcagttccgc tggatgcagc actgccgtgt gaagatctga ttgatctgct gaatcgtagc    300
gatagcgcag cactgtttct gagccccgaa actgcgtccgt atctggatgc atttctgggt    360
aattgtccta aactgcagaa agtttggatg ctgcaagaag aagttgagga cgcaccggca    420
aaagtttatg gtattggtga actgcgtaat gcaggtaaaa gcgcaagcgc agatagcgtt    480
tgtccggatg cagaagatat tgcaaccatt atctttacca gcggcaccac cggtaaaagc    540
aaaggtgtta tgctgaccca gaataatctg gcaagcaatg ttgaagcagt gaaaattacc    600
gcagaaccgg gtacagcagt tctgagcgtt ctgccgattc atcatgcatt ttgtctggtt    660
atggattggc tgaaaggttt tagcctgggt gcaaccctgt gtattaatga tagcctgctg    720
cacatggttc gtaacatgag catctttaaa ccggatatca tgctgatggt tccgatgatg    780
attgaaacca tctataaacg tctggcagca gcagatccga gcattccgaa agccgttctg    840
gcagaaaaag ttttggtgg taaactgcgc attattttca ccggtggcgc acatctggac    900
ccgtattata tcgatcgttt tgttgaatat ggtgtggaag tgctggaagg ttatggtatg    960
agcgaatgta gtccggtgat tagcaataat acgctggaaa accataaaaa aggcagcatt   1020
ggtaaacctc tggaaaatgc cgaaattcgc tttgaaaatg gtgagattct ggttaaaggt   1080
agcagcgtga tgaaaggcta ttatcagatg ccggatgaaa ccgcagaaac cctgaaagat   1140
ggttggctgc ataccggtga taaaggttat atggatgaag atggctacct gtttattaac   1200
ggtcgtgtga aaaatctgat cattctgagc aatggcgaaa atgttagtcc ggaagaaatc   1260
gaaaataaac tggcactgaa tccgctggtt ggtgaagtta ttgttacagg tgaagataac   1320
ggtctgaccg cacgtattta tccggaacag gcagttgttg aagccaaagc actggatgcc   1380
gaagcaattc aggcacagct gcaggccttt ctggatgaat ataatcgtaa tcagccgacc   1440
tatcgtcgca ttaccggtct ggttgttcgt aaaaaatccgt ttattcgtaa caccaccaag   1500
aaaattcgtc gtcaggatgt gctgattgat gaaccgctgg aataa              1545

<210> SEQ ID NO 120
<211> LENGTH: 514
<212> TYPE: PRT
<213> ORGANISM: Blautia wexlerae

<400> SEQUENCE: 120

Met Leu Ile Arg Asn Ile Leu Glu Glu Ser Val Arg Lys Phe Asp Glu
1               5                  10                  15

Val Lys Ala Val Lys Trp Leu Lys Lys Lys Glu Ile Met Glu Arg Ser
                20                  25                  30
```

-continued

```
Tyr Gly Glu Leu Met Glu Asn Val Ser Thr Arg Lys Gly Leu Leu
         35                  40                  45

Ala Glu Gly Phe Glu Gly Lys His Ile Ala Leu Ile Gly Thr Ser Ser
 50                  55                  60

Val Glu Trp Met Glu Ser Tyr Leu Gly Ile Ile Thr Gly Cys Thr Thr
 65                  70                  75                  80

Ala Val Pro Leu Asp Ala Ala Leu Pro Cys Glu Asp Leu Ile Asp Leu
                 85                  90                  95

Leu Asn Arg Ser Asp Ser Ala Ala Leu Phe Leu Ser Pro Lys Leu Arg
                100                 105                 110

Pro Tyr Leu Asp Ala Phe Leu Gly Asn Cys Pro Lys Leu Gln Lys Val
             115                 120                 125

Trp Met Leu Gln Glu Glu Val Glu Asp Ala Pro Ala Lys Val Tyr Gly
         130                 135                 140

Ile Gly Glu Leu Arg Asn Ala Gly Lys Ser Ala Ser Ala Asp Ser Val
145                 150                 155                 160

Cys Pro Asp Ala Glu Asp Ile Ala Thr Ile Ile Phe Thr Ser Gly Thr
                165                 170                 175

Thr Gly Lys Ser Lys Gly Val Met Leu Thr Gln Asn Asn Leu Ala Ser
             180                 185                 190

Asn Val Glu Ala Val Lys Ile Thr Ala Glu Pro Gly Thr Ala Val Leu
         195                 200                 205

Ser Val Leu Pro Ile His His Ala Phe Cys Leu Val Met Asp Trp Leu
     210                 215                 220

Lys Gly Phe Ser Leu Gly Ala Thr Leu Cys Ile Asn Asp Ser Leu Leu
225                 230                 235                 240

His Met Val Arg Asn Met Ser Ile Phe Lys Pro Asp Ile Met Leu Met
                245                 250                 255

Val Pro Met Met Ile Glu Thr Ile Tyr Lys Arg Leu Ala Ala Ala Asp
             260                 265                 270

Pro Ser Ile Pro Lys Ala Val Leu Ala Glu Lys Val Phe Gly Gly Lys
         275                 280                 285

Leu Arg Ile Ile Phe Thr Gly Gly Ala His Leu Asp Pro Tyr Tyr Ile
     290                 295                 300

Asp Arg Phe Val Glu Tyr Gly Val Glu Val Leu Glu Gly Tyr Gly Met
305                 310                 315                 320

Ser Glu Cys Ser Pro Val Ile Ser Asn Asn Thr Leu Glu Asn His Lys
                325                 330                 335

Lys Gly Ser Ile Gly Lys Pro Leu Glu Asn Ala Glu Ile Arg Phe Glu
             340                 345                 350

Asn Gly Glu Ile Leu Val Lys Gly Ser Ser Val Met Lys Gly Tyr Tyr
         355                 360                 365

Gln Met Pro Asp Glu Thr Ala Glu Thr Leu Lys Asp Gly Trp Leu His
     370                 375                 380

Thr Gly Asp Lys Gly Tyr Met Asp Glu Asp Gly Tyr Leu Phe Ile Asn
385                 390                 395                 400

Gly Arg Val Lys Asn Leu Ile Ile Leu Ser Asn Gly Glu Asn Val Ser
                405                 410                 415

Pro Glu Glu Ile Glu Asn Lys Leu Ala Leu Asn Pro Leu Val Gly Glu
             420                 425                 430

Val Ile Val Thr Gly Glu Asp Asn Gly Leu Thr Ala Arg Ile Tyr Pro
         435                 440                 445

Glu Gln Ala Val Val Glu Ala Lys Ala Leu Asp Ala Glu Ala Ile Gln
```

```
                450             455             460
Ala Gln Leu Gln Ala Phe Leu Asp Glu Tyr Asn Arg Asn Gln Pro Thr
465                 470                 475                 480

Tyr Arg Arg Ile Thr Gly Leu Val Val Arg Lys Asn Pro Phe Ile Arg
                485                 490                 495

Asn Thr Thr Lys Lys Ile Arg Arg Gln Asp Val Leu Ile Asp Glu Pro
            500                 505                 510

Leu Glu

<210> SEQ ID NO 121
<211> LENGTH: 1386
<212> TYPE: DNA
<213> ORGANISM: Lachnospiraceae bacterium

<400> SEQUENCE: 121
atgcgcaaag aatatccgct gaccgcagca cagaatatgc attatcagtg gatcaaagag      60
tacaagaccc agcaggttag cggtgttagc attgttgcaa gcctgaaagc agaactggat     120
tttggtctgc tgaaaaaatg tatccagctt gagatggaac gttatggttg tctgcgtctg     180
cgttttacca aaccggatga aaaaggtgag atcaaacagt acctgatcaa acatgatagc     240
cgtgatattc cgctgaaaga tatgaccggt atgaccctgg ccgaagcaga tgacatgatg     300
cagcattggg cctatgaaac cctggatggt gataatcgtc cgatgtgtga atttatgatg     360
gttaaactgc cggaaggcta taacggcttt tttatccaca tggatcatcg tctgattgat     420
agctgtggtc tggttgttat ggttaatgat ctgatgcagc tgtatacccca ttatcgtttt     480 ggtgccgaat atccggcaga tctggcagat tttgaaaaag ttctggaaag cgatctgcag     540
aaagccggta tgaaaaaacg ctttgcacgc gataaaaagt tttgggatga tcagctggat     600
gcactgggtg aaccgctgta tagcgatatt cagggtccga gcgttctgga agaagcacgt     660
aaaaaacaca gaacaaaaa actgcgtgca gccgatattg aacgcaaaga actgtttgtt     720
gccgtgaaag attatgttct ggaaccggaa ccgaccaaag gtctgatgga tttttgtatg     780
aatcatcagc tgagcatgac caatctgctg ctgctgggta ttcgtaccta tctgagcaaa     840
gttaataacg ccaagagga tattaccatc gaaaactta ttagccgtcg tagcaccccat     900 gatgaatgga ccagcggtgg tagccgtacc attatgtttc cgtgtcgtac cgttattcct     960
gccgatatgg attttatgag cgcagcgtat gaaattcaga atgtgcagaa tcgcatctac    1020
atgcacagca attatgatcc ggcactgatt cgtgaagaaa tgaagaaacg ttacaaaaca    1080
ccggatgata ccacctatga aagctgttat ctgacctatc agccgatgcc ggttcacatg    1140
gataatccgt ttctgaatgg tattcagatg catagcaaat ggtttgcaaa tggtgcagcc    1200
accaaaaaga tgtatctgac cgttagccat accgataatg gtggtatgaa cttcagctat    1260
cattatcaaa ccgcacgtct gaccgaaaaa gatatggaac tgctgtatta ttacatgatg    1320
cgtatcctgt ttatgggcat tagcaatccg gatatgaaaa tcggcgatat tatggaacag    1380
gtgtaa                                                              1386

<210> SEQ ID NO 122
<211> LENGTH: 461
<212> TYPE: PRT
<213> ORGANISM: Lachnospiraceae bacterium

<400> SEQUENCE: 122

Met Arg Lys Glu Tyr Pro Leu Thr Ala Ala Gln Asn Met His Tyr Gln
1               5                   10                  15
```

-continued

```
Trp Ile Lys Glu Tyr Lys Thr Gln Gln Val Ser Gly Val Ser Ile Val
         20                  25                  30

Ala Ser Leu Lys Ala Glu Leu Asp Phe Gly Leu Leu Lys Lys Cys Ile
         35                  40                  45

Gln Leu Glu Met Glu Arg Tyr Gly Cys Leu Arg Leu Arg Phe Thr Lys
 50                  55                  60

Pro Asp Glu Lys Gly Glu Ile Lys Gln Tyr Leu Ile Lys His Asp Ser
 65                  70                  75                  80

Arg Asp Ile Pro Leu Lys Asp Met Thr Gly Met Thr Leu Ala Glu Ala
                 85                  90                  95

Asp Asp Met Met Gln His Trp Ala Tyr Glu Thr Leu Asp Gly Asp Asn
            100                 105                 110

Arg Pro Met Cys Glu Ile Met Met Val Lys Leu Pro Glu Gly Tyr Asn
            115                 120                 125

Gly Phe Phe Ile His Met Asp His Arg Leu Ile Asp Ser Cys Gly Leu
130                 135                 140

Val Val Met Val Asn Asp Leu Met Gln Leu Tyr Thr His Tyr Arg Phe
145                 150                 155                 160

Gly Ala Glu Tyr Pro Ala Asp Leu Ala Asp Phe Glu Lys Val Leu Glu
                165                 170                 175

Ser Asp Leu Gln Lys Ala Gly Asn Glu Lys Arg Phe Ala Arg Asp Lys
            180                 185                 190

Lys Phe Trp Asp Asp Gln Leu Asp Ala Leu Gly Glu Pro Leu Tyr Ser
            195                 200                 205

Asp Ile Gln Gly Pro Ser Val Leu Glu Glu Ala Arg Lys Lys His Lys
            210                 215                 220

Asn Lys Lys Leu Arg Ala Ala Asp Ile Glu Arg Lys Glu Leu Phe Val
225                 230                 235                 240

Ala Val Lys Asp Tyr Val Leu Glu Pro Glu Pro Thr Lys Gly Leu Met
                245                 250                 255

Asp Phe Cys Met Asn His Gln Leu Ser Met Thr Asn Leu Leu Leu Leu
            260                 265                 270

Gly Ile Arg Thr Tyr Leu Ser Lys Val Asn Asn Gly Gln Glu Asp Ile
            275                 280                 285

Thr Ile Glu Asn Phe Ile Ser Arg Arg Ser Thr His Asp Glu Trp Thr
            290                 295                 300

Ser Gly Gly Ser Arg Thr Ile Met Phe Pro Cys Arg Thr Val Ile Pro
305                 310                 315                 320

Ala Asp Met Asp Phe Met Ser Ala Ala Tyr Glu Ile Gln Asn Val Gln
                325                 330                 335

Asn Arg Ile Tyr Met His Ser Asn Tyr Asp Pro Ala Leu Ile Arg Glu
            340                 345                 350

Glu Met Lys Lys Arg Tyr Lys Thr Pro Asp Asp Thr Thr Tyr Glu Ser
            355                 360                 365

Cys Tyr Leu Thr Tyr Gln Pro Met Pro Val His Met Asp Asn Pro Phe
370                 375                 380

Leu Asn Gly Ile Gln Met His Ser Lys Trp Phe Ala Asn Gly Ala Ala
385                 390                 395                 400

Thr Lys Lys Met Tyr Leu Thr Val Ser His Thr Asp Asn Gly Gly Met
                405                 410                 415

Asn Phe Ser Tyr His Tyr Gln Thr Ala Arg Leu Thr Glu Lys Asp Met
            420                 425                 430
```

```
Glu Leu Leu Tyr Tyr Tyr Met Met Arg Ile Leu Phe Met Gly Ile Ser
            435                 440                 445

Asn Pro Asp Met Lys Ile Gly Asp Ile Met Glu Gln Val
    450                 455                 460

<210> SEQ ID NO 123
<211> LENGTH: 237
<212> TYPE: DNA
<213> ORGANISM: Lachnospiraceae bacterium

<400> SEQUENCE: 123
atgaatcgtg ccgaagagtt caaaaacatt gttgcacagt atagcagcgt tgcagccgaa     60
gatatgaccg atgaaatgag cctgcgtgaa gatctgggtc tgagcagcct ggattttatg    120
acctttctgg gtgaaatcga ggatacctttt gatgttgaac tggatctgga tcgtgcagtt    180
cagattcgta ccgttggtga agcaattagc atgatgaatg cactggttac cgcataa       237

<210> SEQ ID NO 124
<211> LENGTH: 78
<212> TYPE: PRT
<213> ORGANISM: Lachnospiraceae bacterium

<400> SEQUENCE: 124

Met Asn Arg Ala Glu Glu Phe Lys Asn Ile Val Ala Gln Tyr Ser Ser
1               5                   10                  15

Val Ala Ala Glu Asp Met Thr Asp Glu Met Ser Leu Arg Glu Asp Leu
            20                  25                  30

Gly Leu Ser Ser Leu Asp Phe Met Thr Phe Leu Gly Glu Ile Glu Asp
        35                  40                  45

Thr Phe Asp Val Glu Leu Asp Leu Asp Arg Ala Val Gln Ile Arg Thr
    50                  55                  60

Val Gly Glu Ala Ile Ser Met Met Asn Ala Leu Val Thr Ala
65                  70                  75

<210> SEQ ID NO 125
<211> LENGTH: 1527
<212> TYPE: DNA
<213> ORGANISM: Lachnospiraceae bacterium

<400> SEQUENCE: 125
atgaacacca ttcgcgaaat ttgggatagc gcactgaata actatagcga actgcctgcc     60
gttcgttggc tggaaaaaaa agatatcatt gaacgtagct atcgcgagct gaacaacgat    120
attgaagaaa ttcgtaaagg cctgaaagcc gaaggtctgg atggtgtgca tattagcctg    180
attggcaccg caagcattag ctggattggt acatatctgg gtattaccac cggtaataat    240
gttgcagttc cgctggatgc aggtctgcct gcagaagatc tgattgaact gctgaatgat    300
agtgatgcag aagcactgtt tctggcaccg aaaggtaaag cactggcaga agcagttaaa    360
gcaagctgtc cgaaaatccg taaaatttgg ctgctgcaag aagaaccgga agaaggtttt    420
agcaccctgg cagatctgaa agatatgagc aaaggtcgtc aggatgttga aggtcgtaaa    480
gcagaagata ttgcgacccct gatttatacc agcggtacaa ccggtaaaag caaaggtgtt    540
atgctgaccc agagcaatct gagccagaat gttgaaagcg ttccgtatag cgcagaaccg    600
ggttgtgttc tgctgagcgt tctgccggtt catcatgcat tttgtctggt tatggattgg    660
ctgaaaggtt ttcactgggt gcaaccgtt tgtatcaacg atagctttat gcatatcatc    720
cgcaacatga gcatctttaa accggatgtg atgctgatgg ttccgctgat gattgaaacc    780
```

```
atctataaac gtctgagcgc agttgatccg gcactgccga aagaagccgt tgcagcaaac   840
gtttttggtg gtaatctgaa aatcatcttt acaggcggtg cacatctgga cccgttttat   900
atcgaaaaac tggccgaata tggtgtgaaa gttctggaag ttatggtat gagcgaatgt    960
agtccggtta ttagcagcaa acaccggaa gatcacaaaa ttggtagcat ggtaaaccg    1020
ctgccgaatg ttaaagttcg ttttgaagat ggtgaaattc aggttcaggg tagcagcgtt  1080
atgaaaggct attacaaaat gcctgccgaa accgaagaaa ccctgaaaga tggttggctg  1140
cataccggtg ataaaggtta tctggatgaa gatggctttc tgtttattaa cggtcgcgtg  1200
aaaaatctga ttattctgag caatggcgaa acatcagtc cggaagaaat tgaaaataag  1260
ctgggcatta atccgctggt tggtgaagtt attgttaccg gtgaaaataa tggtctgacc  1320
gcacgtattt atccggatca ggatgtggtt aaagccaccg gtctggccga agatgccgtt  1380
aaagcagcac tggataatat cctgaaagag tataatcaga acagccgac ctatcgtcag  1440
attattgcac tggttgttcg caaaaatccg tttcatcgta atgcaaccgg caaaattgtt  1500
cgtgcagatg cagaaattga tgaataa                                     1527
```

<210> SEQ ID NO 126
<211> LENGTH: 508
<212> TYPE: PRT
<213> ORGANISM: Lachnospiraceae bacterium

<400> SEQUENCE: 126

```
Met Asn Thr Ile Arg Glu Ile Trp Asp Ser Ala Leu Asn Asn Tyr Ser
1               5                   10                  15

Glu Leu Pro Ala Val Arg Trp Leu Glu Lys Lys Asp Ile Ile Glu Arg
            20                  25                  30

Ser Tyr Arg Glu Leu Asn Asn Asp Ile Glu Glu Ile Arg Lys Gly Leu
        35                  40                  45

Lys Ala Glu Gly Leu Asp Gly Val His Ile Ser Leu Ile Gly Thr Ala
    50                  55                  60

Ser Ile Ser Trp Ile Gly Thr Tyr Leu Gly Ile Thr Thr Gly Asn Asn
65                  70                  75                  80

Val Ala Val Pro Leu Asp Ala Gly Leu Pro Ala Glu Asp Leu Ile Glu
                85                  90                  95

Leu Leu Asn Asp Ser Asp Ala Glu Ala Leu Phe Leu Ala Pro Lys Gly
            100                 105                 110

Lys Ala Leu Ala Glu Ala Val Lys Ala Ser Cys Pro Lys Ile Arg Lys
        115                 120                 125

Ile Trp Leu Leu Gln Glu Glu Pro Glu Glu Gly Phe Ser Thr Leu Ala
    130                 135                 140

Asp Leu Lys Asp Met Ser Lys Gly Arg Gln Asp Val Glu Gly Arg Lys
145                 150                 155                 160

Ala Glu Asp Ile Ala Thr Leu Ile Tyr Thr Ser Gly Thr Thr Gly Lys
                165                 170                 175

Ser Lys Gly Val Met Leu Thr Gln Ser Asn Leu Ser Gln Asn Val Glu
            180                 185                 190

Ser Val Pro Tyr Ser Ala Glu Pro Gly Cys Val Leu Leu Ser Val Leu
        195                 200                 205

Pro Val His His Ala Phe Cys Leu Val Met Asp Trp Leu Lys Gly Phe
    210                 215                 220

Ser Leu Gly Ala Thr Val Cys Ile Asn Asp Ser Phe Met His Ile Ile
225                 230                 235                 240
```

```
Arg Asn Met Ser Ile Phe Lys Pro Asp Val Met Leu Met Val Pro Leu
                245                 250                 255

Met Ile Glu Thr Ile Tyr Lys Arg Leu Ser Ala Val Asp Pro Ala Leu
            260                 265                 270

Pro Lys Glu Ala Val Ala Ala Asn Val Phe Gly Gly Asn Leu Lys Ile
        275                 280                 285

Ile Phe Thr Gly Gly Ala His Leu Asp Pro Phe Tyr Ile Glu Lys Leu
    290                 295                 300

Ala Glu Tyr Gly Val Lys Val Leu Glu Gly Tyr Gly Met Ser Glu Cys
305                 310                 315                 320

Ser Pro Val Ile Ser Ser Asn Thr Pro Glu Asp His Lys Ile Gly Ser
                325                 330                 335

Ile Gly Lys Pro Leu Pro Asn Val Lys Val Arg Phe Glu Asp Gly Glu
            340                 345                 350

Ile Gln Val Gln Gly Ser Ser Val Met Lys Gly Tyr Tyr Lys Met Pro
        355                 360                 365

Ala Glu Thr Glu Glu Thr Leu Lys Asp Gly Trp Leu His Thr Gly Asp
    370                 375                 380

Lys Gly Tyr Leu Asp Glu Asp Gly Phe Leu Phe Ile Asn Gly Arg Val
385                 390                 395                 400

Lys Asn Leu Ile Ile Leu Ser Asn Gly Glu Asn Ile Ser Pro Glu Glu
                405                 410                 415

Ile Glu Asn Lys Leu Gly Ile Asn Pro Leu Val Gly Glu Val Ile Val
            420                 425                 430

Thr Gly Glu Asn Asn Gly Leu Thr Ala Arg Ile Tyr Pro Asp Gln Asp
        435                 440                 445

Val Val Lys Ala Thr Gly Leu Ala Glu Asp Ala Val Lys Ala Ala Leu
    450                 455                 460

Asp Asn Ile Leu Lys Glu Tyr Asn Gln Lys Gln Pro Thr Tyr Arg Gln
465                 470                 475                 480

Ile Ile Ala Leu Val Val Arg Lys Asn Pro Phe His Arg Asn Ala Thr
                485                 490                 495

Gly Lys Ile Val Arg Ala Asp Ala Glu Ile Asp Glu
            500                 505

<210> SEQ ID NO 127
<211> LENGTH: 1386
<212> TYPE: DNA
<213> ORGANISM: Ruminococcus sp.

<400> SEQUENCE: 127
atgaacagcg ttaacaaacc ggtgtatccg ctgattccgc ctcaagaaat gattcagttt     60
atgctgaaat acagcttttt tcataaacag gtgacccaga ttccggatag cattattgtt    120
agccagaaaa tcgacttcga tgttatgacc gaagccttta acattgaaat cgaacgtaat    180
gattgtctgc gcctggtttt tttcaaacag aatggcaaca tcatgcagta ttttcgtgat    240
ccgtatcgta ttggtagcgt tccggtttat aactttaaat ccgatgaaga acgcgagaaa    300
gttctgaccg cagatgcaca gaaaccgatt aaaatgctga aggcgaaat cttccgcctg    360 aaatactttt ccacctatga tggtcgttat ggcgtgtata tcaacattca tcatctggtg    420
atggataacg cagcagtttt tgcctttttc aatgacctgt tgccgtgta tgatcatctg    480 aaaaatggta aaccgatgcc gaaaccgctg gtagctatg aagatcgtat taaacgtgaa    540
ctggcctacg ttgaagataa aagcaatctg gaaaagaaa aagaggccta caccgaatat    600
```

```
atcacccgta atggtgaacc ggtttatctg ggtgttgaag gtccgaaact gctggaagca    660
gaacgcaaaa aaaagaaaga tccgagtatt aatgcaccga gcctgtttga tccgattcat    720
gataaagcag aactgaccaa aaccacctt t agtccggaac tgagcgaaaa attctttagc   780
ttttgcgaga caataacgt gagtccggaa tgtctggttc agctggcact gcgtatgcat     840
ctgagcaaaa ttaataatgg tcacctggac acctatttca tttgtctgtg tacccgtcgt    900
cgtaccctga ccgaaaaacg tagcggtggc accgttaccg caccgctgcc gtggcgtgtt    960
catctggaag aggatgatac ctttatgagc gcactggata aaatggcaga tgcccaggtt   1020
tgggcatttc gtcacatgga ttatccgtat ctggaatatc gtgatctgca gcgtgaactg   1080
tttaactata gcgcagcagc aggtagcagc accatgatgt ttagctggat gccgattaac   1140
gaaaaaagca ttaatggctg ggagtatgag tatgttggtt atggtctggg tcgctatatt   1200
atggttctgt atcctttgc aatgaaagat gcacatagcg gctgtctgaa aattagctgt    1260
ctgcatcgta ccaaatttgt gagcgtggaa gatattaaag cactgcataa tggcaccaaa   1320
aaggttctgg aaattgcact gaatgaaccg gatatcagca ttaaagatct gctggaaaag   1380
atgtaa                                                              1386
```

<210> SEQ ID NO 128
<211> LENGTH: 461
<212> TYPE: PRT
<213> ORGANISM: Ruminococcus sp.

<400> SEQUENCE: 128

```
Met Asn Ser Val Asn Lys Pro Val Tyr Pro Leu Ile Pro Pro Gln Glu
1               5                   10                  15

Met Ile Gln Phe Met Leu Lys Tyr Ser Phe Phe His Lys Gln Val Thr
            20                  25                  30

Gln Ile Pro Asp Ser Ile Ile Val Ser Gln Lys Ile Asp Phe Asp Val
        35                  40                  45

Met Thr Glu Ala Phe Asn Ile Glu Ile Glu Arg Asn Asp Cys Leu Arg
    50                  55                  60

Leu Val Phe Phe Lys Gln Asn Gly Asn Ile Met Gln Tyr Phe Arg Asp
65                  70                  75                  80

Pro Tyr Arg Ile Gly Ser Val Pro Val Tyr Asn Phe Lys Ser Asp Glu
                85                  90                  95

Glu Arg Glu Lys Val Leu Thr Ala Asp Ala Gln Lys Pro Ile Lys Met
            100                 105                 110

Leu Lys Gly Glu Ile Phe Arg Leu Lys Tyr Phe Thr Thr Tyr Asp Gly
        115                 120                 125

Arg Tyr Gly Val Tyr Ile Asn Ile His His Leu Val Met Asp Asn Ala
    130                 135                 140

Ala Val Phe Ala Phe Phe Asn Asp Leu Phe Ala Val Tyr Asp His Leu
145                 150                 155                 160

Lys Asn Gly Lys Pro Met Pro Lys Pro Leu Gly Ser Tyr Glu Asp Arg
                165                 170                 175

Ile Lys Arg Glu Leu Ala Tyr Val Glu Asp Lys Ser Asn Leu Glu Lys
            180                 185                 190

Glu Lys Glu Ala Tyr Thr Glu Tyr Ile Thr Arg Asn Gly Glu Pro Val
        195                 200                 205

Tyr Leu Gly Val Glu Gly Pro Lys Leu Leu Glu Ala Glu Arg Lys Lys
    210                 215                 220

Lys Lys Asp Pro Ser Ile Asn Ala Pro Ser Leu Phe Asp Pro Ile His
```

```
                225                 230                 235                 240
Asp Lys Ala Glu Leu Thr Lys Thr Thr Phe Ser Pro Glu Leu Ser Glu
                245                 250                 255

Lys Phe Phe Ser Phe Cys Glu Asn Asn Asn Val Ser Pro Glu Cys Leu
            260                 265                 270

Val Gln Leu Ala Leu Arg Met His Leu Ser Lys Ile Asn Asn Gly His
        275                 280                 285

Leu Asp Thr Tyr Phe Ile Cys Leu Cys Thr Arg Arg Thr Leu Thr
    290                 295                 300

Glu Lys Arg Ser Gly Gly Thr Val Thr Ala Pro Leu Pro Trp Arg Val
305                 310                 315                 320

His Leu Glu Glu Asp Asp Thr Phe Met Ser Ala Leu Asp Lys Met Ala
                325                 330                 335

Asp Ala Gln Val Trp Ala Phe Arg His Met Asp Tyr Pro Tyr Leu Glu
            340                 345                 350

Tyr Arg Asp Leu Gln Arg Glu Leu Phe Asn Tyr Ser Ala Ala Ala Gly
        355                 360                 365

Ser Ser Thr Met Met Phe Ser Trp Met Pro Ile Asn Glu Lys Ser Ile
    370                 375                 380

Asn Gly Trp Glu Tyr Glu Tyr Val Gly Tyr Gly Leu Gly Arg Tyr Ile
385                 390                 395                 400

Met Val Leu Tyr Thr Phe Ala Met Lys Asp Ala His Ser Gly Cys Leu
                405                 410                 415

Lys Ile Ser Cys Leu His Arg Thr Lys Phe Val Ser Val Glu Asp Ile
            420                 425                 430

Lys Ala Leu His Asn Gly Thr Lys Lys Val Leu Glu Ile Ala Leu Asn
        435                 440                 445

Glu Pro Asp Ile Ser Ile Lys Asp Leu Leu Glu Lys Met
    450                 455                 460

<210> SEQ ID NO 129
<211> LENGTH: 225
<212> TYPE: DNA
<213> ORGANISM: Ruminococcus sp.

<400> SEQUENCE: 129
atgctggaaa cctttcgcaa catcatttgc aactatgtgg atatcgatcc ggaagatatt       60
accgaagata gcaaactgcg tagcgatatt gaactgaaca gctttgatat ggttaatgtt      120
gccgtggatc tggaaaatca gtatggcgtt aaaatcgata gcaaaaaatt cggtggtctg      180
aaaaccgttg gtgatctgat gagctatatc gagagcatca aataa                      225

<210> SEQ ID NO 130
<211> LENGTH: 74
<212> TYPE: PRT
<213> ORGANISM: Ruminococcus sp.

<400> SEQUENCE: 130

Met Leu Glu Thr Phe Arg Asn Ile Ile Cys Asn Tyr Val Asp Ile Asp
1               5                   10                  15

Pro Glu Asp Ile Thr Glu Asp Ser Lys Leu Arg Ser Asp Ile Glu Leu
            20                  25                  30

Asn Ser Phe Asp Met Val Asn Val Ala Val Asp Leu Glu Asn Gln Tyr
        35                  40                  45

Gly Val Lys Ile Asp Ser Lys Lys Phe Gly Gly Leu Lys Thr Val Gly
    50                  55                  60
```

Asp Leu Met Ser Tyr Ile Glu Ser Ile Lys
65                  70

<210> SEQ ID NO 131
<211> LENGTH: 1548
<212> TYPE: DNA
<213> ORGANISM: Ruminococcus sp.

<400> SEQUENCE: 131

| | |
|---|---|
| atgaagaaat tgatgcacc gagcgttcgt gaactgctgg ataccggtgc agaaaaattt | 60 |
| ggtgatgcaa ccttcatcaa attcattcgc gacggcaaaa ttgaagaacg cagcttcaaa | 120 |
| aaagttcgta gcgatagcct ggcagtttgt cgttggattc gtagcctgag cgataaacgt | 180 |
| atgcatattg ccattattgg caagagcaac tatgagtata ttacctgtct gagcggtatt | 240 |
| ctgattagcg gtaatgttgc agttccgttt gcaccggata ttagcgttga agaagccgca | 300 |
| gaactgttta acgtgcaga tattgaaatg ctgctgtatg aagatgaatt taccgaaaac | 360 |
| gccgagaaac tgaaagaact gtgtccgttt ctgcgtttta gcgtgaattt aggtaatggc | 420 |
| gaagaattca accgcatcta taccgattat agcgaaaata gcgaatatgc agcactgtct | 480 |
| gatatcaccg ttgataaaaa tgcctgctgc gtgattatct ttaccagcgg tacaaccggt | 540 |
| atcaaaaaag gtgttgaact gagcaccctg gcactggttg caatattat gtatcatgat | 600 |
| tattgcaccg acatctttct gccgaatgat gttagcctga tgttctgcc gatgtatcac | 660 |
| atttattgtt tcagcggtga ctatatcaag aacctgaaag atggtctgca ggtttgtctg | 720 |
| aatggtagca tgatggatct gattcacaac ctgaaaatct ttgaaccgaa agttgttcgt | 780 |
| gtggttccga tgattgcaca gagcctgctg cagcgtgtta agttattct ggcaaaagaa | 840 |
| ccggaaacca gcgttaaaga tgcagttgca caggttttg gtcgcaacat taaatggctg | 900 |
| attagtggtg gtgcatatct gaatccggaa ctgattgatg aatatgagaa actgggtatt | 960 |
| ttcctgcgtc aaggttatgg tatgaccgaa gcaggttgtc gtattagcgt gccggataat | 1020 |
| accgcaagcc gtgaaagcgt tggtcgtgtt accgatgttt gtaccgttcg tattcagaat | 1080 |
| ggtgaaattc aggttaatac cccgaccgtt atgctgggtt attacaaaat gccggaagaa | 1140 |
| accaaagaaa tgtttaccga agatggttgg ctgaaaaccg gtgatattgg tgaactgacc | 1200 |
| gaagataacc agctgtttat taccggtcgt gtgaaaaacc tgattattct gagcaatggc | 1260 |
| gaaaatgtta gtccggaagc cattgaaaaa aagtttgcag ataatcgtct ggtgagcgaa | 1320 |
| gttctggttt atggtgaaaa agatcgcatt atcgccgaaa tctatccgga ttatgagtat | 1380 |
| gcaaaactgg aaggcattga tgatattcag ggtgaactgg aaaaaaccgt ggatcgtatg | 1440 |
| aataaaaccg caaagcagc acatattatc agcgaagtgc gtgttcgtac cgaaccgtta | 1500 |
| gaaaaaacag gtagcggtaa aatcaaacgt aaagcaaccg ttctgtaa | 1548 |

<210> SEQ ID NO 132
<211> LENGTH: 515
<212> TYPE: PRT
<213> ORGANISM: Ruminococcus sp.

<400> SEQUENCE: 132

Met Lys Lys Phe Asp Ala Pro Ser Val Arg Glu Leu Leu Asp Thr Gly
1               5                   10                  15

Ala Glu Lys Phe Gly Asp Ala Thr Phe Ile Lys Phe Ile Arg Asp Gly
            20                  25                  30

Lys Ile Glu Glu Arg Ser Phe Lys Lys Val Arg Ser Asp Ser Leu Ala

```
              35                  40                  45
Val Cys Arg Trp Ile Arg Ser Leu Ser Asp Lys Arg Met His Ile Ala
 50                  55                  60
Ile Ile Gly Lys Ser Asn Tyr Glu Tyr Ile Thr Cys Leu Ser Gly Ile
 65                  70                  75                  80
Leu Ile Ser Gly Asn Val Ala Val Pro Phe Ala Pro Asp Ile Ser Val
                 85                  90                  95
Glu Glu Ala Ala Glu Leu Phe Lys Arg Ala Asp Ile Glu Met Leu Leu
                100                 105                 110
Tyr Glu Asp Glu Phe Thr Glu Asn Ala Glu Lys Leu Lys Glu Leu Cys
                115                 120                 125
Pro Phe Leu Arg Phe Ser Val Asn Leu Gly Asn Gly Glu Glu Phe Asn
130                 135                 140
Arg Ile Tyr Thr Asp Tyr Ser Glu Asn Ser Glu Tyr Ala Ala Leu Ser
145                 150                 155                 160
Asp Ile Thr Val Asp Lys Asn Ala Cys Cys Val Ile Ile Phe Thr Ser
                165                 170                 175
Gly Thr Thr Gly Ile Lys Lys Gly Val Glu Leu Ser Thr Leu Ala Leu
                180                 185                 190
Val Gly Asn Ile Met Tyr His Asp Tyr Cys Thr Asp Ile Phe Leu Pro
                195                 200                 205
Asn Asp Val Ser Leu Ser Val Leu Pro Met Tyr His Ile Tyr Cys Phe
210                 215                 220
Ser Gly Asp Tyr Ile Lys Asn Leu Lys Asp Gly Leu Gln Val Cys Leu
225                 230                 235                 240
Asn Gly Ser Met Met Asp Leu Ile His Asn Leu Lys Ile Phe Glu Pro
                245                 250                 255
Lys Val Val Arg Val Val Pro Met Ile Ala Gln Ser Leu Leu Gln Arg
                260                 265                 270
Val Lys Val Ile Leu Ala Lys Glu Pro Glu Thr Ser Val Lys Asp Ala
                275                 280                 285
Val Ala Gln Val Phe Gly Arg Asn Ile Lys Trp Leu Ile Ser Gly Gly
                290                 295                 300
Ala Tyr Leu Asn Pro Glu Leu Ile Asp Glu Tyr Glu Lys Leu Gly Ile
305                 310                 315                 320
Phe Leu Arg Gln Gly Tyr Gly Met Thr Glu Ala Gly Cys Arg Ile Ser
                325                 330                 335
Val Pro Asp Asn Thr Ala Ser Arg Glu Ser Val Gly Arg Val Thr Asp
                340                 345                 350
Val Cys Thr Val Arg Ile Gln Asn Gly Glu Ile Gln Val Asn Thr Pro
                355                 360                 365
Thr Val Met Leu Gly Tyr Tyr Lys Met Pro Glu Thr Lys Glu Met
                370                 375                 380
Phe Thr Glu Asp Gly Trp Leu Lys Thr Gly Asp Ile Gly Glu Leu Thr
385                 390                 395                 400
Glu Asp Asn Gln Leu Phe Ile Thr Gly Arg Val Lys Asn Leu Ile Ile
                405                 410                 415
Leu Ser Asn Gly Glu Asn Val Ser Pro Glu Ala Ile Glu Lys Lys Phe
                420                 425                 430
Ala Asp Asn Arg Leu Val Ser Glu Val Leu Val Tyr Gly Glu Lys Asp
                435                 440                 445
Arg Ile Ile Ala Glu Ile Tyr Pro Asp Tyr Glu Tyr Ala Lys Leu Glu
450                 455                 460
```

Gly Ile Asp Asp Ile Gln Gly Glu Leu Glu Lys Thr Val Asp Arg Met
465                 470                 475                 480

Asn Lys Thr Ala Lys Ala Ala His Ile Ile Ser Glu Val Arg Val Arg
            485                 490                 495

Thr Glu Pro Leu Glu Lys Thr Gly Ser Gly Lys Ile Lys Arg Lys Ala
        500                 505                 510

Thr Val Leu
    515

<210> SEQ ID NO 133
<211> LENGTH: 1389
<212> TYPE: DNA
<213> ORGANISM: Clostridium sp.

<400> SEQUENCE: 133

```
atgatgatga acagtatcc gctgaccgca gcacagaaaa tgcatgatga ttggatcaaa      60
aagtacaaaa cccagcaggt tagcggtgtt agcgttgttg caagcctgaa agcagaactg     120
gattttggtc tgctgaaaaa atgtatccaa ctggaatatg aacgctatgg ttgtatgcgt    180
attcgtttta ccaaacgcga taaaaatggt gacgttaaac agtacctgac cgaaaaagaa    240
acccgtgata ttccgctgaa agatctgagc ggtatgcaca tggaagaggc agataatctg    300
atgcagcagt gggcctatga aacctttgat ggtgatgata tcccgctgtg tgatattgtt    360
atggttaaac tgccggatgg ctataacggc ttttttatcc acatggatca tcgtctgatt    420
gatagctgtg gtctggttgt gatgattaat gatcttatgc agctgtacac ccactacaaa    480
tttaacaccc cgtatccgca gaaactggca gattttgaag aagtgctggt taaagacctg    540
aatcgtgcca ataatgaaaa acgctttgcc aaagacaaaa aattctggga tgatcagctg    600
gatgcatggg gtgaaccgct gtatagcgat attcaaggtc tggatgttct ggaagcaagc    660
cgtaaactgc atcgtaataa aaccctgcgt gcagcagata ttgaactgga tcagctgttt    720
gttgccgtga agattatca actggaaccg gaaccgacca aaaacctgat tgattttgt     780
atgaatcatc agctgagcat gaccaatctg ctgctgctgg gtattcgtac ctatctgagc    840
aaaatgaatc atggccaaga agatatcacc atcgaaaact ttattagccg tcgtagcacc    900
catgatgaat ggaccagcgg tggtagccgt accattatgt ttccgtgtcg taccgttatt    960
agcgcagata ccgattttct gagcgcagcg tatgaaattc agaatatgca gaaccgcatc   1020
tacatgcaca gcaattatga tccggcactg attcgtgaag aaatgcagaa acgttatcat   1080
accccgaaaa acaccgctta tgaaagctgt tatctgaccc tcagccgat gccggtgaaa   1140
ctggataatc cgcatctggt tcagattccg cagcatgcaa atggtttgc aaatggtgca   1200
gcaaccaaaa gatgtatct gaccgttagc ataccgata tggtggtat gaacttcagc    1260
tatcattacc agaccgcaca tctggcagaa catgatatgg aactgctgta ttattacatg   1320
atgcgcattc tgtttaaagg cattgccgaa ccggatatga gcattggtga aattatggaa   1380
caggtgtaa                                                           1389
```

<210> SEQ ID NO 134
<211> LENGTH: 462
<212> TYPE: PRT
<213> ORGANISM: Clostridium sp.

<400> SEQUENCE: 134

Met Met Met Lys Gln Tyr Pro Leu Thr Ala Ala Gln Lys Met His Asp
1               5                   10                  15

-continued

Asp Trp Ile Lys Lys Tyr Lys Thr Gln Gln Val Ser Gly Val Ser Val
              20                  25                  30

Val Ala Ser Leu Lys Ala Glu Leu Asp Phe Gly Leu Leu Lys Lys Cys
         35                  40                  45

Ile Gln Leu Glu Tyr Glu Arg Tyr Gly Cys Met Arg Ile Arg Phe Thr
50                  55                  60

Lys Arg Asp Lys Asn Gly Asp Val Lys Gln Tyr Leu Thr Glu Lys Glu
65                  70                  75                  80

Thr Arg Asp Ile Pro Leu Lys Asp Leu Ser Gly Met His Met Glu Glu
                 85                  90                  95

Ala Asp Asn Leu Met Gln Gln Trp Ala Tyr Glu Thr Phe Asp Gly Asp
             100                 105                 110

Asp Ile Pro Leu Cys Asp Ile Val Met Val Lys Leu Pro Asp Gly Tyr
         115                 120                 125

Asn Gly Phe Phe Ile His Met Asp His Arg Leu Ile Asp Ser Cys Gly
130                 135                 140

Leu Val Val Met Ile Asn Asp Leu Met Gln Leu Tyr Thr His Tyr Lys
145                 150                 155                 160

Phe Asn Thr Pro Tyr Pro Gln Lys Leu Ala Asp Phe Glu Glu Val Leu
                 165                 170                 175

Val Lys Asp Leu Asn Arg Ala Asn Asn Glu Lys Arg Phe Ala Lys Asp
             180                 185                 190

Lys Lys Phe Trp Asp Asp Gln Leu Asp Ala Trp Gly Glu Pro Leu Tyr
         195                 200                 205

Ser Asp Ile Gln Gly Leu Asp Val Leu Glu Ala Ser Arg Lys Leu His
210                 215                 220

Arg Asn Lys Thr Leu Arg Ala Ala Asp Ile Glu Leu Asp Gln Leu Phe
225                 230                 235                 240

Val Ala Val Lys Asp Tyr Gln Leu Glu Pro Glu Pro Thr Lys Asn Leu
                 245                 250                 255

Ile Asp Phe Cys Met Asn His Gln Leu Ser Met Thr Asn Leu Leu Leu
             260                 265                 270

Leu Gly Ile Arg Thr Tyr Leu Ser Lys Met Asn His Gly Gln Glu Asp
         275                 280                 285

Ile Thr Ile Glu Asn Phe Ile Ser Arg Arg Ser Thr His Asp Glu Trp
290                 295                 300

Thr Ser Gly Gly Ser Arg Thr Ile Met Phe Pro Cys Arg Thr Val Ile
305                 310                 315                 320

Ser Ala Asp Thr Asp Phe Leu Ser Ala Ala Tyr Glu Ile Gln Asn Met
                 325                 330                 335

Gln Asn Arg Ile Tyr Met His Ser Asn Tyr Asp Pro Ala Leu Ile Arg
             340                 345                 350

Glu Glu Met Gln Lys Arg Tyr His Thr Pro Lys Asn Thr Ala Tyr Glu
         355                 360                 365

Ser Cys Tyr Leu Thr Tyr Gln Pro Met Pro Val Lys Leu Asp Asn Pro
370                 375                 380

His Leu Val Gln Ile Pro Gln His Ala Lys Trp Phe Ala Asn Gly Ala
385                 390                 395                 400

Ala Thr Lys Lys Met Tyr Leu Thr Val Ser His Thr Asp Asn Gly Gly
                 405                 410                 415

Met Asn Phe Ser Tyr His Tyr Gln Thr Ala His Leu Ala Glu His Asp
             420                 425                 430

```
Met Glu Leu Leu Tyr Tyr Tyr Met Met Arg Ile Leu Phe Lys Gly Ile
            435                 440                 445

Ala Glu Pro Asp Met Ser Ile Gly Glu Ile Met Glu Gln Val
        450                 455                 460

<210> SEQ ID NO 135
<211> LENGTH: 243
<212> TYPE: DNA
<213> ORGANISM: Clostridium sp.

<400> SEQUENCE: 135
atgacccaag agatgcagtt caaaaaaatc attgcccagt attgcgacgt gaaaccggaa      60
gaaatgacca acgatatgaa atttcgtgaa gatctgggtt ttagcagcct ggattttatg     120
agctttctgg cgaaattga agatacccttt gatatcgaac tggaagagga tgatgcactg     180 catgtttttta ccattgttga agcactggat ctgctggaac gtctgcagca agaaaccgtt     240
taa                                                                    243

<210> SEQ ID NO 136
<211> LENGTH: 80
<212> TYPE: PRT
<213> ORGANISM: Clostridium sp.

<400> SEQUENCE: 136

Met Thr Gln Glu Met Gln Phe Lys Lys Ile Ile Ala Gln Tyr Cys Asp
1               5                   10                  15

Val Lys Pro Glu Glu Met Thr Asn Asp Met Lys Phe Arg Glu Asp Leu
            20                  25                  30

Gly Phe Ser Ser Leu Asp Phe Met Ser Phe Leu Gly Glu Ile Glu Asp
        35                  40                  45

Thr Phe Asp Ile Glu Leu Glu Glu Asp Ala Leu His Val Phe Thr
    50                  55                  60

Ile Val Glu Ala Leu Asp Leu Leu Glu Arg Leu Gln Gln Glu Thr Val
65                  70                  75                  80

<210> SEQ ID NO 137
<211> LENGTH: 1545
<212> TYPE: DNA
<213> ORGANISM: Clostridium sp.

<400> SEQUENCE: 137
atgctgattc gcgatattct ggaagaaagc gagaaaaaat tcagcgaaat caaagccgtt      60
aagtggctga aaagaaaga aattcgtgat cgtagctatc gcgaactgat ggaaaatgca     120
aaaagcgttc gtaaaggtct gtgcgaagaa agttttcagg gtaaacatat tgcactgatt     180
ggtagcagca gcgttgaatg gattgaagca tatctgggta ttattaccgg tcaggcagtt     240
gcagttccgc tggatgcagg tctgcctgca gaagatctga ttgatctgct gaatcgtagt     300
gatgcagaag cactgttttct gagccccgaaa attcagaccc tgagcgaacg tatcctggaa     360
gaatgtccga aactgaagaa aatctggatt ctgcaagaag aaaacatcga accaaccag     420 aaaaaagttg caagcgttgc agaactgatg atgagcggta ttaatggcac cgatgatttt     480
gcagcacctg atccggaaga tattgcaacc attatcttta ccagcggcac caccggtaaa     540
agcaaaggtg ttatgctgac ccagcgtaat ctggcagaaa atgttaaaag cgtgaactat     600
accgcagaac cgggtacgat tgttctgagc gttctgccga ttcatcatgc atttgtctg     660 gttatggatt ggctgaaagg ttttagcttt ggtgcaaccg tttgcattaa tgatagcctg     720
```

```
ctgcacatgg tgaaaaatat gggtgttttt catccggaca ttatgctgat ggttccgctg    780
atggtggaaa ccatctataa acgtctgagc gcaatgaatc cgctgattcc gaaaaaaatc    840
gttgcagcaa aagcctttgg tggcaaactg aaaaccattt ttacaggtgg cgcacatctg    900
gacccgtttt atatcgaaaa atttgccgaa tatggcgtga acatctatga aggttatggt    960
atgagcgaat gcagtccggt tattagcagc aatgtgccgg aagatcataa aaccggtagc   1020
attggtcgtc cgctgagcaa tgttgaaatt agctttgaag atggcgaaat tctggttcgt   1080
ggtagcagtg ttatgaaagg ctattatcag atgcctgaag aaacagccga agcactgcgt   1140
ggtggttggc tgcataccgg tgataaaggt tatctggata agatggcttc ctgtttatt    1200 aacggtcgca tcaaaaacct gattattctg agtaacggcg aaaacattag tccggaagaa   1260
atcgaaaata aactggcact gggtaaactg gttggtgaag ttattgttac cggtgaaaat   1320
aatggtctga tcgcacgtat ttatccggat caagatgcag ttagcgcaaa acgtatgaat   1380
gaagaagcaa ttcgtagcga actgcaggca tttattgata gctataacaa tacccagccg   1440
acctatcgtc gtattacagg tctggtgatt cgtaaatatc cgtttatcaa aagcgccacc   1500
aaaaagatca aacgtcaaga ggtgctgatt gatgaagcac cgtaa              1545

<210> SEQ ID NO 138
<211> LENGTH: 514
<212> TYPE: PRT
<213> ORGANISM: Clostridium sp.

<400> SEQUENCE: 138

Met Leu Ile Arg Asp Ile Leu Glu Glu Ser Glu Lys Lys Phe Ser Glu
1               5                   10                  15

Ile Lys Ala Val Lys Trp Leu Lys Lys Lys Glu Ile Arg Asp Arg Ser
            20                  25                  30

Tyr Arg Glu Leu Met Glu Asn Ala Lys Ser Val Arg Lys Gly Leu Cys
        35                  40                  45

Glu Glu Ser Phe Gln Gly Lys His Ile Ala Leu Ile Gly Ser Ser Ser
    50                  55                  60

Val Glu Trp Ile Glu Ala Tyr Leu Gly Ile Ile Thr Gly Gln Ala Val
65                  70                  75                  80

Ala Val Pro Leu Asp Ala Gly Leu Pro Ala Glu Asp Leu Ile Asp Leu
                85                  90                  95

Leu Asn Arg Ser Asp Ala Glu Ala Leu Phe Leu Ser Pro Lys Ile Gln
            100                 105                 110

Thr Leu Ser Glu Arg Ile Leu Glu Glu Cys Pro Lys Leu Lys Lys Ile
        115                 120                 125

Trp Ile Leu Gln Glu Glu Asn Ile Glu Thr Asn Gln Lys Lys Val Ala
    130                 135                 140

Ser Val Ala Glu Leu Met Met Ser Gly Ile Asn Gly Thr Asp Asp Phe
145                 150                 155                 160

Ala Ala Pro Asp Pro Glu Asp Ile Ala Thr Ile Phe Thr Ser Gly
                165                 170                 175

Thr Thr Gly Lys Ser Lys Gly Val Met Leu Thr Gln Arg Asn Leu Ala
            180                 185                 190

Glu Asn Val Lys Ser Val Asn Tyr Thr Ala Glu Pro Gly Thr Ile Val
        195                 200                 205

Leu Ser Val Leu Pro Ile His His Ala Phe Cys Leu Val Met Asp Trp
    210                 215                 220

Leu Lys Gly Phe Ser Phe Gly Ala Thr Val Cys Ile Asn Asp Ser Leu
```

-continued

```
225                 230                 235                 240

Leu His Met Val Lys Asn Met Gly Val Phe His Pro Asp Ile Met Leu
                245                 250                 255
Met Val Pro Leu Met Val Glu Thr Ile Tyr Lys Arg Leu Ser Ala Met
            260                 265                 270

Asn Pro Leu Ile Pro Lys Lys Ile Val Ala Ala Lys Ala Phe Gly Gly
        275                 280                 285

Lys Leu Lys Thr Ile Phe Thr Gly Gly Ala His Leu Asp Pro Phe Tyr
    290                 295                 300

Ile Glu Lys Phe Ala Glu Tyr Gly Val Asn Ile Tyr Glu Gly Tyr Gly
305                 310                 315                 320
Met Ser Glu Cys Ser Pro Val Ile Ser Ser Asn Val Pro Glu Asp His
                325                 330                 335
Lys Thr Gly Ser Ile Gly Arg Pro Leu Ser Asn Val Glu Ile Ser Phe
            340                 345                 350

Glu Asp Gly Glu Ile Leu Val Arg Gly Ser Ser Val Met Lys Gly Tyr
        355                 360                 365

Tyr Gln Met Pro Glu Glu Thr Ala Glu Ala Leu Arg Gly Gly Trp Leu
    370                 375                 380

His Thr Gly Asp Lys Gly Tyr Leu Asp Lys Asp Gly Phe Leu Phe Ile
385                 390                 395                 400
Asn Gly Arg Ile Lys Asn Leu Ile Ile Leu Ser Asn Gly Glu Asn Ile
                405                 410                 415
Ser Pro Glu Glu Ile Glu Asn Lys Leu Ala Leu Gly Lys Leu Val Gly
            420                 425                 430

Glu Val Ile Val Thr Gly Glu Asn Asn Gly Leu Ile Ala Arg Ile Tyr
        435                 440                 445

Pro Asp Gln Asp Ala Val Ser Ala Lys Arg Met Asn Glu Glu Ala Ile
    450                 455                 460

Arg Ser Glu Leu Gln Ala Phe Ile Asp Ser Tyr Asn Asn Thr Gln Pro
465                 470                 475                 480
Thr Tyr Arg Arg Ile Thr Gly Leu Val Ile Arg Lys Tyr Pro Phe Ile
                485                 490                 495
Lys Ser Ala Thr Lys Lys Ile Lys Arg Gln Glu Val Leu Ile Asp Glu
            500                 505                 510

Ala Pro
```

<210> SEQ ID NO 139
<211> LENGTH: 1386
<212> TYPE: DNA
<213> ORGANISM: Clostridium sp.

<400> SEQUENCE: 139

```
atgaagaact attatccgct gaccgcagca cagaaaatgc attataactg gatcaagaag      60
tacaaaaccc agcaggttag cggtgttagc gttgttgcaa gcctgaaagc agcactggat     120
tttggtctgc tgaaaaaatg tattcagctg gaatttgaac gctatggttg tatgcgtctg     180
cgttttacca aaccggatga aaattgtgat gtgatgcagt atattgccag caatgatagc     240
cgtgatattc cgattaaaga tctgagcaat atgcgtatgg cagatgcaga taaactgatg     300
cagcagtggg cctatgaaac catggatggt aatgatatcc cgatgtgtga tgttaccatg     360
ctgaaactgc cggatggtta taatggcttt tttatccaca tggatcaccg cctgattgat     420
agctgtggtc tgattgttat gatcaacgat ctgatgcaac tgtataccca ttatcgtttt     480
```

```
ggtagcgatt ttccgaaaga tctggcagat tttgaaaccg ttctgagcaa agacctggaa      540
aaagcagcaa acaaaaaacg cttcctgaaa gacaaaaaat tctgggatga tcagctggat      600
attctgggtg aaccgctgta tagcgatatt cagggtcctg caattctgga agaaagccgt      660
aaactgcata acgataaaaa tctgcgtgca gccgatatcg aactgaaaaa cctgtttgtt      720
gccgtgaaag attattacct ggaaccggaa ccgaccaaga atctgctgga tttttgtacc      780
aatcatcagc tgagcatgac caatctgctg ctgctgggta ttcgtaccta tctgagtaaa      840
gttaatgatg gccaagagga tatcaccatc cagaacttta ttagccgtcg tagcacccat      900
gatgaatgga ccagcggtgg tagccgtacc attatgtttc cgtgtcgtac cgttattagc      960
gcagataccg atttctgac agcagcccat gaaattcagg atattcagaa ccgcatttac      1020
atgcacagca attatgatcc ggcactgatt gaagaagaaa tgcgtcgtcg ttataaaaca      1080
ccggaaaaca ccagctatga aagctgttat ctgacctatc agccgatgac cgtgaaaatg      1140
gataatccgc atctggaaaa tattccgcag catagcaaat ggtttgcaaa tggtgcagcc      1200
accaaaaaga tgtatctgac cgttagccat accgataatg gtggcaccaa ttttagctat      1260
cattatcaga ccgccaacct gaaagaacat gatatggaac tgctgtatta ctatatgatg      1320
cgcattctgt ttaaaggcat tgcagaaccg gatatgacca ttggcgaaat tattgaacag      1380
gtgtaa                                                                 1386
```

<210> SEQ ID NO 140
<211> LENGTH: 461
<212> TYPE: PRT
<213> ORGANISM: Clostridium sp.

<400> SEQUENCE: 140

```
Met Lys Asn Tyr Tyr Pro Leu Thr Ala Ala Gln Lys Met His Tyr Asn
1               5                   10                  15

Trp Ile Lys Lys Tyr Lys Thr Gln Gln Val Ser Gly Val Ser Val Val
                20                  25                  30

Ala Ser Leu Lys Ala Ala Leu Asp Phe Gly Leu Leu Lys Lys Cys Ile
            35                  40                  45

Gln Leu Glu Phe Glu Arg Tyr Gly Cys Met Arg Leu Arg Phe Thr Lys
        50                  55                  60

Pro Asp Glu Asn Cys Asp Val Met Gln Tyr Ile Ala Ser Asn Asp Ser
65                  70                  75                  80

Arg Asp Ile Pro Ile Lys Asp Leu Ser Asn Met Arg Met Ala Asp Ala
                85                  90                  95

Asp Lys Leu Met Gln Gln Trp Ala Tyr Glu Thr Met Asp Gly Asn Asp
            100                 105                 110

Ile Pro Met Cys Asp Val Thr Met Leu Lys Leu Pro Asp Gly Tyr Asn
        115                 120                 125

Gly Phe Phe Ile His Met Asp His Arg Leu Ile Asp Ser Cys Gly Leu
    130                 135                 140

Ile Val Met Ile Asn Asp Leu Met Gln Leu Tyr Thr His Tyr Arg Phe
145                 150                 155                 160

Gly Ser Asp Phe Pro Lys Asp Leu Ala Asp Phe Glu Thr Val Leu Ser
                165                 170                 175

Lys Asp Leu Glu Lys Ala Ala Asn Lys Lys Arg Phe Leu Lys Asp Lys
            180                 185                 190

Lys Phe Trp Asp Asp Gln Leu Asp Ile Leu Gly Glu Pro Leu Tyr Ser
        195                 200                 205
```

Asp Ile Gln Gly Pro Ala Ile Leu Glu Glu Ser Arg Lys Leu His Asn
210                 215                 220

Asp Lys Asn Leu Arg Ala Ala Asp Ile Glu Leu Lys Asn Leu Phe Val
225                 230                 235                 240

Ala Val Lys Asp Tyr Tyr Leu Glu Pro Glu Thr Lys Asn Leu Leu
            245                 250                 255

Asp Phe Cys Thr Asn His Gln Leu Ser Met Thr Asn Leu Leu Leu Leu
            260                 265                 270

Gly Ile Arg Thr Tyr Leu Ser Lys Val Asn Asp Gly Gln Glu Asp Ile
            275                 280                 285

Thr Ile Gln Asn Phe Ile Ser Arg Arg Ser Thr His Asp Glu Trp Thr
290                 295                 300

Ser Gly Gly Ser Arg Thr Ile Met Phe Pro Cys Arg Thr Val Ile Ser
305                 310                 315                 320

Ala Asp Thr Asp Phe Leu Thr Ala Ala His Glu Ile Gln Asp Ile Gln
            325                 330                 335

Asn Arg Ile Tyr Met His Ser Asn Tyr Asp Pro Ala Leu Ile Glu Glu
            340                 345                 350

Glu Met Arg Arg Arg Tyr Lys Thr Pro Glu Asn Thr Ser Tyr Glu Ser
            355                 360                 365

Cys Tyr Leu Thr Tyr Gln Pro Met Thr Val Lys Met Asp Asn Pro His
370                 375                 380

Leu Glu Asn Ile Pro Gln His Ser Lys Trp Phe Ala Asn Gly Ala Ala
385                 390                 395                 400

Thr Lys Lys Met Tyr Leu Thr Val Ser His Thr Asp Asn Gly Gly Thr
            405                 410                 415

Asn Phe Ser Tyr His Tyr Gln Thr Ala Asn Leu Lys Glu His Asp Met
            420                 425                 430

Glu Leu Leu Tyr Tyr Tyr Met Met Arg Ile Leu Phe Lys Gly Ile Ala
            435                 440                 445

Glu Pro Asp Met Thr Ile Gly Glu Ile Ile Glu Gln Val
            450                 455                 460

<210> SEQ ID NO 141
<211> LENGTH: 231
<212> TYPE: DNA
<213> ORGANISM: Clostridium sp.

<400> SEQUENCE: 141

```
atgaccaaag agatgcagtt caaaaacatt gttgcccagt attgcgaagt gaaaccggaa     60
gatatgaatg gtgatatgcg ttttcgtgaa gatctgggtt ttagcagcct ggattttatg    120
agctttctgg gtgaactgga agataccttt gatgttgagc tggaagatga agaagcactg    180
aaaattcgta atgttagcga agcactggaa ctgctgaata ccctggttta a             231
```

<210> SEQ ID NO 142
<211> LENGTH: 76
<212> TYPE: PRT
<213> ORGANISM: Clostridium sp.

<400> SEQUENCE: 142

```
Met Thr Lys Glu Met Gln Phe Lys Asn Ile Val Ala Gln Tyr Cys Glu
1               5                   10                  15

Val Lys Pro Glu Asp Met Asn Gly Asp Met Arg Phe Arg Glu Asp Leu
            20                  25                  30

Gly Phe Ser Ser Leu Asp Phe Met Ser Phe Leu Gly Glu Leu Glu Asp
```

```
                35                  40                  45
Thr Phe Asp Val Glu Leu Glu Asp Glu Glu Ala Leu Lys Ile Arg Asn
        50                  55                  60

Val Ser Glu Ala Leu Glu Leu Leu Asn Thr Leu Val
65                  70                  75

<210> SEQ ID NO 143
<211> LENGTH: 1608
<212> TYPE: DNA
<213> ORGANISM: Clostridium sp.

<400> SEQUENCE: 143
atggaaaaac tgatccgcga cattattgaa gaaagcgcat gtcgttttgc agaactgacc      60
gcagttaaat ggctgaaaaa gaaagaaatc ttcgagatca attacgccag cctgaatgaa     120
aacattaccg caattcgtaa agccctgctg aaagaaggtt ttctgaaaaa acatattgcc     180
ctgattggca ccagcagcgt tgaatggatt gaaagctatc tgggtattat taccggtggt     240
tgtgttgcag ttccgctgga tgcaggtctg ccggataaag atctgaccga tctgattaat     300
cgtagcgata gcgaagcact gtttctgagc ccgaaaaatc tgagcctgct gagcagcatt     360
ctggcagatt gtccgaaact gaaaaacatc tggattctga cagcgataa taacgacacc      420 gaaaaaaaca gcatcctgaa caaaattagc gcctttgcca ataacagcat caacaatagc     480 ataccgtta gctttgtgag cgatctgaaa atgttgttc gcacgagcga taatgatgca      540
gatcgtccgg caccggatga taccgcaacc attatcttta ccagcggtac aaccggtaaa     600
agcaaaggtt tatgctgac ccataataat ctggcaagca atgttcagag cgtgaactat     660
tacaccgaaa gcggcaccgt gatgctgagc gttctgccgg ttcatcatgt ttattgtctg     720
gttatggatt ggctgaaagg ttttagcctg gtgcaacca tttgtattaa tgatagcctg     780
atgcacatga tgcgcaatat tggtgttttt aaaccggaag tgattctgat ggttccgatg     840
atggttgaaa ccatctataa acgtctggca gcagcagatc cgagcattcc gcctaatatt     900
ctggccaata aaatctttgg tggcaacctg catatcatct ttatgggtgg tgcacatctg     960
gacccgtttt atatcgataa atttgccgaa tatggcatcg acatctatga aggttatggt    1020
atgagcgaat gtagtccggt tattagcagc aatctgcctg gttgtcataa accggtagc     1080 attggtcgtc cgctgagcaa tgcagaaatt agctttgata tggcgaaat tctggttcgt     1140 ggtacaagcg ttatgaaagg ctattataac atgccgaaag aaaccgcaga accctgcgt     1200 gatggttggc tgcataccgg tgataaaggt tatattgatg aagatggctt cctgtttatt     1260
aacggtcgcg ttaaaaacct gattattctg tccaatggcg agaacattag tccggaagaa     1320
attgaaaata actggcccct ggatgatctg gttggtgaag ttattgtgac cggtgaaaaa     1380
aatggtctga ccgcacgtat ttatccggaa caagaactgg ttattgcagc caatatgacc     1440
gaagatgaag tgcgtaaaaa tctgcaggcc tttatcgaca atataacag cgaacagccg     1500 acctatcgtc gcattaccgg tctggtgatt cgcaaaaatc cgtttattcg tagcagcacc     1560
aaaaagatca aacgtcaaga ggcactgatc gatgaaccga tgatttaa               1608

<210> SEQ ID NO 144
<211> LENGTH: 535
<212> TYPE: PRT
<213> ORGANISM: Clostridium sp.

<400> SEQUENCE: 144

Met Glu Lys Leu Ile Arg Asp Ile Ile Glu Glu Ser Ala Cys Arg Phe
```

-continued

```
1               5                   10                  15
Ala Glu Leu Thr Ala Val Lys Trp Leu Lys Lys Glu Ile Phe Glu
                20                  25                  30
Ile Asn Tyr Ala Ser Leu Asn Glu Asn Ile Thr Ala Ile Arg Lys Ala
                35                  40                  45
Leu Leu Lys Glu Gly Phe Leu Lys Lys His Ile Ala Leu Ile Gly Thr
50                  55                  60
Ser Ser Val Glu Trp Ile Glu Ser Tyr Leu Gly Ile Ile Thr Gly Gly
65                  70                  75                  80
Cys Val Ala Val Pro Leu Asp Ala Gly Leu Pro Asp Lys Asp Leu Thr
                85                  90                  95
Asp Leu Ile Asn Arg Ser Asp Ser Glu Ala Leu Phe Leu Ser Pro Lys
                100                 105                 110
Asn Leu Ser Leu Leu Ser Ser Ile Leu Ala Asp Cys Pro Lys Leu Lys
                115                 120                 125
Asn Ile Trp Ile Leu Asn Ser Asp Asn Asp Thr Glu Lys Asn Ser
                130                 135                 140
Ile Leu Asn Lys Ile Ser Ala Phe Ala Asn Asn Ser Ile Asn Asn Ser
145                 150                 155                 160
Asn Thr Val Ser Phe Val Ser Asp Leu Lys Asn Val Val Arg Thr Ser
                165                 170                 175
Asp Asn Asp Ala Asp Arg Pro Ala Pro Asp Asp Thr Ala Thr Ile Ile
                180                 185                 190
Phe Thr Ser Gly Thr Thr Gly Lys Ser Lys Gly Val Met Leu Thr His
                195                 200                 205
Asn Asn Leu Ala Ser Asn Val Gln Ser Val Asn Tyr Tyr Thr Glu Ser
                210                 215                 220
Gly Thr Val Met Leu Ser Val Leu Pro Val His Val His Val Tyr Cys Leu
225                 230                 235                 240
Val Met Asp Trp Leu Lys Gly Phe Ser Leu Gly Ala Thr Ile Cys Ile
                245                 250                 255
Asn Asp Ser Leu Met His Met Met Arg Asn Ile Gly Val Phe Lys Pro
                260                 265                 270
Glu Val Ile Leu Met Val Pro Met Val Glu Thr Ile Tyr Lys Arg
                275                 280                 285
Leu Ala Ala Ala Asp Pro Ser Ile Pro Pro Asn Ile Leu Ala Asn Lys
                290                 295                 300
Ile Phe Gly Gly Asn Leu His Ile Ile Phe Met Gly Gly Ala His Leu
305                 310                 315                 320
Asp Pro Phe Tyr Ile Asp Lys Phe Ala Glu Tyr Gly Ile Asp Ile Tyr
                325                 330                 335
Glu Gly Tyr Gly Met Ser Glu Cys Ser Pro Val Ile Ser Ser Asn Leu
                340                 345                 350
Pro Gly Cys His Lys Thr Gly Ser Ile Gly Arg Pro Leu Ser Asn Ala
                355                 360                 365
Glu Ile Ser Phe Asp Asn Gly Glu Ile Leu Val Arg Gly Thr Ser Val
                370                 375                 380
Met Lys Gly Tyr Tyr Asn Met Pro Lys Glu Thr Ala Glu Thr Leu Arg
385                 390                 395                 400
Asp Gly Trp Leu His Thr Gly Asp Lys Gly Tyr Ile Asp Glu Asp Gly
                405                 410                 415
Phe Leu Phe Ile Asn Gly Arg Val Lys Asn Leu Ile Ile Leu Ser Asn
                420                 425                 430
```

```
Gly Glu Asn Ile Ser Pro Glu Ile Glu Asn Lys Leu Ala Leu Asp
            435                 440                 445

Asp Leu Val Gly Glu Val Ile Val Thr Gly Glu Lys Asn Gly Leu Thr
    450                 455                 460

Ala Arg Ile Tyr Pro Glu Gln Glu Leu Val Ile Ala Ala Asn Met Thr
465                 470                 475                 480

Glu Asp Glu Val Arg Lys Asn Leu Gln Ala Phe Ile Asp Lys Tyr Asn
                485                 490                 495

Ser Glu Gln Pro Thr Tyr Arg Arg Ile Thr Gly Leu Val Ile Arg Lys
            500                 505                 510

Asn Pro Phe Ile Arg Ser Ser Thr Lys Lys Ile Lys Arg Gln Glu Ala
            515                 520                 525

Leu Ile Asp Glu Pro Met Ile
            530                 535

<210> SEQ ID NO 145
<211> LENGTH: 352
<212> TYPE: PRT
<213> ORGANISM: E. rectale

<400> SEQUENCE: 145

Met His Asn Gln Thr Ala Ile Leu Phe Phe Tyr Lys Gly Lys Lys Met
1               5                   10                  15

Lys Leu Leu Ser Phe Ala Ile Pro Cys Tyr Asn Ser Lys Asp Tyr Met
            20                  25                  30

Glu His Cys Ile Glu Ser Ile Leu Pro Gly Gly Asp Asp Val Glu Ile
        35                  40                  45

Ile Ile Val Asp Asp Gly Ser Lys Asp Glu Thr Ala Ala Ile Ala Asp
    50                  55                  60

Arg Tyr Ala Ala Glu Tyr Pro Asp Ile Val Lys Ala Val His Gln Glu
65                  70                  75                  80

Asn Gly Gly His Gly Glu Ala Val Asn Thr Gly Leu Lys Asn Ala Thr
                85                  90                  95

Gly Lys Tyr Phe Lys Val Val Asp Ser Asp Asp Trp Val Asp Leu Asp
            100                 105                 110

Ser Tyr Lys Lys Ile Leu Asp Lys Leu Arg Glu Phe Glu Gln Glu Asn
            115                 120                 125

Thr Gln Ile Asp Met Leu Leu Ala Asn Tyr Val Tyr Glu Lys Glu Gly
        130                 135                 140

Ala Lys Arg Lys Val Met Arg Gln Thr Gly Phe Pro Arg Asn Glu
145                 150                 155                 160

Ile Phe Thr Trp Ser Asp Ile Lys His Ile Tyr Lys Gly His Tyr Ile
                165                 170                 175

Leu Met His Ser Val Ile Tyr Arg Thr Glu Leu Leu Arg Ser Cys Gly
            180                 185                 190

Leu Lys Leu Pro Lys His Thr Phe Tyr Val Asp Asn Ile Tyr Val Tyr
        195                 200                 205

Lys Pro Leu Pro Tyr Val Arg Thr Met Tyr Tyr Leu Asp Val Asp Phe
    210                 215                 220

Tyr Arg Tyr Phe Ile Gly Arg Asp Asp Gln Ser Val Asn Glu Gln Val
225                 230                 235                 240

Met Ile Arg Arg Ile Asp Gln Gln Ile Arg Val Asn Lys Ile Met Phe
                245                 250                 255

Asp Asp Val Lys Leu His Glu Ile Thr Asn Glu Met Cys Arg Lys Tyr
```

```
            260                 265                 270
Met Tyr Ser Tyr Leu Glu Ile Ile Thr Thr Ile Ser Thr Ile Leu Ala
            275                 280                 285

Ile Ile Ser Gly Thr Asp Glu Asn Met Ala Lys Lys Asp Glu Leu Trp
            290                 295                 300

Ala Tyr Met Lys Glu His Asp Glu Glu Thr Tyr Lys Lys Leu Arg His
305                 310                 315                 320

Gly Val Met Gly Gln Leu Met Asn Leu Pro Gly Lys Gly Arg Lys
                325                 330                 335

Val Ala Ile Gly Ala Tyr Lys Leu Ser Gln Lys Val Val Gly Phe Asn
            340                 345                 350

<210> SEQ ID NO 146
<211> LENGTH: 431
<212> TYPE: PRT
<213> ORGANISM: Artificial Sequence
<220> FEATURE:
<223> OTHER INFORMATION: Synthetic

<400> SEQUENCE: 146

Met Lys Arg Asn Thr Tyr Phe Leu Thr His Ala Gln Arg Arg Val Trp
1               5                   10                  15

Phe Thr Glu Leu Leu Glu Pro Gly Thr Ser Ile Cys Asn Leu Ala Ala
                20                  25                  30

Cys Val Lys Phe Arg Gly Thr Ile Asp Leu Glu Val Leu Gln Gln Ala
            35                  40                  45

Leu Asn Leu Ser Ile Ser Arg Asn Asp Ala Ile Arg Phe Arg Leu Thr
        50                  55                  60

Glu Gly Thr Asp Thr Glu Pro His Leu Tyr Leu Thr Glu His Glu Pro
65                  70                  75                  80

Met Ser Ile Glu Ile Ile Asp Phe Ala Asn Lys Ser Leu Glu Glu Val
                85                  90                  95

Glu Lys Trp Ile His Val Gln Thr Ser Ile Pro Phe Lys Leu Phe His
            100                 105                 110

Ser Pro Leu Tyr Gln Phe Tyr Phe Leu Arg Ile Asn Thr Glu Glu Ile
        115                 120                 125

Trp Leu Tyr Ala Lys Phe His His Ile Ile Met Asp Gly Ile Ser Leu
    130                 135                 140

Asn Leu Met Gly Asn Gln Ile Ile Asp Leu Tyr Leu Thr Leu Ile Arg
145                 150                 155                 160

Lys Asp Pro Val Pro Thr His His Glu Pro Ser Tyr Leu Ser Tyr Ile
                165                 170                 175

Glu Lys Glu Asn Gln Tyr Leu His Ser Ser Arg Phe Glu Lys Asp Arg
            180                 185                 190

Leu Phe Trp Thr Gln Ala Tyr Arg Lys Pro Pro Glu Tyr His Ser Leu
        195                 200                 205

Thr Asp Gln Ala Ser Val Gln Thr His Gly Thr Thr Ala Ser Arg Asp
    210                 215                 220

Thr Leu Thr Leu Ser His Asp Val Glu Arg Asn Ile Arg Asp Phe Cys
225                 230                 235                 240

Gln Glu Gln Gln Ile Ser Ile Ile Ser Leu Phe Met Ala Ser Leu Tyr
                245                 250                 255

Ile Cys Ile Ser Arg Leu Thr Ser Lys Asn Asp Leu Ala Ile Gly Thr
            260                 265                 270

Tyr Tyr Gly Asn Arg Gly Ser Lys Ala Glu Lys Glu Thr Leu Gly Met
```

```
                275                 280                 285
Phe Val Ser Thr Leu Pro Ile Arg Met Thr Val Asp Pro Lys Asp
    290                 295                 300
Phe Leu Ser Phe Val Arg Ser Val Gly Arg Glu Gln Leu Ser Val Met
305                 310                 315                 320
Arg His Gln Arg Phe Pro Asn Leu Leu Val Asn Glu Leu Arg Lys Glu
                325                 330                 335
Tyr Lys Asp Leu His Asn Leu Val Gly Ile Ser Met Gln Tyr Gln Pro
                340                 345                 350
Leu Gln Trp Gln Gln Ala Asp Cys Leu Asn Tyr Glu Thr Ala Met Tyr
                355                 360                 365
Phe Ser Gly His Thr Ala Asn Glu Leu Ser Ile Leu Ile Lys Glu Arg
                370                 375                 380
Ile Asp Thr Gly Thr Ile Gln Leu Asn Phe Asp Tyr Gln Thr Ser Leu
385                 390                 395                 400
Phe Thr Pro Asp Glu Ile Lys Arg Ile Gln His His Leu Leu Thr Val
                405                 410                 415
Leu Lys Asn Ala Leu Asn Asp Pro Ser Gln Leu Ile Lys Asp Met
                420                 425                 430

<210> SEQ ID NO 147
<211> LENGTH: 55
<212> TYPE: PRT
<213> ORGANISM: Artificial Sequence
<220> FEATURE:
<223> OTHER INFORMATION: Synthetic

<400> SEQUENCE: 147

Ile Ser Val Thr Asp His Phe Phe Glu Asn Gly Gly His Ser Leu Lys
1               5                   10                  15
Ala Ile Met Leu Leu Ser Arg Ile His Lys Ile Phe Asp Val Glu Met
                20                  25                  30
Ser Leu Arg Gln Ile Phe Glu Met Pro Thr Ile Lys Glu Gln Ala Thr
            35                  40                  45
Tyr Leu Arg Asn Ala Glu Lys
        50                  55

<210> SEQ ID NO 148
<211> LENGTH: 413
<212> TYPE: PRT
<213> ORGANISM: Artificial Sequence
<220> FEATURE:
<223> OTHER INFORMATION: Synthetic

<400> SEQUENCE: 148

Val Asn Asn His Met Thr Tyr Arg Glu Leu Asn Glu Lys Ser Asn Arg
1               5                   10                  15
Leu Ala Arg Thr Leu Arg Asn Tyr Gly Val Gln Ala Asp Thr Leu Val
                20                  25                  30
Ala Ile Met Ala Glu Arg Ser Leu Glu Met Ile Val Ser Ile Met Ala
            35                  40                  45
Ile Trp Lys Ala Gly Gly Ala Tyr Val Pro Leu Asp Pro Glu Tyr Pro
        50                  55                  60
Glu Glu Arg Leu Gln Tyr Val Leu Asn Asp Ala Asn Ala Asp Val Leu
65                  70                  75                  80
Val Val Gln Arg His Phe Lys Asn Ser Leu Val Phe Asp Gly Pro Met
                85                  90                  95
```

```
Ile Asp Leu Asn Asp Glu Thr Ser Tyr His Ala Asp Cys Ser Leu Leu
            100                 105                 110

Ser Pro Ile Ala Glu His Ser His Leu Ala Tyr Val Ile Tyr Thr Ser
        115                 120                 125

Gly Thr Thr Gly Lys Pro Lys Gly Val Met Val Glu His Gly Gly Ile
    130                 135                 140

Val Asn Ser Leu Gln Trp Lys Lys Ala Phe Phe Lys His Ser Ala Glu
145                 150                 155                 160

Asp Arg Val Leu Val Leu Tyr Pro Tyr Val Phe Asp Ala Phe Ile Leu
                165                 170                 175

Asn Phe Phe Gly Pro Leu Ile Ser Gly Ala Ala Leu Tyr Leu Leu Pro
                180                 185                 190

Asn Glu Asp Asn Lys Asp Leu Phe Ala Ile Gln Asn Val Leu Lys Leu
            195                 200                 205

Glu Arg Ile Thr His Phe Ser Thr Ser Pro Arg Leu Leu Gln Ala Met
            210                 215                 220

Thr Glu Gln Met Asn Ala Glu Asp Phe Tyr His Val Gln His Val Val
225                 230                 235                 240

Val Gly Gly Glu Lys Leu Glu Pro Asp Thr Val Glu Arg Leu Phe Ser
                245                 250                 255

Leu Gln Pro Gln Ile Arg Ile Asn Asn Glu Tyr Gly Pro Thr Glu Asn
                260                 265                 270

Ser Val Val Ser Thr Phe Gln Pro Val Tyr Ser Ala Asp Glu Gln Ile
            275                 280                 285

Thr Ile Gly Lys Pro Val Ala Asn His Gln Ala Tyr Ile Leu Gly Ala
            290                 295                 300

His Arg Gln Ile Gln Pro Ile Gly Val Pro Gly Glu Leu Tyr Val Gly
305                 310                 315                 320

Gly Ser Gly Val Ala Arg Gly Tyr Leu Asn Gln Pro Asp Leu Thr Glu
                325                 330                 335

Glu Lys Phe Val Asp His Leu Leu Ile Pro Arg Arg Lys Met Tyr Lys
                340                 345                 350

Thr Gly Asp Leu Ala Arg Trp Leu Pro Asp Gly Arg Ile Glu Tyr Leu
            355                 360                 365

Gly Arg Ile Asp His Gln Val Lys Ile Arg Gly Tyr Arg Ile Glu Leu
            370                 375                 380

Gly Glu Val Glu Ala Ala Leu Ser Asn Leu Glu Val Arg Glu Thr
385                 390                 395                 400

Thr Val Glu Ser Arg Glu Gly Ile Asp Gly Thr Lys Gln
                405                 410

<210> SEQ ID NO 149
<211> LENGTH: 31
<212> TYPE: PRT
<213> ORGANISM: E. rectale

<400> SEQUENCE: 149

Phe Met Glu Asp Leu Gly Phe Thr Ser Phe Asp Phe Met Ser Met Leu
1               5                   10                  15

Gly Glu Ile Glu Asp Thr Phe Asp Val Glu Ile Glu Gln Thr Lys
                20                  25                  30

<210> SEQ ID NO 150
<211> LENGTH: 59
<212> TYPE: PRT
<213> ORGANISM: Artificial Sequence
```

```
<220> FEATURE:
<223> OTHER INFORMATION: Synthetic

<400> SEQUENCE: 150

Asn Leu Lys Val Phe Phe Glu Asn Ser Leu Asn Val Thr Glu Lys Asp
1               5                   10                  15

Arg Ile Gly Gln Phe Ala Ser Ile Ser Phe Asp Ala Ser Val Trp Glu
            20                  25                  30

Met Phe Met Ala Leu Leu Thr Gly Ala Ser Leu Tyr Ile Ile Leu Lys
        35                  40                  45

Asp Thr Ile Asn Asp Phe Val Lys Phe Glu Gln
    50                  55

<210> SEQ ID NO 151
<211> LENGTH: 59
<212> TYPE: PRT
<213> ORGANISM: Artificial Sequence
<220> FEATURE:
<223> OTHER INFORMATION: Synthetic

<400> SEQUENCE: 151

Asn Ser Leu Gln Trp Lys Lys Ala Phe Phe Lys His Ser Ala Glu Asp
1               5                   10                  15

Arg Val Leu Val Leu Tyr Pro Tyr Val Phe Asp Ala Phe Ile Leu Asn
            20                  25                  30

Phe Phe Gly Pro Leu Ile Ser Gly Ala Ala Leu Tyr Leu Leu Pro Asn
        35                  40                  45

Glu Asp Asn Lys Asp Leu Phe Ala Ile Gln Asn
    50                  55

<210> SEQ ID NO 152
<211> LENGTH: 53
<212> TYPE: PRT
<213> ORGANISM: Artificial Sequence
<220> FEATURE:
<223> OTHER INFORMATION: Synthetic

<400> SEQUENCE: 152

Gln Asn Val Glu Asn Val Tyr Val Asn Leu Gly Pro Gly Val Thr Ile
1               5                   10                  15

Leu Ser Val Leu Pro Ile His His Ala Phe Cys Leu Thr Met Glu Trp
            20                  25                  30

Met Lys Gly Ile Ser Leu Gly Ala Thr Ile Cys Ile Asn Asp Ser Leu
        35                  40                  45

Leu His Met Leu Lys
    50

<210> SEQ ID NO 153
<211> LENGTH: 53
<212> TYPE: PRT
<213> ORGANISM: Artificial Sequence
<220> FEATURE:
<223> OTHER INFORMATION: Synthetic

<400> SEQUENCE: 153

Glu Asn Val Lys Ser Val Gln Tyr Thr Ala Glu Pro Gly Ser Val Leu
1               5                   10                  15

Leu Ser Val Leu Pro Ile His His Ala Phe Cys Leu Val Met Asp Trp
            20                  25                  30

Leu Lys Gly Phe Ser Leu Gly Thr Val Cys Ile Asn Asp Ser Leu
        35                  40                  45
```

Leu His Met Val Lys
    50

<210> SEQ ID NO 154
<211> LENGTH: 53
<212> TYPE: PRT
<213> ORGANISM: Artificial Sequence
<220> FEATURE:
<223> OTHER INFORMATION: Synthetic

<400> SEQUENCE: 154

Asp Asn Ala Val Cys Leu Asp Met Lys Ile Pro Ala Gly Thr Val Ser
1               5                   10                  15

Met Thr Leu Leu Pro Ile Asn His Val Tyr Cys Leu Thr Met Asp Ile
            20                  25                  30

Ile Lys Gly Leu Tyr Ile Gly Met Ile Ile Cys Ile Asn Asp Ser Ile
        35                  40                  45

Met His Val Gln Arg
    50

<210> SEQ ID NO 155
<211> LENGTH: 53
<212> TYPE: PRT
<213> ORGANISM: Artificial Sequence
<220> FEATURE:
<223> OTHER INFORMATION: Synthetic

<400> SEQUENCE: 155

Asp Asn Ala Val Cys Leu Asp Met Lys Ile Pro Ala Gly Thr Val Ser
1               5                   10                  15

Met Thr Leu Leu Pro Ile His His Ala Tyr Cys Phe Thr Met Asp Ile
            20                  25                  30

Leu Lys Gly Ile Tyr Ile Gly Met Val Ile Cys Ile Asn Asp Ser Ile
        35                  40                  45

Met His Val Ser Lys
    50

<210> SEQ ID NO 156
<211> LENGTH: 53
<212> TYPE: PRT
<213> ORGANISM: Artificial Sequence
<220> FEATURE:
<223> OTHER INFORMATION: Synthetic

<400> SEQUENCE: 156

Asp Asn Ala Ile Ala Phe Asp Val Gln Leu Lys Ala Gly Thr Val Ser
1               5                   10                  15

Met Thr Val Leu Pro Ile Asn His Val Phe Cys Phe Thr Met Asp Ile
            20                  25                  30

Leu Lys Gly Ile His Leu His Leu Cys Ile Cys Ile Asn Asp Ser Val
        35                  40                  45

Met Arg Val Leu Lys
    50

<210> SEQ ID NO 157
<211> LENGTH: 53
<212> TYPE: PRT
<213> ORGANISM: Artificial Sequence
<220> FEATURE:
<223> OTHER INFORMATION: Synthetic

<400> SEQUENCE: 157

-continued

```
Glu Asn Ala Gly Ser Ile Asn Met Asp Leu Pro Arg Met Val Leu
1               5                   10                  15

Leu Ser Val Leu Pro Ile His His Ala Tyr Cys Leu Cys Leu Asp Val
            20                  25                  30

Leu Lys Ala Ile Ser Leu Gly Ser Ile Ile Cys Ile Asn Asp Ser Leu
        35                  40                  45

Leu Arg Val Met Lys
        50

<210> SEQ ID NO 158
<211> LENGTH: 53
<212> TYPE: PRT
<213> ORGANISM: Artificial Sequence
<220> FEATURE:
<223> OTHER INFORMATION: Synthetic

<400> SEQUENCE: 158

Asp Asn Ala Val Cys Leu Asp Met Lys Ile Pro Ala Gly Thr Ile Ser
1               5                   10                  15

Met Thr Leu Leu Pro Ile Asn His Val Tyr Cys Leu Thr Met Asp Ile
            20                  25                  30

Ile Lys Gly Leu His Ile Gly Leu Val Ile Cys Ile Asn Asp Ser Ile
        35                  40                  45

Met His Val Gln Arg
        50

<210> SEQ ID NO 159
<211> LENGTH: 53
<212> TYPE: PRT
<213> ORGANISM: Artificial Sequence
<220> FEATURE:
<223> OTHER INFORMATION: Synthetic

<400> SEQUENCE: 159

Glu Asn Ala Thr Cys Leu Asp Met Lys Ile Gly Pro His Thr Val Ile
1               5                   10                  15

Leu Ser Val Leu Pro Ile His His Ala Tyr Cys Leu Ser Met Asp Ile
            20                  25                  30

Leu Lys Gly Ile Ser Leu Gly Ser Val Ile Cys Ile Asn Asp Ser Ile
        35                  40                  45

Met Arg Met Ala Lys
        50

<210> SEQ ID NO 160
<211> LENGTH: 60
<212> TYPE: PRT
<213> ORGANISM: Artificial Sequence
<220> FEATURE:
<223> OTHER INFORMATION: Synthetic

<400> SEQUENCE: 160

Lys Arg Ala Asp Gln Glu Arg Thr Phe His Leu Ala Lys Asp Pro Leu
1               5                   10                  15

Met Arg Val Ala Leu Phe Gln Met Ser Gln His Asp Tyr Gln Val Ile
            20                  25                  30

Trp Ser Phe His His Ile Leu Met Asp Gly Trp Cys Phe Ser Ile Ile
        35                  40                  45

Phe Asp Asp Leu Leu Ala Ile Tyr Leu Ser Leu Gln
        50                  55                  60
```

<210> SEQ ID NO 161
<211> LENGTH: 55
<212> TYPE: PRT
<213> ORGANISM: Artificial Sequence
<220> FEATURE:
<223> OTHER INFORMATION: Synthetic

<400> SEQUENCE: 161

Thr Ser Ile Pro Phe Lys Leu Phe His Ser Pro Leu Tyr Gln Phe Tyr
1               5                   10                  15

Phe Leu Arg Ile Asn Thr Glu Glu Ile Trp Leu Tyr Ala Lys Phe His
            20                  25                  30

His Ile Ile Met Asp Gly Ile Ser Leu Asn Leu Met Gly Asn Gln Ile
        35                  40                  45

Ile Asp Leu Tyr Leu Thr Leu
    50                  55

<210> SEQ ID NO 162
<211> LENGTH: 56
<212> TYPE: PRT
<213> ORGANISM: Artificial Sequence
<220> FEATURE:
<223> OTHER INFORMATION: Synthetic

<400> SEQUENCE: 162

Ser Arg Ile Pro Phe Asp Gly Asp Asn Ile Pro Met Asn Val Ile Lys
1               5                   10                  15

Met Ile Ser Leu Pro Gly Gly Tyr Asn Gly Leu Tyr Ile Lys Ile Asp
            20                  25                  30

His Arg Leu Met Asp Ser Cys Gly Ala Ile Val Met Val Asn Asp Ile
        35                  40                  45

Met Glu Leu Tyr Cys His Tyr Lys
    50                  55

<210> SEQ ID NO 163
<211> LENGTH: 56
<212> TYPE: PRT
<213> ORGANISM: Artificial Sequence
<220> FEATURE:
<223> OTHER INFORMATION: Synthetic

<400> SEQUENCE: 163

Ala Tyr Glu Thr Phe Asp Gly Asp Asp Ile Pro Leu Cys Asp Val Thr
1               5                   10                  15

Met Leu Lys Leu Pro Asp Gly Tyr Asn Gly Phe Phe Ile His Met Asp
            20                  25                  30

His Arg Leu Ile Asp Ser Cys Gly Leu Val Val Met Ile Asn Asp Leu
        35                  40                  45

Met Gln Leu Tyr Thr His Tyr Arg
    50                  55

<210> SEQ ID NO 164
<211> LENGTH: 56
<212> TYPE: PRT
<213> ORGANISM: Artificial Sequence
<220> FEATURE:
<223> OTHER INFORMATION: Synthetic

<400> SEQUENCE: 164

Thr Glu Val Pro Phe Glu Arg Tyr Asp Ser Pro Met His His Ile Val
1               5                   10                  15

Met Ile Arg Met Pro Asp Gly Tyr Gln Gly Leu Tyr Ile Cys Val Asp
            20                  25                  30

His Met Thr Met Asp Ala Gln Ser Leu Ile Leu Phe Phe Arg Asp Val
        35                  40                  45

Ile Glu Leu Tyr Ala Ser Lys Leu
    50                  55

<210> SEQ ID NO 165
<211> LENGTH: 55
<212> TYPE: PRT
<213> ORGANISM: Artificial Sequence
<220> FEATURE:
<223> OTHER INFORMATION: Synthetic

<400> SEQUENCE: 165

Thr Ser Val Pro Phe Glu Arg Phe Asp Ser Pro Leu Asn Arg Val Val
1               5                   10                  15

Met Ile Ile Thr Pro Asp Gly Phe Gln Gly Ile Tyr Leu Leu Val Asp
            20                  25                  30

His Met Thr Met Asp Ala Gln Ser Leu Ile Leu Phe Leu Asp Val Ile
        35                  40                  45

Glu Ile Tyr Ala Asn Met Lys
    50                  55

<210> SEQ ID NO 166
<211> LENGTH: 56
<212> TYPE: PRT
<213> ORGANISM: Artificial Sequence
<220> FEATURE:
<223> OTHER INFORMATION: Synthetic

<400> SEQUENCE: 166

Thr Glu Thr Pro Phe Glu Arg Glu Asn Lys Pro Leu Asn Lys Val Val
1               5                   10                  15

Met Ile Ser Met Pro Glu Gly Tyr Lys Gly Ile Tyr Leu Leu Val Asp
            20                  25                  30

His Met Thr Met Asp Ala Gln Ser Leu Ile Val Phe Met Lys Asp Ile
        35                  40                  45

Ile Glu Ile Tyr Cys His Leu Lys
    50                  55

<210> SEQ ID NO 167
<211> LENGTH: 56
<212> TYPE: PRT
<213> ORGANISM: Artificial Sequence
<220> FEATURE:
<223> OTHER INFORMATION: Synthetic

<400> SEQUENCE: 167

Thr Thr Val Pro Phe Pro Met Glu Asp Ala Pro Leu Thr Arg Val Val
1               5                   10                  15

Met Ile Ser Leu Pro Asp Gly Phe Asn Gly Val Tyr Phe Leu Gly His
            20                  25                  30

His Met Ile Val Asp Ala Gln Ser Leu Ile Gly Phe Leu Lys Asp Ile
        35                  40                  45

Ile Glu Leu Tyr Cys Ser Gln Lys
    50                  55

<210> SEQ ID NO 168
<211> LENGTH: 56
<212> TYPE: PRT

```
<213> ORGANISM: Artificial Sequence
<220> FEATURE:
<223> OTHER INFORMATION: Synthetic

<400> SEQUENCE: 168

Thr Glu Ile Pro Phe Glu Arg Tyr Asp Ser Pro Met His Arg Ile Val
1               5                   10                  15

Met Ile Lys Thr Pro Asp Gly Tyr Gln Gly Leu Tyr Ile Cys Val Asp
            20                  25                  30

His Met Thr Met Asp Ala Gln Ala Leu Ile Val Phe Phe Lys Asp Val
        35                  40                  45

Ile Glu Leu Tyr Cys Ser Arg Leu
    50                  55

<210> SEQ ID NO 169
<211> LENGTH: 56
<212> TYPE: PRT
<213> ORGANISM: Artificial Sequence
<220> FEATURE:
<223> OTHER INFORMATION: Synthetic

<400> SEQUENCE: 169

Thr Gln Val Pro Phe Glu Phe Glu Asp Ser Pro Met Thr Lys Ile Val
1               5                   10                  15

Met Ile Lys Met Pro Asp Gly Phe Asn Gly Val Tyr Phe Leu Gly His
            20                  25                  30

His Met Val Val Asp Ala Gln Ser Leu Ile Ala Phe Leu Lys Asp Ile
        35                  40                  45

Ile Glu Ile Tyr Cys Asn Ala Met
    50                  55
```